United States Patent
Cianchetta et al.

(10) Patent No.: US 11,464,775 B2
(45) Date of Patent: *Oct. 11, 2022

(54) PYRUVATE KINASE MODULATORS AND USE THEREOF

(71) Applicant: Agios Pharmaceuticals, Inc., Cambridge, MA (US)

(72) Inventors: Giovanni Cianchetta, Boxford, MA (US); Charles Kung, Arlington, MA (US); Tao Liu, Wellesley, MA (US); Anil Kumar Padyana, Lexington, MA (US); Zhihua Sui, Somerville, MA (US); Zhenwei Cai, Shanghai (CN); Dawei Cui, Shanghai (CN); Jingjing Ji, Shanghai (CN)

(73) Assignee: Agios Pharmaceuticals, Inc., Cambridge, MA (US)

(*) Notice: Subject to any disclaimer, the term of this patent is extended or adjusted under 35 U.S.C. 154(b) by 86 days.

This patent is subject to a terminal disclaimer.

(21) Appl. No.: 16/639,086

(22) PCT Filed: Aug. 15, 2018

(86) PCT No.: PCT/US2018/000129
§ 371 (c)(1),
(2) Date: Feb. 13, 2020

(87) PCT Pub. No.: WO2019/035865
PCT Pub. Date: Feb. 21, 2019

(65) Prior Publication Data
US 2020/0206225 A1 Jul. 2, 2020

Related U.S. Application Data

(60) Provisional application No. 62/673,526, filed on May 18, 2018, provisional application No. 62/673,533, filed on May 18, 2018.

(30) Foreign Application Priority Data

Aug. 15, 2017 (WO) ............... PCT/CN2017/097496

(51) Int. Cl.
| | |
|---|---|
| *A61K 31/5025* | (2006.01) |
| *A61K 31/506* | (2006.01) |
| *A61K 31/519* | (2006.01) |
| *C07D 241/36* | (2006.01) |
| *C07D 513/14* | (2006.01) |
| *A61K 45/06* | (2006.01) |

(52) U.S. Cl.
CPC ........ *A61K 31/5025* (2013.01); *A61K 31/506* (2013.01); *A61K 31/519* (2013.01); *C07D 241/36* (2013.01); *C07D 513/14* (2013.01); *A61K 45/06* (2013.01)

(58) Field of Classification Search
CPC .................. C07D 513/14; A61K 31/5025
See application file for complete search history.

(56) References Cited

U.S. PATENT DOCUMENTS

| | | | |
|---|---|---|---|
| 4,405,635 A | 9/1983 | Schnettler et al. | |
| 4,883,914 A | 11/1989 | Alvarado et al. | |
| 11,040,036 B2* | 6/2021 | Cianchetta ........... | A61K 31/506 |
| 2010/0331307 A1 | 12/2010 | Salituro et al. | |
| 2012/0142717 A1 | 6/2012 | Jin et al. | |
| 2014/0155374 A1 | 6/2014 | Su | |
| 2020/0207785 A1 | 7/2020 | Cianchetta et al. | |
| 2021/0130371 A1 | 5/2021 | Cianchetta et al. | |

FOREIGN PATENT DOCUMENTS

| | | |
|---|---|---|
| EA | 201590881 A1 | 8/2015 |
| WO | 2001/009121 A2 | 2/2001 |
| WO | 2001/017956 A1 | 3/2001 |
| WO | 2010/042867 A2 | 4/2010 |
| WO | 2011/002817 A1 | 1/2011 |
| WO | 2011/137089 A1 | 11/2011 |
| WO | 2012/092442 A1 | 7/2012 |
| WO | 2012/151448 A1 | 11/2012 |
| WO | 2012/151450 A1 | 11/2012 |
| WO | 2012/151451 A1 | 11/2012 |

(Continued)

OTHER PUBLICATIONS

Su et al., The role of pyruvate kinase M2 in anticancer therapeutic treatments (Review), Oncology Letters, 18, pp. 5663-5672, 2019.*
Marelli et al., Tumor targeting via integrin ligands, Frontiers in Oncology, vol. 3, Article 222, pp. 1-12, 2013.*
Wang et al., Mathematical modeling in cancer drug discovery, Drug Discovery Today, vol. 19, No. 2, pp. 145-150, 2014.*
Pearce et al., Failure modes in anticancer drug discovery and development, Cancer Drug Design and Discovery Edited by Stephen Neidle, Chapter 18, pp. 424-435 (2008).*
Gura, Systems for identifying new drugs are often faulty, Science, Nov. 7, 1997, 278(5340): 1041-2.*
Johnson et al., Relationships between drug activity in NCI preclinical in vitro and in vivo models and early clinical trials, Br J Cancer. May 18, 2001, 84(10): 1424-31.*

(Continued)

*Primary Examiner* — Deepak R Rao
(74) *Attorney, Agent, or Firm* — Steven G. Davis; Michael J. DeGrazia; Christopher D. Bayne

(57) ABSTRACT

Described herein are methods of using compounds of Formula (I) to modulate PKM2 activity in a subject. These compounds are represented by Formula (I): wherein $R^1$, $R^2$, $L^1$, and $L^2$ are as defined herein.

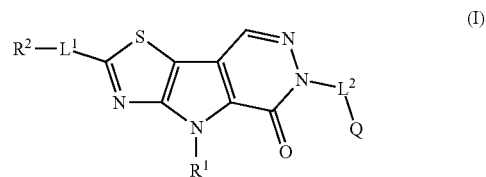

21 Claims, 14 Drawing Sheets

(56) References Cited

FOREIGN PATENT DOCUMENTS

| WO | 2012/151452 A1 | 11/2012 |
| --- | --- | --- |
| WO | 2014/074848 A1 | 5/2014 |
| WO | 2014/139144 A1 | 9/2014 |
| WO | 2014/139325 A1 | 9/2014 |
| WO | 2019/008025 A1 | 1/2019 |
| WO | 2019/034690 A1 | 2/2019 |
| WO | 2019/035865 A1 | 2/2019 |
| WO | 2019/035911 A1 | 2/2019 |

OTHER PUBLICATIONS

Simone, Introduction, Omenn, Cancer Prevention, Part XIV. Oncology, Cecil Textbook of Medicine, 20th Edition, vol. 1, pp. 1004-1010 (1996).*

Acute Leukemia, Merck Manual (Online Edition) 6 pages, pp. 1-6 (2013).*

U.S. Appl. No. 16/639,075, filed Feb. 13, 2020, Pending.

U.S. Appl. No. 16/639,081, filed Feb. 13, 2020, 2020-0207785, Published.

U.S. Appl. No. 16/952,257, filed Nov. 19, 2020, Pending.

U.S. Appl. No. 16/639,081, filed Feb. 13, 2020, Pending.

Adem et al., Pyruvate kinase activators as a therapy target: a patent review 2011-2017. Expert Opin Ther Pat. Jan. 2018;28(1):61-68.

Gupta et al., Human pyruvate kinase M2: a multifunctional protein. Protein Sci. Nov. 2010;19(11):2031-44.

Jiang et al., Evaluation of thieno[3,2-b]pyrrole[3,2-d]pyridazinones as activators of the tumor cell specific M2 isoform of pyruvate kinase. Bioorg Med Chem Lett. Jun. 1, 2010;20(11):3387-93.

Linghu et al., Development of a Practical Synthesis of ERK Inhibitor GDC-0994. 2017;21:387-98.

Palsson-McDermott et al., Pyruvate kinase M2 regulates Hif-1a activity and IL-1 beta induction and is a critical determinant of the warburg effect in LPS-activated macrophages Cell Metab. Jan. 6, 2015;21(1):65-80.

Sofan et al., Antimicrobial Activity of Newly Synthesized Thiadiazoles, 5-benzyl-2H-tetrazole and Their Nucleosides. Der Pharma Chemica. 2012;4(3): 1064-73.

International Search Report and Written Opinion for Application No. PCT/US2018/000129, dated Nov. 29, 2018, 10 pages.

* cited by examiner

FIGURE 4 - Continued

| | | |
|---|---|---|
| E7-10 | 3-methylacetophenone → NBS AIBN CCl₄, 80°C, 2h → 3-(bromomethyl)acetophenone | |
| E7-12 | 5-methylbenzoxazole → NBS, AIBN, CCl₃ → 5-(bromomethyl)benzoxazole | |
| E7-14 | methyl 3-amino-2-nitrobenzoate → 1) Pd H₂, MeOH, r.t; 2) CDI, DMF, r.t, 2h; 3) NaH, SEMCl, DMF, r.t, 1h; 4) LiBH₄, THF, r.t, 4h; 5) CBr₄, PPh₃, DCM, r.t → 4-(bromomethyl)-1,3-bis-SEM-benzimidazol-2(3H)-one | |
| E7-15 | 3-methyl-1H-pyrazolo[3,4-b]pyridine → 1) DMAP, Et₃N, Boc₂O, ACN, rt, 2h; 2) NBS, AIBN, CCl₄, 80°C, 16h → 3-(bromomethyl)-1-Boc-pyrazolo[3,4-b]pyridine | |
| E7-17 | 5-chloro-1H-pyrazolo[4,3-b]pyridine → 1) NaH, SEMCl, THF; 2) CO, Pd(dppf)Cl₂, MeOH/DMF, 90 °C; 3) DIBAL, THF; 4) SOCl₂, DCM → 5-(chloromethyl)-1-SEM-pyrazolo[4,3-b]pyridine | |
| E7-18 | 2-aminopyrimidine + 1,3-dichloroacetone → (CH₂OMe)₂, 45°C overnight → 2-(chloromethyl)imidazo[1,2-a]pyrimidine | |
| E7-20 | methyl 1H-indazole-4-carboxylate → 1) KOH, DMF, I₂, rt, 14h; 2) 3,4-Dihydro-2H-pyran, TsOH, THF, 85°C, 14 h; 3) CuI, Cs₂CO₃, MeOH, MW, 105°C, 2 h; 4) LAH, THF, ice-bath; 5) MsCl, TEA, DCM → 4-(chloromethyl)-3-methoxy-1-THP-indazole | |
| E7-22 | 5-bromo-1H-pyrazolo[4,3-b]pyridine → 1) nBuLi, THF, -30°C; 2) I₂, KOH, DMF, rt; 3) SEMCl, DMF, NaH; 4) CO, PdCl₂dppf, Et₃N, MeOH, DMF, 60°C; 5) LiAlH₄ → (1-SEM-pyrazolo[4,3-b]pyridin-3-yl)methanol | |
| E7-23 | 5-chloro-1H-pyrazolo[4,3-b]pyridine → 1) KOH, Acetone, MeI, rt; 2) CO, Pd(DPPF)Cl₂, MeOH, DMF; 3) NaBH₄; 4) SOCl₂, DCM → 5-(chloromethyl)-1-methyl-pyrazolo[4,3-b]pyridine | |

FIGURE 4 - Continued

| | | |
|---|---|---|
| E8-13<br>E8-14 | Imidazole-CH2OH | 1) (Boc)2O, Et3N<br>2) SOCl2, DMF<br>3) PhSNa<br>4) THF, H2O, rt → Boc-imidazole-CH2SO2Ph |
| E8-15 | 2-(2,5-dimethylpyrrol-1-yl)thiazole-5-carboxylic acid ethyl ester | 1) LiAlH4, THF<br>2) NCS, PPh3<br>3) PhSO2Na, DMF → 2-(2,5-dimethylpyrrol-1-yl)-5-(phenylsulfonylmethyl)thiazole |
| E8-17 | methyl 3-(chlorosulfonyl)benzoate | 1) PMB-NH-PMB, DIEPA, MeCN<br>2) LiAlH4<br>3) CBr4, PPh3<br>4) PhSNa, DMF<br>5) Oxone, THF → 3-((phenylsulfonyl)methyl)-N,N-bis(PMB)benzenesulfonamide |
| E8-18 | methyl 1H-indazole-6-carboxylate | 1) NaH, SEMCl<br>2) LiAlH4, THF<br>3) PPh3, CBr4<br>4) PhSNa, DMF<br>5) Oxone, THF → 1-SEM-6-((phenylsulfonyl)methyl)indazole |
| E8-20 | ethyl 5-fluoro-1H-pyrazole-3-carboxylate | 1) TrtCl, TEA<br>2) LiAlH4, THF<br>3) MsCl, TEA, DCM<br>4) PhSO2Na, DMSO → 1-Trt-5-fluoro-3-((SO2Ph)methyl)pyrazole |
| E8-21 | methyl 1H-indazole-4-carboxylate | 1) NaH, MeI, DMF<br>2) LAH, THF<br>3) SOCl2, DCM → 4-(chloromethyl)-1-methyl-1H-indazole |
| E8-22 | methyl 1H-indazole-5-carboxylate | 1) NaH, MeI, DMF<br>2) LAH, THF<br>3) SOCl2, DCM → 5-(chloromethyl)-1-methyl-1H-indazole |
| E8-24 | methyl 1H-indole-4-carboxylate | 1) NaBH3CN, AcOH<br>2) Boc2O, DMAP, MeCN<br>3) DIBAL-H, THF<br>4) CBr4, PPh3, DCM → 4-(bromomethyl)-1-Boc-indoline |
| E8-26 | methyl 4-(bromomethyl)thiazole-2-carboxylate | PhSO2Na, DMSO<br>DMSO, rt, 2h → methyl 4-((phenylsulfonyl)methyl)thiazole-2-carboxylate |

FIGURE 4 - Continued
| | |
|---|---|
| E8-27 | 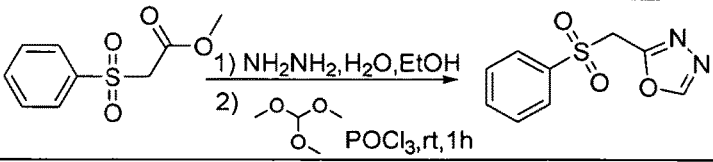 |
| E8-31 | 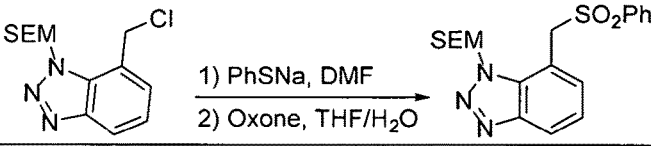 |
| E8-34 | 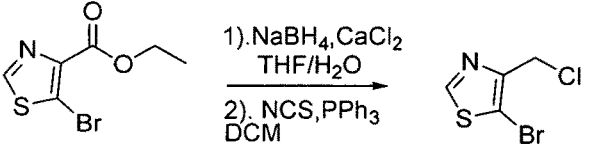 |
| E8-35 | 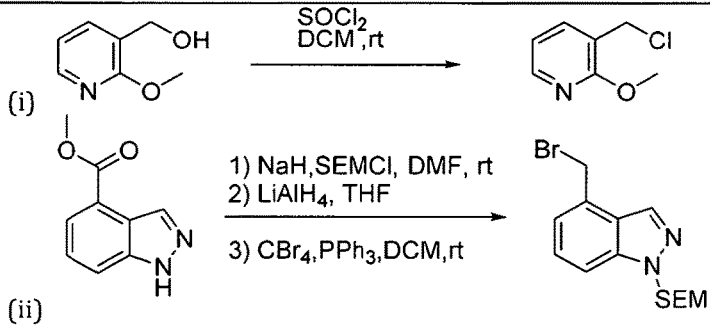 |
| E8-38 | 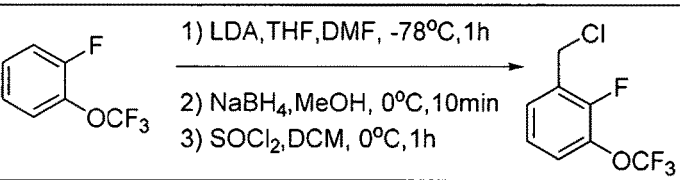 |
| E9-9 | 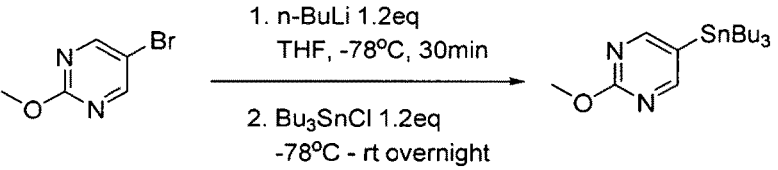 |
| E9-14<br>E9-28 | 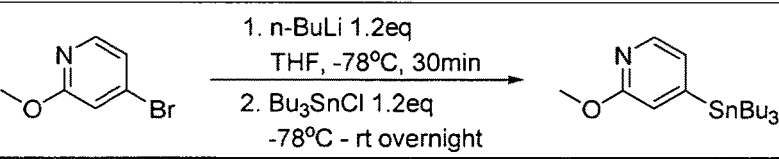 |
| E7-39 | 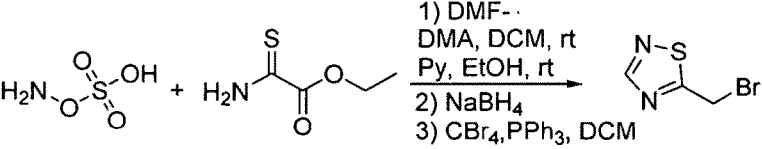 |

FIGURE 4 - Continued

| | | |
|---|---|---|
| E7-40 | ethyl 2-aminothiazole-4-carboxylate + hexane-2,5-dione → 1) TsOH, toluene MW, 150°C, 1h; 2) LiAlH₄, THF; 3) NCS, PPh₃ → 2-(2,5-dimethyl-1H-pyrrol-1-yl)-5-(chloromethyl)thiazole | |
| E7-41 | (1-trityl-1H-imidazol-4-yl)methanol → SOCl₂, CHCl₃ → 4-(chloromethyl)-1-trityl-1H-imidazole | |
| E7-42 | ethyl 1H-pyrazole-4-carboxylate → 1) TrtCl, NaH, THF; 2) LiAlH4, THF; 3) CBr₄, PPh₃, DCM → 4-(bromomethyl)-1-trityl-1H-pyrazole | |
| E7-44 | methyl 4-methylthiazole-2-carboxylate → 1) NBS, AIBN, BPO, CCl₄, reflux overnight; 2) DIBAL-H, THF; 3) DHP, PTSA, DCM → 4-(bromomethyl)-2-((tetrahydro-2H-pyran-2-yloxy)methyl)thiazole | |
| E7-47 | 6-methylpyridin-2-amine → 1) (Boc)₂O, DMAP, THF, rt, 12h; 2) NBS, AIBN, CCl₄, 80°C, 14h → di-Boc protected 6-(bromomethyl)pyridin-2-amine | |
| E7-49 | ethyl 5-bromothiazole-4-carboxylate → 1) NaBH₄, CaCl₂, THF/H₂O; 2) NCS, PPh₃, DCM → 5-bromo-4-(chloromethyl)thiazole | |
| E7-51 | 4-methylthiazole-5-carbaldehyde → 1) NH₂OH·HCl, DMSO, 90°C, 1.5 h; 2) NBS, AIBN, CCl₄, 80°C, 16hr → 4-(bromomethyl)thiazole-5-carbonitrile | |
| E7-53 | methyl 5-methylthiazole-4-carboxylate → 1) LAH, THF, 0°C; 2) Ph₃PBr₂, DCM → 4-(bromomethyl)-5-methylthiazole | |
| E7-54 | (6-chloropyridin-2-yl)methanol → 1) dimethylamine in THF, t-BuONa, Xantphos, Pd(oAc)₂; 2) SOCl₂, DCM → 6-(chloromethyl)-N,N-dimethylpyridin-2-amine | |

FIGURE 4 - Continued

| | | |
|---|---|---|
| E7-55 | ethyl 2-aminothiazole-4-carboxylate | 1) NIS, DCM r.t, 24 h<br>2) t-BuNO₂, THF, 50 °C-r.t, 2h<br>3) Methyl 2,2-difluoro-2-(fluorosulfonyl)acetate CuI, DMF, 85 °C, sealed tube<br>4) LiAlH₄, THF, 0 °C-r.t, 1h<br>5) Dibromo triphenyl phosphine DCM, 0 °C-r.t → 4-(bromomethyl)-5-(trifluoromethyl)thiazole |
| E7-56 | 4-methylthiazole | 1) NCS, CCl₄, reflux, 1h<br>2) NBS, BPO, CCl₄, reflux, 3h → 4-(bromomethyl)-5-chlorothiazole |
| E7-57 | ethyl 5-bromothiazole-4-carboxylate | 1) CH₃ONa, MeOH, 50 °C, 3 h<br>2) LiAlH₄, THF → (5-methoxythiazol-4-yl)methanol |
| E7-59 | 6-methyl-2-nitropyridin-3-ol | 1) MeI, K₂CO₃, DMF, rt<br>2) NBS, BPO → 6-(bromomethyl)-3-methoxy-2-nitropyridine |
| E7-60 | 2,6-dibromo-4-nitropyridine | 1) Cs₂CO₃, Pd(OAc)₂, BINAP, toluene, reflux [with bis(2,4-dimethoxybenzyl)amine]<br>2) TBAF, DMF, 65 °C<br>3) CO, Pd(dppf)Cl₂, TEA, MeOH<br>4) LiAlH₄, THF<br>5) NBS, PPh₃, DCM → 6-(bromomethyl)-N,N-bis(2,4-dimethoxybenzyl)-4-fluoropyridin-2-amine |
| E7-61 | methyl 5-methylpicolinate | 1) m-CPBA, DCM, r.t,<br>2) POCl₃, toluene, reflux<br>3) LiAlH₄, THF, 0 °C → (6-chloro-5-methylpyridin-2-yl)methanol |
| E7-62 | methyl 4-fluoro-1H-pyrazole-3-carboxylate | 1) TrtCl, TEA, DCM<br>2) LiAlH₄, THF, rt<br>3) MsCl, DIPEA, DCM → 3-(chloromethyl)-4-fluoro-1-trityl-1H-pyrazole |
| E7-73 | benzyloxyacetaldehyde | 1) ≡—MgBr<br>2) 2-Iodoxybenzoic acid<br>3) HOSO₂ONH₂<br>4) BBr₃ DCM → isothiazol-3-ylmethanol |
| E7-75 | methyl propiolate | 1) NaN₃ CH₃I CuSO₄ sodium ascorbate<br>2) LAH THF → (1-methyl-1H-1,2,3-triazol-4-yl)methanol |

FIGURE 4 - Continued

| E7-78 | dimethyl 1H-pyrazole-3,5-dicarboxylate → 1) SEMCl, DIPEA; 2) NaBH₄, MeOH → methyl 5-(hydroxymethyl)-1-SEM-pyrazole-3-carboxylate + methyl 3-(hydroxymethyl)-1-SEM-pyrazole-5-carboxylate |
| --- | --- |
| E7-87 | methyl 1-Trt-1,2,4-triazole-3-carboxylate → 1) LAH, THF, 0°C, 1 h; 2) MsCl, TEA, DCM, r.t. 15 h; 3) LiCl, DMSO, r.t. 2h → 3-(chloromethyl)-1-Trt-1,2,4-triazole |
| E7-88 | ClCH₂C(O)CH₂OBn → 1) H₂N-NH-CHO, DCM, 0 °C, 2 hr; 2) P₂S₅, dioxane, 45 °C, 2 hr → 2-(benzyloxymethyl)-1,3,4-thiadiazole → 3) BBr₃; 4) PBr₃, DCM → 2-(bromomethyl)-1,3,4-thiadiazole |
| E8-16 | 2-amino-6-methylpyridine → 1) (Boc)₂O; 2) (Boc)₂O, DMAP, THF; 3) NBS, AIBN, DCE; 4) diethyl phosphite, DIPEA, CH₃CN → N,N-di-Boc-6-(bromomethyl)pyridin-2-amine |
| E8-70 | thiazole-2-carbaldehyde → 1) NaBH₄, MeOH; 2) SOCl₂, DCM → 2-(chloromethyl)thiazole |
| E8-77 | methyl 4-methylthiazole-2-carboxylate → 1) NBS, AIBN, BPO, CCl₄, reflux overnight; 2) DIBAL-H, THF; 3) DHP, PTSA, DCM; 4) PhSO₂Na, DMSO → THPO-CH₂-thiazole-CH₂-SO₂Ph |
| E8-82 | methyl 1H-1,2,3-triazole-4-carboxylate → 1) SEM-Cl, NaH; 2) LAH, THF; 3) SOCl₂, DCM; 4) PhSO₂Na, DMSO → SEM-N-triazole-CH₂SO₂Ph |
| E8-86, E8-87, E8-96, E8-97 | 2-amino-5-bromo-4-methylthiazole → 1) (Boc)₂O DCM, TEA, DMAP, r.t; 2) N-fluorobenzenesulfonimide, n-BuLi, THF; 3) NCS, BPO, 80 °C, 2 h → BocHN-4-(chloromethyl)-5-fluorothiazol-2-yl |
| E8-86, E8-87, E8-91, E8-99 | methyl 1H-1,2,3-triazole-4-carboxylate → 1) SEM-Cl, NaH, THF, 0°C, 2hr; 2) LAH, THF, 0°C, 1hr; 3) SOCl₂, DCM, 0°C, 1hr → 1-SEM-4-(chloromethyl)-1,2,3-triazole |

FIGURE 4 - Continued
| E8-89 | 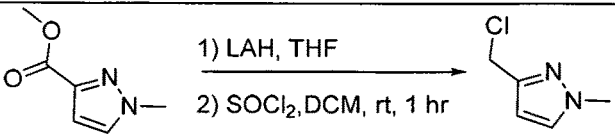 |
|---|---|
| E8-90 | 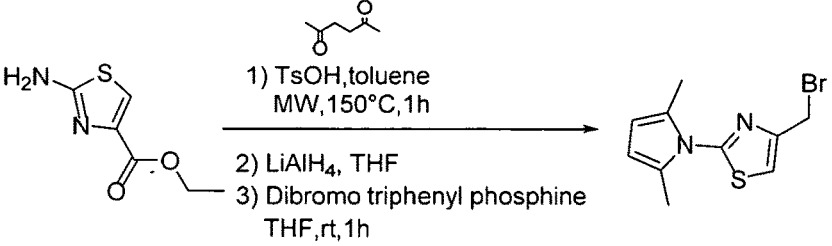 |
| E8-91<br>E8-92 | 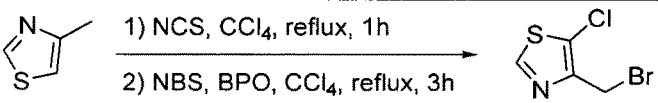 |
| E8-95 | 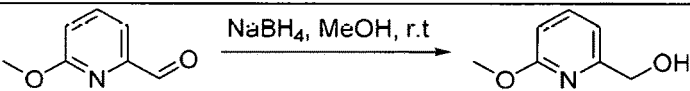 |
| E8-111 | 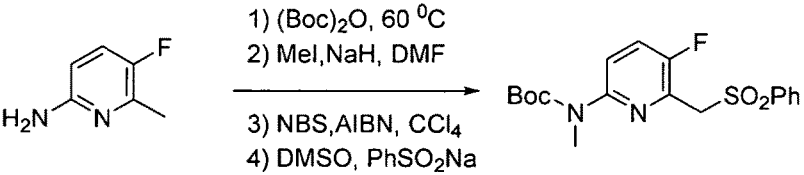 |
| E8-112 | 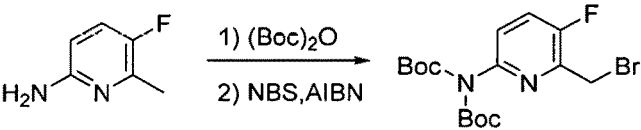 |

PYRUVATE KINASE MODULATORS AND USE THEREOF

CROSS-REFERENCE TO RELATED APPLICATIONS

This application is a 35 U.S.C. § 371 national stage filing of International Application No. PCT/US2018/000129, filed on Aug. 15, 2018 which in turn claims the benefit of priority of U.S. Provisional Patent Application Nos. 62/673,526 and 62/673,533, both filed May 18, 2018. This application also claims the benefit of priority of International Patent Application No. PCT/CN2017/097496, filed Aug. 15, 2017. The entire contents of each of the aforementioned priority applications are hereby incorporated by reference.

BACKGROUND

Pyruvate kinase (PK) is a metabolic enzyme that converts phosphoenolpyruvate to pyruvate during glycolysis. Four PK isoforms exist in mammals: the L and R isoforms (from the PKLR gene) are expressed in liver and red blood cells respectively, and the PKM gene encodes two splice variants, the M1 isoform that is expressed in most adult tissues, and the M2 isoform that is expressed during embryonic development and in some adult tissues including the kidney and hematopoietic stem cells. Many tumor cells also express PKM2. This tetrameric allosterically regulated isoform is intrinsically designed to downregulate its activity, through post-translational modification, allosteric modulation by small molecule ligands including some amino acids, and by subunit dissociation (into the dimeric form), which results in partial inhibition of glycolysis at the last step. This accumulates upstream glycolytic intermediates as an anabolic carbon source for synthesis of lipids and nucleic acids, whereas reassociation of PKM2 into active tetramer replenishes the normal catabolic state as a feedback after cell division (Protein Sci. 2010 November; 19(11): 2031-2044). Modulation (e.g. inhibition or activation) of PKM2 may be effective in the treatment of a number of disorders, e.g., cancer, obesity, diabetic diseases (e.g. diabetic nephropathy (DN)), coronary artery disease (CAD), Bloom Syndrome (BS), autoimmune conditions, and proliferation-dependent diseases (e.g., benign prostatic hyperplasia (BPH)).

SUMMARY

Described herein are methods of modulating pyruvate kinase M2 (PKM2) activity in a subject in need thereof, comprising administering an effective amount of a compound of Formulas (I), (II), (III), (IV), (V-a), (V-b), (VI), or (IX) (collectively referred to herein as "Formulas (I)-(IX)") or a pharmaceutically acceptable salt thereof, or a compound of Formulas (I'), (II'), (III'), (IV'), (V'), (collectively referred to herein as Formulas (I')-(V')" or a pharmaceutically acceptable salt thereof, that regulate PKM2, wild type and/or mutant enzymes (such as those described herein).

In one embodiment, the invention provides a method of modulating pyruvate kinase M2 (PKM2) activity in a subject, comprising administering an effective amount of a compound of Formula (I) or a pharmaceutically acceptable salt thereof:

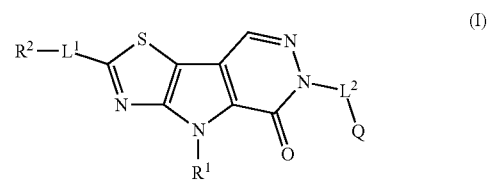

wherein Q, $R^1$, $R^2$, $L^1$, $L^2$ and Q are as defined herein.

In one embodiment, the compound or pharmaceutically acceptable salt thereof is selected from the compounds of Table 1, and FIGS. 1A-1C, 2A-2C, and 3.

Also provided is a method of modulating pyruvate kinase M2 (PKM2) activity in a subject in need thereof, comprising administering a pharmaceutical composition comprising an effective amount of a compound of Formulas (I)-(IX) or a pharmaceutically acceptable salt thereof, or a compound of Formulas (I')-(V') or a pharmaceutically acceptable salt thereof, and a pharmaceutically acceptable carrier.

In another embodiment, provided is a method of modulating (e.g., increasing or decreasing) the level of PKM2 activity in a subject in need thereof comprising administering an effective amount of a compound described herein to the subject. In some embodiments, a compound or a composition described herein is used to maintain PKM2 in its active conformation or activate pyruvate kinase activity in proliferating cells as means to divert glucose metabolites into catabolic rather than anabolic processes in the patient. In certain embodiments, the provided method increases the level of (i.e. activating) PKM2 activity in the subject. In certain embodiments, the provided method decreases the level of PKM2 activity in the subject.

In another embodiment, provided is a method of modulating (e.g., increasing or decreasing) the level of plasma glucose in a subject in need thereof comprising administering an effective amount of a compound described herein to the subject. In certain embodiments, the provided method increases the level of plasma glucose in the subject. In certain embodiments, the provided method decreases the level of plasma glucose in the subject.

In another embodiment, provided is a method of inhibiting cell proliferation in a subject in need thereof comprising administering an effective amount of a compound described herein to the subject. E.g., this method can inhibit growth of a transformed cell, e.g., a cancer cell, or generally inhibiting growth in a PKM2-dependent cell that undergoes aerobic glycolysis.

In another embodiment, provided is a method of treating a subject suffering from or susceptible to a disease or disorder associated with the function of PKM2 comprising administering an effective amount of a compound described herein to the subject. In certain embodiment, the method further comprises identifying or selecting a subject who would benefit from modulation (e.g., activation) of PKM2 and/or plasma glucose. E.g., the patient can be identified on the basis of the level of PKM2 activity in a cell of the patient for treatment of cancer associated with PKM2 function. In another embodiment, the selected patient is a subject suffering from or susceptible to a disorder or disease identified herein, e.g., a disorder characterized by unwanted cell growth or proliferation. In certain embodiments, the disease is a neoplastic disorder. In certain embodiments, the disease is cancer, obesity, a diabetic disease (e.g. diabetic nephropathy (DN)), atherosclerosis, restenosis, coronary artery disease (CAD), Bloom Syndrome (BS), benign prostatic hyperplasia (BPH), or an autoimmune disease. In certain embodiments, the disease is cancer. In certain embodiments, the disease is a diabetic disease. In certain embodiments, the diabetic disease is diabetic nephropathy (DN). In certain embodiments, the disease is coronary artery disease (CAD).

In one embodiment, provided is use of a compound described herein or a pharmaceutically acceptable salt thereof or a pharmaceutical composition comprising the same in any of the methods of the invention described above. In one embodiment, provided is a compound described herein or a pharmaceutically acceptable salt thereof or a pharmaceutical composition comprising the same for use in any of the method of the invention described above. In another embodiment, provided is use of a compound described herein or a pharmaceutically acceptable salt thereof or a pharmaceutical composition comprising the same for the manufacture of a medicament for any of the method of the invention described.

DETAILED DESCRIPTION OF THE INVENTION

Figure 1A:
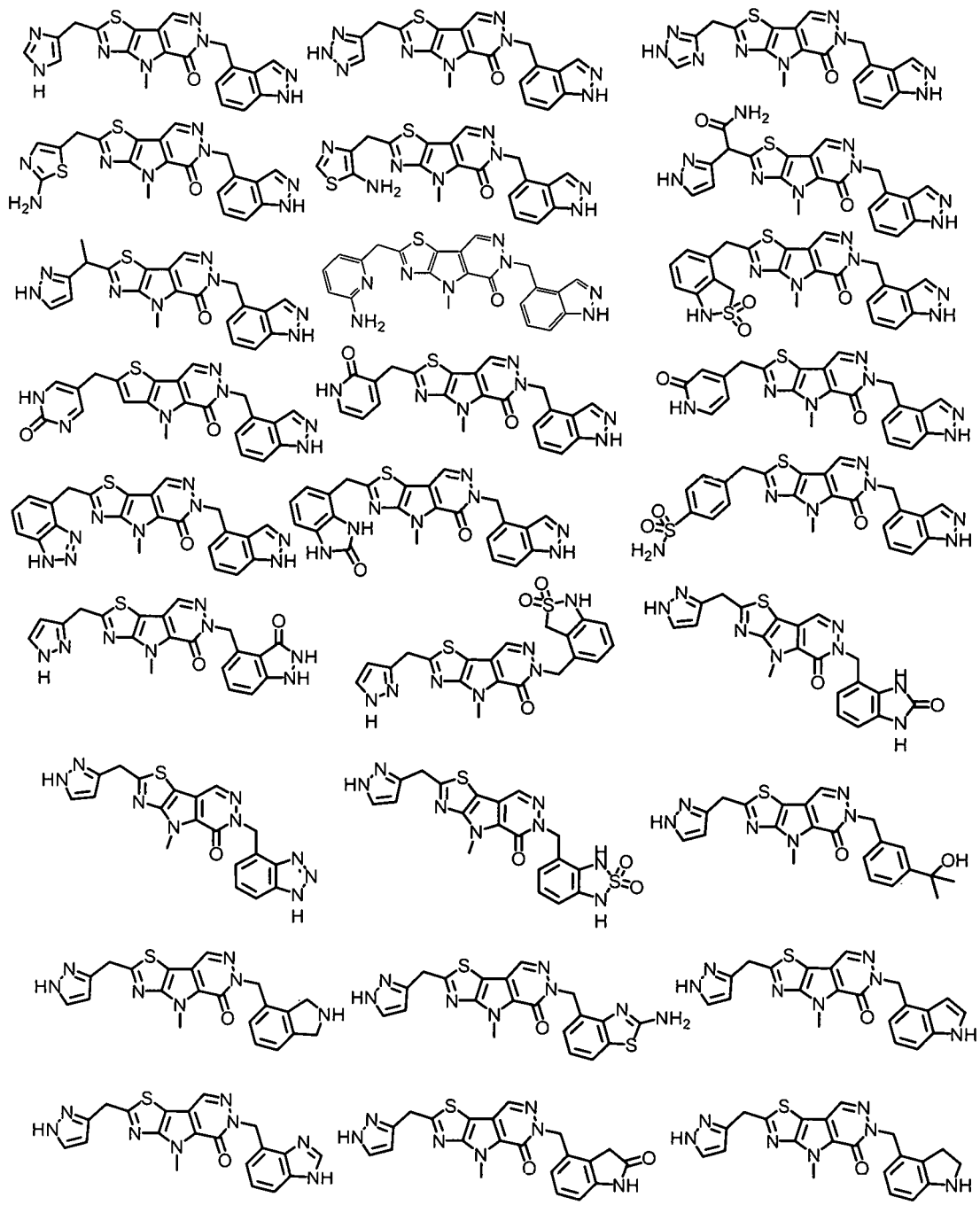
FIGS. 1A-1C are listings of the structures of other exemplary compounds used in the methods of the invention.

The details of construction and the arrangement of components set forth in the following description or illustrated in the drawings are not meant to be limiting. Embodiments can be practiced or carried out in various ways. The phraseology and terminology used herein is for purpose of description and shouldn't be regarded as limiting.

Definitions

Compounds described herein, which are used in the methods of the invention, can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, N Y, 1962); and Wilen, S. H. Tables of Resolving Agents and Optical Resolutions p. 268 (E. L. Eliel, Ed., Univ. of Notre Dame Press, Notre Dame, Ind. 1972).

In one embodiment, the compounds described herein may also comprise one or more isotopic substitutions. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

The compounds described herein may also be represented in multiple tautomeric forms, in such instances, expressly includes all tautomeric forms of the compounds described herein, even though only a single tautomeric form may be represented (e.g., alkylation of a ring system may result in alkylation at multiple sites; all such reaction products are expressly included). All such isomeric forms of such compounds are expressly included. If a tautomer of a compound is aromatic, this compound is aromatic. Similarly, if a tautomer of a substitutent is a heteroaryl, this substituent is heteroaryl.

The term "alkyl" refers to a radical of a straight-chain or branched saturated hydrocarbon group having from 1 to 10 carbon atoms ("$C_{1-10}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is unsubstituted —$C_{1-10}$ alkyl. In certain embodiments, the alkyl group is substituted —$C_{1-10}$ alkyl.

The term "haloalkyl" refers to a substituted alkyl group, wherein one or more of the hydrogen atoms are independently replaced by a halogen, e.g., fluoro, bromo, chloro, or iodo and includes alkyl moieties in which all hydrogens have been replaced by halo (e.g., perfluoroalkyl). In some embodiments, the haloalkyl moiety has 1 to 8 carbon atoms ("$C_{1-8}$ haloalkyl").

The term "alkoxy" or "alkoxyl" refers to an —O-alkyl radical. E.g., with between 1 and 6 carbon atoms.

The term "aryloxy" refers to an —O-aryl radical. In some embodiments the aryloxy group is phenoxy.

"Hydroxyalkyl" or "hydroxylalkyl" can include alkyl structures that are substituted with one or more hydroxyl groups.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). The one or more carbon-carbon double bonds can be internal (such as in 2-butenyl) or terminal (such as in 1-butenyl). Examples of —$C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted —$C_{2-10}$ alkenyl. In certain embodiments, the alkenyl group is a substituted —$C_{2-10}$ alkenyl. In an alkenyl group, a C=C double bond may be an (E)- or (Z)-double bond.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). Examples of alkynyl groups include ethynyl ($C_2$), 1-propynyl ($C_3$), 2-propynyl ($C_3$), 1-butynyl ($C_4$), 2-butynyl ($C_4$), pentynyl ($C_5$), hexynyl ($C_6$) heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted —$C_{2-10}$ alkynyl. In certain embodiments, the alkynyl group is a substituted —$C_{2-10}$ alkynyl.

The term "carbocyclyl" or "carbocyclic" refers to a radical of a non-aromatic monocyclic, bicyclic, or tricyclic or polycyclic hydrocarbon ring system having from 3 to 14 ring carbon atoms ("$C_{3-14}$ carbocyclyl") and zero heteroatoms in the non-aromatic ring system. Carbocyclyl groups include fully saturated ring systems (e.g., cycloalkyls), and partially saturated ring systems. In some embodiments, a carbocyclyl group has 3 to 10 ring carbon atoms ("$C_{3-10}$ carbocyclyl").

The term "cycloalkyl" as employed herein includes saturated cyclic, bicyclic, tricyclic, or polycyclic hydrocarbon groups having 3 to 14 carbons containing the indicated number of rings and carbon atoms (for example a $C_3$-$C_{14}$ monocyclic, $C_4$-$C_{14}$ bicyclic, $C_5$-$C_{14}$ tricyclic, or $C_6$-$C_{14}$ polycyclic cycloalkyl). In some embodiments "cycloalkyl" is a monocyclic cycloalkyl. Examples of monocyclic cycloalkyl groups include cyclopentyl ($C_5$), cyclohexyl ($C_5$). cyclopropyl ($C_3$) cyclobutyl ($C_4$), cycloheptyl ($C_7$) and cyclooctyl ($C_8$). In some embodiments "cycloalkyl" is a bicyclic cycloalkyl. Examples of bicyclic cycloalkyls include bicyclo[1.1.0]butane ($C_4$), bicyclo[1.1.1]pentane ($C_5$), spiro[2.2]pentane ($C_5$), bicyclo[2.1.0]pentane ($C_5$), bicyclo[2.1.1]hexane ($C_6$), bicyclo[3.3.3]undecane ($C_{11}$), decahydronaphthalene ($C_{10}$), bicyclo[4.3.2]undecane ($C_{11}$), spiro[5.5]undecane ($C_{11}$) and bicyclo[4.3.3]dodecane ($C_{12}$). In some embodiments "cycloalkyl" is a tricyclic cycloalkyl. Examples of tricyclic cycloalkyls include adamantine ($C_{12}$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl").

Exemplary heterocyclyl groups include aziridinyl, oxiranyl, thiiranyl, azetidinyl, oxetanyl, thietanyl, tetrahydrofuranyl, dihydrofuranyl, tetrahydrothiophenyl, dihydrothiophenyl, pyrrolidinyl, dihydropyrrolyl, pyrrolyl-2,5-dine, dioxolanyl, oxathiolanyl, dithiolanyl, triazolinyl, oxadiazolinyl, thiadiazolinyl, piperidinyl, tetrahydropyranyl, dihydropyridinyl, thianyl, piperazinyl, morpholinyl, dithianyl, dioxanyl, triazinanyl, azepanyl, oxepanyl, thiepanyl, azocanyl, oxecanyl, thiocanyl, indolinyl, isoindolinyl, dihydrobenzofuranyl, dihydrobenzothienyl, tetrahydrobenzo-thienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 it electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Arylalkyl" or "aralkyl" is a subset of "alkyl" and refers to an alkyl group substituted by an aryl group, wherein the point of attachment is on the alkyl moiety. Examples of "arylalkyl" or "aralkyl" include benzyl, 2-phenylethyl, 3-phenylpropyl, 9-fluorenyl, benzhydryl, and trityl groups The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In some embodiments the heteroaryl can be a 5-8 membered monocyclic heteroaryl containing 1-4 heteroatoms. In some embodiments the heteroaryl can be an 8-12 membered bicyclic heteroaryl having 1-6 heteroatoms. In some embodiments the heteroaryl can be an 11-14 membered tricyclic heteroaryl ring system having 1-9 heteroatoms. In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continues to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a monocyclic 5-10 membered aromatic ring system having ring carbon atoms and 1-4 ring heteroatoms provided in the aromatic ring system, wherein each heteroatom is independently selected from nitrogen, oxygen, and sulfur ("5-10 membered monocyclic heteroaryl"). In some embodiments, a heteroaryl group is a bicyclic 8-12 membered aromatic ring system having ring carbon atoms and 1-6 ring heteroatoms provided in the aromatic ring system, wherein each heteroatom is independently selected from nitrogen, oxygen, and sulfur ("8-12 membered bicyclic heteroaryl"). Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl. In certain embodiments, the heteroaryl group is an optionally substituted 5-membered monocyclic heteroaryl. In certain embodiments, the heteroaryl group is an optionally substituted 6-membered monocyclic heteroaryl.

Exemplary monocyclic heteroaryl groups include pyrrolyl, furanyl, thiophenyl, imidazolyl, pyrazolyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, triazinyl, tetrazinyl, azepinyl, oxepinyl, thiepinyl, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, purinyl, naphthyridinyl, pteridinyl, quinolinyl, isoquinolinyl, cinnolinyl, quinoxalinyl, phthalazinyl, quinazolinylphenanthridinyl, dibenzofuranyl, carbazolyl, acridinyl, phenothiazinyl, phenoxazinyl and phenazinyl.

"Heteroaralkyl" or "heteroarylalkyl" refers to an alkyl group substituted by a heteroaryl group, wherein the point of attachment is on the alkyl moiety.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

The term "optionally substituted" refers to being substituted or unsubstituted. In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent (e.g. $C_{1-6}$ alkyl, halogen, nitro, cyano, hydroxyl, $C_{1-6}$ haloalkyl, $C_{1-6}$ haloalkoxy, $C_{1-6}$ acyl, $C_{3-6}$ cycloalkyl, $C_{6-10}$ aryl, monocyclic or bicyclic heteroaryl, and monocyclic or bicyclic heterocyclyl), at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valences of the heteroatoms and results in the formation of a stable moiety. The disclosure is not intended to be limited in any manner by the exemplary substituents described herein.

The term "halo" or "halogen" refers to fluorine, chlorine, bromine, or iodine.

The term "acyl" refers to a group having the general formula $-C(=O)R^{X1}$, $-C(=O)OR^{X1}$, $-C(=O)-O-C(=O)R^{X1}$, $-C(=O)SR^{X1}$, $-C(=O)N(R^{X1})_2$, $-C(=S)R^{X1}$, $-C(=S)N(R^{X1})_2$, and $-C(=S)S(R^{X1})$, $-C(=NR^{X1})R^{X1}$, $-C(=NR^{X1})OR^{X1}$, $-C(=NR^{X1})SR^{X1}$, and $-C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched $C_{1-10}$ alkyl; cyclic or acyclic, substituted or unsubstituted, branched or unbranched $C_{2-10}$ alkenyl; substituted or unsubstituted $C_{2-10}$ alkynyl; substituted or unsubstituted $C_{6-12}$ aryl, substituted or unsubstituted heteroaryl, when valency permits. Exemplary acyl groups include aldehydes (—CHO), carboxylic acids (—CO$_2$H), ketones, acyl halides, esters, amides, imines, carbonates, carbamates, and ureas.

In certain embodiments, the substituent present on a nitrogen atom, on an oxygen atom or on a sulfur atom is a nitrogen protecting group, an oxygen protecting group or a sulfur protecting group, respectively. Nitrogen, oxygen and sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups include, but are not limited to, formamide, acetamide, chloroacetamide, trichloroacetamide, trifluoroacetamide, phenylacetamide, methyl carbamate, ethyl carbamate, 9-fluorenylmethyl carbamate (Fmoc), t-butyl carbamate (BOC or Boc), 1-adamantyl carbamate (Adoc), vinyl carbamate (Voc), allyl carbamate (Alloc), 2-(trimethylsilyl)ethoxy]methyl (SEM), p-toluenesulfonamide (Ts), benzenesulfonamide, 2,3,6-trimethyl-4-methoxybenzenesulfonamide (Mtr), 2,4,6-trimethoxybenzenesulfonamide (Mtb), phenothiazinyl-(10)-acyl derivative, N'-p-toluenesulfonylaminoacyl derivative, Exemplary oxygen and sulfur protecting groups include, but are not limited to, methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), tetrahydropyranyl (THP), methanesulfonate (mesylate), benzylsulfonate, and tosylate (Ts).

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), ortrifluoromethanesulfonate (triflate, —OTf).

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N$^+$(C$_{1-4}$ alkyl)$_4$$^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomologus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. In certain embodiments, the subject is a patient. The term "patient" refers to a human subject in need of treatment of a disease. In certain embodiments, the term "patient" is a human adult over 18 years old in need of treatment of a disease. In certain embodiments, the term "patient" is a human child no more than 18 years old in need of treatment of a disease. In certain embodiments, the patient is not under regularly transfusion (e.g. having had no more than 4 transfusion episodes in the 12-month period). In certain embodiments, the patient is under regularly transfusion (e.g. having had ate least 4 transfusion episodes in the 12-month period).

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed (i.e., therapeutic treatment). In other embodiments, treatment may be administered in the absence of signs or symptoms of the disease. For example, treatment may be administered to a susceptible subject prior to the onset of symptoms (i.e., prophylactic treatment) (e.g., in light of a history of symptoms and/or in light of exposure to a pathogen). Treatment may also be continued after symptoms have resolved, for example, to delay or prevent recurrence. In certain embodiments, treatment includes delaying onset of at least one symptom of the disorder for a period of time.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, the effective amount is to generate a subject's hemoglobin response of ≥1.5 g/dL increase in Hb concentration from baseline. The subject's baseline Hb concentration is the average of all available Hb concentrations before the treatment with the compound. In certain embodiments, the effective amount is to generate a subject's hemoglobin response of ≥1.0 g/dL increase in Hb concentration from baseline. In certain embodimetns, the effective amount is to generate a subject's hemoglobin response of ≥2.0 g/dL increase in Hb concentration from baseline. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for eliciting measurable activation of wild-type or mutant PKM2. In certain embodiments, a therapeutically effective amount is an amount sufficient for regulating (e.g. lowering) plasma glucose in a subject in need thereof. In certain embodiments, a therapeutically effective amount is an amount sufficient for eliciting measurable efficacy to treat a proliferative disease (e.g. cancer, an autoimmune disease). In certain embodiments, a therapeutically effective amount is an amount sufficient for eliciting measurable efficacy to treat and/or prevent a diabetic disease (e.g. DN). In certain embodiments, a therapeutically effective amount is an amount sufficient for eliciting measurable efficacy to treat and/prevent CAD.

The term "activator" as used herein means an agent that (measurably) increases the activity of a pyruvate kinase (e.g., PKM2) or causes pyruvate kinase (e.g., PKM2) activity to increase to a level that is greater than PKM2's basal levels of activity. For example, the activator may mimic the effect caused by a natural ligand (e.g., FBP). The activator effect caused by a compound provided herein may be to the same, or to a greater, or to a lesser extent than the activating effect caused by a natural ligand, but the same type of effect is caused. A compound provided herein can be evaluated to determine if it is an activator by measuring either directly or indirectly the activity of the pyruvate kinase when subjected to said compound. The activity of a compound provided herein can be measured, for example, against a control substance. In some instances, the activity measured of the test compound is for activation of PKM2. The activity of PKM2 can be measured, for example, by monitoring the concentration of a product such as ATP or levels of a cofactor such as NADH used in a coupled enzyme assay system (see PCT/US2010/040486).

The term "inhibitor" as used herein means an agent that (measurably) slows, stops, decreases, or inactivates the enzymatic activity of a pyruvate kinase (e.g., PKM2) to decrease to a level that is less than the pyruvate kinases (e.g. PKM2's) basal levels or activity.

The term "ex vivo" referring to a method as used herein means that the method takes place outside an organism. For example, a cell or a tissue may be extracted from the organism to be contacted with one or more compounds provided herein or a pharmaceutically acceptable salt thereof or a pharmaceutical composition thereof, optionally under artificially controlled conditions (e.g., temperature).

The term "in vitro" referring to a method as used herein means that the method takes place outside an organism and is contained within an artificial environment. For example, a cell or a tissue may be extracted from the organism to be contacted with one or more compounds provided herein or a pharmaceutically acceptable salt thereof or a pharmaceutical composition thereof, in a contained, artificial environment (e.g., a culture system), such as in a test tube, in a culture, in flask, in a microtiter plate, on a Petri dish, and the like.

Compounds

Described herein are methods related to compounds and pharmaceutical compositions that modulate PKM2, and use of these compounds and pharmaceutical compositions for these methods. Specifically, these methods include a method of modulating pyruvate kinase M2 (PKM2) activity in a subject, a method of modulating (e.g., increasing or decreasing) the level of PKM2 activity in a subject in need thereof, a method of modulating (e.g., increasing or decreasing) the level of plasma glucose in a subject in need thereof, a method of inhibiting cell proliferation in a subject in need thereof (a transformed cell, e.g., a cancer cell, or generally inhibiting growth in a PKM2-dependent cell that undergoes aerobic glycolysis), a method of treating a subject suffering from or susceptible to a disease or disorder associated with the function of PKM2. In one embodiment, the compounds and compositions described herein modulate PKM2 by binding in an allosteric binding pocket. In one embodiment, the compounds and compositions described herein inhibit PKM2. In one embodiment, the compounds and compositions described herein activate PKM2. In one embodiment, the compound described herein is a compound of Formulas (I)-(IX), or a compound of Formulas (I')-(V'), or a pharmaceutically acceptable salt thereof, or a pharmaceutical composition comprising a compound of Formulas (I)-(IX), or a compound of Formulas (I')-(V'), or a pharmaceutically acceptable salt thereof. In one embodiment, the compound used in the methods of the invention is a compound described in International Patent Application No. PCT/CN2017/09496 and U.S. Provisional Patent Application Nos. 62/673,533 and 62/673,526, the disclosure of each of which is incorporated herein by reference in its entirety.

In a first embodiment of the invention, provided is a method of modulating pyruvate kinase M2 (PKM2) activity in a subject in need thereof comprising administering an effective amount of a compound of Formula (I) or a pharmaceutically acceptable salt thereof, wherein:

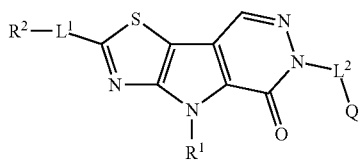

(I)

Q is hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl;

$R^1$ is hydrogen, optionally substituted alkyl, optionally substituted haloalkyl, optionally substituted alkenyl, optionally substituted alkynyl, optionally substituted cycloalkyl, optionally substituted heterocyclyl, optionally substituted aryl, —$OR^{o1}$, —$C(=O)R^{c1}$, or a nitrogen protecting group;

$L^1$ is a bond, optionally substituted alkylene, —O—, —S—, —S—CH$_2$—, —S(=O)CH$_2$—, —S(=O)$_2$CH$_2$—, —NR$^3$—, —NR$^3$C(=O)—, —C(=O)NR$^3$—, —C(=O)—, —OC(=O)—, —C(=O)O—, —NR$^3$C(=O)O—, —OC(=O)NR$^3$—, —NR$^3$C(=O)NR$^3$—, —OC(R$^4$)$_2$—, —C(R$^4$)$_2$O—, —NR$^3$C(R$^4$)$_2$—, —C(R$^4$)$_2$NR$^3$—, —S(=O)$_2$—, —S(=O)—, —S(=O)$_2$O—, —OS(=O)$_2$—, —S(=O)O—, —OS(=O)—, —S(=O)$_2$NR$^3$—, —NR$^3$S(=O)$_2$—, —S(=O)NR$^3$—, —NR$^3$S(=O)—, —NR$^3$S(=O)$_2$O—, —OS(=O)$_2$NR$^3$—, —NR$^3$S(=O)O—, —OS(=O)NR$^3$—, or —S(=O)(=NR$^3$)—, wherein the point of the attachment to $R^2$ is on the left-hand side;

$L^2$ is a bond, optionally substituted alkylene, —C(=O)—, —S(=O)$_2$—, or —S(=O)—, wherein the point of the attachment to Q is on the right-hand side;

$R^2$ is hydrogen, halogen, optionally substituted alkyl, optionally substituted alkoxy, optionally substituted alkenyl, optionally substituted alkynyl, optionally substituted cycloalkyl, optionally substituted heterocyclyl, optionally substituted aryl, or optionally substituted heteroaryl, or a nitrogen protecting group when $L^1$ is —NR$^3$—, —NR$^3$C(=O)—, —NR$^3$C(=O)O—, —NR$^3$C(R$^4$)$_2$—, —NR$^3$S(=O)$_2$—, —NR$^3$S(=O)—, —NR$^3$C(=O)NR$^3$—, —NR$^3$S(=O)$_2$O—, or —NR$^3$S(=O)O—, an oxygen protecting group when $L^1$ is —O—, —OC(=O)—, —OC(=O)NR$^3$—, —OC(R$^4$)$_2$—, —OS(=O)$_2$—, —OS(=O)$_2$NR$^3$—, —OS(=O)NR$^3$—, or —OS(=O)—, or a sulfur protecting group when $L^1$ is —S—;

each instance of $R^3$ is independently hydrogen, —$OR^{o2}$, optionally substituted alkyl, optionally substituted alkenyl, optionally substituted alkynyl, optionally substituted cycloalkyl, optionally substituted heterocyclyl, optionally substituted aryl, optionally substituted heteroaryl, or a nitrogen protecting group;

each instance of $R^{o1}$, and $R^{o2}$ is independently hydrogen, optionally substituted alkyl, or an oxygen protecting group;

each instance of $R^{c1}$ is independently optionally substituted alkyl or —N($R^{cn}$)$_2$, wherein each instance of $R^{cn}$ is independently hydrogen, —C$_{1-6}$ alkyl, or a nitrogen protecting group; and each instance of $R^4$ is independently hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl.

In a second embodiment of the invention, provided is a method of modulating the level of plasma glucose in a subject in need thereof comprising administering an effective amount of a compound of Formula (I) or a pharmaceutically acceptable salt thereof, wherein Formula (I) is as defined in the first embodiment.

In a third embodiment of the invention, provided is a method of inhibiting cell proliferation in a subject suffering from or susceptible to a disease or disorder associated with function of PKM2 comprising administering an effective amount of a compound of Formula (I) or a pharmaceutically acceptable salt thereof, wherein Formula (I) is as defined in the first embodiment.

In a fourth embodiment of the invention, provided is a method of treating a disease associated with the aberrant activity of PKM2 in a subject in need thereof comprising administering an effective amount of a compound of Formula (I) or a pharmaceutically acceptable salt thereof, wherein Formula (I) is as defined in the first embodiment.

In a fifth embodiment of the invention, provided is a method in accordance with the fourth embodiment as described above, wherein the disease is a proliferative disease.

In a sixth embodiment of the invention, provided is a method in accordance with the fourth embodiment as described above, wherein the disease is cancer, obesity, a diabetic disease (e.g. diabetic nephropathy (DN)), atherosclerosis, restenosis, coronary artery disease (CAD), Bloom Syndrome (BS), benign prostatic hyperplasia (BPH), or an autoimmune disease.

In a seventh embodiment of the invention, provided is a method of treating hyperglycemia in a subject in need thereof comprising administering an effective amount of a compound of Formula (I) or a pharmaceutically acceptable salt thereof, wherein Formula (I) is as defined in the first embodiment.

In an eighth embodiment of the invention, provided is a method of treating a diabetic disease in a subject in need thereof comprising administering an effective amount of a compound of Formula (I) or a pharmaceutically acceptable salt thereof, wherein Formula (I) is as defined in the first embodiment.

In a ninth embodiment of the invention, provided is a method in accordance with the eighth embodiment as described above, wherein the diabetic disease is diabetic nephropathy.

In a tenth embodiment of the invention, provided is a method in accordance with any one of the first through ninth embodiments as described above, wherein the method further comprises identifying a subject who would benefit from modulation of PKM2.

In an eleventh embodiment of the invention, provided is a method in accordance with the first embodiment as described above, wherein the modulating is activating.

In a twelfth embodiment of the invention, provided is a method in accordance with any one of the first through eleventh embodiments as described above, wherein:

Q is hydrogen, optionally substituted —C$_1$-C$_6$ alkyl, optionally substituted C$_3$-C$_{12}$ cycloalkyl, optionally substituted 3- to 14-membered heterocyclyl, optionally substituted 6- to 14-membered aryl, or optionally substituted 5- to 14-membered heteroaryl;

$R^1$ is hydrogen, optionally substituted —C$_1$-C$_6$ alkyl, optionally substituted —C$_1$-C$_6$ haloalkyl, optionally substituted —C$_2$-C$_6$ alkenyl, optionally substituted —C$_2$-C$_6$ alkynyl, optionally substituted C$_3$-C$_{12}$ cycloalkyl, optionally substituted 3- to 14-membered heterocyclyl, optionally substituted 6- to 12-membered aryl, —$OR^{o1}$, —$C(=O)R^{c1}$, or a nitrogen protecting group;

$L^1$ is a bond, optionally substituted $C_{1-6}$ alkylene, —O—, —S—, —S—CH$_2$—, —S(=O)CH$_2$—, —S(=O)$_2$CH$_2$—, —NR$^3$—, —NR$^3$C(=O)—, —C(=O)NR$^3$—, —C(=O)—, —OC(=O)—, —C(=O)O—, —NR$^3$C(=O)O—, —OC(=O)NR$^3$—, —NR$^3$C(=O)NR$^3$—, —OC(R$^4$)$_2$—, —C(R$^4$)$_2$O—, —NR$^3$C(R$^4$)$_2$—, —C(R$^4$)$_2$NR$^3$—, —S(=O)$_2$—, —S(=O)—, —S(=O)$_2$O—, —OS(=O)$_2$—, —S(=O)O—, —OS(=O)—, —S(=O)$_2$NR$^3$—, —NR$^3$S(=O)$_2$—, —S(=O)NR$^3$—, —NR$^3$S(=O)—, —NR$^3$S(=O)$_2$O—, —OS(=O)$_2$NR$^3$—, —NR$^3$S(=O)O—, —OS(=O)NR$^3$—, or —S(=O)(=NR$^3$)—, wherein the point of the attachment to R$^2$ is on the left-hand side;

$L^2$ is a bond, optionally substituted $C_1$-$C_6$ alkylene, —C(=O)—, —S(=O)$_2$—, or —S(=O)—, wherein the point of the attachment to Q is on the right-hand side;

R$^2$ is hydrogen, halogen, optionally substituted —$C_1$-$C_6$ alkyl, optionally substituted —$C_1$-$C_6$ alkoxy, optionally substituted —$C_3$-$C_{12}$ cycloalkyl, optionally substituted 3- to 14-membered heterocyclyl, optionally substituted —$C_6$-$C_{12}$ aryl, or optionally substituted 3- to 14-membered heteroaryl, or a nitrogen protecting group when $L^1$ is —NR$^3$—, —NR$^3$C(=O)—, —NR$^3$C(=O)O—, —NR$^3$C(R$^4$)$_2$—, —NR$^3$S(=O)$_2$—, —NR$^3$S(=O)—, —NR$^3$C(=O)NR$^3$—, —NR$^3$S(=O)$_2$O—, or —NR$^3$S(=O)O—, an oxygen protecting group when $L^1$ is —O—, —OC(=O)—, —OC(=O)NR$^3$—, —OC(R$^4$)$_2$—, —OS(=O)—, —OS(=O)$_2$—, —OS(=O)$_2$NR$^3$—, —OS(=O)NR$^3$—, or —OS(=O)—, or a sulfur protecting group when $L^1$ is —S—;

each instance of R$^3$ is independently hydrogen, —OR$^{o2}$, optionally substituted —$C_1$-$C_6$ alkyl, optionally substituted —$C_2$-$C_6$ alkenyl, optionally substituted —$C_2$-$C_6$ alkynyl, optionally substituted $C_3$-$C_{12}$ cycloalkyl, optionally substituted $C_3$-$C_{12}$ heterocyclyl, optionally substituted $C_6$-$C_{12}$ aryl, optionally substituted $C_5$-$C_{12}$ heteroaryl, or a nitrogen protecting group;

each instance of R$^{o1}$ and R$^{o2}$ is independently hydrogen, optionally substituted —$C_1$-$C_6$ alkyl, or an oxygen protecting group;

each instance of R' is independently optionally substituted —$C_1$-$C_6$ alkyl or —N(R$^{cn}$)$_2$, wherein each instance of R$^{cn}$ is independently hydrogen, —$C_1$-$C_6$ alkyl, or a nitrogen protecting group;

each instance of R$^4$ is independently hydrogen, optionally substituted —$C_1$-$C_6$ alkyl, optionally substituted —$C_2$-$C_6$ alkenyl, optionally substituted —$C_2$-$C_6$ alkynyl, optionally substituted $C_3$-$C_{12}$ cycloalkyl, optionally substituted 3- to 14-membered heterocyclyl, optionally substituted $C_6$-$C_{12}$ aryl, or optionally substituted 5- to 14-membered heteroaryl.

In a thirteenth embodiment of the invention, provided is a method in accordance with any one of the first through twelfth embodiments as described above, wherein:

Q is $C_6$-$C_{12}$ aryl, 5- to 6-membered monocyclic heteroaryl, or 8- to 12-membered bicyclic heteroaryl, each of which is substituted with 0-3 occurrences of R$^{c1}$;

R$^1$ is selected from hydrogen, —$C_1$-$C_6$ alkyl, —$C_1$-$C_6$ haloalkyl, $C_3$-$C_7$ monocyclic cycloalkyl and 3- to 14-membered heterocyclyl, —OR$^{o1}$, —C(=O)R$^{c1}$, or a nitrogen protecting group; wherein each alkyl, cycloalkyl or heterocyclyl is substituted with 0-3 occurrences of R$^d$;

R$^2$ is selected from hydrogen, halogen, —$C_1$-$C_6$ alkyl, —$C_1$-$C_6$ alkoxy, $C_3$-$C_7$ monocyclic cycloalkyl, $C_6$-$C_{12}$ bicyclic cycloalkyl, 3- to 14-membered heterocyclyl, $C_6$-$C_{12}$ aryl, 5- to 6-membered monocyclic heteroaryl, 8- to 12-membered bicyclic heteroaryl, wherein each alkyl, cycloalkyl, heterocyclyl, aryl and heteroaryl is substituted with 0-3 occurrences of R$^e$, or a nitrogen protecting group when $L^1$ is —NR$^3$-, —NR$^3$C(=O)—, —NR$^3$C(=O)O—, —NR$^3$C(R$^4$)$_2$—, —NR$^3$S(=O)$_2$—, —NR$^3$S(=O)—, —NR$^3$C(=O)NR$^3$—, —NR$^3$S(=O)$_2$O—, or —NR$^3$S(=O)O—, an oxygen protecting group when $L^1$ is —O—, —OC(=O)—, —OC(=O)NR$^3$—, —OC(R$^4$)$_2$—, —OS(=O)—, —OS(=O)$_2$—, —OS(=O)$_2$NR$^3$—, —OS(=O) NR$^3$—, or —OS(=O)—, or a sulfur protecting group when $L^1$ is —S—;

R$^3$ is selected from hydrogen, —OR$^{o2}$, —$C_1$-$C_6$ alkyl, $C_3$-$C_7$ monocyclic cycloalkyl, $C_6$-$C_{12}$ bicyclic cycloalkyl, 3- to 14-membered heterocyclyl, $C_6$-$C_{12}$ aryl, 5- to 6-membered monocyclic heteroaryl, and 8- to 12-membered bicyclic heteroaryl, wherein each alkyl, cycloalkyl, heterocyclyl, aryl and heteroaryl is substituted with 0-3 occurrences of R$^f$;

R$^4$ is selected from hydrogen, —$C_1$-$C_6$ alkyl, $C_3$-$C_7$ monocyclic cycloalkyl, and 3- to 14-membered heterocyclyl, wherein each alkyl, cycloalkyl or heterocyclyl is substituted with 0-1 occurrences of R$^g$;

$L^1$ is a bond, an alkylene substituted with 0-3 occurrences of R$^h$, —O—, —S—, —S—CH$_2$—, —S(=O)CH$_2$—, —S(=O)$_2$CH$_2$—, —NR$^3$—, —NR$^3$C(=O)—, —C(=O) NR$^3$—, —C(=O)—, —OC(=O)—, —C(=O)O—, —NR$^3$C(=O)O—, —OC(=O)NR$^3$—, —NR$^3$C(=O) NR$^3$—, —OC(R$^4$)$_2$—, —C(R$^4$)$_2$O—, —NR$^3$C(R$^4$)$_2$—, —C(R$^4$)$_2$NR$^3$—, —S(=O)$_2$—, —S(=O)—, —S(=O)$_2$O—, —OS(=O)$_2$—, —S(=O)O—, —OS(=O)—, —S(=O)$_2$NR$^3$—, —NR$^3$S(=O)$_2$—, —S(=O) NR$^3$—, —NR$^3$S(=O)—, —NR$^3$S(=O)$_2$O—, —OS(=O)$_2$NR$^3$—, —NR$^3$S(=O)O—, —OS(=O)NR$^3$—, or —S(=O)(=NR$^3$)—, wherein the point of the attachment to R$^2$ is on the left-hand side;

$L^2$ is a bond, an alkylene substituted with 0-3 occurrences of R$^h$, —C(=O)—, —S(=O)$_2$—, or —S(=O)—, wherein the point of the attachment to Q is on the right-hand side;

each R$^c$ is independently selected from halo, —$C_1$-$C_6$ alkyl, —$C_1$-$C_6$ haloalkyl, —$C_1$-$C_6$ hydroxyalkyl, —OH, —OC$_1$-$C_6$ alkyl, —$C_1$-$C_6$ aminoalkyl, —NH($C_1$-$C_6$ alkyl), —N($C_1$-$C_6$ alkyl)$_2$, —C(=O)OC$_1$-$C_6$ alkyl, —C(=O)OH, —C(=O)$C_1$-$C_6$ alkyl, —C(=O)NH$_2$, —C(=O)NH($C_1$-$C_6$ alkyl), —C(=O)N($C_1$-$C_6$ alkyl)$_2$, —NHC(=O)NH$_2$, —NHC(=O)NH($C_1$-$C_6$ alkyl), —NH(C=O)N($C_1$-$C_6$ alkyl)$_2$, —NHC(=O)($C_1$-$C_6$ alkyl), —N($C_1$-$C_6$ alkyl)C (=O)($C_1$-$C_6$ alkyl), —S(=O)$_2$NH$_2$, —S(=O)$_2$NH($C_1$-$C_6$ alkyl), —S(=O)$_2$N($C_1$-$C_6$ alkyl)$_2$, —NHS(=O)$_2$($C_1$-$C_6$ alkyl), —NH$_2$, —CN, and —NO$_2$; or two instances of RC attached to the same or adjacent carbon atoms, are taken together with the carbon atoms to which they are attached form a cycloalkyl or a heterocyclylC(=O)OH;

each R$^d$ is independently selected from halo, —$C_1$-$C_6$ alkyl, —OH, —OC$_1$-$C_6$ alkyl, —NH$_2$ and —CN;

each R$^e$ is independently selected from halo, —$C_1$-$C_6$ alkyl, —$C_1$-$C_6$ haloalkyl, —$C_1$-$C_6$ hydroxyalkyl, —OH, —OC$_1$-$C_6$ alkyl, —$C_1$-$C_6$ aminoalkyl, —NH($C_1$-$C_6$ alkyl), —N($C_1$-$C_6$ alkyl)$_2$, —C(=O)OC$_1$-$C_6$ alkyl, —C(=O)OH, —C(=O)$C_1$-$C_6$ alkyl, —C(=O)NH$_2$, —C(=O)NH($C_1$-$C_6$ alkyl), —C(=O)N($C_1$-$C_6$ alkyl)$_2$, —NHC(=O)NH$_2$, —NHC(=O)NH($C_1$-$C_6$ alkyl), —NH(C=O)N($C_1$-$C_6$ alkyl)$_2$, —NHC(=O)($C_1$-$C_6$ alkyl), —N($C_1$-$C_6$ alkyl)C (=O)($C_1$-$C_6$ alkyl), —S(=O)$_2$NH$_2$, —S(=O)$_2$NH($C_1$-$C_6$ alkyl), —S(=O)$_2$N($C_1$-$C_6$ alkyl)$_2$, —NHS(=O)$_2$($C_1$-$C_6$ alkyl), —NH$_2$, —CN, and —NO$_2$; or two instances of R$^e$ attached to the same or adjacent carbon atoms, are taken together with the carbon atoms to which they are attached form a cycloalkyl or a heterocyclyl;

each $R^f$ is independently selected from halo, —$C_1$-$C_6$ alkyl, —$C_1$-$C_6$ haloalkyl, —$C_1$-$C_6$ alkoxy, —OH, —$NH_2$, —CN and —$NO_2$;

each $R^g$ is independently selected from halo, —$C_1$-$C_6$ alkyl, —$C_1$-$C_6$ haloalkyl, —$C_1$-$C_6$ alkoxy, —OH, $NH_2$, —CN and $NO_2$ and;

each $R^h$ is independently selected from halo, —$C_1$-$C_6$ alkyl, —$C_1$-$C_6$ haloalkyl, —$C_1$-$C_6$ hydroxyalkyl, —OH, —$OC_1$-$C_6$ alkyl, —$C_1$-$C_6$ aminoalkyl, —NH($C_1$-$C_6$ alkyl), —N($C_1$-$C_6$ alkyl)$_2$, —C(=O)O$C_1$-$C_6$ alkyl, —C(=O)OH, —C(=O)$C_1$-$C_6$ alkyl, —C(=O)$NH_2$, —C(=O)NH($C_1$-$C_6$ alkyl), —C(=O)N($C_1$-$C_6$ alkyl)$_2$, —NHC(=O)$NH_2$, —NHC(=O)NH($C_1$-$C_6$ alkyl), —NH(C=O)N($C_1$-$C_6$ alkyl)$_2$, —NHC(=O)($C_1$-$C_6$ alkyl), —N($C_1$-$C_6$ alkyl)C(=O)($C_1$-$C_6$ alkyl), —S(=O)$_2$$NH_2$, —S(=O)$_2$NH($C_1$-$C_6$ alkyl), —S(=O)$_2$N($C_1$-$C_6$ alkyl)$_2$, —NHS(=O)$_2$($C_1$-$C_6$ alkyl), —$NH_2$, —CN, and —$NO_2$, S(=O)$_2$aryl, S(=O)$_2$heteroaryl and =NOH or two instances of $R^h$ attached to the same or adjacent carbon atoms, are taken together with the carbon atoms to which they are attached form a cycloalkyl or a heterocyclyl.

In a fourteenth embodiment of the invention, provided is a method in accordance with any one of the first through thirteenth embodiments as described above, wherein the compound is a compound represented by Formula (II):

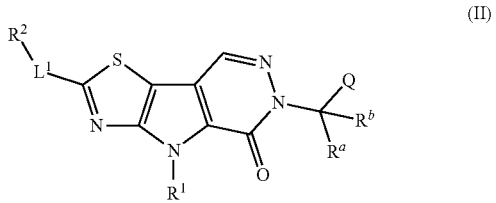

(II)

or a pharmaceutically acceptable salt thereof; wherein:

$R^a$ and $R^b$ are each independently hydrogen, halogen, —CN, —$NO_2$, —$N_3$, optionally substituted alkyl, —$OR^{o3}$, —N($R^{n1}$)$_2$, —C(=O)N($R^{n1}$)$_2$, or —C(=O)$R^{c2}$, or $R^a$ and $R^b$ can be taken together with the carbon atom to form optionally substituted cycloalkyl or optionally substituted heterocyclyl;

each instance of $R^{n1}$ is independently hydrogen, optionally substituted —$C_1$-$C_6$ alkyl, or a nitrogen protecting group;

each instance of $R^{o3}$ is independently hydrogen, optionally substituted —$C_1$-$C_6$ alkyl, or an oxygen protecting group; and each instance of $R^{c2}$ is independently optionally substituted —$C_1$-$C_6$ alkyl;

wherein the remainder of the variables are as defined in any one of the first through twelfth embodiments.

In a fifteenth embodiment of the invention, provided is a method in accordance with any one of the first through thirteenth embodiments as described above, wherein $L^1$ is a bond, optionally substituted —$C_{1-6}$ alkylene, —C(=O)—, —S(=O)—, —S(=O)$_2$—, —$NR^3$C(=O)—, or —C(=O)$NR^3$—; and wherein the remainder of the variables are as defined in any one of the first through fourteenth embodiments.

In a sixteenth embodiment of the invention, provided is a method in accordance with any one of the first through fourteenth embodiments as described above, wherein $L^1$ is $C_1$_alkylene substituted with R' and $R^k$;

wherein each instance of R and $R^k$ is independently selected from H, halogen, —CN, —$OR^{o7}$, —N($R^{n5}$)$_2$, —N($R^{n5}$)C(=O) $R^{c5}$, —C(=O)N($R^{n5}$)$_2$, —C(=O)$R^{c5}$, —C(=O)$OR^{o7}$, —$SR^{js}$, —S(=O)$_2$$R^{js}$, or —S(=O)$R^{js}$, optionally substituted —$C_1$-$C_6$ alkyl; or $R^j$ and $R^k$ can be taken together with the carbon atom to form C=O, C=$NR^{jn}$, an optionally substituted $C_3$-$C_6$ monocyclic cycloalkyl ring or an optionally substituted $C_3$-$C_6$ monocyclic heterocyclyl ring;

each of $R^{n5}$ and $R^{jn}$ is independently hydrogen, optionally substituted —$C_1$-$C_6$ alkyl, —$OR^{o8}$, or a nitrogen protecting group;

each instance of $R^{o7}$ is independently hydrogen, optionally substituted —$C_1$-$C_6$ alkyl, or an oxygen protecting group;

each instance of $R^{c5}$ is independently optionally substituted —$C_1$-$C_6$ alkyl; and each instance of $R^{js}$ is independently optionally substituted —$C_1$-$C_6$ alkyl, optionally substituted $C_{6-12}$ aryl, optionally substituted heteroaryl, or a sulfur protecting group; and wherein the remainder of the variables are as defined in any one of the first through fifteenth embodiments.

In a seventeenth embodiment of the invention, provided is a method in accordance with any one of the first through sixteenth embodiments as described above, wherein the compound represented by Formula (I'):

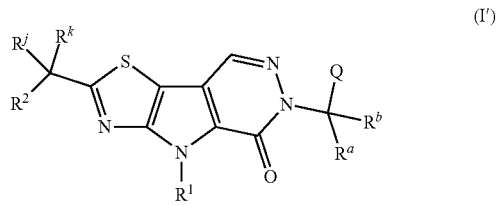

(I')

or a pharmaceutically acceptable salt thereof, wherein:

$R^1$ is hydrogen, an optionally substituted alkyl, an optionally substituted haloalkyl, an optionally substituted alkenyl, an optionally substituted alkynyl, an optionally substituted cycloalkyl, an optionally substituted heterocyclyl, an optionally substituted aryl, —$OR^{o1}$, —C(=O)$R^{c1}$, or a nitrogen protecting group; wherein:
  $R^{o1}$ is hydrogen, optionally substituted alkyl, or an oxygen protecting group;
  $R^{c1}$ is optionally substituted alkyl or —N($R^{cn}$)$_2$, wherein each instance of $R^{cn}$ is independently hydrogen, —$C_{1-6}$ alkyl, or a nitrogen protecting group;

$R^2$ and Q are each independently an optionally substituted 5- or 6-membered monocyclic heteroaryl;

$R^a$ and $R^b$ are each independently hydrogen, a halogen, —CN, —$NO_2$, —$N_3$, an optionally substituted alkyl, —$OR^{o3}$, —N($R^{n1}$)$_2$, —C(=O)N($R^{n1}$)$_2$, or —C(=O)$R^{c2}$; or alternatively $R^a$ and $R^b$ can be taken together with the carbon atom to which they are attached to form an optionally substituted cycloalkyl or an optionally substituted heterocyclyl; wherein:
  each instance of $R^{n1}$ is independently hydrogen, an optionally substituted —$C_1$-$C_6$ alkyl, or a nitrogen protecting group;
  $R^{o3}$ is hydrogen, an optionally substituted —$C_1$-$C_6$ alkyl, or an oxygen protecting group; and
  $R^{c2}$ is an optionally substituted —$C_1$-$C_6$ alkyl; and R$^j$ and R$^k$ are each independently hydrogen, a halogen, —CN, —OR$^{o7}$, —N(R$^{n5}$)$_2$, —N(R$^{n5}$)C(=O) R$^{c5}$, —C(=O)N(R$^{n5}$)$_2$, —C(=O)R$^{c5}$, —C(=O)OR$^{o7}$, —SR$^{js}$, —S(=O)$_2$R$^{js}$, —S(=O)R$^{js}$, or an optionally substituted —C$_1$-C$_6$ alkyl; or alternatively R$^j$ and R$^k$ can be taken together with the carbon atom to which they are attached to form C=O, an optionally substituted C$_1$-C$_6$ monocyclic cycloalkyl ring, or an optionally substituted C$_3$-C$_6$ monocyclic heterocyclyl ring; wherein:

each instance of R$^{n5}$ is independently hydrogen, an optionally substituted —C$_1$-C$_6$ alkyl, —OR$^{o8}$, or a nitrogen protecting group, wherein R$^{o8}$ is hydrogen, an optionally substituted —C$_1$-C$_6$ alkyl, or an oxygen protecting group;
  each instance of R$^{o7}$ is independently hydrogen, an optionally substituted —C$_1$-C$_6$ alkyl, or an oxygen protecting group;
  each instance of R$^{c5}$ is independently an optionally substituted —C$_1$-C$_6$ alkyl; and
  each instance of R$^{js}$ is independently an optionally substituted —C$_1$-C$_6$ alkyl, an optionally substituted C$_{6-12}$ aryl, an optionally substituted heteroaryl, or
  a sulfur protecting group.

In an eighteenth embodiment of the invention, provided is a method in accordance with the seventeenth embodiment as described above, wherein the compound is a compound represented by Formula (I') or a pharmaceutically acceptable salt thereof, wherein the 5- or 6-membered monocyclic heteroaryl represented by R$^2$ is optionally substituted at each substitutable ring carbon atom by R$^p$ and optionally substituted at each substitutable ring nitrogen atom by R$^{n6}$; wherein:

each instance of R$^p$ is independently hydrogen, a halogen, —CN, —NO$_2$, —N$_3$, an optionally substituted alkyl, an optionally substituted alkenyl, an optionally substituted alkynyl, an optionally substituted cycloalkyl, an optionally substituted aryl, an optionally substituted heterocyclyl, an optionally substituted heteroaryl, —OR$^{o6}$, —SR$^{s2}$, —N(R$^{n3}$)$_2$, —C(=O)N(R$^{n3}$)$_2$, —N(R$^{n3}$)C(=O)R$^{c4}$, —C(=O)R$^{c4}$, —C(=O)OR$^{o6}$, —OC(=O)R$^{c4}$, —S(=O)R$^{s2}$, —S(=O)$_2$R$^{s2}$, —S(=O)OR$^{o6}$, —OS(=O)R$^{c4}$, —S(=O)$_2$OR$^{o6}$, —OS(=O)$_2$R$^{c4}$, —S(=O)N(R$^{n3}$)$_2$, —S(=O)$_2$N(R$^{n3}$)$_2$, —N(R$^{n3}$) S(=O)R$^{s2}$, —N(R$^{n3}$) S(=O)$_2$R$^{s2}$, —N(R$^{n3}$)C(=O)OR$^{o6}$, —OC(=O)N(R$^{n3}$)$_2$, —N(R$^{n3}$)C(=O)N(R$^{n3}$)$_2$, —N(R$^{n3}$)S(=O)N(R$^{n3}$)$_2$, —N(R$^3$) S(=O)$_2$N(R$^{n3}$)$_2$, —N(R$^{n3}$)S(=O)OR$^{o6}$, —N(R$^{n3}$) S(=O)$_2$OR$^{o6}$, —OS(=O)N(R$^{n3}$)$_2$, or —OS(=O)$_2$N (R$^{n3}$)$_2$; or alternatively two instances of R$^p$ attached to the same or adjacent carbon atoms, can be taken together with the carbon atom(s) to which they are attached to form an optionally substituted cycloalkyl or a heterocycloalkyl; wherein:

each instance of R$^{n3}$ is independently hydrogen, an optionally substituted —C$_1$-C$_6$ alkyl, or a nitrogen protecting group;
  each instance of R$^{o6}$ is independently hydrogen, an optionally substituted —C$_1$-C$_6$ alkyl, or an oxygen protecting group; and
  each instance of R$^{o4}$ is an optionally substituted —C$_1$-C$_6$ alkyl;
  each instance of R$^{s2}$ is independently an optionally substituted —C$_1$-C$_6$ alkyl or a sulfur protecting group; and
  R$^{n6}$ is hydrogen, an optionally substituted —C$_1$-C$_6$ alkyl, or a nitrogen protecting group; and wherein the remainder of the variables are as defined in the seventeenth embodiment.

In a nineteenth embodiment of the invention, provided is a method in accordance with any one of the first through eighteenth embodiments as described above, wherein wherein Q is optionally substituted 5- to 6-membered monocyclic heteroaryl; and wherein the remainder of the variables are as defined in any one of the first through eighteenth embodiments.

In a twentieth embodiment of the invention, provided is a method in accordance with any one of the first through nineteenth embodiments as described above, wherein Q is of one of the following formulae:

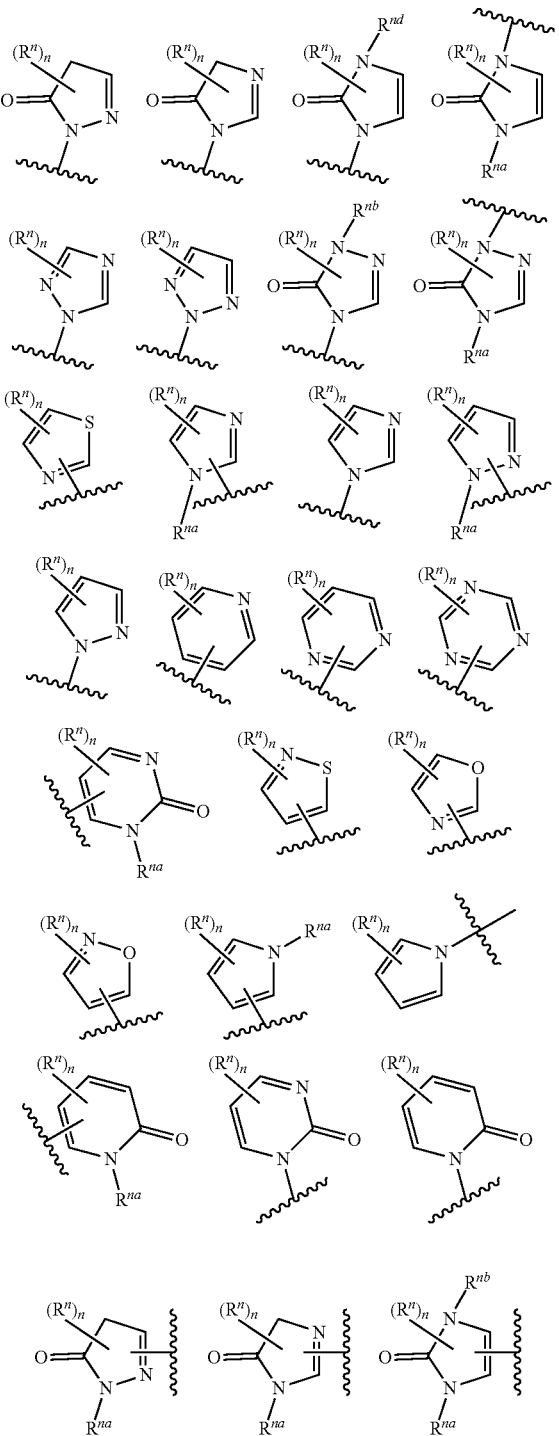

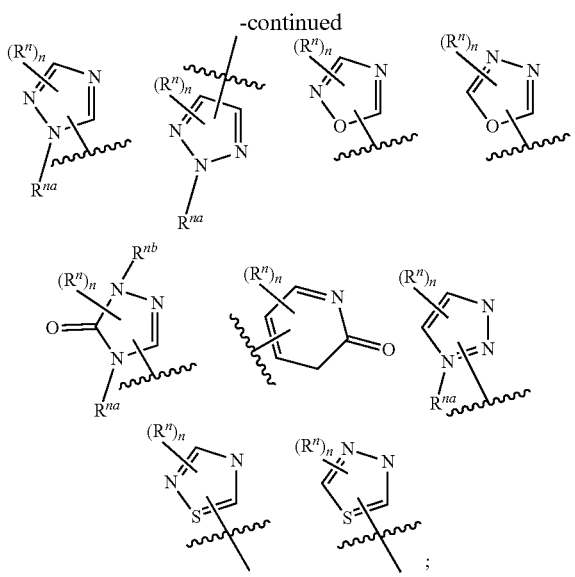

wherein:

each instance of $R^n$ is independently hydrogen, halogen, —CN, —NO$_2$, —N$_3$, an optionally substituted alkyl, an optionally substituted alkenyl, an optionally substituted alkynyl, an optionally substituted cycloalkyl, an optionally substituted aryl, an optionally substituted heterocyclyl, an optionally substituted heteroaryl, —OR$^{o4}$, —SR$^{s1}$, —N(R$^{n2}$)$_2$, —C(=O)N(R$^{n2}$)$_2$, —N(R$^{n2}$)C(=O)R$^{c3}$, —C(=O)R$^{c3}$, —C(=O)OR$^{o4}$, —OC(=O)R$^{c3}$, —S(=O)R$^{s1}$, —S(=O)$_2$R$^{s1}$, —S(=O)OR$^{o4}$, —OS(=O)R$^{c3}$, —S(=O)$_2$OR$^{o4}$, —OS(=O)$_2$R$^{c3}$, —S(=O)N(R$^{n2}$)$_2$, —S(=O)$_2$N(R$^{n2}$)$_2$, —N(R$^{n2}$)S(=O)R$^{s1}$, —N(R$^{n2}$)S(=O)$_2$R$^{s1}$, —N(R$^{n2}$)C(=O)OR$^{o4}$, —OC(=O)N(R$^{n2}$)$_2$, —N(R$^{n2}$)C(=O)N(R$^{n2}$)$_2$, —N(R$^{n2}$)S(=O)N(R$^{n2}$)$_2$, —(R$^{n2}$)S(=O)$_2$N(R$^{n2}$)$_2$, —N(R$^{n2}$)S(=O)OR$^{o4}$, —N(R$^{n2}$)(=O)OR$^{o4}$, —OS(=O)N(R$^{n2}$)$_2$, —OS(=N(R$^{n2}$)$_2$; or two instances of $R^n$ attached to the same or adjacent carbon atoms, taken together with the carbon atoms to which they are attached to form an optionally substituted cycloalkyl or a heterocycloalkyl; wherein:

each instance of $R^{n2}$ is independently hydrogen, an optionally substituted —C$_1$-C$_6$ alkyl, or a nitrogen protecting group;

each instance of $R^{o4}$ is independently hydrogen, an optionally substituted —C$_1$-C$_6$ alkyl, or an oxygen protecting group;

each instance of $R^{c3}$ independently an optionally substituted —C$_1$-C$_6$ alkyl;

each instance of $R^{s1}$ is independently an optionally substituted —C$_1$-C$_6$ alkyl or a sulfur protecting group;

n is 0, 1, 2, or 3, as valency permits; and each of $R^{na}$, $R^{nb}$, and $R^{nd}$ is independently hydrogen, an optionally substituted —C$_1$-C$_6$ alkyl, or a nitrogen protecting group; and wherein the remainder of the variables are as defined in any one of the first through nineteenth embodiments.

In a twenty-first embodiment of the invention, provided is a method in accordance with any one of the first through twentieth embodiments as described above, wherein the 5- or 6-membered monocyclic heteroaryl represented by Q is selected from the following:

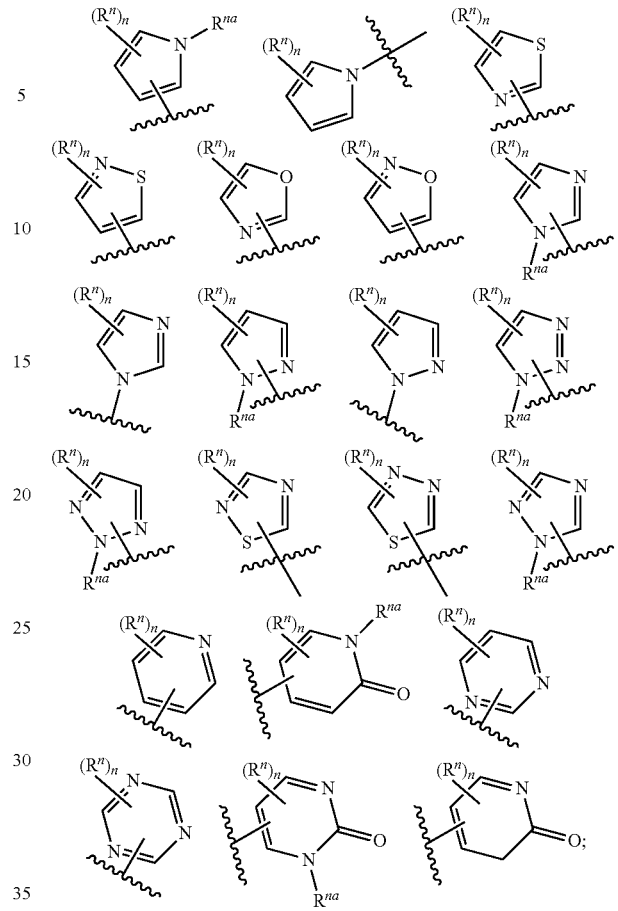

wherein the remainder of the variables are as defined in any one of the first through twentieth embodiments.

In a twenty-second embodiment of the invention, provided is a method in accordance with any one of the first through twenty-first embodiments as described above, wherein the 5- or 6-membered monocyclic heteroaryl represented by Q is selected from the following:

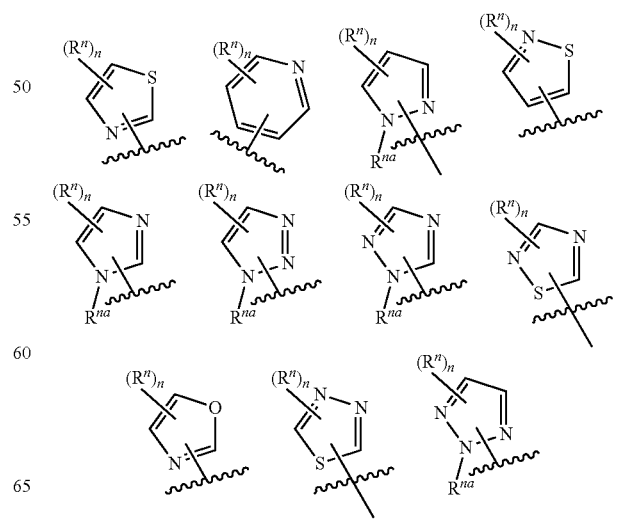

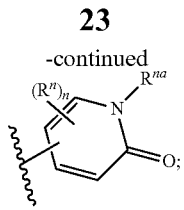

and wherein the remainder of the variables are as defined in any one of the first through twenty-first embodiments.

In a twenty-third embodiment of the invention, provided is a method in accordance with any one of the first through twenty-second embodiments as described above, wherein the 5- or 6-membered monocyclic heteroaryl represented by Q is selected from the following:

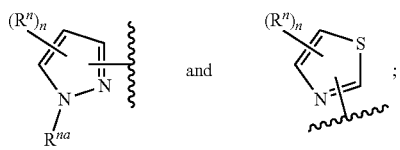

and wherein the remainder of the variables are as defined in any one of the first through twenty-second embodiments.

In a twenty-fourth embodiment of the invention, provided is a method in accordance with any one of the first through twenty-third embodiments as described above, wherein the 5- or 6-membered monocyclic heteroaryl represented by Q is

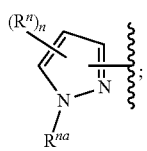

and wherein the remainder of the variables are as defined in any one of the first through twenty-third embodiments.

In a twenty-fifth embodiment of the invention, provided is a method in accordance with any one of the first through sixteenth embodiments as described above, wherein Q is optionally substituted 8- to 12-membered bicyclic heteroaryl or optionally substituted 8- to 12-membered bicyclic heterocyclyl; and wherein the remainder of the variables are as defined in any one of the first through sixteenth embodiments.

In a twenty-sixth embodiment of the invention, provided is a method in accordance with any one of the first through sixteenth and twenty-fifth embodiments as described above, wherein Q is of one of the following formulae:

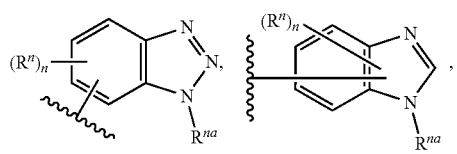

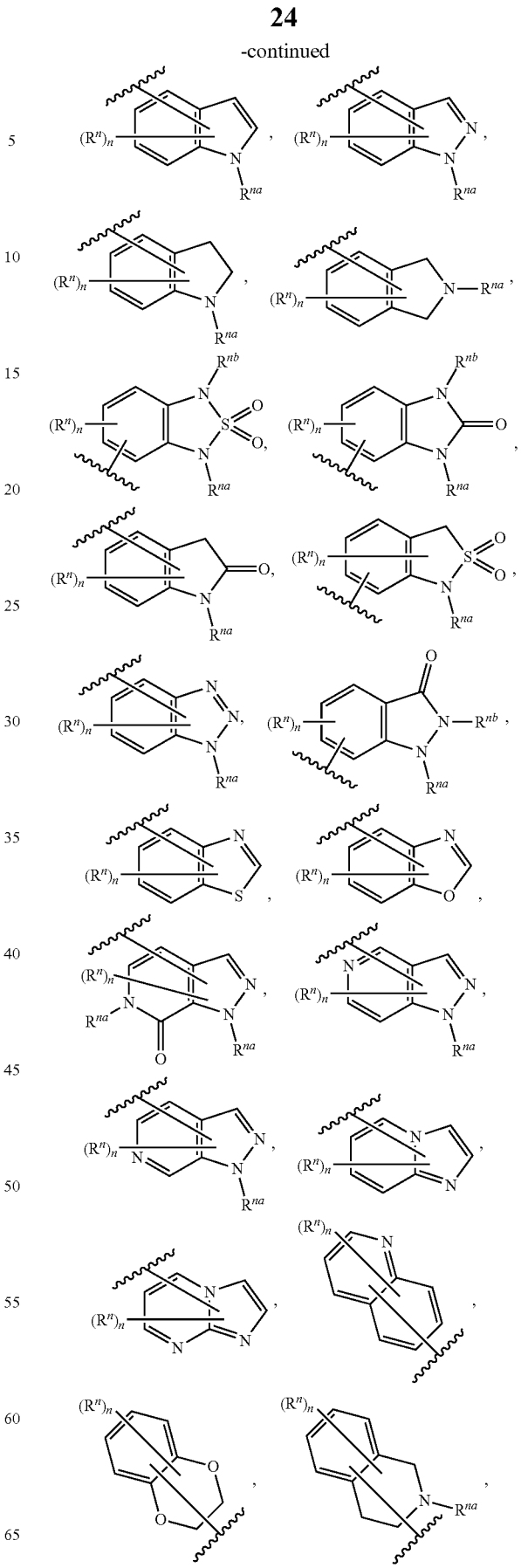

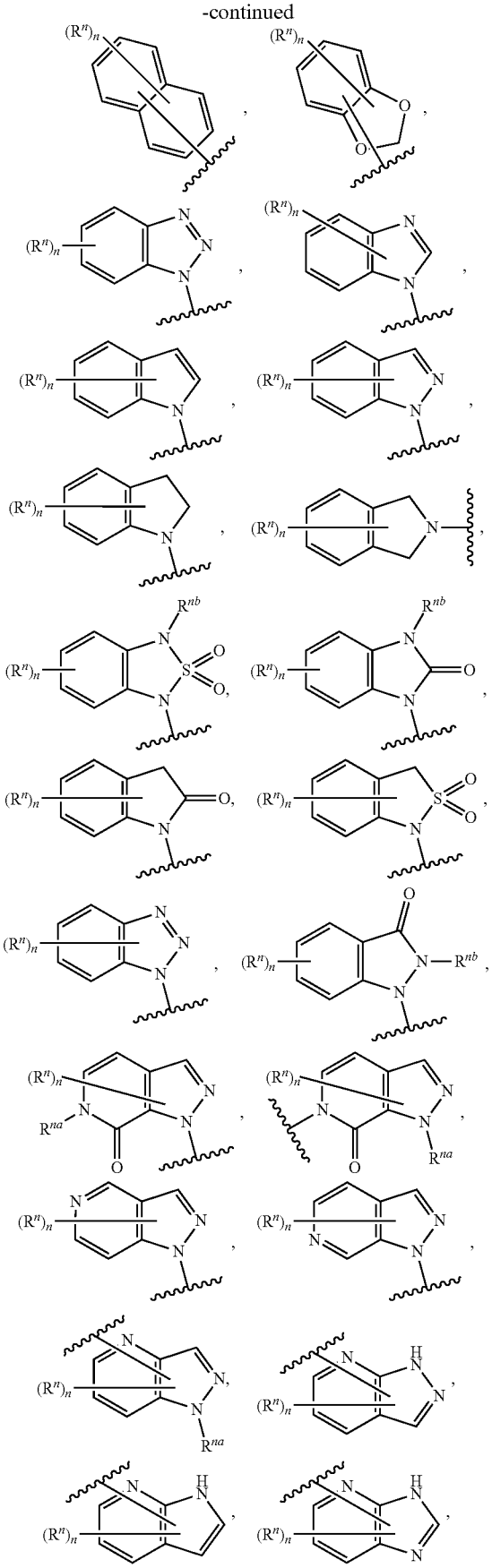
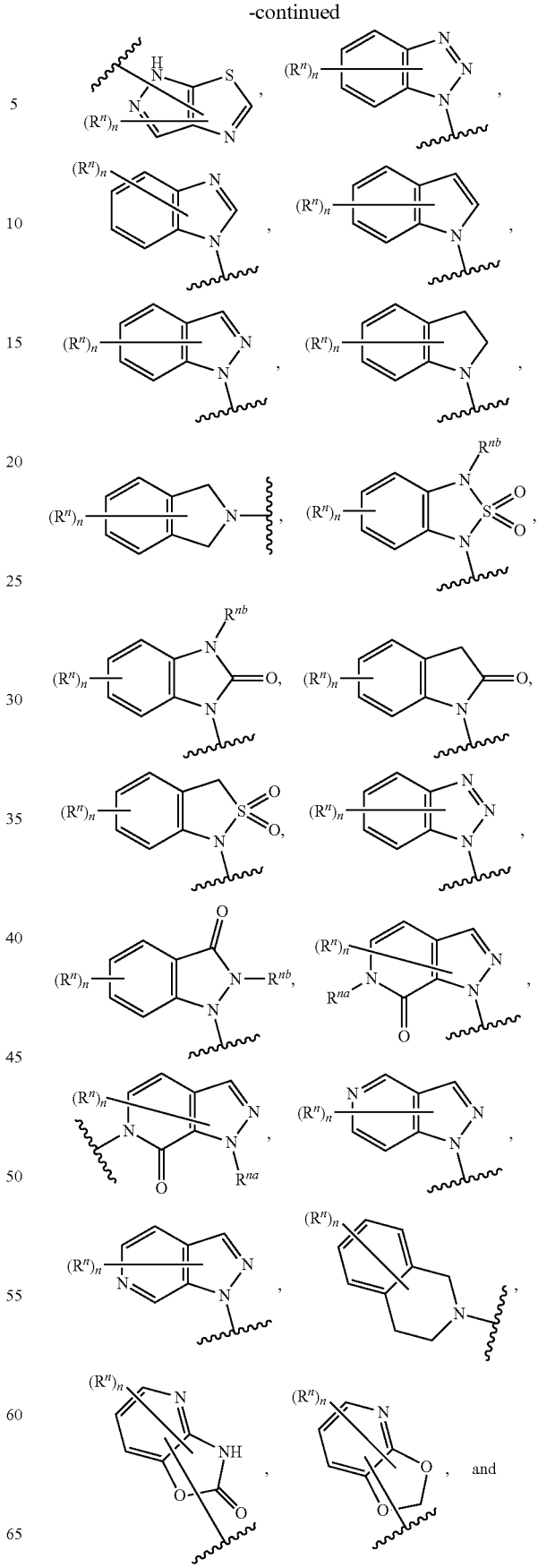

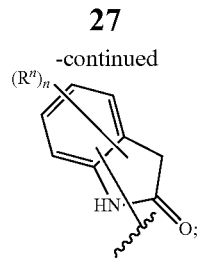

wherein each instance of $R^n$ is independently selected from hydrogen, halogen, —CN, —NO$_2$, —N$_3$, optionally substituted alkyl, optionally substituted alkenyl, optionally substituted alkynyl, optionally substituted cycloalkyl, optionally substituted aryl, optionally substituted heterocyclyl, optionally substituted heteroaryl, —OR$^{o4}$, —SR$^{s1}$, —N(R$^{n2}$)$_2$, —C(=O)N(R$^{n2}$)$_2$, —N(R$^{n2}$)C(=O)R$^{c3}$, —C(=O)R$^{c3}$, —C(=O)OR$^{o4}$, —OC(=O)R$^{c3}$, —S(=O)R$^{s1}$, —S(=O)$_2$R$^{s1}$, —S(=O)OR$^{o4}$, —OS(=O)R$^{c3}$, —S(=O)$_2$R$^{o4}$, —OS(=O)$_2$R$^{c3}$, —S(=O)N(R$^{n2}$)$_2$, —S(=O)$_2$N(R$^{n2}$)$_2$, —N(R$^{n2}$)S(=O)R$^{s1}$, —N(R$^{n2}$)S(=O)$_2$R$^{s1}$, —N(R$^{n2}$)C(=O)OR$^{o4}$, —OC(=O)N(R$^{n2}$)$_2$, —N(R$^{n2}$)C(=O)N(R$^{n2}$)$_2$, —N(R$^{n2}$)S(=O)N(R$^{n2}$)$_2$, —N(R$^{n2}$)S(=O)$_2$N(R$^{n2}$)$_2$, —N(R$^{n2}$)S(=O)OR$^{o4}$, —N(R$^{n2}$)S(=O)$_2$OR$^{o4}$, —OS(=O)N(R$^{n2}$)$_2$, —OS(=O)$_2$N(R$^{n2}$)$_2$, or two instances of $R^n$ attached to the same or adjacent carbon atoms, taken together with the atoms to which they are attached form an optionally substituted cycloalkyl or a heterocycloalkyl;

each instance of $R^{na}$ and $R^{nb}$ is independently hydrogen, optionally substituted —C$_1$-C$_6$ alkyl, or a nitrogen protecting group;

each instance of $R^{n2}$ is independently hydrogen, optionally substituted —C$_1$-C$_6$ alkyl, or a nitrogen protecting group;

each instance of $R^{o4}$ is independently hydrogen, optionally substituted —C$_1$-C$_6$ alkyl, or an oxygen protecting group;

each instance of $R^{c3}$ is independently optionally substituted —C$_1$-C$_6$ alkyl;

each instance of $R^{s1}$ is independently optionally substituted —C$_1$-C$_6$ alkyl, or a sulfur protecting group;

n is 0, 1, 2, or 3, as valency permits; and wherein the remainder of the variables are as defined in any one of the first through sixteenth and twenty-fifth embodiments.

In a twenty-seventh embodiment of the invention, provided is a method in accordance with any one of the first through twenty-sixth embodiments as described above, wherein $R^2$ is selected from hydrogen, hydroxyl, halogen, —C$_1$-C$_6$ alkyl, —C$_2$-C$_6$ alkenyl, —C$_2$-C$_6$ alkoxyl, phenyl, naphthalenyl, C$_{3-6}$ cycloalkyl, 5-membered heteroaryl, 6-membered heteroaryl, 8-membered bicyclic heteroaryl, 9-membered bicyclic heteroaryl, wherein each alkyl, alkenyl, phenyl, and heteroaryl is substituted with 0-3 occurrences of $R^e$; and wherein the remainder of the variables are as defined in any one of the first through twenty-sixth embodiments.

In a twenty-eighth embodiment of the invention, provided is a method in accordance with any one of the first through twenty-seventh embodiments as described above, wherein $R^2$ is of one of the following formulae:

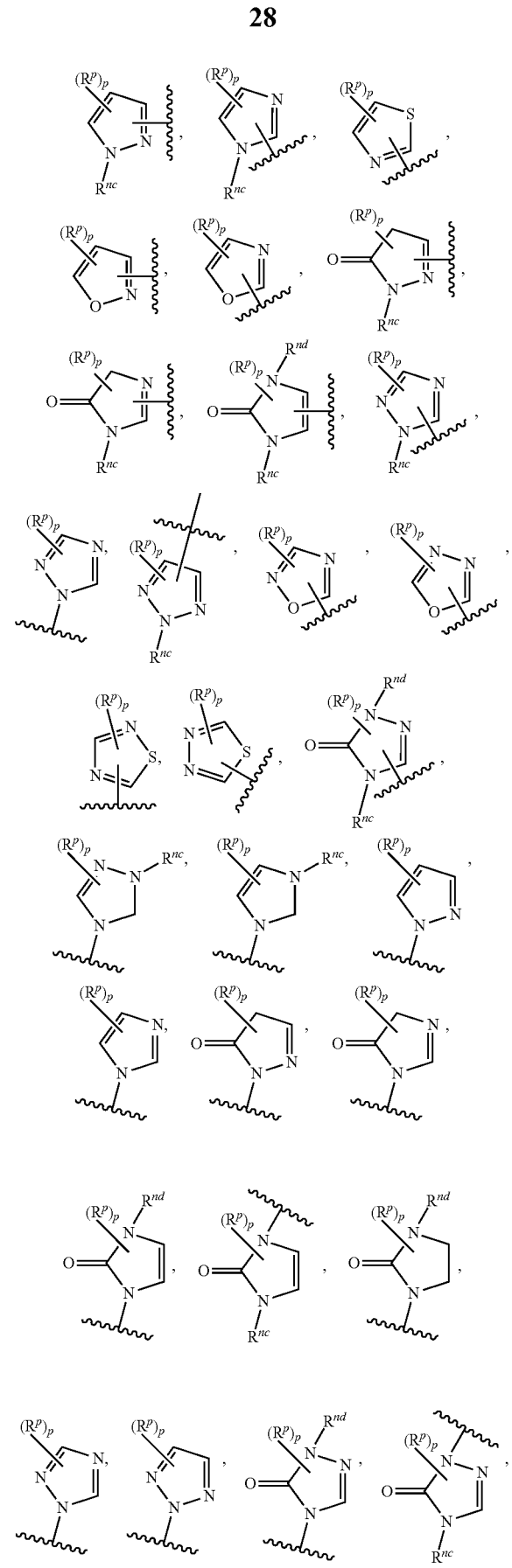

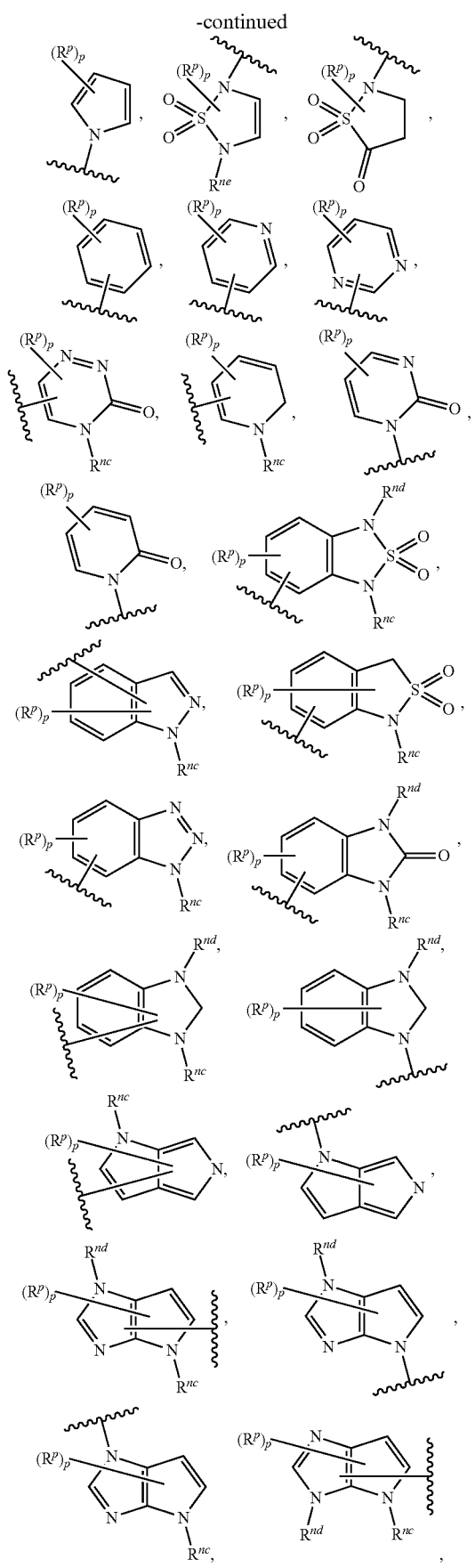

-continued

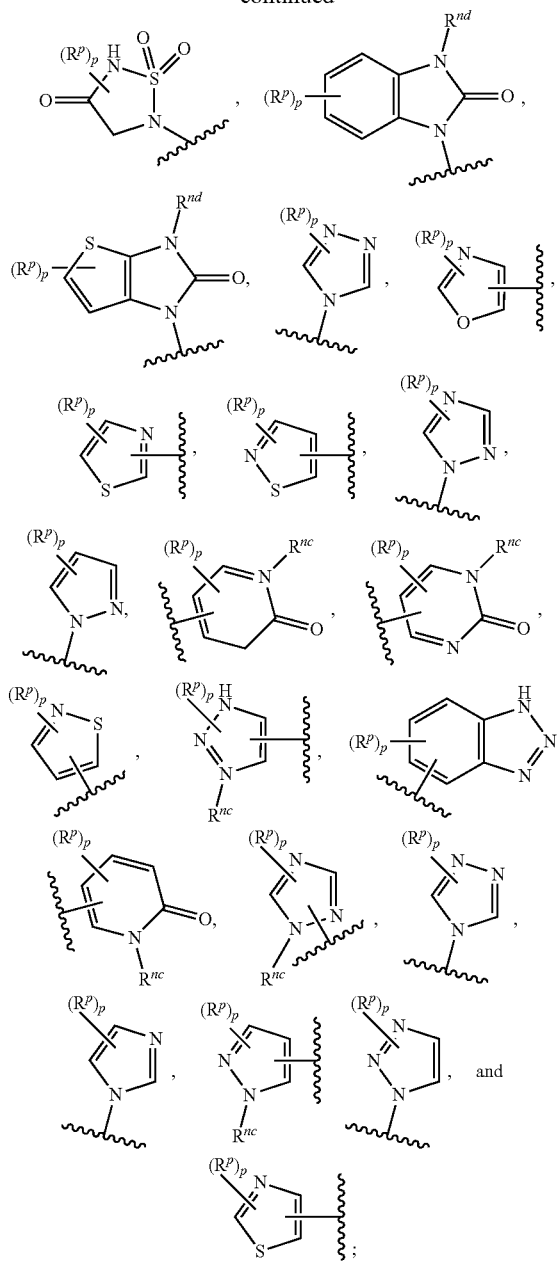

wherein each instance of R is independently selected from hydrogen, halogen, —CN, —NO$_2$, —N$_3$, optionally substituted alkyl, optionally substituted alkenyl, optionally substituted alkynyl, optionally substituted cycloalkyl, optionally substituted aryl, optionally substituted heterocyclyl, optionally substituted heteroaryl, —OR$^{o6}$, —SR$^{s2}$, —N(R$^{n3}$)$_2$, —C(=O)N(R$^{n3}$)$_2$, —N(R$^{n3}$) C(=O)R$^{c4}$, —C(=O)R$^{c4}$, —C(=O)OR$^{o6}$, —OC(=O)R$^{c4}$, —S(=O) R$^{s2}$, —S(=O)$_2$R$^{s2}$, —S(=O)OR$^{o6}$, —OS(=O)R$^{c4}$, —S(=O)$_2$OR$^{o6}$, —OS(=O)$_2$R$^{c4}$, —S(=O)N(R$^{n3}$)$_2$, —S(=O)$_2$N(R$^{n3}$)$_2$, —N(R$^{n3}$)S(=O)R$^{s2}$, —N(R$^{n3}$) S(=O)$_2$R$^{s2}$, —N(R$^{n3}$)C(=O)OR$^{o6}$, —OC(=O)N(R$^{n3}$)$_2$, —N(R$^{n3}$)C(=O)N(R$^{n3}$)$_2$, —N(R$^{n3}$)S(=O)N(R$^{n3}$)$_2$, —N(R$^{n3}$) S(=O)$_2$N(R$^{n3}$)$_2$, —N(R$^{n3}$)S(=O)OR$^6$, —N(R$^{n3}$) S(=O)$_2$OR$^{o6}$, —OS(=O)N(R$^{n3}$)$_2$, —OS(=O)$_2$N(R$^{n3}$)$_2$, or two instances of R$^p$ attached to the same or adjacent carbon atoms, taken together with the atoms to which they are attached form an optionally substituted cycloalkyl or a heterocycloalkyl;

each instance of R$^{n3}$, R$^{nc}$, and R$^{nd}$ is independently hydrogen, optionally substituted —C$_1$-C$_6$ alkyl, or a nitrogen protecting group;

each instance of R$^{o6}$ is independently hydrogen, optionally substituted —C$_1$-C$_6$ alkyl, or an oxygen protecting group;

each instance of R$^{c4}$ is independently optionally substituted —C$_1$-C$_6$ alkyl;

each instance of R$^{s2}$ is independently optionally substituted —C$_1$-C$_6$ alkyl, or a sulfur protecting group;

p is 0, 1, 2, or 3, as valency permits; and wherein the remainder of the variables are as defined in any one of the first through twenty-seventh embodiments.

In a twenty-ninth embodiment of the invention, provided is a method in accordance with any one of the first through twenty-eighth embodiments as described above, wherein the 5- or 6-membered monocyclic heteroaryl represented by R$^2$ is selected from one of the following:

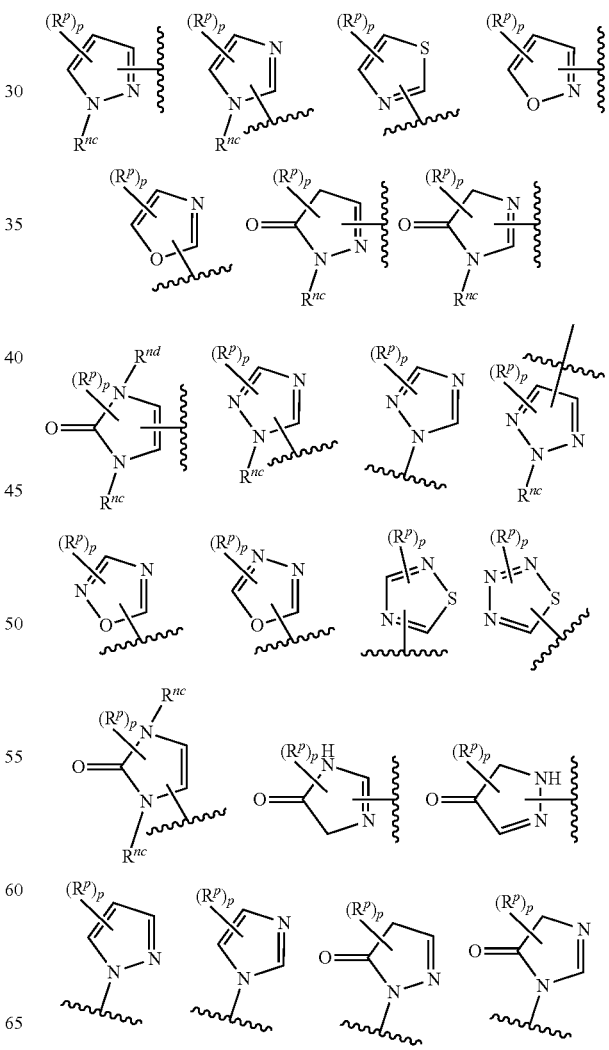

-continued

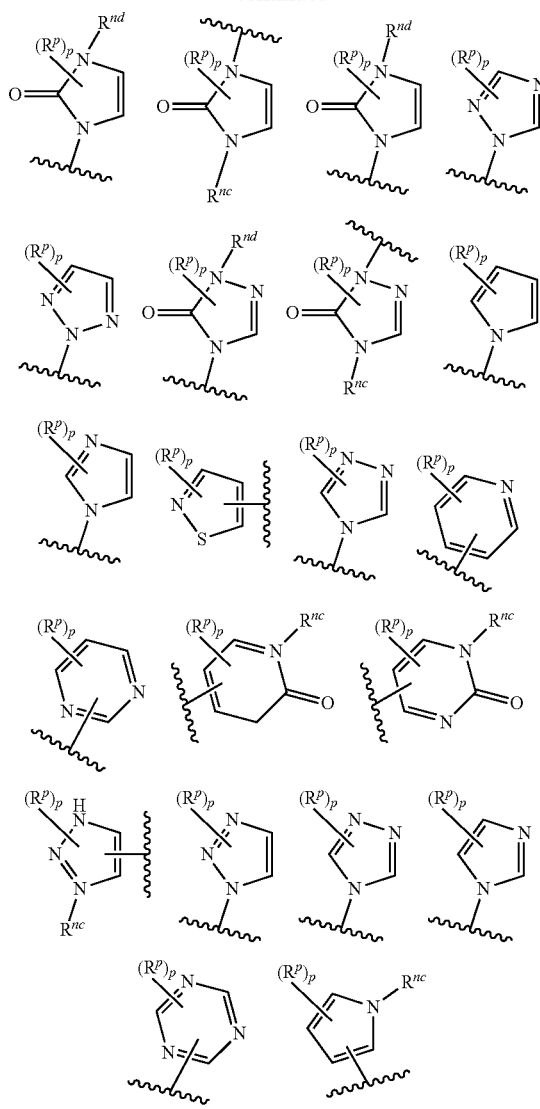

wherein:

each instance of $R^{nc}$ and $R^{nd}$ is independently hydrogen, optionally substituted —$C_1$-$C_6$ alkyl, or a nitrogen protecting group;

p is 0, 1, 2, 3, or 4, as valency permits;

wherein the remaining variables are as defined in any one of the first through twenty-eighth embodiments.

In a thirtieth embodiment of the invention, provided is a method in accordance with any one of the first through twenty-ninth embodiments as described above, wherein the 5- or 6-membered monocyclic heteroaryl represented by $R^2$ is selected from one of the following:

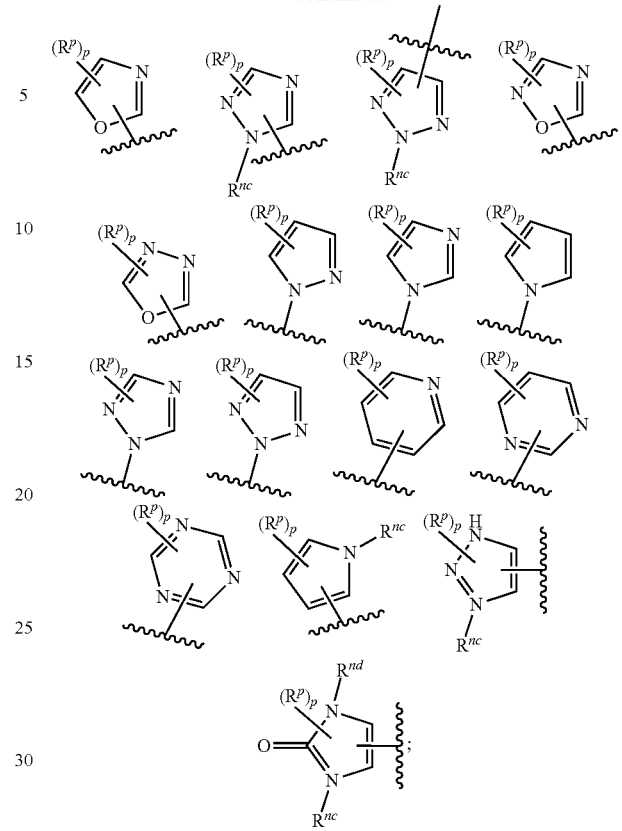

wherein the remainder of the variables are as defined in any one of the first through twenty-ninth embodiments.

In a thirty-first embodiment of the invention, provided is a method in accordance with any one of the first through thirtieth embodiments as described above, wherein $R^2$ is selected from one of the following:

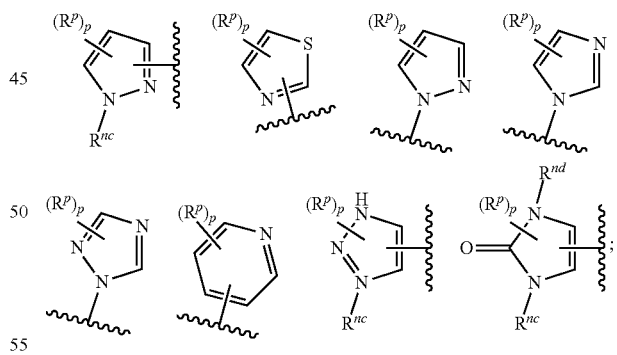

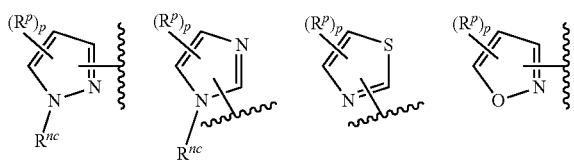

and wherein the remainder of the variables are as defined in any one of the first through twenty-thirtieth embodiments.

In a thirty-second embodiment of the invention, provided is a method in accordance with any one of the twenty-seventh through thirty-first embodiments as described above, wherein each instance of $R^p$ is independently hydrogen, halogen, optionally substituted $C_{1-4}$ alkyl, —CN, —$NO_2$, —$N_3$, —$OR^{o4}$, —$N(R^{n2})_2$, —$C(=O)N(R^{n2})_2$, —$C(=O)R^{c3}$, or —$C(=O)OR^{o4}$; and wherein the remainder of the variables are as defined in any one of the twenty-eighth through thirty-first embodiments.

In a thirty-third embodiment of the invention, provided is a method in accordance with any one of the first through sixteenth and twenty-seventh through thirty-second embodiments as described above, wherein the compound is a compound of Formula (III):

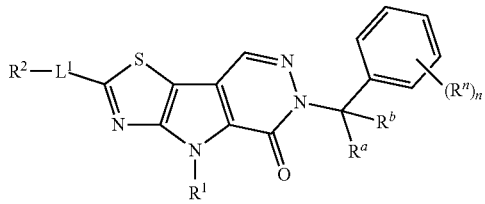

(III)

or a pharmaceutically acceptable salt thereof, wherein the variables are as defined in any one of the first through sixteenth and twenty-seventh through thirty-second embodiments.

In a thirty-fourth embodiment of the invention, provided is a method in accordance with any one of the first through twenty-fourth and twenty-seventh through thirty-second embodiments as described above, wherein the compound is a compound of Formula (IV):

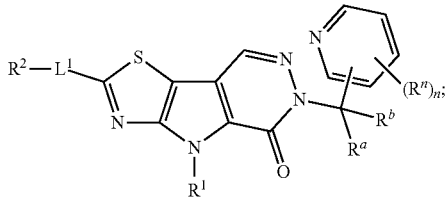

(IV)

or a pharmaceutically acceptable salt thereof, wherein the variables are as defined in any one of the first through twenty-fourth and twenty-seventh through thirty-second embodiments.

In a thirty-fifth embodiment of the invention, provided is a method in accordance with any one of the first through twenty-fourth and twenty-seventh through thirty-second embodiments as described above, wherein the compound is a compound of Formula (V-a):

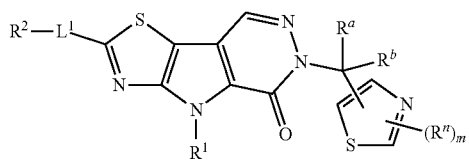

(V-a)

or a pharmaceutically acceptable salt thereof, wherein m is 0, 1, or 2; and the remainder of the variables are as defined in any one of the first through twenty-fourth and twenty-seventh through thirty-second embodiments.

In a thirty-sixth embodiment of the invention, provided is a method in accordance with any one of the first through twenty-fourth and twenty-seventh through thirty-second embodiments as described above, wherein the compound is a compound of Formula (V-b):

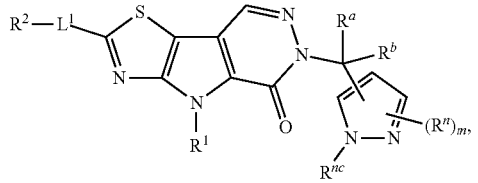

(V-b)

or a pharmaceutically acceptable salt thereof, wherein m is 0, 1, or 2; $R^{nc}$ is independently hydrogen, optionally substituted —$C_1$-$C_6$ alkyl, or a nitrogen protecting group; and wherein the remainder of the variables are as defined in any one of the first through twenty-fourth and twenty-seventh through thirty-second embodiments.

In a thirty-seventh embodiment of the invention, provided is a method in accordance with any one of the first through sixteenth and twenty-fifth through thirty-second embodiments as described above, wherein the compound is a compound of Formula (VI):

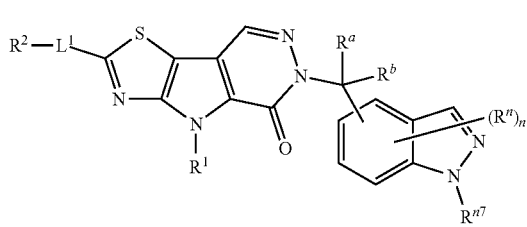

(VI)

or a pharmaceutically acceptable salt thereof, wherein $R^{n7}$ is hydrogen, optionally substituted —$C_1$-$C_6$ alkyl, or a nitrogen protecting group; and wherein the remainder of the variables are as defined in any one of the first through sixteenth and twenty-fifth through thirty-second embodiments.

In a thirty-eighth embodiment of the invention, provided is a method in accordance with any one of the first through twenty-fourth and twenty-seventh through thirty-second embodiments as described above, wherein the compound is a compound of Formula (IX):

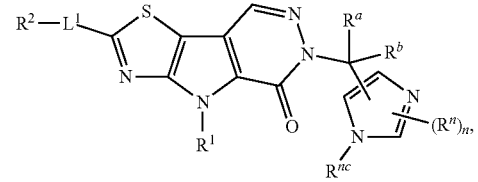

(IX)

or a pharmaceutically acceptable salt thereof, wherein $R^{nc}$ is independently hydrogen, optionally substituted —$C_1$-$C_6$ alkyl, or a nitrogen protecting group; and wherein the remainder of the variables are as defined in any one of the first through twenty-fourth and twenty-seventh through thirty-second embodiments.

In a thirty-ninth embodiment of the invention, provided is a method in accordance with any one of the first through thirty-eighth embodiments as described above, wherein the compound is a compound of Formula (II'):

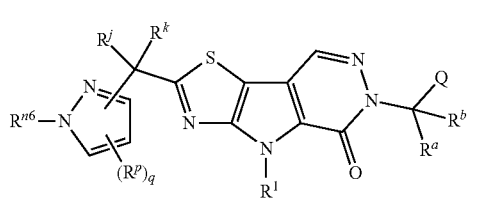

(II')

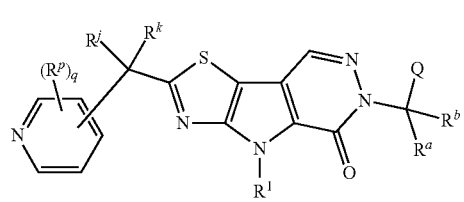

(V')

or a pharmaceutically acceptable salt thereof, wherein $R^{n6}$ is hydrogen, an optionally substituted —$C_1$-$C_6$ alkyl, or a nitrogen protecting group; q is 0, 1, 2, or 3; and wherein the remainder of the variables are as defined in any one of the first through thirty-eighth embodiments. Alternatively, the variables are as described in any one of the seventeenth, eighteenth, twenty-ninth, thirtieth, and thirty-first embodiments.

In a fortieth embodiment of the invention, provided is a method in accordance with any one of the first through thirty-eighth embodiments as described above, wherein the compound is a compound of Formula (III'):

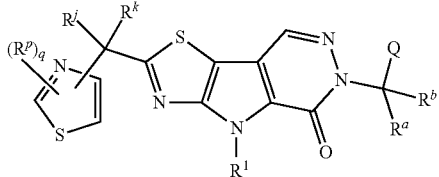

(III')

or a pharmaceutically acceptable salt thereof, wherein q is 0, 1, 2, or 3; and wherein the remainder of the variables are as defined in any one of the first through thirty-eighth embodiments.

In a forty-first embodiment of the invention, provided is a method in accordance with any one of the first through thirty-eighth embodiments as described above, wherein the compound is a compound of Formula (IV'):

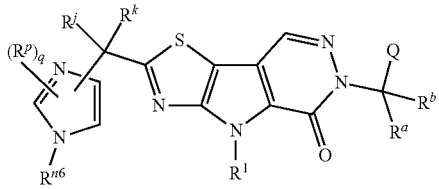

(IV')

or a pharmaceutically acceptable salt thereof, wherein $R^{n6}$ is hydrogen, an optionally substituted —$C_1$-$C_6$ alkyl, or a nitrogen protecting group; q is 0, 1, 2, or 3; and wherein the remainder of the variables are as defined in any one of the first through thirty-eighth embodiments.

In a forty-second embodiment of the invention, provided is a method in accordance with any one of the first through thirty-eighth embodiments as described above, wherein the compound is a compound of Formula (V')

or a pharmaceutically acceptable salt thereof, wherein q is 0, 1, 2, or 3; and wherein the remainder of the variables are as defined in any one of the first through thirty-eighth embodiments.

In a forty-third embodiment of the invention, provided is a method in accordance with any one of the thirty-ninth through forty-second embodiments as described above, wherein $R^{n6}$ is hydrogen or a —$C_{1-4}$ alkyl; and wherein the remainder of variables are as defined in any one of the thirty-ninth through forty-second embodiments.

In a forty-fourth embodiment of the invention, provided is a method in accordance with any one of the thirty-ninth through forty-second embodiments as described above, wherein each instance of R is independently hydrogen, halogen, optionally substituted $C_{1-4}$ alkyl, —CN, —$NO_2$, —$N_3$, —$OR^{o4}$, —$N(R^{n2})_2$, —C(=O)$N(R^{n2})_2$, —C(=O)$R^{c3}$, or —C(=O)$OR^{o4}$; and wherein the remainder of variables are as defined in any one of the thirty-ninth through forty-second embodiments.

In a forty-fifth embodiment of the invention, provided is a method in accordance with any one of the twenty-sixth through forty-second embodiments as described above, wherein $R^{na}$ is hydrogen or —$C_{1-4}$ alkyl; and wherein the remainder of the variables are as defined in any one of the twenty-sixth through forty-second embodiments.

In a forty-sixth embodiment of the invention, provided is a method in accordance with any one of the twentieth through forty-fifth embodiments as described above, wherein each instance of R" is independently hydrogen, halogen, optionally substituted $C_{1-4}$ alkyl, —CN, —$NO_2$, —$N_3$, —$OR^{o4}$, —$N(R^{n2})_2$, —C(=O)$N(R^{n2})_2$, —C(=O)$R^{c3}$, or —C(=O)$OR^{o4}$; and wherein the remainder of the variables are as defined in any one of the twentieth through forty-fifth embodiments.

In a forty-seventh embodiment of the invention, provided is a method in accordance with any one of the first through forty-sixth embodiments as described above, wherein R' is hydrogen or a —$C_1$-$C_4$ alkyl; and wherein the remainder of the variables are as defined in any one of the first through forty-sixth embodiments.

In a forty-eighth embodiment of the invention, provided is a method in accordance with any one of the sixteenth through forty-seventh embodiments as described above, wherein $R^j$ and $R^k$ are each independently hydrogen, a halogen, —$OR^{o7}$, or a —$C_1$-$C_4$ alkyl; or $R^j$ and $R^k$ are joined together to form =O; and wherein the remainder of the variables are as defined in any one of the sixteenth through forty-seventh embodiments.

In a forty-ninth embodiment of the invention, provided is a method in accordance with any one of the sixteenth through forty-eighth embodiments as described above, wherein $R^j$ and $R^k$ are each hydrogen; and wherein the remainder of the variables are as defined in any one of the sixteenth through forty-eighth embodiments.

In a fiftieth embodiment of the invention, provided is a method in accordance with any one of the fourteenth through forty-ninth embodiments as described above, wherein $R^a$ and $R^b$ are each hydrogen; and wherein the remainder of the variables are as defined in any one of the fourteenth through forty-ninth embodiments.

In a fifty-first embodiment of the invention, provided is a method in accordance with any one of the thirty-fifth through fiftieth embodiments as described above, wherein q is 0 or 1; and wherein the remainder of the variables are as defined in any one of the thirty-fifth through fiftieth embodiments.

In a fifty-second embodiment of the invention, provided is a method in accordance with any one of the twentieth through fifty-first embodiments as described above, wherein n is 0 or 1; and wherein the remainder of the variables are as defined in any one of the twentieth through fifty-first embodiments.

In a fifty-third embodiment of the invention, provided is a method in accordance with any one of the first through fifty-second embodiments as described above, wherein the compound is a compound selected from Table 1 or a pharmaceutically acceptable salt thereof.

In a fifty-fourth embodiment of the invention, provided is a method of modulating the activity of pyruvate kinase M2 (PKM2), comprising contacting the PKM2 with an effective amount of a compound as described in any one of the above first through fifty-third embodiments, or a pharmaceutically acceptable salt thereof.

In a fifty-fifth embodiment of the invention, provided is a method of inhibiting proliferation of a cell expressing pyruvate kinase M2 (PKM2), comprising contacting the cel with an effective amount of a compound as described in any one of the above first through fifty-third embodiments, or a pharmaceutically acceptable salt thereof.

In a fifty-sixth embodiment of the invention, provided is a method in accordance with any one of the fifty-fourth and fifty-fifth embodiments as described above, wherein the method Is an ex vivo method.

In a fifty-seventh embodiment of the invention, provided is a method in accordance with any one of the fifty-fourth and fifty-fifth embodiments as described above, wherein the method is an in vitro method.

In a fifty-eighth embodiment of the invention, provided is a method in accordance with any one of the fifty-fourth through fifty-seventh embodiments, wherein the method inhibits the activity of PKM2.

In a fifty-ninth embodiment of the invention, provided is a method in accordance with any one of the fifty-fourth through fifty-seventh embodiments, wherein the method activates the activity of PKM2.

In a sixtieth embodiment of the invention, provided is a method in accordance with any one of the fifty-fourth through fifty-ninth embodiments, wherein the PKM2 is expressed in a cell that is not a red blood cell.

In a sixty-first embodiment of the invention, provided is a method in accordance with any one of the fifty-fourth through sixtieth embodiments, wherein the cell is derived or obtained from a subject suffering from or susceptible to a disease or disorder associated with function of PKM2.

In a sixty-second embodiment of the invention, provided is a method in accordance with the sixty-first embodiment, wherein the disease or disorder is associated with aberrant activity of PKM2.

In a sixty-third embodiment of the invention, provided is a method in accordance with the sixty-first embodiment, wherein the disease or disorder is cancer, obesity, a diabetic disease (e.g. diabetes, diabetic nephropathy (DN)), atherosclerosis, restenosis, coronary artery disease (CAD), Bloom Syndrome (BS), benign prostatic hyperplasia (BPH), or an autoimmune disease.

In a sixty-fourth embodiment of the invention, provided is a method in accordance with the sixty-third embodiment, wherein the diabetic disease is diabetic nephropathy.

In a sixty-fifth embodiment of the invention, provided is a method in accordance with any one of the fifty-fifth through sixty-fourth embodiments, wherein the cell is a cell that overexpresses PKM2.

In a sixty-sixth embodiment of the invention, provided is a method in accordance with any one of the fifty-fifth through sixty-fifth embodiments, wherein the cell is a cell that expresses PKM2 that has aberrant activity.

In a sixty-seventh embodiment of the invention, provided is a method in accordance with any one of the fifty-fifth through sixty-sixth embodiments, wherein the cell is a cancer cell, a pancreatic cell, a liver cell, a nerve cell or a kidney cell.

In certain embodiments of the compounds of Formulas (I)-(IX), (I')-(V') or pharmaceutically acceptable salts thereof, $R^2$ and Q are each independently optionally substituted 5- or 6-membered monocyclic heteroaryl. In certain embodiments of the compounds of Formulas (I)-(IX), (I')-(V') or pharmaceutically acceptable salts thereof, $R^2$ and Q are both optionally substituted 5- or 6-membered monocyclic heteroaryl; and $L^1$ and $L^2$ are each independently optionally substituted C1-4 alkylene. In certain embodiments, $R^2$ and Q are the same. In certain embodiments, $R^2$ and Q are different.

In certain embodiments, compounds described herein are useful as activators of PKM2 utilized in the methods and compositions described herein and operate by or has one or more of the following mechanisms or properties:

a. it is an allosteric activator of PKM2;
   b. it modulates (e.g., stabilizes) the binding of FBP in a binding pocket of PKM2;
   c. it modulates (e.g., promotes) the release of FBP from a binding pocket of PKM2;
   d. it is a modulator (e.g., an agonist), e.g., an analog, of FBP, e.g., an agonist which binds PKM2 with a lower, about the same, or higher affinity than does FBP;
   e. it modulates (e.g., promotes) the dissolution of tetrameric PKM2;
   f. it modulates (e.g., promotes) the assembly of tetrameric PKM2;
   g. it modulates (e.g., stabilizes) the tetrameric conformation of PKM2;
   h. it modulates (e.g., promotes) the binding of a phosphotyrosine containing polypeptide to PKM2;
   i. it modulates (e.g., promotes) the ability of a phosphotyrosine containing polypeptide to induce release of FBP from PKM2, e.g., by inducing a change in the conformation of PKM2, e.g., in the position of Lys 433, thereby hindering the release of FBP;
   j. modulates the propensity of PKM2 to undergo post-translational modifications (e.g. oxidation at Cys358 or acetylation on Lys305) that affect activity of the enzyme.
   k. it binds to or changes the position of Lys 433 relative to the FBP binding pocket;
   l. it selectively modulates (e.g., activates) PKM2 over at least one other isoform of PK, e.g., it is selective for PKM2 over one or more of PKR, PKM1, or PKL;

m. it has an affinity for PKM2 which is greater than its affinity for at least one other isoform of PK, e.g., PKR, PKM1, or PKL.

A compound described herein may be tested for its ability to activate PKM2. For simplicity, the activation activity of these compounds is represented as an $AC_{50}$ in Table 2. In Tables 2, a compound described herein may have an AC50 of wild type PKM2. "A" refers to an AC50 less than 0.300 μM; "B" refers to an AC50 from 0.301 μM to 0.800 μM, and "C" refers to an AC50 greater than 0.800 μM.

TABLE 1

Exemplary Compounds as PKM2 Modulators

| Cpd Nr | Compound |
|---|---|
| 1 | *(structure)* |
| 2 | *(structure)* |
| 3 | *(structure)* |
| 4 | *(structure)* |
| 5 | *(structure)* |
| 6 | *(structure)* |

TABLE 1-continued

Exemplary Compounds as PKM2 Modulators

| Cpd Nr | Compound |
|---|---|
| 7 | |
| 8 | |
| 9 | |
| 10 | |
| 11 | |
| 12 | |
| 13 | |

TABLE 1-continued

Exemplary Compounds as PKM2 Modulators

| Cpd Nr | Compound |
|---|---|
| 14 | |
| 15 | |
| 16 | |
| 17 | |
| 18 | |
| 19 | |

TABLE 1-continued

Exemplary Compounds as PKM2 Modulators

| Cpd Nr | Compound |
|---|---|
| 20 | |
| 21 | |
| 22 | |
| 23 | |
| 24 | |
| 25 | |
| 26 | |

TABLE 1-continued

Exemplary Compounds as PKM2 Modulators

| Cpd Nr | Compound |
|---|---|
| 27 | (structure) |
| 28 | (structure) |
| 29 | (structure) |
| 30 | (structure) |
| 31 | (structure) |
| 32 | (structure) |

TABLE 1-continued
Exemplary Compounds as PKM2 Modulators
| Cpd Nr | Compound |
|---|---|
| 33 | 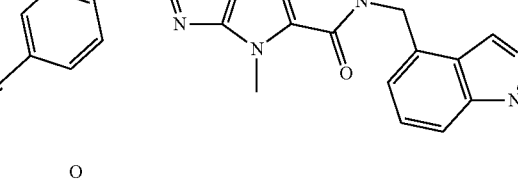 |
| 34 | 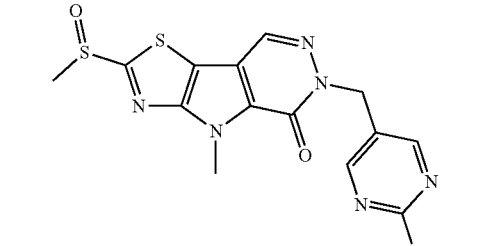 |
| 35 | 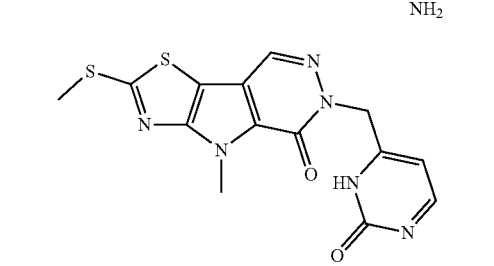 |
| 36 | 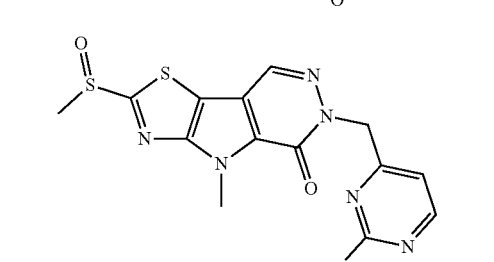 |
| 37 |  |
| 38 | 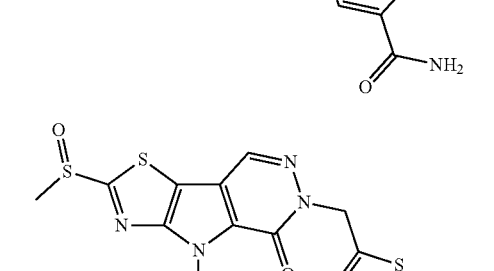 |

TABLE 1-continued

Exemplary Compounds as PKM2 Modulators

| Cpd Nr | Compound |
|---|---|
| 39 | |
| 40 | |
| 41 | |
| 42 | |
| 43 | |
| 44 | |

TABLE 1-continued

Exemplary Compounds as PKM2 Modulators

| Cpd Nr | Compound |
|---|---|
| 45 | |
| 46 | |
| 47 | |
| 48 | |
| 49 | |
| 50 | |

TABLE 1-continued

Exemplary Compounds as PKM2 Modulators

| Cpd Nr | Compound |
|---|---|
| 51 | |
| 52 | |
| 53 | |
| 54 | |
| 55 | |
| 56 | |
| 57 | |

TABLE 1-continued

Exemplary Compounds as PKM2 Modulators

| Cpd Nr | Compound |
|---|---|
| 58 | |
| 59 | |
| 60 | |
| 61 | |
| 62 | |
| 63 | |

TABLE 1-continued

Exemplary Compounds as PKM2 Modulators

| Cpd Nr | Compound |
|---|---|
| 64 | |
| 65 | |
| 66 | |
| 67 | |
| 68 | |
| 69 | |
| 70 | |

TABLE 1-continued

Exemplary Compounds as PKM2 Modulators

| Cpd Nr | Compound |
|---|---|
| 71 | |
| 72 | |
| 73 | |
| 74 | |
| 75 | |
| 76 | |

TABLE 1-continued
Exemplary Compounds as PKM2 Modulators
| Cpd Nr | Compound |
|---|---|
| 77 | 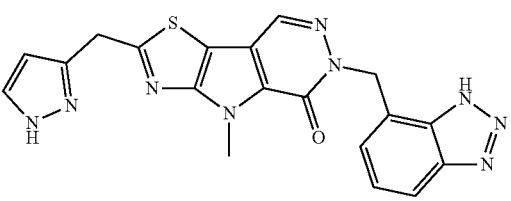 [SMILES: Cn1c2nc(Cc3cc[nH]n3)sc2c2cnn(Cc3cccc4nn[nH]c34)c(=O)c21] |
| 78 | 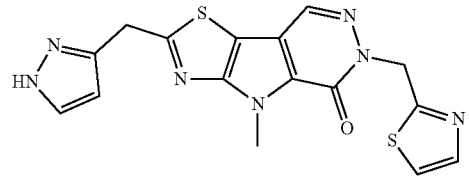 [SMILES: Cn1c2nc(Cc3cc[nH]n3)sc2c2cnn(Cc3nccs3)c(=O)c21] |
| 79 | 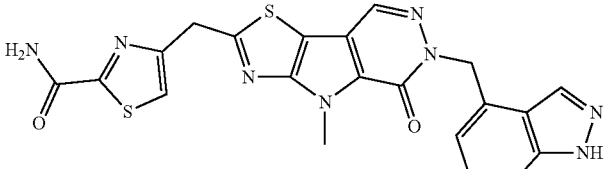 |
| 80 | 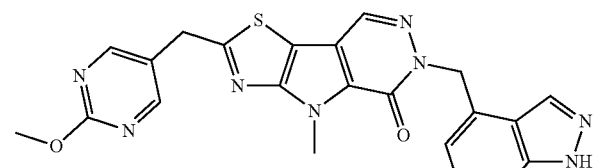 |
| 81 | 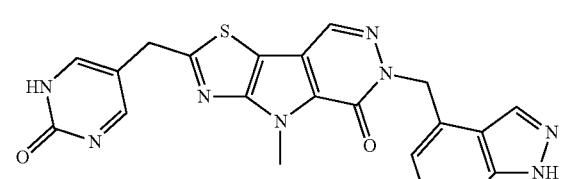 |
| 82 | 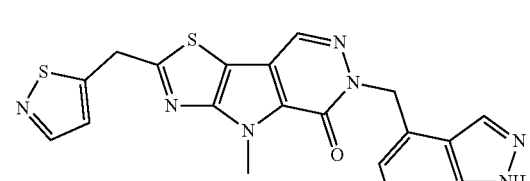 |
| 83 | 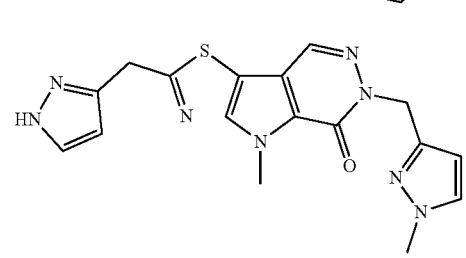 |

TABLE 1-continued

Exemplary Compounds as PKM2 Modulators

| Cpd Nr | Compound |
|---|---|
| 84 | |
| 85 | |
| 86 | |
| 87 | |
| 88 | |
| 89 | |
| 90 | |

TABLE 1-continued

Exemplary Compounds as PKM2 Modulators

| Cpd Nr | Compound |
|---|---|
| 91 | |
| 92 | |
| 93 | |
| 94 | |
| 95 | |
| 96 | |
| 97 | |

TABLE 1-continued

Exemplary Compounds as PKM2 Modulators

| Cpd Nr | Compound |
|---|---|
| 98 | |
| 99 | |
| 100 | |
| 101 | |
| 102 | |
| 103 | |
| 104 | |

TABLE 1-continued

Exemplary Compounds as PKM2 Modulators

| Cpd Nr | Compound |
|---|---|
| 105 | |
| 106 | |
| 107 | |
| 108 | |
| 109 | |
| 110 | |
| 111 | |

TABLE 1-continued

Exemplary Compounds as PKM2 Modulators

| Cpd Nr | Compound |
|---|---|
| 112 | |
| 113 | |
| 114 | |
| 115 | |
| 116 | |
| 117 | |

TABLE 1-continued

Exemplary Compounds as PKM2 Modulators

| Cpd Nr | Compound |
|---|---|
| 118 | |
| 119 | |
| 120 | |
| 121 | |
| 122 | |
| 123 | |

TABLE 1-continued

Exemplary Compounds as PKM2 Modulators

| Cpd Nr | Compound |
|---|---|
| 124 | |
| 125 | |
| 126 | |
| 127 | |
| 128 | |
| 129 | |

TABLE 1-continued

Exemplary Compounds as PKM2 Modulators

| Cpd Nr | Compound |
|---|---|
| 130 | |
| 131 | |
| 132 | |
| 133 | |
| 134 | |
| 135 | |

TABLE 1-continued

Exemplary Compounds as PKM2 Modulators

| Cpd Nr | Compound |
|---|---|
| 136 | |
| 137 | |
| 138 | |
| 139 | |
| 140 | |
| 141 | |
| 142 | |

TABLE 1-continued

Exemplary Compounds as PKM2 Modulators

| Cpd Nr | Compound |
|---|---|
| 143 | |
| 144 | |
| 145 | |

TABLE 2

$AC_{50}$ of Exemplary compounds for Wild Type PKM2

| Cpd No. | PKM2 WT AC50 | Cpd No. | PKM2 WT AC50 | Cpd No. | PKM2 WT AC50 | Cpd No. | PKM2 WT AC50 |
|---|---|---|---|---|---|---|---|
| 1 | A | 74 | A | 33 | C | 106 | C |
| 2 | A | 75 | A | 34 | C | 107 | A |
| 3 | B | 76 | A | 35 | C | 108 | A |
| 4 | B | 77 | A | 36 | B | 109 | A |
| 5 | C | 78 | A | 37 | C | 110 | A |
| 6 | B | 79 | C | 38 | A | 111 | A |
| 7 | C | 80 | A | 39 | A | 112 | A |
| 8 | A | 81 | C | 40 | C | 113 | A |
| 9 | B | 82 | B | 41 | B | 114 | C |
| 10 | A | 83 | A | 42 | C | 115 | A |
| 11 | A | 84 | A | 43 | A | 116 | C |
| 12 | C | 85 | A | 44 | C | 117 | C |
| 13 | B | 86 | A | 45 | B | 118 | B |
| 14 | C | 87 | A | 46 | A | 119 | B |
| 15 | C | 88 | A | 47 | C | 120 | C |
| 16 | B | 89 | A | 48 | C | 121 | B |
| 17 | C | 90 | A | 49 | B | 122 | A |
| 18 | C | 91 | A | 50 | C | 123 | A |
| 19 | C | 92 | A | 51 | A | 124 | B |
| 20 | C | 93 | A | 52 | C | 125 | C |
| 21 | A | 94 | A | 53 | C | 126 | A |
| 22 | C | 95 | C | 54 | A | 127 | B |
| 23 | B | 96 | A | 55 | C | 128 | A |
| 24 | C | 97 | C | 56 | C | 129 | A |
| 25 | C | 98 | B | 57 | C | 130 | C |
| 26 | B | 99 | A | 58 | C | 131 | B |
| 27 | B | 100 | A | 59 | C | 132 | A |
| 28 | A | 101 | A | 60 | C | 133 | C |
| 29 | B | 102 | B | 61 | C | 134 | A |
| 30 | A | 103 | A | 62 | C | 135 | A |
| 31 | A | 104 | A | 63 | A | 136 | B |
| 32 | A | 105 | A | 64 | C | 137 | B |

TABLE 2-continued
AC₅₀ of Exemplary compounds for Wild Type PKM2
| Cpd No. | PKM2 WT AC50 | Cpd No. | PKM2 WT AC50 |
|---|---|---|---|
| 65 | A | 138 | C |
| 66 | A | 139 | C |
| 67 | C | 140 | C |
| 68 | A | 141 | C |
| 69 | A | 142 | C |
| 70 | A | 143 | C |
| 71 | C | 144 | C |
| 72 | A | 145 | C |
| 73 | A | | |
In certain embodiments, the compound of Formulas (I)-(IX), (I')-(V') are selected from any one of the compounds set forth in Table 1 and in the Examples. In certain embodiments, the compound of Formulas (I)-(IX), (I')-(V') are of the formula of any one below:
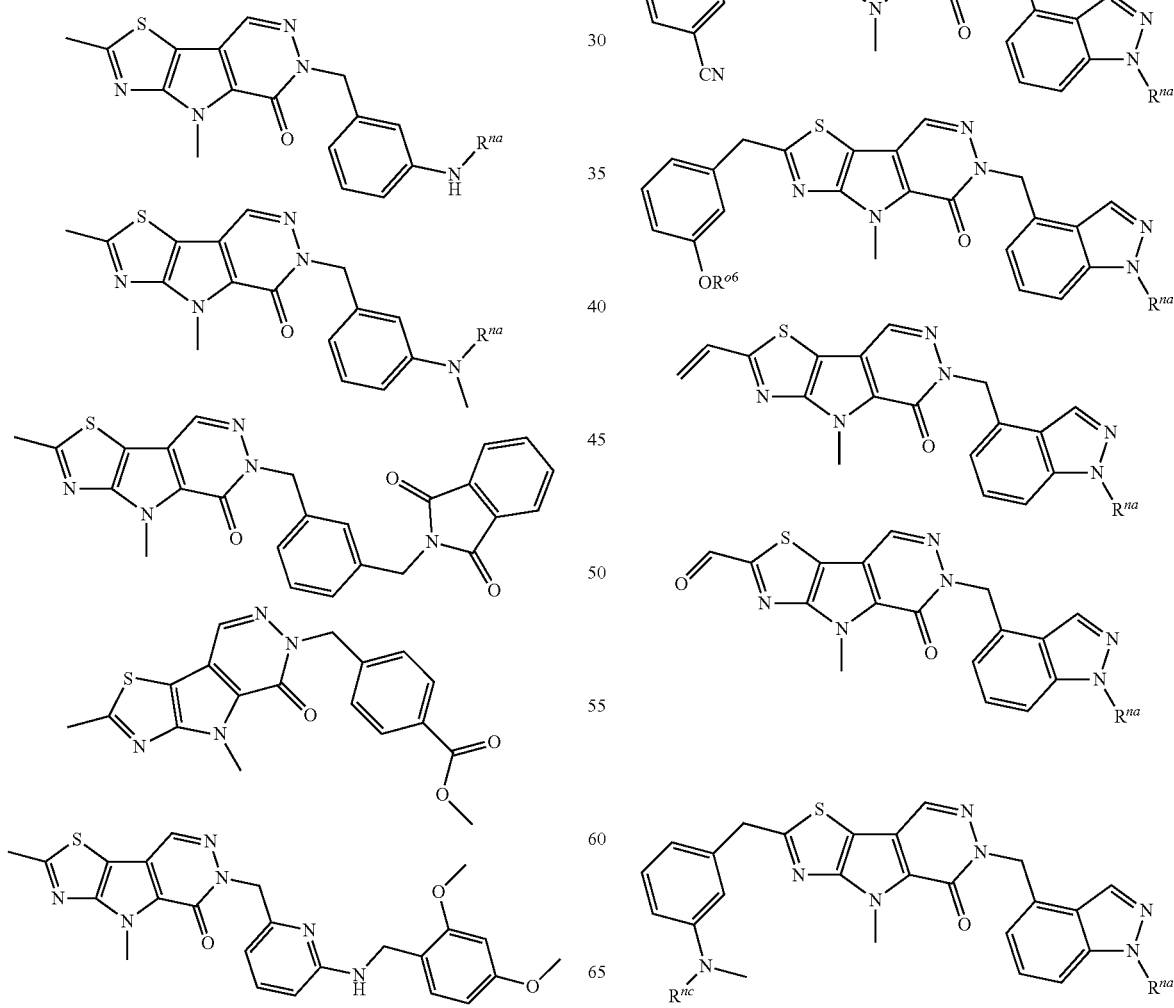

89
-continued
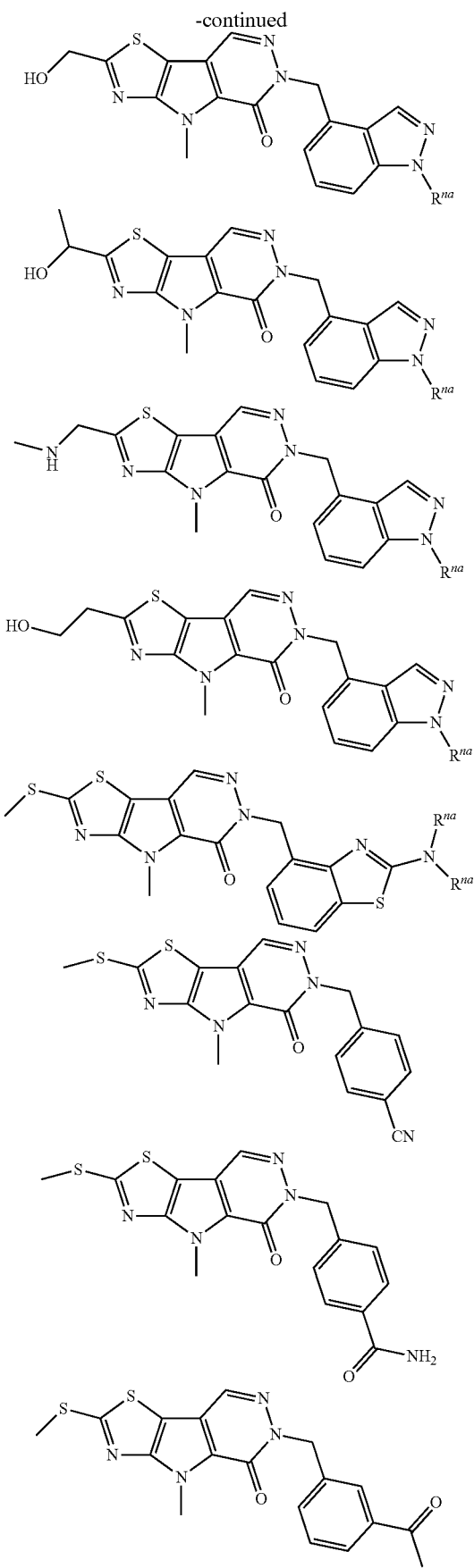
90
-continued
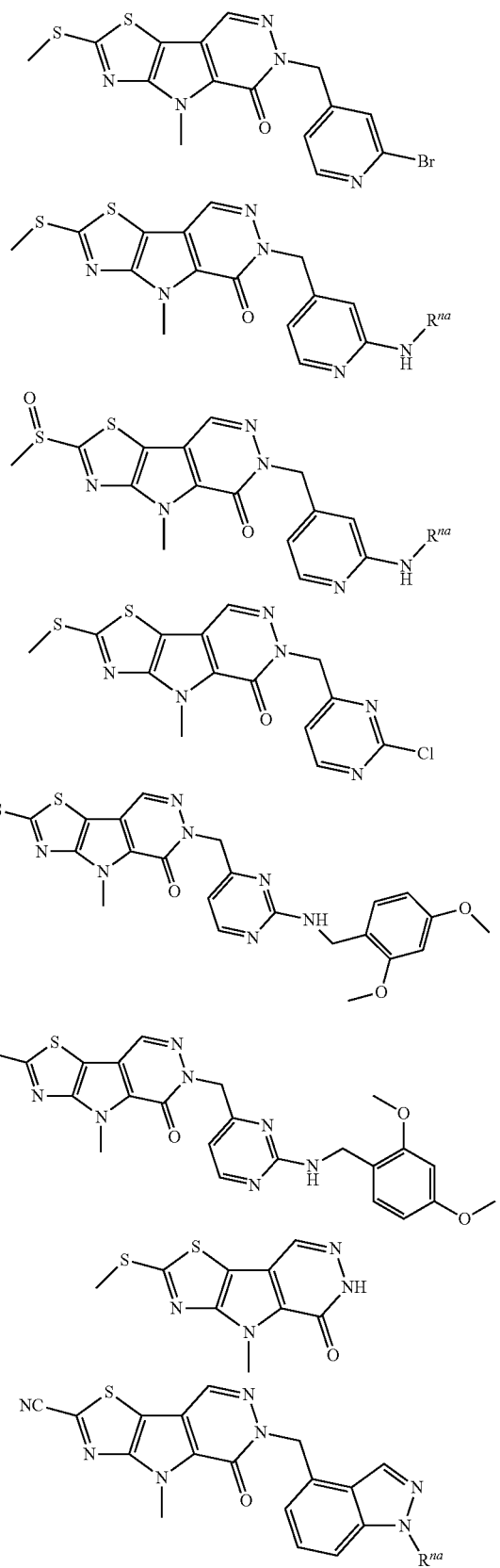

91
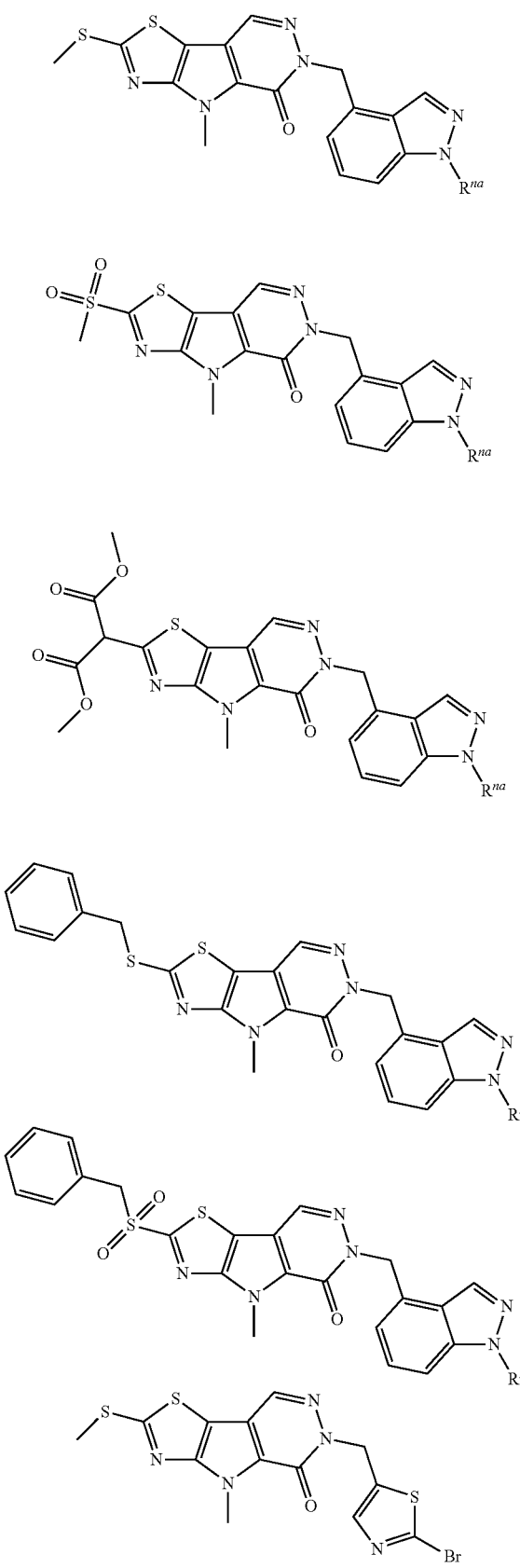
-continued
92
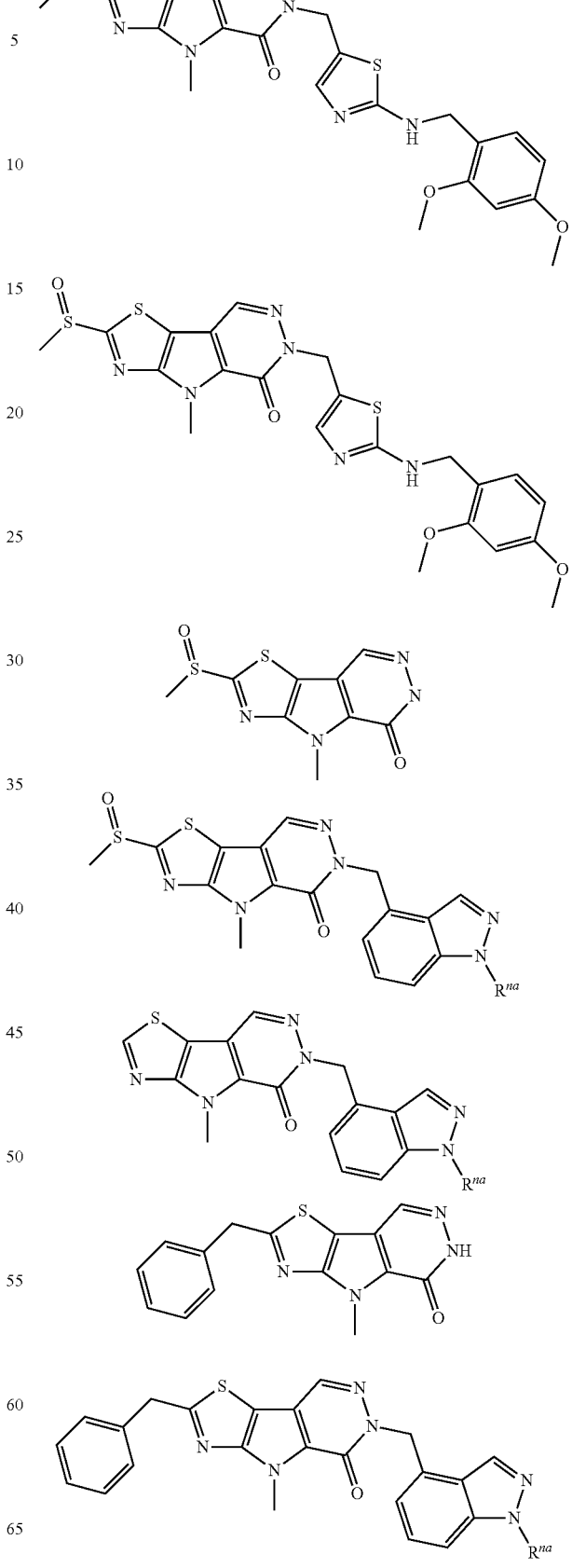
-continued

93
-continued
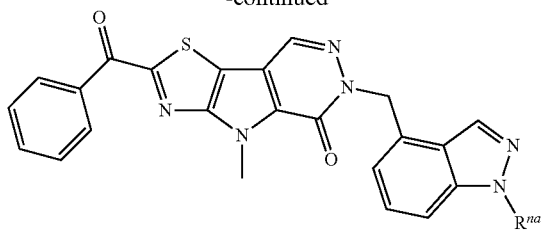
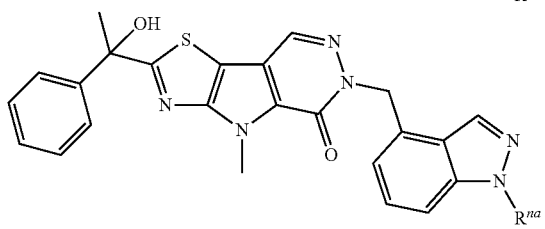
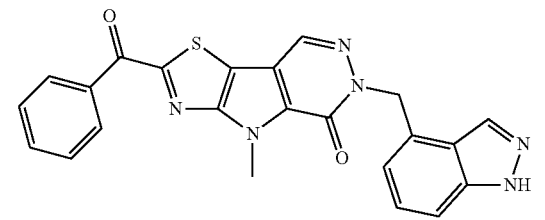
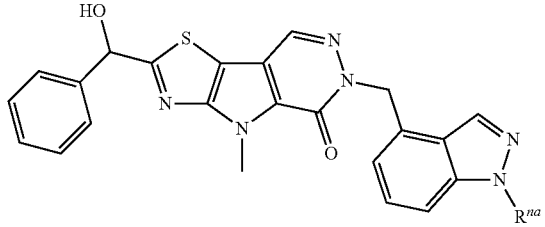
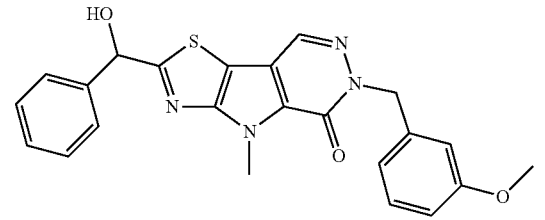
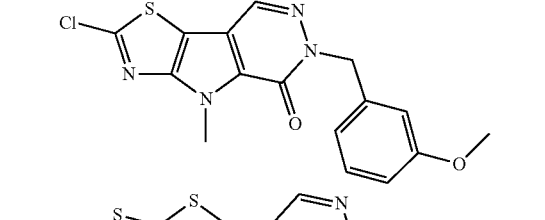
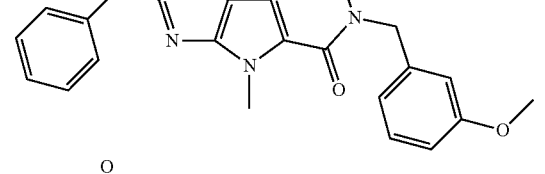
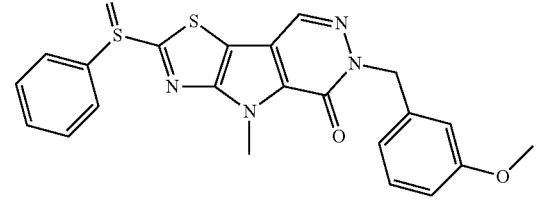
94
-continued
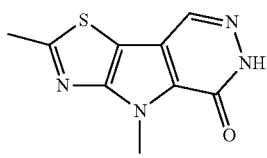
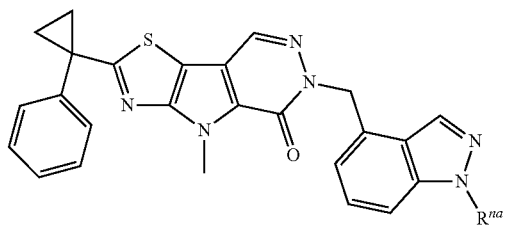
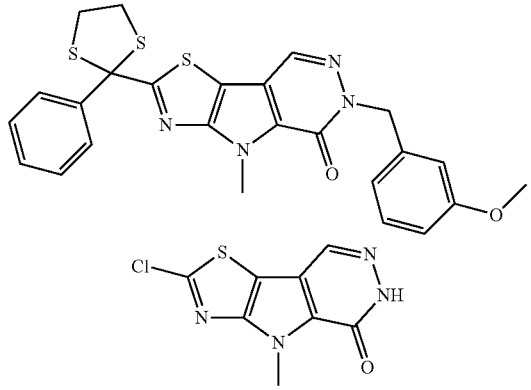
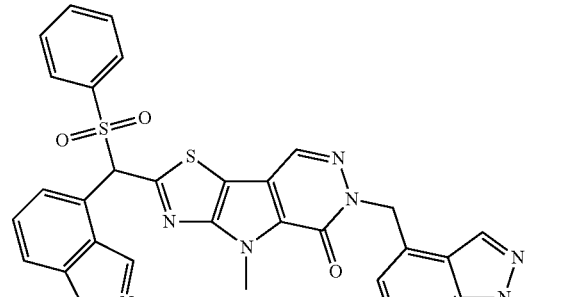
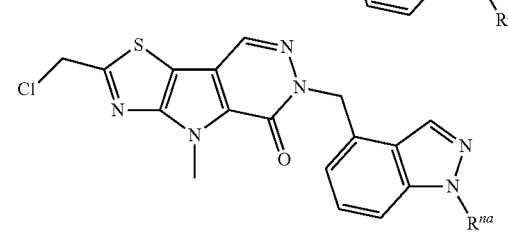

-continued
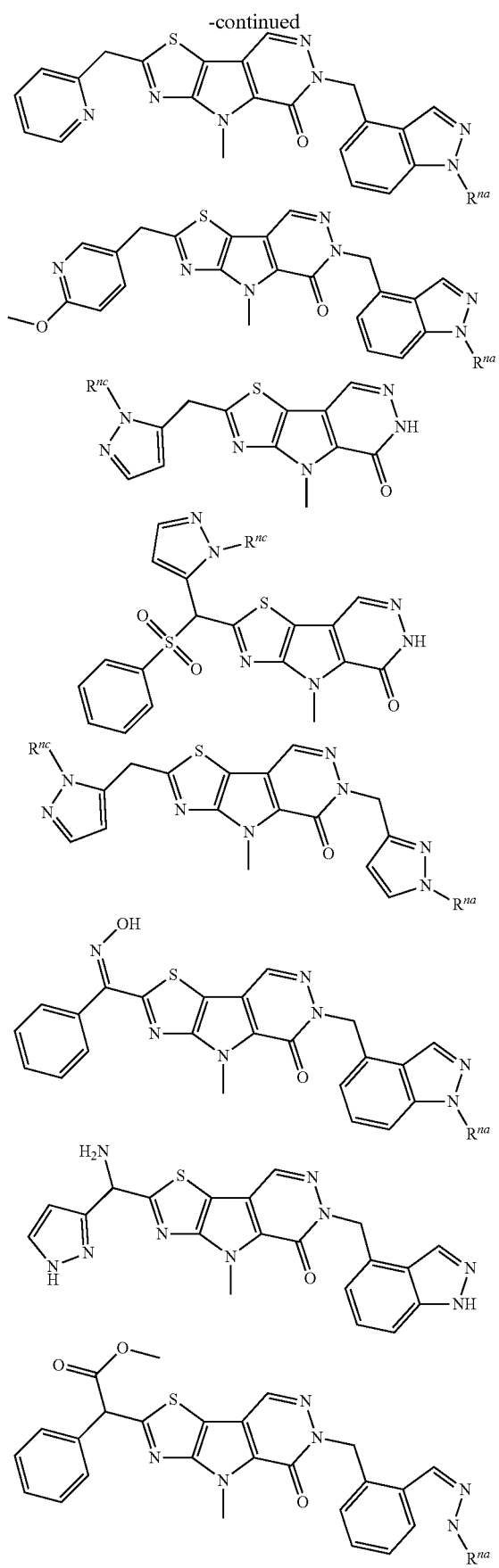
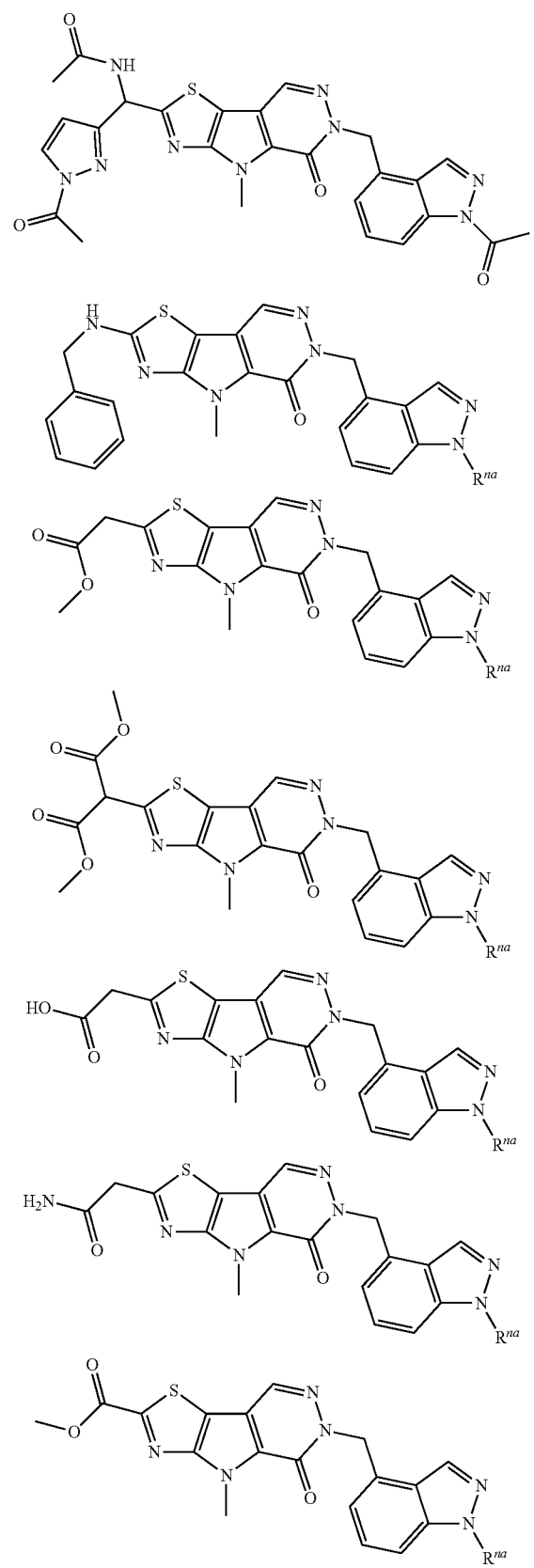

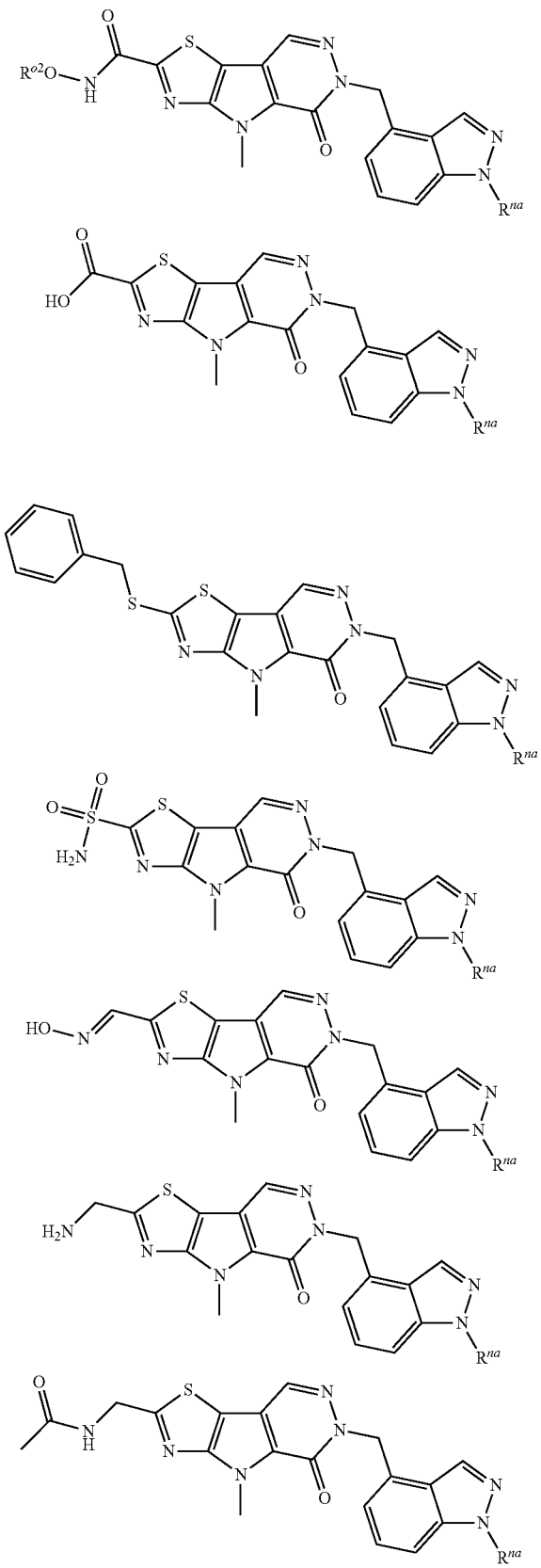

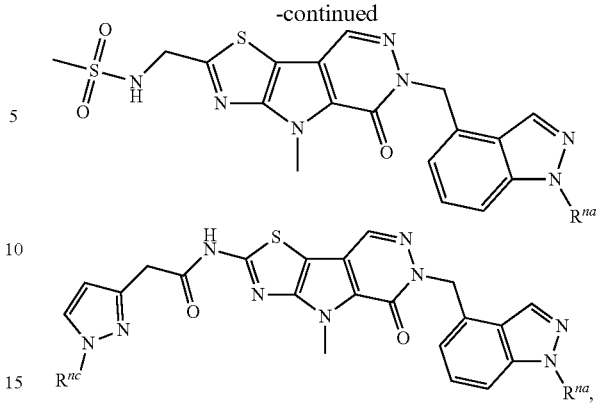

wherein $R^{na}$, $R^{nc}$, $R^{o2}$, and $R^{o6}$ are as defined herein, and $R^{ox}$ is hydrogen or an oxygen protecting group. In certain embodiments, $R^{na}$ is a nitrogen protecting group (e.g. SEM or BOC). In certain embodiments, $R^{nc}$ is a nitrogen protecting group (e.g. SEM or BOC). In certain embodiments, $R^{o2}$ is an oxygen protecting group (e.g. THP). In certain embodiments, $R^{o6}$ is an oxygen protecting group (e.g. TBS). In certain embodiments, $R^{ox}$ is an oxygen protecting group (e.g. THP).

The compounds described herein can be made using a variety of synthetic techniques as set forth in the Examples. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Certain activator compounds useful as PKM2 wild type and/or mutant activators are those that demonstrate specificity and activation of PKM2 enzyme (wild type and/or a mutant enzyme) in the absence of FBP to a level greater than that of 10, 15, 20, 25, 30, 35, 40, 45, 50, 55, 60, 65, 70, 75, 80, 85, 90, 95, 99, or 100% in the presence of FBP.

In some embodiments, compounds of Formula (I) can be prepared using methods illustrated in Scheme 1. Thiazolyl aldehyde of formula S1 reacts with ethyl azidoacetate under nucleophilic addition conditions (e.g. a base) in an appropriate solvent (e.g. ethanol) to give intermediates of formula S2. The hydroxyl group of formula S2 can be converted to a leaving group and subject to elimination to give formula S3. Cyclization and subsequent functionalization of the amino group provides bicyclic compound of formula S5, which undergoes nucleophilic displacement with sodium methanethiolate, followed by oxidation to give formula S7. Further cyclization of formula S7 in the presence of hydrazine, followed by nucleophilic displacement with $LG^1$-$CH_2$-$Q^1$ in the presence of a base provides intermediates of formula S9. The sulfur group in formula S9 can be oxidized to sulfinyl or sulfonyl to provide formula S10 or S11, which is a substrate for further nucleophilic displacement to generate a general formula S12. As used herein, $X^1$ is a leaving group as defined herein. In certain embodiments, $X^1$ is halogen, alkanesulfonyloxy, arenesulfonyloxy, diazonium, alkyl diazenes, aryl diazenes, alkyl triazenes, aryl triazenes, nitro, alkyl nitrate, aryl nitrate, alkyl phosphate, aryl phosphate, alkyl carbonyl oxy, aryl carbonyl oxy, alkoxcarbonyl oxy, aryoxcarbonyl oxy ammonia, alkyl amines, aryl amines, hydroxyl group, alkyloxy group, aryloxy group; $LG^1$ is a leaving group as defined herein; $Q^1$ is optionally substituted cycloalkyl, optionally substituted heterocyclyl, optionally substituted aryl, or optionally substituted heteroaryl; and $Nu^1$ is a nucleophile as defined herein. $Nu^1$ of compound of formula S12 can be further converted to other functionalities with standard chemical transformations. $R^1$ is as defined in the first embodiment.

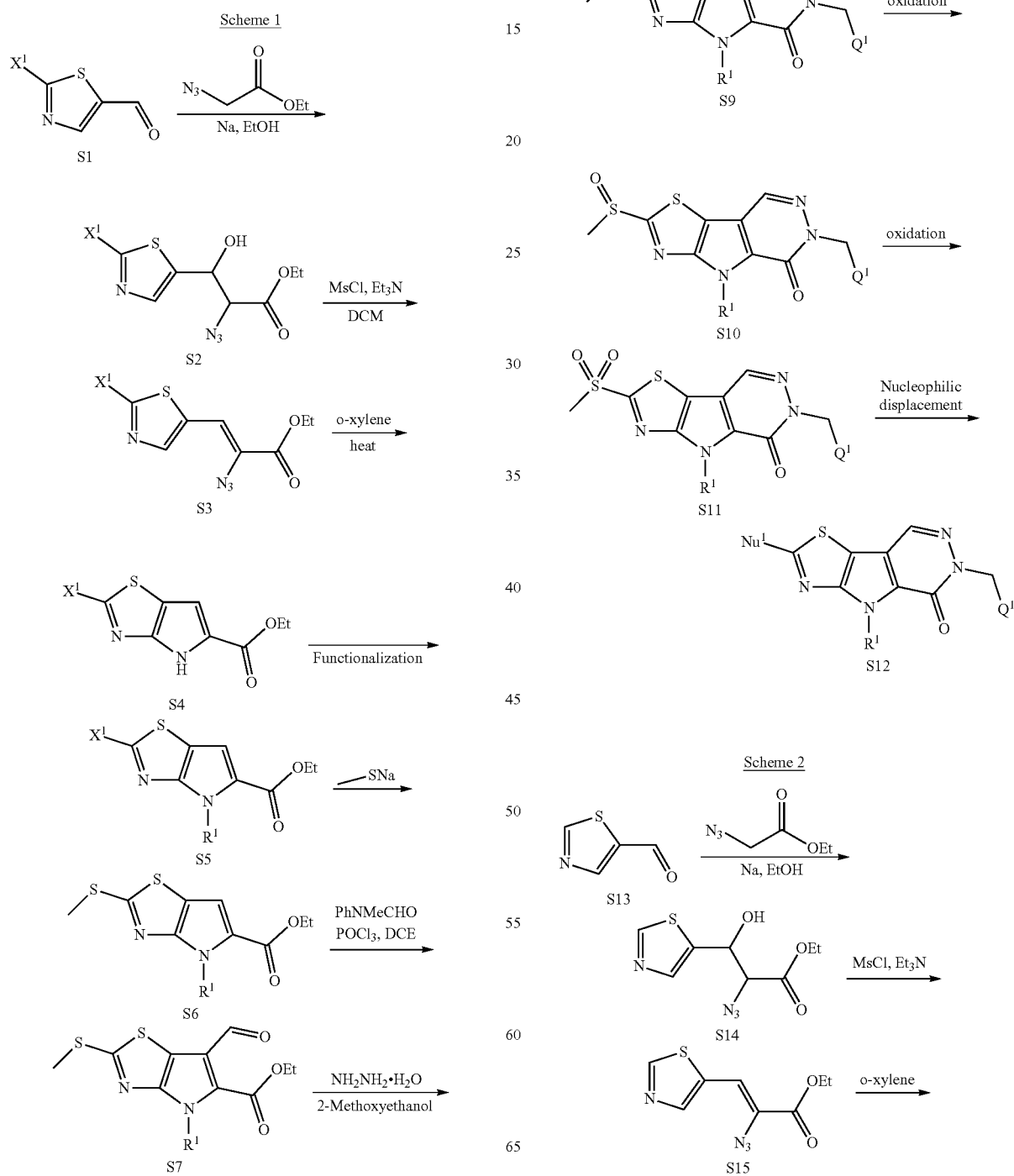

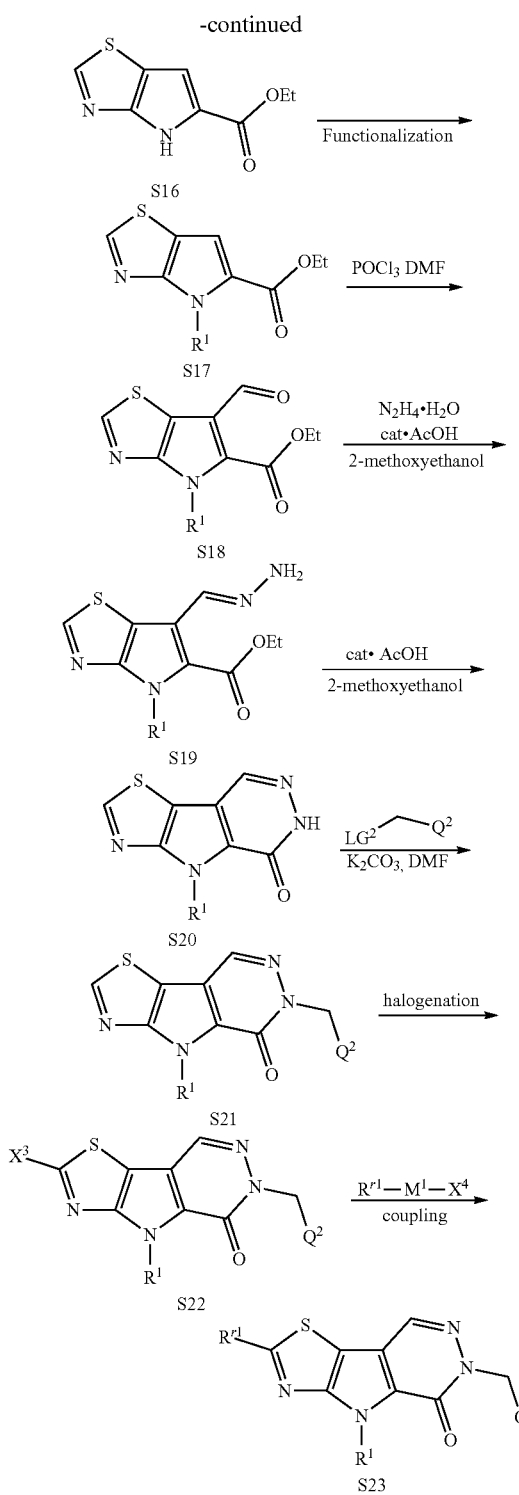

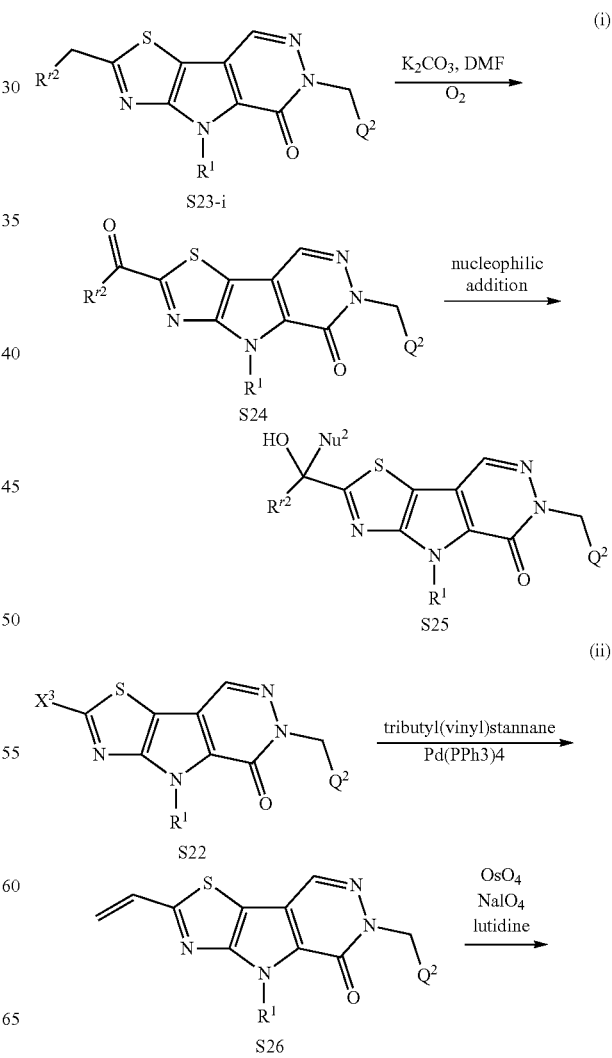

herein; $Q^2$ is optionally substituted cycloalkyl, optionally substituted heterocyclyl, optionally substituted aryl, or optionally substituted heteroaryl; $M^1$ is a metal (e.g. Li, Na, K, Mg, Zn, Sn, B, Pd, Si, Cu etc.), $X^4$ is halogen or alkyl sulfonic acid ester or an aryl sulfonic acid ester; $R^1$ is optionally substituted alkyl, optionally substituted alkenyl, optionally substituted alkynyl, optionally substituted cycloalkyl, optionally substituted heterocyclyl, optionally substituted aryl, or optionally substituted heteroaryl. In certain embodiments, the organo coupling reaction is Negishi reaction; $X^3$ is I; and $M^1$ is Zn.

Compounds of formula S22 and S23 are useful intermediates to introduce more functionalities at $X^3$ and/or $R^{r1}$ position (Scheme 3). In certain embodiments, the compound of formula 23-i can be further oxidized to form formula S24. Nucleophilic addition of S24 with an appropriate nucleophile generates a compound of S25. In another embodiment, compounds of formula S22 can be coupled with vinyl metal to introduce the vinyl group to the thiazole ring. Oxidation of the vinyl group followed by nucleophilic addition provides a compound of formula S28. As used herein, $Nu^2$ is a nucleophile.

In some embodiments, compounds of Formula (I) can be prepared using methods shown in Scheme 2. Similar to Scheme 1, formula S21 can be prepared from thiazole aldehyde of formula S13. Halogenation of formula S21 gives formula S22, which can undergo an organo coupling reaction with an alkyl metal, alkenyl metal, alkynyl metal, aryl metal, heteroaryl metal, heterocyclyl metal, or cycloalkyl metal to give a compound of formula S23. As used herein; $X^3$ is a halogen; $R^1$ is as defined in the first embodiment of the invention; $LG^2$ is a leaving group as defined

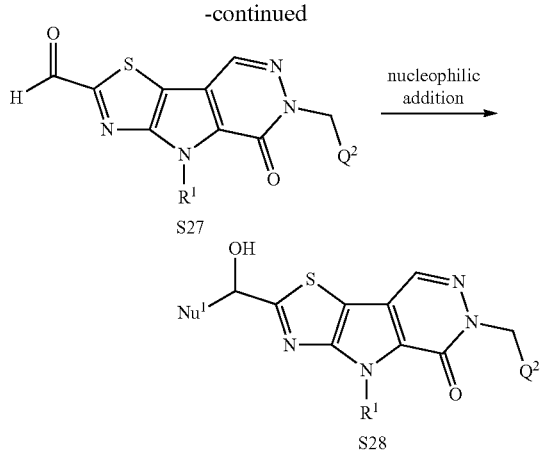

As used herein, $R^{r2}$ is optionally substituted alkyl, optionally substituted alkenyl, optionally substituted alkynyl, optionally substituted cycloalkyl, optionally substituted heterocyclyl, optionally substituted aryl, or optionally substituted heteroaryl. $Nu^1$ and Q2 is as defined in Scheme 2.

As used herein, a nucleophile is a chemical species that donates an electron pair to an electrophile to form a chemical bond in relation to a reaction. All molecules or ions with a free pair of electrons or at least one pi bond can act as nucleophiles. Exemplary nucleophiles comprise at least one group possessing nucleophilic functionality, for example, an alpha carbon (e.g. the carbon adjacent to carbonyl, sulfonyl, sulfinyl, aryl group, or heteroaryl), a thiol group, a hydroxyl group, a primary amine group, a secondary amine group, a halide, cyanide, azide, alcoxide, organic metal, or inorganic base.

In some embodiments, compounds of Formula (I) can be prepared using methods shown in Scheme 4. Nucleophilic displacement of formulae S30 with a secondary cyclic amine provides formulae S31. Organo-coupling reactions (e.g. Suzuki coupling, Pd coupling etc.) of compound S32 provide a compound of formulae S33 (i)-(iii). Further, the sulfinyl group of formula S34 can be functionalized with ammonium carbamate to give imino-sulfanone of formula S35.

Scheme 4

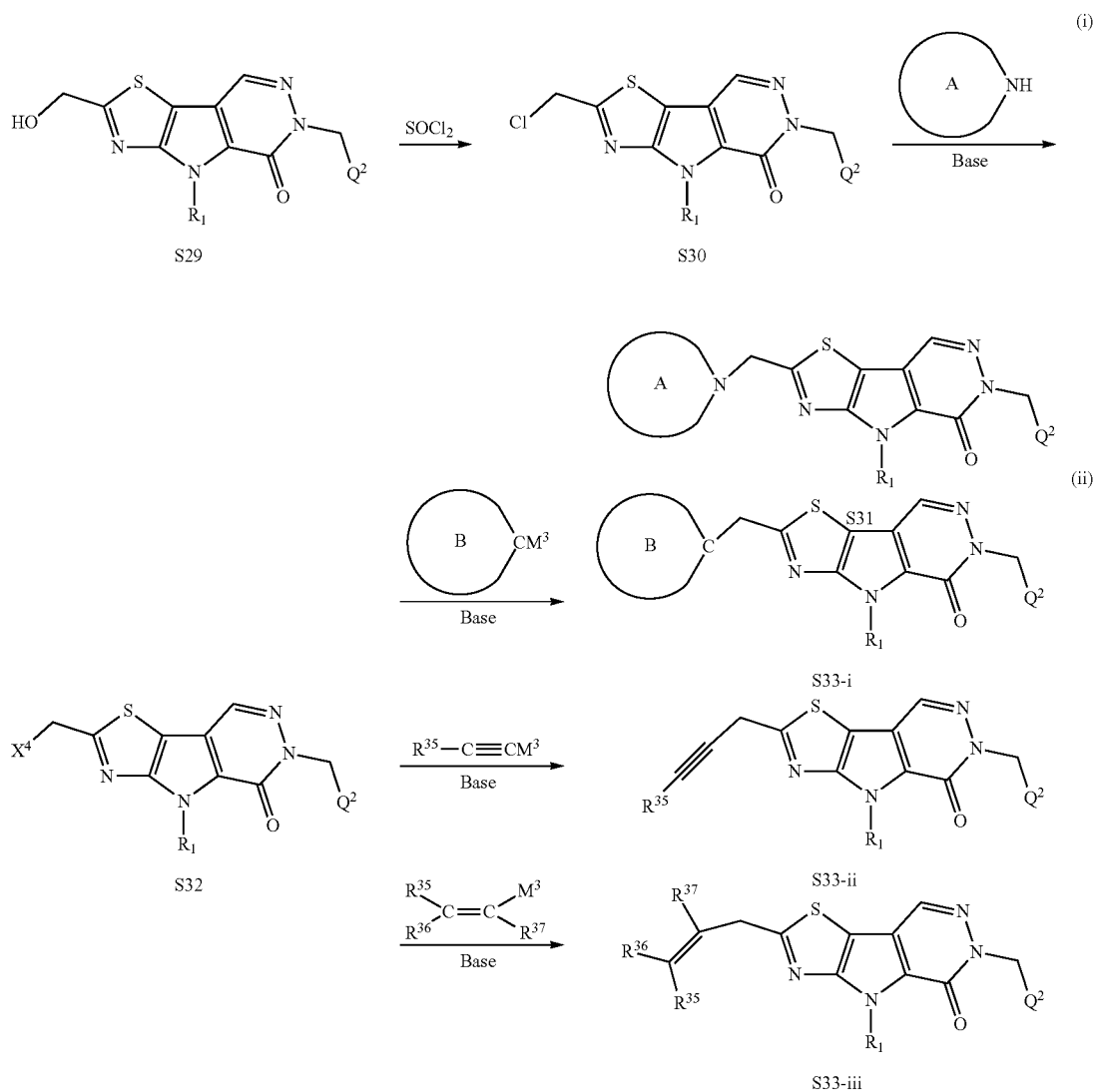

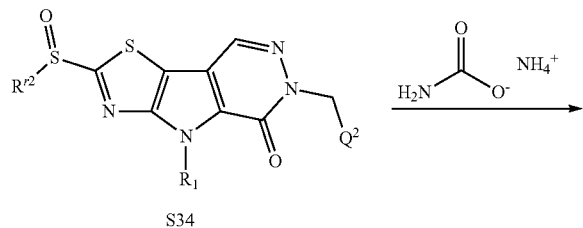

S34

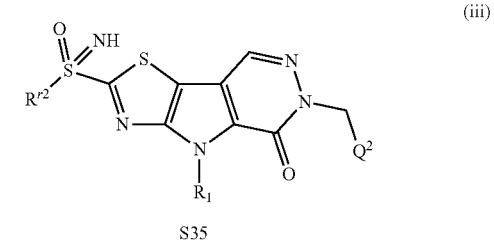

(iii)

S35

As used herein,

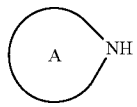

represents Ring A with a nitrogen as a ring atom.

As used herein,

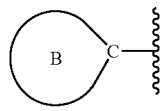

represents Ring B with the point of attachment on the carbon ring atom.

$R^1$ is as defined in the first embodiment. Each instance of $R^{35}$, $R^{36}$, and $R^{37}$ is independently hydrogen, optionally substituted alkyl, optionally substituted alkenyl, optionally substituted alkynyl, optionally substituted aryl, optionally substituted heteroaryl, optionally substituted heterocyclyl, or optionally substituted cycloalkyl.

$X^4$ is halogen or —OTf. $M^4$ is an organic metal with appropriate ligands if needed (organic or inorganic) as valency permits. Exemplified $M^4$ includes, but is not limited to organic Li, Sn, B (e.g. boronic acids and boronic esters), Zn, Mg, Si, Pd, and Cu.

Figure 1B:
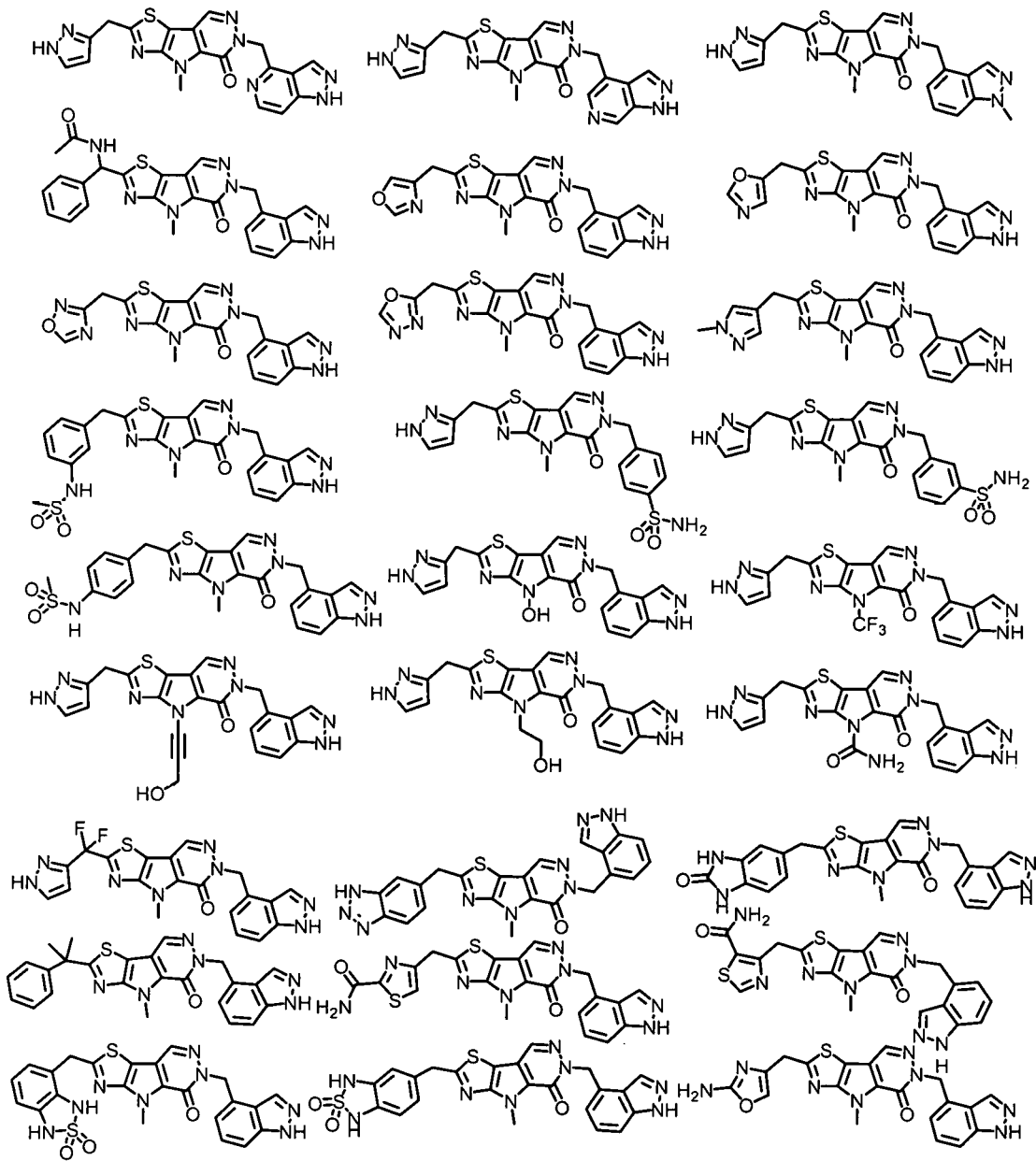
Figure 1C:
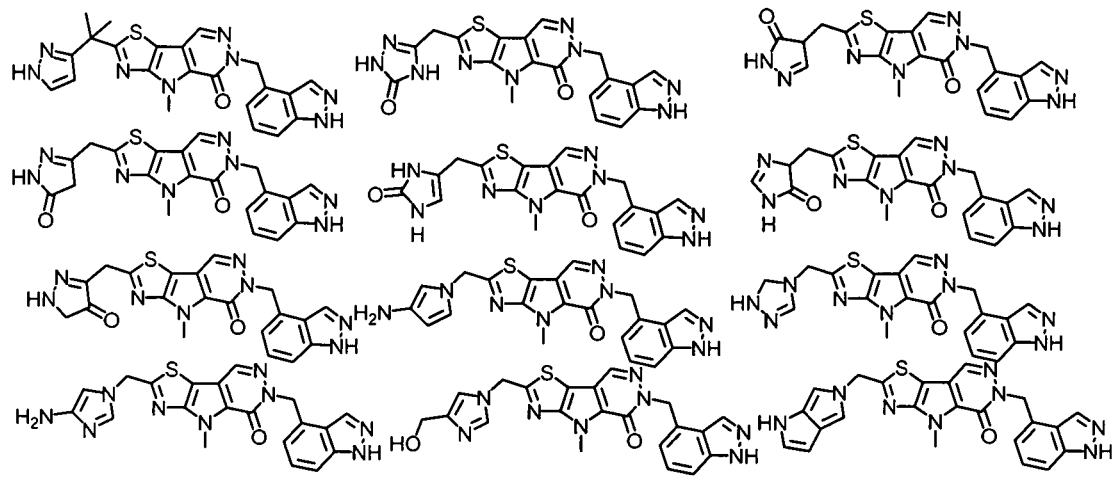
Figure 2A:
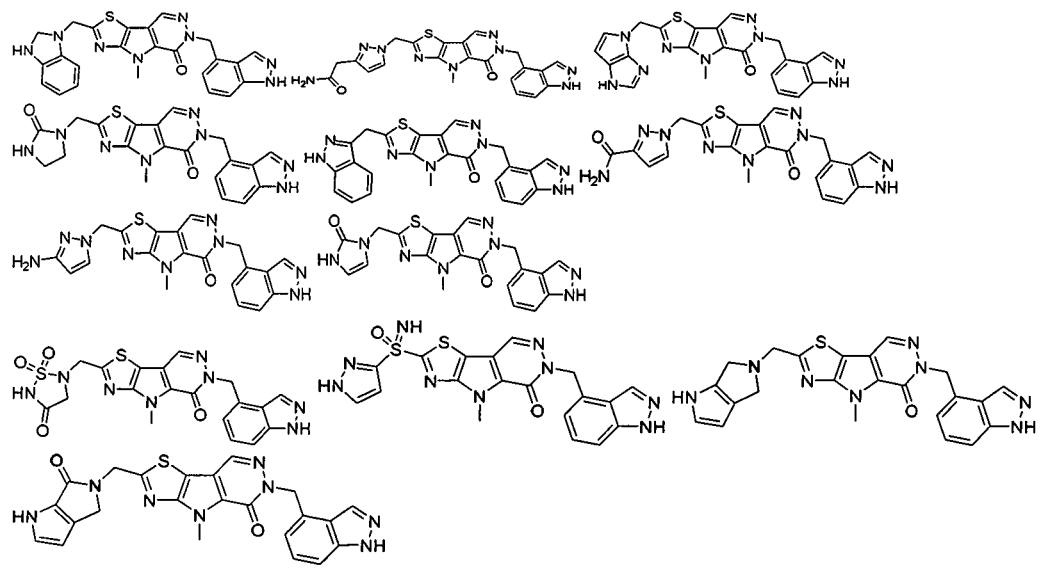
FIGS. 2A-2C are listings of the structures of other exemplary compounds used in the methods of the invention.
Figure 2B:
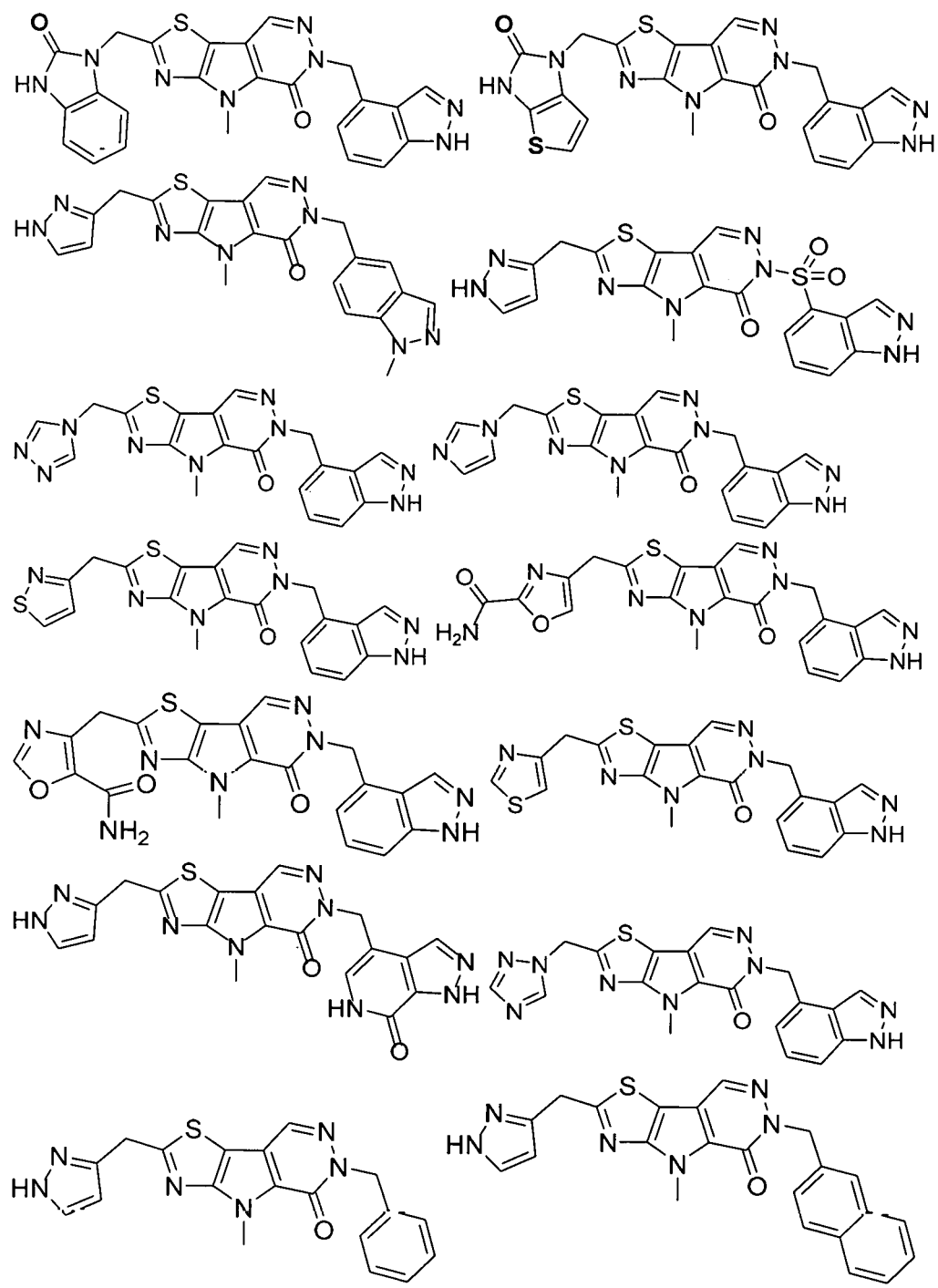
Figure 2C:
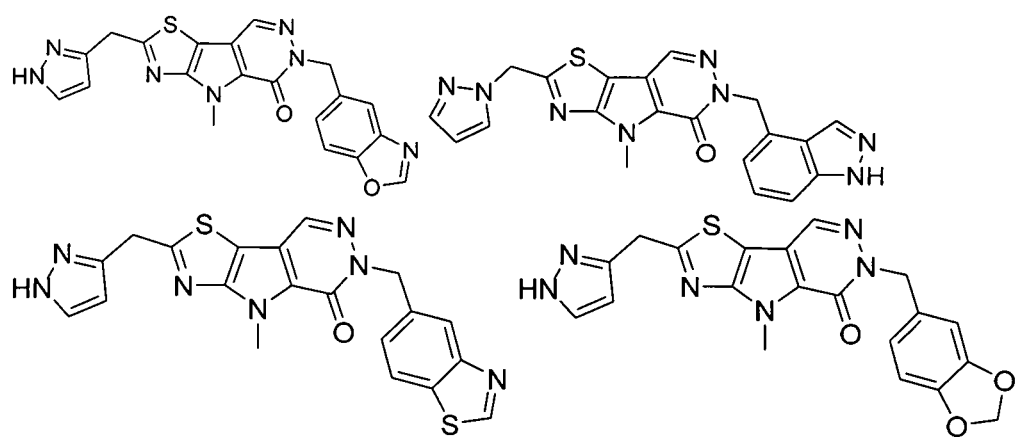
Figure 3:
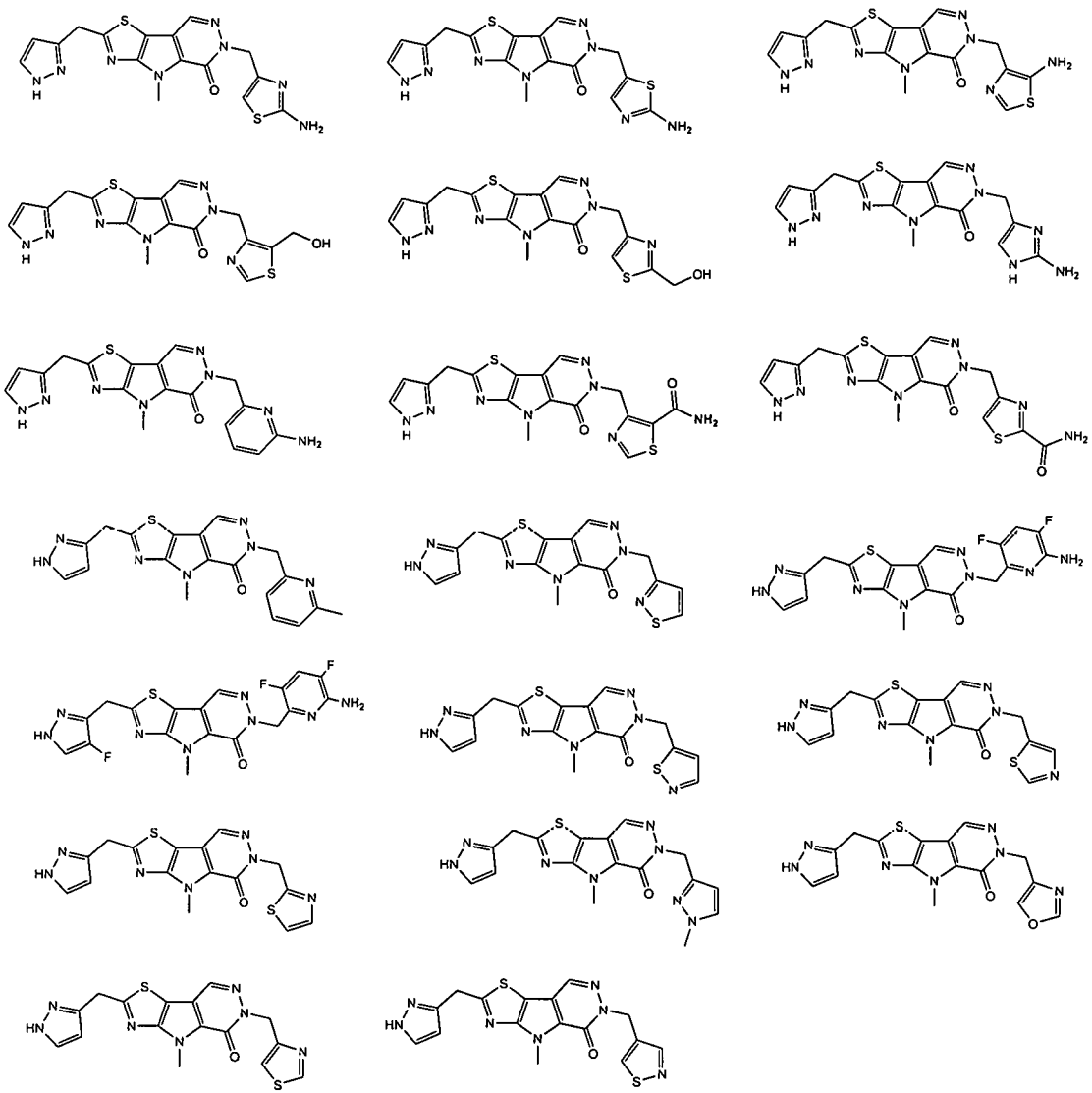
FIG. 3 is a listing of the structures of other exemplary compounds used in the methods of the invention.
Figure 4:
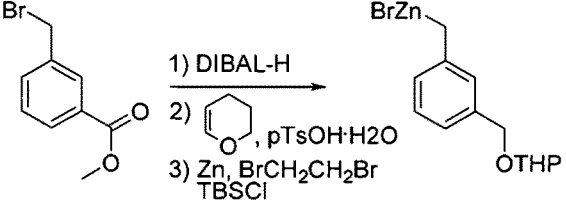
FIG. 4 shows synthesis of exemplary intermediates used in Examples 1-10.

Methods of Treatment In one embodiment, provided is a method for treating a disease, condition or disorder as described herein (e.g., treating) comprising administering a compound, a pharmaceutically acceptable salt of a compound or pharmaceutical composition comprising a compound described herein (e.g., a compound of Formulas (I)-(IX), (I')-(V'), in the Examples, and in Table 1, and FIGS. 1A-1C, 2A-2C, 3).

The compounds and compositions described herein can be administered to cells in culture, e.g. in vitro or ex vivo, or to a subject, e.g., in vivo, to treat, and/or diagnose a variety of disorders, including those described herein below.

Proliferative Disease

In some embodiments, provided is a method of treating a proliferative disease comprising administering to a subject a compound, a pharmaceutically acceptable salt thereof, or pharmaceutical composition thereof, as described herein. As used here, "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases. In certain embodiments, the proliferative diease is cancer. In certain embodiments, the proliferative diease is an autoimmune disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include solid tumors, soft tissue tumors, and metastases thereof. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small. intestine. Other exemplary cancers include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primaiy; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated or prevented in accordance with the methods described herein.

Cancer Combination Therapies

In some embodiments, the provided method further comprises administering one or more additional cancer treatments. Exemplary cancer treatments include, for example: chemotherapy, targeted therapies such as antibody therapies, immunotherapy, and hormonal therapy. Examples of each of these treatments are provided below.

In some embodiments, a compound described herein is administered with one or more chemotherapies. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Satraplatin, Streptozocin, Talaporfin, Tegafur-uracil, Temoporfin, Temozolomide, Teniposide, Tesetaxel, Testolactone, Tetranitrate, Thiotepa, Tiazofurin, Tioguanine, Tipifarnib, Topotecan, Trabectedin, triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

In some embodiments, a compound described herein is administered with one or more targeted therapies. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rittiximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

In some embodiments, a compound described herein is administered with one or more immunotherapies. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

In some embodiments, a compound described herein is administered with one or more hormonal therapies. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Obesity and Fat Disorders

In some embodiments, provided is a method of treating or preventing obesity in a human subject (e.g. a child or adult) by administering to the human subject an effective amount of the compound, pharmaceutically acceptable salt, or pharmaceutical composition thereof as described herein. "Obesity" refers to a condition in which a subject has a body mass index of greater than or equal to 30. Many compounds described herein can be used to treat or prevent an over-weight condition. "Over-weight" refers to a condition in which a subject has a body mass index of greater or equal to 25.0. The body mass index (BMI) and other definitions are according to the "NIH Clinical Guidelines on the Identification and Evaluation, and Treatment of Overweight and Obesity in Adults" (1998). Treatment with the compound may be in an amount effective to alter the weight of the subject, e.g., by at least 2, 5, 7, 10, 12, 15, 20, 25, 30, 25, 40, 45, 50, or 55%. Treatment with a compound may be in an amount effective to reduce the body mass index of the subject, e.g., to less than 30, 28, 27, 25, 22, 20, or 18. The compounds can be used to treat or prevent aberrant or inappropriate weight gain, metabolic rate, or fat deposition, e.g., anorexia, bulimia, obesity, diabetes, or hyperlipidemia (e.g., elevated triglycerides and/or elevated cholesterol), as well as disorders of fat or lipid metabolism.

A compound or composition described herein can be administered to treat obesity associated with Prader-Willi Syndrome (PWS). PWS is a genetic disorder associated with obesity (e.g., morbid obesity).

A compound or composition described herein can be used to reduce body fat, prevent increased body fat, reduce cholesterol (e.g., total cholesterol and/or ratios of total cholesterol to HDL cholesterol), and/or reduce appetite in individuals having PWS associated obesity, and/or reduce comorbidities such as diabetes, cardiovascular disease, and stroke.

Hyperglycemia

High glucose levels induce metabolic abnormalities in glucose metabolic pathways and induce mitochondrial dysfunction. This also overproduces reactive oxygen species (ROS). Elevated intracellular glucose leads to accumulation of the toxic glucose metabolites sorbitol, methylglyoxal (MG) and diacylglycerol (DAG), which have been proposed to contribute to microvascular complication, e.g., DN. Small-molecule PKM2 activators were found to reverse hyperglycemia-induced elevation in toxic glucose metabolites and mitochondrial dysfunction (Nat Med. 2017, 23(6): 753-762; U.S. Pat. No. 9,921,221).

In certain embodiments, provided herein is a method of treating treat hyperglycemia in a subject comprising comprising administering a therapeutic effective amount of the compound, pharmaceutically acceptable salt, or pharmaceutical composition thereof.

In certain embodiments, provided herein is a method of treating a diabetic disease in a subject comprising comprising administering a therapeutic effective amount of the compound, pharmaceutically acceptable salt, or pharmaceutical composition thereof. A "diabetic disease" as used herein refers to diabetes and pre-diabetes as well as diabetic implications. Diabetes refers to a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger). There are several types of diabetes. Type I diabetes results from the body's failure to produce insulin, and presently requires the person to inject insulin or wear an insulin pump. Type II diabetes results from insulin resistance a condition in which cells fail to use insulin properly, sometimes combined with an absolute insulin deficiency. Gestational diabetes occurs when pregnant women without a previous diagnosis of diabetes develop a high blood glucose level. Other forms of diabetes include congenital diabetes, which is due to genetic defects of insulin secretion, cystic fibrosis-related diabetes, steroid diabetes induced by high doses of glucocorticoids, and several forms of monogenic diabetes, e.g., mature onset diabetes of the young (e.g., MODY 1, 2, 3, 4, 5, 6, 7, 8, 9, or 10). Pre-diabetes indicates a condition that occurs when a person's blood glucose levels are higher than normal but not high enough for a diagnosis of diabetes. All forms of diabetes increase the risk of long-term complications. These typically develop after many years, but may be the first symptom in those who have otherwise not received a diagnosis before that time. The major long-term complications relate to damage to blood vessels. Exemplary diabetic implications include cardiovascular disease, macrovascular diseases such as ischemic heart disease (angina, myocardial infarction), stroke, and peripheral vascular disease, microvascular complications (e.g., damage to the small blood vessels), diabetic retinopathy (i.e. the impact of diabetes on blood vessel formation in the retina of the eye), diabetic nephropathy (i.e. the impact of diabetes on the kidneys), diabetic neuropathy (e.g. the impact of diabetes on the nervous system, most commonly causing numbness, tingling and pain in the feet and also increasing the risk of skin damage due to altered sensation), diabetic foot ulcers, and syndrome X. In certain embodiments, a "diabetic disease" includes one or more selected from hyperglycemia, hyperinsulinaemia, diabetes, insulin resistance, impaired glucose metabolism, conditions of impaired glucose tolerance (IGT), conditions of impaired fasting plasma glucose, diabetic retinopathy, diabetic nephropathy, glomerulosclerosis, diabetic neuropathy and syndrome X.

In certain embodiments, the compound or composition described herein can be used to lower the reactive oxygen species (ROS) and/or at least one of the glucose metabolites (e.g. sorbitol, methylglyoxal (MG) and diacylglycerol (DAG)) in a subject.

In certain embodiments, the compound or composition described herein can be used to treat a microvascular complication.

In certain embodiments, the compound or composition described herein can be used to treat DN. In certain embodiments, the treatment of DN can include lessening of any symptom associated with DN, including, but not limited to, changes in appetite, change in sleep, protein in serum, weakness, and/or nausea.

In certain embodiments, the method further comprises administering to the subject a therapeutically effective amount of one or more secondary agents that increase the level or activity of one or more of the DN protective factors. Exemplary DN protective factors include, but are not limited to SOD1-Superoxide dismutase; TPI1—Triosephosphate isomerase isoform 2; SORD—Sorbitol dehydrogenase; ALDOA—Aldolase A, fructose-bisphosphate; GAPDH—Glyceraldehyde-3-phosphate dehydrogenase; PKM—Pyruvate kinase isozymes M1/M2; ENO1—Alpha-enolase; FGB—Fibrinogen beta chain; SELENBP1—Selenium binding protein 1; PEBP1—Phosphatidylethanolamine-binding protein 1; CRYL1—Lambda-crystallin homolog (U.S. Pat. No. 9,921,221, which is incorporated by reference on its entirety). A secondary agent may increase the level or activity of a protective factor or decrease the level or activity of a risk factor by at least 50%, 100% (1-fold), 1'/2-fold, 2-fold, 3-fold, 4-fold, 5-fold, 10-fold, 15-fold, 20-fold or more. In certain embodiments, the provided method comprises bringing the level or activity of a protective factor essentially to its level or activity in a subject that is protected from the development of a microvascular complication. "Essentially within its level," refers to within less than 5%, 10%, 20%, 30%, 40%, 50%, 60%, 70%, 80%, 90% or 100% of the control value. The secondary agent may be a small molecule, a protein comprising the protective factor or a biologically active variant (e.g., fragment) thereof, or a nucleic acid encoding a protein comprising the protective factor or a biologically active variant (e.g., fragment) thereof. Biologically active variants of the proteins of protective factors also include full length immature and mature forms or fragments thereof that comprise an amino acid sequence that differs from the naturally occurring sequence or fragment thereof in at most 1, 2, 3, 4, 5, 10, 15, 20, 25, 30, 35, 40, 45, 50 or 100 amino acid deletions, additions or substitutions, such as conservative amino acid substitutions.

Biologically active variants of the proteins of the DN protective factors may also include variants that are at least 70%, 80%, 85%, 90%, 95%, 97%, 98% or 99% identical to the full length mature or precursor human PEBP1 protein (or other biomarker identified in this specification) or a fragment thereof.

In some embodiments, the method provided further comprises selecting a subject for treatment. For example, a subject can be selected if the subject has or is at risk for developing DN, e.g., a subject having diabetes, e.g., type 1 or type 2 diabetes, or a subject who is prediabetic, e.g., having metabolic syndrome, insulin resistance, hyperglycemia, hyperlipidemia or a subject who is overweight or obese, e.g., having a BMI≥25. In some instances, a subject can be selected if the subject has or is at risk for developing type 1 and/or type 2 diabetes. In some instances, a subject can be selected if the subject is taking or will take insulin, e.g., to treat diabetes.

Cardiovascular disease is a chronic inflammatory condition. Increased glucose uptake and glycolytic flux promotes reactive oxygen species in mitochondria. ROS promotes dimerization of PKM2 and enable its nuclear translocation. Nuclear PKM2 functions as protein kinase and boosts IL-6 and IL-1β production. This results in systemic and tissue inflammation. Reducing glycolysis and enforcing PKM2 tetramerization was found to correct proinflammatory phenotype of coronary artery disease (CAD) macrophages (J. Exp. Med. 2016, 213(3): 337-354).

In certain embodiments, provided herein is a method of treating a cardiovascular disease in a subject comprising administering a therapeutic effective amount of the compound, pharmaceutically acceptable salt, or pharmaceutical composition thereof. The compounds or composition described herein can lower the plasma glucose level in a subject. A "cardiovascular disease" as defined in this application comprises, but is not limited to hypertension, congestive heart failure, diabetes, glomerulosclerosis, chronic renal failure, coronary heart disease, angina pectoris, myocardial infarction, stroke, vascular restenosis endothelial dysfunction, impaired vascular compliance and congestive heart failure. In certain embodiments, the cardiovascular disease is coronary artery disease (CAD). In certain embodiments, the compound or composition described herein can be used to lower the reactive oxygen species (ROS) in mitochondria in a subject.

In certain embodiments, provided herein is a method of treating an autoimmune disease in a subject comprising comprising administering a therapeutic effective amount of the compound, pharmaceutically acceptable salt, or pharmaceutical composition thereof. It was found that activation of PKM2 attenuated an LPS-induced proinflammatory M1 macrophage phenotype while promoting traits typical of an M2 macrophage. Additionally, it was found activation of PKM2 by TEPP-46 in vivo inhibited LPS and IL-1β production, whilst boosting production of IL-10. (Cell Metab. 2015, 21(1): 65-80) Accordingly, PKM2 activators can be useful to treat an autoimmune disease by promoting IL-1β and/or IL-10 production.

An "autoimmune disease" refers to a disease arising from an inappropriate immune response of the body of a subject against substances and tissues normally present in the body. Exemplary autoimmune diseases include, but are not limited to, glomerulonephritis, Goodpasture's syndrome, necrotizing vasculitis, lymphadenitis, peri-arteritis *nodosa*, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

EXPERIMENTAL

Abbreviations List:

| abbrv. | Full Name | abbrv. | Full Name |
| --- | --- | --- | --- |
| anhy. | anhydrous | aq. | aqueous |
| min | minute(s) | satd. | saturated |
| mL | milliliter | hrs | hours |
| mmol | millimole(s) | mol | mole(s) |
| MS | mass spectrometry | NMR | nuclear magnetic resonance |
| TLC | thin layer chromatography | HPLC | high-performance liquid chromatography |
| LCMS | Liquid chromatography-mass spectrometry | CMBP | Cyanomethylenetributylphosphorane |
| DAST | Diethylaminosulfurtrifluoride | $CHCl_3$ | chloroform |
| DCM | dichloromethane | DMF | dimethylformamide |
| Et2O | diethyl ether | EtOH | ethyl alcohol |
| EtOAc | ethyl acetate | MeOH | methyl alcohol |
| MeCN | acetonitrile | PE | petroleum ether |
| THF | tetrahydrofuran | DMSO | dimethyl sulfoxide |
| AcOH | acetic acid | HCl | hydrochloric acid |
| $H_2SO_4$ | sulfuric acid | $NH_4Cl$ | ammonium chloride |
| KOH | potassium hydroxide | NaOH | sodium hydroxide |
| $K_2CO_3$ | potassium carbonate | $Na_2CO_3$ | sodium carbonate |
| TFA | trifluoroacetic acid | $Na_2SO_4$ | sodium sulfate |
| $NaBH_4$ | sodium borohydride | $NaHCO_3$ | sodium bicarbonate |
| LiHMDS | lithium hexamethyldisilylamide | $NaBH_4$ | sodium borohydride |
| TEA | Triethylamine | Py or Pyr | pyridine |
| DMAP | 4-(dimethylamino)pyridine | DIPEA | N,N-diisopropylethylamine |
| BINAP | 2,2'bis(diphenylphosphanyl)-1,1'-binaphthyl | dppf | 1,1'-bis(diphenylphosphino)ferrocene |
| PEP | Phospho(enol)pyruvic acid | LDH | Lactate Dehydrogenase |
| DTT | DL-Dithiothreitol | BSA | Bovine serum Albumin |
| NADH | β-Nicotinamide adenine dinucleotide, reduced | SEM | 2-(Trimethylsilyl)ethoxymethyl |
| p-TsOH | p-Toluenesulfonic acid | DCE | 1,2-dichloroethane |
| MTBE | Methyl tert-butyl ether | | |

General Experimental

In the following examples, the chemical reagents were purchased from commercial sources (such as Alfa, Acros, Sigma Aldrich, TCI and Shanghai Chemical Reagent Company), and used without further purification. Flash chromatography was performed on an Ez Purifier III via column with silica gel particles of 200-300 esh. Analytical and preparative thin layer chromatography plates (TLC) were HSGF 254 (0.15-0.2 mm thickness, Shanghai Anbang Company, China). Nuclear magnetic resonance (NMR) spectra were recorded using Brucker AMX-300 or AMX-400 NMR (Brucker, Switzerland). Chemical shifts were reported in parts per million (ppm, δ) etero (ESI) from a Waters LCT TOF Mass Spectrometer (Waters, USA). HPLC chromatographs were recorded on Agilent 1200 Liquid Chromatography (Agilent, USA, column: Ultimate 4.6 m×50 mm, 5 M, mobile phase A: 0.1% formic acid in water; mobile phase B: acetonitrile). Microwave reactions were run on an Initiator 2.5 Microwave Synthesizer (Biotage, Sweden).

HPLC conditions used in the experiments described herein are as follows:

Method 1:
Instrument: Shimadzu LC-2010AHT
Column: YMC-Triart C18, 50×4.6 mm, 5 μm
Mobilephase: Solvent A:$H_2O$/$CH_3OH$/TFA=90/10/0.1,
  Solvent B: $H_2O$/$CH_3OH$/TFA=90/10/0.1
Flow rate: 2.5 mL/min
Column temperature: 35° C.
Wavelength: 220 nm/254 nm Method 2:
Instrument: Shimadzu LC-2010AHT
Column: YMC-Triart C18, 50×4.6 mm, 5 μm
Mobilephase: Solvent A:$H_2O$/$CH_3OH$/TFA=90/10/0.1,
  Solvent B: $H_2O$/$CH_3OH$/TFA=90/10/0.1
Flow rate: 2.5 mL/min
Column temperature: 35° C.
Wavelength: 220 nm/254 nm Prep-HPLC conditions used in the experiments described herein are as follows:
Instrument: Waters 2545B/2767
Column: YMC-Triart C18, 50×4.6 mm, 5 μm
Mobilephase: Solvent A:$H_2O$ (01.% FA),
  Solvent B: $CH_3OH$ or $CH_3CN$
Flow rate: 20 mL/min
Column temperature: 35° C.
Wavelength: 220 nm/254 nm

Example 1. Preparation of Compounds E1-vii with Scheme E1

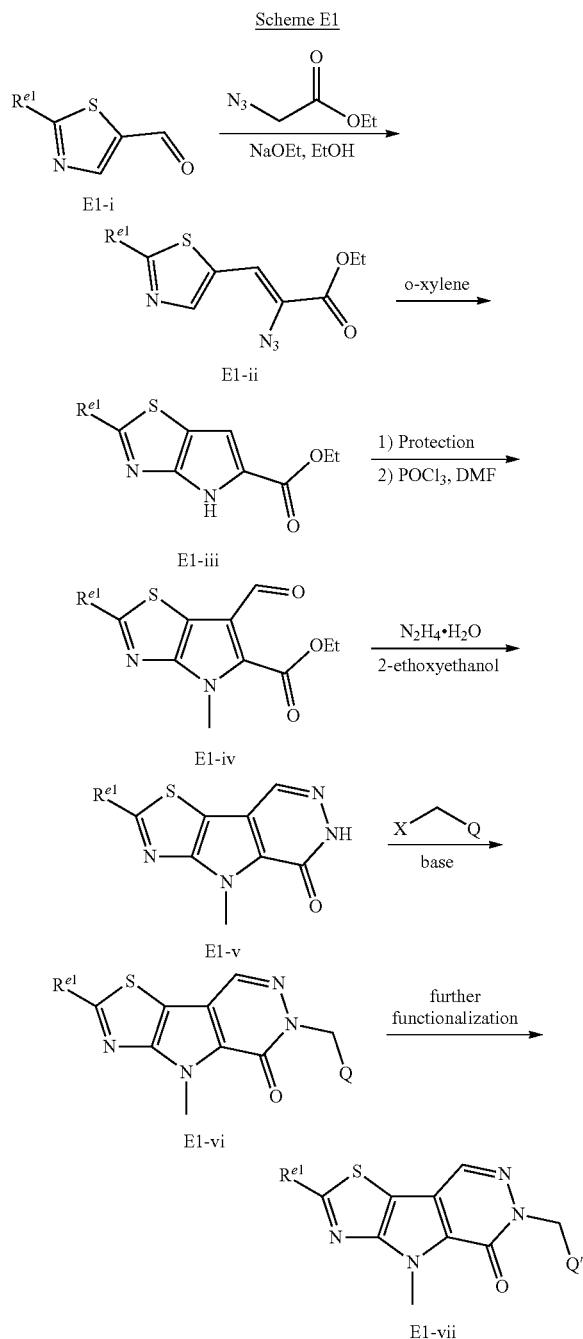

wherein $R^{e1}$ is optionally substituted alkyl (e.g. $C_{1-3}$ alkyl); Q is as defined in any one of the first to twenty-sixth embodiments of the invention; Q' is a further functionalized Q, and X is a leaving group (e.g. halogen such as Br or I; OMs; or OTs). Thiazole 5-carbaldehyde E1-i undergoes condensation with 2-azidoacetate to give a compound of Formula E1-ii. Compound E1-ii undergoes cyclization in heated o-xylene to give a bicyclic system of E1-iii, followed by methylation of the amino group and subsequent oxidation to give a compound E1-iv. Compound E1-iv reacts with hydrazine followed by cyclization to give a compound of E1-v. Compound E1-v can react with a nucleophile such as X—$CH_2$-Q to give E1-vi, which can be further functionalized to E1-vii having Q'.

Example 1A. Synthesis of 6-(3-methoxybenzyl)-2,4-dimethyl-4,6-dihydro-5H-thiazolo[5',4':4,5]pyrrolo[2,3-d]pyridazin-5-one

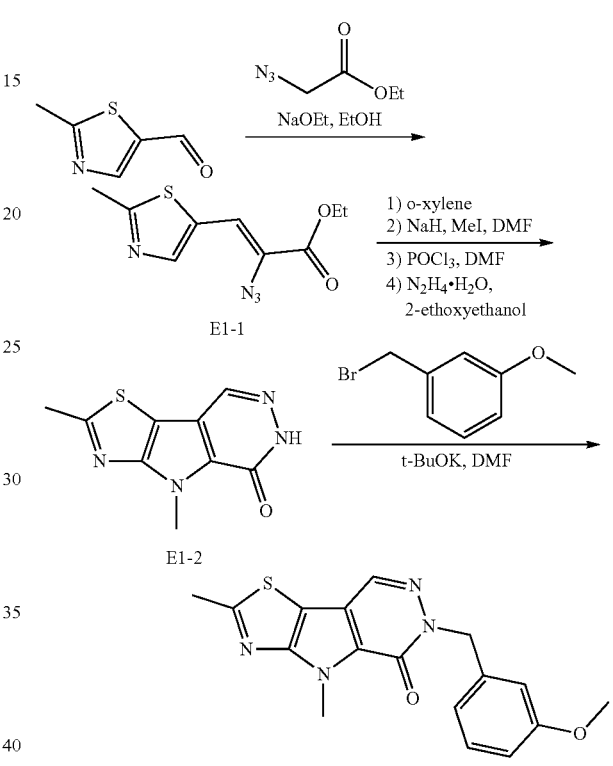

Step A. Ethyl (Z)-2-azido-3-(2-methylthiazol-5-yl)acrylate

To a solution of NaOEt (803 mg, 11.79 mmol) in EtOH (10 mL) between about −10° C. and about −5° C. was added drop wise a solution of 2-methylthiazole-5-carbaldehyde (500 mg, 3.93 mmol) and ethyl 2-azidoacetate (1.53 g, 11.79 mmol) in anhydrous EtOH (3 mL). The reaction mixture was stirred for about 1 hr. while the temperature maintained below 0° C., then warmed to r.t. and stirred for another 2 hr. The resulting mixture was poured into saturated aqueous $NH_4Cl$ (50 mL) at 0° C. and extracted with EtOAc. The combined organic layers were washed with brine, dried over anhydrous $Na_2SO_4$ and concentrated under reduced pressure to give the desired product (500 mg) which was directly used in the next step without any purification. LCMS: m/z 239 $(M+H)^+$.

Step B. Ethyl 2-methyl-4H-pyrrolo[2,3-d]thiazole-5-carboxylate

A mixture of ethyl (Z)-2-azido-3-(2-methylthiazol-5-yl)acrylate (500 mg, 2.1 mmol) in o-xylene (5 mL) was stirred at 140° C. for 2 hr. then cooled down to r.t. and then directly purified by column chromatography on silica gel (eluent: pentane/EtOAc=6/1 to give the desired product (220 mg, 49.8% yield). LCMS: m/z 211 (M+H)+.

Step C. Ethyl 2,4-dimethyl-4H-pyrrolo[2,3-d]thiazole-5-carboxylate

To a solution of ethyl 2-methyl-4H-pyrrolo[2,3-d]thiazole-5-carboxylate (160 mg, 0.76 mmol) in DMF (3 mL) at 0° C. was added NaH (36.5 mg, 1.52 mmol). The reaction mixture was stirred at r.t. for 0.5 hr., followed by addition of $CH_3I$ (47 μL, 0.76 mmol). The resulting mixture was stirred at r.t for 0.5 hr. then poured into saturated aqueous $NH_4Cl$ at 0° C. and extracted with EtOAc. The combined organic layers were washed with brine, dried over anhydrous $Na_2SO_4$ and concentrated under reduced pressure. The residue was purified by column chromatography on silica gel (eluent: pentane/ethyl acetate=6/1) to give the desired product (124 mg, 72.6% yield). LCMS: m/z 225 (M+H)+.

Step D. Ethyl 6-formyl-2,4-dimethyl-4H-pyrrolo[2,3-d]thiazole-5-carboxylate

To a mixture of ethyl 2,4-dimethyl-4H-pyrrolo[2,3-d]thiazole-5-carboxylate (100 mg, 0.446 mmol) in DMF (1 mL)) at 0° C. was added $POCl_3$ (122.5 μL, 1.338 mmol). The reaction mixture was stirred at 100° C. for 2 hr. then poured into saturated aqueous $NaHCO_3$ at 0° C. and extracted with EtOAc. The combined organic layers were washed with brine, dried over anhydrous $Na_2SO_4$ and concentrated under reduced pressure. The residue was purified by column chromatography on silica gel (eluent: pentane/ethyl acetate=5/1) to give the desired product (57 mg, 50.7% yield). LCMS: m/z 253 (M+H)+.

Step E. 2,4-Dimethyl-4,6-dihydro-5H-thiazolo[5,4': 4,5]pyrrolo[2,3-d]pyridazin-5-one To a mixture of ethyl 6-formyl-2,4-dimethyl-4H-pyrrolo[2,3-d]thiazole-5-carboxylate (57 mg, 0.226 mmol) in 2-ethoxyethanol (2 mL) was added $N_2H_4 \cdot H_2O$ (53.7 μL, 1.130 mmol). The reaction mixture was stirred at 100° C. for 1 hr. then poured into $H_2O$ and extracted with EtOAc. The combined organic layers were washed with brine, dried over anhydrous $Na_2SO_4$ and concentrated under reduced pressure. The residue was purified by column chromatography on silica gel (eluent: pentane/ethyl acetate=5/1) to give the desired product (49 mg, 98.4% yield). LCMS: m/z 221 (M+H)+.

Step F. 6-(3-Methoxybenzyl)-2,4-dimethyl-4,6-dihydro-5H-thiazolo[5',4':4,5]pyrrolo[2,3-d]pyridazin-5-one To a mixture of 2,4-dimethyl-4,6-dihydro-5H-thiazolo[5',4':4,5]pyrrolo[2,3-d]pyridazin-5-one (49 mg, 0.223 mmol) in DMF (1 mL) at 0° C. was added t-BuOK (50.8 mg, 0.454 mmol). The reaction mixture was stirred at r.t. for 0.5 hr., followed by addition of 1-(chloromethyl)-3-methoxybenzene (34.9 mg, 0.223 mmol). The resulting mixture was stirred at r.t. for 1 hr. then poured into saturated aqueous $NH_4Cl$ solution at 0° C. and extracted with EtOAc. The combined organic layers were washed with brine, dried over anhydrous $Na_2SO_4$ and concentrated under reduced pressure. The residue was purified by column chromatography on silica gel (eluent: pentane/ethyl acetate=3/1) to give the desired product. LCMS: m/z 341 (M+H)+. $^1$H NMR (400 MHz, DMSO-$d_6$) δ 8.56 (s, 1H), 7.23 (t, 1H), 6.92-6.72 (m, 3H), 5.32 (s, 2H), 4.26 (s, 3H), 3.72 (s, 3H), 2.85 (s, 3H).

The procedure set forth above was used to produce the following compounds using the appropriate starting materials. Standard protection and deprotection can be used when necessary.

| Cpd No. | Structure | Characterization |
|---|---|---|
| E1-4 | 6-(4-Methoxybenzyl)-2,4-dimethyl-4,6-dihydro-5H-thiazolo[5',4':4,5]pyrrolo[2,3-d]pyridazin-5-one | LC-MS: 341 (M + H)+. $^1$H NMR (400 MHz, DMSO-$d_6$) δ 8.54 (s, 1H), 7.29 (d, 2H), 6.88 (d, 2H), 5.27 (s, 2H), 4.26 (s, 3H), 3.72 (s, 3H), 2.85 (s, 3H). |
| E1-5 | 6-(4-Fluorobenzyl)-2,4-dimethyl-4H-thiazolo[5',4':4,5]pyrrolo[2,3-d]pyridazin-5(6H)-one | LCMS: m/z 329 (M + H)+. $^1$H NMR (400 MHz, DMSO-$d_6$) δ 8.56 (s, 1H), 7.38 (dd, 2H), 7.15 (t, 2H), 5.33 (s, 2H), 4.25 (s, 3H), 2.85 (s, 3H). |

| Cpd No. | Structure | Characterization |
|---|---|---|
| E1-6 | 6-(3-Fluorobenzyl)-2,4-dimethyl-4H-thiazolo[5',4':4,5]pyrrolo[2,3-d]pyridazin-5(6H)-one | LCMS: m/z 329 (M + H)$^+$.<br>$^1$H NMR (400 MHz, DMSO-d$_6$) δ 8.58 (s, 1H), 7.38 (m, 1H), 7.12 (m, 3H), 5.37 (s, 2H), 4.26 (s, 3H), 2.85 (s, 3H). |
| E1-7 | 6-(2-Fluorobenzyl)-2,4-dimethyl-4H-thiazolo[5',4':4,5]pyrrolo[2,3-d]pyridazin-5(6H)-one | LCMS: m/z 329 (M + H)$^+$.<br>$^1$H NMR (400 MHz, DMSO-d$_6$) δ 8.58 (s, 1H), 7.43-7.30 (m, 1H), 7.25-7.06 (m, 3H), 5.41 (s, 2H), 4.26 (s, 3H), 2.86 (s, 3H) |
| E1-8 | Ethyl-3-((2,4-dimethyl-5-oxo-4H-thiazolo[5',4':4,5]pyrrolo[2,3-d]pyridazin-6(5H)-yl)methyl)benzoate | LCMS: m/z 383 (M + H)$^+$.<br>$^1$H NMR (400 MHz, DMSO-d$_6$) δ 8.59 (s, 1H), 8.00-7.83 (m, 2H), 7.54 (dd, 1H), 7.48 (m, 1H), 5.42 (s, 2H), 4.48-4.16 (m, 5H), 2.85 (s, 3H), 1.30 (t, 3H). |
| E1-9 | 3-((2,4-Dimethyl-5-oxo-4H-thiazolo[5',4':4,5]pyrrolo[2,3-d]pyridazin-6(5H)-yl)methyl)benzoic acid | LCMS: m/z 355 (M + H)$^+$.<br>$^1$H NMR (400 MHz, DMSO-d$_6$) δ 8.60 (s, 1H), 8.0-7.87 (m, 2H), 7.55-7.40 (m, 2H), 5.40 (s, 2H), 4.26 (s, 3H), 2.85 (s, 3H). |
| E1-10 | 2,4-Dimethyl-6-(3-nitrobenzyl)-4H-thiazolo[5',4':4,5]pyrrolo[2,3-d]pyridazin-5(6H)-one | LCMS: m/z 356 (M + H)$^+$.<br>$^1$H NMR (400 MHz, CDCl$_3$) δ 8.20 (s, 1H), 8.16 (s, 1H), 8.08 (d, 1H), 7.70 (d, 1H), 7.44 (t, 1H), 5.46 (S, 2H), 4.32 (s, 3H), 2.80 (s, 3H). |

| Cpd No. | Structure | Characterization |
|---|---|---|
| E1-11 | 2,4-Dimethyl-6-(4-nitrobenzyl)-4,6-dihydro-5H-thiazolo[5',4':4,5]pyrrolo[2,3-d]pyridazin-5-one | LCMS: m/z 356 (M + H)$^+$. $^1$H NMR (400 MHz, DMSO-d$_6$) δ 8.62 (s, 1H), 8.20 (d, 2H), 7.55 (d, 2H), 5.50 (s, 2H), 4.26 (s, 3H), 2.86 (s, 3H). |
| E1-12 | 6-(2-Methoxybenzyl)-2,4-dimethyl-4,6-dihydro-5H-thiazolo[5',4':4,5]pyrrolo[2,3-d]pyridazin-5-one | LC-MS: m/z 341 (M + H)$^+$. $^1$H NMR (400 MHz, DMSO-d$_6$) δ 8.58 (s, 1H), 7.25 (s, 1H), 7.04 (d, 1H), 6.83 (d, 1H), 6.74 (d, 1H), 5.34 (s, 2H), 4.27 (s, 3H), 3.85 (s, 3H), 2.87 (s, 3H). |
| E1-13 | 6-(3-Acetylbenzyl)-2,4-dimethyl-4H-thiazolo[5',4':4,5]pyrrolo[2,3-d]pyridazin-5(6H)-one | LC-MS: m/z 353 (M + H)$^+$. $^1$H NMR (400 MHz, DMSO-d$_6$) δ 8.59 (s, 1H), 7.89 (d, 2H), 7.56 (d, 1H), 7.50 (d, 1H), 5.43 (s, 2H), 4.26 (s, 3H), 2.85 (s, 3H), 2.56 (s, 3H). |
| E1-14 | 2,4-Dimethyl-6-((1-methyl-1H-indazol-4-yl)methyl)-4H-thiazolo[5',4':4,5]Pyrrolo[2,3-d]pyridazin-5(6H)-one | LCMS: m/z 365 (M + H)$^+$. $^1$H NMR (400 MHz, DMSO-d$_6$) δ 8.56 (s, 1H), 8.12 (s, 1H), 7.56 (d, 1H), 7.38-7.24 (m, 1H), 6.98 (d, 1H), 5.66 (s, 2H), 4.24 (s, 3H), 4.02 (s, 3H), 2.86 (s, 3H). |
| E1-15 | 6-((1H-indazol-5-yl)methyl)-2,4-dimethyl-4,6-dihydro-5H-thiazolo[5',4':4,5]pyrrolo[2,3-d]pyridazin-5-one | LC-MS: m/z 351 (M + H)$^+$. $^1$H NMR (400 MHz, DMSO-d$_6$) δ 13.02 (s, 1H), 8.58 (s, 1H), 8.04 (s, 1H), 7.70 (s, 1H), 7.50 (d, 1H), 7.40 (d, 1H), 5.44 (s, 2H), 4.28 (s, 3H), 2.86 (s, 3H). |

| Cpd No. | Structure | Characterization |
|---|---|---|
| E1-16 | 6-((1H-indazol-4-yl)methyl)-2,4-dimethyl-4,6-dihydro-5H-thiazolo[5',4':4,5]pyrrolo[2,3-d]pyridazin-5-one | LCMS: m/z 351 (M + H)+. $^1$H NMR (400 MHz, DMSO-$d_6$) δ 13.11 (s, 1H), 8.58 (s, 1H), 8.15 (s, 1H), 7.45 (d, 1H), 7.33-7.22 (m, 1H), 6.96 (d, 1H), 5.66 (s, 2H), 4.26 (s, 3H), 2.85 (s, 3H). |
| E1-17 | 6-((1H-indazol-7-yl)methyl)-2,4-dimethyl-4H-thiazolo[5',4':4,5]pyrrolo[2,3-d]pyridazin-5(6H)-one | LCMS: m/z 351 (M + H)+. $^1$H NMR (400 MHz, DMSO-$d_6$) δ 13.14 (s, 1H), 8.60 (s, 1H), 8.13 (s, 1H), 7.75-7.60 (m, 1H), 7.11-6.92 (m, 2H), 5.68 (s, 2H), 4.27 (s, 3H), 2.85 (s, 3H). |
| E1-18 | 6-((1H-Indazol-6-yl)methyl)-2,4-dimethyl-4H-thiazolo[5',4':4,5]pyrrolo[2,3-d]pyridazin-5(6H)-one | LCMS: m/z 351 (M + H)+. $^1$H NMR (400 MHz, DMSO-$d_6$) δ 12.96 (s, 1H), 8.59 (s, 1H), 8.03 (s, 1H), 7.71 (d, 1H), 7.42 (s, 1H), 7.13 (d, 1H), 5.48 (s, 2H), 4.27 (s, 3H), 2.86 (s, 3H). |
| E1-19 | 6-((1H-Benzo[d][1,2,3]triazol-6-yl)methyl)-2,4-dimethyl-4H-thiazolo[5',4':4,5]pyrrolo[2,3-d]pyridazin-5(6H)-one | LCMS: m/z 352 (M + H)+. $^1$H NMR (400 MHz, DMSO-$d_6$) 16.0-15.55 (m, 1H), δ 8.59 (s, 1H), 8.08-7.31 (m, 3H), 5.53 (s, 2H), 4.27 (s, 3H), 2.85 (s, 3H). |
| E1-20 | 6-((1H-Benzo[d]imidazol-5-yl)methyl)-2,4-dimethyl-4H-thiazolo[5',4':4,5]pyrrolo[2,3-d]pyridazin-5(6H)-one | LCMS: m/z 351 (M + H)+. $^1$H NMR (400 MHz, DMSO-$d_6$) δ 12.37 (s, 1H), 8.56 (s, 1H), 8.19 (s, 1H), 7.54 (m, 2H), 7.23 (s, 1H), 5.45 (s, 2H), 4.26 (s, 3H), 2.87 (s, 3H). |

| Cpd No. | Structure | Characterization |
|---|---|---|
| E1-21 | 6-((1H-indol-6-yl)methyl)-2,4-dimethyl-4,6-dihydro-5H-thiazolo[5',4':4,5]pyrrolo[2,3-d]pyridazin-5-one | LCMS: m/z 350 (M + H)+. $^1$H NMR (400 MHz, DMSO-d$_6$) δ 11.01 (s, 1H), 8.56 (s, 1H), 7.46 (d, 1H), 7.36 (s, 1H), 7.30 (t, 1H), 7.03 (d, 1H), 6.37 (s, 1H), 5.42 (s, 2H), 4.27 (s, 3H), 2.84 (s, 3H). |
| E1-22 | 2,4-Dimethyl-6-((2-oxo-2,3-dihydro-1H-benzo[d]imidazol-5-yl)methyl)-4,6-dihydro-5H-thiazolo[5',4':4,5]pyrrolo[2,3-d]pyridazin-5-one | LC-MS: m/z 367 (M + H)+. $^1$H NMR (DMSO-d$_6$) δ: 10.57 (s, 1H), 10.52 (s, 1H), 8.55 (s, 1H), 6.94-6.95 (m, 2H), 6.85-6.87 (m, 1H), 5.31 (s, 2H), 4.27 (s, 3H), 2.85 (s, 3H). |
| E1-23 | 2,4-Dimethyl-6-((6-methylpyridin-2-yl)methyl)-4,6-dihydro-5H-thiazolo[5',4':4,5]pyrrolo[2,3-d]pyridazin-5-one | LC-MS: 326 (M + H)+. $^1$H NMR (400 MHz, DMSO-d$_6$) δ 8.58 (s, 1H), 7.60 (t, 1H), 7.13 (d, 1H), 6.83 (d, 1H), 5.40 (s, 2H), 4.26 (s, 3H), 2.86 (s, 3H), 2.44 (s, 3H). |
| E1-24 | 6-((6-Methoxypyridin-2-yl)methyl)-2,4-dimethyl-4,6-dihydro-5H-thiazolo[5',4':4,5]pyrrolo[2,3-d]pyridazin-5-one | LC-MS: 342 (M + H)+. $^1$H NMR (400 MHz, DMSO-d$_6$) δ 8.59 (s, 1H), 7.65-7.58 (m, 1H), 6.69 (d, 1H), 6.61 (d, 1H), 5.37 (s, 2H), 4.26 (s, 3H), 3.77 (s, 3H), 2.86 (s, 3H). |
| E1-25 | 6-((6-Fluoropyridin-2-yl)methyl)-2,4-dimethyl-4,6-dihydro-5H-thiazolo[5',4':4,5]pyrrolo[2,3-d]pyridazin-5-one | LC-MS: 330 (M + H)+. $^1$H NMR (400 MHz, DMSO-d$_6$) δ 8.58 (s, 1H), 7.96-7.88 (m, 1H), 7.13 (dd, 1H), 7.07 (dd, 1H), 5.42 (s, 2H), 4.25 (s, 3H), 2.86 (s, 3H). |

| Cpd No. | Structure | Characterization |
|---|---|---|
| E1-26 | 2,8-Dimethyl-6-(1H-pyrazol-3-ylmethyl)-6,8-dihydro-3-thia-1,5,6,8-tetraaza-cyclopenta[a]inden-7-one | LC-MS: m/z 301 (M + H)+. <br> 1H NMR (400 MHz, DMSO-d6) δ 12.70 (s, 1H), 8.58 (s, 1H), 7.67 (s, 1H) 6.18 (s, 1H), 5.38 (s, 2H), 4.32 (s, 3H), 2.91 (s, 3H). |
| E1-27 | 6-((1H-pyrazol-4-yl)methyl)-2,4-dimethyl-4H-thiazolo[5',4':4,5]pyrrolo[2,3-d]pyridazin-5(6H)-one | LCMS: m/z 301 (M + H)+. <br> 1H NMR (400 MHz, DMSO-d6) δ 8.59 (s, 1H), 7.70 (s, 2H), 5.28 (s, 2H), 4.32 (s, 3H), 2.91 (s, 3H). |
| E1-28 | 6-((1H-Imidazol-4-yl)methyl)-2,4-dimethyl-4,6-dihydro-5H-thiazolo[5',4':4,5]pyrrolo[2,3-d]pyridazin-5-one | LCMS: m/z 301 (M + H)+. <br> 1H NMR (400 MHz, DMSO-d6): 12.08 (brs, 1H), δ 8.51 (s, 1H), 7.52 (s, 1H), 6.92 (s, 1H), 5.25 (s, 2H), 4.26 (s, 3H), 2.85 (s, 3H). |
| E1-29 | 6-(2-(2-hydroxyethoxy)ethyl)-2,4-dimethyl-4H-thiazolo[5',4':4,5]pyrrolo[2,3-d]pyridazin-5(6H)-one | LCMS: 309 (M + H)+. <br> 1H NMR (400 MHz, DMSO-d6) δ 8.54 (s, 1H), 4.32 (t, 2H), 4.26 (s, 3H), 3.79 (t, 2H), 3.45 (s, 4H), 2.86 (s, 3H). |
| E1-30 | 6-(3-Hydroxypropyl)-2,4-dimethyl-4,6-dihydro-5H-thiazolo[5',4':4,5]pyrrolo[2,3-d]pyridazin-5-one | LCMS: m/z 279 (M + H)+. <br> 1H NMR (400 MHz, DMSO-d6) δ 8.52 (s, 1H), 4.52 (t, 1H), 4.26 (s, 3H), 4.21 (t, 2H), 3.46 (dd, 2H), 2.85 (s, 3H), 1.92-1.82 (m, 2H). |

| Cpd No. | Structure | Characterization |
|---|---|---|
| E1-31 | Ethyl-2-(2,4-dimethyl-5-oxo-4H-thiazolo[5',4':4,5]pyrrolo[2,3-d]pyridazin-6(5H)-yl)acetate | LCMS: 307 (M + H)⁺. ¹H NMR (400 MHz, DMSO-d₆) δ 8.63 (s, 1H), 5.00 (s, 2H), 4.40-4.12 (m, 5H), 2.92 (s, 3H), 1.35-1.21 (m, 3H). |

Example 1B. Synthesis of 1-(3-((2,4-dimethyl-5-oxo-4H-thiazolo[5',4':4,5]pyrrolo[2,3-d]pyridazin-6(5H)-yl)methyl)phenyl)urea

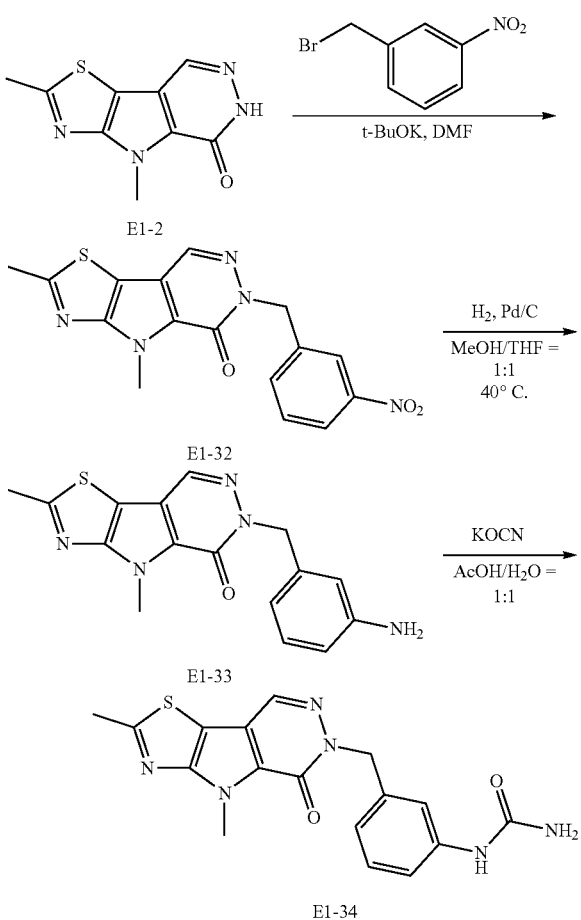

Step A. 2,4-Dimethyl-6-(3-nitrobenzyl)-4H-thiazolo[5',4':4,5]pyrrolo[2,3-d]pyridazin-5(6H)-one To a mixture of 2,4-dimethyl-4H-thiazolo[5',4':4,5]pyrrolo[2,3-d]pyridazin-5(6H)-one (100 mg, 0.45 mmol) in DMF (5 mL) were added 1-(bromomethyl)-3-nitrobenzene (194 mg, 0.9 mmol) and t-BuOK (76 mg, 0.68 mmol). The reaction was stirred at r.t. for 1 hr. then poured into water and extracted with EtOAc. The combined organic layers were washed with brine, dried over anhydrous Na₂SO₄ and concentrated under reduced pressure. The residue was purified by prep-TLC to give the desired product (100 mg, 62.5% yield). LCMS: m/z 356 (M+H)⁺.

Step B. 6-(3-Aminobenzyl)-2,4-dimethyl-4H-thiazolo[5',4':4,5]pyrrolo[2,3-d]pyridazin-5(6H)-one To a mixture of 2,4-dimethyl-6-(3-nitrobenzyl)-4H-thiazolo[5',4':4,5]pyrrolo[2,3-d]pyridazin-5(6H)-one (100 mg, 0.28 mmol) in MeOH/THF (10 mL/10 mL) under N₂ was added Pd/C (10%, 50 mg). The reaction mixture was stirred at 40° C. under H₂ for 12 hr. then filtered through Celite. The filtrate was concentrated under reduced pressure and the residue was purified by prep-TLC to afford the desired compound (80 mg, 88% yield). LCMS: m/z 326 (M+H)⁺. ¹H NMR (400 MHz, DMSO-d₆) δ 8.54 (s, 1H), 6.94 (t, 1H), 6.57-6.32 (m, 3H), 5.19 (s, 2H), 5.04 (s, 2H), 4.26 (s, 3H), 2.85 (s, 3H).

Step C. 1-(3-((2,4-Dimethyl-5-oxo-4H-thiazolo[5,4':4,5]pyrrolo[2,3-d]pyridazin-6(5H)-yl)methyl)phenyl) urea To a mixture of 6-(3-aminobenzyl)-2,4-dimethyl-4H-thiazolo[5',4':4,5]pyrrolo[2,3-d]pyridazin-5(6H)-one (65 mg, 0.2 mmol) in HOAc (2 mL) was added KOCN (160 mg, in HOAc:H₂O=2 mL:4 mL). The reaction mixture was stirred at r.t. for 2 hr. then poured into saturated aqueous NaHCO₃ and extracted with EtOAc. The organic layers were concentrated under reduced pressure. The residue was purified by prep-HPLC to afford the desired compound (4 mg, 5% yield). LCMS: m/z 369 (M+H)⁺. ¹H NMR (400 MHz, DMSO-d₆) δ 8.60-8.50 (m, 2H), 7.39 (d, 1H), 7.23 (s, 1H), 7.16 (t, 1H), 6.85 (d, 1H), 5.78 (s, 2H), 5.28 (s, 2H), 4.27 (s, 3H), 2.86 (s, 3H).

Example 1C. Synthesis of 2,4-dimethyl-6-(3-(methylamino)benzyl)-4,6-dihydro-5H-thiazolo[5',4':4,5]pyrrolo[2,3-d]pyridazin-5-one

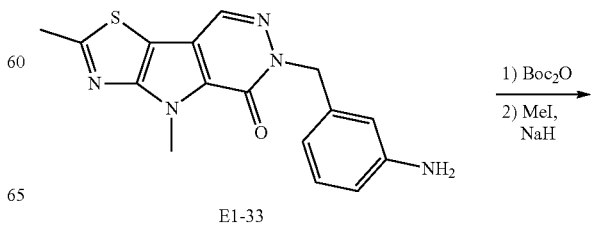

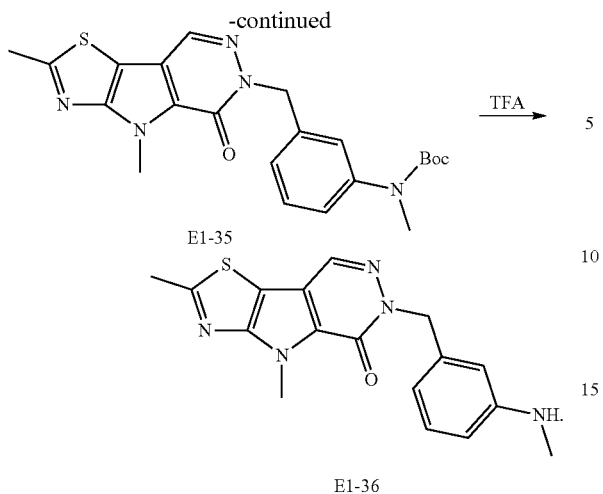

E1-35

E1-36

Step A. Tert-butyl (3-((2,4-dimethyl-5-oxo-4,5-dihydro-6H-thiazolo[5',4':4,5]pyrrolo[2,3-d]pyridazin-6-yl)methyl)phenyl)carbamate To a mixture of 6-(3-aminobenzyl)-2,4-dimethyl-4,6-dihydro-5H-thiazolo[5',4':4,5]pyrrolo[2,3-d]pyridazin-5-one (90 mg, 0.28 mmol) in 1,4-dioxane (10 mL) was added Boc$_2$O (73 mg, 0.33 mmol). The reaction mixture was stirred at reflux overnight then concentrated under reduced pressure. The residue was purified by column chromatography on silica gel (eluent: PE/EtOAc—3/1) to give the desired product (90 mg, 76.3% yield). LCMS: m/z 426 (M+H)$^+$.

Step B. Tert-butyl (3-((2,4-dimethyl-5-oxo-4,5-dihydro-6H-thiazolo[5',4':4,5]pyrrolo[2,3-d]pyridazin-6-yl)methyl)phenyl)(methyl) carbamate To a mixture of tert-butyl (3-((2,4-dimethyl-5-oxo-4,5-dihydro-6H-thiazolo[5',4':4,5]pyrrolo[2,3-d]pyridazin-6-yl)methyl)phenyl)carbamate (90 mg, 0.21 mmol) in anhydrous DMF (5 mL) at 0° C. was added NaH (13 mg, 0.32 mmol, 60% wt). The mixture was stirred at 0° C. for 1 hr., followed by drop wise addition of MeI. The resulting mixture was stirred at 0-5° C. for 3 hr. then poured into cold saturated aqueous NH$_4$Cl and extracted with EtOAc. The combined organic layers were washed with brine, dried over anhydrous Na$_2$SO$_4$ and concentrated under reduced pressure. The residue was purified by prep-TLC to give the desired product (70 mg, 75.2% yield). LCMS: m/z 440 (M+H)$^+$.

Step C. 2,4-Dimethyl-6-(3-(methylamino)benzyl)-4,6-dihydro-5H-thiazolo[5',4':4,5]pyrrolo[2,3-d]pyridazin-5-one To a mixture of tert-butyl (3-((2,4-dimethyl-5-oxo-4,5-dihydro-6H-thiazolo[5',4':4,5]pyrrolo[2,3-d]pyridazin-6-yl)methyl)phenyl)(methyl)carbamate (90 mg, 0.21 mmol) in DCM (3 mL) was added TFA (1 mL). The mixture was stirred at r.t. for 2 hr. then concentrated under reduced pressure. The residue was purified by prep-HPLC to give the desired product (25 mg, 46.4% yield). LCMS: m/z 340 (M+H)$^+$. $^1$H NMR (400 MHz, DMSO-d$_6$) δ 8.54 (s, 1H), 7.12 (t, 1H), 6.66-6.61 (m, 3H), 5.26 (s, 2H), 4.26 (s, 3H), 2.85 (s, 3H), 2.68 (d, 3H).

The procedure set forth above was used to produce the following compound using the appropriate starting materials. Standard protection and deprotection can be used when necessary.

| Cpd No. | Structure | Characterization |
|---|---|---|
| E1-37 | ![structure] 6-(4-aminobenzyl)-2,4-dimethyl-4,6-dihydro-5H-thiazolo[5',4':4,5]pyrrolo[2,3-d]pyridazin-5-one | LCMS: m/z 326 (M + H)$^+$. $^1$H NMR (400 MHz, DMSO-d$_6$) δ 8.52 (s, 1H), 7.04 (d, 2H), 6.49 (d, 2H), 5.15 (s, 2H), 5.01 (s, 2H), 4.25 (s, 3H), 2.85 (s, 3H). |
| E1-38 | ![structure] 2,4-Dimethyl-6-(4-(methylamino)benzyl)-4,6-dihydro-5H-thiazolo[5',4':4,5]pyrrolo[2,3-d]pyridazin-5-one | LCMS: m/z 340 (M + H)$^+$. $^1$H NMR (400 MHz, DMSO-d$_6$) δ 8.51 (s, 1H), 7.11 (d, 2H), 6.46 (d, 2H), 5.58 (d, 1H), 5.17 (s, 2H), 4.25 (s, 3H), 2.84 (s, 3H), 2.62 (d, 3H). |

Example 1D. Synthesis of 6-(3-hydroxybenzyl)-2,4-dimethyl-4H-thiazolo[5',4':4,5]pyrrolo[2,3-d]pyridazin-5(6H)-one

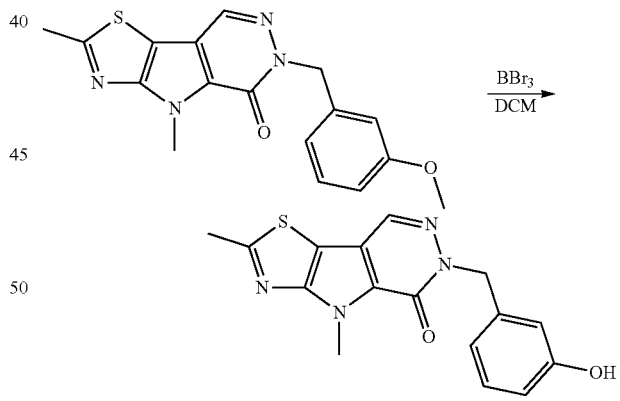

E1-39

To a mixture of 6-(3-methoxybenzyl)-2,4-dimethyl-4H-thiazolo[5',4':4,5]pyrrolo[2,3-d]pyridazin-5(6H)-one (53 mg, 0.16 mmol) in DCM (4 mL) at 0° C. was added BBr$_3$ (195 mg, 0.778 mmol). The mixture was stirred r.t. for 2 hr. then quenched with MeOH. The resulting mixture was concentrated under reduced pressure. The residue was purified by prep-HPLC to give the desired product (15.6 mg, 30.70% yield). LCMS: m/z 327 (M+H)$^+$. $^1$H NMR (400 MHz, DMSO-d$_6$) δ 9.34 (s, 1H), 8.58 (s, 1H), 7.12 (t, 1H), 6.78-6.56 (m, 3H), 5.26 (s, 2H), 4.278 (s, 3H), 2.86 (s, 3H).

The procedure set forth above was used to produce the following compounds using the appropriate starting materials. Standard protection and deprotection can be used when necessary.

| Cpd No. | Structure | Characterization |
|---|---|---|
| E1-40 | 6-(2-Hydroxybenzyl)-2,4-dimethyl-4,6-dihydro-5H-thiazolo[5',4':4,5]pyrrolo[2,3-d]pyridazin-5-one | LC-MS: m/z 327 (M + H)$^+$. $^1$H NMR (400 MHz, DMSO-d$_6$) δ 9.67 (s, 1H), 8.59 (s, 1H), 7.07 (d, 1H), 6.85-6.60 (m, 3H), 5.32 (s, 2H), 4.27 (s, 3H), 2.87 (s, 3H). |
| E1-41 | 6-(4-Hydroxybenzyl)-2,4-dimethyl-4,6-dihydro-5H-thiazolo[5',4':4,5]pyrrolo[2,3-d]pyridazin-5-one | LC-MS: 327 (M + H)$^+$. $^1$H NMR (400 MHz, DMSO-d$_6$) δ 9.36 (s, 1H), 8.53 (s, 1H), 7.17 (d, 2H), 6.70 (d, 2H), 5.22 (s, 2H), 4.26 (s, 3H), 2.85 (s, 3H). |

Example 1E. Synthesis of 6-[3-(1-Amino-ethyl)-benzyl]-2,8-dimethyl-6,8-dihydro-3-thia-1,5,6,8-tetraaza-cyclopenta[a]inden-7-one

E1-42

To a stirred mixture of 6-(3-acetylbenzyl)-2,4-dimethyl-4H-thiazolo[5',4':4,5]pyrrolo[2,3-d]pyridazin-5(6H)-one (50 mg, 0.142 mmol) in MeOH (4 mL) were added NH$_4$OAc (109 mg, 1.42 mmol) and NaBH$_3$CN (18 mg, 0.284 mmol). The reaction mixture was stirred at 35° C. for 13 hr. then concentrated under reduced pressure. The residue was purified by prep-HPLC to afford the desired product (20 mg, 40.0% yield). LC-MS: m/z 354 (M+H)$^+$. $^1$H NMR (400 MHz, DMSO-d$_6$) δ 8.48 (s, 1H), 7.25 (dd, 3H), 7.12 (d, 1H), 5.26 (s, 2H), 4.17 (s, 3H), 4.15-4.06 (m, 1H), 2.76 (s, 3H), 1.27 (d, 3H).

Example 1F. Synthesis of 6-(3-(aminomethyl)benzyl)-2,4-dimethyl-4,6-dihydro-5H-thiazolo[5',4':4,5]pyrrolo[2,3-d]pyridazin-5-one

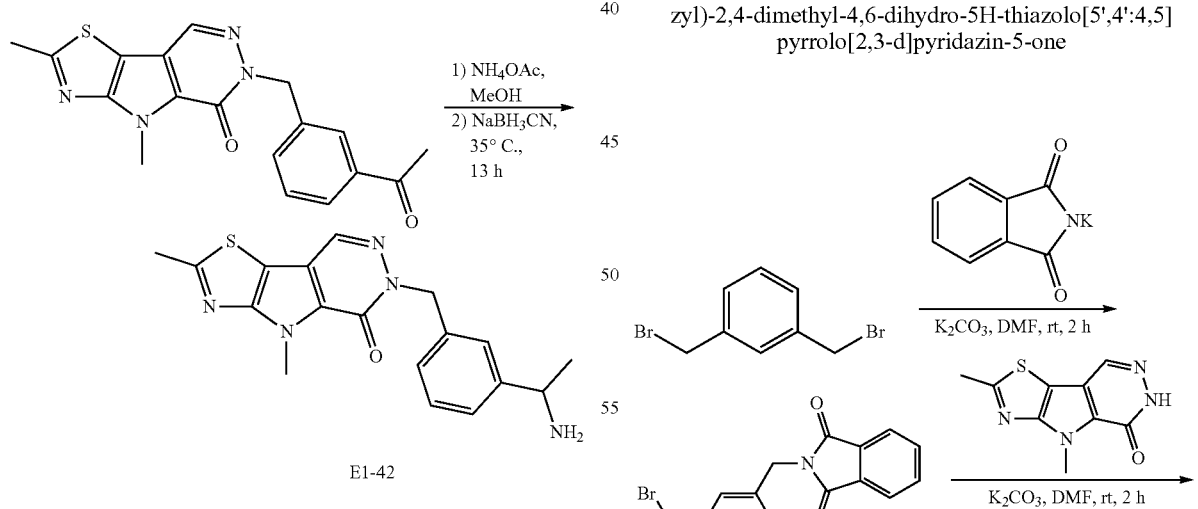

-continued

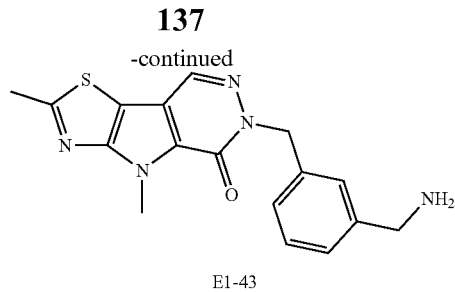

E1-43

Step A. 2-(3-(Bromomethyl)benzyl)isoindoline-1,3-dione

To a stirred mixture of 1,3-bis(bromomethyl)benzene (1.3 g, 4.96 mmol) in DMF (20 mL) were added potassium 1,3-dioxoisoindolin-2-ide (0.918 g, 4.96 mmol) and $K_2CO_3$ (1.03 g, 7.44 mol). The reaction mixture was stirred at r.t. for 2 hr. then poured into saturated aqueous $NH_4Cl$ (30 mL) and extracted with DCM. The combined organic layers were washed with brine, dried over anhydrous $Na_2SO_4$ and concentrated under reduced pressure. The residue was purified by column chromatography on silica gel (eluent: PE/EtOAc=30/1) to give the desired product (1.1 g, 67.4% yield). LC-MS: m/z 330 (M+H)+.

Step B. 2-(3-((2,4-Dimethyl-5-oxo-4H-thiazolo[5',4':4,5]pyrrolo[2,3-d]pyridazin-6(5H)-yl)methyl)benzyl)isoindoline-1,3-dione To a stirred mixture of 2-(3-(bromomethyl)benzyl)isoindoline-1,3-dione (100 mg, 0.303 mmol) in DMF (4 mL) were added 2,4-dimethyl-4H-thiazolo[5',4':4,5]pyrrolo[2,3-d]pyridazin-5(6H)-one (66.7 mg, 0.303 mmol) and $K_2CO_3$ (83.6 mg, 0.606 mol). The reaction mixture was stirred at r.t. for 2 hr. then poured into saturated aqueous $NH_4Cl$ (15 mL) and extracted with DCM. The combined organic layers were washed with brine, dried over anhydrous $Na_2SO_4$ and concentrated under reduced pressure. The residue was purified by column chromatography on silica gel (eluent: PE/EtOAc=5/1) to give the desired product (80 mg, 56.3% yield). LC-MS: m/z 470 (M+H)+.

Step C. 6-(3-(Aminomethyl)benzyl)-2,4-dimethyl-4H-thiazolo[5',4':4,5]pyrrolo[2,3-d]pyridazin-5(6H)-one To a stirred mixture of 2-(3-((2,4-dimethyl-5-oxo-4H-thiazolo[5',4':4,5]pyrrolo[2,3-d]pyridazin-6(5H)-yl)methyl)benzyl)isoindoline-1,3-dione (80 mg, 0.17 mmol) in EtOH (5 mL) was added $N_2H_4 \cdot H_2O$ (44 mg, 98% wt, 0.85 mmol). The reaction mixture was stirred at 100° C. for 2 hr. then poured into saturated aqueous $NH_4Cl$ (15 mL) and extracted with DCM twice. The organic layers were washed with brine twice, dried over anhydrous $Na_2SO_4$, and concentrated under reduced pressure. The residue was purified by prep-HPLC to afford the desired product (30 mg, 52.1% yield). LC-MS: m/z 324 (M+H—$NH_3$)+. $^1H$ NMR (400 MHz, DMSO-$d_6$) δ 8.57 (s, 1H), 7.32 (m, 3H), 7.23 (d, 1H), 5.35 (s, 2H), 4.27 (s, 3H), 3.84 (s, 2H), 2.86 (s, 3H).

Example 1G. Synthesis of 6-(4-(hydroxymethyl)benzyl)-2,4-dimethyl-4,6-dihydro-5H-thiazolo[5',4':4,5]pyrrolo[2,3-d]pyridazin-5-one

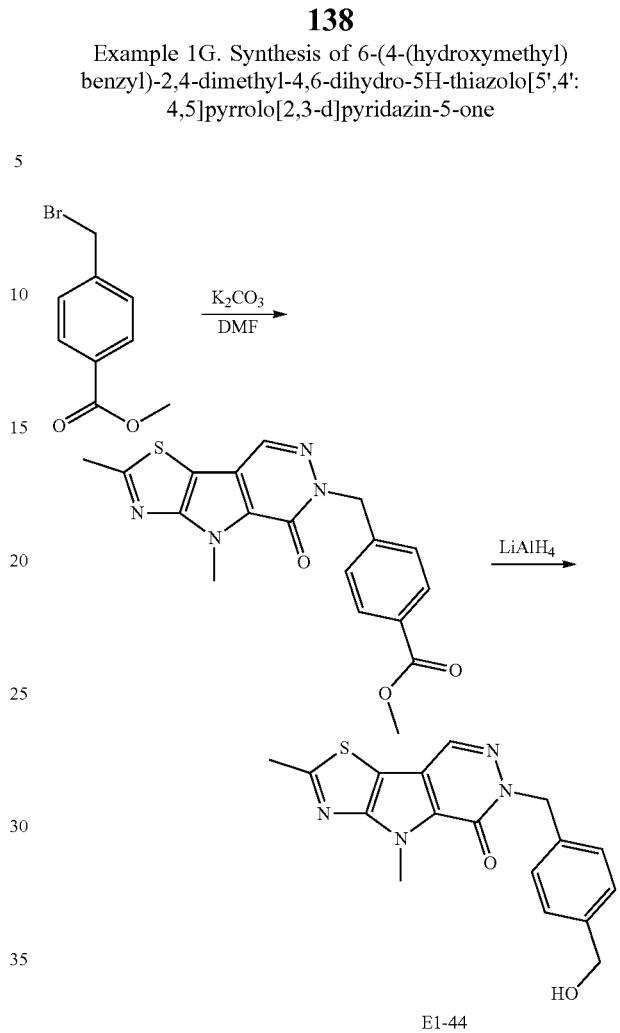

E1-44

Step A. Methyl 4-((2,4-dimethyl-5-oxo-4H-thiazolo[5',4':4,5]pyrrolo[2,3-d]pyridazin-6(5H)-yl)methyl)benzoate To a mixture of 2,4-dimethyl-4H-thiazolo[5',4':4,5]pyrrolo[2,3-d]pyridazin-5(6H)-one (100 mg, 0.4 mmol) in DMF (20 mL) was added $K_2CO_3$ (181 mg, 1.3 mmol). The mixture was stirred at 60° C. for 30 min, followed by addition of methyl 4-(bromomethyl)benzoate (100 mg, 0.4 mmol) at 0° C. The resulting mixture was stirred at 60° C. for 18 hr. then poured into ice-water and extracted with EtOAc The combined organic layers were washed with brine, dried over anhydrous $Na_2SO_4$ and concentrated under reduced pressure. The residue was purified by column chromatography on silica gel (eluent: PE/EtOAc=50/1 to 10/1) to give the desired product (120 mg, 74.61%). LCMS: m/z 369 (M+H)+.

Step B. 6-(4-(hydroxymethyl)benzyl)-2,4-dimethyl-4H-thiazolo[5',4':4,5]pyrrolo[2,3-d]pyridazin-5(6H)-one To a mixture of 4-((2,4-dimethyl-5-oxo-4H-thiazolo[5',4':4,5]pyrrolo[2,3-d]pyridazin-6(5H)-yl)methyl)benzoate (100 mg, 0.3 mmol) in THF (20 mL) at 0° C. was added LAH (30 mg, 0.8 mmol). The reaction was stirred at 0° C. under $N_2$ for 30 min then quenched with $NaSO_4 \cdot 10H_2O$ and filtered.

The filtrate was concentrated under reduced pressure. The residue was purified by prep-TLC to give the desired product (3 mg, 3.25%). LCMS: m/z 341 (M+H)+. $^1$H NMR (400 MHz, CDCl$_3$) δ 8.12 (s, 1H), 7.36 (d, 2H), 7.25 (d, 2H), 5.37 (s, 2H), 4.59 (s, 2H), 4.31 (s, 3H), 2.80 (s, 3H).

The procedure set forth above was used to produce the following compounds using the appropriate starting materials. Standard protection and deprotection can be used when necessary.

| Cpd No. | Structure | Characterization |
|---|---|---|
| E1-45 | 6-(3-(Hydroxymethyl)benzyl)-2,4-dimethyl-4,6-dihydro-5H-thiazolo[5',4':4,5]pyrrolo[2,3-d]pyridazin-5-one | LCMS: m/z 341 (M + H)+. $^1$H NMR (400 MHz, CDCl$_3$) δ 8.22 (s, 1H), 7.44 (s, 1H), 7.40-7.29 (m, 3H), 5.47 (s, 2H), 4.69 (s, 2H), 4.39 (s, 3H), 2.90 (s, 3H). |
| E1-46 | 6-(2-hydroxyethyl)-2,4-dimethyl-4H-thiazolo[5',4':4,5]pyrrolo[2,3-d]pyridazin-5(6H)-one | LCMS: 265 (M + H)+. $^1$H NMR (400 MHz, DMSO-d$_6$) δ 8.52 (s, 1H), 4.80 (t, 1H), 4.45-4.15 (m, 5H), 3.74 (q, 2H), 2.85 (s, 3H). |

Example 1H. Synthesis of 6-((6-aminopyridin-2-yl)methyl)-2,4-dimethyl-4,6-dihydro-5H-thiazolo[5',4':4,5]pyrrolo[2,3-d]pyridazin-5-one Step A: 6-((6-((2,4-dimethoxybenzyl)amino)pyridin-2-yl)methyl)-2,4-dimethyl-4H-thiazolo[5',4':4,5]pyrrolo[2,3-d]pyridazin-5(6H)-one A mixture of 6-((6-fluoropyridin-2-yl)methyl)-2,4-dimethyl-4H-thiazolo[5',4':4,5]-pyrrolo[2,3-d]pyridazin-5(6H)-one (40 mg, 0.12 mmol) and (2,4-dimethoxyphenyl)methanamine (102 mg, 0.6 mmol) in NMP (1 mL) was stirred at 140° C. until completion. The resulting mixture was concentrated under reduced pressure. The residue was purified by prep-TLC to obtain the desired product (20 mg, 34.5% yield). LC-MS: 477 (M+H)+.

Step B: 6-((6-aminopyridin-2-yl)methyl)-2,4-dimethyl-4H-thiazolo[5',4':4,5]pyrrolo[2,3-d]pyridazin-5(6H)-one A mixture of 6-((6-((2,4-dimethoxybenzyl)amino)pyridin-2-yl)methyl)-2,4-dimethyl-4H-thiazolo[5',4':4,5]pyrrolo[2,3-d]pyridazin-5(6H)-one (20 mg, 0.042 mmol) and TFA (45 mg, 0.42 mmol) in DCM (1 mL) was stirred at r.t. until completion. The resulting mixture was concentrated under reduced pressure. The residue was purified by prep-HPLC to obtain the desired product (20 mg, 34.5% yield). LC-MS: 327 (M+H)+. $^1$H NMR (400 MHz, DMSO-d$_6$) δ 8.55 (s, 1H), 7.26 (t, 1H), 6.30 (d, 1H), 6.09 (d, 1H), 5.90 (s, 2H), 5.19 (s, 2H), 4.25 (s, 3H), 2.85 (s, 3H).

Example 1I. Synthesis of 6-(hydroxymethyl)-2,4-dimethyl-4H-thiazolo[5',4':4,5]pyrrolo[2,3-d]pyridazin-5(6H)-one

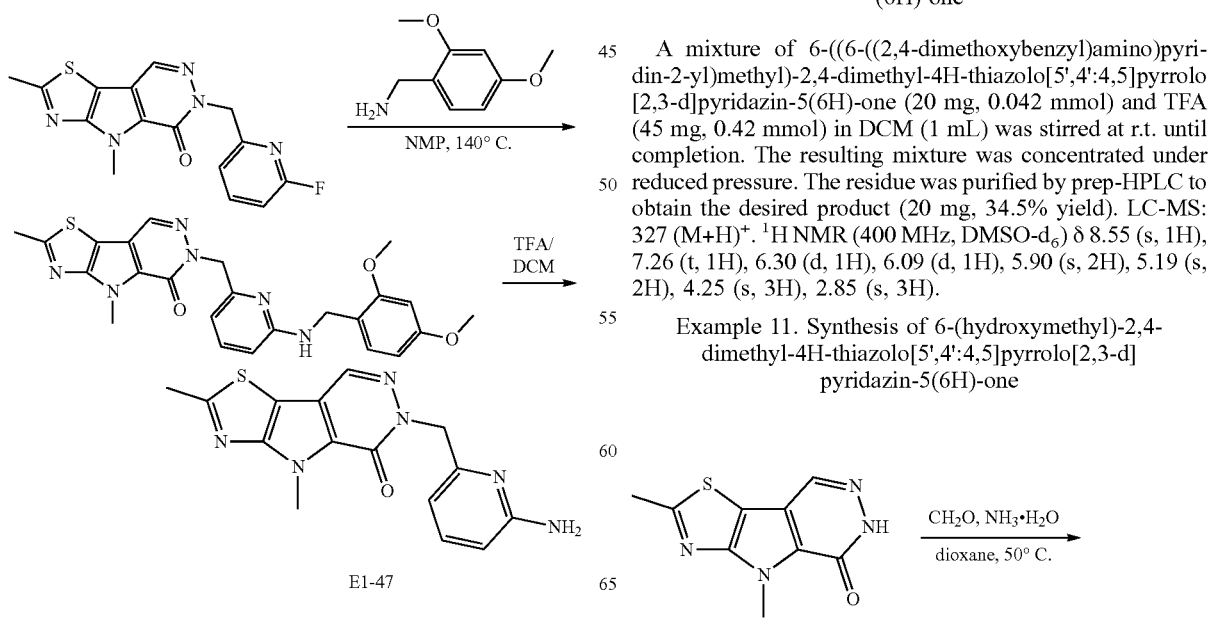

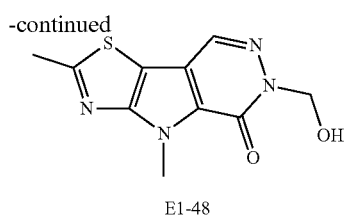

A mixture of 2,4-dimethyl-4H-thiazolo[5',4':4,5]pyrrolo[2,3-d]pyridazin-5(6H)-one (30 mg, 0.14 mmol), formaldehyde (1.5 mL, 40% wt) and NH$_3$ (0.75 mL, 33% wt) in dioxane (2 mL) was stirred at 50° C. for 1 hr. then poured into water and extracted with DCM. The organic layer was concentrated under reduced pressure. The residue was purified by prep-TLC to give the desired product (4.40 mg, 17% yield). LCMS: 251 (M+H). $^1$H NMR (400 MHz, DMSO-d$_6$) δ 8.55 (s, 1H), 6.63 (t, 1H), 5.44 (d, 2H), 4.27 (s, 3H), 2.85 (s, 3H).

Example 2. Preparation of Compounds of Formula E2-vii with Scheme E2

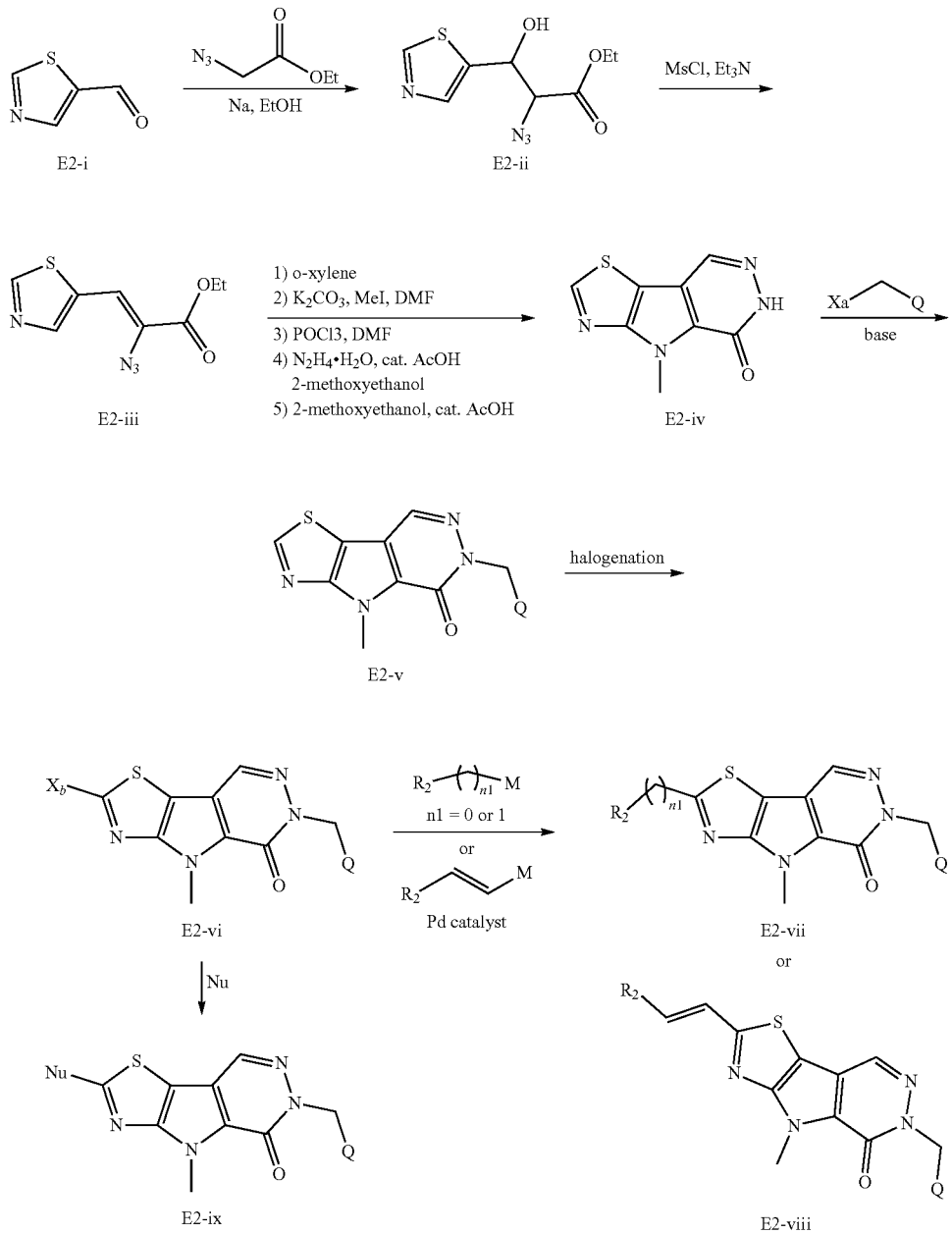

wherein Xa is a leaving group (e.g. halogen such as Br or I; OMs; or OTs); $X_b$ is halogen (e.g. Cl, Br or I); n1 is 0 or 1; M is hydrogen (for example for Heck reaction) or an organic metal complex (e.g. organoboron complex such as boronic acid or pinaco boron complex; organotin complex such as —Sn(Bu$^t$)$_3$; organozinc complex such as —Zn(halogen)); Q and R$^2$ are as defined in any one of the first to twenty-sixth embodiments of the invention. In certain embodiments, Q and R$^2$ are each independently optionally substituted aryl, optionally substituted heteroaryl, optionally substituted carbocycle or optionally substituted heterocyclyl, optionally substituted alkyl. Similar to the synthesis of compounds of Formula E1-v in Example 1, compound E2-iv can be synthesized from thiazole aldehyde E2-i with a few modifications (e.g. reaction of compound E2-ii with MsCl followed by elimination to give compound E2-iii; the tricyclic system can be formed with cat. AcOH in 2-methoxyethanol). Substitution and halogenation (e.g. CBr$_4$ or Cl$_3$CCCl$_3$ in the presence of LiHMDS; or 1,2,3,4,5-pentafluoro-6-iodobenzene in the presence of t-BuOK and toluene) of compound E2-iv provides compound E2-vi. Coupling reactions of compound E2-vi with organometal in the presence of a catalyst gives compound E2-vii or E2-viii. Direct nucleophilic reaction of E2-vi with a neucleophile (Nu) can generate compound E2-ix.

Example 2A. Synthesis of 2-(4-fluorobenzyl)-6-(3-methoxybenzyl)-4-methyl-4H-thiazolo[5',4':4,5]pyrrolo[2,3-d]pyridazin-5(6H)-one

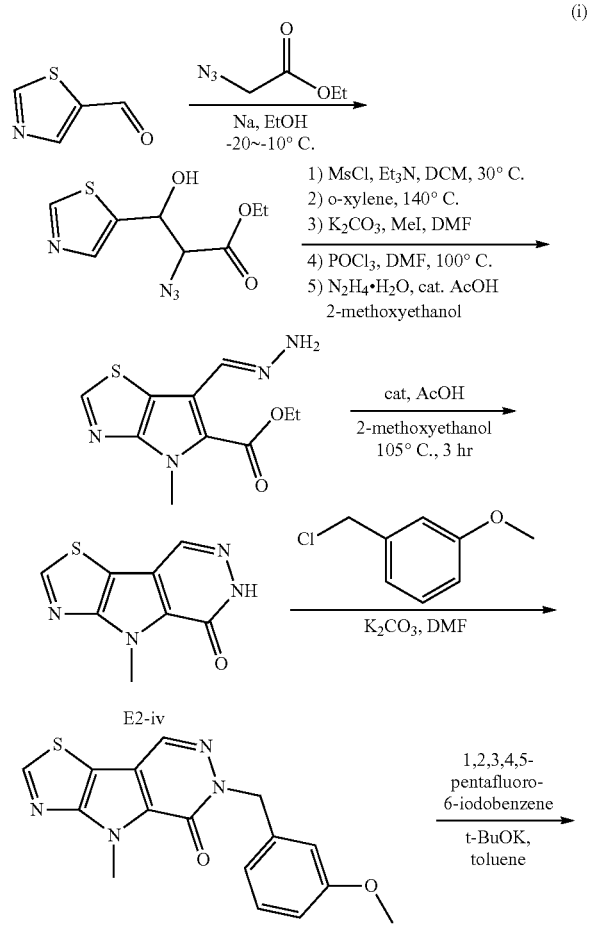

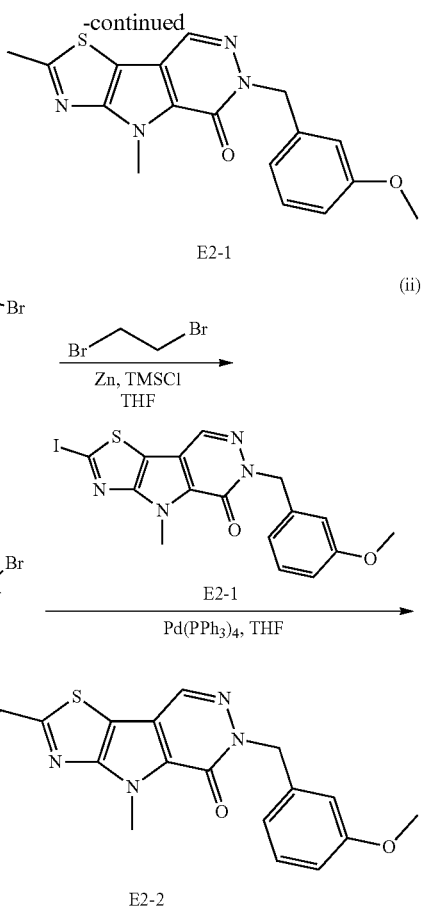

Step A. Ethyl 2-azido-3-hydroxy-3-(thiazol-5-yl)propanoate

Sodium (12.2 g, 0.531 mol) was slowly added at r.t. to a stirred solution of dry EtOH (300 mL). The reaction mixture was then cooled to −20° C., followed by drop wise addition of a solution of ethyl 2-azidoacetate (68.5 g, 0.531 mol) and thiazole-5-carbaldehyde (20.0 g, 0.177 mol) in anhydrous EtOH (100 mL) while keeping the temperature between −20° C. to −15° C. After the addition, the reaction mixture was stirred at −20° C. for additional 1 hr. and then poured into saturated aqueous NH$_4$Cl (1 L). The resulting mixture was saturated with NaCl and extracted with EtOAc. The combined organic phase was washed with brine, dried over anhydrous Na$_2$SO$_4$ and concentrated under reduced pressure. The residue was purified by column chromatography on silica gel using (eluent: PE/EtOAc=6/1 to 5/1 to 1/1) to afford desired product (34 g) as pale. LCMS: m/z=243 (M+H)$^+$.

Step B. Ethyl (Z)-2-azido-3-(thiazol-5-yl)acrylate

To a stirred mixture of ethyl 2-azido-3-hydroxy-3-(thiazol-5-yl)propanoate (103 g, 0.426 mol) in dry DCM (1.5 L) at −35° C. was added MsCl (146 g, 1.28 mol), followed by drop wise addition of TEA (301 g, 2.98 mol) while keeping the temperature between −35° C. to −30° C. After the addition, the reaction mixture was stirred at −30° C. for another 15 min then poured into saturated aqueous NH₄Cl (1.5 L). The resulting mixture was saturated with NaCl and extracted with DCM twice. The combined organic layers were washed in sequence with aqueous HCl (1 M) and brine, dried over anhydrous Na₂SO₄ and concentrated under reduced pressure. The residue was purified by column chromatography on silica gel using (eluent: PE/EtOAc=5/1) to afford the desired product (82.0 g, 86.3% yield). LCMS: m/z=225 (M+H)⁺.

Steps C-E to synthesize ethyl 4H-pyrrolo[2,3-d]thiazole-5-carboxylate, ethyl 4-methyl-4H-pyrrolo[2,3-d]thiazole-5-carboxylate, and ethyl 6-formyl-4-methyl-4H-pyrrolo[2,3-d]thiazole-5-carboxylate were similar to the procedures in Example 1A.

Step F. Ethyl (E)-6-(hydrazonomethyl)-4-methyl-4H-pyrrolo[2,3-d]thiazole-5-carboxylate To a stirred mixture of N₂H₄. H₂O (2.0 g, 98%, 40 mmol) in 2-methoxyethanol (50 mL) at r.t. was added ethyl 6-formyl-4-methyl-4H-pyrrolo[2,3-d]thiazole-5-carboxylate (4.8 g, 20 mmol), followed by addition of 20 drops of AcOH. The reaction mixture was stirred at r.t. for about 30 min till the mixture turned clear. The resulting mixture was poured into water (100 mL) with stirring and extracted with DCM. The combined organic layers were dried over anhydrous Na₂SO₄ and concentrated under reduced pressure to afford the desired product which was used in the next step without further purification. LCMS: m/z=253 (M+H)⁺.

Step G. 4-Methyl-4,6-dihydro-5H-thiazolo[5,4':4,5]pyrrolo[2,3-d]pyridazin-5-one To a stirred suspension of ethyl (E)-6-(hydrazonomethyl)-4-methyl-4H-pyrrolo[2,3-d]thiazole-5-carboxylate (4.8 g, 0.19 mol) in 2-methoxyethanol (50 mL) at r.t. was added AcOH (20 drops). The reaction suspension was stirred at 105° C. for 3 hr. and then filtered. The filter cake was washed with water and dried under high vacuum to get the first batch of the desired product. The filtrate was diluted with water and extracted with DCM twice. The organic layers were washed with brine, dried over anhydrous Na₂SO₄ and concentrated under reduced pressure to afford the second batch of the desired product. The combined two batches of the desired product (2.5 g) was directly used in the next step without further purification. LCMS: m/z=207 (M+H)⁺. 1H NMR (400 MHz, DMSO) δ 12.68 (s, 1H), 9.35 (s, 1H), 8.55 (s, 1H), 4.30 (s, 3H).

Step H. 6-(3-Methoxybenzyl)-4-methyl-4,6-dihydro-5H-thiazolo[5',4':4,5]pyrrolo[2,3-d]pyridazin-5-one To a stirred mixture of 4-methyl-4,6-dihydro-5H-thiazolo[5',4':4,5]pyrrolo[2,3-d]pyridazin-5-one (2 g, 10.0 mmol) and K₂CO₃ (2.7 g, 20 mmol) in DMF (15 mL) was added 1-(chloromethyl)-3-methoxybenzene (2.3 g, 15 mmol). The reaction mixture was stirred at 50° C. for 3 hr. then poured into water and extracted with EtOAc twice. The combined organic layers were washed with brine, dried over anhydrous Na₂SO₄ and concentrated under reduced pressure. The residue was purified by column chromatography on silica gel (eluent: PE/EtOAc=5/1) to give the desired product (2 g, 67% yield). LCMS: m/z=327 (M+H)⁺. ¹H NMR (400 MHz, DMSO-d₆) 9.36 (s, 1H), 8.64 (s, 1H), 7.24 (t, 1H), 6.88-6.80 (m, 3H), 5.33 (s, 2H). 4.31 (s, 3H) 3.72 (s, 3H).

Step I. 2-Iodo-6-(3-methoxybenzyl)-4-methyl-4,6-dihydro-5H-thiazolo[5',4':4,5]pyrrolo[2,3-d]pyridazin-5-one To a stirred mixture of 6-(3-methoxybenzyl)-4-methyl-4,6-dihydro-5H-thiazolo[5',4':4,5]pyrrolo[2,3-d]pyridazin-5-one (1 g, 3 mmol) and t-BuOK (688 mg, 6 mmol) in toluene (30 mL) at r.t. was added 1,2,3,4,5-pentafluoro-6-iodobenzene (3.6 g, 12 mmol). The reaction mixture was stirred at 135° C. for 4 hr. (oil bath was pre-heated) and then concentrated under reduced pressure. The residue was purified by column chromatography on silica gel (eluent: PE/EtOAc=6/1) to afford the desired product (1 g, 72% yield). LCMS: m/z=453 (M+H)⁺. ¹H NMR (400 MHz, DMSO-d₆) δ 8.61 (s, 1H), 7.23 (t, 1H), 6.88-6.80 (m, 3H), 5.31 (s, 2H). 4.26 (s, 3H) 3.71 (s, 3H).

Step J. (4-Fluorobenzyl)zinc(II) Bromide

To a 25 mL three-necked round bottom flask was added Zn powder (1300 mg, 20 mmol). The mixture was degassed under high vacuum and back purged with N₂ three times. Dry THF (15 mL), TMSCl (108 mg, 1 mmol), and 1,2-dibromoethane (186 mg, 1 mmol) were added via syringe at room temperature. The suspension was heated to 65° C. for 30 min then cooled to 0° C., followed by drop wise addition of 1-(bromomethyl)-4-fluorobenzene (1.89 g, 10 mmol). The resulting mixture was stirred at r.t. for 1.5 hr. The supernatant solution was directly used for the next step.

Step K. 2-(4-Fluorobenzyl)-6-(3-methoxybenzyl)-4-methyl-4H-thiazolo[5',4':4,5]pyrrolo[2,3-d]pyridazin-5(6H)-one To a 25 mL three-necked round bottom flask were added 2-iodo-6-(3-methoxybenzyl)-4-methyl-4H-thiazolo[5',4':4,5]pyrrolo[2,3-d]pyridazin-5(6H)-one (100 mg, 0.22 mmol) and Pd(PPh₃)₄ (25.4 mg, 10 mol %). The flask was degassed under high vacuum and back purged with N₂ three times. The supernatant solution of (4-fluorobenzyl)zinc(II) bromide (6 mL) was added in via syringe to the flask. The resulting mixture was stirred under N₂ at 65° C. for 0.5 hr. then concentrated under reduced pressure. The residue was purified by prep-TLC to give the desired product (6 mg). LCMS: m/z=435 (M+H)⁺. ¹H NMR (400 MHz, DMSO-d₆) δ 8.53 (s, 1H), 7.75-7.50 (m, 1H), 7.47 (s, 2H), 7.23 (s, 3H), 6.84 (s, 2H), 5.31 (s, 2H), 4.52 (s, 2H), 4.26 (s, 3H), 3.71 (s, 3H).

The procedure set forth above was used to produce the following compounds using the appropriate starting materials. Standard amino group protection and deprotection can be used when appropriate. Examples of amino protecting group include but not limited to SEM. Deprotection of SEM can be carried in TFA and DCM.

| Cpd No. | Structure | Characterization |
|---|---|---|
| E2-3 | 6-(3-Methoxybenzyl)-4-methyl-2-(4-methylbenzyl)-4,6-dihydro-5H-thiazolo[5',4':4,5]pyrrolo[2,3-d]pyridazin-5-one | LCMS: m/z 431 (M + H)+. $^1$H NMR (400 MHz, DMSO-$d_6$) δ 8.52 (s, 1H), 7.29 (d, 2H), 7.23 (d, 1H), 7.18 (d, 2H), 6.84 (s, 2H), 6.82 (s, 1H), 5.31 (s, 2H), 4.46 (s, 2H), 4.26 (s, 3H), 3.71 (s, 3H), 2.29 (s, 3H). |
| E2-4 | 6-(3-Methoxybenzyl)-4-methyl-2-(4-(trifluoromethyl)benzyl)-5,6-dihydro-4H-thiazolo[5',4':4,5]pyrrolo[2,3-d]pyridazine | LC-MS: m/z 485 [M + 1]+. $^1$H NMR (400 MHz, DMSO-$d_6$) δ 8.55 (s, 1H), 7.75 (d, 2H), 7.65 (d, 2H), 7.22 (t, 1H), 6.84 (s, 2H), 6.82 (s, 1H), 5.31 (s, 2H), 4.65 (s, 2H), 4.26 (s, 3H), 3.71 (s, 3H). |
| E2-5 | 4-((6-(3-Methoxybenzyl)-4-methyl-5-oxo-5,6-dihydro-4H-thiazolo[5',4':4,5]pyrrolo[2,3-d]pyridazin-2-yl)methyl)benzonitrile | LC-MS: m/z 442 [M + 1]+. $^1$H NMR (400 MHz, DMSO-$d_6$) δ 8.56 (s, 1H), 7.85 (s, 2H), 7.63 (s, 2H), 7.23 (s, 1H), 6.84 (s, 3H), 5.31 (s, 2H), 4.65 (s, 2H), 4.25 (s, 3H), 3.71 (s, 3H). |
| E2-6 | 2-(4-Chlorobenzyl)-6-(3-methoxybenzyl)-4-methyl-4H-thiazolo[5',4':4,5]pyrrolo[2,3-d]pyridazin-5(6H)-one | LCMS: m/z 451 (M + H)+. $^1$H NMR (400 MHz, DMSO-$d_6$) δ 8.54 (s, 1H), 7.44 (s, 4H), 7.22 (t, 1H), 6.84-6.82 (m, 3H), 5.31 (s, 2H), 4.53 (s, 2H), 4.26 (s, 3H), 3.71 (s, 3H). |
| E2-7 | 2-(Cyclohexylmethyl)-6-(3-methoxybenzyl)-4-methyl-4H-thiazolo[5',4':4,5]pyrrolo[2,3-d]pyridazin-5(6H)-one | LCMS: m/z 423 (M + H)+. $^1$H NMR (400 MHz, DMSO-$d_6$) δ 8.55 (s, 1H), 7.23 (t, 1H), 6.84-6.82 (m, 3H), 5.32 (s, 2H), 4.26 (s, 3H), 3.71 (s, 3H), 3.02 (d, 2H), 1.76-1.59 (m, 5H), 1.25-1.00 (m, 6H). |

| Cpd No. | Structure | Characterization |
|---|---|---|
| E2-8 | 6-((1H-indazol-4-yl)methyl)-2-((1H-pyrazol-3-yl)methyl)-4-methyl-4,6-dihydro-5H-thiazolo[5',4':4,5]pyrrolo[2,3-d]pyridazin-5-one | LCMS: m/z = 417 (M + H)$^+$.<br>$^1$H NMR (400 MHz, DMSO-d$_6$) δ 13.12 (s, 1H), δ 12.72 (s, 1H), 8.55 (s, 1H), 8.15 (s, 1H), 7.67 (s, 1H), 7.45 (d, 1H), 7.28 (dd, 1H), 6.96 (d, 1H), 6.26 (d, 1H), 5.65 (s, 2H), 4.50 (s, 2H), 4.28 (s, 3H). |
| E2-9 | 2-((1H-pyrazol-3-yl)methyl)-6-((2,3-dihydrobenzo[b][1,4]dioxin-6-yl)methyl)-4-methyl-4,6-dihydro-5H-thiazolo[5',4':4,5]pyrrolo[2,3-d]pyridazin-5-one | LCMS: 435 (M + H)$^+$.<br>$^1$H NMR (400 MHz, DMSO-d$_6$) δ 12.77 (s, 1H), 8.51 (s, 1H), 7.71 (s, 1H), 6.78-6.65 (m, 3H), 6.26 (s, 1H), 5.21 (s, 2H), 4.47 (s, 2H), 4.26 (s, 3H), 4.19 (s, 4H). |
| E2-10 | 2-((1H-pyrazol-3-yl)methyl)-6-(4-methoxybenzyl)-1-methyl 4,6 dihydro-5H-thiazolo[5',4':4,5]pyrrolo[2,3-d]pyridazin-5-one | LCMS: m/z 407 (M + H)$^+$.<br>$^1$H NMR (400 MHz, DMSO-d$_6$) δ 12.94 (s, 1H), 8.56 (s, 1H), 7.72 (s, 1H), 7.31 (d, 2H), 6.91 (d, 2H), 6.29 (s, 1H), 5.30 (s, 2H), 4.50 (s, 2H), 4.30 (s, 3H), 3.75 (s, 3H). |
| E2-11 | 2-((1H-pyrazol-3-yl)methyl)-4-methyl-6-(quinolin-2-ylmethyl)-4,6-dihydro-5H-thiazolo[5',4':4,5]pyrrolo[2,3-d]pyridazin-5-one | LCMS: 428 (M + H)$^+$.<br>$^1$H NMR (400 MHz, DMSO-d$_6$) δ 12.78 (s, 1H), δ 8.58 (s, 1H), 8.31 (d, 1H), 7.94 (t, 2H), 7.71-7.50 (m, 3H), 7.28 (d, 1H), 6.27 (d, 1H), 5.64 (s, 2H), 4.51 (s, 2H), 4.27 (s, 3H). |

| Cpd No. | Structure | Characterization |
|---|---|---|
| E2-12 | 6-((1H-indazol-4-yl)methyl)-2-((6-chloropyridin-3-yl)methyl)-4-methyl-4,6-dihydro-5H-thiazolo[5',4':4,5]pyrrolo[2,3-d]pyridazin-5-one | LCMS: m/z 462 (M + H)$^+$.<br>$^1$H NMR (400 MHz, DMSO-d$_6$) δ 13.12 (s, 1H), 8.57 (s, 1H), 8.50 (d, 1H), 8.13 (s, 1H), 7.91 (dd, 1H), 7.54 (d, 1H), 7.45 (d, 1H), 7.26 (d, 1H), 6.95 (d, 1H), 5.65 (s, 2H), 4.59 (s, 2H), 4.26 (s, 3H). |
| E2-13 | 2-((1H-pyrazol-3-yl)methyl)-6-(3-methoxybenzyl)-4-methyl-4,6-dihydro-5H-thiazolo[5',4':4,5]pyrrolo[2,3-d]pyridazin-5-one | LCMS: m/z 407 (M + H)$^+$.<br>$^1$H NMR (400 MHz, DMSO-d$_6$) δ 12.79 (s, 1H), 8.54 (s, 1H), 8.43 (s, 1H), 7.73 (s, 1H), 7.23 (dd, 1H), 6.84-6.74 (m, 2H), 6.26 (d, 1H), 5.31 (s, 2H), 4.49 (s, 2H), 4.27 (s, 3H), 3.71 (s, 3H). |
| E2-14 | 6-((1H-indazol-4-yl)methyl)-2-(3-(hydroxymethyl)benzyl)-4-methyl-4,6-dihydro-5H-thiazolo[5',4':4,5]pyrrolo[2,3-d]pyridazin-5-one. | LCMS: m/z 457 (M + H)$^+$.<br>$^1$H NMR (400 MHz, DMSO-d$_6$) δ 13.12 (s, 1H), 8.54 (s, 1H), 8.14 (s, 1H), 7.45 (d, 1H), 7.38-7.21 (m, 5H), 6.96 (d, 1H), 5.65 (s, 2H), 5.21 (t, 1H), 4.49 (d, 4H), 4.28 (s, 3H). |
| E2-15 | 3-((6-((1H-indazol-4-yl)methyl)-4-methyl-5-oxo-5,6-dihydro-4H-thiazolo[5',4':4,5]pyrrolo[2,3-d]pyridazin-2-yl)methyl)benzamide | LCMS: m/z 470 (M + H)$^+$.<br>$^1$H NMR (400 MHz, DMSO-d$_6$) δ 13.11 (s, 1H), 8.55 (s, 1H), 8.13 (s, 1H), 7.97 (s, 1H), 7.91 (s, 1H), 7.80 (d, 1H), 7.57 (d, 1H), 7.47-7.43 (m, 2H), 7.37 (s, 1H), 7.28 (t, 1H), 6.95 (d, 1H), 5.65 (s, 2H), 4.57 (s, 2H), 4.27 (s, 3H). |

-continued

| Cpd No. | Structure | Characterization |
|---|---|---|
| E2-16 | 3-((6-((1H-Indazol-4-yl)methyl)-4-methyl-5-oxo-5,6-dihydro-4H-thiazolo[5',4':4,5]pyrrolo[2,3-d]pyridazin-2-yl)methyl)benzonitrile | LCMS: m/z 452 (M + H)+. $^1$H NMR (400 MHz, DMSO-$d_6$) δ 13.11 (s, 1H), 8.56 (s, 1H), 8.13 (s, 1H), 7.91 (s, 1H), 7.78 (m, 2H), 7.60 (t, 1H), 7.45 (d, 1H), 7.28 (t, 1H), 6.95 (d, 1H), 5.65 (s, 2H), 4.61 (s, 2H), 4.27 (s, 3H). |
| E2-17 | 4-((6-((1H-Indazol-4-yl)methyl)-4-methyl-5-oxo-5,6-dihydro-4H-thiazolo[5',4':4,5]pyrrolo[2,3-d]pyridazin-2-yl)methyl)benzonitrile | LCMS: m/z 452 (M + H)+. $^1$H NMR (400 MHz, DMSO-$d_6$) δ 13.21 (s, 1H), 8.66 (s, 1H), 8.23 (s, 1H), 7.94 (d, 2H), 7.73 (d, 2H), 7.54 (m, 1H), 7.38 (m, 1H), 7.04 (m, 1H), 5.75 (s, 2H), 4.74 (s, 2H), 3.05 (s, 3H). |
| E2-18 | 4-((6-((1H-indazol-4-yl)methyl)-4-methyl-5-oxo-5,6-dihydro-4H-thiazolo[5',4':4,5]pyrrolo[2,3-d]pyridazin-2-yl)methyl)benzamide | LC-MS: m/z 470 (M + H)+. $^1$H NMR (400 MHz, DMSO-$d_6$) δ 13.12 (s, 1H), 8.55 (s, 1H), 8.13 (s, 1H), 7.96 (s, 1H), 7.86 (d, 2H), 7.60-7.43 (m, 3H), 7.35 (s, 1H), 7.27 (d, 1H), 6.95 (d, 1H), 5.65 (s, 2H), 4.57 (s, 2H), 4.27 (s, 3H). |
| E2-19 | 6-((1H-indazol-4-yl)methyl)-2-(3-hydroxybenzyl)-4-methyl-4,6-dihydro-5H-thiazolo[5',4':4,5]pyrrolo[2,3-d]pyridazin-5-one | LCMS: 443 (M + H)+. $^1$H NMR (400 MHz, DMSO-$d_6$) δ 13.12 (s, 1H), 9.46 (s, 1H), 8.54 (s, 1H), 8.13 (s, 1H), 7.44 (d, 1H), 7.30-7.24 (m, 1H), 7.15 (t, 1H), 6.95 (d, 1H), 6.83-6.77 (m, 2H), 6.68 (dd, 1H), 5.65 (s, 2H), 4.41 (s, 2H), 4.28 (s, 3H). |
| E2-20 | 6-((1H-indazol-4-yl)methyl)-2-(4-hydroxybenzyl)-4-methyl-4H-thiazolo[5',4':4,5]pyrrolo[2,3-d]pyridazin-5(6H)-one | LCMS: m/z 443 (M + H)+. $^1$H NMR (400 MHz, DMSO-$d_6$) δ 13.12 (s, 1H), 9.43 (s, 1H), 8.53 (s, 1H), 8.14 (s, 1H), 7.45 (d, 1H), 7.30-7.25 (t, 1H), 7.20 (d, 2H), 6.95 (d, 1H), 6.76 (d, 2H), 5.65 (s, 2H), 4.37 (s, 2H), 4.27 (s, 3H). |

-continued

| Cpd No. | Structure | Characterization |
|---|---|---|
| E2-21 | 6-(1H-Indazol-4-ylmethyl)-8-methyl-2-(3-methylamino-benzyl)-6,8-dihydro-3-thia-1,5,6,8-tetraaza-cyclopenta[a]inden-7-one | LC-MS: m/z 456 (M + H)$^+$. $^1$H NMR (400 MHz, DMSO-d$_6$) δ 13.10 (s, 1H), 8.54 (s, 1H), 8.13 (s, 1H), 7.45 (d, 1H), 7.27 (t, 1H), 7.12 (t, 1H), 6.94 (d, 1H), 6.67 (s, 2H), 6.58 (d, 1H), 5.65 (s, 2H), 4.38 (s, 2H), 4.27 (s, 3H), 2.68 (s, 3H). |
| E2-22 | 6-((1H-Indazol-4-yl)methyl)-4-methyl-2-(4-(methylamino)benzyl)-4,6-dihydro-5H-thiazolo[5',4':4,5]pyrrolo[2,3-d]pyridazin-5-one | LC-MS: m/z 456 (M + 1)$^+$. $^1$H NMR (400 MHz, DMSO-d6) δ 13.11 (s, 1H), 8.51 (s, 1H), 8.13 (s, 1H), 7.44 (d, 1H), 7.31-7.21 (m, 1H), 7.11 (d, 2H), 6.95 (d, 1H), 6.52 (d, 2H), 5.64 (s, 3H), 4.30 (s, 2H), 4.27 (s, 3H), 2.66 (d, 3H). |
| E2-23 | 2-chloro-6-(3-methoxybenzyl)-4-methyl-4H-thiazolo[5',4':4,5]pyrrolo[2,3-d]pyridazin-5(6H)-one | LCMS: m/z 361 (M + H)$^+$. $^1$H NMR (400 MHz, DMSO-d$_6$) δ 8.65 (s, 1H), 7.24 (t, 1H), 6.86-6.83 (m, 3H), 5.32 (s, 2H), 4.25 (s, 3H), 3.72 (s, 3H). |
| E2-24 | 6-((1H-indazol-4-yl)methyl)-2-benzyl-4-methyl-4H-thiazolo[5',4':4,5]pyrrolo[2,3-d]pyridazin-5(6H)-one | LCMS: m/z 427 (M + H)$^+$. $^1$H NMR (400 MHz, DMSO-d$_6$) δ 13.11 (s, 1H), 8.55 (s, 1H), 8.13 (s, 1H), 7.51-7.35 (m, 5H), 7.25-7.33 (m, 2H), 6.95 (d, 1H), 5.65 (s, 2H), 4.51 (s, 2H), 4.28 (s, 3H). |

Example 2B. Synthesis of 2-benzyl-6-(3-methoxybenzyl)-4-methyl-4H-thiazolo[5',4':4,5]pyrrolo[2,3-d]pyridazin-5(6H)-one

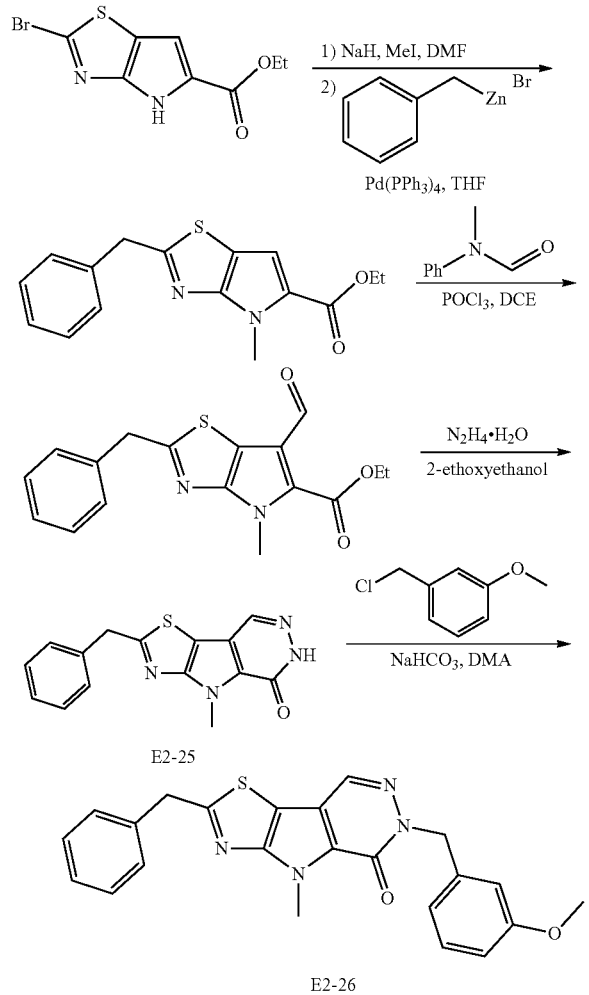

E2-25

E2-26

Step A. Ethyl 2-bromo-4-methyl-4H-pyrrolo[2,3-d]thiazole-5-carboxylate

To a solution of ethyl 2-bromo-4H-pyrrolo[2,3-d]thiazole-5-carboxylate (1.1 g, 4 mmol) in anhydrous DMF (10 mL) was added NaH (320 mg, 60% in oil, 8 mmol). The reaction mixture was stirred at r.t. for 15 min, followed by addition of MeI (852 mg, 6 mmol). The resulting mixture was stirred at r.t. for another 2 hr. then quenched with saturated aqueous NH₄Cl and extracted with EtOAc. The combined organic layers were washed with water and brine, dried over anhydrous Na₂SO₄ and concentrated under reduced pressure. The residue was purified by column chromatography on silica gel (eluent: PE/EtOAc=5/1) to give the desired product (950 mg, 82.2% yield). LCMS: m/z 289 (M+H)⁺.

Step B. Ethyl 2-benzyl-4-methyl-4H-pyrrolo[2,3-d]thiazole-5-carboxylate

To a mixture of ethyl 2-bromo-4-methyl-4H-pyrrolo[2,3-d]thiazole-5-carboxylate (720 mg, 2.5 mmol) and Pd(PPh₃)₄ (145 mg, 0.125 mmol) in dry THF under N₂ was added benzylzinc bromide (20 mL, 0.5 M). The reaction mixture stirred at 65° C. for 1 hr. then quenched with saturated aqueous NH₄Cl and extracted with EtOAc. The combined organic layers were washed with brine, dried over anhydrous Na₂SO₄ and concentrated under reduced pressure. The residue was purified by column chromatography on silica gel (eluent: PE/EtOAc=4/1) to give the desired product (600 mg, 80.0% yield). LCMS: m/z 301 (M+H)⁺.

Step C. Ethyl 2-benzyl-6-formyl-4-methyl-4H-pyrrolo[2,3-d]thiazole-5-carboxylate To a solution of ethyl 2-benzyl-4-methyl-4H-pyrrolo[2,3-d]thiazole-5-carboxylate (600 mg, 2 mmol) in 1,2-dichloroethane (6 mL) were added a mixture of phosphorus oxychloride (612 mg, 4 mmol) and N-methyl-N-phenylformamide (540 mg, 4 mmol). The reaction mixture was refluxed overnight then cooled down and poured into ice-water, and then extracted with DCM. The combined organic layers were washed with brine, dried over anhydrous Na₂SO₄ and concentrated under reduced pressure. The residue was purified by column chromatography on silica gel (eluent: PE/EtOAc=3/1) to give the desired product (140 mg) as yellow oil. LCMS: m/z 329 (M+H)⁺.

Step D. 2-Benzyl-4-methyl-4H-thiazolo[5,4':4,5]pyrrolo[2,3-d]pyridazin-5(6H)-one To a solution of ethyl 2-benzyl-6-formyl-4-methyl-4H-pyrrolo[2,3-d]thiazole-5-carboxylate (140 mg, crude) in 2-ethoxyethanol (3 mL) was added hydrazine hydrate (0.5 mL, 98% wt). The reaction mixture was stirred at 110° C. for 1 hr. then cooled to r.t. The precipitate was collected by filtration and washed with MeOH to give the desired product (60 mg, 10.1% yield over 2 steps). LCMS: m/z 297 (M+H)⁺.

Step E. 2-Benzyl-6-(3-methoxybenzyl)-4-methyl-4H-thiazolo[5',4':4,5]pyrrolo[2,3-d]pyridazin-5(6H)-one To a mixture of 2-benzyl-4-methyl-4H-thiazolo[5',4':4,5]pyrrolo[2,3-d]pyridazin-5(6H)-one (50 mg, 0.169 mmol) and NaHCO₃ (28 mg, 0.338 mmol) in DMA (1 mL) under N₂ was added 1-(chloromethyl)-3-methoxybenzene (40 mg, 0.254 mmol). The reaction mixture was stirred at 120° C. for 3 hr. then quenched with saturated aqueous NH₄Cl and extracted with EtOAc. The combined organic layers were concentrated under reduced pressure and the residue was purified by prep-HPLC to give the desired product (8 mg, 11.4% yield). LCMS: m/z 417 (M+H)⁺. ¹H NMR (400 MHz, DMSO-d₆) δ 8.53 (s, 1H), 7.36-7.43 (m, 4H), 7.30-7.32 (m, 1H), 7.20-7.25 (m, 1H), 6.82-6.85 (m, 3H), 5.31 (s, 2H), 4.51 (s, 2H), 4.27 (s, 3H), 3.71 (s, 3H).

Example 2C. Synthesis of 6-((1H-indazol-4-yl)methyl)-4-methyl-2-(1-phenylethyl)-4H-thiazolo[5',4':4,5]pyrrolo[2,3-d]pyridazin-5(6H)-one

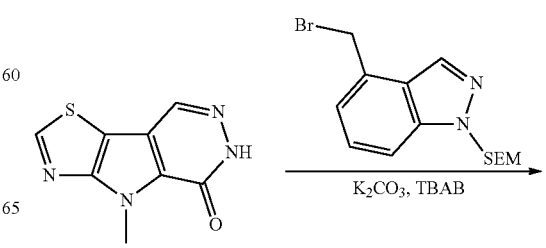

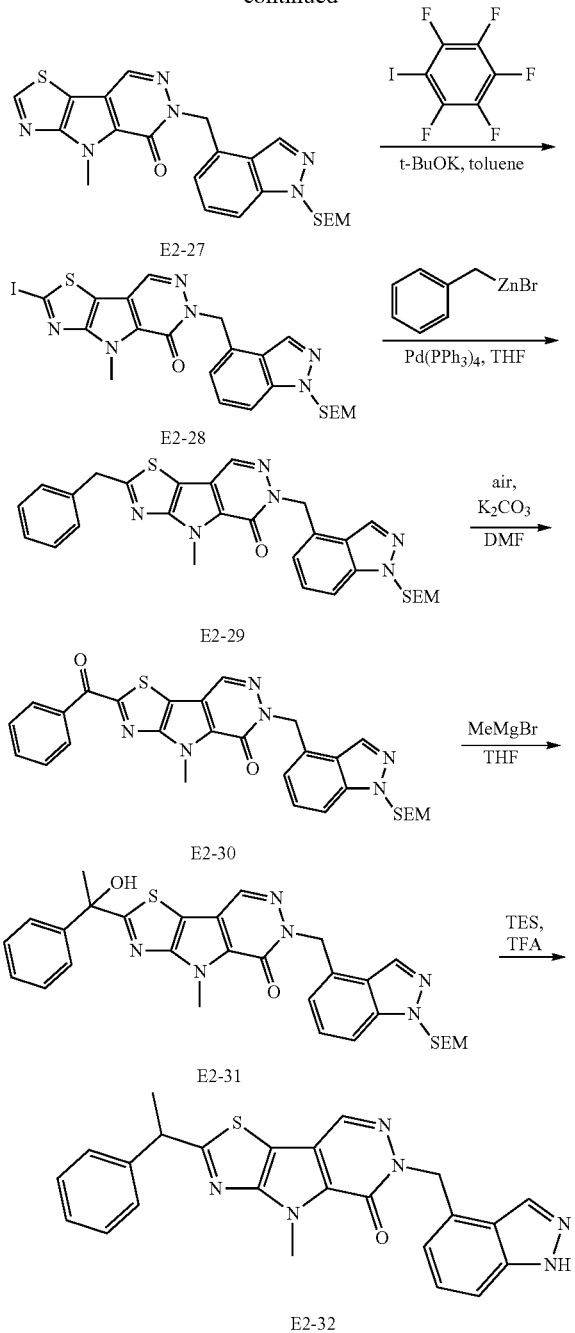

Step A

4-Methyl-6-((1-((2-(trimethylsilyl)ethoxy)methyl)-1H-indazol-4-yl)methyl)-4,6-dihydro-5H-thiazolo[5',4':4,5]pyrrolo[2,3-d]pyridazin-5-one was synthesized using the procedure similar to Example 2A. LCMS: m/z 467 (M+H)+.

Step B

2-Iodo-4-methyl-6-((1-((2-(trimethylsilyl)ethoxy)methyl)-1H-indazol-4-yl)methyl)-4,6-dihydro-5H-thiazolo[5',4':4,5]pyrrolo[2,3-d]pyridazin-5-one was synthesized using the procedure similar to Example 2A. LCMS: 593 (M+H)+.

Step C. 2-Benzyl-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one Zinc powder (1.3 g, 20 mmol) was suspended in anhydrous THF (5 mL) under N₂, followed by addition of 1,2-dibromoethane (0.01 mL). The mixture was heated at 65° C. for 5 min, followed by addition of chlorotrimethylsilane (0.01 mL). The resulting mixture was heated at 65° C. for another 15 min then cooled to 0° C., followed by drop wise addition of a solution of (bromomethyl)benzene (1.7 g, 10 mmol) in anhydrous THF (5 mL). The resulting mixture was stirred for 1 hr. at 65° C. then cooled down to afford benzylzinc (II) bromide (around 1 M in THF) which was used directly in the next step. To a mixture of 2-iodo-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (300 mg, 0.5 mmol) in dry THF (2 mL) under N₂ was added in sequence Pd(PPh₃)₄ (58 mg, 0.05 mmol) and the above benzylzinc(II) bromide (5 ml, 1 M). The resulting mixture was heated at 65° C. for 1 hr. then poured into water and extracted with EtOAc. The combined organic layers were washed with brine, dried over anhydrous Na₂SO₄ and concentrated under reduced pressure. The residue was purified by column chromatography on silica gel (eluent: PE/EtOAc=5/2) to give the desired product (230 mg, 82.7% yield). LCMS: 557 (M+H)+.

Step D. 2-Benzoyl-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one To a mixture of 2-benzyl-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (100 mg, 0.18 mmol) in DMF (5 mL) was added K₂CO₃ (74 mg, 0.53 mmol). The mixture was stirred at 50° C. under air for 4 hr. then poured into water. The precipitate was collected by filtration, washed with PE, and dried under high vacuum to afford the desired product (100 mg, 98% yield). LCMS: 571 (M+H)+.

Step E. 2-(1-Hydroxy-1-phenylethyl)-4-methyl-6-((1-((2-(trimethylsilyl) ethoxy)methyl)-1H-indazol-4-yl)methyl)-4H-thiazolo[5',4':4,5]pyrrolo[2,3-d]pyridazin-5(6H)-one To a mixture of methyl magnesium bromide (0.6 mL, 1.5 M) in dry THF (2 mL) under ice bath was added a solution of 2-benzoyl-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (100 mg, 0.175 mmol) in dry THF. The mixture was stirred for 1 hr. and poured into saturated aqueous NH₄Cl and extracted with EtOAc. The combined organic layers were washed with brine, dried over anhydrous Na₂SO₄ and concentrated under reduced pressure. The residue was purified by prep-TLC to give the desired product (30 mg, 29.4% yield) as oil. LCMS: 587 (M+H)+.

Step F. 6-((1H-indazol-4-yl)methyl)-4-methyl-2-(1-phenyethyl)-4H-thiazolo[5',4':4,5]pyrrolo[2,3-d]pyridazin-5(6H)-one A solution of 2-(1-hydroxy-1-phenylethyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5

(6H)-one (30 mg, 0.05 mmol) in a mixed solution of TFA/TES (2 mL/0.5 mL) was stirred at r.t. for 2 hr. then concentrated under reduced pressure. The residue was purified by prep-HPLC to afford the desired product (5 mg, 22.7% yield). LCMS: m/z 441 (M+H)+. $^1$H NMR (400 MHz, DMSO-d$_6$) δ 13.11 (s, 1H), 8.53 (s, 1H), 8.12 (s, 1H), 7.46-7.41 (m, 3H), 7.37 (t, 2H), 7.28 (m, 2H), 6.95 (d, 1H), 5.65 (s, 2H), 4.71 (q, 1H), 4.28 (s, 3H), 1.78 (d, 3H).

A byproduct, 4-methyl-6-((1-methyl-1H-indazol-4-yl)methyl)-2-(1-phenylethyl)-4,6-dihydro-5H-thiazolo[5',4':4,5]pyrrolo[2,3-d]pyridazin-5-one was also obtained by prep-HPLC:

E2-33

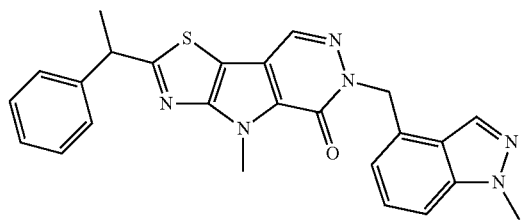

LCMS: m/z 455 (M+H)+. $^1$H NMR (400 MHz, DMSO-d$_6$) δ 8.52 (s, 2260 (s, 1H), 7.41 (d, 1H), 7.42-7.30 (m, 6H), 6.97 (d, 1H), 5.64 (s, 2H), 4.70 (q, 1H), 4.27 (s, 3H), 4.09 (s, 3H), 1.77 (d, 3H).

| Cpd No. | Structure | Characterization |
|---|---|---|
| E2-34 | 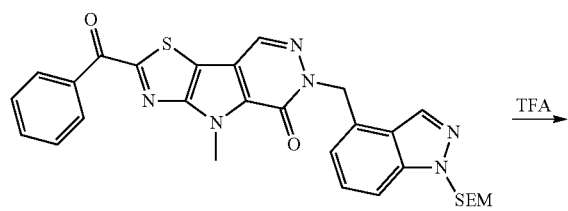<br>6-((1H-indazol-4-yl)methyl)-2-(1-(1H-pyrazol-3-yl)ethyl)-4-methyl-4,6-dihydro-5H-thiazolo[5',4':4,5]pyrrolo[2,3-d]pyridazin-5-one | LCMS: m/z 431 (M + H)+.<br>$^1$H NMR (400 MHz, DMSO-d$_6$) δ 13.12 (s, 1H), 12.71 (s, 1H), 8.54 (s, 1H), 8.14 (s, 1H), 7.68 (s, 1H), 7.45 (d, 1H), 7.28 (dd, 1H), 6.95 (d, 1H), 6.28 (d, 1H), 5.65 (s, 2H), 4.72 (s, 1H), 4.30 (s, 3H), 1.76 (d, 3H), |

Example 2D. Synthesis of 6-((1H-indazol-4-yl)methyl)-2-(1-hydroxy-1-phenylethyl)-4-methyl-4,6-dihydro-5H-thiazolo[5',4':4,5]pyrrolo[2,3-d]pyridazin-5-one

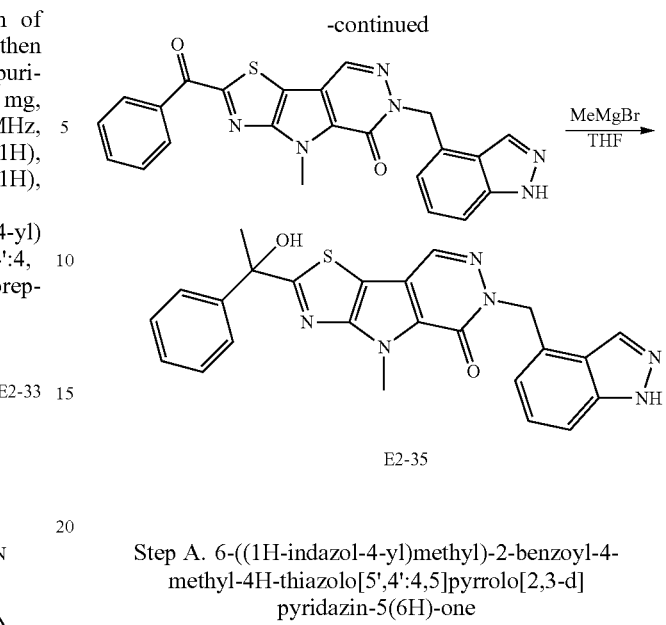

Step A. 6-((1H-indazol-4-yl)methyl)-2-benzoyl-4-methyl-4H-thiazolo[5',4':4,5]pyrrolo[2,3-d]pyridazin-5(6H)-one To a mixture of 2-benzoyl-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (75 mg, 0.13 mmol) in DCM (2 mL) was added TFA (2 mL). The mixture was stirred at r.t. for 2 hr. then concentrated under reduced pressure. The residue was purified by prep-TLC to afford the desired product (30 mg, 52.6% yield). LCMS: 441 (M+H)+.

Step B. 6-((1H-indazol-4-yl)methyl)-2-(1-hydroxy-1-phenylethyl)-4-methyl-4H-thiazolo[5',4':4,5]pyrrolo[2,3-d]pyridazin-5(6H)-one To a mixture of methyl magnesium bromide (0.22 mL, 1.5 M) in dry THF (1 mL) under ice bath was added a solution of 6-((1H-indazol-4-yl)methyl)-2-benzoyl-4-methyl-4H-thiazolo[5',4':4,5]pyrrolo[2,3-d]pyridazin-5(6H)-one (30 mg, 0.068 mmol) in dry THF. The mixture was stirred for 30 min then poured into saturated aqueous NH$_4$Cl and extracted with EtOAc. The combined organic layers were concentrated under reduced pressure. The residue was purified by prep-HPLC to afford the desired product (8 mg, 25.8% yield). LCMS: 457 (M+H)+. $^1$H NMR (400 MHz, DMSO-d$_6$) δ 13.11 (s, 1H), 8.56 (s, 1H), 8.13 (s, 1H), 7.62 (d, 2H), 7.45 (d, 1H), 7.34 (t, 2H), 7.29-7.23 (m, 2H), 6.99-6.93 (m, 2H), 5.65 (s, 2H), 4.26 (s, 3H), 2.01 (s, 3H).

The procedure set forth above was used to produce the following compounds using the appropriate starting materials.

| Cpd No. | Structure | Characterization |
|---|---|---|
| E2-36 | 6-((1H-indazol-4-yl)methyl)-2-(1-hydroxy-1-(1H-pyrazol-3-yl)ethyl)-4-methyl-4,6-dihydro-5H-thiazolo[5',4':4,5]pyrrolo[2,3-d]pyridazin-5-one | LCMS: m/z 447 (M + H)$^+$. $^1$H NMR (400 MHz, DMSO-d$_6$) δ 13.11 (s, 1H), 8.58 (s, 1H), 8.13 (d, 1H), 7.56 (d, 1H), 7.45 (d, 1H), 7.28 (dd, 1H), 6.97-6.86 (m, 2H), 6.22 (d, 1H), 5.66 (s, 2H), 4.23 (s, 3H), 2.00 (s, 3H). |
| E2-37 | 6-((1H-indazol-4-yl)methyl)-2-(hydroxy(pyridin-2-yl)methyl)-4-methyl-4,6-dihydro-5H-thiazolo[5',4':4,5]pyrrolo[2,3-d]pyridazin-5-one | LCMS: m/z 444 (M + H)$^+$. $^1$H NMR (400 MHz, DMSO-d$_6$) δ 13.12 (s, 1H), 8.60 (s, 1H), 8.53 (d, 1H), 8.14 (s, 1H), 7.85 (d, 1H), 7.59 (d, 1H), 7.45 (d, 1H), 7.35 (s, 1H), 7.29 (d, 1H), 7.16 (d, 1H), 6.96 (d, 1H), 6.09 (d, 1H), 5.66 (s, 2H), 4.22 (s, 3H). |
| E2-38 | 2-(3-hydroxybenzoyl)-6-(3-methoxybenzyl)-4-methyl-4,6-dihydro-5H-thiazolo[5',4':4,5]pyrrolo[2,3-d]pyridazin-5-one | LCMS: m/z 447 (M + H)$^+$. $^1$H NMR (400 MHz, DMSO-d$_6$) δ 9.97 (s, 1H), 8.76 (s, 1H), 7.96 (d, 1H), 7.88 (s, 1H), 7.44 (dd, 1H), 7.23 (dd, 1H), 7.17 (d, 1H), 6.90-6.83 (m, 3H), 5.35 (s, 2H), 4.37 (s, 3H), 3.72 (s, 3H). |

Example 2E. Synthesis of 2-(hydroxy(phenyl)methyl)-6-(3-methoxybenzyl)-4-methyl-4H-thiazolo[5',4':4,5]pyrrolo[2,3-d]pyridazin-5(6H)-one

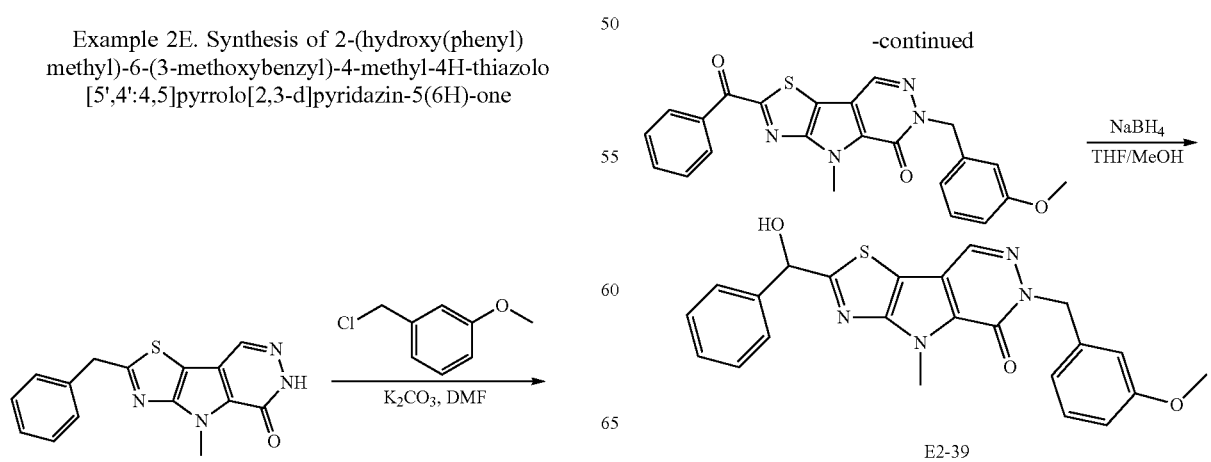

E2-39

Step A. 2-Benzoyl-6-(3-methoxybenzyl)-4-methyl-4H-thiazolo[5',4':4,5]pyrrolo[2,3-d]pyridazin-5(6H)-one To a solution of 2-benzyl-4-methyl-4H-thiazolo[5',4':4,5]pyrrolo[2,3-d]pyridazin-5(6H)-one (40 mg, 0.135 mmol) and $K_2CO_3$ (37 mg, 0.27 mmol) in DMF (1 mL) was added 1-(chloromethyl)-3-methoxybenzene (31 mg, 0.2 mmol). The reaction mixture was stirred at r.t. in the air overnight then poured into water. The precipitate was collected by filtration and washed with EtOAc to give desired product (30 mg, 51.7% yield). LCMS: m/z 431 (M+H)$^+$. $^1$H NMR (400 MHz, DMSO-d$_6$) δ 8.76 (s, 1H), 8.46-8.49 (m, 2H), 7.78 (t, 1H), 7.66 (t, 2H), 7.25 (t, 1H), 6.84-6.89 (m, 3H), 5.36 (s, 2H), 4.37 (s, 3H), 3.73 (s, 3H).

Step B. 2-(Hydroxy(phenyl)methyl)-6-(3-methoxybenzyl)-4-methyl-4H-thiazolo[5',4':4,5]pyrrolo[2,3-d]pyridazin-5(6H)-one To a mixture of 2-benzoyl-6-(3-methoxybenzyl)-4-methyl-4H-thiazolo[5',4':4,5]pyrrolo[2,3-d]pyridazin-5(6H)-one (20 mg, 0.047 mmol) in THF (1 mL) and MeOH (1 mL) was added NaBH$_4$ (3.5 mg, 0.093 mmol). The mixture was stirred at rt. for 15 min, quenched with water and extracted with EtOAc. The organic layer was separated and concentrated under reduced pressure. The residue was purified by prep-TLC to give desired product (13 mg, 64.0% yield). LCMS: m/z 433 (M+H)$^+$. $^1$H NMR (400 MHz, DMSO-d$_6$) δ 8.58 (s, 1H), 7.49-7.53 (m, 2H), 7.36-7.40 (m, 2H), 7.28-7.33 (m, 1H), 7.20-7.25 (m, 1H), 7.07 (d, 1H), 6.82-6.85 (m, 3H), 6.08 (d, 1H), 5.31 (d, 2H), 4.21 (s, 3H), 3.71 (s, 3H).

The procedure set forth above was used to produce the following compounds using the appropriate starting materials.

Example 2F. Synthesis of 6-((1H-indazol-4-yl)methyl)-2-(hydroxy(phenyl)methyl)-4-methyl-4,6-dihydro-5H-thiazolo[5',4':4,5]pyrrolo[2,3-d]pyridazin-5-one

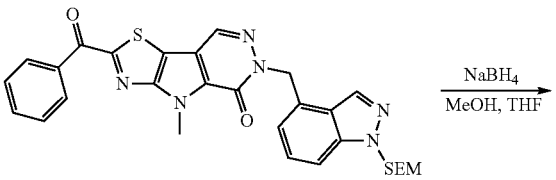

NaBH$_4$
MeOH, THF

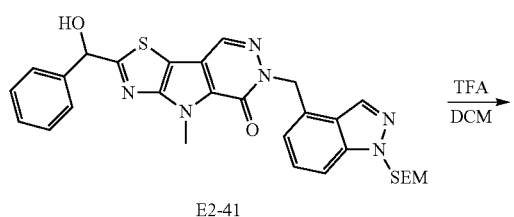

E2-41

TFA
DCM

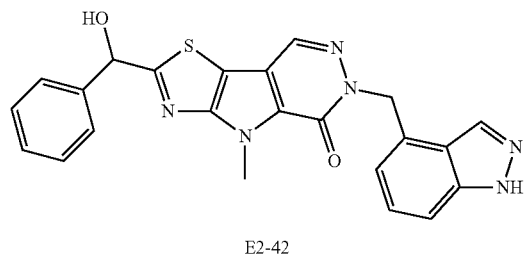

E2-42

| Cpd No. | Structure | Characterization |
|---|---|---|
| E2-40 | 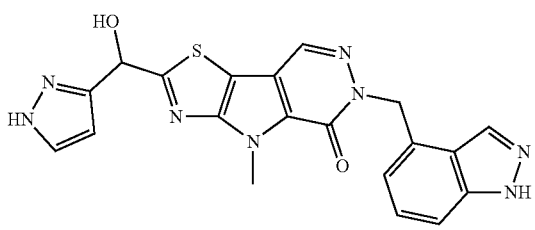 [SMILES: Cn1c2nc(C(O)c3cc[nH]n3)sc2c2cnn(Cc3cccc4[nH]ncc34)c(=O)c21]<br>6-((1H-indazol-4-yl)methyl)-2-(hydroxy(1H-pyrazol-3-yl)methyl)-4-methyl-4,6-dihydro-5H-thiazolo[5',4':4,5]pyrrolo[2,3-d]pyridazin-5-one | LCMS: m/z 433 (M + H)$^+$.<br>$^1$H NMR (400 MHz, DMSO-d$_6$) δ 13.12 (s, 1H), 12.75 (s, 1H), 8.60 (s, 1H), 8.14 (s, 1H), 7.65 (s, 1H), 7.45 (d, 1H), 7.28 (dd, 1H), 6.96 (d, 1H), 6.85 (s, 1H), 6.21 (s, 1H), 6.09 (s, 1H), 5.66 (s, 2H), 4.23 (s, 3H). |

Step A 2-(Hydroxy(phenyl)methyl)-4-methyl-6-((1-((2-(trimethylsilyl)ethoxy) methyl)-1H-indazol-4-yl)methyl)-4H-thiazolo[5',4':4,5]pyrrolo[2,3-d]pyridazin-5(6H)-one was synthesized using the procedure similar to Example 2E. LCMS: m/z 573 (M+H)+.

Step B 6-((1H-indazol-4-yl)methyl)-2-(hydroxy(phenyl)methyl)-4-methyl-4H-thiazolo[5',4':4,5]pyrrolo[2,3-d]pyridazin-5(6H)-one was synthesized using the procedure similar to Example 2D. LCMS: m/z 443 (M+H)+. $^1$H NMR (400 MHz, DMSO-$d_6$) δ 13.12 (s, 1H), 8.59 (s, 1H), 8.13 (s, 1H), 7.56-7.42 (m, 3H), 7.37 (s, 2H), 7.28 (m, 2H), 7.07 (s, 1H), 6.95 (s, 1H), 6.08 (s, 1H), 5.65 (s, 2H), 4.21 (s, 3H).

Example 2G. Synthesis of methyl 6-(3-methoxybenzyl)-4-methyl-5-oxo-5,6-dihydro-4H-thiazolo[5',4':4,5]pyrrolo[2,3-d]pyridazine-2-carboxylate

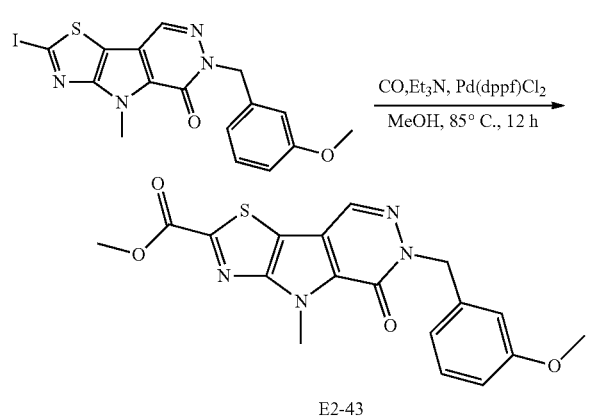

E2-43

To a stirred mixture of 2-iodo-6-(3-methoxybenzyl)-4-methyl-4H-thiazolo[5',4':4,5]pyrrolo[2,3-d]pyridazin-5(6H)-one (40 mg, 0.088 mmol) in MeOH (5 mL) were added Et$_3$N (27 mg, 0.264 mmol) and Pd(dppf)Cl$_2$ (6.5 mg, 0.009 mmol). The reaction mixture was stirred at 85° C. under CO for 12 hr. then concentrated under reduced pressure. The residue was purified by prep-HPLC to afford the desired product (2 mg, 5.88% yield). LC-MS: m/z 385 (M+H)+. $^1$H NMR (400 MHz, DMSO-$d_6$) δ 8.72 (s, 1H), 7.24 (t, 1H), 6.95-6.81 (m, 3H), 5.34 (s, 2H), 4.29 (s, 3H), 3.99 (s, 3H), 3.72 (s, 3H).

A similar reaction was carried out with 2-chloro-6-(3-methoxybenzyl)-4-methyl-4H-thiazolo[5',4':4,5]pyrrolo[2,3-d]pyridazin-5(6H)-one, which generated 2-methoxy-6-(3-methoxybenzyl)-4-methyl-4,6-dihydro-5H-thiazolo[5',4':4,5]pyrrolo[2,3-d]pyridazin-5-one as the major byproduct. LC-MS: m/z 357 (M+H)+. $^1$H NMR (400 MHz, DMSO-$d_6$) δ 8.50 (s, 1H), 7.26-7.21 (m, 1H), 6.88-6.80 (m, 3H), 5.30 (s, 2H), 4.19 (brs, 6H), 3.72 (s, 3H).

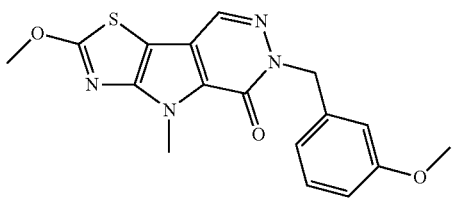

Example 2H. Synthesis of 2-(fluoro(phenyl)methyl)-6-(3-methoxybenzyl)-4-methyl-4H-thiazolo[5',4':4,5]pyrrolo[2,3-d]pyridazin-5(6H)-one

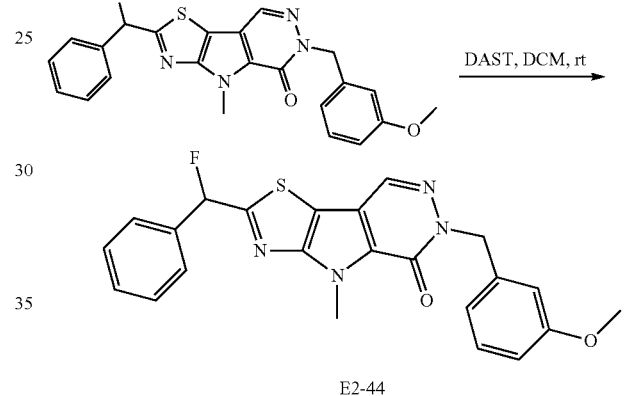

E2-44

To a solution of 2-(hydroxy(phenyl)methyl)-6-(3-methoxybenzyl)-4-methyl-4H-thiazolo[5',4':4,5]pyrrolo[2,3-d]pyridazin-5(6H)-one (20 mg, 0.046 mmol) in DCM (2 mL) under −78° C. was added DAST (0.3 mL). The mixture was stirred at r.t. for 30 min then concentrated under reduced pressure. The residue was purified by prep-TLC to give the desired product (2.5 mg, 12.5% yield). LCMS: 435. (M+H)+. $^1$H NMR (400 MHz, DMSO-$d_6$) δ 8.64 (s, 1H), 7.55-7.48 (m, 5H), 7.26-7.07 (m, 2H), 6.92-6.74 (m, 3H), 5.32 (s, 2H), 4.25 (s, 3H), 3.71 (s, 3H).

Example 2I. Synthesis of 6-((1H-indazol-4-yl)methyl)-2-(amino(phenyl)methyl)-4-methyl-4,6-dihydro-5H-thiazolo[5',4':4,5]pyrrolo[2,3-d]pyridazin-5-one

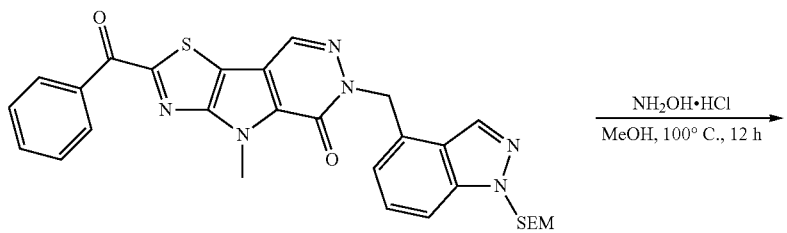

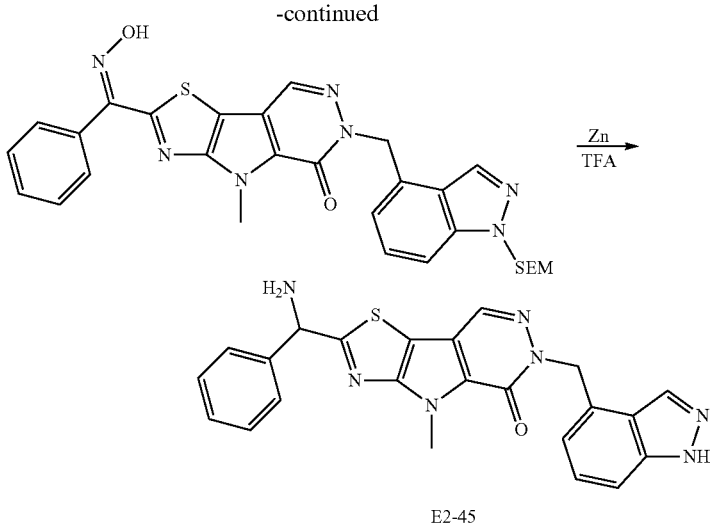

E2-45

Step A. (Z)-2-((Hydroxyimino) (phenyl)methyl)-4-methyl-6-((1-((2-(trimethylsilyl) ethoxy)methyl)-1H-indazol-4-yl)methyl)-4H-thiazolo[5',4':4,5]pyrrolo[2,3-d]pyridazin-5(6H)-one A mixture of 2-benzoyl-4-methyl-6-((1-((2-(trimethylsilyl) ethoxy)methyl)-1H-indazol-4-yl)methyl)-4H-thiazolo[5',4':4,5]pyrrolo[2,3-d]pyridazin-5(6H)-one (100 mg, 0.175 mmol) and NH$_2$OH.HCl (123 mg, 1.75 mmol). in anhydrous MeOH (5 mL) was stirred at 100° C. in a sealed tube for 12 hr. Then poured into saturated aqueous NH$_4$Cl (20 mL) and extracted with DCM. The combined organic layers were washed with brine, dried over anhydrous Na$_2$SO$_4$, and concentrated under reduced pressure. The residue was purified by column chromatography on silica gel (eluent: PE/EA=2/1) to afford the desired product (40 mg, 39.1% yield). LC-MS: m/z 586 (M+H)$^+$.

Step B. 6-((1H-Indazol-4-yl)methyl)-2-(amino(phenyl)methyl)-4-methyl-4H-thiazolo[5',4':4,5]pyrrolo[2,3-d]pyridazin-5(6H)-one To a stirred mixture of (Z)-2-((hydroxyimino)(phenyl)methyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (40 mg, 0.068 mmol) in TFA (3 mL) was added Zn (44 mg, 0.68 mmol). The reaction mixture was stirred at r.t. for 16 hr. then poured into saturated aqueous NaHCO$_3$ (20 mL) and extracted with DCM. The combined organic layers were washed with brine, dried over anhydrous Na$_2$SO$_4$, and concentrated under reduced pressure. The residue was purified by prep-HPLC to afford the desired product (4.6 mg, 14.8% yield). LC-MS: m/z 442 (M+H)$^+$.
$^1$H NMR (400 MHz, DMSO-d$_6$) δ 13.11 (s, 1H), 8.58 (s, 1H), 8.13 (s, 1H), 7.52-7.40 (m, 3H), 7.39-7.32 (m, 2H), 7.30-7.22 (m, 2H), 6.95 (d, 1H), 5.65 (s, 2H), 5.49 (s, 1H), 4.20 (s, 3H).

The procedure set forth above was used to produce the following compounds using the appropriate starting materials.

| Cpd No. | Structure | Characterization |
|---|---|---|
| E2-46 | ![structure] 6-((1H-indazol-4-yl)methyl)-2-(amino(1H-pyrazol-3-yl)methyl)-4-methyl-4,6-dihydro-5H-thiazolo[5',4':4,5]pyrrolo[2,3-d]pyridazin-5-one | LC-MS: m/z: 432 (M + H)$^+$. $^1$H NMR (400 MHz, DMSO-d$_6$): δ 8.62 (s, 1H), 8.15 (s, 1H), 7.88 (s, 1H), 7.56 (d, 1H), 7.29 (t, H), 6.99 (d, 1H), 6.51 (s, 1H), 6.28 (s, 1H), 5.66 (s, 2H), 4.33 (s, 3H). |

Example 2J. Synthesis of N-((6-((1H-indazol-4-yl)methyl)-4-methyl-5-oxo-5,6-dihydro-4H-thiazolo[5',4':4,5]pyrrolo[2,3-d]pyridazin-2-yl)(1H-pyrazol-3-yl)methyl)acetamide

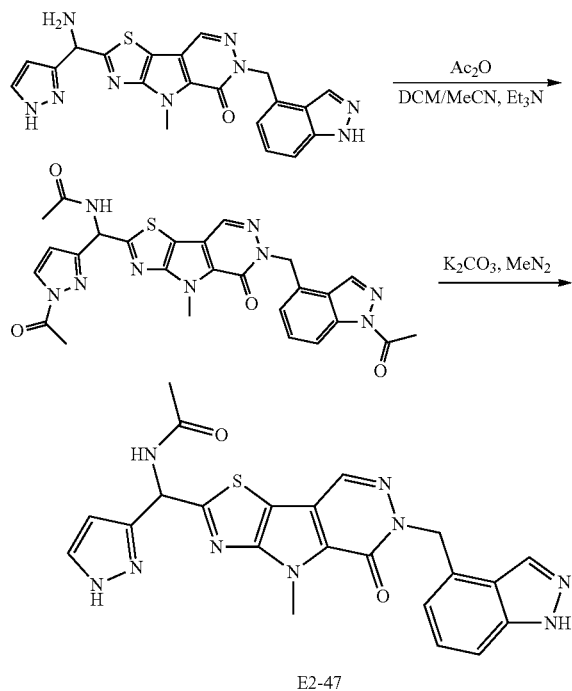

E2-47

Step A. N-((6-((1-acetyl-1H-indazol-4-yl)methyl)-4-methyl-5-oxo-5,6-dihydro-4H-thiazolo[5',4':4,5]pyrrolo[2,3-d]pyridazin-2-yl)(1-acetyl-1H-pyrazol-3-yl)methyl) acetamide To a stirred mixture of 6-((1H-indazol-4-yl)methyl)-2-(amino(1H-pyrazol-3-yl)methyl)-4-methyl-4H-thiazolo[5',4':4,5]pyrrolo[2,3-d]pyridazin-5(6H)-one (20 mg, 0.046 mmol) in DCM/MeCN (1 mL/1 mL) was added Et₃N (14 mg, 0.139 mmol) and acetic anhydride (24 mg, 0.23 mmol). The resulting mixture was stirred at 23° C. for 1 hr. then quenched with water and extracted with DCM. The combined organic layers were dried over anhydrous Na₂SO₄ and concentrated under reduced pressure to afford the crude product (30 mg) which was directly used in the next step without any further purification. LCMS: m/z 558 (M+H)⁺.

Step B. N-((6-((1H-indazol-4-yl)methyl)-4-methyl-5-oxo-5,6-dihydro-4H-thiazolo[5',4':4,5]pyrrolo[2,3-d]pyridazin-2-yl)(1H-pyrazol-3-yl)methyl)acetamide To a stirred mixture of N-((6-((1-acetyl-1H-indazol-4-yl)methyl)-4-methyl-5-oxo-5,6-dihydro-4H-thiazolo[5',4':4,5]pyrrolo[2,3-d]pyridazin-2-yl)(1-acetyl-1H-pyrazol-3-yl)methyl)acetamide (30 mg, 0.053 mmol) in MeOH (3 mL) under N₂ was added K₂CO₃ (22 mL, 0.16 mmol). The mixture was stirred at 23° C. for 30 min then quenched with saturated aqueous NH₄Cl and extracted with DCM. The combined organic layers were dried over anhydrous Na₂SO₄ and concentrated under reduced pressure. The residue was purified by prep-HPLC to afford the desired product (2.0 mg, 9% yield). LC-MS: m/z: 474 (M+H)⁺. ¹H NMR (400 MHz, DMSO-d₆): δ 8.57 (s, 1H), 8.13 (s, 1H), 7.46 (s, 1H), 7.48-7.60 (d, 1H), 7.31-7.27 (t, 1H), 7.00-6.98 (d, 1H), 6.51 (s, 1H), 6.28 (s, 1H), 5.66 (s, 2H), 4.33 (s, 3H), 1.97 (s, 3H).

Example 2K. Synthesis of 2-(difluoro(phenyl)methyl)-6-(3-methoxybenzyl)-4-methyl-4,6-dihydro-5H-thiazolo[5',4':4,5]pyrrolo[2,3-d]pyridazin-5-one

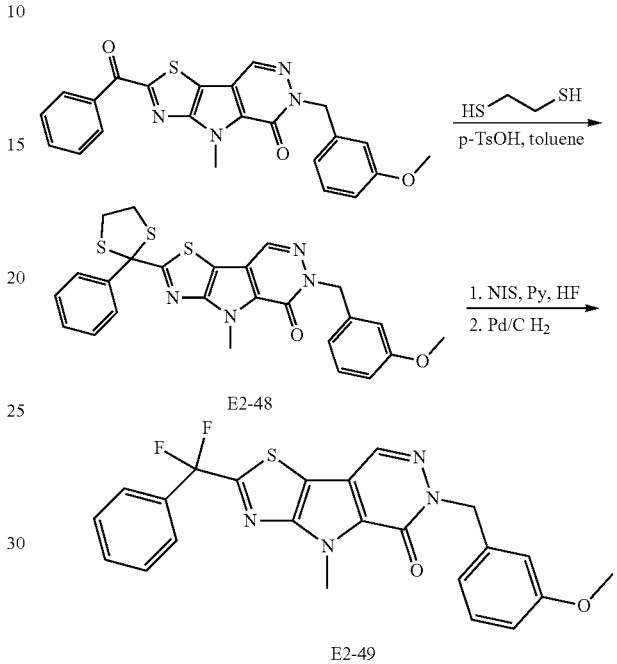

E2-49

Step A. 6-(3-Methoxybenzyl)-4-methyl-2-(2-phenyl-1,3-dithiolan-2-yl)-4,6-dihydro-5H-thiazolo[5',4':4,5]pyrrolo[2,3-d]pyridazin-5-one To a mixture of 2-benzoyl-6-(3-methoxybenzyl)-4-methyl-4,6-dihydro-5H-thiazolo[5',4':4,5]pyrrolo[2,3-d]pyridazin-5-one (86 mg, 0.2 mmol) in toluene (3 mL) was added p-TsOH (36 mg, 0.2 mmol) and ethane-1,2-dithiol (39 mg, 0.4 mmol). The mixture was stirred at 110° C. for 4 hr. then poured into water and extracted with EtOAc. The combined organic layers were washed with brine, dried over anhydrous Na₂SO₄ and concentrated under reduced pressure. The residue was purified by column chromatography on silica gel (eluent: PE/EtOAc=3/1) to give the desired product (80 mg, 80% yield). LCMS: m/z 507 (M+H)⁺.

Step B. 2-(Difluoro(phenyl)methyl)-6-(3-methoxybenzyl)-4-methyl-4,6-dihydro-5H-thiazolo[5,4':4,5]pyrrolo[2,3-d]pyridazin-5-one To a mixture of 6-(3-Methoxybenzyl)-4-methyl-2-(2-phenyl-1,3-dithiolan-2-yl)-4,6-dihydro-5H-thiazolo[5',4':4,5]pyrrolo[2,3-d]pyridazin-5-one (65 mg, 0.13 mmol) and NIS (little) in DCM (5 mL) was added Py.HF (1 mL). The reaction mixture was stirred at r.t. under N₂ for 2 hr. then poured into water and extracted with DCM. The combined organic layers were washed with brine, dried over anhydrous Na₂SO₄ and concentrated under reduced pressure. The residue was purified by column chromatography on silica gel (eluent: PE/EtOAc=3/1) to give a solid (50 mg, 76% yield). LCMS: m/z 595 (M+H)⁺.

To a mixture of the above solid (25 mg, 0.04 mmol) in THF/MeOH (3 mL/2 mL) was added Pd/C (5 mg). The mixture was stirred at r.t. under H₂ for 40 min then filtered. The filtrate was concentrated under reduced pressure and the residue was purified by prep-TLC to afford the desired product (7 mg, 36.8% yield). LCMS: 453 (M+H)⁺. ¹H NMR (400 MHz, DMSO-d₆) 8.70 (s, 1H), 7.74-7.70 (m, 2H), 7.64-7.56 (m, 3H), 7.26-7.20 (m, 1H), 6.88-6.84 (m, 3H), 5.33 (s, 2H), 4.25 (s, 3H), 3.71 (s, 3H).

Example 2L. Synthesis of 6-((1H-indazol-4-yl) methyl)-4-methyl-2-(1-phenylcyclo-propyl)-4,6-dihydro-5H-thiazolo[5',4':4,5]pyrrolo[2,3-d] pyridazin-5-one

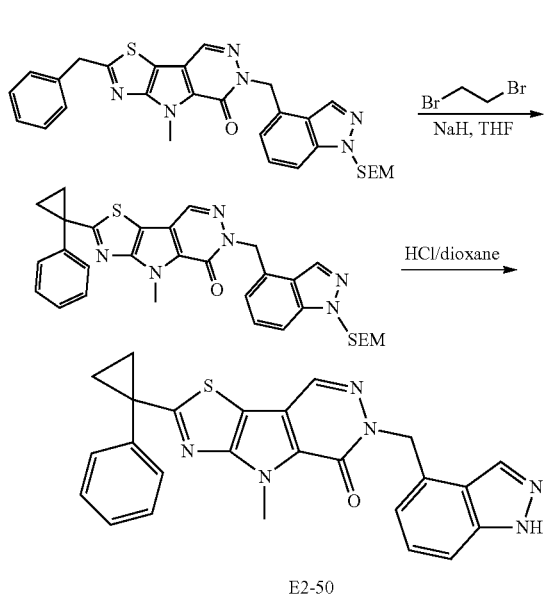

E2-50

Step A. 4-Methyl-2-(1-phenylcyclopropyl)-6-((1-((2-(trimethylsilyl)ethoxy) methyl)-1H-indazol-4-yl) methyl)-4H-thiazolo[5',4':4,5]pyrrolo[2,3-d] pyridazin-5(6H)-one To a mixture of 2-benzyl-4-methyl-6-((1-((2-(trimethylsilyl)methoxy)methyl)-1H-indazol-4-yl)methyl)-4H-thiazolo [5',4':4,5]pyrrolo[2,3-d]pyridazin-5(6H)-one (60 mg, 0.1 mmol) in dry DMF (2 mL) were added 1,2-dibromoethane (10 μL, 0.1 mmol) and TBAB (3 mg, 0.01 mmol). The mixture was stirred at r.t. for 30 min, followed by addition of NaH (8 mg, 0.2 mmol). The mixture was stirred at r.t. for 3 hr. then poured into saturated aqueous NH₄Cl and extracted with EtOAc. The combined organic layers were concentrated under reduced pressure. The residue was purified by prep-TLC to afford the desired product (26 mg, 44.7% yield). LCMS: 583 (M+H)⁺.

Step B. 6-((1H-indazol-4-yl)methyl)-4-methyl-2-(1-phenylcyclopropyl)-4H-thiazolo[5',4':4,5]pyrrolo[2,3-d]pyridazin-5(6H)-one A mixture of 4-methyl-2-(1-phenylcyclopropyl)-6-((1-((2-(trimethylsilyl)ethoxy)methyl)-1H-indazol-4-yl) methyl)-4H-thiazolo[5',4':4,5]pyrrolo[2,3-d]pyridazin-5 (6H)-one (26 mg, 0.044 mmol) in a solution of HCl in dioxane (4M, 2 mL) was stirred at r.t. for 3 hr. then concentrated under reduced pressure. The residue was purified by prep-HPLC to afford the desired product (3 mg, 15% yield). LCMS: 453 (M+H)⁺. ¹H NMR (400 MHz, DMSO-d₆) δ 13.11 (s, 1H), 8.47 (s, 1H), 8.12 (s, 1H), 7.59-7.52 (m, 2H), 7.50-7.38 (m, 4H), 7.32-7.23 (m, 1H), 6.95 (d, 1H), 5.63 (s, 2H), 4.24 (s, 3H), 1.84-1.81 (m, 2H), 1.59-1.57 (m, 2H).

Example 2M. Synthesis of 3-((2,4-dimethyl-5-oxo-4H-thiazolo[5',4':4,5]pyrrolo[2,3-d]pyridazin-6(5H)-yl)methyl)benzamide

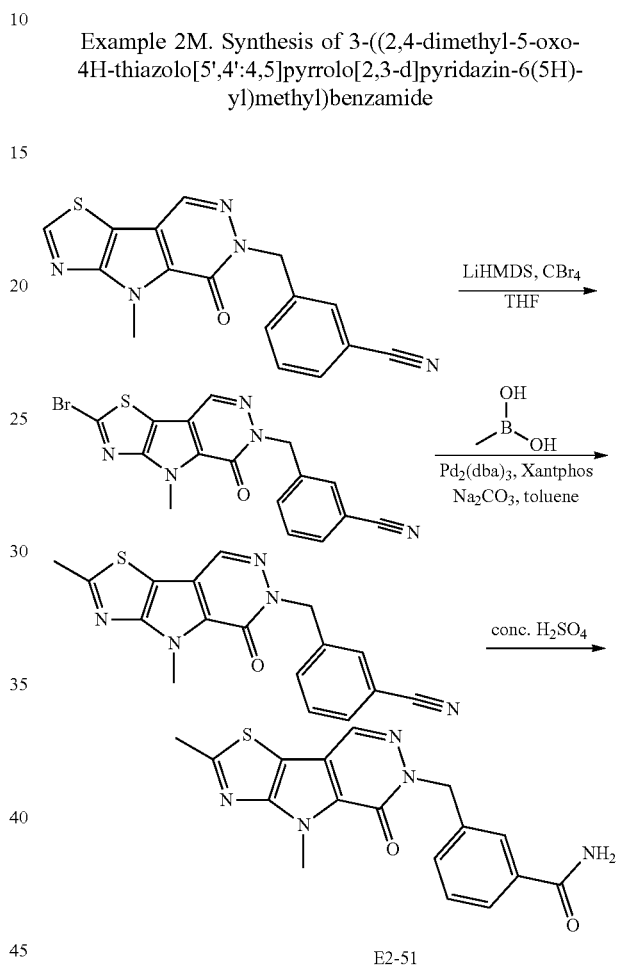

E2-51

Step A. Synthesis of 3-((2-bromo-4-methyl-5-oxo-4H-thiazolo[5',4':4,5]pyrrolo[2,3-d]pyridazin-6(5H)-yl)methyl)benzonitrile At −40° C. under N₂ atmosphere, to a mixture of 3-((4-methyl-5-oxo-4H-thiazolo[5',4':4,5]pyrrolo[2,3-d] pyridazin-6(5H)-yl)methyl) benzonitrile (200 mg, 0.62 mmol) and CBr₄ (1.03 g, 3.11 mmol) in THF (15 mL) was added LiHMDS (1.24 mL, 1 M in THF) by dropwise. The reaction mixture was stirred at −40° C. for 2 hrs, quenched by satd. NH₄Cl and extracted with EtOAc. The combined organic layers were washed with brine, dried over anhy. Na₂SO₄ and concentrated under reduced pressure. The residue was purified by column chromatography (silica gel, 0~25% EtOAc in PE) to afford 3-((2-bromo-4-methyl-5-oxo-4H-thiazolo[5',4':4,5]pyrrolo[2,3-d]pyridazin-6(5H)-yl)methyl)benzonitrile (200 mg, 80.6% yield). LC-MS (ESI): m/z 400 (M+H)⁺.

Step B. Synthesis of 3-((2,4-dimethyl-5-oxo-4H-thiazolo[5',4':4,5]pyrrolo[2,3-d]pyridazin-6(5H)-yl)methyl)benzonitrile To a mixture of 3-((2-bromo-4-methyl-5-oxo-4H-thiazolo[5',4':4,5]pyrrolo[2,3-d]pyridazin-6(5H)-yl)methyl)benzonitrile (100 mg, 0.25 mmol) and methylboronic acid (45 mg, 0.75 mmol) in toluene (2 mL) was added Na$_2$CO$_3$ (53 mg, 0.5 mmol), followed by Pd$_2$(dba)$_3$ (23 mg, 0.025 mmol) and xantphos (14 mg, 0.025 mmol). The reaction mixture was stirred at 100° C. for 15 hr. The reaction mixture was filtered and the filtrate was evaporated. The residue was purified by column chromatography (silica gel, 0~50% EtOAc in petroleum ether) to afford 3-((2,4-dimethyl-5-oxo-4H-thiazolo[5',4':4,5]pyrrolo[2,3-d]pyridazin-6(5H)-yl)methyl)benzonitrile (60 mg, 71.4% yield). LC-MS (ESI): m/z 336 (M+H)$^+$.

Step C. Synthesis of 3-((2,4-dimethyl-5-oxo-4H-thiazolo[5',4':4,5]pyrrolo[2,3-d]pyridazin-6(5H)-yl)methyl)benzamide A solution of 3-((2,4-dimethyl-5-oxo-4H-thiazolo[5',4':4,5]pyrrolo[2,3-d]pyridazin-6(5H)-yl)methyl)benzonitrile (60 mg, 0.18 mmol) in H$_2$SO$_4$ (1 mL) was stirred at 30° C. overnight. The reaction was quenched by satd. NaHCO$_3$ and extracted with EtOAc. The combined organic layers were washed with brine, dried over anhy. Na$_2$SO$_4$ and evaporated. The residue was purified by pre-TLC (10% MeOH in DCM) to afford 3-((2,4-dimethyl-5-oxo-4H-thiazolo[5',4':4,5]pyrrol[2,3-d]pyridazin-6(5H)-yl)methyl)benzamide (10 mg, 15.7% yield). LC-MS (ESI): m/z 354 (M+H)$^+$. $^1$H NMR (400 MHz, DMSO-d6) δ 8.59 (s, 1H), 7.98 (s, 1H), 7.81 (s, 1H), 7.77 (d, 1H), 7.46 (d, 1H), 7.41 (t, 1H), 7.35 (s, 1H), 5.40 (s, 2H), 4.26 (s, 3H), 2.86 (s, 3H).

Example 2N. Synthesis of 2-(2-(1H-pyrazol-3-yl)ethyl)-4-methyl-6-((1-methyl-1H-pyrazol-3-yl)methyl)-4,6-dihydro-5H-thiazolo[5',4':4,5]pyrrolo[2,3-d]pyridazin-5-one

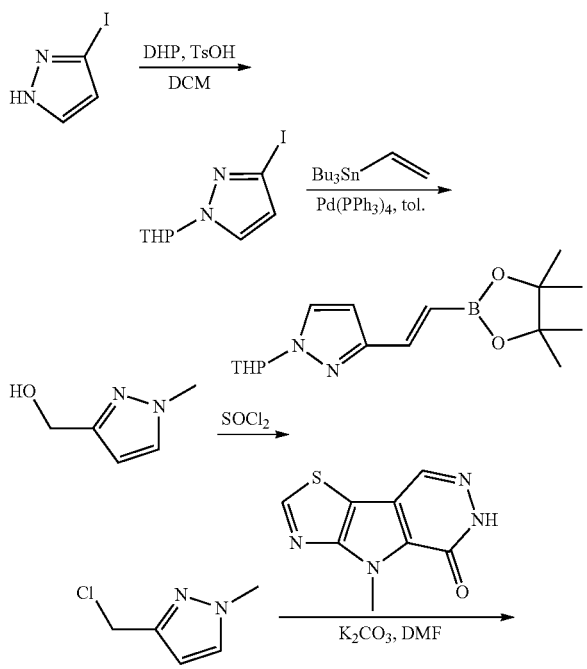

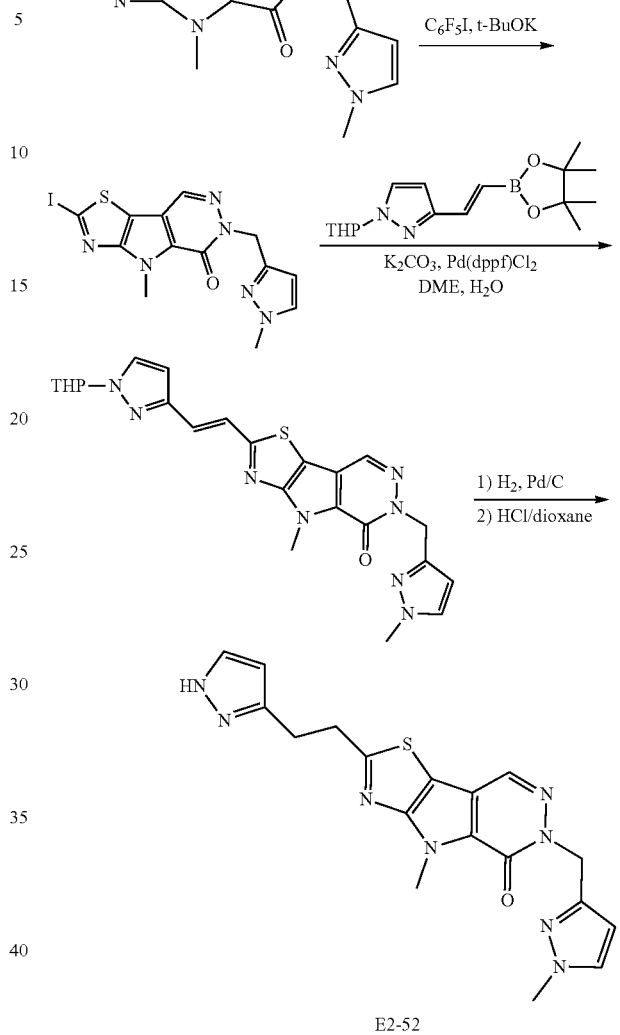

E2-52

Step A. Synthesis of 3-iodo-1-(tetrahydro-2H-pyran-2-yl)-1H-pyrazole

To a mixture of 3-iodo-1H-pyrazole (1 g, 5.16 mmol) and p-TsOH (88 mg, 0.52 mmol) in DCM (15 mL) was added DHP (0.56 mL, 6.19 mmol) and stirred at r.t. for 2 hr. The reaction mixture was washed with satd. NaHCO$_3$ and brine, dried over anhy. Na$_2$SO$_4$ and concentrated. The residue was purified by flash chromatography (silica gel, 0~10% EtOAc in PE) to give 3-iodo-1-(oxan-2-yl)-1H-pyrazole (1.4 g). LC-MS (m/z 279 (M+H)$^+$.

Step B. Synthesis of (E)-1-(tetrahydro-2H-pyran-2-yl)-3-(2-(4,4,5,5-tetramethyl-1,3,2-dioxaborolan-2-yl)vinyl)-1H-pyrazole Under nitrogen, to a mixture of 3-iodo-1-(tetrahydro-2H-pyran-2-yl)-1H-pyrazole (150 mg, 0.54 mmol) in toluene (3 mL) was added 2-ethenyl-4,4,5,5-tetramethyl-1,3,2-dioxaborolane (0.18 mL, 1.08 mmol), Et$_3$N (0.37 mL, 2.7 mmol) and Pd(PBu$_3$)$_2$ (14 mg, 0.03 mmol). The reaction was stirred at 100° C. for 3 hr. The mixture was concentrated and purified by prep-TLC (35% EtOAc in PE) to give 1-(oxan-2-yl)-3-[(E)-2-(tetramethyl-1,3,2-dioxaborolan-2-yl)ethenyl]-1H-pyrazole (60 mg, 37% yield). LC-MS (ESI): m/z 305 (M+H)+.

Step C. Synthesis of 4-methyl-6-((1-methyl-1H-pyrazol-3-yl)methyl)-4H-thiazolo[5',4':4,5]pyrrolo[2,3-d]pyridazin-5(6H)-one To a mixture of 4-methyl-4H-thiazolo[5',4':4,5]pyrrolo[2,3-d]pyridazin-5(6H)-one (500 mg, 2.42 mmol) in DMF (15 mL) was added $K_2CO_3$ (335 mg, 2.42 mmol). After stirred at 50° C. for 30 min, a solution of 3-(bromomethyl)-1-methyl-1H-pyrazole (636 mg, 3.64 mmol) in DMF (2 mL) was added. The reaction was stirred at 50° C. overnight. The suspension was poured into satd. $NH_4Cl$, extracted with EtOAc. The organic layer was dried over anhy. $Na_2SO_4$, filtered and concentrated. The residue was purified by flash chromatography (silica gel, 0~100 EtOAc in PE) to give 4-methyl-6-((1-methyl-1H-pyrazol-3-yl)methyl)-4H-thiazolo[5',4':4,5]pyrrolo[2,3-d]pyridazin-5(6H)-one (280 mg). LC-MS (ESI): m/z 301 (M+H)+.

Step D. Synthesis of 2-iodo-4-methyl-6-((1-methyl-1H-pyrazol-3-yl)methyl)-4H-thiazolo[5',4':4,5]pyrrolo[2,3-d]pyridazin-5(6H)-one To a mixture of 4-methyl-6-((1-methyl-1H-pyrazol-3-yl)methyl)-4H-thiazolo[5',4':4,5]pyrrolo[2,3-d]pyridazin-5(6H)-one (280 mg, 0.93 mmol) in toluene (10 mL) was added pentafluoroiodobenzene (0.50 mL, 3.73 mmol) and t-BuOK (209 mg, 1.86 mmol). The reaction was stirred at 135° C. for 2 hr under nitrogen. The mixture was cooled to r.t. and concentrated. The residue was purified by flash chromatography (silica gel, 0~100% EtOAc in PE) to give 2-iodo-4-methyl-6-((1-methyl-1H-pyrazol-3-yl)methyl)-4H-thiazolo[5',4':4,5]pyrrolo[2,3-d]pyridazin-5(6H)-one (300 mg). LC-MS (ESI): m/z 427 (M+H)+.

Step E. Synthesis of (E)-4-methyl-6-((1-methyl-1H-pyrazol-3-yl)methyl)-2-(2-(1-(tetrahydro-2H-pyran-2-yl)-1H-pyrazol-3-yl)vinyl)-4H-thiazolo[5',4':4,5]pyrrolo[2,3-d]pyridazin-5(6H)-one Under nitrogen, to a mixture of 2-iodo-4-methyl-6-((1-methyl-1H-pyrazol-3-yl)methyl)-4H-thiazolo[5',4':4,5]pyrrolo[2,3-d]pyridazin-5(6H)-one (300 mg, 0.71 mmol) and (E)-1-(tetrahydro-2H-pyran-2-yl)-3-(2-(4,4,5,5-tetramethyl-1,3,2-dioxaborolan-2-yl)vinyl)-1H-pyrazole (300 mg, 0.99 mmol) in DME (5 mL) and water (1 mL) were added $Na_2CO_3$ (149 mg, 1.41 mmol) and $Pd(PPh_3)_2Cl_2$ (49 mg, 0.071 mmol). The mixture was stirred at 80° C. for 3 hr. Then the mixture was cooled down, diluted with EtOAc, washed with water and brine. The organic layer was dried over anhy. $Na_2SO_4$, filtered and concentrated. The residue was purified by flash chromatography (silica gel, 0~100% EtOAc in PE) to give (E)-4-methyl-6-((1-methyl-1H-pyrazol-3-yl)methyl)-2-(2-(1-(tetrahydro-2H-pyran-2-yl)-1H-pyrazol-3-yl)vinyl)-4H-thiazolo[5',4':4,5]pyrrolo[2,3-d]pyridazin-5(6H)-one (170 mg). LC-MS (ESI): m/z 477 (M+H)+.

Step F. Synthesis of 4-methyl-6-((1-methyl-1H-pyrazol-3-yl)methyl)-2-(2-(1-(tetrahydro-2H-pyran-2-yl)-1H-pyrazol-3-yl)ethyl)-4H-thiazolo[5',4':4,5]pyrrolo[2,3-d]pyridazin-5(6H)-one To a mixture of (E)-4-methyl-6-((1-methyl-1H-pyrazol-3-yl)methyl)-2-(2-(1-(tetrahydro-2H-pyran-2-yl)-1H-pyrazol-3-yl)vinyl)-4H-thiazolo[5',4':4,5]pyrrolo[2,3-d]pyridazin-5(6H)-one (80 mg, 0.17 mmol) in THF (3 mL) and MeOH (3 mL) was added Pd/C (10 mg). The reaction was stirred under $H_2$ at r.t. for 6 hr. The mixture was filtered and the filtrate was concentrated. The residue was purified by prep-TLC (EtOAc) to give 4-methyl-6-((1-methyl-1H-pyrazol-3-yl)methyl)-2-(2-(1-(tetrahydro-2H-pyran-2-yl)-1H-pyrazol-3-yl)ethyl)-4H-thiazolo[5',4':4,5]pyrrolo[2,3-d]pyridazin-5(6H)-one (20 mg). LC-MS (ESI): m/z 479 (M+H)+.

Step G. Synthesis of 2-(2-(1H-pyrazol-3-yl)ethyl)-4-methyl-6-((1-methyl-1H-pyrazol-3-yl)methyl)-4H-thiazolo[5',4':4,5]pyrrolo[2,3-d]pyridazin-5(6H)-one To a mixture of 4-methyl-6-((1-methyl-1H-pyrazol-3-yl)methyl)-2-(2-(1-(tetrahydro-2H-pyran-2-yl)-1H-pyrazol-3-yl)ethyl)-4H-thiazolo[5',4':4,5]pyrrolo[2,3-d]pyridazin-5(6H)-one (20 mg, 0.042 mmol) in ethanol (2 mL) was added HCl (0.5 mL, 4 M in dioxane). The reaction mixture was stirred at 50° C. for 30 min. The reaction mixture was cooled down and poured into satd. $NaHCO_3$, extracted with EtOAc. The organic layer was dried over anhy. $Na_2SO_4$, filtered and concentrated. The residue was purified by prep-TLC (10% MeOH in DCM) to give 2-(2-(1H-pyrazol-3-yl)ethyl)-4-methyl-6-((1-methyl-1H-pyrazol-3-yl)methyl)-4H-thiazolo[5',4':4,5]pyrrolo[2,3-d]pyridazin-5(6H)-one (10 mg, 61% yield). LC-MS (ESI): m/z 395 (M+H)+. 1H NMR (400 MHz, DMSO-d6) δ 12.56 (s, 1H), 8.51 (s, 1H), 7.56 (d, 1H), 7.52 (s, 1H), 6.12 (d, 1H), 6.08 (d, 1H), 5.27 (s, 2H), 4.27 (s, 3H), 3.77 (s, 3H), 3.48 (t, 2H), 3.13 (t, 2H).

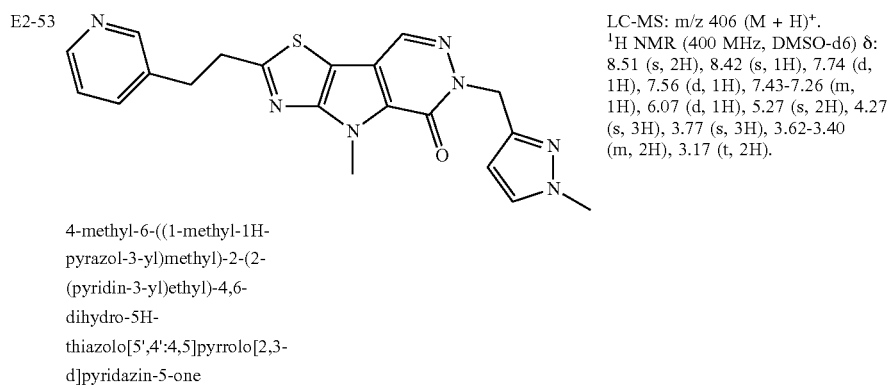

E2-53

4-methyl-6-((1-methyl-1H-pyrazol-3-yl)methyl)-2-(2-(pyridin-3-yl)ethyl)-4,6-dihydro-5H-thiazolo[5',4':4,5]pyrrolo[2,3-d]pyridazin-5-one LC-MS: m/z 406 (M + H)+.
1H NMR (400 MHz, DMSO-d6) δ: 8.51 (s, 2H), 8.42 (s, 1H), 7.74 (d, 1H), 7.56 (d, 1H), 7.43-7.26 (m, 1H), 6.07 (d, 1H), 5.27 (s, 2H), 4.27 (s, 3H), 3.77 (s, 3H), 3.62-3.40 (m, 2H), 3.17 (t, 2H).

Example 2O. Synthesis of 2-((1H-pyrazol-5-yl)oxy)-6-((6-aminopyridin-2-yl)methyl)-4-methyl-4H-thiazolo[5',4':4,5]pyrrolo[2,3-d]pyridazin-5(6H)-one

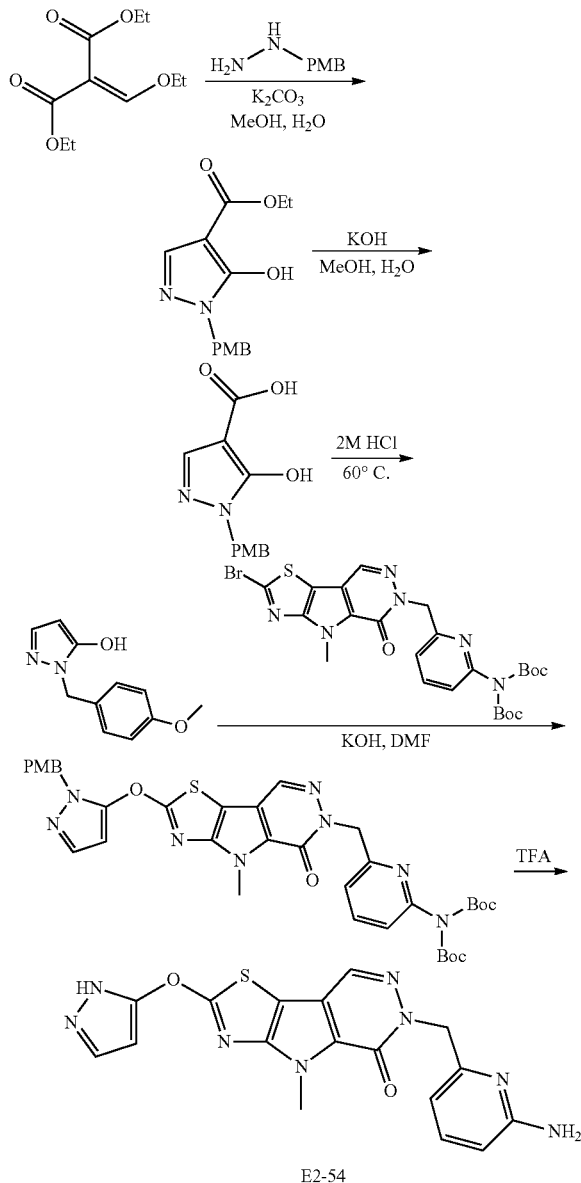

E2-54

Step A. Synthesis of ethyl 5-hydroxy-1-(4-methoxybenzyl)-1H-pyrazole-4-carboxylate To a mixture of (4-methoxybenzyl)hydrazine dihydrochloride (2.25 g, 10 mmol) and K$_2$CO$_3$ (4.14 g, 30 mmol) in methanol (50 mL) and water (10 mL) was added diethyl 2-(ethoxymethylene)malonate (2.16 g, 10 mmol). The mixture was stirred at 80° C. for 5 hr. Then the mixture was quenched with aq. NH$_4$Cl and extracted with EtOAc. The organic layers were washed with brine, dried over Na$_2$SO$_4$ and concentrated. The residue was purified by column chromatography (silica gel, 0~50% EtOAc in PE) to afford 1.1 g of ethyl 5-hydroxy-1-(4-methoxybenzyl)-1H-pyrazole-4-carboxylate.

Step B. Synthesis of 5-hydroxy-1-(4-methoxybenzyl)-1H-pyrazole-4-carboxylic acid To a solution of ethyl 5-hydroxy-1-(4-methoxybenzyl)-1H-pyrazole-4-carboxylate (800 mg, 2.9 mmol) in methanol (10 mL) was added a solution of KOH (800 mg, 15 mmol) in water (10 mL). The mixture was stirred at room temperature for 16 hr. Then the mixture was concentrated and the residue was used directly in next step. LC-MS (ESI): m/z 249 (M+H)$^+$.

Step C. Synthesis of 1-(4-methoxybenzyl)-1H-pyrazol-5-ol

A mixture of 5-hydroxy-1-(4-methoxybenzyl)-1H-pyrazole-4-carboxylic acid was dissolve in 2 M HCl (50 mL) was stirred at 60° C. for 16 hr. The solvent was removed and the residue was purified by pre-TLC to give 120 mg of 1-(4-methoxybenzyl)-1H-pyrazol-5-ol. LC-MS (ESI): m/z 205 (M+H)$^+$.

Step D. Synthesis of tert-butyl N-(tert-butoxy)carbonyl (6-((2-((1-(4-methoxybenzyl)-1H-pyrazol-5-yl)oxy)-4-methyl-5-oxo-4H-thiazolo[5',4':4,5]pyrrolo[2,3-d]pyridazin-6(5H)-yl)methyl)pyridin-2-yl)carbamate To a solution of 1-[(4-methoxyphenyl)methyl]-1H-pyrazol-5-ol (60 mg, 0.29 mmol) in DMF (8 mL) was added KOH (18 mg, 0.32 mmol) at 5° C. The reaction mixture was stirred at 5° C. for 30 min, a solution of tert-butyl N-(tert-butoxy)carbonyl (6-((2-bromo-4-methyl-5-oxo-4H-thiazolo[5',4':4,5]pyrrolo[2,3-d]pyridazin-6(5H)-yl)methyl)pyridin-2-yl)carbamate (174 mg, 0.29 mmol) in DMF (2 mL) was added. The reaction was stirred at r.t. for 16 hr and then poured into 1 M aqueous citric acid, extracted with EtOAc. The combined organic layers were washed with brine, dried over anhy. Na$_2$SO$_4$ and evaporated. The residue was purified by pre-TLC (EA:PE=1:1) to afford 80 mg of tert-butyl N-(tert-butoxy)carbonyl (6-((2-((1-(4-methoxybenzyl)-1H-pyrazol-5-yl)oxy)-4-methyl-5-oxo-4H-thiazolo[5',4':4,5]pyrrolo[2,3-d]pyridazin-6(5H)-yl)methyl)pyridin-2-yl)carbamate. LC-MS: m/z 715 (M+H)$^+$.

Step E. Synthesis of 2-((1H-pyrazol-5-yl)oxy)-6-((6-aminopyridin-2-yl)methyl)-4-methyl-4H-thiazolo[5',4':4,5]pyrrolo[2,3-d]pyridazin-5(6H)-one A solution of tert-butyl N-(tert-butoxy)carbonyl(6-((2-((1-(4-methoxybenzyl)-1H-pyrazol-5-yl)oxy)-4-methyl-5-oxo-4H-thiazolo[5',4':4,5]pyrrolo[2,3-d]pyridazin-6(5H)-yl)methyl)pyridin-2-yl)carbamate (60 mg, 0.08 mmol) in TFA (2 mL) was stirred at r.t. overnight. The 0.15 reaction was concentrated and purified by prep-HPLC to give 15 mg of 2-((1H-pyrazol-5-yl)oxy)-6-((6-aminopyridin-2-yl)methyl)-4-methyl-4H-thiazolo[5',4':4,5]pyrrolo[2,3-d]pyridazin-5(6H)-one. LC-MS (ESI): m/z 395 (M+H)$^+$. $^1$H NMR (400 MHz, Methanol-d4) δ 8.41 (s, 1H), 7.76-7.63 (m, 2H), 6.79 (d, 1H), 6.64 (d, 1H), 6.31 (d, 1H), 5.42 (s, 2H), 4.26 (s, 3H).

Example 3. Preparation of Compounds of Formula E3-ii and Derivatives with Scheme E3

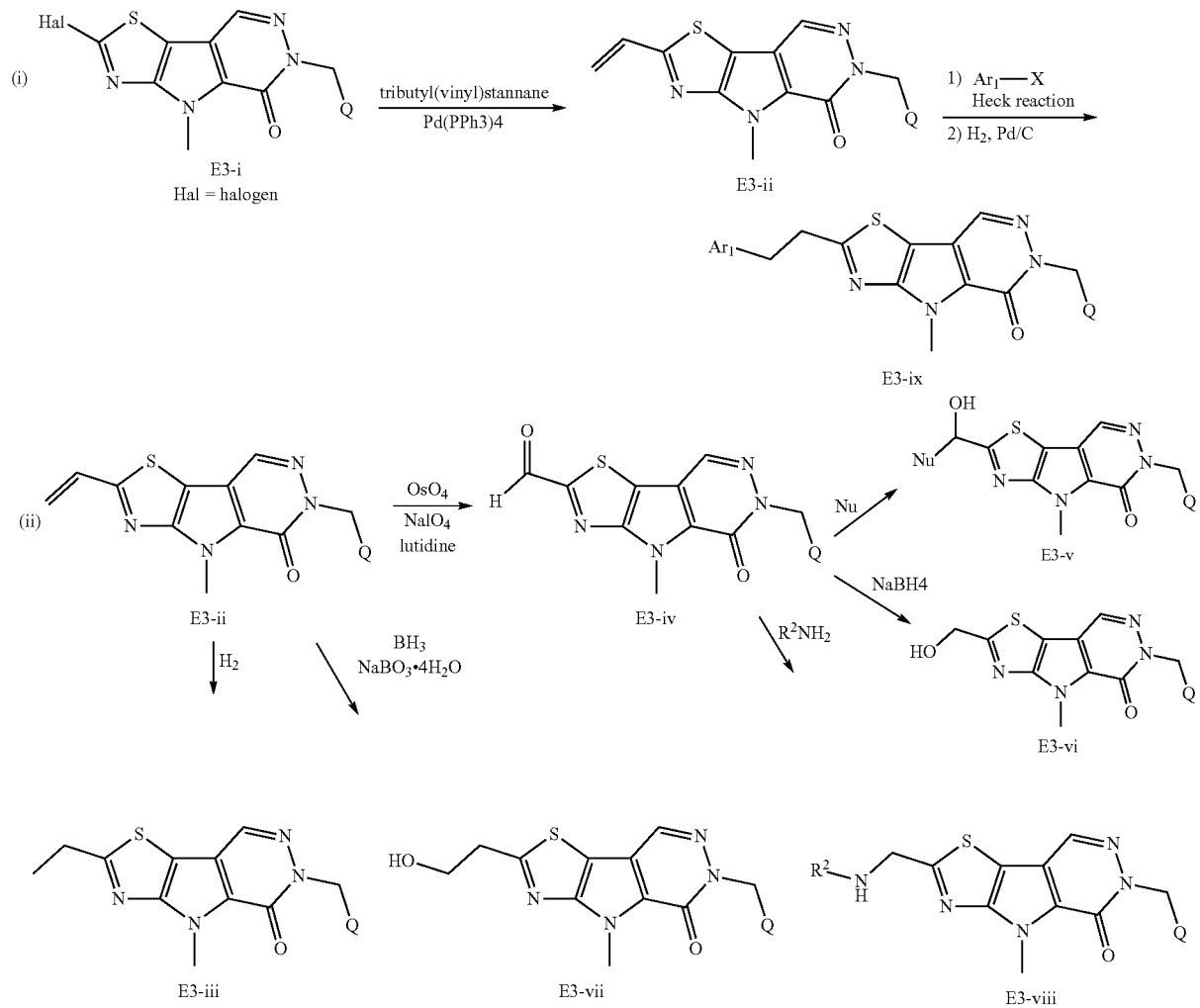

Compound E3-ii can be synthesized by a Stille reaction between compound E3-i and tributyl(vinyl)stannane. Heck reaction of E3-ii in the presence of a catalyst (e.g. Palladium catalyst such as Pd(Pt-Bu3)$_2$, DMF) followed by reduction of the alkenyl group can generate compound E3-ix. Alternatively, standard hydrogenation of compound E3-ii generates compound E3-iii. Hydroboration of compound E3-ii followed by oxidation with sodium perborate gives product E3-vii. Direct oxidation of compound E3-ii with osmium (VIII) oxide and sodium periodate provides aldehyde E3-iv. Nucleophilic addition of aldehyde E3-iv gives product E3-v. Standard reduction of compound E3-iv with sodium borohydride affords compound E3-vi. Reductive amination of compound E3-iv gives compound E3-viii. Wherein Q and $R^2$ are as defined in the any one of the first to the twenty-sixth embodiments of the invention. In certain embodiments, Q and $R^2$ are each independently optionally substituted aryl, optionally substituted heteroaryl, optionally substituted carbocycle or optionally substituted heterocyclyl.

Example 3A. Synthesis of 2-ethyl-6-(3-methoxy-benzyl)-4-methyl-4H-thiazolo[5',4':4,5]pyrrolo[2,3-d]pyridazin-5(6H)-one

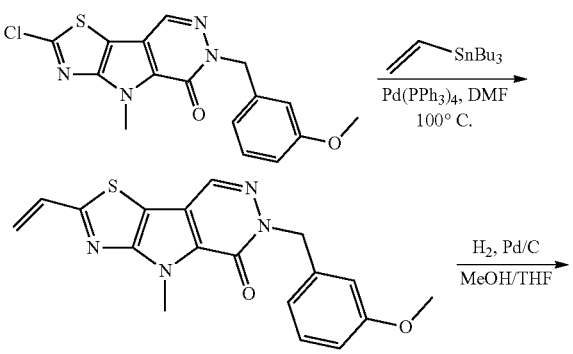

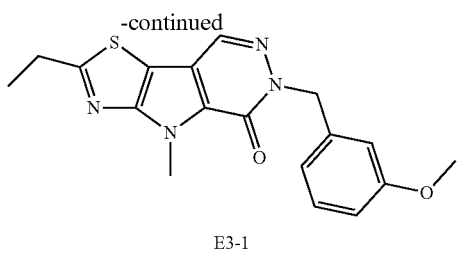

E3-1

Step A. 6-(3-Methoxybenzyl)-4-methyl-2-vinyl-4H-thiazolo[5,4':4,5]pyrrolo[2,3-d]pyridazin-5(6H)-one To a mixture of 2-chloro-6-(3-methoxybenzyl)-4-methyl-4H-thiazolo[5',4':4,5]pyrrolo[2,3-d]pyridazin-5(6H)-one (600 mg, 1.67 mmol) and tributyl(vinyl)stannane (1 mL, 3.4 mmol) in DMF (6 mL) was added Pd(PPh$_3$)$_4$. The mixture was stirred at 100° C. overnight under N$_2$ then poured into water and extracted with EtOAc. The combined organic layers were washed with brine, dried over anhydrous Na$_2$SO$_4$ and concentrated under reduced pressure. The residue was purified by column chromatography on silica gel (eluent: PE/EtOAc=5/2) to give desired product (410 mg, 68% yield). LCMS: m/z 353 (M+H)$^+$. $^1$H NMR (400 MHz, DMSO-d6) δ 8.61 (s, 1H), 7.23 (t, 1H), 7.10 (dd, 1H), 6.89-6.80 (m, 3H), 6.28 (d, 1H), 5.75 (d, 1H), 5.32 (s, 2H), 4.27 (s, 3H), 3.72 (s, 3H).

Step B. 2-Ethyl-6-(3-methoxybenzyl)-4-methyl-4H-thiazolo[5',4':4,5]pyrrolo[2,3-d]pyridazin-5(6H)-one To a mixture of 6-(3-methoxybenzyl)-4-methyl-2-vinyl-4H-thiazolo[5',4':4,5]pyrrolo[2,3-d]pyridazin-5(6H)-one (30 mg, 0.88 mmol) in MeOH (1 mL) and THF (1 mL) under N$_2$ was added Pd/C (10 mg). The mixture was stirred under H$_2$ at r.t. for 1 hr. then filtered through Celite. The filtrate was concentrated under reduced pressure and the residue was purified by prep-TLC to afford the desired product (5 mg, 16.7% yield).

LCMS: m/z 355 (M+H)$^+$. $^1$H NMR (400 MHz, DMSO-d$_6$) δ 8.56 (s, 1H), 7.23 (t, 1H), 6.89-6.78 (m, 3H), 5.32 (s, 2H), 4.26 (s, 3H), 3.72 (s, 3H), 3.17 (q, 2H), 1.38 (t, 3H).

The procedure set forth above was used to produce the following compounds using the appropriate starting materials.

Example 3B. Synthesis of 2-(hydroxymethyl)-6-(3-methoxybenzyl)-4-methyl-4H-thiazolo[5',4':4,5]pyrrolo[2,3-d]pyridazin-5(6H)-one

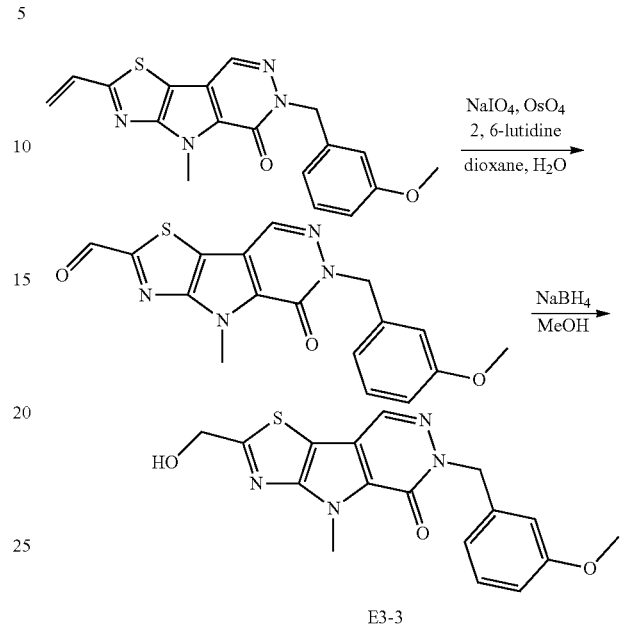

E3-3

Step A. 6-(3-Methoxybenzyl)-4-methyl-5-oxo-5,6-dihydro-4H-thiazolo[5',4':4,5]pyrrolo[2,3-d]pyridazine-2-carbaldehyde To a mixture of 6-(3-methoxybenzyl)-4-methyl-2-vinyl-4H-thiazolo[5',4':4,5]pyrrolo[2,3-d]pyridazin-5(6H)-one (410 mg, 1.16 mmol) in dioxane (6 mL) and water (2 mL) were added NaIO$_4$ (1 g, 4.6 mmol), 2,6-dimethylpyridine (0.27 mL, 2.32 mmol) and OsO$_4$ (cat.). The mixture was stirred at r.t. for 4 hr. then quenched with saturated aqueous Na$_2$S$_2$O$_3$ and extracted with EtOAc. The combined organic layers were washed with brine, dried over anhydrous Na$_2$SO$_4$ and concentrated under reduced pressure. The residue was purified by column chromatography on silica gel (eluent: PE/EtOAc=1/1) to give the desired product (130 mg, 31.7% yield). LCMS: m/z 387 (M+MeOH+H)$^+$. $^1$H NMR (400 MHz, DMSO-d$_6$) δ 10.08 (s, 1H), 8.75 (s, 1H), 7.24 (t, 1H), 6.88-6.83 (m, 3H), 5.34 (s, 2H), 4.34 (s, 3H), 3.72 (s, 3H).

| Cpd No. | Structure | Characterization |
|---|---|---|
| E3-2 | 6-((1H-indazol-4-yl)methyl)-4-methyl-2-vinyl-4,6-dihydro-5H-thiazolo[5',4':4,5]pyrrolo[2,3-d]pyridazin-5-one | LC-MS: m/z 363 (M + H)$^+$. $^1$H NMR (400 MHz, DMSO-d$_6$) δ 13.13 (s, 1H), 8.63 (s, 1H), 8.16 (s, 1H), 7.46 (d, 1H), 7.31-7.27 (m, 1H), 7.14-7.07 (m, 1H), 6.98 (d, H), 6.28 (d1H), 5.76 (d, 1H), 5.67 (s, 2H), 4.29 (s, 3H). |

Step B. 2-(Hydroxymethyl)-6-(3-methoxybenzyl)-4-methyl-4H-thiazolo[5',4':4,5] pyrrolo[2,3-d]pyridazin-5(6H)-one To a mixture of 6-(3-methoxybenzyl)-4-methyl-5-oxo-5,6-dihydro-4H-thiazolo[5',4':4,5]pyrrolo[2,3-d]pyridazine-2-carbaldehyde (30 mg, 0.08 mmol) in methanol (2 mL) was added NaBH$_4$ (6 mg, 0.16 mmol). The mixture was stirred at r.t. for 10 min then poured into water and extracted with EtOAc. The organic layer was concentrated under reduced pressure and the residue was purified by prep-HPLC to afford the desired product (10 mg, 35.7% yield). LCMS: m/z 357 (M+H)$^+$. $^1$H NMR (400 MHz, DMSO-d$_6$) δ 8.59 (s, 1H), 7.23 (t, 1H), 6.86-6.82 (m, 3H), 6.34 (t, 1H), 5.32 (s, 2H), 4.89 (d, 2H), 4.26 (s, 3H), 3.72 (s, 3H).

The procedure set forth above was used to produce the following compounds using the appropriate starting materials. Standard protection and deprotection can be used when necessary.

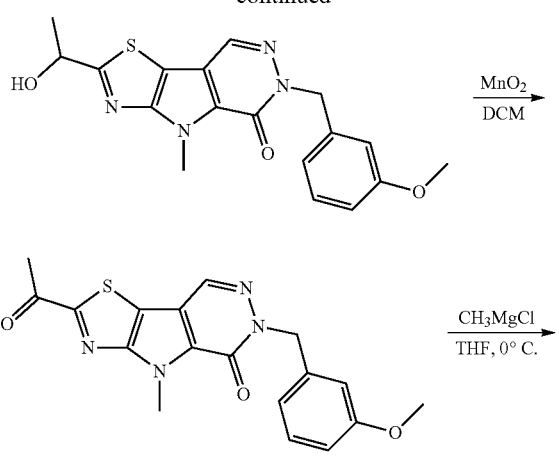

| Cpd No. | Structure | Characterization |
|---|---|---|
| E3-4 | ![structure] 6-((1H-indazol-4-yl)methyl)-2-(hydroxymethyl)-4-methyl-4,6-dihydro-5H-thiazolo[5',4':4,5]pyrrolo[2,3-d]pyridazin-5-one | LC-MS: m/z 367 (M + H)$^+$. $^1$H NMR (400 MHz, DMSO-d$_6$) δ 13.12 (s, 1H), 8.62 (s, 1H), 8.16 (s, 1H), 7.45 (d, 1H), 7.31-7.27 (m, 1H), 6.98-6.97 (m, 1H), 6.34 (t, 1H), 5.67 (s, 2H), 4.89 (d, 2H), 4.27 (s, 3H). |
| E3-5 | ![structure] 6-((1H-indazol-4-yl)methyl)-2-(1-hydroxyethyl)-4-methyl-4,6-dihydro-5H-thiazolo[5',4':4,5]pyrrolo[2,3-d]pyridazin-5-one | LC-MS: m/z 381 (M + H)$^+$. $^1$H NMR (400 MHz, DMSO-d$_6$) δ 13.13 (s, 1H), 8.60 (s, 1H), 8.15 (s, 1H), 7.45 (d, 1H), 7.30-7.26 (m, 1H), 6.97-6.95 (m, 1H), 6.42 (d, 1H), 5.66 (s, 2H), 5.10-5.07 (m, 1H), 4.26 (s, 3H), 1.53 (d, 3H). |

Example 3C: Synthesis of 2-(2-hydroxypropan-2-yl)-6-(3-methoxybenzyl)-4-methyl-4H-thiazolo[5',4':4,5]pyrrolo[2,3-d]pyridazin-5(6H)-one

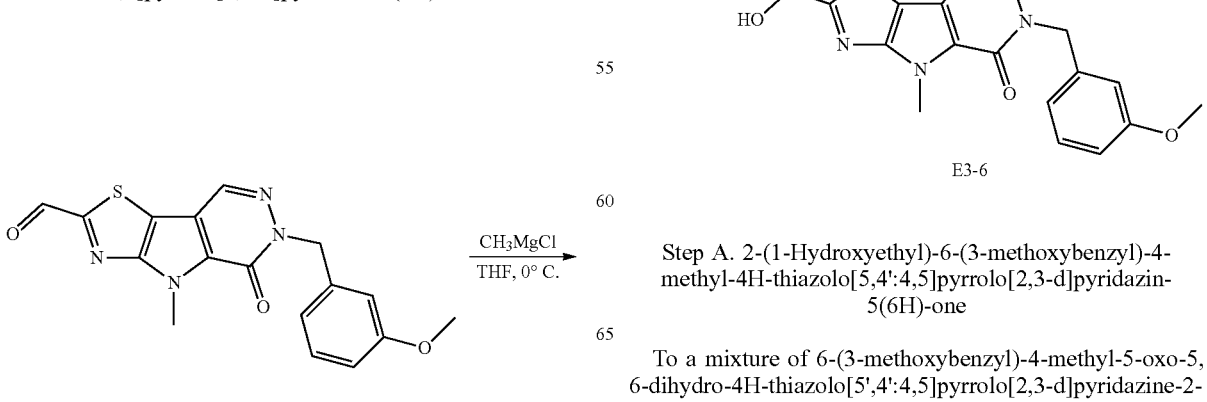

E3-6

Step A. 2-(1-Hydroxyethyl)-6-(3-methoxybenzyl)-4-methyl-4H-thiazolo[5',4':4,5]pyrrolo[2,3-d]pyridazin-5(6H)-one To a mixture of 6-(3-methoxybenzyl)-4-methyl-5-oxo-5,6-dihydro-4H-thiazolo[5',4':4,5]pyrrolo[2,3-d]pyridazine-2- carbaldehyde (100 mg, 0.28 mmol) in THF (3 mL) at 0° C. was added drop wise methylmagnesium chloride (0.19 mL, 0.56 mmol). The mixture was stirred at r.t. for 10 min then poured into saturated aqueous NH₄Cl and extracted with EtOAc. The combined organic layers were washed with brine, dried over anhydrous Na₂SO₄ and concentrated under reduced pressure. The residue was purified by column chromatography on silica gel (eluent: PE/EtOAc=5/2) to give the desired product (40 mg). LCMS: m/z 371 (M+H)⁺. ¹H NMR (400 MHz, DMSO-d₆) δ 8.58 (s, 1H), 7.24 (t, 1H), 6.97-6.77 (m, 3H), 6.41 (d, 1H), 5.40-5.23 (m, 2H), 5.18-5.02 (m, 1H), 4.26 (s, 3H), 3.72 (s, 3H), 1.55 (d, 3H).

Step B. 2-Acetyl-6-(3-methoxybenzyl)-4-methyl-4H-thiazolo[5',4':4,5]pyrrolo[2,3-d]pyridazin-5(6H)-one To a mixture of 2-(1-hydroxyethyl)-6-(3-methoxybenzyl)-4-methyl-4H-thiazolo[5',4':4,5]pyrrolo[2,3-d]pyridazin-5(6H)-one (30 mg, 0.08 mmol) in DCM (3 mL) was added manganese (IV) oxide (35 mg, 0.4 mmol). The mixture was stirred at r.t. for 1 hr. then filtered through Celite. The filtrate was concentrated under reduced pressure to give the desired product (25 mg). LCMS: m/z 369 (M+H)⁺. ¹H NMR (400 MHz, DMSO-d₆) δ 8.83 (s, 1H), 7.35 (t, 1H), 6.99-6.94 (m, 3H), 5.45 (s, 2H), 4.45 (s, 3H), 3.83 (s, 3H), 2.85 (s, 3H).

Step C. 2-(2-Hydroxypropan-2-yl)-6-(3-methoxybenzyl)-4-methyl-4H-thiazolo[5',4':4,5]pyrrolo[2,3-d]pyridazin-5(6H)-one To a mixture of 2-acetyl-6-(3-methoxybenzyl)-4-methyl-4H-thiazolo[5',4':4,5]pyrrolo[2,3-d]pyridazin-5(6H)-one (20 mg, 0.05 mmol) in THF (1 mL) at 0° C. was added drop wise methylmagnesium chloride (0.08 mL, 0.15 mmol). The mixture was stirred at r.t. for 10 then poured into saturated aqueous NH₄Cl and extracted with EtOAc. The combined organic layers were washed with brine, dried over anhydrous Na₂SO₄ and concentrated under reduced pressure. The residue was purified by prep-TLC to give the desired product (10 mg). LCMS: m/z 385 (M+H)⁺. ¹H NMR (400 MHz, DMSO-d₆) δ 8.58 (s, 1H), 7.24 (t, 1H), 6.89-6.81 (m, 3H), 6.28 (s, 1H), 5.33 (s, 2H), 4.26 (s, 3H), 3.72 (s, 3H), 1.60 (s, 6H).

Example 3D. Synthesis of 6-((1H-indazol-4-yl)methyl)-2-(2-hydroxyethyl)-4-methyl-4,6-dihydro-5H-thiazolo[5',4':4,5]pyrrolo[2,3-d]pyridazin-5-one

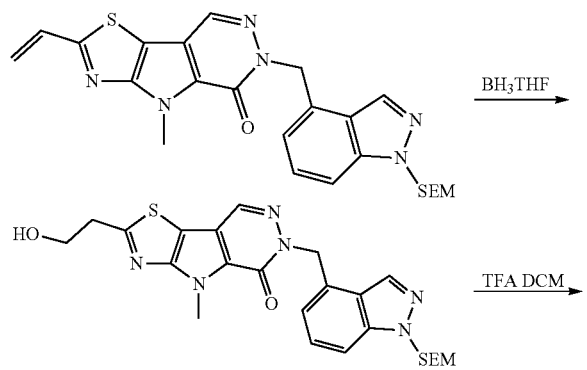

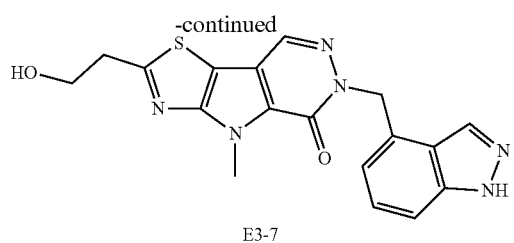

E3-7

Step A. 2-(2-Hydroxyethyl)-4-methyl-6-((1-((2-(trimethylsilyl)ethoxy)methyl)-1H-indazol-4-yl)methyl)-4,6-dihydro-5H-thiazolo[5',4':4,5]pyrrolo[2,3-d]pyridazin-5-one To a mixture of 4-methyl-6-((1-((2-(trimethylsilyl)ethoxy)methyl)-1H-indazol-4-yl)methyl)-2-vinyl-4,6-dihydro-5H-thiazolo[5',4':4,5]pyrrolo[2,3-d]pyridazin-5-one (100 mg, 0.20 mmol) in THF (2 mL) at 0° C. under N₂ was added BH₃-THF (0.2 mL, 1 mol/L, 0.20 mmol). The mixture was stirred at r.t. for 2 h, then cooled to 0° C., followed by addition of water (1 mL) and NaBO₃·4H₂O (154 mg, 1.00 mmol). The mixture was slowly warmed to r.t. and stirred at that temperature for 3 h. The resulting mixture was poured into saturated aqueous NH₄Cl and extracted with EtOAc. The combined organic layers were washed with brine, dried over anhydrous Na₂SO₄ and concentrated under reduced pressure. The residue was purified by column chromatography on silica gel (eluent: PE/EtOAc=5/1) to give the desired product (30 mg). LC-MS: m/z 511 (M+H)⁺.

Step B. 6-((1H-indazol-4-yl)methyl)-2-(2-hydroxyethyl)-4-methyl-4,6-dihydro-5H-thiazolo[5',4':4,5]pyrrolo[2,3-d]pyridazin-5-one To a solution of 2 (30 mg, 0.18 mmol) in DCM (3 mL) at 0° C. was added drop wise TFA (1 mL). The resulting mixture was stirred at r.t. for 16 hr. then concentrated under reduced pressure. The residue was purified by prep-HPLC to give the desired product (2.0 mg). LC-MS: m/z 381 (M+H)⁺. ¹H NMR (400 MHz, DMSO-d₆) δ 13.11 (s, 1H), 8.58 (s, 1H), 8.14 (s, 1H), 7.45 (d, 1H), 7.30-7.26 (m, 1H), 6.96 (d, 1H), 5.66 (s, 2H), 5.02-5.00 (m, 1H), 4.27 (s, 3H), 3.85-3.81 (m, 2H), 3.32-3.25 (m, 2H).

Example 3E. Synthesis of 6-((1H-indazol-4-yl)methyl)-4-methyl-2-((methylamino) methyl)-4,6-dihydro-5H-thiazolo[5',4':4,5]pyrrolo[2,3-d]pyridazin-5-one

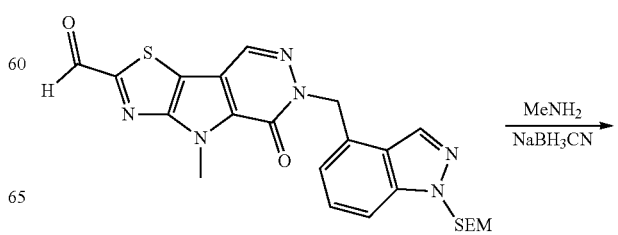

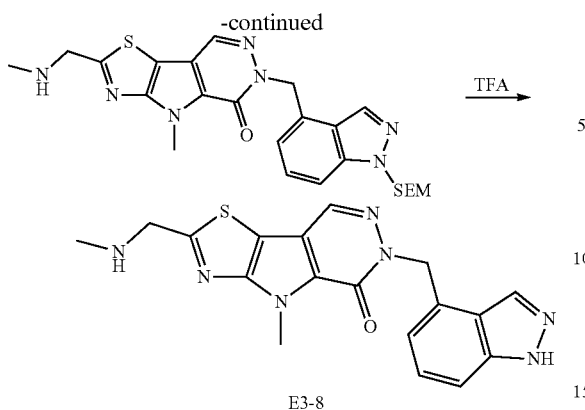

E3-8

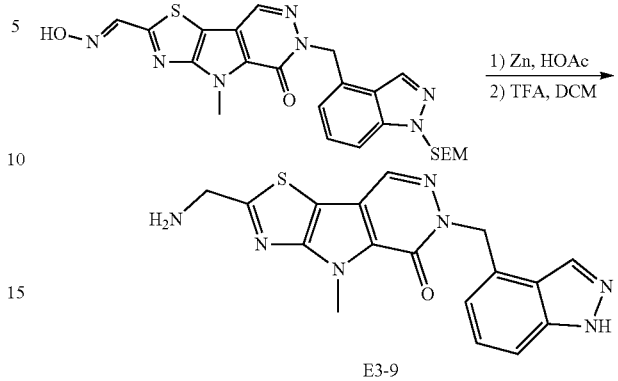

E3-9

Step A. 4-Methyl-2-((methylamino)methyl)-6-((1-((2-(trimethylsilyl)ethoxy) methyl)-1H-indazol-4-yl)methyl)-4H-thiazolo[5',4':4,5]pyrrolo[2,3-d]pyridazin-5(6H)-one To a mixture of 4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-carbaldehyde (50 mg, 0.1 mmol) in THF (10 mL) at 0° C. was added drop wise MeNH$_2$ (30% in MeOH, 21 mg, 0.2 mmol). The reaction mixture was stirred r.t. for 2 hr., followed by addition of sodium cyanoborohydride (19 mg, 0.3 mmol). The resulting mixture was stirred at r.t. overnight then quenched with saturated aqueous NH$_4$Cl and extracted with EtOAc. The combined organic layers were dried over anhydrous Na$_2$SO$_4$, and concentrated under reduced pressure. The residue was purified by prep-TLC to give desired product (35 mg). LCMS: m/z 511 (M+H)$^+$.

Step B. 6-((1H-indazol-4-yl)methyl)-4-methyl-2-((methylamino)methyl)-4H-thiazolo[5',4':4,5]pyrrolo[2,3-d]pyridazin-5(6H)-one To a mixture of 4-methyl-((methylamino)methyl)-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (35 mg, 0.07 mmol) in DCM (10 mL) at 0° C. was added drop wise TFA (3 mL). The reaction mixture was stirred at r.t. for 2 hr. then concentrated under reduced pressure. The residue was purified by prep-HPLC to give the desired product (5 mg). LCMS: m/z 380 (M+H)$^+$. $^1$H NMR (400 MHz, DMSO-d$_6$) 13.13 (s, 1H), 8.59 (s, 1H), 8.16 (d, 1H), 7.45 (d, 1H), 7.31-7.25 (m, 1H), 6.96 (d, 1H), 5.66 (s, 2H), 4.26 (s, 3H), 4.09 (s, 2H), 2.40 (s, 3H).

Example 3F. Synthesis of 6-((1H-indazol-4-yl)methyl)-2-(aminomethyl)-4-methyl-4,6-dihydro-5H-thiazolo[5',4':4,5]pyrrolo[2,3-d]pyridazin-5-one

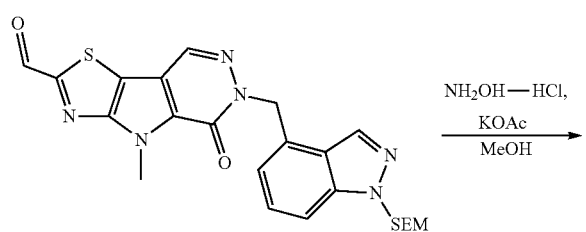

NH$_2$OH—HCl,
KOAc
MeOH

Step A. (E)-4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-carbaldehyde oxime To a mixture of 4-methyl-5-oxo-6-((1-((2-(trimethylsilyl)ethoxy) methyl)-1H-indazol-4-yl)methyl)-5,6-dihydro-4H-thiazolo[5',4':4,5]pyrrolo[2,3-d]pyridazine-2-carbaldehyde (120 mg, 0.24 mmol) in MeOH (10 mL) at 0° C. was added hydroxylamine hydrochloride (50 mg, 0.73 mmol), followed by addition of KOAc (71 mg, 0.73 mmol). The reaction mixture was stirred st r.t. for 8 hr. then quenched with saturated aqueous NH$_4$Cl and extracted with EtOAc. The combined organic layers were washed with brine, dried over anhydrous Na$_2$SO$_4$ and concentrated under reduced pressure. The residue was purified by prep-TLC to give the desired product (90 mg). LCMS: m/z 510 (M+H)$^+$.

Step B. 2-(Aminomethyl)-4-methyl-6-((1-((2-(trimethylsilyl) ethoxy)methyl)-1H-indazol-4-yl)methyl)-4H-thiazolo[5',4':4,5]pyrrolo[2,3-d]pyridazin-5(6H)-one To a mixture of (E)-4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-carbaldehyde oxime (90 mg, 0.18 mmol) in acetic acid (10 mL) was added Zn power (58 mg, 0.88 mmol). The reaction mixture was stirred at r.t. overnight then filtered through Celite. The filtrate was concentrated under reduced pressure and the residue was purified by prep-HPLC to give the desired product (70 mg). LCMS: m/z 496 (M+H)$^+$.

Step C. 6-((1H-indazol-4-yl)methyl)-2-(aminomethyl)-4-methyl-4H-thiazolo[5',4':4,5]pyrrolo[2,3-d]pyridazin-5(6H)-one was synthesized using the procedure in Example 3D. LCMS: m/z 366 (M+H)$^+$. $^1$H NMR (400 MHz, DMSO-d$_6$) δ 13.13 (s, 1H), 8.59 (s, 1H), 8.15 (s, 1H), 7.45 (d, 1H), 7.33-7.20 (m, 1H), 6.97 (d, 1H), 5.66 (s, 2H), 4.24 (d, 3H), 4.17 (s, 2H).

Example 3G. Synthesis of N-((6-((1H-indazol-4-yl)methyl)-4-methyl-5-oxo-5,6-dihydro-4H-thiazolo[5',4':4,5]pyrrolo[2,3-d]pyridazin-2-yl)methyl)acetamide

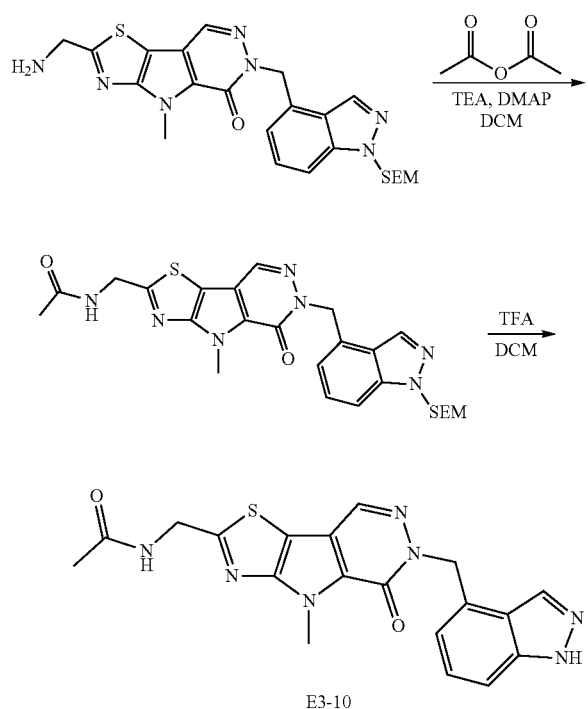

E3-10

Step A. N-((4-methyl-5-oxo-6-((1-((2-(trimethylsilyl)ethoxy)methyl)-1H-indazol-4-yl)methyl)-5,6-dihydro-4H-thiazolo[5,4':4,5]pyrrolo[2,3-d]pyridazin-2-yl)methyl)acetamide To a mixture of 2-(aminomethyl)-4-methyl-6-((1-((2-(trimethylsilyl) ethoxy)methyl)-1H-indazol-4-yl)methyl)-4H-thiazolo[5',4':4,5]pyrrolo[2,3-d]pyridazin-5(6H)-one (35 mg, 0.07 mmol) in DCM (10 mL) at 0° C. was added acetic anhydride (22 mg, 0.21 mmol), followed by addition of triethylamine (22 mg, 0.21 mmol) and DMAP (0.8 mg, 0.007 mmol). The reaction mixture was stirred at r.t. for 2 hr. then quenched with water and extracted with DCM. The combined organic layers were washed with brine, dried over anhydrous Na₂SO₄, and concentrated under reduced pressure. The residue was purified by prep-TLC to give the desired product (25 mg) as yellow oil. LCMS: m/z 538 (M+H)⁺.

Step B

N-((4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)methyl)acetamide was synthesized using the procedure in Example 3D. LCMS: m/z 408 (M+H)⁺. ¹H NMR (400 MHz, DMSO-d₆) δ 13.12 (s, 1H), 8.67 (s, 1H), 8.29 (s, 1H), 8.16 (s, 1H), 7.46 (d, 1H), 7.31-7.21 (m, 1H), 6.97 (d, 1H), 5.67 (s, 2H), 4.31 (s, 3H), 1.93 (s, 3H).

Example 3H. Synthesis of N-((6-((1H-indazol-4-yl)methyl)-4-methyl-5-oxo-5,6-dihydro-4H-thiazolo[5',4':4,5]pyrrolo[2,3-d]pyridazin-2-yl)methyl)methanesulfonamide

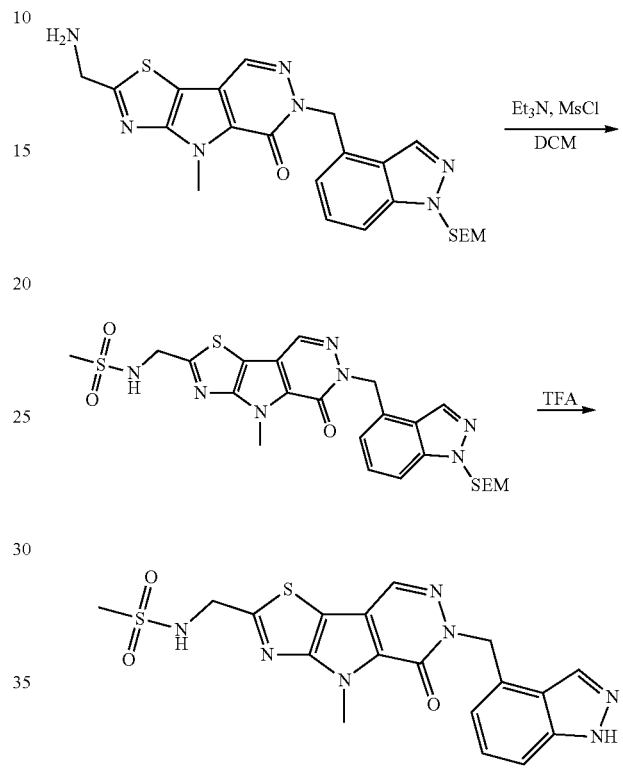

E3-11

Step A. N-((4-methyl-5-oxo-6-((1-((2-(trimethylsilyl) ethoxy)methyl)-1H-indazol-4-yl)methyl)-5,6-dihydro-4H-thiazolo[5,4':4,5]pyrrolo[2,3-d]pyridazin-2-yl)methyl)methanesulfonamide To a mixture of 2-(aminomethyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (50 mg, 0.1 mmol) in DCM (5 mL) at 0° C. was added Et₃N (30.62 mg, 0.3 mmol), followed by addition of MsCl (9.24 mg, 0.081 mmol). The mixture was stirred at 20° C. for 2 hr. then concentrated under reduced pressure. The residue was purified by prep-TLC to give the desired product (20 mg).

Step B

N-((6-((1H-indazol-4-yl)methyl)-4-methyl-5-oxo-5,6-dihydro-4H-thiazolo[5',4':4,5]pyrrolo[2,3-d]pyridazin-2-yl)methyl)methanesulfonamid was synthesized using the procedure in Example 3D. LCMS: m/z 444 (M+H)⁺. ¹H NMR (400 MHz, DMSO-d₆) δ 13.11 (s, 1H), 8.62 (s, 1H), 8.22 (s, 1H), 8.17 (d, 1H), 7.45 (d, 1H), 7.34-7.20 (m, 1H), 6.97 (d, 1H), 5.66 (s, 2H), 4.64 (d, 2H), 4.27 (s, 3H), 3.04 (s, 3H).

Example 3I. Synthesis of 2-(2-(1H-pyrazol-3-yl)ethyl)-6-((6-aminopyridin-2-yl)methyl)-4-methyl-4H-thiazolo[5',4':4,5]pyrrolo[2,3-d]pyridazin-5(6H)-one

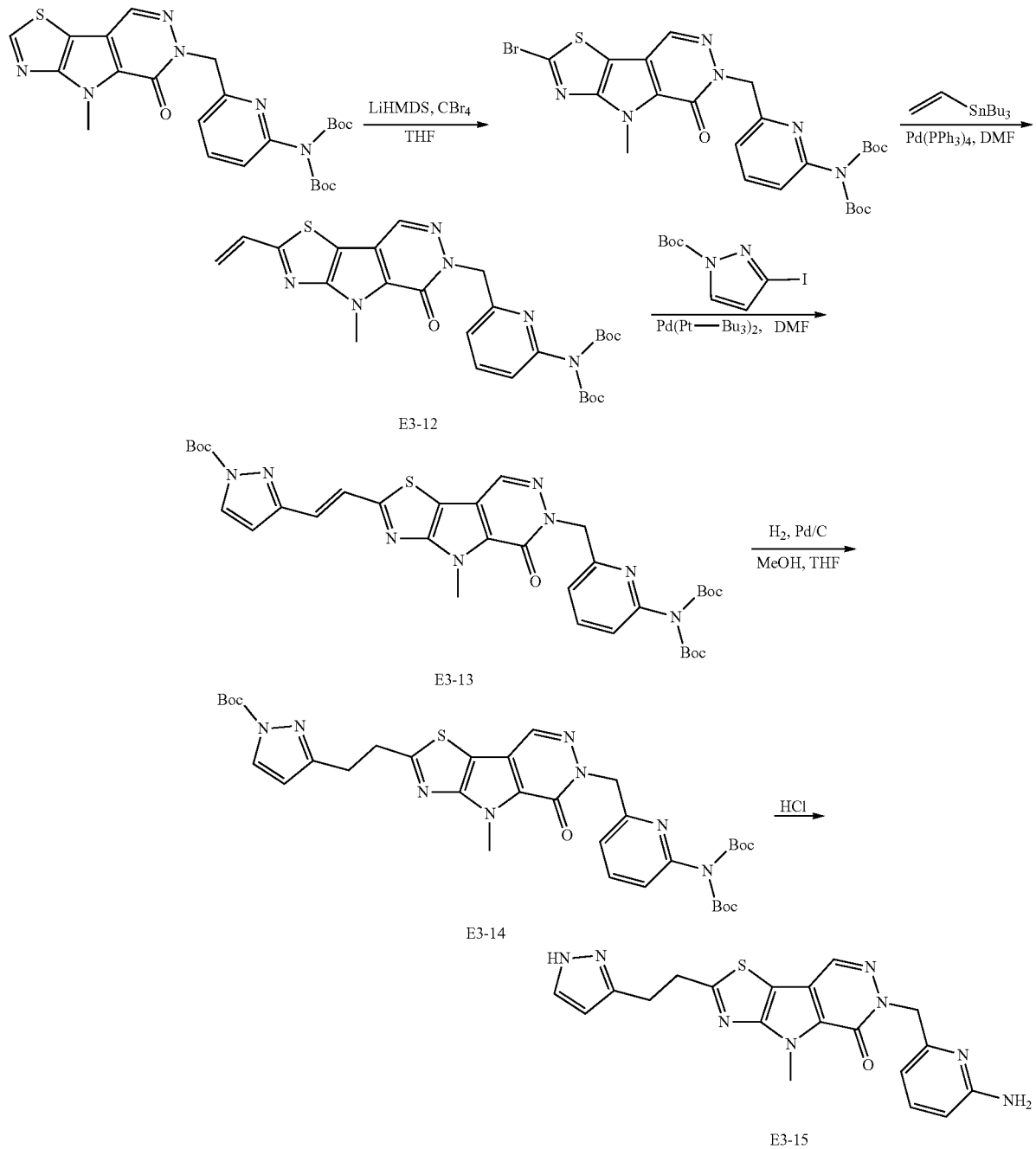

Step A. Synthesis of tert-butyl N-[(tert-butoxy)carbonyl]-N-[6-({4-bromo-7-methyl-9-oxo-3-thia-5,7,10,11-tetraazatricyclo[6.4.0.0{2,6}]dodeca-1(8),2(6),4,11-tetraen-10-yl}methyl)pyridin-2-yl]carbamate At −40° C. under $N_2$ atmosphere, to a mixture of tert-butyl N-[(tert-butoxy)carbonyl]-N-[6-({7-methyl-9-oxo-3-thia-5,7,10,11-tetraazatricyclo[6.4.0.0 {2,6}]dodeca-1 (8),2(6),4,11-tetraen-10-yl}methyl)pyridin-2-yl]carbamate (1.4 g, 2.73 mmol) and $CBr_4$ (4.52 g, 13.65 mmol) in THF (20 mL) was added LiHMDS (5.46 mL, 5.46 mmol) by dropwise. The reaction mixture was stirred at −40° C. for 30 min, then quenched by water (4 mL) and extracted with EtOAc. The combined organic layers were washed with brine, dried over anhy. $Na_2SO_4$ and concentrated under reduced pressure. The residue was purified by flash chromatography (silica gel, PE/EA=10:1~3:1) to afford 500 mg of tert-butyl N-[(tert-butoxy)carbonyl]-N-[6-({4-bromo-7-methyl-9-oxo-3-thia-5,7,10,11-tetraazatricyclo[6.4.0.0 {2,6}]dodeca-1(8),2(6),4,11-tetraen-10-yl}methyl)pyridin-2-yl]carbamate. LC-MS: m/z 591 (M+H)$^+$.

Step B. Synthesis of tert-butyl N-[(tert-butoxy)carbonyl]-N-[6-({4-vinyl-7-methyl-9-oxo-3-thia-5,7,10,11-tetraazatricyclo[6.4.0.0 {2,6}]dodeca-1(8),2(6),4,11-tetraen-10-yl}methyl)pyridin-2-yl]carbamate To a solution of tert-butyl N-[(tert-butoxy)carbonyl]-N-[6-({4-bromo-7-methyl-9-oxo-3-thia-5,7,10,11-tetraazatricyclo[6.4.0.0 {2,6}]dodeca-1(8),2(6),4,11-tetraen-10-yl}methyl)pyridin-2-yl]carbamate (500 mg, 0.85 mmol) in DMF (10 mL) was added tributyl(ethenyl)stannane (536 mg, 1.69 mmol) and DIPEA (327 mg, 2.53 mmol), followed by Pd(PPh$_3$)$_4$(105 mg, 0.08 mmol). The reaction mixture was stirred under N$_2$ atmosphere at 80° C. for 3 hr, then quenched by H$_2$O and extracted with EtOAc. The combined organic layers were washed with brine, dried over anhy. Na$_2$SO$_4$ and concentrated under reduced pressure. The residue was purified by flash chromatography (silica gel, PE/EA=10:1~5:1) to afford 300 mg oftert-butyl N-[(tert-butoxy)carbonyl]-N-[6-({4-vinyl-7-methyl-9-oxo-3-thia-5,7,10,11-tetraazatricyclo[6.4.0.0 {2,6}]dodeca-1(8),2(6),4,11-tetraen-10-yl}methyl)pyridin-2-yl]carbamate. LC-MS: m/z 539 (M+H)$^+$.

Step C. Synthesis of tert-butyl (E)-3-(2-(6-((6-((tert-butoxycarbonyl)[(tert-butoxy)carbonyl]amino)pyridin-2-yl)methyl)-4-methyl-5-oxo-5,6-dihydro-4H-thiazolo[5',4':4,5]pyrrolo[2,3-d]pyridazin-2-yl)vinyl)-1H-pyrazole-1-carboxylate To a solution of tert-butyl N-[(tert-butoxy)carbonyl]-N-[6-({4-vinyl-7-methyl-9-oxo-3-thia-5,7,10,11-tetraazatricyclo[6.4.0.0 {2,6}]dodeca-1 (8),2(6),4,11-tetraen-10-yl}methyl)pyridin-2-yl]carbamate (300 mg, 0.56 mmol) in DMF (4 mL) was added tert-butyl 3-iodo-1H-pyrazole-1-carboxylate (180 mg, 0.61 mmol). The reaction mixture was stirred at 100° C. overnight. After cooled down to r.t., the reaction mixture was quenched by H$_2$O and extracted with EtOAc. The combined organic layers were washed with brine, dried over anhy. Na$_2$SO$_4$ and concentrated under reduced pressure. The residue was purified by pre-TLC (PE/EA=1:1) to afford 200 mg of tert-butyl (E)-3-(2-(6-((6-((tert-butoxycarbonyl) [(tert-butoxy)carbonyl]amino)pyridin-2-yl)methyl)-4-methyl-5-oxo-5,6-dihydro-4H-thiazolo[5',4':4,5]pyrrolo[2,3-d]pyridazin-2-yl)vinyl)-1H-pyrazole-1-carboxylate. LC-MS: m/z 705 (M+H)$^+$.

Step D. Synthesis of tert-butyl 3-(2-(6-((6-((tert-butoxycarbonyl)[(tert-butoxy)carbonyl]amino)pyridin-2-yl)methyl)-4-methyl-5-oxo-5,6-dihydro-4H-thiazolo[5',4':4,5]pyrrolo[2,3-d]pyridazin-2-yl)ethyl)-1H-pyrazole-1-carboxylate To a solution of tert-butyl (E)-3-(2-(6-((6-((tert-butoxycarbonyl)[(tert-butoxy)carbonyl]amino)pyridin-2-yl)methyl)-4-methyl-5-oxo-5,6-dihydro-4H-thiazolo[5',4':4,5]pyrrolo[2,3-d]pyridazin-2-yl)vinyl)-1H-pyrazole-1-carboxylate (200 mg, 0.28 mmol) in THF/MeOH (4 mL, 10:1) was added Pd/C (6 mg, 10% wt.). The reaction mixture was stirred under hydrogen at r.t. for 12 hr. The mixture was filtered through a pad of celite, and the filtrate was concentrated. The residue was purified by pre-TLC (PE/EA=1:1) to afford 100 mg of tert-butyl 3-(2-(6-((6-((tert-butoxycarbonyl) [(tert-butoxy)carbonyl]amino)pyridin-2-yl)methyl)-4-methyl-5-oxo-5,6-dihydro-4H-thiazolo[5',4':4,5]pyrrolo[2,3-d]pyridazin-2-yl)ethyl)-1H-pyrazole-1-carboxylate. LC-MS: m/z 707 (M+H)$^+$.

Step E. Synthesis of 2-(2-(1H-pyrazol-3-yl)ethyl)-6-((6-aminopyridin-2-yl)methyl)-4-methyl-4H-thiazolo[5',4':4,5]pyrrolo[2,3-d]pyridazin-5(6H)-one At 0° C. under N$_2$ atmosphere, to a mixture of tert-butyl 3-(2-(6-((6-((tert-butoxycarbonyl)[(tert-butoxy)carbonyl] amino)pyridin-2-yl)methyl)-4-methyl-5-oxo-5,6-dihydro-4H-thiazolo[5',4':4,5]pyrrolo[2,3-d]pyridazin-2-yl)ethyl)-1H-pyrazole-1-carboxylate (100 mg, 0.14 mmol) in EtOH (2 mL) was added HCl (2 mL, 4 M in dioxane). After stirred at 80° C. for 1 hr, the mixture was poured in to satd. NaHCO$_3$, extracted with EtOAc. The combined organic layers were washed with brine, dried over anhy. Na$_2$SO$_4$ and concentrated under reduced pressure. The residue was purified by pre-TLC (DCM/MeOH=10:1) to afford 10 mg of 2-(2-(1H-pyrazol-3-yl)ethyl)-6-((6-aminopyridin-2-yl)methyl)-4-methyl-4H-thiazolo[5',4':4,5]pyrrolo[2,3-d]pyridazin-5 (6H)-one. LC-MS: m/z 407 (M+H)$^+$. $^1$H NMR (400 MHz, DMSO-d6) δ 12.52 (s, 1H), 8.55 (s, 1H), 7.60-7.10 (m, 2H), 6.30 (d, 1H), 6.18-6.02 (m, 2H), 5.90 (s, 2H), 5.19 (s, 2H), 4.26 (s, 3H), 3.61-3.41 (m, 2H), 3.19-3.12 (m, 2H).

Example 4. Synthesis of Compounds E4-vii and E4-viii

Scheme E4

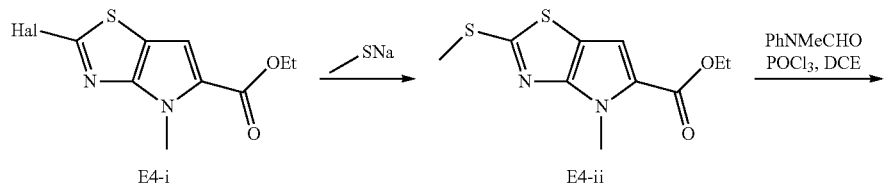

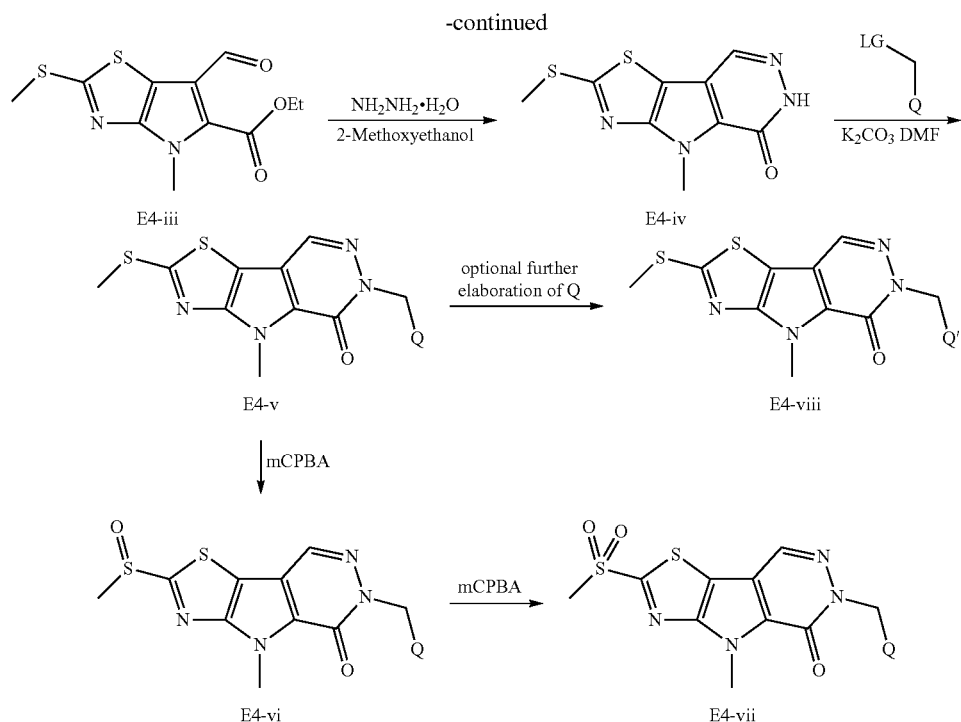

wherein Hal is halogen (e.g. Br or I); LG is a leaving group (e.g. halogen such as Br or I; OMs; or OTs); Q is as defined in any one of the first to twenty-sixth embodiments; and $Q^1$ is further functionalized Q (e.g. optionally substituted aryl, optionally substituted heteroaryl, optionally substituted carbocycle or optionally substituted heterocyclyl). Aromatic substitution reaction of compound E4-i with sodium methanethiolate provides compound E4-ii, which can be converted to compound E4-v using the synthesis of compound E1-iii to E1-vi. Oxidation of compound E4-v with mCPBA gives compound E4-vi and E4-vii respectively. Compound E4-viii can be converted from E4-v by further functionalizing Q to Q'.

Example 4A. Synthesis of 6-(3-methoxybenzyl)-4-methyl-2-(methylthio)-4,6-dihydro-5H-thiazolo[5',4': 4,5]pyrrolo[2,3-d]pyridazin-5-one

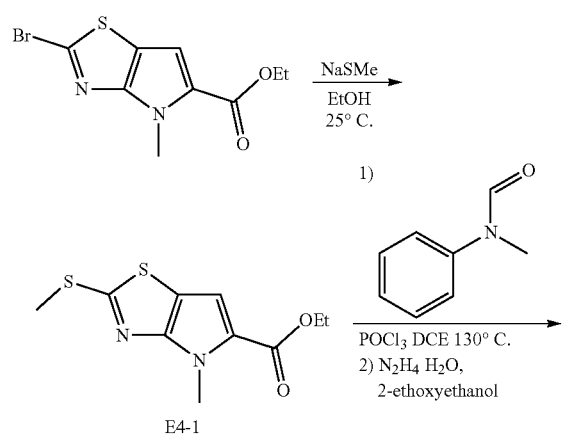

Step A: Ethyl 4-methyl-2-(methylthio)-4H-pyrrolo[2,3-d]thiazole-S-carboxylate To a mixture of ethyl 2-bromo-4-methyl-4H-pyrrolo[2,3-d]thiazole-5-carboxylate (500.0 mg, 1.73 mmol) in EtOH (10.0 mL) was added NaSMe (240.0 mg, 3.5 mmol). The reaction mixture was stirred at 25° C. for 3 hr then quenched with ice water and extracted with DCM. The combined organic layers were washed with brine, dried over anhydrous $Na_2SO_4$ and concentrated under reduced pressure to afford desired product (460 mg) which was directly used in the next step without any purification. LC-MS: m/z 257 (M+H)⁺.

Step B: Ethyl 6-formyl-4-methyl-2-(methylthio)-4H-pyrrolo[2,3-d]thiazole-5-carboxylate To a solution of ethyl 4-methyl-2-(methylthio)-4H-pyrrolo[2,3-d]thiazole-5-carboxylate (460.0 mg, 1.8 mmol) and N-methyl-N-phenylformamide (490 mg, 3.6 mmol) in DCE (10 mL) was added $POCl_3$ (550.0 mg, 3.6 mmol). The resulting mixture was stirred at 130° C. for 3 hr. then quenched with ice water and extracted with DCM. The combined organic layers were washed with brine, dried over anhydrous $Na_2SO_4$ and concentrated under reduced pressure. The residue was purified by column chromatography on silica gel (eluent: PE/EtOAc=8/1) to give the desired product (320.0 mg). LC-MS: m/z 285 $(M+H)^+$.

Step C: 4-Methyl-2-(methylthio)-4,6-dihydro-5H-thiazolo[5',4':4,5]pyrrolo[2,3-d]pyridazin-5-one To a solution of ethyl 6-formyl-4-methyl-2-(methylthio)-4H-pyrrolo[2,3-d]thiazole-5-carboxylate (300.0 mg, 1.06 mmol) in EtOH (5.0 mL) was added $N_2H_4 \cdot H_2O$ (2 mL, 98% wt). The reaction mixture was stirred at r.t. for 1 hr. then heated to 60° C. for overnight then cooled down. The solid was collected by filtration and dried under high vacuum to afford the desired product (180.0 mg). LC-MS: m/z 253 $(M+H)^+$. $^1H$ NMR (400 MHz, DMSO-$d_6$) δ 12.61 (s, 1H), 8.48 (s, 1H), 4.22 (s, 3H), 2.81 (s, 3H).

Step D: 6-(3-Methoxybenzyl)-4-methyl-2-(methylthio)-4,6-dihydro-5H-thiazolo[5',4':4,5]pyrrolo[2,3-d]pyridazin-5-one To a solution of 4-methyl-2-(methylthio)-4,6-dihydro-5H-thiazolo[5',4':4,5]pyrrolo[2,3-d]pyridazin-5-one (180.0 mg, 0.7 mmol) in DMF (5.0 mL) was added potassium carbonate (200 mg, 1.4 mmol). The mixture was stirred at 60° C. for 1 hr., followed by addition of 1-(chloromethyl)-3-methoxybenzene (170 mg, 1.07 mmol). The resulting mixture was stirred at 60° C. for 3 hr. then quenched with ice water (100.0 mL) and extracted with DCM. (10.0 mL×3). The combined organic layers were washed with brine, dried over anhydrous $Na_2SO_4$ and concentrated under reduced pressure. The residue was purified by column chromatography on silica gel (eluent: DCM/MeOH=10/1) to give the desired product (200.0 mg). LC-MS: m/z 373 $(M+H)^+$. $^1H$ NMR (400 MHz, DMSO-$d_6$) δ 8.57 (s, 11H), 7.24 (t, 1H), 6.88-6.82 (m, 3H), 5.32 (s, 2H), 4.24 (s, 3H), 3.72 (s, 3H), 2.82 (s, 3H).

The procedure set forth above was used to produce following compounds using appropriate starting materials. Standard protection and deprotection can be used when necessary.

| Cpd No. | Structure | Characterization |
|---|---|---|
| E4-4 | 6-(Imidazo[1,2-a]pyrimidin-2-ylmethyl)-4-methyl-2-(methylthio)-4,6-dihydro-5H-thiazolo[5',4':4,5]pyrrolo[2,3-d]pyridazin-5-one | LC-MS: m/z 384 $(M + H)^+$. $^1H$ NMR (400 MHz, DMSO-$d_6$) δ 8.87 (dd, 1H), 8.58 (s, 1H), 8.49 (dd, 1H), 7.70 (s, 1H), 7.02 (dd, 1H), 5.49 (s, 2H), 4.25 (s, 3H), 2.82 (s, 3H). |
| E4-5 | 3-((4-Methyl-2-(methylthio)-5-oxo-4H-thiazolo[5',4':4,5]pyrrolo[2,3-d]pyridazin-6(5H)-yl)methyl)benzenesulfonamide | LCMS: m/z 422$(M + H)^+$. $^1H$ NMR (400 MHz, DMSO-$d_6$) δ 8.60 (s, 1H), 7.75-7.72 (m, 2H), 7.55-7.53 (m, 2H), 7.36 (s, 2H), 5.42 (s, 2H), 4.23 (s, 3H), 2.81 (s, 3H). |
| E4-6 | 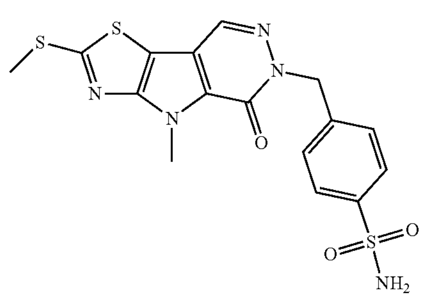 [SMILES: CSc1nc2c(s1)c1cnn(Cc3ccc(S(N)(=O)=O)cc3)c(=O)c1n2C] | LCMS: m/z 422 $(M + H)^+$. $^1H$ NMR (400 MHz, DMSO-$d_6$) δ 8.59 (s, 1H), 7.77 (d, 2H), 7.46 (d, 2H), 7.31 (s, 2H), 5.41 (s, 2H), 4.23 (s, 3H), 2.82 (s, 3H). |

| Cpd No. | Structure | Characterization |
|---|---|---|
| | 4-((4-Methyl-2-(methylthio)-5-oxo-4,5-dihydro-6H-thiazolo[5',4':4,5]pyrrolo[2,3-d]pyridazin-6-yl)methyl)benzenesulfonamide | |
| E4-7 | 6-((2-aminobenzo[d]thiazol-4-yl)methyl)-4-methyl-2-(methylthio)-4,6-dihydro-5H-thiazolo[5',4':4,5]pyrrolo[2,3-d]pyridazin-5-one | LCMS: m/z 415 (M + H)+. 1H NMR (400 MHz, DMSO-d6) δ 8.59 (s, 1H), 7.65 (s, 2H), 7.55 (d, 1H), 6.89 (t, 1H), 6.68 (d, 1H), 5.61 (s, 2H), 4.24 (s, 3H), 2.82 (s, 3H). |
| E4-8 | 6-(3-methoxybenzyl)-4-methyl-2-(phenylthio)-4,6-dihydro-5H-thiazolo[5',4':4,5]pyrrolo[2,3-d]pyridazin-5-one | LC-MS: m/z 435(M + H)+. 1H NMR (400 MHz, DMSO-d6) δ 8.50 (s, 1H), 7.80 (dd, 2H), 7.61 (dd, 3H), 7.21 (d, 1H), 6.83 (d, 3H), 5.29 (s, 2H), 4.23 (s, 3H), 3.71 (s, 3H). |
| E4-9 | 6-((2-(2,5-dimethyl-1H-pyrrol-1-yl)thiazol-4-yl)methyl)-4-methyl-2-(methylthio)-4,6-dihydro-5H-thiazolo[5',4':4,5]pyrrolo[2,3-d]pyridazin-5-one | LC-MS: m/z 443(M + H)+. 1H NMR (400 MHz, CDCl3) δ 8.13 (s, 1H), 7.05 (s, 1H), 5.77 (s, 2H), 5.32 (d, 2H), 4.31 (s, 3H), 2.74 (s, 3H), 2.10 (s, 6H). |

Example 4B. Synthesis of 4-methyl-2-(methylthio)-6-((2-oxo-2,3-dihydropyrimidin-4-yl)methyl)-4H-thiazolo[5',4':4,5]pyrrolo[2,3-d]pyridazin-5(6H)-one

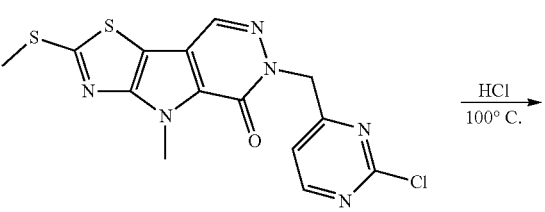

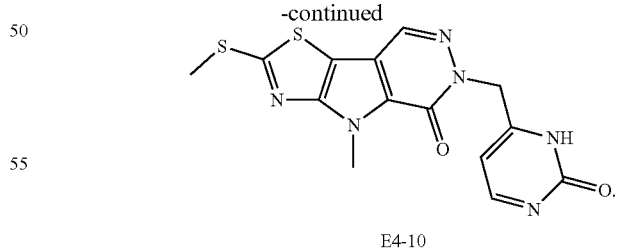

E4-10

A mixture of 6-((2-chloropyrimidin-4-yl)methyl)-4-methyl-2-(methylthio)-4H-thiazolo[5',4':4,5]pyrrolo[2,3-d]pyridazin-5(6H)-one (50 mg, 0.132 mmol) in HCl (10 mL) was stirred at 100° C. for 1 hr. then concentrated under reduced pressure. The residue was purified by prep-HPLC to give the desired product (5.0 mg, 10.51% yield). LCMS: m/z 361 (M+H)+. 1H NMR (400 MHz, DMSO-d6) δ 11.82 (s, 1H), 8.60 (s, 1H), 7.82 (s, 1H), 6.14 (s, 1H), 5.22 (s, 2H), 4.24 (s, 3H), 2.82 (s, 4H).

The procedure set forth above was used to produce the following compounds using the appropriate starting materials.

| Cpd No. | Structure | Characterization |
|---|---|---|
| E4-11 | 4-Methyl-2-(methylthio)-6-((2-oxo-1,2-dihydropyrimidin-5-yl)methyl)-4,6-dihydro-5H-thiazolo[5',4':4,5]pyrrolo[2,3-d]pyridazin-5-one | LC-MS: 361(M + H)+.<br>1H NMR (400 MHz, DMSO-d6) δ 11.95 (s, 1H), 8.57 (s, 1H), 8.31 (s, 2H), 5.12 (s, 2H), 4.23 (s, 3H), 2.81 (s, 3H). |

Example 4C. Synthesis of 6-(3-methoxybenzyl)-4-methyl-2-(methylsulfinyl)-4,6-dihydro-5H-thiazolo[5',4':4,5]pyrrolo[2,3-d]pyridazin-5-one

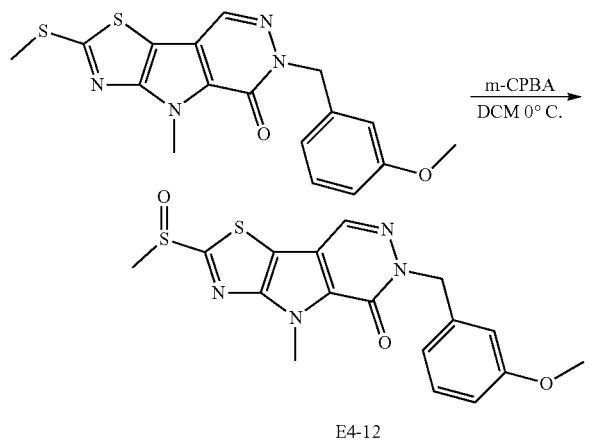

E4-12

To a solution of 6-(3-methoxybenzyl)-4-methyl-2-(methylthio)-4,6-dihydro-5H-thiazolo[5',4':4,5]pyrrolo[2,3-d]pyridazin-5-one (30.0 mg, 0.08 mmol) in DCM (3.0 mL) at 0° C. was added m-CPBA (14.0 mg, 0.08 mmol). The resulting mixture was stirred at 0° C. for 1 hr. then quenched with ice water and extracted with DCM. The combined organic layers were washed with brine, dried over anhydrous $Na_2SO_4$ and concentrated under reduced pressure. The residue was purified by column chromatography on silica gel (eluent: DCM/MeOH=10/1) to give the desired product (15.0 mg). LC-MS: m/z 389 (M+H)+. H NMR (400 MHz, DMSO-d6) δ 8.74 (s, 1H), 7.25 (t, 1H), 6.86 (dd, 3H), 5.35 (s, 2H), 4.30 (s, 3H), 3.73 (s, 3H), 3.11 (s, 3H).

The procedure set forth above was used to produce following compounds using appropriate starting materials. Standard protection and deprotection can be used when necessary.

| Cpd No. | Structure | Characterization |
|---|---|---|
| E4-13 | 6-(3-methoxybenzyl)-4-methyl-2-(phenylsulfinyl)-4,6-dihydro-5H-thiazolo[5',4':4,5]pyrrolo[2,3-d]pyridazin-5-one | LC-MS: m/z 451(M + H)+.<br>1H NMR (400 MHz, DMSO-d6) δ 8.67 (s, 1H), 7.90 (dd, 2H), 7.70-7.62 (m, 3H), 7.22 (t, 1H), 6.83 (d, 3H), 5.31 (s, 2H), 4.25 (s, 3H), 3.70 (s, 3H). |

-continued

| Cpd No. | Structure | Characterization |
|---|---|---|
| E4-14 | 6-(3-Acetylbenzyl)-4-methyl-2-(methylsulfinyl)-4H-thiazolo[5',4':4,5]pyrrolo[2,3-d]pyridazin-5(6H)-one | LCMS: m/z 401 (M + H)$^+$. $^1$H NMR (400 MHz, DMSO-d$_6$) δ 8.75 (s, 1H), 7.92-7.87 (m, 2H), 7.58-7.56 (m, 1H), 7.49 (t, 1H), 5.45 (s, 2H), 4.29 (s, 3H), 3.11 (s, 3H), 2.56 (s, 3H). |
| E4-15 | 6-(3-(1-hydroxyethyl)benzyl)-4-methyl-2-(methylsulfinyl)-4H-thiazolo[5',4':4,5]pyrrolo[2,3-d]pyridazin-5(6H)-one | LCMS: m/z 425 (M + Na)$^+$. $^1$H NMR (400 MHz, DMSO-d$_6$) δ 8.73 (s, 1H), 7.32 (s, 1H), 7.28-7.21 (m, 2H), 7.15-7.13 (m, 1H), 5.34 (s, 2H), 5.14 (d, 1H), 4.70-4.64 (m, 1H), 4.30 (s, 3H), 3.11 (s, 3H), 1.28 (d, 3H). |
| E4-16 | 6-((1H-indazol-4-yl)methyl)-4-methyl-2-(methylsulfinyl)-4,6-dihydro-5H-thiazolo[5',4':4,5]pyrrolo[2,3-d]pyridazin-5-one | LCMS: m/z 399 (M + H)$^+$. $^1$H NMR (400 MHz, DMSO-d$_6$) δ 13.14 (s, 1H), 8.74 (s, 1H), 8.15 (s, 1H), 7.47 (d, 1H), 7.29 (t, 1H), 6.98 (d, 1H), 5.68 (s, 2H), 4.31 (s, 3H), 3.11 (s, 3H). |
| E4-17 | 4-((4-Methyl-2-(methylsulfinyl)-5-oxo-4,5-dihydro-6H-thiazolo[5',4':4,5]Pyrrolo[2,3-d]pyridazin-6-yl)methyl)benzonitrile | LC-MS: 384(M + H)$^+$. $^1$H NMR (400 MHz, DMSO-d$_6$) δ 8.81 (s, 1H), 7.86 (d, 2H), 7.53 (d, 2H), 5.52 (d, 2H), 4.34 (s, 3H), 3.17 (s, 3H). |

| Cpd No. | Structure | Characterization |
|---|---|---|
| E4-18 | 4-Methyl-2-(methylsulfinyl)-6-(quinolin-2-ylmethyl)-4,6-dihydro-5H-thiazolo[5',4':4,5]pyrrolo[2,3-d]pyridazin-5-one | LCMS: 410 (M + H)⁺. ¹H NMR (400 MHz, DMSO-d₆) δ 8.78 (s, 1H), 8.32 (d, 1H), 7.94 (dd, 2H), 7.82-7.68 (m, 1H), 7.59 (dd, 1H), 7.33 (d, 1H), 5.75-5.56 (s, 2H), 4.30 (s, 3H), 3.12 (s, 3H). |
| E4-19 | 6-((2,3-Dihydrobenzo[b][1,4]dioxin-6-yl)methyl)-4-methyl-2-(methylsulfinyl)-4,6-dihydro-5H-thiazolo[5',4':4,5]Pyrrolo[2,3-d]pyridazin-5-one | LCMS: 417 (M + H)⁺. ¹H NMR (400 MHz, DMSO-d₆) δ 8.71 (s, 1H), 8.45 (s, 1H), 6.83 (s, 1H), 6.80 (d, 1H), 5.24 (d, 2H), 4.30 (s, 3H), 4.20 (s, 4H), 3.11 (s, 3H), |
| E4-20 | 6-(2,3-Dihydro-1H-indol-4-ylmethyl)-2-methanesulfinyl-8-methyl-6,8-dihydro-3-thia-1,5,6,8-tetraaza-cyclopenta[a]inden-7-one | LC-MS: m/z 400 (M + H)⁺. ¹H NMR (400 MHz, DMSO-d₆) δ 8.71 (s, 1H), 6.83 (dd, 1H), 6.38 (d, 1H), 5.50 (s, 1H), 5.25 (s, 2H), 4.29 (s, 3H), 3.41 (t, 2H), 3.11 (s, 3H), 2.96 (t, 2H). |
| E4-21 | 2-Methanesulfinyl-8-methyl-6-(1,2,3,4-tetrahydro-isoquinolin-5-ylmethyl)-6,8-dihydro-3-thia-1,5,6,8-tetraaza-cyclopenta[a]inden-7-one | LC-MS: m/z 414 (M + H)⁺. ¹H NMR (400 MHz, DMSO-d₆) δ 8.73 (s, 1H), 7.03 (t, 1H), 6.95 (d, 1H), 6.77 (d, 1H), 5.32 (s, 2H), 4.29 (s, 3H), 3.90 (s, 2H), 3.11 (s, 3H), 3.06 (t, 2H), 2.78 (t, 2H). |

Example 4D. Synthesis of 4-((4-methyl-2-(methyl-sulfinyl)-5-oxo-4,5-dihydro-6H-thiazolo[5',4':4,5]pyrrolo[2,3-d]pyridazin-6-yl)methyl)benzamide

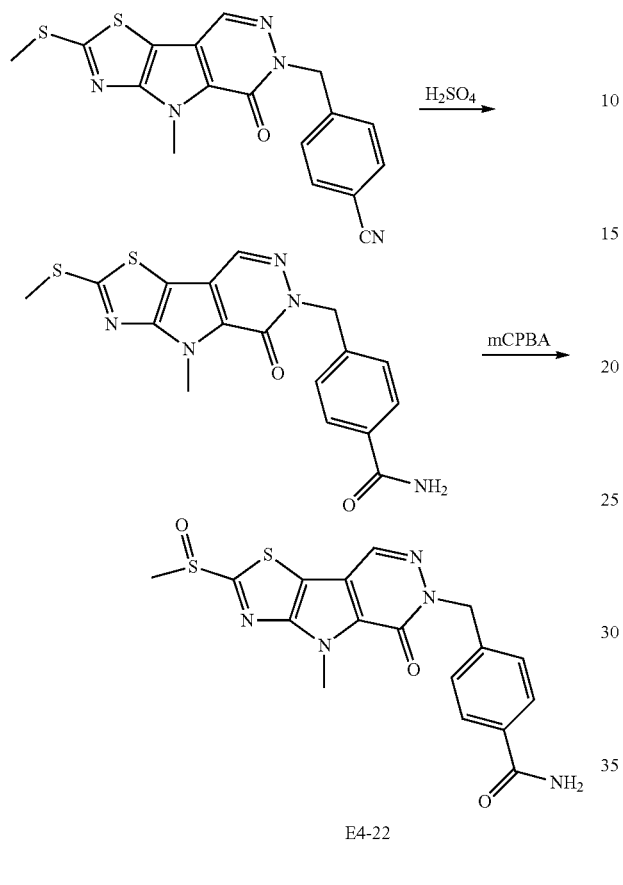

E4-22

Step A: 4-((4-Methyl-2-(methylthio)-5-oxo-4,5-dihydro-6H-thiazolo[5',4':4,5]pyrrolo[2,3-d]pyridazin-6-yl)methyl)benzamide A mixture of 4-((4-methyl-2-(methylthio)-5-oxo-4,5-dihydro-6H-thiazolo[5',4':4,5]pyrrolo[2,3-d]pyridazin-6-yl)methyl)benzonitrile (50.0 mg, 0.13 mmol) in $H_2SO_4$ (1.0 mL) was stirred at 0° C. for 1 hr. then neutralized with saturated aqueous $NaHCO_3$ and extracted with DCM. The combined organic layers were washed with brine, dried over anhydrous $Na_2SO_4$ and concentrated under reduced pressure. The residue was purified by column chromatography on silica gel (eluent: DCM/MeOH=10/1) to give the desired product (20.0 mg). LC-MS: m/z 386 $(M+H)^+$.

Step B: 4-((4-Methyl-2-(methylsulfinyl)-5-oxo-4,5-dihydro-6H-thiazolo[5',4':4,5]pyrrolo[2,3-d]pyridazin-6-yl)methyl)benzamide To a solution of 4-((4-methyl-2-(methylthio)-5-oxo-4,5-dihydro-6H-thiazolo[5',4':4,5]pyrrolo[2,3-d]pyridazin-6-yl)methyl)benzamide (20.0 mg, 0.052 mmol) in DCM (2.0 mL) at 0° C. was added m-CPBA (10.0 mg, 0.052 mmol). The resulting mixture was stirred at 0° C. for 1 hr then quenched with ice water (10.0 mL) and extracted with DCM. The combined organic layers were washed with brine, dried over anhydrous $Na_2SO_4$ and concentrated under reduced pressure. The residue was purified by column chromatography on silica gel (eluent: DCM/MeOH=10/1) to give the desired product (5.0 mg). LC-MS: m/z 402 $(M+H)^+$. $^1$H NMR (400 MHz, DMSO-$d_6$) δ 8.75 (s, 1H), 7.93 (s, 1H), 7.82 (d, 2H), 7.38-7.33 (m, 3H), 5.42 (s, 2H), 4.29 (s, 3H), 3.11 (s, 3H).

Example 4E. Synthesis of 6-(3-(2-hydroxypropan-2-yl)benzyl)-4-methyl-2-(methylsulfinyl)-4H-thiazolo[5',4':4,5]pyrrolo[2,3-d]pyridazin-5(6H)-one

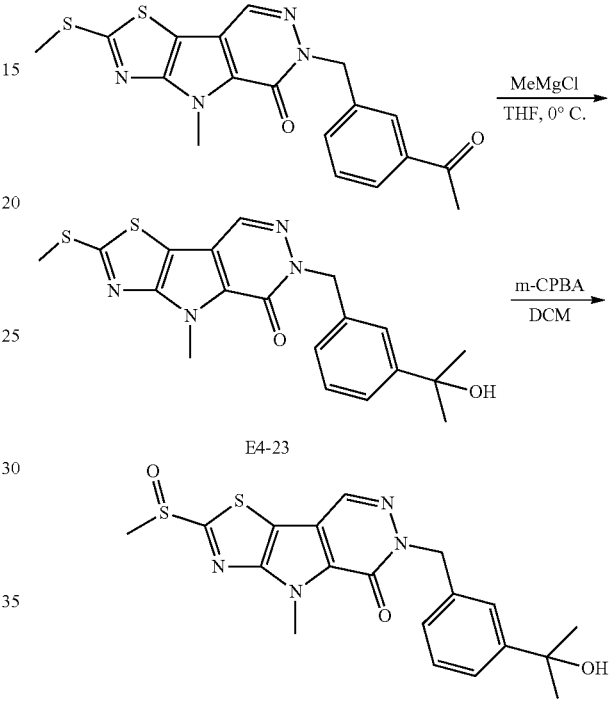

E4-23

E4-24

Step A. 6-(3-(2-Hydroxypropan-2-yl)benzyl)-4-methyl-2-(methylthio)-4H-thiazolo[5',4':4,5]pyrrolo[2,3-d]pyridazin-5(6H)-one To a mixture of 6-(3-acetylbenzyl)-4-methyl-2-(methylthio)-4H-thiazolo[5',4':4,5]pyrrolo[2,3-d]pyridazin-5(6H)-one (120 mg, 0.31 mmol) in dry THF (5 mL) at 0° C. was added dropwise methylmagnesium chloride (0.3 mL, 0.9 mmol). The mixture was stirred at r.t. for 30 min then poured into saturated aq. $NH_4Cl$ and extracted with EtOAc. The organic layer was separated and concentrated under reduced pressure. The residue was purified by prep-TLC to afford desired product (70 mg). LCMS: m/z 401 $(M+H)^+$. $^1$H NMR (400 MHz, DMSO-$d_6$) δ 8.56 (s, 1H), 7.49 (s, 1H), 7.33 (d, 1H), 7.23 (t, 1H), 7.09 (d, 1H), 5.33 (s, 2H), 4.98 (s, 1H), 4.24 (s, 3H), 2.81 (s, 3H), 1.39 (s, 6H).

Step B. 6-(3-(2-Hydroxypropan-2-yl)benzyl)-4-methyl-2-(methylsulfinyl)-4H-thiazolo[5',4':4,5]pyrrolo[2,3-d]pyridazin-5(6H)-one To a mixture of 6-(3-(2-hydroxypropan-2-yl)benzyl)-4-methyl-2-(methylthio)-4H-thiazolo[5',4':4,5]pyrrolo[2,3-d]pyridazin-5 (6H)-one (46 mg, 0.115 mmol) in DCM (3 mL) at 0° C. was added m-CPBA (20 mg, 0.1 mmol, 85% w/w).

The mixture was stirred at r.t. for 30 min then quenched with saturated aq. Na$_2$S$_2$O$_3$ and extracted with DCM. The organic layer was separated and concentrated under reduced pressure. The residue was purified by prep-HPLC to afford desired product (10 mg). LCMS: m/z 417 (M+H)$^+$. $^1$H NMR (400 MHz, DMSO-d$_6$) δ 8.73 (s, 1H), 7.49 (s, 1H), 7.34 (d, 1H), 7.24 (t, 1H), 7.09 (d, 1H), 5.37 (s, 2H), 4.98 (s, 1H), 4.30 (s, 3H), 3.11 (s, 311), 1.39 (s, 611).

Example 4F. Synthesis of 6-((2-aminopyridin-4-yl)methyl)-4-methyl-2-(methylsulfinyl)-4H-thiazolo[5',4':4,5]pyrrolo[2,3-d]pyridazin-5(6H)-one

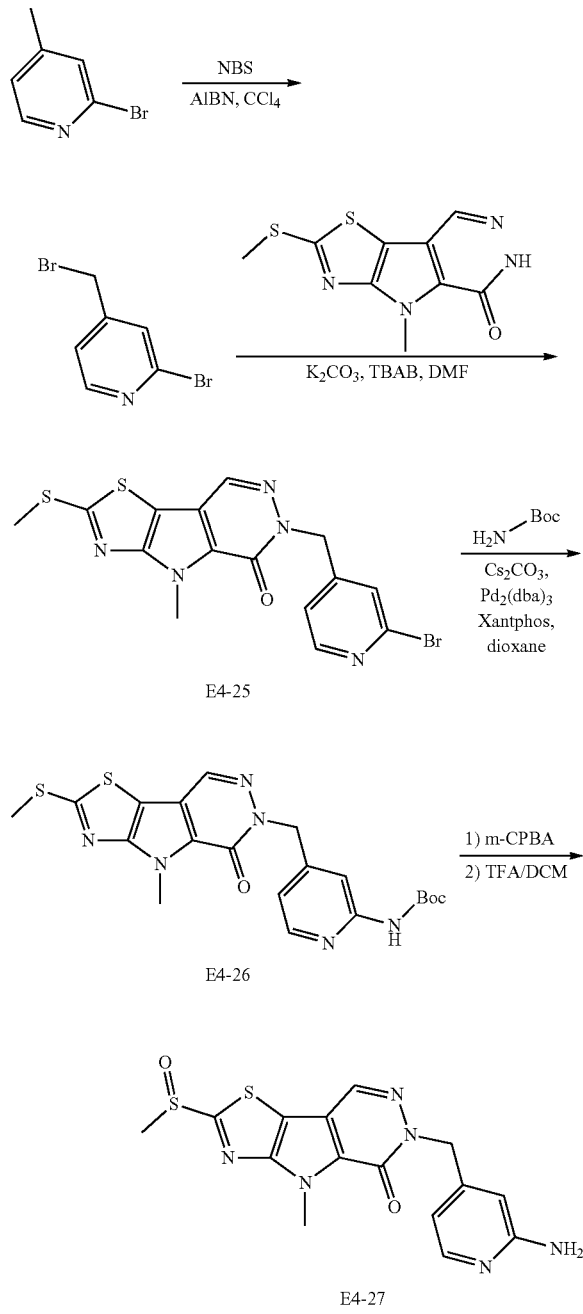

Step A. 2-Bromo-4-(bromomethyl)pyridine

A mixture of 2-bromo-4-methylpyridine (1 g, 5.81 mmol), NBS (1.1 g, 6.39 mmol) and a catalytic amount of AIBN (100 mg) in CCl$_4$ (10 mL) was stirred at 80° C. overnight. The resulting mixture was concentrated under reduced pressure and the residue was purified by column chromatography on silica gel (eluent: PE/EtOAc=200/1) to give the desired product (500 mg).

Step B. 6-((2-Bromopyridin-4-yl)methyl)-4-methyl-2-(methylthio)-4H-thiazolo[5',4':4,5]pyrrolo[2,3-d]pyridazin-5(6H)-one A mixture of 4-methyl-2-(methylthio)-4H-thiazolo[5',4':4,5]pyrrolo[2,3-d]pyridazin-5(6H)-one (100 mg, 0.40 mmol), and K$_2$CO$_3$ (164 mg, 1.19 mmol) in DMF (8 mL) was stirred at 60° C. for 2 hr., followed by addition of a solution of 2-bromo-4-(bromomethyl)pyridine (199 mg, 0.80 mmol) in DMF (2 mL) and a catalytic amount of TBAB (13 mg). The mixture was stirred at 60° C. overnight then quenched with water (20 mL) and extracted with EtOAc. The combined organic layers were washed with saturated aqueous NH$_4$Cl, dried over anhydrous Na$_2$SO$_4$ and concentrated under reduced pressure. The residue was purified by column chromatography on silica gel (eluent: PE/EtOAc=10/1) to give the desired product (150 mg). LCMS: m/z 423 (M+H)$^+$.

Step C. Tert-butyl (4-((4-methyl-2-(methylthio)-5-oxo-4H-thiazolo[5',4':4,5]pyrrolo[2,3-d]pyridazin-6(5H)-yl)methyl)pyridin-2-yl)carbamate A mixture of 6-((2-bromopyridin-4-yl)methyl)-4-methyl-2-(methylthio)-4H-thiazolo[5',4':4,5]pyrrolo[2,3-d]pyridazin-5(6H)-one (100 mg, 0.24 mmol), tert-butyl carbamate (83 mg, 0.71 mmol), K$_3$PO$_4$ (201 mg, 0.95 mmol), Pd$_2$(dba)$_3$ (18 mg, 0.02 mmol) and Xantphos (11 mg, 0.02 mmol) in dioxane (10 mL) was stirred at 100° C. under nitrogen overnight. The resulting mixture was quenched with water and extracted with EtOAc. The combined organic layers were washed with brine, dried over anhydrous Na$_2$SO$_4$ and concentrated under reduced pressure. The residue was purified by column chromatography on silica gel (eluent: PE/EtOAc=3/1) to give the desired product (100 mg). LCMS: m/z 459 (M+H)$^+$.

Step D-E

Tert-butyl (4-((4-methyl-2-(methylsulfinyl)-5-oxo-4H-thiazolo[5',4':4,5]pyrrolo[2,3-d]pyridazin-6(5H)-yl)methyl)pyridin-2-yl)carbamate was synthesized using procedure similar to Example 4C and 6-((2-Aminopyridin-4-yl)methyl)-4-methyl-2-(methylsulfinyl)-4H-thiazolo[5',4':4,5]pyrrolo[2,3-d]pyridazin-5(6H)-one were synthesized using the procedure similar to Example 3G. LCMS: m/z 375 (M+H)$^+$. $^1$H NMR (400 MHz, DMSO-d$_6$) δ 8.67 (s, 1H), 7.73 (d, 1H), 6.30 (d, 1H), 6.12 (s, 1H), 5.89 (s, 2H), 5.24-5.03 (m, 2H), 4.29 (s, 3H), 3.03 (s, 3H).

The procedure set forth above was used to produce following compounds using appropriate starting materials. Standard protection and deprotection can be used when necessary

| Cpd No. | Structure | Characterization |
|---|---|---|
| E4-28 | 6-((2-aminopyrimidin-4-yl)methyl)-4-methyl-2-(methylsulfinyl)-4H-thiazolo[5',4':4,5]pyrrolo[2,3-d]pyridazin-5(6H)-one | LC-MS: m/z 376 (M + H)+. 1H NMR (400 MHz, DMSO-d6) δ 8.76 (s, 1H), 8.12 (d, 1H), 6.60 (s, 2H), 6.22 (d, 1H), 5.20 (t, 2H), 4.28 (s, 3H), 3.12 (s, 3H). |
| E4-29 | 6-((2-Aminopyrimidin-5-yl)methyl)-4-methyl-2-(methylsulfinyl)-4,6-dihydro-5H-thiazolo[5',4':4,5]pyrrolo[2,3-d]pyridazin-5-one | LC-MS: 376(M + H)+. 1H NMR (400 MHz, DMSO-d6) δ 8.70 (s, 1H), 8.29 (s, 2H), 6.66 (s, 2H), 5.16 (s, 2H), 4.28 (s, 3H), 3.10 (s, 3H). |

Example 4G. Synthesis of 6-((2-aminothiazol-5-yl)methyl)-4-methyl-2-(methyl sulfinyl)-4H-thiazolo[5',4':4,5]pyrrolo[2,3-d]pyridazin-5(6H)-one -continued

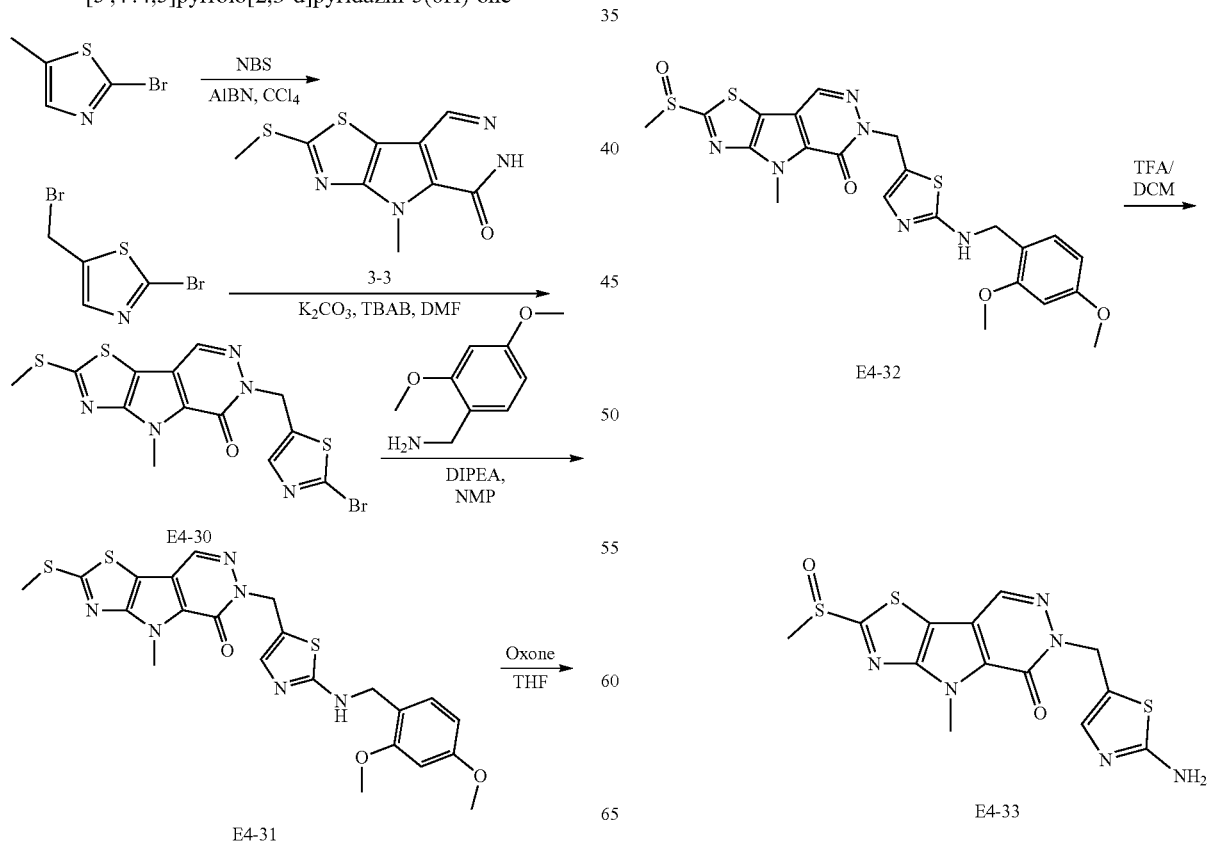

Step A-B

2-Bromo-5-(bromomethyl)thiazole and 6-((2-Bromothiazol-5-yl)methyl)-4-methyl-2-(methylthio)-4H-thiazolo[5',4':4,5]pyrrolo[2,3-d]pyridazin-5(6H)-one were synthesized similar to Example 4F.

Step C. 6-((2-((2,4-dimethoxybenzyl)amino)thiazol-5-yl)methyl)-4-methyl-2-(methylthio)-4H-thiazolo[5',4':4,5]pyrrolo[2,3-d]pyridazin-5(6H)-one A mixture of 6-((2-bromothiazol-5-yl)methyl)-4-methyl-2-(methylthio)-4H-thiazolo[5',4':4,5]pyrrolo[2,3-d]pyridazin-5(6H)-one (130 mg, 0.30 mmol) and DIPEA (0.1 mL) in NMP (0.1 mL) and (2,4-dimethoxyphenyl)methanamine (0.1 mL) was stirred at 150° C. for 4 hr. Then the traction mixture was quenched with water (10 mL), extracted with EtOAc. The combined organic layers were washed with brine, dried over anhydrous $Na_2SO_4$ and concentrated under reduced pressure. The residue was purified by column chromatography on silica gel (eluted with PE/EtOAc=5/1) to give the desired product (60 mg, 38.4% yield). LC-MS: m/z 515 (M+H)$^+$.

Step D. 6-((2-((2,4-dimethoxybenzyl)amino)thiazol-5-yl)methyl)-4-methyl-2-(methylsulfinyl)-4H-thiazolo[5',4':4,5]pyrrolo[2,3-d]pyridazin-5(6H)-one To a mixture of 6-((2-((2,4-dimethoxybenzyl)amino)thiazol-5-yl)methyl)-4-methyl-2-(methylthio)-4H-thiazolo[5',4':4,5]pyrrolo[2,3-d]pyridazin-5(6H)-one (50 mg, 0.10 mmol) in THF (3 mL) at 0° C. was added oxone (61 mg, 0.10 mmol). The mixture was stirred at 0° C. for 1 hr, then quenched with saturated aqueous $Na_2S_2O_3$ solution (5 mL) and extracted with DCM. The combined organic layers were washed with brine, dried over anhydrous $Na_2SO_4$ and concentrated under reduced pressure to give the desired product (30 mg, 50.1% yield) which was used directly in the next step without further purification. LC-MS: m/z 531 (M+H)$^+$.

Step E 6-((2-Aminothiazol-5-yl)methyl)-4-methyl-2-(methylsulfinyl)-4H-thiazolo[5',4':4,5]pyrrolo[2,3-d]pyridazin-5(6H)-one was synthesized similar to Example 3G. LC-MS: m/z 381 (M+H)$^+$. $^1$H NMR (400 MHz, DMSO-d$_6$) δ 8.70 (s, 1H), 6.97 (s, 1H), 6.87 (s, 2H), 5.28 (s, 2H), 4.29 (s, 3H), 3.11 (s, 3H).

The procedure set forth above was used to produce following compounds using appropriate starting materials. Standard protection and deprotection can be used when necessary.

Example 4H. Synthesis of 6-(3-methoxybenzyl)-4-methy-2-(methylsulfonyl)-4,6-dihydro-5H-thiazolo[5',4':4,5]pyrrolo[2,3-d]pyridazin-5-one

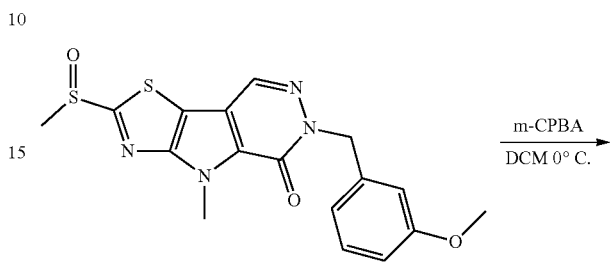

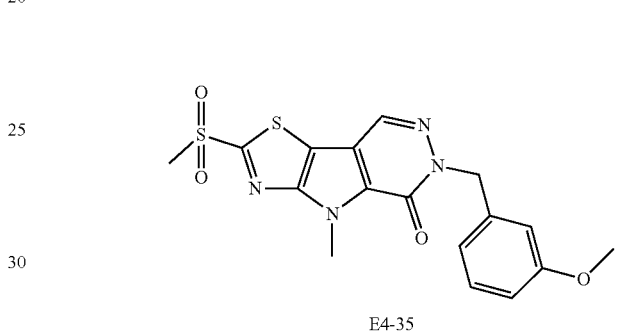

E4-35

To a solution of 6-(3-methoxybenzyl)-4-methyl-2-(methylsulfinyl)-4,6-dihydro-5H-thiazolo[5',4':4,5]pyrrolo[2,3-d]pyridazin-5-one (30.0 mg, 0.08 mmol) in DCM (3.0 mL) at 0° C. was m-CPBA (35.0 mg, 0.2 mmol). The resulting mixture was stirred at 0° C. for 1 hr. then quenched with ice water and extracted with DCM. The combined organic layers were washed with brine, dried over anhydrous $Na_2SO_4$ and concentrated under reduced pressure. The residue was purified by column chromatography on silica gel (eluent: DCM/MeOH=10/1) to give the desired product (10.0 mg, 32% yield). LC-MS: m/z 405 (M+H)$^+$. $^1$H NMR (400 MHz, DMSO-d$_6$) δ 8.78 (s, 1H), 7.24 (t, 1H), 6.92-6.82 (m, 3H), 5.35 (s, 2H), 4.33 (s, 3H), 3.72 (s, 3H), 3.57 (s, 3H).

| Cpd No. | Structure | Characterization |
|---|---|---|
| E4-34 | ![structure] 6-((1H-indazol-4-yl)methyl)-4-methyl-2-(methylsulfinyl)-4,6-dihydro-5H-thiazolo[5',4':4,5]pyrrolo[2,3-d]pyridazin-5-one | LCMS: m/z 381 (M + H)$^+$. $^1$H NMR (400 MHz, DMSO-d$_6$) δ 8.69 (s, 1H), 6.92 (s, 2H), 6.21 (s, 1H), 5.26-5.05 (m, 2H), 4.30 (s, 3H), 3.11 (s, 3H). |

| Cpd No. | Structure | Characterization |
|---|---|---|
| E4-36 | 6-(3-methoxybenzyl)-4-methyl-2-(phenylsulfonyl)-4,6-dihydro-5H-thiazolo[5',4':4,5]pyrrolo[2,3-d]pyridazin-5-one | LC-MS: m/z 467(M + H)⁺. ¹H NMR (400 MHz, DMSO-$d_6$) δ 8.75 (s, 1H), 8.11 (d, 2H), 7.81 (dd, 1H), 7.73 (dd, 2H), 7.23 (s, 1H), 6.86-6.83 (m, 3H), 5.32 (s, 2H), 4.24 (s, 3H), 3.70 (s, 3H). |
| E4-37 | 6-((1H-indazol-4-yl)methyl)-4-methyl-2-(methylsulfonyl)-4,6-dihydro-5H-thiazolo[5',4':4,5]pyrrolo[2,3-d]pyridazin-5-one | LCMS: m/z 415 (M + H)⁺. ¹H NMR (400 MHz, DMSO-$d_6$) δ 13.13 (s, 1H), 8.79 (s, 1H), 8.15 (s, 1H), 7.46 (d, 1H), 7.31-7.25 (m, 1H), 6.99 (d, 1H), 5.69 (s, 2H), 4.34 (s, 3H), 3.56 (s, 3H). |
| E4-38 | 6-((1H-indazol-4-yl)methyl)-2-(benzylsulfonyl)-4-methyl-4,6-dihydro-5H-thiazolo[5',4':4,5]pyrrolo[2,3-d]pyridazin-5-one | LCMS: m/z 491 (M + H)⁺. ¹H NMR (400 MHz, DMSO-$d_6$) δ 13.16 (s, 1H), 8.74 (s, 1H), 8.18 (s, 1H), 7.47 (d, 1H), 7.35-7.27 (m, 4H), 7.24 (d, 2H), 7.00 (d, 1H), 5.68 (s, 2H), 5.05 (s, 2H), 4.36 (s, 3H). |

Example 5. Synthesis of Compounds of Formula E5-ii and Derivatives with Scheme E5

Scheme E5

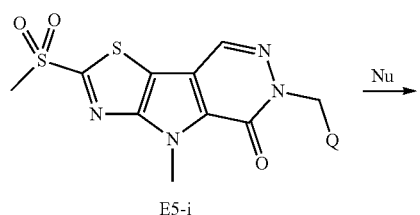

-continued

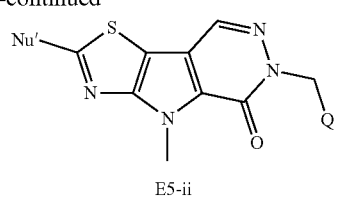

Wherein Q is as defined in any one of the first to twenty-sixth embodiments of the invention; Nu is a nucleophile (i.e. a chemical species that donates an electron pair to an electrophile to form a chemical bond in relation to a reaction). Nu' is optionally substituted alkoxyl, optionally substituted thiol, optionally substituted amino, or optionally functionalized carbon nucleophiles.

Example 5A. Synthesis of 6-((1H-indazol-4-yl)methyl)-2-(benzylthio)-4-methyl-4,6-dihydro-5H-thiazolo[54':4,5]pyrrolo[2,3-d]pyridazin-5-one

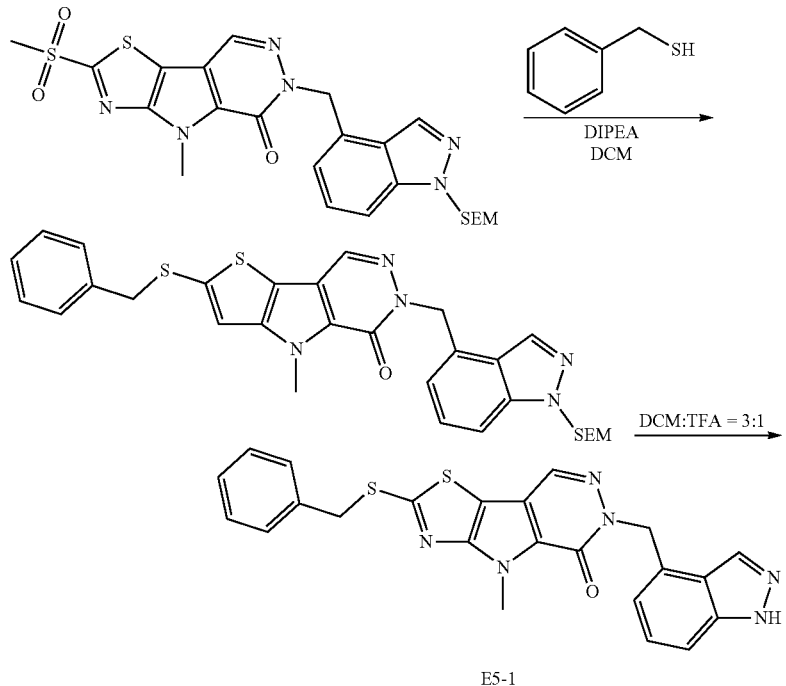

E5-1

Step A. 2-(Benzylthio)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one To solution of phenylmethanethiol (91.21 mg, 734.32 μmol) in DCM (5 mL) at 0° C. were added DIPEA (142.3 mg, 1.10 mmol) and 4-methyl-2-(methylsulfonyl)-6-((1-((2-(trimethylsilyl) ethoxy)methyl)-1H-indazol-4-yl)methyl)-4H-thiazolo[5',4':4,5]pyrrolo[2,3-d]pyridazin-5(6H)-one (200 mg, 0.37 mmol). The mixture was stirred at 20° C. for 1 hr. then quenched with water and extracted with EtOAc. The combined organic layers were washed with brine, dried over anhydrous $Na_2SO_4$ and concentrated under reduced pressure. The residue was purified by column chromatography on silica gel (eluent: PE/EtOAc=5/1 to 3/1) to give the desired product (200 mg). LCMS: m/z 589 (M+H)$^+$ Step B. 6-((1H-indazol-4-yl)methyl)-2-(benzylthio)-4-methyl-4,6-dihydro-5H-thiazolo[5',4':4,5]pyrrolo[2,3-d]pyridazin-5-one A mixture of 2-(benzylthio)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (30 mg, 50.95 μmol) in DCM/TFA (V:V=3:1) was stirred at 20° C. for 2 hr. then concentrated under reduced pressure. The residue was purified by prep-HPLC to give the desired product (5 mg). LCMS: m/z 459 (M+H)$^+$. $^1$H NMR (400 MHz, DMSO-$d_6$) δ 13.11 (s, 1H), 8.57 (s, 1H), 8.14 (s, 1H), 7.49 (d, 2H), 7.45 (d, 1H), 7.34 (t, 2H), 7.28 (dd, 2H), 6.95 (d, 1H), 5.65 (s, 2H), 4.62 (s, 2H), 4.26 (s, 3H).

Example 5B. Synthesis of 6-((1H-indazol-4-yl)methyl)-4-methyl-5-oxo-5,6-dihydro-4H-thiazolo[5',4':4,5]pyrrolo[2,3-d]pyridazine-2-sulfonamide

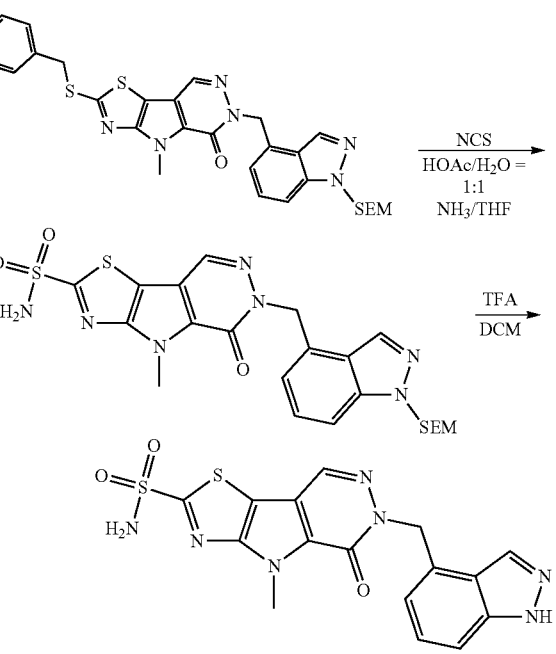

E5-2

Step A. 4-Methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-sulfonamide To a solution of 2-(benzylthio)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (100 mg, 0.169 mmol) in HOAc/H₂O (V:V=1:1, 10 mL) was added NCS (45 mg, 0.34 mmol). The mixture was stirred at 40° C. for 3 hr. then cooled to 0° C., followed by slow addition of NH₃/THF (5 mL) till pH 9 at that temperature. The resulting mixture was stirred at 20° C. for 0.5 hr. then extracted with EtOAc. The combined organic layers were concentrated under reduced pressure. The residue was purified by prep-TLC (eluent: PE/EtOAc=1/1) to afford the desired product (20 mg). LCMS: m/z 546 (M+H)⁺.

Step B. 6-((1H-indazol-4-yl)methyl)-4-methyl-5-oxo-5,6-dihydro-4H-thiazolo[5',4':4,5]pyrrolo[2,3-d]pyridazine-2-sulfonamide A mixture of 4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-sulfonamide (20 trig, 36.65 μmol) in DCM/TFA (V/V=3/1) was stirred at 20° C. for 2 hr. then concentrated under reduced pressure. The residue was purified by prep-HPLC to give the desired product (1.7 mg). LCMS: m/z 416 (M+H)⁺. ¹H NMR (400 MHz, DMSO-d₆) δ 13.13 (s, 1H), 8.73 (s, 1H), 8.31 (brs, 2H), 8.17 (s, 1H), 7.47 (d, 1H), 7.36-7.20 (m, 1H), 6.99 (d, 1H), 5.68 (s, 2H), 4.30 (s, 3H).

| Cpd No. | Structure | Characterization |
| --- | --- | --- |
| E5-3 | 6-((1H-indazol-4-yl)methyl)-2-(benzylamino)-4-methyl-4,6-dihydro-5H-thiazolo[5',4':4,5]pyrrolo[2,3-d]pyridazin-5-one | LCMS: m/z 442 (M + H)⁺. ¹H NMR (400 MHz, DMSO-d₆) δ 13.10 (s, 1H), 8.96 (s, 1H), 8.33 (s, 1H), 8.12 (s, 1H), 7.46-7.34 (m, 5H), 7.32-7.24 (m, 2H), 6.93 (d, 1H), 5.61 (s, 2H), 4.59 (d, 2H), 4.12 (d, 3H) |
| E5-4 | 6-((1H-indazol-4-yl)methyl)-4-methyl-2-(phenylamino)-4,6-dihydro-5H-thiazolo[5',4':4,5]pyrrolo[2,3-d]pyridazin-5-one | LCMS: m/z 428 (M + H)⁺. ¹H NMR (400 MHz, DMSO-d₆) δ 13.11 (s, 1H), 10.81 (brs, 1H), 8.44 (s, 1H), 8.14 (s, 1H), 7.75 (d, 2H), 7.45 (d, 1H), 7.38 (dd, 2H), 7.32-7.24 (m, 1H), 7.06 (dd, 1H), 6.95 (d, 1H), 5.63 (s, 2H), 4.22 (s, 3H) |
| E5-5 | N-(6-((1H-indazol-4-yl)methyl)-4-methyl-5-oxo-5,6-dihydro-4H-thiazolo[5',4':4,5]pyrrolo[2,3-d]pyridazin-2-yl)-2-(1H-pyrazol-3-yl)acetamide | LCMS: m/z 460 (M + H)⁺. ¹H NMR (400 MHz, DMSO-d₆) δ 13.12 (s, 1H), 8.55 (s, 1H), 8.14 (s, 1H), 7.59 (s, 1H), 7.45 (d, 1H), 7.28 (dd, 1H), 6.95 (d, 1H), 6.22 (s, 1H), 5.65 (s, 2H), 4.22 (s, 3H), 3.84 (s, 2H). |
| E5-6 | 6-((1H-indazol-4-yl)methyl)-4-methyl-5-oxo-5,6-dihydro-4H-thiazolo[5',4':4,5]pyrrolo[2,3-d]pyridazine-2-carbonitrile | LC-MS: m/z 362(M + H)⁺. ¹H NMR (400 MHz, DMSO-d₆) δ 13.14 (s, 1H), 8.80 (s, 1H), 8.18 (s, 1H), 7.46 (d, 1H), 7.34-7.22 (m, 1H), 6.98 (d, 1H), 5.70 (s, 2H), 4.32 (d, 3H). |

| Cpd No. | Structure | Characterization |
|---|---|---|
| E5-7 | 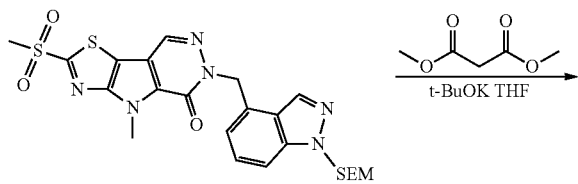<br>6-((2-Aminothiazol-4-yl)methyl)-4-methyl-5-oxo-5,6-dihydro-4H-thiazolo[5',4':4,5]pyrrolo[2,3-d]pyridazine-2-carbonitrile | LCMS: m/z 344 (M + H)$^+$.<br>$^1$H NMR (400 MHz, DMSO-$d_6$) δ 8.75 (s, 1H), 6.92 (s, 2H), 6.24 (s, 1H), 5.15 (s, 2H), 4.31 (s, 3H). |
| E5-8 | 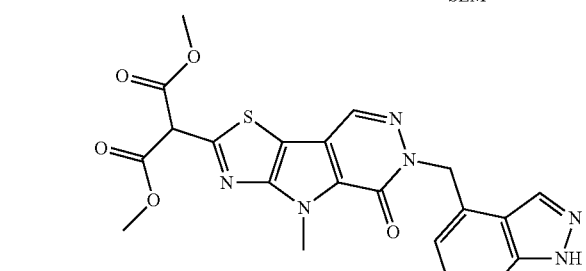<br>6-((6-Aminopyridin-2-yl)methyl)-4-methyl-5-oxo-5,6-dihydro-4H-thiazolo[5',4':4,5]pyrrolo[2,3-d]pyridazine-2-carbonitrile | LCMS: m/z 338 (M + H)$^+$.<br>$^1$H NMR (400 MHz, DMSO-$d_6$) δ 8.79 (s, 1H), 7.34-7.18 (m, 1H), 6.31 (d, 1H), 6.14 (d, 1H), 5.91 (s, 2H), 5.22 (s, 2H), 4.31 (s, 3H). |

Example 5C. Synthesis of dimethyl 2-(6-((1H-indazol-4-yl)methyl)-4-methyl-5-oxo-5,6-dihydro-4H-thiazolo[5',4':4,5]pyrrolo[2,3-d]pyridazin-2-yl)malonate Step A. Dimethyl 2-(4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl) malonate To a mixture of t-BuOK (103 mg, 0.92 mmol) and dimethyl malonate (91 mg, 0.69 mmol) in THF (5 mL) under N$_2$ was added 4-methyl-2-(methylsulfonyl)-6-((1-((2-(trimethylsilyl)ethoxy)methyl)-1H-indazol-4-yl)methyl)-4,6-dihydro-5H-thiazolo[5',4':4,5]pyrrolo[2,3-d]pyridazin-5-one (250 mg, 0.46 mmol). The reaction mixture was stirred at 60° C. for 16 hr. then, poured into ice water and extracted with EtOAc The combined organic layers were washed with brine, dried over anhydrous Na$_2$SO$_4$ and concentrated under reduced pressure. The residue was purified by column chromatography on silica gel to give the desired product (100 mg, 36.48% yield).

LC-MS: m/z 597 (M+H)$^+$.

Step B 2-(6-((1H-indazol-4-yl)methyl)-4-methyl-5-oxo-5,6-dihydro-4H-thiazolo[5',4':4,5]pyrrolo[2,3-d]pyridazin-2-yl) malonate was synthesized similar to Example 5A. LC-MS: m/z 467 (M+H)$^+$. $^1$H NMR (400 MHz, DMSO-$d_6$) δ 13.12 (s, 1H), 8.65 (s, 1H), 8.15 (s, 1H), 7.45 (d, 1H), 7.30-7.26 (m, 1H), 6.96 (d, 1H), 5.84 (s, 1H), 5.67 (s, 2H), 4.27 (s, 3H), 3.77 (s, 6H).

Example 5D. Synthesis of methyl 2-(6-((1H-indazol-4-yl)methyl)-4-methyl-5-oxo-5,6-dihydro-4H-thiazolo[5',4':4,5]pyrrolo[2,3-d]pyridazin-2-yl)acetate

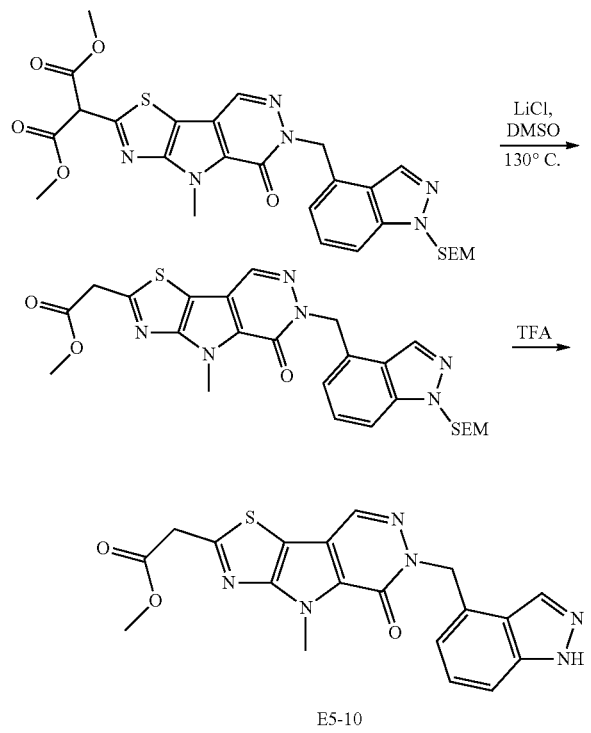

E5-10

Step A. Methyl 2-(4-methyl-5-oxo-6-((1-((2-(trimethylsilyl)ethoxy)methyl)-1H-indazol-4-yl)methyl)-5,6-dihydro-4H-thiazolo[5,4':4,5]pyrrolo[2,3-d]pyridazin-2-yl)acetate To a solution of dimethyl 2-(4-methyl-5-oxo-6-((1-((2-(trimethylsilyl) ethoxy)methyl)-1H-indazol-4-yl)methyl)-5,6-dihydro-4H-thiazolo[5',4':4,5]pyrrolo[2,3-d]pyridazin-2-yl)malonate (130 mg, 0.22 mmol) in DMSO (2 mL) under $N_2$ was added saturated aqueous LiCl (0.1 mL). The resulting mixture was stirred at 130° C. for 10 min then poured into ice water and extracted with EtOAc. The combined organic layers were washed with brine, dried over anhydrous $Na_2SO_4$ and concentrated under reduced pressure. Then the residue was purified by column chromatography on silica gel to afford the desired product (100 mg). LC-MS: m/z 539 $(M+H)^+$.

Step B

Methyl 2-(6-((1H-indazol-4-yl)methyl)-4-methyl-5-oxo-5,6-dihydro-4H-thiazolo[5',4':4,5]pyrrolo[2,3-d]pyridazin-2-yl)acetate was synthesized as in Example 5A. LC-MS: m/z 409 $(M+H)^+$. $^1H$ NMR (400 MHz, DMSO-$d_6$) δ 13.12 (s, 1H), 8.62 (s, 1H), 8.15 (s, 1H), 7.45 (d, 1H), 7.30-7.26 (m, 1H), 6.96 (d, 1H), 5.67 (s, 2H), 4.39 (s, 2H), 4.27 (s, 3H), 3.70 (s, 3H).

Example 5E. Synthesis of 2-(6-((1H-indazol-4-yl)methyl)-4-methyl-5-oxo-5,6-dihydro-4H-thiazolo[5',4':4,5]pyrrolo[2,3-d]pyridazin-2-yl)acetamide

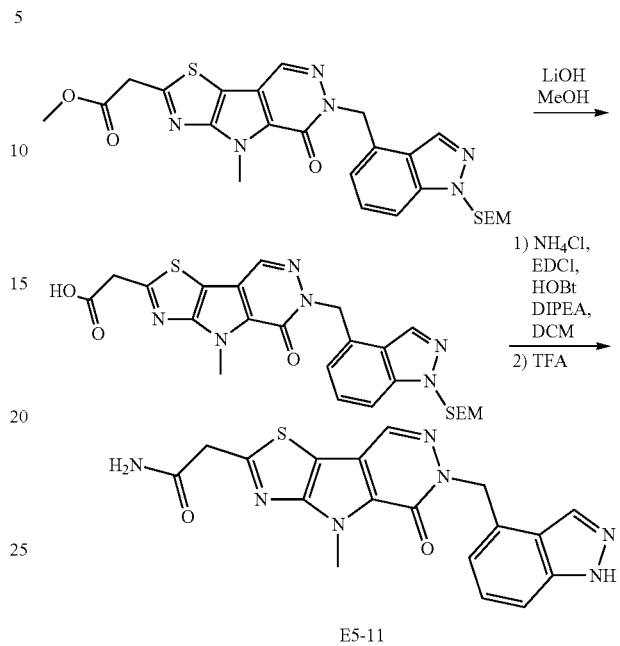

E5-11

Step A. 2-(4-Methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)acetic acid To a mixture of methyl 2-(4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)acetate (100 mg, 0.186 mmol) in MeOH/$H_2O$ (3 mL/1 mL) at 0° C. under $N_2$ was added LiOH (23 mg, 0.558 mmol). The resulting mixture was stirred at r.t. for 16 hr. then concentrated under reduced pressure. The residue was acidified with aqueous HCl (1 M) and extracted with EtOAc. The combined organic layers were washed with brine, dried over anhydrous $Na_2SO_4$ and concentrated under reduced pressure. The residue was directly used in next step without further purification. LC-MS: m/z 525 $(M+H)^+$.

Step B. 2-(4-Methyl-5-oxo-6-((1-((2-(trimethylsilyl)ethoxy)methyl)-1H-indazol-4-yl)methyl)-5,6-dihydro-4H-thiazolo[5,4':4,5]pyrrolo[2,3-d]pyridazin-2-yl)acetamide To a mixture of 2-(4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)acetic acid (50 mg, 0.095 mmol), EDCI (37 mg, 0.190 mmol), HOBT (26 mg, 0.190 mmol) and DIPEA (0.05 mL, 0.286 mmol) in DCM (5 mL) at 0° C. was added $NH_4Cl$ (26 mg, 0.477 mmol). The resulting mixture was stirred at r.t. for 16 hr. then poured into ice water and extracted with EtOAc. The combined organic layers were washed with brine, dried over anhydrous $Na_2SO_4$ and concentrated under reduced pressure. The residue was purified by column chromatography on silica gel to afford the desired product (20 mg). LC-MS: m/z 524 $(M+H)^+$.

Step C 2-(6-((1H-Indazol-4-yl)methyl)-4-methyl-5-oxo-5,6-dihydro-4H-thiazolo[5',4':4,5]pyrrolo[2,3-d]pyridazin-2-yl)acetamide was synthesized using the procedure as in Example 5A. LCMS: m/z 394 (M+H)$^+$. $^1$H NMR (400 MHz, DMSO-d$_6$) δ 13.12 (s, 1H), 8.59 (s, 1H), 8.15 (s, 1H), 7.77 (s, 1H), 7.45 (d, 1H), 7.33-7.22 (m, 2H), 6.96 (d, 1H), 5.66 (s, 2H), 4.27 (s, 3H), 4.07 (s, 2H).

Example 5F. Synthesis of 6-((1H-indazol-4-yl)methyl)-4-methyl-5-oxo-5,6-dihydro-4H-thiazolo[5',4':4,5]pyrrolo[2,3-d]pyridazine-2-carboxamide

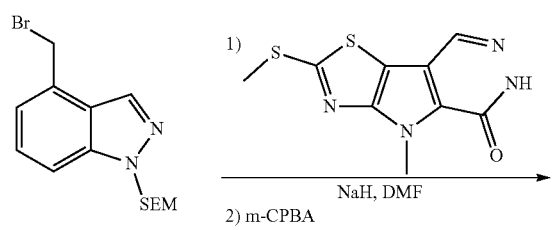

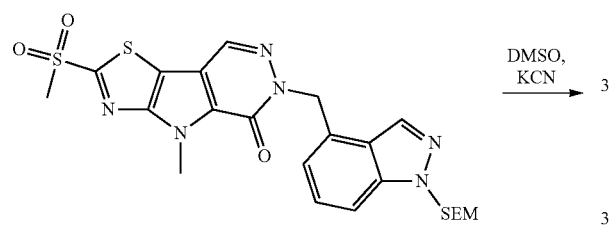

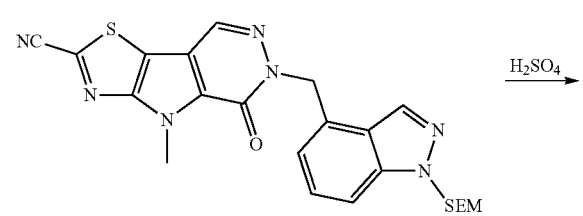

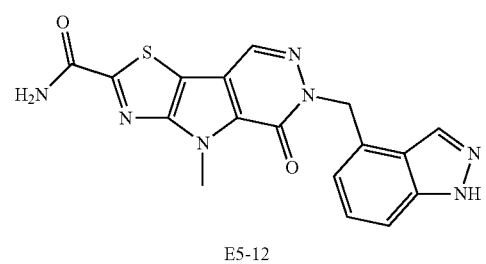

E5-12

Step A. 4-Methyl-2-(methylthio)-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one To a mixture of 4-methyl-2-(methylthio)-4H-thiazolo[5',4':4,5]pyrrolo[2,3-d]pyridazin-5 (6H)-one (1 g, 3.96 mmol) in DMF (25 mL) at 0° C. was added NaH (318 mg, 7.93 mmol). The mixture was stirred at r.t. for 30 min. followed by addition of a solution of 4-(bromomethyl)-1-((2-(trimethylsilyl)ethoxy)methyl)-1H-indazole (2 g, 5.94 mmol) in DMF (10 mL) at 0° C. The mixture was stirred at r.t. for 2 hr. then poured into ice-water and extracted with EtOAc. The combined organic layers were washed with brine, dried over anhydrous Na$_2$SO$_4$ and concentrated under reduced pressure. The residue was purified by column chromatography on silica gel (eluent: PE/EtOAc=50/1 to 10/1) to give the desired product (1.85 g). LCMS: m/z 513 (M+H)$^+$.

Step B. 4-Methyl-2-(methylsulfonyl)-6-((1-((2-(trimethylsilyl)ethoxy) methyl)-1H-indazol-4-yl)methyl)-4H-thiazolo[5',4':4,5]pyrrolo[2,3-d]pyridazin-5(6H)-one To a mixture of 4-methyl-2-(methylthio)-6-((1-((2-(trimethylsilyl)ethoxy) methyl)-1H-indazol-4-yl)methyl)-4H-thiazolo[5',4':4,5]pyrrolo[2,3-d]pyridazin-5(6H)-one (700 mg, 1.37 mmol) in DCM (20 mL) at 0° C. was added m-CPBA (831 mg, 4.01 mmol). The mixture was stirred at r.t. overnight then quenched by saturated aqueous Na$_2$SO$_3$ and extracted with EtOAc. The combined organic layers were washed with brine, dried over anhydrous Na$_2$SO$_4$ and concentrated under reduced pressure. The residue was purified by column chromatography on silica gel to give the desired product (360 mg). LCMS: m/z 545 (M+H)$^+$.

Step C. 4-Methyl-5-oxo-6-((1-((2-(trimethylsilyl)ethoxy)methyl)-1H-indazol-4-yl)methyl)-5,6-dihydro-4H-thiazolo[5'4':4,5]pyrrolo[2,3-d]pyridazine-2-carbonitrile To a mixture of 4-methyl-2-(methylsulfonyl)-6-((1-((2-(trimethylsilyl)ethoxy) methyl)-1H-indazol-4-yl)methyl)-4H-thiazolo[5',4':4,5]pyrrolo[2,3-d]pyridazin-5(6H)-one (300 mg, 0.552 mmol) in DMF (10 mL) at 0° C. was added KCN (72 mg, 1.10 mmol). The mixture was stirred at r.t. for 2 hr. then quenched by water and extracted with EtOAc. The combined organic layers were washed with brine, dried over anhydrous Na$_2$SO$_4$ and concentrated under reduced pressure. The residue was purified by column chromatography on silica gel (eluent: PE/EtOAc=5/1) to give the desired product (210 mg). LCMS: m/z 492 (M+H)$^+$.

Step D. 6-((1H-indazol-4-yl)methyl)-4-methyl-5-oxo-5,6-dihydro-4H-thiazolo[5',4':4,5]pyrrolo[2,3-d]pyridazine-2-carboxamide A mixture of 4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-carbonitrile (50 mg, 0.1 mmol) in conc. H$_2$SO$_4$ (3 mL) was stirred at r.t. for 12 hr. then quenched with saturated aqueous NaHCO$_3$ (aq) and extracted with DCM. The combined organic layers were washed with brine, dried over anhydrous Na$_2$SO$_4$ and concentrated under reduced pressure. The residue was purified by prep-HPLC to give the desired product (6 mg). LCMS: m/z 380 (M+H)$^+$. $^1$H NMR (400 MHz, DMSO) δ 13.12 (s, 1H), 8.71 (s, 1H), 8.39 (s, 1H), 8.16 (s, 1H), 8.07 (s, 1H), 7.46 (d, 1H), 7.33-7.23 (m, 1H), 6.98 (d, 1H), 5.68 (s, 2H), 4.33 (s, 3H).

The procedure set forth above was used to produce following compounds using appropriate starting materials. Standard protection and deprotection can be used when necessary.

| Cpd No. | Structure | Characterization |
|---|---|---|
| E5-13 | 6-((2-Aminothiazol-4-yl)methyl)-4-methyl-5-oxo-5,6-dihydro-4H-thiazolo[5',4':4,5]pyrrolo[2,3-d]pyridazine-2-carboxamide | LCMS: m/z 362 (M + H)$^+$. $^1$H NMR (400 MHz, DMSO-d$_6$) δ 8.65 (s, 1H), 8.40 (s, 1H), 8.07 (s, 1H), 6.92 (s, 2H), 6.22 (s, 1H), 5.15 (s, 2H), 4.33 (s, 3H). |
| E5-14 | 6-((6-Aminopyridin-2-yl)methyl)-4-methyl-5-oxo-5,6-dihydro-4H-thiazolo[5',4':4,5]pyrrolo[2,3-d]pyridazine-2-carboxamide | LCMS: m/z 356 (M + H)$^+$. $^1$H NMR (400 MHz, DMSO-d$_6$) δ 8.69 (s, 1H), 8.40 (s, 1H), 8.08 (s, 1H), 7.34-7.19 1H), 6.30 (d, 1H), 6.12 (d, 1H), 5.91 (s, 2H), 5.21 (s, 2H), 4.32 (s, 3H). |

Example 5G. Synthesis of 6-((1H-indazol-4-yl)methyl)-N-hydroxy-4-methyl-5-oxo-5,6-dihydro-4H-thiazolo[5',4':4,5]pyrrolo[2,3-d]pyridazine-2-carboxamide

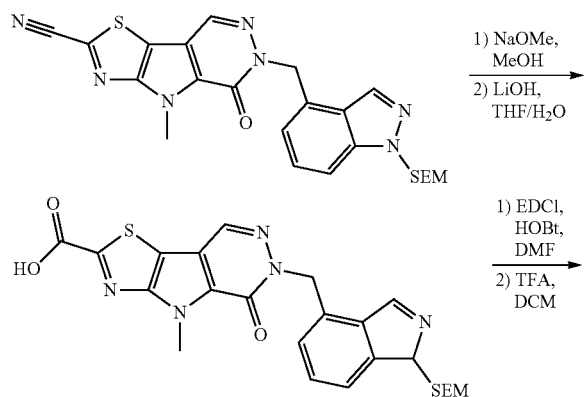

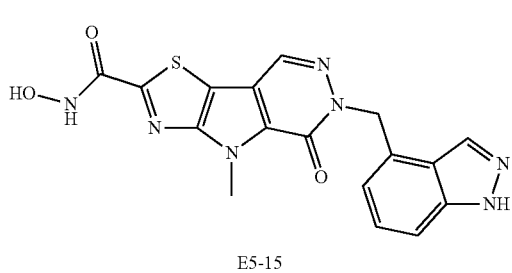

E5-15

Step A. Methyl 4-methyl-5-oxo-6-((1-((2-(trimethylsilylethoxy)methyl)-1H-indazol-4-yl)methyl)-5,6-dihydro-4H-thiazolo[5',4':4,5]pyrrolo[2,3-d]pyridazine-2-carboxylate To a mixture of 4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-carbonitrile (100 mg, 0.20 mmol) in MeOH (10 mL) at 0° C. was added MeONa (110 mg, 0.61 mmol, 30% wt). The reaction mixture was stirred at r.t. for 1.5 hr. then quenched with saturated HCl (1 M) and extracted with DCM (30 mL). The combined organic layers were dried over anhydrous Na$_2$SO$_4$, and concentrated under reduced pressure to give the desired product (85 mg) as yellow oil which was directly used in next step without further purification. LCMS: m/z 525 (M+H)$^+$.

Step B. 4-Methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-carboxylic acid To a mixture of methyl 4-methyl-5-oxo-6-((1-((2-(trimethylsilyl)ethoxy) methyl)-1H-indazol-4-yl)methyl)-5,6-dihydro-4H-thiazolo[5',4':4,5]pyrrolo[2,3-d]pyridazine-2-carboxylate (90 mg, 0.18 mmol) in THF (10 mL) at 0° C. was added a solution of LiOH (12 mg, 0.48 mmol) in H$_2$O (10 mL). The reaction mixture was stirred at r.t. overnight, then slowly adjusted to pH 5 with aqueous HCl (1 M) and extracted with DCM. The combined organic layers were washed with brine, dried over anhydrous Na$_2$SO$_4$, and concentrated under reduced pressure to give the desired product (70 mg, 84% crude yield) as a white oil which was directly used in the next step without any further purification. LCMS: m/z 511 (M+H)$^+$.

Step C. 4-Methyl-5-oxo-N-((tetrahydro-2H-pyran-2-yl)oxy)-6-((1-((2-(trimethyl silyl)ethoxy)methyl)-1H-indazol-4-yl)methyl)-5,6-dihydro-4H-thiazolo[5',4':4,5]pyrrolo[2,3-d]pyridazine-2-carboxamide To a mixture of 4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-carboxylic acid (70 mg, 0.14 mmol) in DCM (10 mL) at 0° C. were added O-(tetrahydro-2H-pyran-2-yl)hydroxylamine (24 mg, 0.21 mmol), EDCI (39 mg, 0.21 mmol) and HOBT (28 mg, 0.21 mmol). The reaction mixture was stirred at r.t. overnight then quenched with water and extracted with DCM. The combined organic layers were washed with brine, dried over anhydrous $Na_2SO_4$, and concentrated under reduced pressure. The residue was purified by prep-TLC to give the desired product (35 mg) as yellow oil. LCMS: m/z 610 (M+H)$^+$.

Step D 6-((1H-indazol-4-yl)methyl)-N-hydroxy-4-methyl-5-oxo-5,6-dihydro-4H-thiazolo[5',4':4,5]pyrrolo[2,3-d]pyridazine-2-carboxamide was synthesized using the procedure in Example 5A. LCMS: m/z 396 (M+H)$^+$. $^1$H NMR (400 MHz, DMSO-d$_6$) δ 13.12 (s, 1H), 8.67 (s, 1H), 8.29 (s, 1H), 8.16 (s, 1H), 7.46 (d, 1H), 7.31-7.25 (m, 1H), 6.97 (d, 1H), 5.67 (s, 2H), 4.31 (s, 3H).

Example 5H. Synthesis of 2-(6-((1H-indazol-4-yl)methyl)-4-methyl-5-oxo-5,6-dihydro-4H-thiazolo[5',4':4,5]pyrrolo[2,3-d]pyridazin-2-yl)-2-phenylacetamide

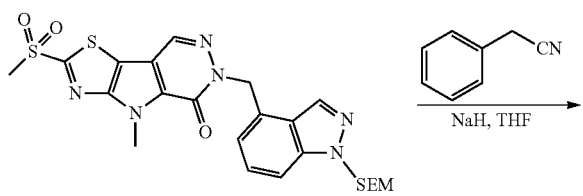

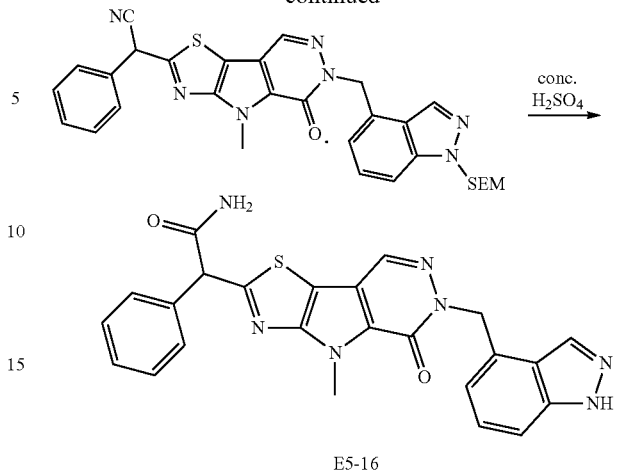

Step A. 2-(4-Methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)-2-phenylacetonitrile To a mixture of 2-phenylacetonitrile (43 mg, 0.36 mmol) in THF (3 mL) was added NaH (14 mg, 0.36 mmol). The mixture was stirred at r.t. for 30 min, followed by addition of 4-methyl-2-(methylsulfonyl)-6-((1-((2-(trimethylsilyl)ethoxy)methyl)-1H-indazol-4-yl)methyl)-4,6-dihydro-5H-thiazolo[5',4':4,5]pyrrolo[2,3-d]pyridazin-5-one (100 mg, 0.18 mmol). The reaction mixture was stirred at rt. for another 3 hr. then quenched with water and extracted with EtOAc. The combined organic layers were washed with brine, dried over anhydrous $Na_2SO_4$ and concentrated under reduced pressure. The residue was purified by column chromatography on silica gel (eluent: PE/EtOAc=3/1) to give the product (63 mg, 59% yield). LCMS: 582 (M+H)$^+$.

Step B 2-(6-((1H-indazol-4-yl)methyl)-4-methyl-5-oxo-5,6-dihydro-4H-thiazolo[5',4':4,5]pyrrolo[2,3-d]pyridazin-2-yl)-2-phenylacetamide was synthesized similar to Example 5F. LCMS: m/z 470 (M+H)$^+$. $^1$H NMR (400 MHz, DMSO-d$_6$) δ 13.11 (s, 1H), 8.58 (s, 1H), 8.13 (s, 1H) 8.01 (s, 1H), 7.54-7.24 (m, 8H), 6.94 (d, 1H), 5.65 (s, 2H), 5.51 (s, 1H), 4.24 (s, 3H).

| Cpd No. | Structure | Characterization |
|---|---|---|
| E5-17 | ![structure] 2-(6-((1H-indazol-4-yl)methyl)-4-methyl-5-oxo-5,6-dihydro-4H-thiazolo[5',4':4,5]pyrrolo[2,3-d]pyridazin-2-yl)-2-(1H-pyrazol-3-yl)acetamide | LCMS: 460 (M + H)$^+$. $^1$H NMR (400 MHz, DMSO-d$_6$) δ 13.11 (s, 1H), 12.88 (s, 1H), 8.56 (s, 1H), 8.14 (s, 1H), 7.93 (s, 1H), 7.70 (s, 1H), 7.44 (d, 1H), 7.28 (s, 1H), 7.27 (dd, 1H), 6.95 (d, 1H), 6.34 (s, 1H), 5.65 (s, 2H), 5.56 (s, 1H), 4.27 (s, 3H). |

Example 5I. Synthesis of 2-(6-((1H-indazol-4-yl)methyl)-4-methyl-5-oxo-5,6-dihydro-4H-thiazolo[5',4':4,5]pyrrolo[2,3-d]pyridazin-2-yl)-2-hydroxy-2-phenylacetamide

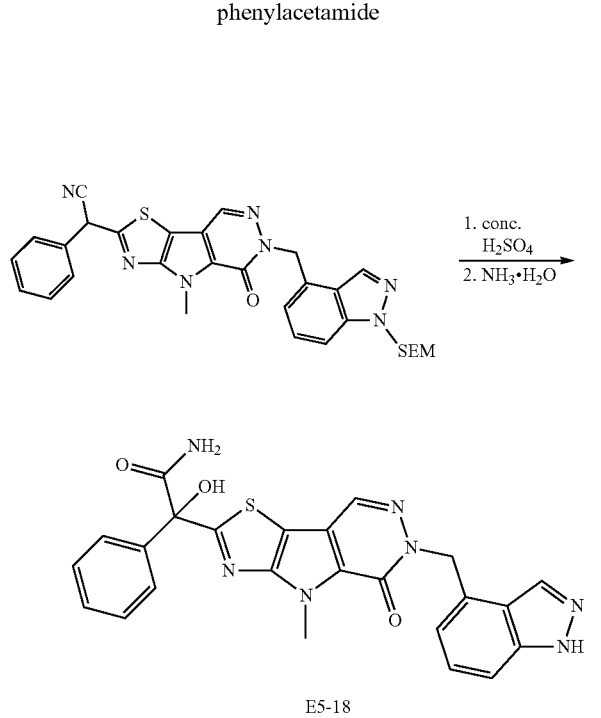

E5-18

A mixture of 2-(4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)-2-phenylacetonitrile (100 mg, 0.18 mmol) in conc. H$_2$SO$_4$ (1 mL) was stirred at r.t. for 2 hr. then poured into water and extracted with DCM. The combined organic layers were concentrated under reduced pressure. The residue was dissolved in MeOH (3 mL), followed by addition of NH$_3$·H$_2$O (3 mL). The reaction mixture was stirred at r.t. for 2 hr. then under reduced pressure. The residue was purified by prep-HPLC to afford the desired product (2 mg). LCMS: 486 (M+H)$^+$. $^1$H NMR (400 MHz, DMSO-d$_6$) δ 13.12 (s, 1H), 8.61 (s, 1H), 8.14 (s, 1H), 7.71 (d, 2H), 7.64 (d, 2H), 7.52 (s, 1H), 7.45 (d, 1H), 7.40-7.24 (m, 4H), 6.95 (d, 1H), 5.66 (s, 2H) 4.27 (s, 3H).

Example 5J. Synthesis of methyl 2-(6-((1H-indazol-4-yl)methyl)-4-methyl-5-oxo-5,6-dihydro-4H-thiazolo[5',4':4,5]pyrrolo[2,3-d]pyridazin-2-yl)-2-phenylacetate

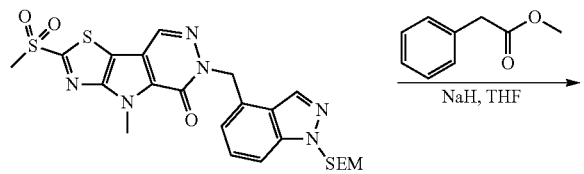

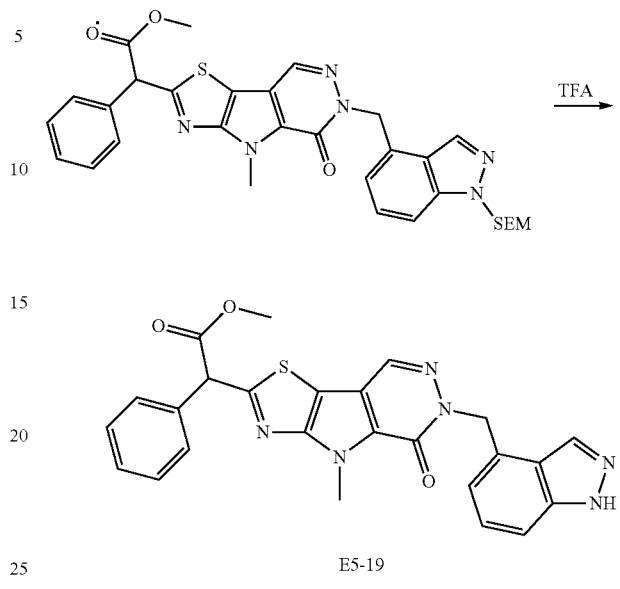

E5-19

Step A. Methyl 2-(4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)-2-phenylacetate To a mixture of methyl 2-phenylacetate (43 mg, 0.29 mmol) in THF (3 mL) was added NaH (11 mg, 0.29 mmol). The mixture was stirred at rt. for 30 min, followed by addition of 4-methyl-2-(methylsulfonyl)-6-((1-((2-(trimethylsilyl) ethoxy) methyl)-1H-indazol-4-yl)methyl)-4,6-dihydro-5H-thiazolo[5',4':4,5]pyrrolo[2,3-d]pyridazin-5-one (82 mg, 0.15 mmol). The resulting mixture was stirred at r.t. for 3 hr. then quenched with water and extracted with EtOAc. The combined organic layers were concentrated under reduced pressure. The residue was purified by column chromatography on silica gel (eluent: PE/EtOAc=3/1) to afford the desired product (20 mg). LCMS: 615 (M+H)$^+$.

Step B. Methyl 2-(6-((1H-indazol-4-yl)methyl)-4-methyl-5-oxo-5,6-dihydro-4H-thiazolo[5',4':4,5]pyrrolo[2,3-d]pyridazin-2-yl)-2-phenylacetate A mixture of methyl 2-(4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazin-2-yl)-2-phenylacetate (40 mg, 0.07 mmol) in DCM/TFA (V:V=1:1, 2 mL) was stirred at r.t. for 2 hr. then poured into water and extracted with DCM. The combined organic layers were concentrated under reduced pressure. The residue was purified by prep-HPLC to afford the desired product (5 mg). LCMS: 485 (M+H)$^+$. $^1$H NMR (400 MHz, DMSO-d$_6$) δ 13.11 (s, 1H), 8.58 (s, 1H), 8.13 (s, 1H) 7.54-7.50 (m, 2H), 7.46-7.36 (m, 4H), 7.30-7.24 (m, 1H), 6.94 (d, 1H), 5.87 (s, 1H), 5.65 (s, 2H), 4.26 (s, 3H), 3.73 (s, 3H).

The procedure set forth above was used to produce the following compounds using the appropriate starting materials.

| Cpd No. | Structure | Characterization |
|---|---|---|
| E5-20 | Methyl 2-(6-((1H-indazol-4-yl)methyl)-4-methyl-5-oxo-5,6-dihydro-4H-thiazolo[5',4':4,5]pyrrolo[2,3-d]pyridazin-2-yl)-2-(1H-pyrazol-3-yl)acetate | LCMS: 475 (M + H)+. 1H NMR (400 MHz, DMSO-d6) δ 8.48 (s, 1H), 8.06 (s, 1H), 7.67 (d, 1H), 7.40 (d, 1H), 7.23 (dd, 1H), 6.89 (d, 1H), 6.32 (d, 1H), 5.58 (s, 2H), 4.19 (s, 3H), 3.63 (s, 3H). |

Example 6. Synthesis of 6-(3-methoxybenzyl)-4-methyl-2-(trifluoromethyl)-4,6-dihydro-5H-thiazolo[5',4':4,5]pyrrolo[2,3-d]pyridazin-5-one Example 7. Synthesis of Compounds E7-v and E7-viii

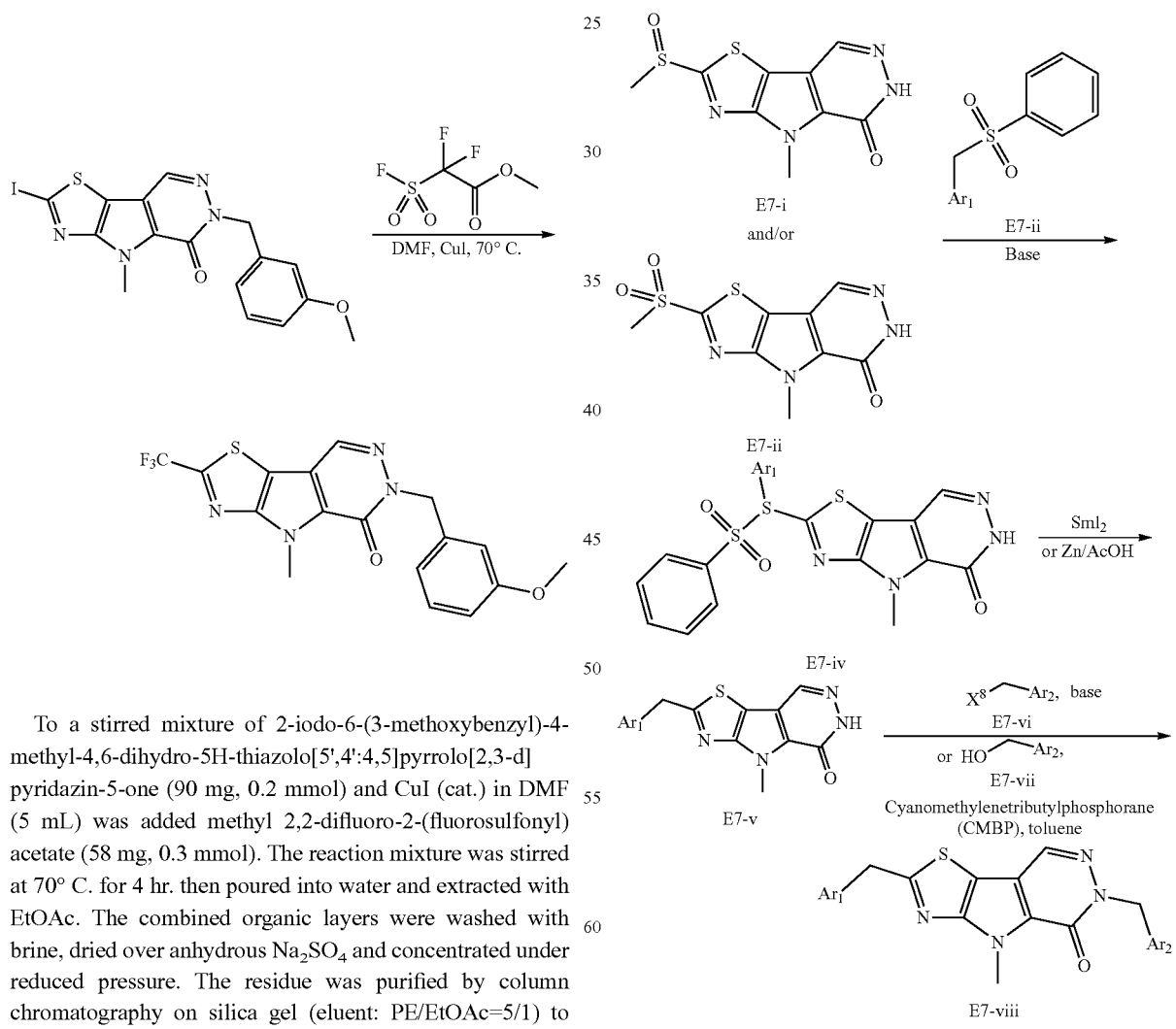

To a stirred mixture of 2-iodo-6-(3-methoxybenzyl)-4-methyl-4,6-dihydro-5H-thiazolo[5',4':4,5]pyrrolo[2,3-d]pyridazin-5-one (90 mg, 0.2 mmol) and CuI (cat.) in DMF (5 mL) was added methyl 2,2-difluoro-2-(fluorosulfonyl)acetate (58 mg, 0.3 mmol). The reaction mixture was stirred at 70° C. for 4 hr. then poured into water and extracted with EtOAc. The combined organic layers were washed with brine, dried over anhydrous Na2SO4 and concentrated under reduced pressure. The residue was purified by column chromatography on silica gel (eluent: PE/EtOAc=5/1) to give the desired product (10 mg). LCMS: m/z=395 (M+H)+. 1H NMR (400 MHz, DMSO-d6) δ 8.78 (s, 1H), 7.24 (t, 1H), 6.90-6.82 (m, 3H), 5.34 (s, 2H), 4.32 (s, 3H) 3.72 (s, 3H).

Nucleophilic aromatic substitution between compound E7-iii and compound E7-i and/or compound E7-ii gives intermediate E7-iv. Reduction of the phenylsulfonyl group of compound E7-iv affords intermediate E7-v. Using standard alkylation reaction of E7-vi and base (e.g. K₂CO₃, K₃PO₄, t-BuOK, or Cs₂CO₃) gives compound E7-viii, wherein $X^a$ is a leaving group such as Cl, Br, I, OMs, OTs; Ar₁ and Ar₂ are each independently optionally substituted aryl, optionally substituted heteroaryl, optionally substituted carbocycle or optionally substituted heterocyclyl; optionally substituted alkyl, optionally substituted alkylaryl, optionally substituted alkylheteroaryl, optionally substituted alkyenyl, and optionally substituted alkynyl groups. Compound E7-viii can also be synthesized from intermediate E7-v through Mitsunobu reaction using Cyanomethylenetributylphosphorane (CMBP) in toluene. In certain embodiments, Ar1 and Ar2 are each independently optionally substituted heteroaryl.

Example 7A. Synthesis of 4-methyl-2-(methylsulfinyl)-4,6-dihydro-5H-thiazolo[5',4':4,5]pyrrolo[2,3-d]pyridazin-5-one (intermediates E7-i)

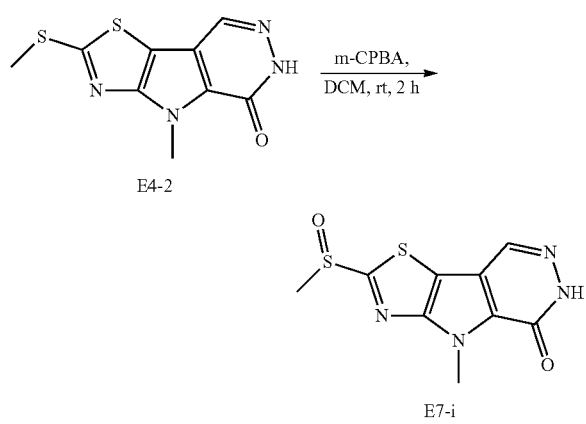

To a stirred suspension of 4-methyl-2-(methylthio)-4,6-dihydro-5H-thiazolo[5',4':4,5]pyrrolo[2,3-d]pyridazin-5-one (1.01 g, 4.0 mmol) in DCM (20 mL) was added 3-chloro-benzoperoxoic acid (0.77 g, 3.8 mmol) at r.t. The mixture stirred at r.t. for 2 hr. Then the mixture was filtered washed with EtOAc and triturated with MeOH to to give 4-methyl-2-(methylsulfinyl)-4,6-dihydro-5H-thiazolo[5',4':4,5]pyrrolo[2,3-d]pyridazin-5-one (600 mg). LCMS: m/z 269 (M+H)⁺. 1H NMR (400 MHz, DMSO) δ 12.78 (s, 1H), 8.64 (s, 1H), 4.28 (s, 3H), 3.11 (s, 3H).

Example 7B. Synthesis of 4-methyl-2-(methylsulfonyl)-4,6-dihydro-5H-thiazolo[5',4':4,5]pyrrolo[2,3-d]pyridazin-5-one(E7-ii)

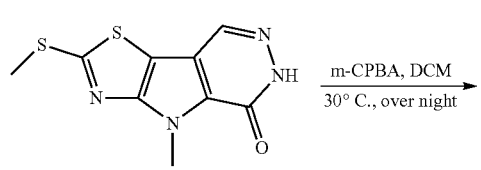

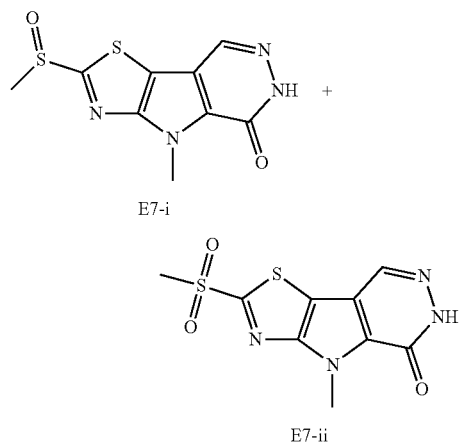

Three necked flask charged with 4-methyl-4,6-dihydro-5H-thiazolo[5',4':4,5]pyrrolo[2,3-d]pyridazin-5-one (30 g, 0.119 mol, 1.0 eq) in DCM (600 mL) m-CPBA (61.5 g, 3 eq) was added at 20° C. in three portions. The mixture was stirred at 30° C. overnight, LC-MS indicated 100% consumption of starting material. The mixture was cooled to r.t., another portion of m-CPBA (1.0 eq) was added. The reaction mixture was stirred at 30° C. for 2 hr, LC-MS indicated E7-ii (LCMS: m/z 269 (M+H)+). The mixture was cooled to r.t. and filtered. The filtered cake was suspension in MeOH (500 mL) and stirred at r.t. for 1 hr. Solid was collected by filtration, washed with ethylacetate, dried in vacuum to afford 28 g of mixture of 5% of E7-i and 95% of E7-ii. The mixture (28 g) was suspended in DMSO (600 mL), heated to 120° C.~130° C. to form a clear solution. Then cooled to r.t., solid precipitated. The mixture was filtered and dried to provide 23 g of pure E5-1, LCMS: m/z 285 (M+H)⁺. 1H NMR (400 MHz, DMSO) δ12.87 (s, 1H), 8.69 (s, 1H), 4.32 (s, 3H), 3.56 (s, 3H).

Example 7C. Synthesis of 3-((phenylsulfonyl)methyl)-1-((2-(trimethylsilyl)ethoxy)methyl)-1H-pyrazole

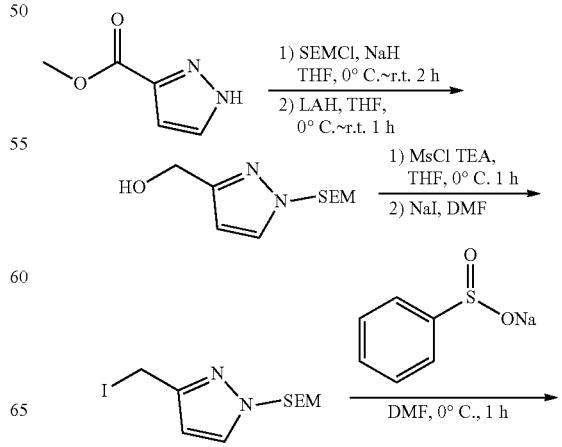

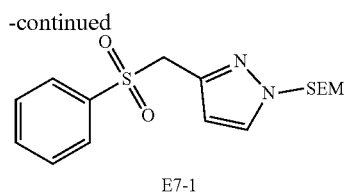

E7-1

Methyl 1-((2-(trimethylsilyl)ethoxy)methyl)-1H-pyrazole-3-carboxylate

At 0° C. under N₂ atmosphere, to a stirred solution of methyl 1H-pyrazole-3-carboxylate (90 g, 0.72 mol) in THF (1 L) was added NaH (20.7 g, 0.864 mol, 60%). The resulting mixture was slowly warmed up to r.t and stirred for 1 h. The reaction mixture was then cooled back to 0° C. and SEMCl (151.5 mL, 0.842 mol) was added drop wise. The stirring was continued for another 2 hr before quenched with sat. NH₄Cl and extracted with ethyl acetate (3×). The combined organic layers were washed with brine and dried over Na₂SO₄. Solvents were removed under vacuum to provide crude product 210 g which was used in the next step without purification.

(1-((2-(trimethylsilyl)ethoxy)methyl)-1H-pyrazol-3-yl)methanol

At 0° C. under N₂ atmosphere, to the suspension of LAH (16.9 g, 0.44 mol) in THF (760 mL) was added the crude methyl 1-((2-(trimethylsilyl)ethoxy)methyl)-1H-pyrazole-3-carboxylate (76 g). The resulting mixture was slowly warmed up to r.t. and stirred for 1 hr. The reaction mixture was cooled back to 0° C. and H₂O (15.6 mL), 10% NaOH (15.6 mL), H₂O (15.6 mL) was added successively. The resulting mixture was filtered through a pad of celite and washed with MTBE (4×). The combined organic fractions were dried over Na₂SO₄. Solvents were removed under reduced pressure to provide crude product 69.4 g which was used in the next step without purification. LC-MS: m/z 229 (M+H)⁺.

3-(iodomethyl)-1-((2-(trimethylsilyl)ethoxy)methyl)-1H-pyrazole

At 0° C. under N₂ atmosphere, to a stirred solution of (1-((2-(trimethylsilyl)ethoxy)methyl)-1H-pyrazol-3-yl)methanol (61.5 g, theoretically 0.262 mol) in THF (310 mL) was added TEA (55.42 mL, 0.393 mol) followed by MsCl (24 mL, 0.314 mol). The reaction was warmed up to r.t and stirred for 1 hr before the introduction of NaI (196.5 g, 1.31 mol, in 310 mL DMF). The resulting mixture was stirred for another 1 hr and quenched with ice-water, extracted with MTBE (3×). The combined organic layers were washed with sat. Na₂S₂O₃ and brine, dried over Na₂SO₄ and concentrated to provide 77.5 g crude product used in the next step without purification. LC-MS: m/z 339 (M+H)⁺.

3-((phenylsulfonyl)methyl)-1-((2-(trimethylsilyl)ethoxy)methyl)-1H-pyrazole

At 0° C. under N₂ atmosphere, to a stirred solution of (1-((2-(trimethylsilyl)ethoxy)methyl)-1H-pyrazol-3-yl)methanol (77.5 g, theoretically 0.229 mol) in DMF (600 mL) was added sodium benzenesulfinate (53.5 g, 0.32 mol) and stirred for 1 hr at 0° C. After warmed up to r.t., the reaction mixture was quenched with ice-water and sat. Na₂S₂O₃, extracted with ethyl acetate (3×). The combined organic layers were washed with sat. NaHCO₃ and brined successively, dried over Na₂SO₄. Solvents were removed under vacuum and the residue was purified by flash chromatography (silica gel, 20%~70% ethyl acetate in petroleum ether) to provide 56.7 g. LCMS: [M+H]+ 353. 1H NMR (400 MHz, DMSO) δ 7.85-7.77 (m, 4H), 7.62 (dd, 2H), 6.19 (d, 1H), 5.35 (d, 2H), 4.70 (d, 2H), 3.44-3.38 (m, 2H), 0.88-0.77 (m, 2H), −0.01 (s, 9H).

Example 7D. Synthesis of 4-methyl-2-((1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one

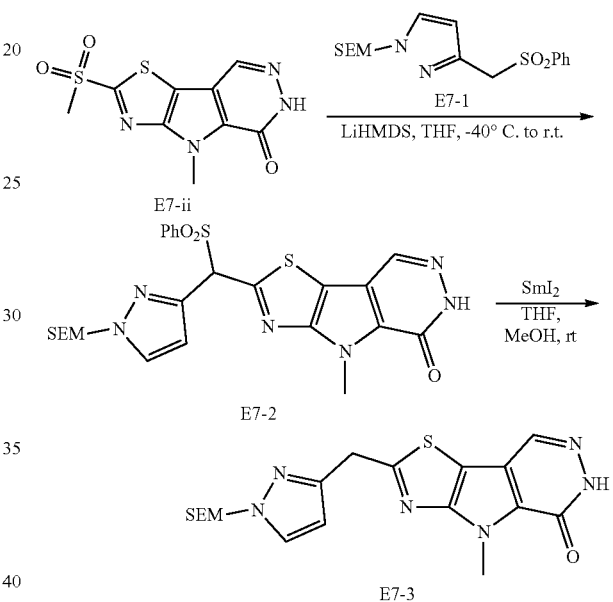

4-methyl-2-((phenylsulfonyl)(1-((2-(trimethylsilyl)ethoxy)methyl)-1H-pyrazol-5-yl)methyl)-4H-thiazolo[5',4':4,5]pyrrolo[2,3-d]pyridazin-5(6H)-one To a solution of 3-((phenylsulfonyl)methyl)-1-((2-(trimethylsilyl)ethoxy)methyl)-1H-pyrazole (1.8 g, 5.1 mmol) in dry THF (30 mL) at −40° C. was added LiHMDS (7.5 mL, 7.5 mmol) drop-wise. The mixture was stirred at room temperature for 30 min, followed by addition of a suspension of 4-methyl-2-(methylsulfinyl)-4H-thiazolo[5',4':4,5]pyrrolo[2,3-d]pyridazin-5(6H)-one (580 mg, 2.7 mmol) in dry THF (30 mL) at room temperature. The mixture was stirred at r.t. for another 1 hr and poured into ice-cooled saturated aqueous NH₄Cl (20 mL) and extracted with EtOAc (3×100 mL). The combined organic layers were washed with water (60 mL), dried over anhydrous Na₂SO₄ and concentrated under reduced pressure. The residue was purified by flash chromatography (silica gel, 0~2.5% methanol in dichloromethane) to give the desired product (800 mg). LC-MS (ESI) found: 557 (M+H)⁺. 1H NMR (400 MHz, DMSO) δ 12.78 (s, 1H), 8.65 (s, 1H), 8.03 (d, 1H), 7.84-7.78 (m, 3H), 7.67-7.59 (m, 2H), 6.94 (s, 1H), 6.72 (d, 1H), 5.48 (d, 2H), 4.29 (s, 3H), 3.56 (dd, 2H), 0.88 (dd, 2H), 0.00 (s, 9H).

4-methyl-2-((1-((2-(trimethylsilyl)ethoxy)methyl)-1H-pyrazol-5-yl)methyl)-4H-thiazolo[5',4':4,5]pyrrolo[2,3-d]pyridazin-5(6H)-one To a mixture of 4-methyl-2-((phenylsulfonyl)(1-((2-(trimethylsilyl)ethoxy)methyl)-1H-pyrazol-5-yl)methyl)-4H-thiazolo[5',4':4,5]pyrrolo[2,3-d]pyridazin-5(6H)-one (0.8 g, 1.41 mmol) in THF (5 mL) and MeOH (10 mL) under N$_2$ was added dropwise SmI$_2$ (0.1M/THF, 45 mL) under ice-bath After stirred for 10 min, the reaction was quenched with saturated aqueous NH$_4$Cl (50 mL) and extracted with EAOAc (50 mL×3). The combined organic layers were washed with water (60 mL), dried over anhydrous Na$_2$SO$_4$ and concentrated under reduced pressure. The residue was purified by flash chromatography (silica gel, 0~3% methanol in dichloromethane) to give the desired product (310 mg). LC-MS) found: 417 (M+H)$^+$. $^1$H NMR (400 MHz, CDCl$_3$) δ 8.31 (s, 1H), 7.60 (d, 1H), 6.39 (d, 1H), 5.49 (s, 2H), 4.58 (s, 2H), 4.43 (s, 3H), 3.62 (t, 2H), 0.95 (t, 2H), 0.0 (s, 9H).

Example 7E. Synthesis of 2-((1H-pyrazol-3-yl)methyl)-6-((1H-pyrazolo[4,3-c]pyridin-4-yl)methyl)-4-methyl-4H-thiazolo[5',4':4,5]pyrrolo[2,3-d]pyridazin-5(6H)-one

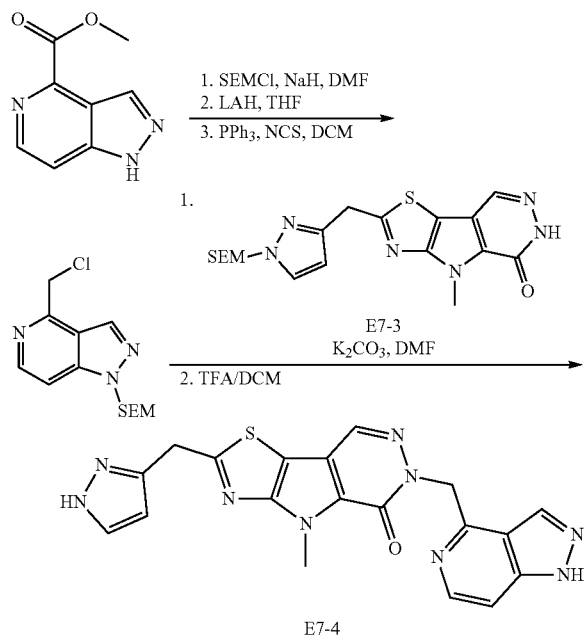

Step A. methyl 1-((2-(trimethylsilyl)ethoxy)methyl)-1H-pyrazolo[4,3-c]pyridine-4-carboxylate To a solution of methyl 1H-pyrazolo[4,3-c]pyridine-4-carboxylate (900 mg, 5.1 mmol) in dry DMF (10 mL) was added NaH (305 mg, 7.6 mmol, 60%) at 0° C. in portions. The suspension was stirred for 15 min under ice bath before the introduction of (2-(chloromethoxy)ethyl)trimethylsilane (1.07 mL, 6.0 mmol) dropwise and stirred for another 1 hr at rt. Then the mixture was poured into sat. NH$_4$Cl (aq.), extracted with ethyl acetate. The combined organic layers was dried with anhydrous Na$_2$SO$_4$, filtered and concentrated. The residue was purified by flash chromatography (silica gel, 0~30% ethyl acetate in petroleum ether) to afford methyl 1-((2-(trimethylsilyl)ethoxy)methyl)-1H-pyrazolo[4,3-c]pyridine-4-carboxylate (1.32 g). LCMS: m/z 308 (M+H)$^+$.

Step B. (1-((2-(trimethylsilyl) ethoxy)methyl)-1H-pyrazolo[4,3-c]pyridin-4-yl)methanol To a solution of methyl 1-((2-(trimethylsilyl)ethoxy)methyl)-1H-pyrazolo[4,3-c]pyridine-4-carboxylate (1 g, 3.2 mmol) in dry THF (10 mL) was added LiHAl$_4$ (146 mg, 3.8 mmol) by portions under ice bath. The mixture was stirred for 30 min at 0° C. Then the suspension was poured into sat. NH$_4$Cl (aq.), extracted with ethyl acetate (2×). The combined organic layers were dried with anhydrous Na$_2$SO$_4$, filtered and concentrated. The residue was purified by flash chromatography (silica gel, 0~60% ethyl acetate in petroleum ether) to afford (1-((2-(trimethylsilyl)ethoxy)methyl)-1H-pyrazolo[4,3-c]pyridin-4-yl)methanol (500 mg). LCMS: m/z 280 (M+H)$^+$.

Step C. 4-(chloromethyl)-1-((2-(trimethylsilyl)ethoxy)methyl)-1H-pyrazolo[4,3-c]pyridine To a solution of (1-((2-(trimethylsilyl)ethoxy)methyl)-1H-pyrazolo[4,3-c]pyridin-4-yl)methanol (120 mg, 0.43 mmol) in dichloromethane (2 mL) was added PPh$_3$ (225 mg, 0.86 mmol). The mixture was cooled down to 0° C. and NCS (114 mg, 0.86 mmol) was added. The suspension was warmed to rt and stirred for another 1 hr. Then the reaction was poured into sat. NaHCO$_3$ (aq.). The aqueous was extracted with dichloromethane. The combined organic layers were dried with anhydrous Na$_2$SO$_4$, filtered and concentrated. The residue was purified by flash chromatography (silica gel, 0~30% ethyl acetate in petroleum ether) to afford 4-(chloromethyl)-1-((2-(trimethylsilyl)ethoxy)methyl)-1H-pyrazolo[4,3-c]pyridine (70 mg) as an oil. LCMS: m/z 298 (M+H)$^+$.

Step D. 4-methyl-2-((1-((2-(trimethylsilyl)ethoxy)methyl)-1H-pyrazol-3-yl)methyl)-6-((1-((2-(trimethylsilyl)ethoxy)methyl)-1H-pyrazolo[4,3-c]pyridin-4-yl)methyl)-4H-thiazolo[5',4':4,5]pyrrolo[2,3-d]pyridazin-5(6H)-one To a mixture of K$_2$CO$_3$ (41 mg, 0.3 mmol) in anhydrous DMF (2 mL) was added 4-methyl-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (41 mg, 0.1 mmol) and stirred at 50° C. for 30 min under argon. A solution of 4-(chloromethyl)-1-((2-(trimethylsilyl)ethoxy)methyl)-1H-pyrazolo[4,3-c]pyridine (30 mg, 0.1 mmol) in DMF (1 mL) was added and stirred for another 4 hrs. The suspension was cooled down to r.t and poured into 0.5 N HCl (aq.). The layers were separated and the aqueous layer was extracted with ethyl acetate. The combined organic layers were dried with anhydrous Na$_2$SO$_4$, filtered and concentrated. The residue was purified by pre-TLC to afford 4-methyl-2-((1-((2-(trimethylsilyl)ethoxy)methyl)-1H-pyrazol-3-yl)methyl)-6-((1-((2-(trimethylsilyl)ethoxy)methyl)-1H-pyrazolo[4,3-c]pyridin-4-yl)methyl)-4H-thiazolo[5',4':4,5]pyrrolo[2,3-d]pyridazin-5(6H)-one (40 mg, 60%). LCMS: m/z 678 (M+H)$^+$.

Step E. 2-((1H-pyrazol-3-yl)methyl)-6-((1H-pyrazolo[4,3-c]pyridin-4-yl)methyl)-4-methyl-4H-thiazolo[5',4':4,5]pyrrolo[2,3-d]pyridazin-5(6H)-one A solution of 4-methyl-2-((1-((2-(trimethylsilyl)ethoxy)methyl)-1H-pyrazol-3-yl)methyl)-6-((1-((2-(trimethylsilyl)ethoxy)methyl)-1H-pyrazolo[4,3-c]pyridin-4-yl)methyl)-4H-thiazolo[5',4':4,5]pyrrolo[2,3-d]pyridazin-5(6H)-one (30 mg, 0.044 mmol) in 35% TFA (1 mL, in dichloromethane) was stirred at r.t overnight. The mixture was concentrated and the residue was purified by pre-HPLC to afford 2-((1H-pyrazol-3-yl)methyl)-6-((1H-pyrazolo[4,3-c]pyridin-4-yl)methyl)-4-methyl-4H-thiazolo[5',4':4,5]pyrrolo[2,3-d]pyridazin-5(6H)-one (3 mg). LCMS: m/z 418 (M+H)$^+$. $^1$H NMR (400 MHz, DMSO-d6) δ 13.51 (s, 1H), 12.78 (s, 1H), 8.55 (s, 1H), 8.18 (d, 1H), 8.00 (s, 1H), 7.68 (s, 1H), 7.43 (d, 1H), 6.27 (d, 1H), 5.78 (s, 2H), 4.51 (s, 2H), 4.25 (s, 3H).

Example 7F. Synthesis of 6-((1H-imidazol-2-yi)methyl)-2-((1H-pyrazol-3-yl)methyl)-4-methyl-4H-thiazolo[5',4':4,5]pyrrolo[2,3-d]pyridazin-5(6H)-one

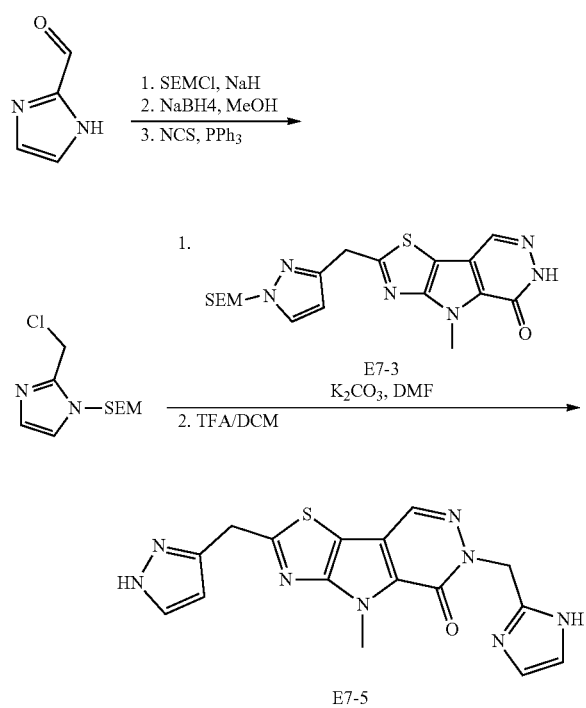

Step A. 1-((2-(trimethylsilyl)ethoxy)methyl)-1H-imidazole-2-carbaldehyde

A sample of NaH was washed with hexane (2×10 mL) under N$_2$. The flask was charged dry DMF (20 mL) and 1H-imidazole-2-carbaldehyde (500 mg, 5.2 mmol) was added in small portions. After stirring at room temperature for 1.5 h, SEMCl (864 mg, 5.2 mmol) was added dropwise. The reaction mixture was stirred at r.t. for 30 min. The reaction mixture was poured into water, extracted with EtOAc. The organic layer was washed with brine, dried over Na$_2$SO$_4$, concentrated under reduced pressure to afford crude 1-((2-(trimethylsilyl)ethoxy)methyl)-1H-imidazole-2-carbaldehyde (800 mg). LCMS: 227 (M+H)$^+$.

Step B. (1-((2-(trimethylsilyl)ethoxy)methyl)-1H-imidazol-2-yl)methanol

To a stirred mixture of 1-((2-(trimethylsilyl)ethoxy)methyl)-1H-imidazole-2-carbaldehyde (1.6 g, 7 mmol) in THF (20 mL) was added NaBH$_4$ (1.34 g, 35 mmol) at 0° C. The reaction mixture was stirred at r.t for 30 min. The reaction mixture was poured into aq. NH$_4$Cl and extracted with EtOAc. The organic layer was washed with brine, dried over Na$_2$SO$_4$, concentrated under reduced pressure to afford crude (1-((2-(trimethylsilyl)ethoxy)methyl)-1H-imidazol-2-yl)methanol (1.3 g).

Step C. 2-(chloromethyl)-1-((2-(trimethylsilyl)ethoxy)methyl)-1H-imidazole

To a stirred mixture of (1-((2-(trimethylsilyl)ethoxy)methyl)-1H-imidazol-2-yl)methanol (400 mg, 1.75 mmol) in DCM (20 mL) were added NCS (466 mg, 3.5 mmol) and PPh$_3$ (920 mg, 3.5 mmol) at r.t. The mixture was stirred at r.t for 2 h. The reaction mixture was poured into water and extracted with DCM. The mixture was washed with water and the organic layer was concentrated under reduced pressure. The residue was purified by Pre-TLC (PE:EtOAc=1:1) to afford 2-(chloromethyl)-1-((2-(trimethylsilyl)ethoxy)methyl)-1H-imidazole. LCMS: 247 (M+H)$^+$. To a stirred mixture of 4-methyl-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (50 mg, 0.12 mmol) in dry DMF (5 mL) was added K$_2$CO$_3$ (66 mg, 0.48 mmol) at 60° C. under N$_2$. After 20 min, compound E7-3 (60 mg, 0.24 mmol), in dry DMF (2 mL) was added at 60° C. under N$_2$. The mixture was stirred at 60° C. for 1.5 h under N$_2$. The reaction mixture was cooled to r.t and adjusted at pH=5~6 with 0.5N aq. HCl. Then the mixture was extracted with EtOAc, washed with water and brine. The organic layer was dried over Na$_2$SO$_4$, concentrated under reduced pressure and purified by Prep-TLC (PE:EtOAc=1:1.5) to afford 4-methyl-6-((1-((2-(trimethylsiyl)ethoxy)methyl)-1H-imidazol-2-yl)methyl)-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (25 mg). LCMS: 627 (M+H)$^+$. A mixture of 4-methyl-6-((1-((2-(trimethylsilyl)ethoxy)methyl)-1H-imidazol-2-yl)methyl)-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (25 mg, 0.04 mmol) in DCM/TFA (2 mL/2 mL) was stirred at r.t for 1 hour. The reaction mixture was concentrated. The residue was purified by prep-HPLC to afford desired product (1.3 mg). LCMS: 367 (M+H)$^+$. $^1$H NMR (400 MHz, DMSO-d6) δ 8.51 (s, 1H), 7.66 (d, 1H), 6.9 (s, 2H), 6.27 (d, 1H), 5.34 (s, 2H), 4.51 (s, 2H), 4.27 (s, 3H).

The following compounds were synthesized according to Scheme E7 and the procedure of Example 7C-7E using the appropriate starting material.

| Cpd No. | Structure | Characterization |
|---|---|---|
| E7-6 | 2-((1H-pyrazol-3-yl)methyl)-6-(benzo[d][1,3]dioxol-5-ylmethyl)-4-methyl-4H-thiazolo[5',4':4,5]pyrrolo[2,3-d]pyridazin-5(6H)-one | LCMS: 421 (M + H)+. 1H NMR (400 MHz, DMSO) δ 12.77 (s, 1H), 8.51 (s, 1H), 7.70 (s, 1H), 6.89 (d, 1H), 6.86-6.80 (m, 2H), 6.26 (d, 1H), 5.97 (s, 2H), 5.24 (s, 2H), 4.49 (s, 2H), 4.26 (s, 3H). |
| E7-7 | 2-((1H-pyrazol-3-yl)methyl)-6-(benzo[d]thiazol-5-ylmethyl)-4-methyl-4,6-dihydro-5H-thiazolo[5',4':4,5]pyrrolo[2,3-d]pyridazin-5-one | LCMS: 434 (M + H)+. 1H NMR (400 MHz, DMSO) δ 12.81 (s, 1H), 9.38 (s, 1H), 8.56 (s, 1H), 8.12 (d, 1H), 7.98 (s, 1H), 7.67 (s, 1H), 7.48 (d, 1H), 6.26 (s, 1H), 5.52 (s, 2H), 4.49 (s, 2H), 4.27 (s, 3H) |
| E7-8 | 2-((1H-pyrazol-3-yl)methyl)-6-((2,2-dioxido-1,3-dihydrobenzo[c][1,2,5]thiadiazol-4-yl)methyl)-4-methyl-4H-thiazolo[5',4':4,5]pyrrolo[2,3-d]pyridazin-5(6H)-one | LCMS: 469 (M + H)+. 1HNMR(400 MHz, DMSO) δ 12.77 (s, 1H), 10.84 (s, 1H), 8.56 (s, 1H), 7.70 (s, 1H), 6.83-6.51 (m, 2H), 6.40 (d, 1H), 6.26 (d, 1H), 5.27 (s, 2H), 4.50 (s, 2H), 4.27 (s, 3H) |
| E7-9 | 6-((1H-benzo[d]imidazol-4-yl)methyl)-2-((1H-pyrazol-3-yl)methyl)-4-methyl-4H-thiazolo[5',4':4,5]pyrrolo[2,3-d]pyridazin-5(6H)-one | LCMS: 417 (M + H)+. 1H NMR (400 MHz, DMSO-d6) δ 12.76 (s, 1H), 12.51 (s, 1H), 8.54 (s, 1H), 8.24 (s, 1H), 7.67 (s, 1H), 7.47 (s, 1H), 7.08 (t, 1H), 6.70 (s, 1H), 6.26 (d, 1H), 5.71 (s, 2H), 4.50 (s, 2H), 4.28 (s, 3H). |
| E7-10 | 2-((1H-pyrazol-3-yl)methyl)-6-(isoindolin-4-ylmethyl)-4-methyl-4H-thiazolo[5',4':4,5]pyrrolo[2,3-d]pyridazin-5(6H)-one | LCMS: m/z 418 (M + H)+. 1H NMR (400 MHz, DMSO-d6) δ 8.54 (s, 1H), 8.27 (s, 1H), 7.66 (s, 1H), 7.24-7.16 (m, 2H), 7.08 (d, 1H), 6.26 (d, 1H), 5.31 (s, 2H), 4.50 (s, 2H), 4.26 (s, 5H), 4.20 (s, 2H) |

| Cpd No. | Structure | Characterization |
|---|---|---|
| E7-11 | 2-((1H-pyrazol-3-yl)methyl)-6-(3-acetylbenzyl)-4-methyl-4H-thiazolo[5',4':4,5]pyrrolo[2,3-d]pyridazin-5(6H)-one | LCMS: m/z 419 (M + H)+. 1H NMR (400 MHz, DMSO-d6) δ 12.78 (s, 1H), 8.56 (s, 1H), 7.89-7.87 (m, 2H), 7.71 (s, 1H), 7.56 (d, 1H), 7.51-7.47 (m, 1H), 6.26 (d, 1H), 5.43 (s, 2H), 4.49 (s, 2H), 4.27 (s, 3H), 2.56 (s, 3H). |
| E7-12 | 6-(3-acetylbenzyl)-2-(2-(3-acetylphenyl)-1-(1H-pyrazol-3-yl)ethyl)-4-methyl-4H-thiazolo[5',4':4,5]pyrrolo[2,3-d]pyridazin-5(6H)-one | LCMS: m/z 551 (M + H)+. 1H NMR (400 MHz, DMSO-d6) δ 12.73 (s, 1H), 8.54 (s, 1H), 7.89-7.87 (m, 2H), 7.83 (s, 1H), 7.73-7.71 (m, 2H), 7.56-7.46 (m, 3H), 7.36-7.33 (m, 1H), 6.32 (d, 1H), 5.42 (s, 2H), 4.99 (s, 1H), 4.27 (s, 3H), 3.67-3.59 (m, 2H), 2.56 (s, 3H), 2.49 (s, 3H). |
| E7-13 | 2-((1H-pyrazol-3-yl)methyl)-6-(3-amino-4-hydroxybenzyl)-4-methyl-4H-thiazolo[5',4':4,5]pyrrolo[2,3-d]pyridazin-5(6H)-one | LCMS: m/z 408 (M + H)+. 1H NMR (400 MHz, DMSO) δ 12.76 (s, 1H), 8.93 (s, 1H), 8.50 (s, 1H), 7.67 (s, 1H), 6.57 (d, 1H), 6.55 (d, 1H), 6.39 (dd, 1H), 6.26 (s, 1H), 5.11 (s, 2H), 4.49 (br s, 4H), 4.27 (s, 3H). |
| E7-14 | 6-((1H-benzo[d][1,2,3]triazol-7-yl)methyl)-2-((1H-pyrazol-3-yl)methyl)-4-methyl-4H-thiazolo[5',4':4,5]pyrrolo[2,3-d]pyridazin-5(6H)-one | LC-MS: 418 (M + H)+. 1H NMR (400 MHz, DMSO) δ 12.76 (s, 1H), 8.55 (s, 1H), 7.78 (d, 1H), 7.65 (d, 1H), 7.36 (dd, 1H), 7.05 (d, 1H), 6.25 (d, 1H), 5.78 (s, 2H), 4.48 (s, 2H), 4.24 (s, 3H). |

| Cpd No. | Structure | Characterization |
|---|---|---|
| E7-15 | 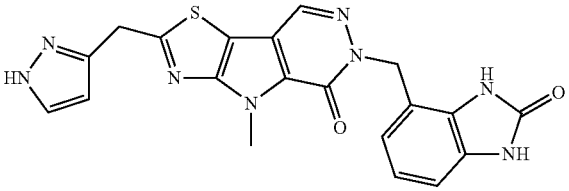 [SMILES: Cn1c2nc(Cc3cc[nH]n3)sc2c2cnn(Cc3cccc4[nH]c(=O)[nH]c34)c(=O)c21]<br>2-((1H-pyrazol-3-yl)methyl)-4-methyl-6-((2-oxo-2,3-dihydro-1H-benzo[d]imidazol-4-yl)methyl)-4H-thiazolo[5',4':4,5]pyrrolo[2,3-d]pyridazin-5(6H)-one | LCMS: m/z 433 (M + H)+. $^1$H NMR (400 MHz, DMSO) δ 12.78 (s, 1H), 10.69 (d, 2H), 8.55 (s, 1H), 7.68 (s, 1H), 6.84 (d, 2H), 6.73-6.59 (m, 1H), 6.27 (d, 1H), 5.41 (s, 2H), 4.50 (s, 2H), 4.28 (s, 3H). |
| E7-16 | 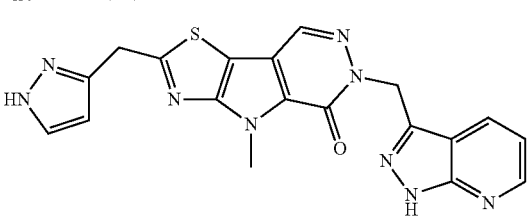<br>2-((1H-pyrazol-3-yl)methyl)-6-((1H-pyrazolo[3,4-b]pyridin-3-yl)methyl)-4-methyl-4H-thiazolo[5',4':4,5]pyrrolo[2,3-d]pyridazin-5(6H)-one | LC-MS: m/z 418 (M + H)$^+$. $^1$H NMR (400 MHz, DMSO) δ 13.52 (s, 1H), 12.77 (s, 1H), 8.53 (s, 1H), 8.50-8.46 (m, 1H), 8.15 (d, 1H), 7.70 (s, 1H), 7.14 (dd, 1H), 6.26 (d, 1H), 5.67 (s, 2H), 4.49 (s, 2H), 4.28 (s, 3H). |
| E7-17 | 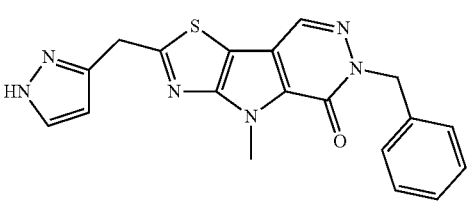 [SMILES: Cn1c2nc(Cc3cc[nH]n3)sc2c2cnn(Cc3ccccc3)c(=O)c21]<br>2-((1H-pyrazol-3-yl)methyl)-6-benzyl-4-methyl-4,6-dihydro-5H-thiazolo[5',4':4,5]pyrrolo[2,3-d]pyridazin-5-one | LCMS: m/z 377(M + 1)$^+$. $^1$H NMR (400 MHz, DMSO-d$_6$) δ 12.77 (s, 1H), 8.53 (s, 1H), 7.70 (s, 1H), 7.35-7.22 (m, 5H), 6.26 (d, 1H), 5.34 (s, 2H), 4.48 (s, 2H), 4.27 (s, 3H). |
| E7-18 | 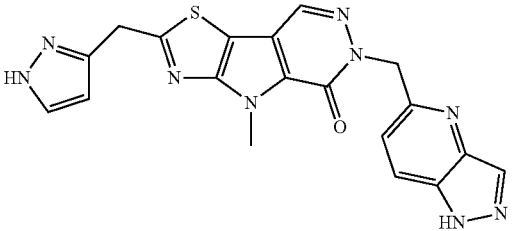 [SMILES: Cn1c2nc(Cc3cc[nH]n3)sc2c2cnn(Cc3ccc4[nH]ncc4n3)c(=O)c21]<br>2-((1H-pyrazol-3-yl)methyl)-6-((1H-pyrazolo[4,3-b]pyridin-5-yl)methyl)-4-methyl-4H-thiazolo[5',4':4,5]pyrrolo[2,3-d]pyridazin-5(6H)-one | LCMS: m/z 418 (M + H)$^+$. $^1$HNMR (400 MHz, DMSO) δ 13.29 (s, 1H), 12.8 (brs, 1H), 8.54 (s, 1H), 8.20 (s, 1H), 7.96 (d, 1H), 7.67 (s, 1H), 7.24 (d, 1H), 6.27 (d, 1H), 5.57 (s, 2H), 4.51 (s, 2H), 4.27 (s, 3H). |
| E7-19 | 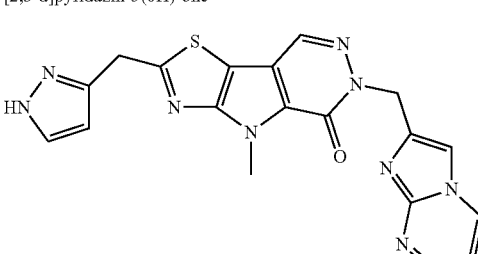<br>2-((1H-pyrazol-3-yl)methyl)-6-(imidazo[1,2-a]pyrimidin-2-ylmethyl)-4-methyl-4,6-dihydro-5H-thiazolo[5',4':4,5]pyrrolo[2,3-d]pyridazin-5-one | LCMS: m/z 418 (M + H)$^+$. $^1$HNMR (400 MHz, DMSO) δ 12.79 (s, 1H), 8.92 (dd, 1H), 8.61 (s, 1H), 8.55 (dd, 1H), 8.31 (s, 1H), 7.75 (s, 1H), 7.73 (s, 1H), 7.08 (dd, 1H), 6.33 (d, 1H), 5.55 (s, 2H), 4.57 (s, 2H), 4.34 (s, 3H). |

| Cpd No. | Structure | Characterization |
|---|---|---|
| E7-20 | 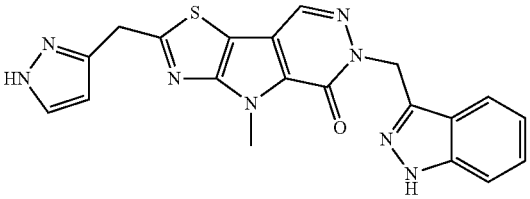 [SMILES: Cn1c2nc(Cc3cc[nH]n3)sc2c2cnn(Cc3n[nH]c4ccccc34)c(=O)c21]<br>6-((1H-indazol-3-yl)methyl)-2-((1H-pyrazol-3-yl)methyl)-4-methyl-4H-thiazolo[5',4':4,5]pyrrolo[2,3-d]pyridazin-5(6H)-one | LCMS: ESI m/z 417 (M + H)⁺. ¹H NMR (400 MHz, DMSO-d$_6$) δ 12.91 (s, 1H), 12.77 (s, 1H), 8.51 (s, 1H), 7.73-7.70 (m, 2H), 7.48 (d, 1H), 7.30 (dd, 1H), 7.04 (t, 1H), 6.25 (d, 1H), 5.68 (s, 2H), 4.48 (s, 2H), 4.28 (s, 3H). |
| E7-21 | 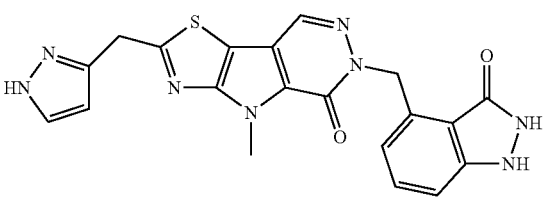 [SMILES: Cn1c2nc(Cc3cc[nH]n3)sc2c2cnn(Cc3cccc4[nH][nH]c(=O)c34)c(=O)c21]<br>2-((1H-pyrazol-3-yl)methyl)-4-methyl-6-((3-oxo-2,3-dihydro-1H-indazol-4-yl)methyl)-4H-thiazolo[5',4':4,5]pyrrolo[2,3-d]pyridazin-5(6H)-one | LCMS: m/z 433(M + H)⁺. ¹H NMR (400 MHz, DMSO) δ 12.78 (s, 1H), 11.37 (s, 1H), 8.57 (s, 1H), 7.70 (s, 1H), 7.13 (d, 2H), 6.38-6.29 (m, 1H), 6.27 (d, 1H), 5.79 (s, 2H), 4.51 (s, 2H), 4.27 (s, 3H). |
| E7-22 | 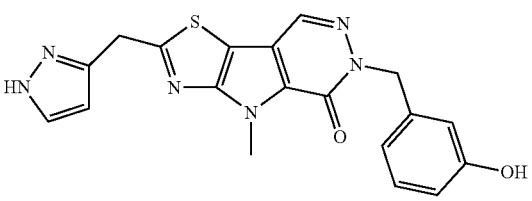 [SMILES: Cn1c2nc(Cc3cc[nH]n3)sc2c2cnn(Cc3cccc(O)c3)c(=O)c21]<br>2-((1H-pyrazol-3-yl)methyl)-6-(3-hydroxybenzyl)-4-methyl-4,6-dihydro-5H-thiazolo[5',4':4,5]pyrrolo[2,3-d]pyridazin-5-one | LCMS: m/z 393 (M + H)⁺. ¹H NMR (400 MHz, DMSO-d$_6$) δ 12.82 (s, 1H), 9.39 (s, 1H), 8.58 (s, 1H), 7.76 (s, 1H), 7.15(s, 1H), 6.92-6.55 (m, 3H), 6.31.(s, 1H), 5.30 (s, 2H), 4.53 (s, 2H), 4.28 (s, 3H) |
| E7-23 | 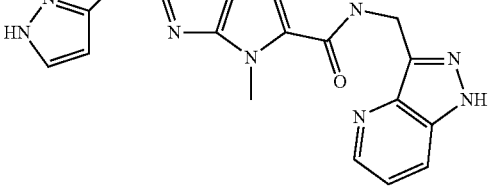<br>2-((1H-pyrazol-3-yl)methyl)-6-((1H-pyrazolo[4,3-b]pyridin-3-yl)methyl)-4-methyl-4,6-dihydro-5H-thiazolo[5',4':4,5]pyrrolo[2,3-d]pyridazin-5-one | LCMS: m/z 418 (M + H)⁺. ¹H NMR (400 MHz, DMSO-d$_6$) δ 13.15 (s, 1H), 12.83 (s, 1H), 8.52(s, 2H), 8.02 (dd, 1H), 7.74 (s, 1H), 7.40 (dd, 1H), 6.32 (d, 1H), 5.81 (s, 2H), 4.55 (s, 2H), 4.33 (s, 3H). |
| E7-24 | 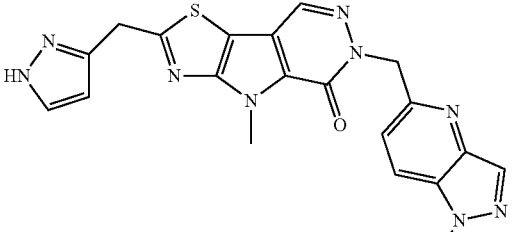<br>2-((1H-pyrazol-3-yl)methyl)-4-methyl-6-((1-methyl-1H-pyrazolo[4,3-b]pyridin-5-yl)methyl)-4,6-dihydro-5H-thiazolo[5',4':4,5]pyrrolo[2,3-d]pyridazin-5-one | LCMS: m/z 432 (M + H)⁺. ¹H NMR (400 MHz, DMSO-d$_6$) δ 12.80 (s, 1H), 8.54 (s, 1H), 8.16 (s, 1H), 8.09 (d, 1H), 7.69 (s, 1H), 7.29 (d, 1H), 6.27 (s, 1H), 5.57 (s, 2H), 4.51 (s, 2H), 4.27 (s, 3H), 4.05 (s, 3H). |

| Cpd No. | Structure | Characterization |
|---|---|---|
| E7-25 | 2-((1H-pyrazol-3-yl)methyl)-4-methyl-6-(naphthalen-2-ylmethyl)-4,6-dihydro-5H-thiazolo[5',4':4,5]pyrrolo[2,3-d]pyridazin-5-one | LCMS: m/z 427 (M + H)$^+$. $^1$H NMR (400 MHz, DMSO-d$_6$) δ 12.78 (s, 1H), 8.56 (s, 1H), 7.89-7.86 (m, 3H), 7.78 (s, 1H), 7.68 (s, 1H), 7.51-7.48 (m, 3H), 6.26 (d, 1H), 5.52 (s, 2H), 4.48 (s, 2H), 4.27 (s, 3H). |
| E7-26 | 2-((1H-pyrazol-3-yl)methyl)-6-((2-aminobenzo[d]thiazol-4-yl)methyl)-4-methyl-4,6-dihydro-5H-thiazolo[5',4':4,5]pyrrolo[2,3-d]pyridazin-5-one | LCMS: m/z 449 (M + H)$^+$. $^1$H NMR (400 MHz, DMSO-d$_6$) δ 12.79 (s, 1H), 8.55 (s, 1H), 7.70 (s, 1H), 7.63 (s, 2H), 7.54 (d, 1H), 6.89 (dd, 1H), 6.66 (d, 1H), 6.27 (d, 1H), 5.59 (s, 2H), 4.50 (s, 2H), 4.27 (s, 3H). |
| E7-27 | 6-((1H-indol-4-yl)methyl)-2-((1H-pyrazol-3-yl)methyl)-4-methyl-4,6-dihydro-5H-thiazolo[5',4':4,5]pyrrolo[2,3-d]pyridazin-5-one | LCMS: m/z 416 (M + H)$^+$. $^1$H NMR (400 MHz, DMSO-d$_6$) δ 12.77 (s, 1H), 11.13 (s, 1H), 8.51 (s, 1H), 7.70 (s, 1H), 7.32-7.28 (m, 2H), 7.00 (dd, 1H), 6.82 (d, 1H), 6.59 (s, 1H), 6.26 (s, 1H), 5.58 (s, 2H), 4.48 (s, 2H), 4.28 (s, 3H). |
| E7-28 | 2-((1H-pyrazol-3-yl)methyl)-6-((1H-pyrrolo[2,3-b]pyridin-6-yl)methyl)-4-methyl-4H-thiazolo[5',4':4,5]pyrrolo[2,3-d]pyridazin-5(6H)-one | LC-MS: m/z 417 (M + H)$^+$. $^1$H NMR (400 MHz, DMSO-d6) δ: 12.79 (s, 1H), 11.59 (s, 1H), 8.53 (s, 1H), 7.89 (d, 1H), 7.69 (s, 1H), 7.40 (s, 1H), 6.92 (d, 1H), 6.40 (s, 1H), 6.27 (s, 1H), 5.51 (s, 2H), 4.50 (s, 2H), 4.27 (s, 3H). |

-continued

| Cpd No. | Structure | Characterization |
|---|---|---|
| E7-29 | 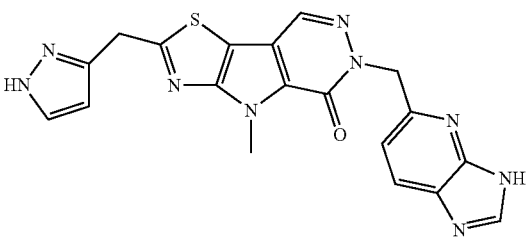 [SMILES: Cn1c2nc(Cc3cc[nH]n3)sc2c2cnn(Cc3ccc4nc[nH]c4n3)c(=O)c21]<br>2-((1H-pyrazol-3-yl)methyl)-6-((3H-imidazo[4,5-b]pyridin-5-yl)methyl)-4-methyl-4H-thiazolo[5',4':4,5]pyrrolo[2,3-d]pyridazin-5(6H)-one | LC-MS: m/z 418 (M + H)$^+$.<br>$^1$H NMR (400 MHz, DMSO-d6) δ: 13.04 (s, 1H), 12.77 (s, 1H), 8.54 (s, 1H), 8.44-8.28 (m, 1H), 8.07-7.88 (m, 1H), 7.69 (s, 1H), 7.10 (d, 1H), 6.27 (d, 1H), 5.55 (s, 2H), 4.50 (s, 2H), 4.27 (s, 3H). |
| E7-30 | 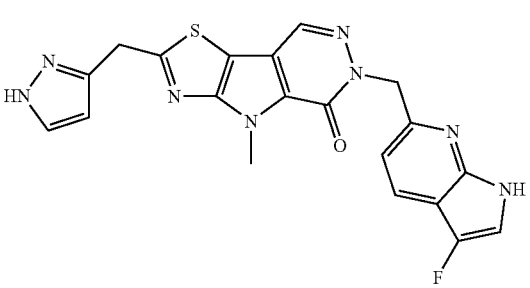 [SMILES: Cn1c2nc(Cc3cc[nH]n3)sc2c2cnn(Cc3ccc4c(F)c[nH]c4n3)c(=O)c21]<br>2-((1H-pyrazol-3-yl)methyl)-6-((3-fluoro-1H-pyrrolo[2,3-b]pyridin-6-yl)methyl)-4-methyl-4H-thiazolo[5',4':4,5]pyrrolo[2,3-d]pyridazin-5(6H)-one | LC-MS: m/z 435 (M + H)$^+$.<br>$^1$H NMR (400 MHz, DMSO-d6) δ: 12.85 (s, 1H), 11.47 (s, 1H), 8.59 (s, 1H), 8.00 (d, 1H), 7.76 (s, 1H), 7.43 (t, 1H), 7.06 (d, 1H), 6.34 (d, 1H), 5.58 (s, 2H), 4.56 (s, 2H), 4.33 (s, 3H). |
| E7-31 | 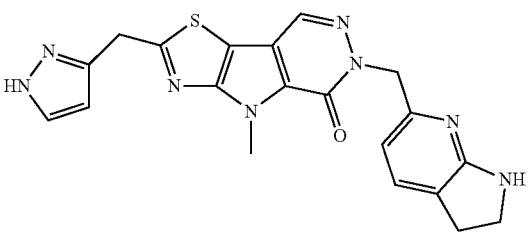 [SMILES: Cn1c2nc(Cc3cc[nH]n3)sc2c2cnn(Cc3ccc4c(n3)NCC4)c(=O)c21]<br>2-((1H-pyrazol-3-yl)methyl)-6-((2,3-dihydro-1H-pyrrolo[2,3-b]pyridin-6-yl)methyl)-4-methyl-4H-thiazolo[5',4':4,5]pyrrolo[2,3-d]pyridazin-5(6H)-one | LC-MS: m/z 419 (M + H)$^+$.<br>$^1$H NMR (400 MHz, DMSO-d6) δ: 8.50 (s, 1H), 7.67 (s, 1H), 7.14 (d, 1H), 6.34 (s, 1H), 6.27 (d, 1H), 6.12 (d, 1H), 5.18 (s, 2H), 4.50 (s, 2H), 4.27 (s, 3H), 3.57 (m, 2H), 2.90 (t, 2H). |
| E7-32 | 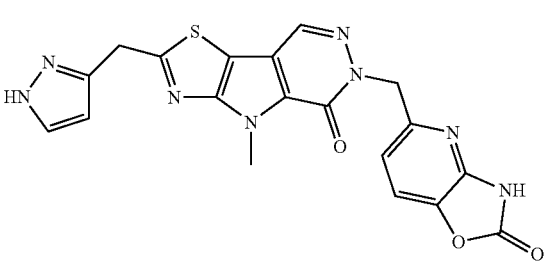 [SMILES: Cn1c2nc(Cc3cc[nH]n3)sc2c2cnn(Cc3ccc4oc(=O)[nH]c4n3)c(=O)c21]<br>5-((2-((1H-pyrazol-3-yl)methyl)-4-methyl-5-oxo-4,5-dihydro-6H-thiazolo[5',4':4,5]pyrrolo[2,3-d]pyridazin-6-yl)methyl)oxazolo[4,5-b]pyridin-2(3H)-one | LC-MS: m/z 435 (M + H)$^+$.<br>$^1$H NMR (400 MHz, DMSO-d6) δ: 12.88 (s, 1H), 8.56 (s, 1H), 7.76 (s, 1H), 6.94 (d, 1H), 6.35-6.29 (m, 2H), 5.32 (s, 2H), 4.55 (s, 2H), 4.33 (s, 3H). |

-continued

| Cpd No. | Structure | Characterization |
|---|---|---|
| E7-33 | 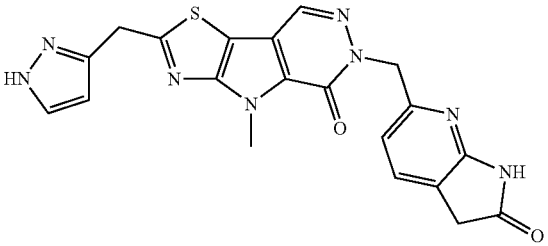 [SMILES: Cn1c2nc(Cc3cc[nH]n3)sc2c2cnn(Cc3ccc4c(n3)NC(=O)C4)c(=O)c21]<br>2-((1H-pyrazol-3-yl)methyl)-4-methyl-6-((2-oxo-2,3-dihydro-1H-pyrrolo[2,3-b]pyridin-6-yl)methyl)-4,6-dihydro-5H-thiazolo[5',4':4,5]pyrrolo[2,3-d]pyridazin-5-one | LC-MS: m/z 433 (M + H)+.<br>$^1$H NMR (400 MHz, DMSO-d6) δ: 12.84 (s, 1H), 11.01 (s, 1H), 8.59 (s, 1H), 7.74 (s, 1H), 7.53 (d, 1H), 6.76 (d, 1H), 6.33 (d, 1H), 5.40 (s, 2H), 4.56 (s, 2H), 4.32 (s, 3H), 3.56 (s, 2H). |
| E7-34 | 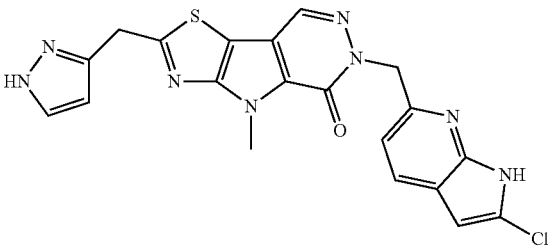 [SMILES: Cn1c2nc(Cc3cc[nH]n3)sc2c2cnn(Cc3ccc4cc(Cl)[nH]c4n3)c(=O)c21]<br>2-((1H-pyrazol-3-yl)methyl)-6-((2-chloro-1H-pyrrolo[2,3-b]pyridin-6-yl)methyl)-4-methyl-4,6-dihydro-5H-thiazolo[5',4':4,5]pyrrolo[2,3-d]pyridazin-5-one | LC-MS: m/z 451 (M + H)+.<br>$^1$H NMR (400 MHz, DMSO-d6) δ: 12.87 (s, 1H), 8.59 (s, 1H), 8.46 (s, 1H), 7.88 (d, 1H), 7.73 (s, 1H), 7.02 (d, 1H), 6.51 (s, 1H), 6.33 (d, 1H), 5.55 (s, 2H), 4.57 (s, 2H), 4.33 (s, 3H) |
| E7-35 | 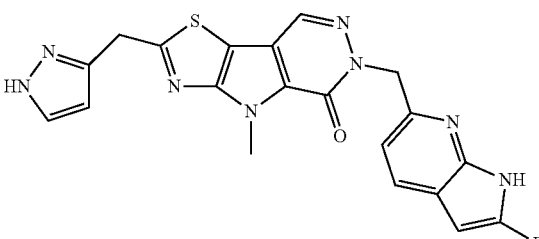<br>2-((1H-pyrazol-3-yl)methyl)-6-((2-fluoro-1H-pyrrolo[2,3-b]pyridin-6-yl)methyl)-4-methyl-4,6-dihydro-5H-thiazolo[5',4':4,5]pyrrolo[2,3-d]pyridazin-5-one | LC-MS: m/z 435 (M + H)+.<br>$^1$H NMR (400 MHz, DMSO-d6) δ: 12.78 (s, 1H), 8.53 (s, 1H), 7.80 (d, 1H), 7.68 (s, 1H), 6.97 (d, 1H), 6.27 (d, 1H), 5.90 (d, 1H), 5.49 (s, 2H), 4.51 (s, 2H), 4.27 (s, 3H) |
| E7-36 | 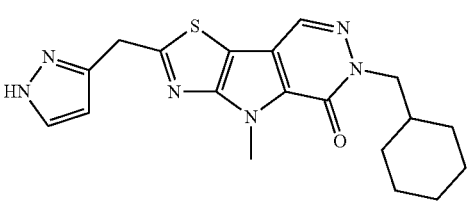 [SMILES: Cn1c2nc(Cc3cc[nH]n3)sc2c2cnn(CC3CCCCC3)c(=O)c21]<br>2-((1H-pyrazol-3-yl)methyl)-6-(cyclohexylmethyl)-4-methyl-4,6-dihydro-5H-thiazolo[5',4':4,5]pyrrolo[2,3-d]pyridazin-5-one | LC-MS: m/z 383 (M + H)+.<br>$^1$H NMR (400 MHz, DMSO-d6) δ: 12.84 (d, 1H), 8.47 (s, 1H), 7.71 (s, 1H), 6.26 (d, 1H), 4.47 (s, 2H), 4.26 (s, 3H), 4.00 (d, 2H), 1.96-1.83 (m, 1H), 1.76-1.40 (m, 6H), 1.33-0.55 (m, 4H) |

| Cpd No. | Structure | Characterization |
|---|---|---|
| E7-37 | 6-benzyl-2-((4-fluoro-1H-pyrazol-3-yl)methyl)-4-methyl-4H-thiazolo[5',4':4,5]pyrrolo[2,3-d]pyridazin-5(6H)-one | LC-MS: m/z 395 (M + H)+. $^1$H NMR (400 MHz, DMSO-d6) δ: 12.82 (s, 1H), 8.55 (s, 1H), 7.84 (s, 1H), 7.35-7.20 (m, 5H), 5.35 (s, 2H), 4.51 (s, 2H), 4.26 (s, 3H). |
| E7-38 | 2-((1H-pyrazol-3-yl)methyl)-4-methyl-6-(thiazol-4-ylmethyl)-4H-thiazolo[5',4':4,5]pyrrolo[2,3-d]pyridazin-5(6H)-one | LCMS: 384 (M + H)+. $^1$H NMR (400 MHz, DMSO) δ 12.78 (s, 1H), 9.03 (d, 1H), 8.52 (s, 1H), 7.71 (s, 1H), 7.42 (d, 1H), 6.27 (d, 1H), 5.48 (s, 2H), 4.48 (s, 2H), 4.27 (s, 3H). |
| E7-39 | 6-((1,2,4-thiadiazol-5-yl)methyl)-2-((1H-pyrazol-3-yl)methyl)-4-methyl-4H-thiazolo[5',4':4,5]pyrrolo[2,3-d]pyridazin-5(6H)-one | LCMS: 385 (M + H)+. 1HNMR(400 MHz, DMSO) δ 12.79 (s, 1H), 8.84 (s, 1H), 8.64 (s, 1H), 7.72 (s, 1H), 6.27 (d, 1H), 5.84 (s, 2H), 4.51 (s, 2H), 4.28 (s, 3H) |
| E7-40 | 2-((1H-pyrazol-3-yl)methyl)-6-((2-aminothiazol-5-yl)methyl)-4-methyl-4H-thiazolo[5',4':4,5]pyrrolo[2,3-d]pyridazin-5(6H)-one | LCMS: m/z 399 (M + H)+. 1H NMR (400 MHz, DMSO-d6) δ 12.78 (s, 1H), 8.52 (s, 1H), 7.70 (s, 1H), 6.91 (s, 1H), 6.87 (br s, 2H), 6.27 (d, 1H), 5.26 (s, 2H), 4.49 (s, 2H), 4.27 (s, 3H). |
| E7-41 | 6-((1H-imidazol-4-yl)methyl)-2-((1H-pyrazol-3-yl)methyl)-4-methyl-4H-thiazolo[5',4':4,5]pyrrolo[2,3-d]pyridazin-5(6H)-one | LCMS: m/z 367 (M + H)+. 1H NMR (400 MHz, DMSO-d6) δ 8.48 (s, 1H), 7.68 (s, 1H), 7.52 (s, 1H), 6.91 (s, 1H), 6.27 (d, 1H), 5.25 (s, 2H), 4.50 (s, 2H), 4.28 (s, 3H). |

| Cpd No. | Structure | Characterization |
|---|---|---|
| E7-42 | 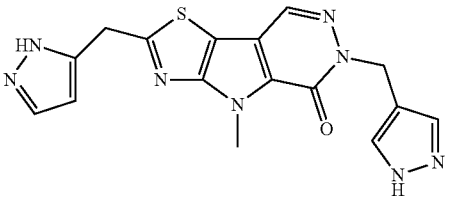 [SMILES: Cn1c2nc(Cc3ccn[nH]3)sc2c2cnn(Cc3cn[nH]c3)c(=O)c21]<br>6-((1H-pyrazol-4-yl)methyl)-2-((1H-pyrazol-5-yl)methyl)-4-methyl-4H-thiazolo[5',4':4,5]pyrrolo[2,3-d]pyridazin-5(6H)-one | LC-MS: m/z 367 (M + H)⁺.<br>1H NMR (400 MHz, DMSO) δ 12.77 (brs, 2H), 8.49 (s, 1H), 7.72-7.35 (m, 3H), 6.25 (s,1H), 5.20 (s, 2H), 4.48 (s, 2H), 4.27 (s, 3H). |
| E7-43 | 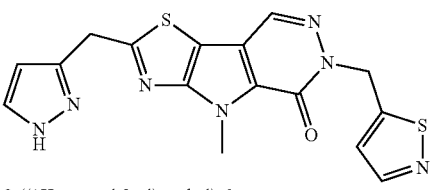<br>2-((1H-pyrazol-3-yl)methyl)-6-(isothiazol-5-ylmethyl)-4-methyl-4H-thiazolo[5',4':4,5]pyrrolo[2,3-d]pyridazin-5(6H)-one | LC-MS: m/z 384(M + 1)⁺.<br>1H NMR (400 MHz, DMSO) δ 12.77 (s, 1H), 8.59 (s, 1H), 8.46 (d, 1H), 7.71 (s, 1H), 7.42 (d, 1H), 6.26 (d, 1H), 5.66 (s, 2H), 4.48 (s, 2H), 4.28 (s, 3H). |
| E7-44 | 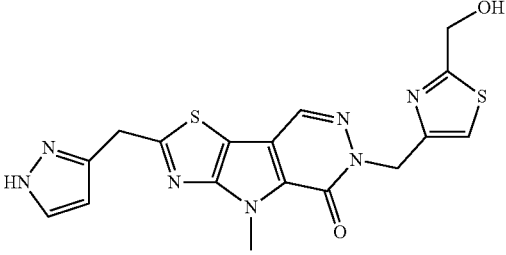 [SMILES: Cn1c2nc(Cc3cc[nH]n3)sc2c2cnn(Cc3csc(CO)n3)c(=O)c21]<br>2-((1H-pyrazol-3-yl)methyl)-6-((2-(hydroxymethyl)thiazol-4-yl)methyl)-4-methyl-4H-thiazolo[5',4':4,5]pyrrolo[2,3-d]pyridazin-5(6H)-one | LCMS: m/z 414 (M + H)⁺.<br>¹H NMR (400 MHz, DMSO) δ 12.78 (s, 1H), 8.48 (s, 1H), 7.70 (s, 1H), 7.28 (s, 1H), 6.26 (d, 1H), 6.15 (t, 1H), 5.39 (s, 2H), 4.66 (d, 2H), 4.49 (s, 2H), 4.25 (s, 3H). |
| E7-45 | 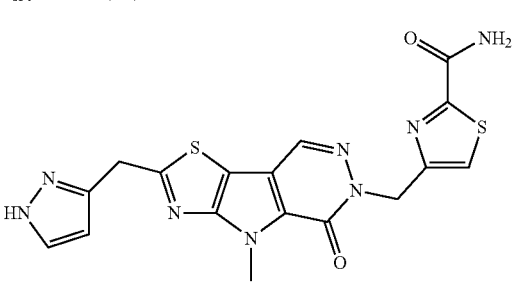<br>4-((2-((1H-pyrazol-3-yl)methyl)-4-methyl-5-oxo-4H-thiazolo[5',4':4,5]pyrrolo[2,3-d]pyridazin-6(5H)-yl)methyl)thiazole-2-carboxamide | LCMS: m/z 427 (M + H)+.<br>1H NMR (400 MHz, DMSO) δ 12.78 (s, 1H), 8.51 (s, 1H), 8.11 (s, 1H), 7.78 (s, 1H), 7.70-7.60 (m, 2H), 6.27 (d, 1H), 5.50 (s, 2H), 4.48 (s, 2H), 4.26 (s, 3H). |
| E7-46 | 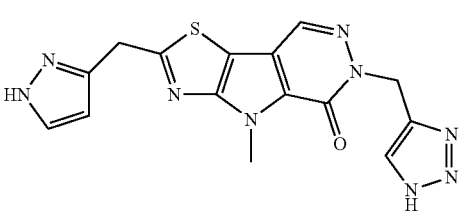 [SMILES: Cn1c2nc(Cc3cc[nH]n3)sc2c2cnn(Cc3c[nH]nn3)c(=O)c21]<br>6-((1H-1,2,3-triazol-4-yl)methyl)-2-((1H-pyrazol-3-yl)methyl)-4-methyl-4H-thiazolo[5',4':4,5]pyrrolo[2,3-d]pyridazin-5(6H)-one | LCMS: m/z 368 (M + H)⁺.<br>1H NMR (400 MHz, DMSO-d6) δ 14.89 (s, 1H), 12.78 (s, 1H), 8.51 (s, 1H), 7.95-7.54 (m, 2H), 6.26 (d, 1H), 5.42 (s, 2H), 4.49 (s, 2H), 4.27 (s, 3H). |

| Cpd No. | Structure | Characterization |
|---|---|---|
| E7-47 | N-(6-((2-((1H-pyrazol-3-yl)methyl)-4-methyl-5-oxo-4H-thiazolo[5',4':4,5]pyrrolo[2,3-d]pyridazin-6(5H)-yl)methyl)-5-fluoropyridin-2-yl)acetamide | LCMS: (ESI) m/z 453 (M + H)$^+$.<br>$^1$H NMR (400 MHz, DMSO-d$_6$) δ 12.84 (s, 1H), 10.41 (s, 1H), 8.57 (s, 1H), 8.06 (s, 1H), 7.71 (s, 2H), 6.34 (s, 1H), 5.52 (s, 2H), 4.58 (s, 2H), 4.33 (s, 3H), 2.08 (s, 3H). |
| E7-48 | 2-((1H-pyrazol-3-yl)methyl)-4-methyl-6-(thiazol-2-ylmethyl)-4H-thiazolo[5',4':4,5]pyrrolo[2,3-d]pyridazin-5(6H)-one | LC-MS: 384 [M + H]+.<br>1H NMR (400 MHz, DMSO) δ 12.78 (s, 1H), 8.58 (s, 1H), 7.75 (d, 1H), 7.70 (s, 1H), 7.64 (d, 1H), 6.27 (s, 1H), 5.65 (s, 2H), 4.48 (s, 2H), 4.27 (s, 3H). |
| E7-49 | 2-((1H-pyrazol-3-yl)methyl)-6-((5-bromothiazol-4-yl)methyl)-4-methyl-4H-thiazolo[5',4':4,5]pyrrolo[2,3-d]pyridazin-5(6H)-one | LCMS: m/z 462, 464 (M, M + 2H)$^+$.<br>$^1$H NMR (400 MHz, DMSO-d$_6$) δ12.77 (s, 1H), 9.04 (s, 1H), 8.49 (s, 1H), 7.71 (s, 1H), 6.26 (d, 1H), 5.41 (s, 2H), 4.48 (s, 2H), 4.25 (s, 3H). |
| E7-50 | 2-((1H-pyrazol-3-yl)methyl)-6-((5-aminothiazol-4-yl)methyl)-4-methyl-4H-thiazolo[5',4':4,5]pyrrolo[2,3-d]pyridazin-5(6H)-one | LCMS: m/z 399 (M + H)$^+$.<br>$^1$H NMR (400 MHz, DMSO-d$_6$) δ 12.78(s, 1H), 8.51 (s, 1H), 7.99 (s, 1H), 7.71 (s, 1H), 6.27 (d, 1H), 5.83(s, 2H), 5.27 (s, 2H), 4.49 (s, 2H), 4.27 (s, 3H) |
| E7-51 | 4-((2-((1H-pyrazol-3-yl)methyl)-4-methyl-5-oxo-4H-thiazolo[5',4':4,5]pyrrolo[2,3-d]pyridazin-6(5H)-yl)methyl)thiazole-5-carbonitrile | LCMS: m/z 409 (M + H)$^+$.<br>$^1$H NMR (400 MHz, DMSO-d$_6$) δ12.77 (s, 1H), 9.36 (s, 1H), 8.56 (s, 1H), 7.71 (s, 1H), 6.26 (d, 1H), 5.61 (s, 2H), 4.49 (s, 2H), 4.25 (s, 3H). |

| Cpd No. | Structure | Characterization |
|---|---|---|
| E7-52 | 4-((2-((1H-pyrazol-3-yl)methyl)-4-methyl-5-oxo-4H-thiazolo[5',4':4,5]pyrrolo[2,3-d]pyridazin-6(5H)-yl)methyl)thiazole-5-carboxamide | LCMS: m/z 427 (M + H)+. $^1$H NMR (400 MHz, DMSO-d$_6$) δ12.78 (s, 1H), 8.97 (s, 1H), 8.51 (s, 1H), 7.70 (s, 1H), 7.75 (d, 2H), 6.26 (d, 1H), 5.67 (s, 2H), 4.49 (s, 2H), 4.25 (s, 3H). |
| E7-53 | 2-((1H-pyrazol-3-yl)methyl)-4-methyl-6-((5-methylthiazol-4-yl)methyl)-4,6-dihydro-5H-thiazolo[5',4':4,5]pyrrolo[2,3-d]pyridazin-5-one | LCMS: m/z 398 (M + H)+. $^1$H NMR (400 MHz, DMSO-d$_6$) δ12.77 (s, 1H), 8.74 (s, 1H), 8.47 (s, 1H), 7.70 (s, 1H), 6.26 (d, 1H), 5.39 (s, 2H), 4.49 (s, 2H), 4.26 (s, 3H), 2.49 (s, 3H). |
| E7-54 | 2-((1H-pyrazol-3-yl)methyl)-6-((6-(dimethylamino)pyridin-2-yl)methyl)-4-methyl-4,6-dihydro-5H-thiazolo[5',4':4,5]pyrrolo[2,3-d]pyridazin-5-one | LCMS: 421 (M + H)+. $^1$H NMR (400 MHz, DMSO) δ 12.78 (s, 1H), 8.53 (s, 1H), 7.68 (s, 1H), 7.39 (dd, 1H), 6.47 (d, 1H), 6.27 (d, 1H), 6.17 (d, 1H), 5.27 (s, 2H), 4.47 (m, 2H), 4.26 (s, 3H), 2.94 (s, 6H). |
| E7-55 | 2-((1H-pyrazol-3-yl)methyl)-4-methyl-6-((5-(trifluoromethyl)thiazol-4-yl)methyl)-4H-thiazolo[5',4':4,5]pyrrolo[2,3-d]pyridazin-5(6H)-one | LCMS: m/z 452 (M + H)+. $^1$H NMR (400 MHz, DMSO) δ 12.85 (s, 1H), 9.24 (s, 1H), 8.50 (s, 1H), 7.67 (s, 1H), 6.27 (d, 1H), 5.57 (s, 2H), 4.50 (s, 2H), 4.25 (s, 3H). |
| E7-56 | 2-((1H-pyrazol-3-yl)methyl)-6-((5-chlorothiazol-4-yl)methyl)-4-methyl-4H-thiazolo[5',4':4,5]pyrrolo[2,3-d]pyridazin-5(6H)-one | LCMS: m/z 418 (M + H)+. $^1$H NMR (400 MHz, DMSO) δ 12.79 (s, 1H), 8.94 (s, 1H), 8.49 (s, 1H), 7.70 (s, 1H), 6.26 (d, 1H), 5.42 (s, 2H), 4.49 (s, 2H), 4.26 (s, 3H). |

| Cpd No. | Structure | Characterization |
|---|---|---|
| E7-57 | 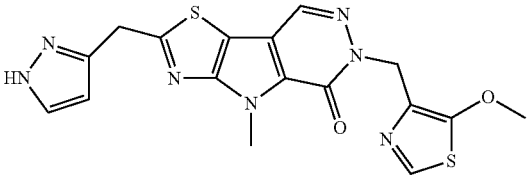 [SMILES: COc1scnc1Cn1ncc2c3sc(Cc4cc[nH]n4)nc3n(C)c2c1=O]<br>2-((1H-pyrazol-3-yl)methyl)-6-((5-methoxythiazol-4-yl)methyl)-4-methyl-4H-thiazolo[5',4':4,5]pyrrolo[2,3-d]pyridazin-5(6H)-one | LCMS (ESI): m/z 414 (M + H)+.<br>$^1$H NMR DMSO-d6 400 MHz δ 8.45 (s, 1H), 8.41 (s, 1H), 8.29 (s, 1H), 7.66 (s, 1H), 6.26 (d, 1H), 5.30 (s, 2H), 4.49 (s, 2H), 4.26 (s, 3H), 3.93 (s, 3H). |
| E7-58 | 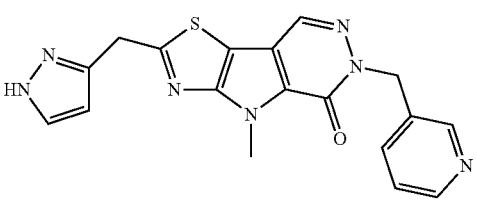 [SMILES: Cn1c2nc(Cc3cc[nH]n3)sc2c2cnn(Cc3cccnc3)c(=O)c21]<br>2-((1H-pyrazol-3-yl)methyl)-4-methyl-6-(pyridin-3-ylmethyl)-4H-thiazolo[5',4':4,5]pyrrolo[2,3-d]pyridazin-5(6H)-one | LCMS (ESI): m/z 378 (M + H).<br>$^1$H NMR (DMSO-d6 400 MHz) δ 12.79 (s, 1H), 8.57 (d, 1H), 8.54 (s, 1H), 8.48 (dd, 1H), 7.71 (ddd, 2H), 7.35 (ddd, 1H), 6.26 (d, 1H), 5.38 (s, 2H), 4.49 (s, 2H), 4.26 (s, 3H). |
| E7-59 | 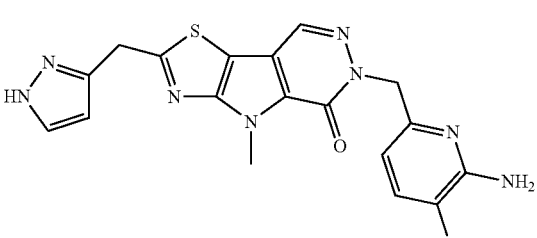<br>2-((1H-pyrazol-3-yl)methyl)-6-((6-amino-5-methoxypyridin-2-yl)methyl)-4-methyl-4H-thiazolo[5',4':4,5]pyrrolo[2,3-d]pyridazin-5(6H)-one | LCMS: m/z 423 (M + H)+.<br>$^1$H NMR (400 MHz, DMSO-$d_6$) δ 12.78 (s, 1H), 8.51 (s, 1H), 7.71 (s, 1H), 6.91 (d, 1H), 6.26 (d, 1H), 6.17 (d, 1H), 5.68 (s, 2H), 5.16 (s, 2H), 4.49 (s, 2H), 4.27 (s, 3H), 3.72 (s, 3H). |
| E7-60 | 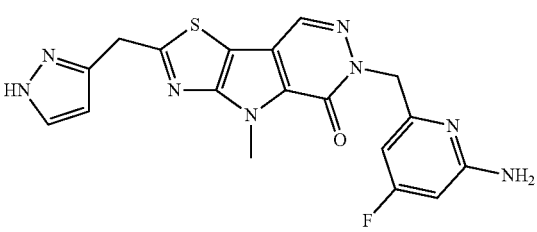 [SMILES: Cn1c2nc(Cc3cc[nH]n3)sc2c2cnn(Cc3cc(F)cc(N)n3)c(=O)c21]<br>2-((1H-pyrazol-3-yl)methyl)-6-((6-amino-4-fluoropyridin-2-yl)methyl)-4-methyl-4H-thiazolo[5',4':4,5]pyrrolo[2,3-d]pyridazin-5(6H)-one | LCMS: m/z 411 (M + H)+.<br>$^1$H NMR (400 MHz, DMSO-$d_6$) δ 8.56 (s, 1H), 7.67 (s, 1H), 6.3-6.2 (m, 2H), 6.18 (d, 1H), 5.27 (s, 2H), 4.51 (s, 2H), 4.27 (s, 3H). |
| E7-61 | 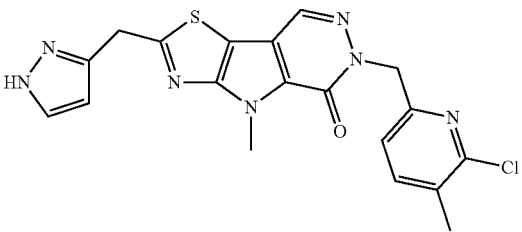 [SMILES: Cc1ccc(Cn2ncc3c4sc(Cc5cc[nH]n5)nc4n(C)c3c2=O)nc1Cl]<br>2-((1H-pyrazol-3-yl)methyl)-6-((6-chloro-5-methylpyridin-2-yl)methyl)-4-methyl-4H-thiazolo[5',4':4,5]pyrrolo[2,3-d]pyridazin-5(6H)-one | LCMS: m/z 426 (M + H)+.<br>$^1$H NMR (400 MHz, DMSO) δ 8.56 (s, 1H), 7.73 (d, 1H), 7.67 (s, 1H), 7.08 (d, 1H), 6.26 (d, 1H), 5.39 (s, 2H), 4.50 (s, 2H), 4.26 (s, 3H), 2.30 (s, 3H). |

| Cpd No. | Structure | Characterization |
|---|---|---|
| E7-62 | 2-((1H-pyrazol-3-yl)methyl)-6-((4-fluoro-1H-pyrazol-3-yl)methyl)-4-methyl-4,6-dihydro-5H-thiazolo[5',4':4,5]pyrrolo[2,3-d]pyridazin-5-one | LCMS: m/z 385 (M + H)+. <br> 1H NMR (400 MHz, DMSO) δ 12.83 (s, 1H), 12.68 (s, 1H), 8.46 (s, 1H), 7.64 (s, 2H), 6.26 (s, 1H), 5.33 (s, 2H), 4.48 (s, 2H), 4.24 (s, 3H). |
| E7-63 | 2-((1H-pyrazol-3-yl)methyl)-4-methyl-6-((2-oxo-1,2-dihydropyridin-3-yl)methyl)-4H-thiazolo[5',4':4,5]pyrrolo[2,3-d]pyridazin-5(6H)-one | LCMS: m/z 394 (M + H)+. <br> 1H NMR (400 MHz, DMSO) δ 12.79 (s, 1H), 11.74 (s, 1H), 8.55 (s, 1H), 7.72 (s, 1H), 7.30 (d, 1H), 6.83 (d, 1H), 6.27 (d, 1H), 6.09 (t, 1H), 5.10 (s, 2H), 4.51 (s, 2H), 4.27 (s, 3H). |
| E7-64 | 2-((1H-pyrazol-3-yl)methyl)-6-((2-methoxy-pyridin-3-yl)methyl)-4-methyl-4H-thiazolo[5',4':4,5]pyrrolo[2,3-d]pyridazin-5(6H)-one | LCMS: m/z 408 (M + H)+. <br> 1H NMR (400 MHz, DMSO) δ 12.78 (s, 1H), 8.56 (s, 1H), 8.08 (dd, 1H), 7.70 (s, 1H), 7.16 (d, 1H), 6.90 (dd, 1H), 6.27 (d, 1H), 5.29 (s, 2H), 4.51 (s, 2H), 4.27 (s, 3H), 3.93 (s, 3H). |
| E7-65 | 2-((1H-pyrazol-3-yl)methyl)-6-((5-fluoro-1H-pyrazol-3-yl)methyl)-4-methyl-4H-thiazolo[5',4':4,5]pyrrolo[2,3-d]pyridazin-5(6H)-one | LCMS: m/z 385 (M + H)+. <br> 1H NMR (400 MHz, DMSO-d6) δ 12.88 (s, 1H), 12.61 (s, 1H), 8.61 (d, 1H), 7.78 (s, 1H), 6.33 (d, 1H), 5.89 (d, 1H), 5.36 (s, 2H), 4.54 (d, 2H), 4.34 (s, 3H). |
| E7-66 | 2-((1H-pyrazol-3-yl)methyl)-6-((6-amino-5-methylpyridin-2-yl)methyl)-4-methyl-4H-thiazolo[5',4':4,5]Pyrrolo[2,3-d]pyridazin-5(6H)-one | LCMS: m/z 407 (M + H)+. <br> 1H NMR (400 MHz, DMSO-d6) δ 12.84 (s, 1H), 8.58 (s, 1H), 7.79 (s, 1H), 7.18 (d, 1H), 6.33(s, 1H), 6.15 (d, 1H), 5.75 (s, 2H), 5.25 (s, 2H), 4.55 (s, 2H), 4.33 (s, 3H), 2.05 (s, 3H). |

| Cpd No. | Structure | Characterization |
|---|---|---|
| E7-67 | 2-((1H-pyrazol-3-yl)methyl)-6-((6-methoxypyridin-3-yl)methyl)-4-methyl-4H-thiazolo[5',4':4,5]pyrrolo[2,3-d]pyridazin-5(6H)-one | LC-MS: m/z 408 (M + H)+. 1H NMR (400 MHz, DMSO) δ 12.87 (s, 1H), 8.60 (s, 1H), 8.27 (d, 1H), 7.84-7.72 (m, 2H), 6.86 (d, 1H), 6.34 (d, 1H), 5.37 (s, 2H), 4.55 (s, 2H), 4.34 (s, 3H), 3.89 (s, 3H). |
| E7-68 | 2-((1H-pyrazol-3-yl)methyl)-4-methyl-6-((6-oxo-1,6-dihydropyridin-3-yl)methyl)-4,6-dihydro-5H-thiazolo[5',4':4,5]pyrrolo[2,3-d]pyridazin-5-one | LC-MS: m/z 394 (M + H)+. 1H NMR (400 MHz, DMSO) δ 12.77 (s, 1H), 11.53 (s, 1H), 8.52 (s, 1H), 7.69 (s, 1H), 7.47 (dd, 1H), 7.40 (d, 1H), 6.27 (dd, 2H), 5.07 (s, 2H), 4.49 (s, 2H), 4.26 (s, 3H). |
| E7-69 | 2-((1H-pyrazol-3-yl)methyl-6-((2-methoxypyridin-4-yl)methyl)-4-methyl-4H-thiazolo[5',4':4,5]pyrrolo[2,3-d]pyridazin-5(6H)-one | LC-MS: m/z 408 (M + H)+. 1H NMR (400 MHz, DMSO) δ 12.86 (s, 1H), 8.65 (d, 1H), 8.17 (d, 1H), 7.80 (s, 1H), 6.94-6.89 (m, 1H), 6.66 (s, 1H), 6.34 (d, 1H), 5.41 (s, 2H), 4.56 (s, 2H), 4.34 (s, 3H), 3.89 (s, 3H). |
| E7-70 | 2-((1H-pyrazol-3-yl)methyl-4-methyl-6-((2-oxo-1,2-dihydropyridin-4-yl)methyl)-4,6-dihydro-5H-thiazolo[5',4':4,5]pyrrolo[2,3-d]pyridazin-5-one | LC-MS: m/z 394 (M + H)+. 1H NMR (400 MHz, DMSO) δ 8.57 (s, 1H), 7.68 (s, 1H), 7.31 (d, 1H), 7.23 (t, 1H), 6.27 (d, 1H), 6.07 (dd, 1H), 5.97 (s, 1H), 5.17 (s, 2H), 4.51 (s, 2H), 4.27 (s, 3H). |

| Cpd No. | Structure | Characterization |
|---|---|---|
| E7-71 | 2-((1H-pyrazol-3-yl)methyl-6-((2-amino-1H-imidazol-4-yl)methyl)-4-methyl-4H-thiazolo[5',4':4,5]pyrrolo[2,3-d]pyridazin-5(6H)-one | LC-MS: m/z 382 (M + H)$^+$. $^1$HNMR (400 MHz, DMSO) δ 12.80 (s, 1H), 8.46 (s, 1H), 8.39 (s, 1H), 7.66 (s, 1H), 6.34 (s, 1H), 6.26 (d, 1H), 5.18 (s, 2H), 5.06 (s, 2H), 4.49 (s, 2H), 4.27 (s, 3H). |
| E7-72 | 2-((1H-pyrazol-3-yl)methyl-6-((6-(hydroxyamino)pyridin-2-yl)methyl)-4-methyl-4H-thiazolo[5',4':4,5]pyrrolo[2,3-d]pyridazin-5(6H)-one | LC-MS: m/z 409 (M + H)$^+$. $^1$HNMR (400 MHz, DMSO) δ 12.83 (s, 1H), 8.74 (s, 1H), 8.55-8.65 (m, 2H), 7.79 (s, 1H), 7.56 (t, 1H), 6.77 (d, 1H), 6.40 (d, 1H), 6.32 (d, 1H), 5.32 (s, 2H), 4.52 (s, 2H), 4.31 (s, 3H) |
| E7-73 | 2-((1H-pyrazol-3-yl)methyl-6-(isothiazol-3-ylmethyl)-4-methyl-4H-thiazolo[5',4':4,5]pyrrolo[2,3-d]pyridazin-5(6H)-one | LC-MS: ESI m/z 384 (M + H)$^+$. $^1$H NMR (400 MHz, DMSO-d$_6$) δ 9.01 (d, 1H), 8.54 (s, 1H), 7.67 (d, 1H), 7.21 (d, 1H), 6.27 (d, 1H), 5.50 (s, 2H), 4.51 (s, 2H), 4.26 (s, 3H). |
| E7-74 | 2-((1H-pyrazol-3-yl)methyl)-4-methyl-6-((1-methyl-1H-1,2,3-triazol-5-yl)methyl)-4H-thiazolo[5',4':4,5]pyrrolo[2,3-d]pyridazin-5(6H)-one | LCMS: ESI m/z 382 (M + H)$^+$. $^1$H NMR (400 MHz, DMSO-d$_6$) δ 12.78 (s, 1H), 8.55 (s, 1H), 7.71 (s, 1H), 7.62 (s, 1H), 6.26 (d, 1H), 5.49 (s, 2H), 4.48 (s, 2H), 4.26 (s, 3H), 4.10 (s, 3H). |
| E7-75 | 2-((1H-pyrazol-3-yl)methyl)-4-methyl-6-((1-methyl-1H-1,2,3-triazol-4-yl)methyl)-4H-thiazolo[5',4':4,5]pyrrolo[2,3-d]pyridazin-5(6H)-one | LCMS: ESI m/z 382 (M + H)$^+$. $^1$H NMR (400 MHz, DMSO-d$_6$) δ 12.78 (s, 1H), 8.51 (s, 1H), 7.96 (s, 1H), 7.71 (s, 1H), 6.27 (d, 1H), 5.38 (s, 2H), 4.49 (s, 2H), 4.27 (s, 3H), 3.99 (s, 3H). |

-continued

| Cpd No. | Structure | Characterization |
|---|---|---|
| E7-76 | 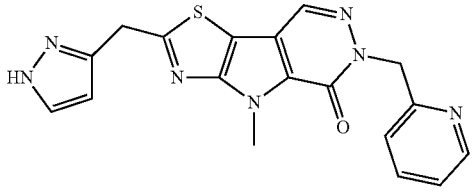 [SMILES: Cn1c2nc(Cc3cc[nH]n3)sc2c2cnn(Cc3ccccn3)c(=O)c21]<br>2-((1H-pyrazol-3-yl)methyl)-4-methyl-6-(pyridin-2-ylmethyl)-4H-thiazolo[5',4':4,5]pyrrolo[2,3-d]pyridazin-5(6H)-one | LCMS: ESI m/z 378 (M + H)$^+$.<br>$^1$H NMR (400 MHz, DMSO-d$_6$) δ 12.94 (s, 1H), 8.64 (s, 1H), 8.57 (d, 1H), 7.82 (m, 2H), 7.36 (m, 1H), 7.23 (d, 1H), 6.36 (d, 1H), 5.55 (s, 2H), 4.58 (s, 2H), 4.36 (s, 3H). |
| E7-77 | 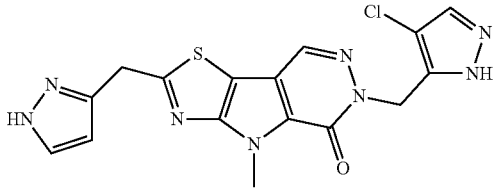 [SMILES: Cn1c2nc(Cc3cc[nH]n3)sc2c2cnn(Cc3[nH]ncc3Cl)c(=O)c21]<br>2-((1H-pyrazol-3-yl)methyl)-6-((4-chloro-1H-pyrazol-5-yl)methyl)-4-methyl-4H-thiazolo[5',4':4,5]pyrrolo[2,3-d]pyridazin-5(6H)-one | LCMS: m/z 401 (M + H)$^+$.<br>$^1$H NMR (400 MHz, DMSO-d6) δ 12.96 (s, 1H), 12.77 (s, 1H), 8.48 (s, 1H), 7.91 (s, 1H), 7.71 (s, 1H), 6.26 (d, 1H), 5.33 (s, 2H), 4.49 (s, 2H), 4.27 (s, 3H). |
| E7-78 | 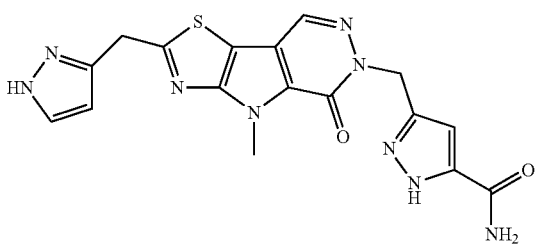 [SMILES: Cn1c2nc(Cc3cc[nH]n3)sc2c2cnn(Cc3cc(C(N)=O)[nH]n3)c(=O)c21]<br>3-((2-((1H-pyrazol-3-yl)methyl)-4-methyl-5-oxo-4,5-dihydro-6H-thiazolo[5',4':4,5]pyrrolo[2,3-d]pyridazin-6-yl)methyl)-1H-pyrazole-5-carboxamide | LCMS: m/z 410 (M + H)$^+$.<br>$^1$H NMR (400 MHz, DMSO-d6) δ 13.34 (s, 1H), 12.81 (s, 1H), 8.54 (s, 1H), 7.70 (s, 2H), 7.26 (m, 1H), 6.64 (s, 1H), 6.27 (s, 1H), 5.35 (s, 2H), 4.50 (s, 2H), 4.28 (s, 3H) |
| E7-79 | 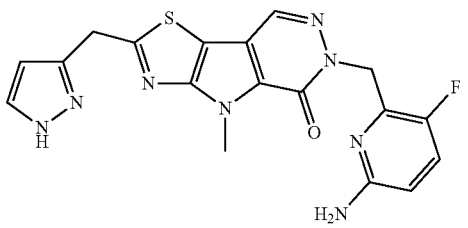 [SMILES: Cn1c2nc(Cc3cc[nH]n3)sc2c2cnn(Cc3nc(N)ccc3F)c(=O)c21]<br>2-((1H-pyrazol-3-yl)methyl)-6-((6-amino-3-fluoropyridin-2-yl)methyl)-4-methyl-4H-thiazolo[5',4':4,5]pyrrolo[2,3-d]pyridazin-5(6H)-one | LC-MS m/z 411.0 (M + H)$^+$.<br>$^1$H NMR (400 MHz, DMSO) δ 12.79 (s, 1H), 8.46 (s, 1H), 7.73 (s, 1H), 7.29 (dd, 1H), 6.34 (dd, 1H), 6.27 (d, 1H), 5.74 (s, 2H), 5.30 (s, 2H), 4.46 (s, 2H), 4.26 (s, 3H) |
| E7-80 | 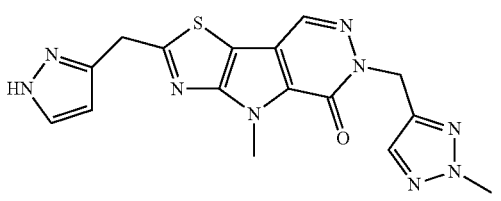 [SMILES: Cn1ncc(Cn2ncc3c4sc(Cc5cc[nH]n5)nc4n(C)c3c2=O)n1]<br>2-((1H-pyrazol-3-yl)methyl)-4-methyl-6-((2-methyl-2H-1,2,3-triazol-4-yl)methyl)-4H-thiazolo[5',4':4,5]pyrrolo[2,3-d]pyridazin-5(6H)-one | LC-MS m/z 382.0 (M + H)$^+$.<br>$^1$H NMR (400 MHz, DMSO) δ 12.79 (s, 1H), 8.51 (s, 1H), 7.68 (s, 1H), 7.68 (s, 1H), 6.26 (d, 1H), 5.38 (s, 2H), 4.50 (s, 2H), 4.26 (s, 3H), 4.08 (s, 3H) |

-continued

| Cpd No. | Structure | Characterization |
|---|---|---|
| E7-81 | 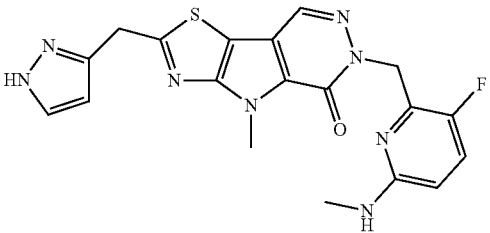 [SMILES: CNc1ccc(F)c(Cn2ncc3c4sc(Cc5cc[nH]n5)nc4n(C)c3c2=O)n1]<br>2-((1H-pyrazol-3-yl)methyl)-6-((3-fluoro-6-(methylamino)pyridin-2-yl)methyl)-4-methyl-4H-thiazolo[5',4':4,5]pyrrolo[2,3-d]pyridazin-5(6H)-one | LC-MS m/z 425 (M + H)$^+$.<br>$^1$H NMR (400 MHz, DMSO) δ 12.77 (s, 1H), 8.47 (s, 1H), 7.71 (s, 1H), 7.31 (t, 1H), 6.33-6.26 (m, 3H), 5.34 (s, 2H), 4.49 (s, 2H), 4.26 (s, 3H), 2.48 (s, 3H) |
| E7-82 | 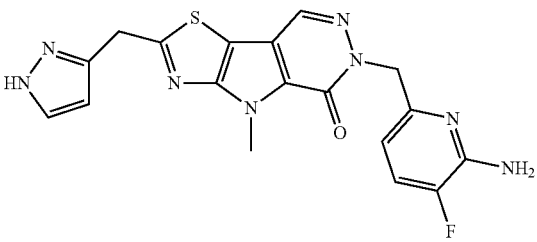 [SMILES: Cn1c2nc(Cc3cc[nH]n3)sc2c2cnn(Cc3ccc(F)c(N)n3)c(=O)c21]<br>2-((1H-pyrazol-3-yl)methyl)-6-((6-amino 5 fluoropyridin-2-yl)methyl)-4-methyl-4H-thiazolo[5',4':4,5]pyrrolo[2,3-d]pyridazin-5(6H)-one | LCMS: (ESI) m/z 411 (M + H)$^+$.<br>$^1$H NMR (400 MHz, DMSO-d$_6$) δ 8.59 (s, 1H), 7.73 (s, 1H), 7.29 (dd, 1H), 6.47-6.06 (m, 4H), 5.26 (s, 2H), 4.56 (s, 2H), 4.32 (s, 3H) |
| E7-83 | 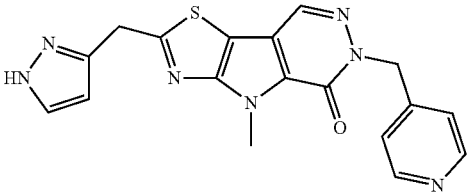 [SMILES: Cn1c2nc(Cc3cc[nH]n3)sc2c2cnn(Cc3ccncc3)c(=O)c21]<br>2-((1H-pyrazol-3-yl)methyl)-4-methyl-6-(pyridin-4-ylmethyl)-4H-thiazolo[5',4':4,5]pyrrolo[2,3-d]pyridazin-5(6H)-one | LCMS: (ESI) m/z 378 (M + H)$^+$.<br>$^1$H NMR (400 MHz, DMSO-d$_6$) δ 12.84 (s, 1H), 8.64 (s, 1H), 8.57 (d, 1H), 8.55 (d, 1H), 7.77 (s, 1H), 7.28 (d, 2H), 6.33 (d, 1H), 5.45 (s, 2H), 4.56 (s, 2H), 4.32 (s, 3H) |
| E7-84 | 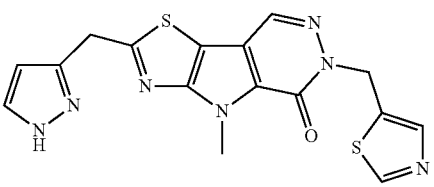 [SMILES: Cn1c2nc(Cc3cc[nH]n3)sc2c2cnn(Cc3cncs3)c(=O)c21]<br>2-((1H-pyrazol-3-yl)methyl)-4-methyl-6-(thiazol-5-ylmethyl)-4,6-dihydro-5H-thiazolo[5',4':4,5]pyrrolo[2,3-d]pyridazin-5-one | LCMS: (ESI) m/z 384 (M + H)$^+$.<br>$^1$H NMR (400 MHz, DMSO-d$_6$) δ 12.85 (s, 1H), 9.01 (s, 1H), 8.54 (d, 1H), 7.95 (d, 1H), 7.74 (s, 1H), 6.24 (s, 1H), 5.55 (s, 2H), 4.46 (s, 2H), 4.30 (s, 3H) |
| E7-85 | 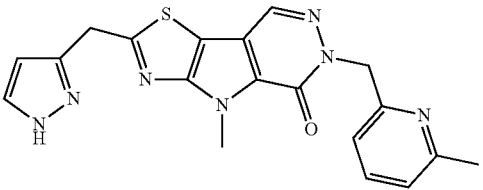 [SMILES: Cc1cccc(Cn2ncc3c4sc(Cc5cc[nH]n5)nc4n(C)c3c2=O)n1]<br>2-((1H-pyrazol-3-yl)methyl)-4-methyl-6-((6-methylpyridin-2-yl)methyl)-4,6-dihydro-5H-thiazolo[5',4':4,5]pyrrolo[2,3-d]pyridazin-5-one | LCMS: (ESI) m/z 392 (M + H)$^+$.<br>$^1$H NMR (400 MHz, DMSO-d$_6$) δ 12.78 (s, 1H), 8.55 (s, 1H), 7.74 (s, 1H), 7.61 (dd, 1H), 7.14 (d, 1H), 6.81 (d, 1H), 6.26 (s, 1H), 5.39 (s, 2H), 4.50 (s, 2H), 4.26 (s, 3H), 2.43 (s, 3H) |

| Cpd No. | Structure | Characterization |
|---|---|---|
| E7-86 | 2-((1H-pyrazol-3-yl)methyl)-6-(isothiazol-4-ylmethyl)-4-methyl-4,6-dihydro-5H-thiazolo[5',4':4,5]pyrrolo[2,3-d]pyridazin-5-one | LCMS: (ESI) m/z 384 (M + H)+. <br> 1H NMR (400 MHz, DMSO-d6) δ 12.78 (s, 1H), 8.91 (s, 1H), 8.56 (s, 1H), 8.53 (s, 1H), 7.71 (s, 1H), 6.26 (s, 1H), 5.48 (s, 2H), 4.49 (s, 2H), 4.31 (s, 3H) |
| E7-87 | 6-((1H-1,2,4-triazol-3-yl)methyl)-2-((1H-pyrazol-3-yl)methyl)-4-methyl-4,6-dihydro-5H-thiazolo[5',4':4,5]pyrrolo[2,3-d]pyridazin-5-one | LCMS: (ESI) m/z 368 (M + H)+. <br> 1H NMR (400 MHz, DMSO-d6) δ 13.85 (s, 1H), 12.78 (s, 1H), 8.51 (s, 1H), 8.49-8.21(m, 1H), 7.71 (s, 1H), 6.27 (d, 1H), 5.41 (s, 2H), 4.49 (s, 2H), 4.26 (s, 3H) |
| E7-88 | 6-((1,3,4-thiadiazol-2-yl)methyl)-2-((1H-pyrazol-3-yl)methyl)-4-methyl-4,6-dihydro-5H-thiazolo[5',4':4,5]pyrrolo[2,3-d]pyridazin-5-one | LCMS: (ESI) m/z 385 (M + H)+. <br> 1H NMR (400 MHz, DMSO-d6) δ 12.79 (s, 1H), 9.57 (s, 1H), 8.61 (s, 1H), 7.71 (s, 1H), 6.26 (d, 1H), 5.80 (s, 2H), 4.49 (s, 2H), 4.27 (s, 3H) |
| E7-89 | 2-((1H-pyrazol-3-yl)methyl)-6-((6-bromo-5-fluoropyridin-2-yl)methyl)-4-methyl-4,6-dihydro-5H-thiazolo[5',4':4,5]pyrrolo[2,3-d]pyridazin-5-one | LCMS: (ESI) m/z 476 (M + 2H)+. <br> 1H NMR (400 MHz, DMSO-d6) δ 12.78 (s, 1H), 8.57 (s, 1H), 7.81 (dd, 1H), 7.71 (s, 1H), 7.30 (dd, 1H), 6.26 (d, 1H), 5.43 (s, 2H), 4.49 (s, 2H), 4.26 (s, 3H) |
| E7-90 | 2-((1H-pyrazol-3-yl)methyl)-6-((5-chloro-1H-pyrazol-3-yl)methyl)-4-methyl-4,6-dihydro-5H-thiazolo[5',4':4,5]pyrrolo[2,3-d]pyridazin-5-one | LCMS: (ESI) m/z 401 (M + H)+. <br> 1H NMR (400 MHz, DMSO-d6) δ 13.01 (s, 1H), 12.95 (s, 1H), 8.53 (s, 1H), 7.68 (dd, 1H), 6.26 (d, 1H), 6.17 (s, 1H), 5.32 (s, 2H), 4.50 (s, 2H), 4.26 (s, 3H) |

-continued

| Cpd No. | Structure | Characterization |
|---|---|---|
| E7-91 | 2-((1H-pyrazol-3-yl)methyl)-6-((4-fluoro-1-methyl-1H-pyrazol-3-yl)methyl)-4-methyl-4,6-dihydro-5H-thiazolo[5',4':4,5]pyrrolo[2,3-d]pyridazin-5-one | LCMS: (ESI) m/z 399 (M + H)$^+$.<br>$^1$H NMR (400 MHz, DMSO-d$_6$) δ 12.77 (s, 1H), 8.47 (s, 1H), 7.75 (d, 1H), 7.71 (s, 1H), 6.26 (s, 1H), 5.29 (s, 2H), 4.47 (s, 2H), 4.26 (s, 3H), 3.70 (s, 3H) |
| E7-92 | 2-((1H-pyrazol-3-yl)methyl)-6-((4-chloro-1-methyl-1H-pyrazol-3-yl)methyl)-4-methyl-4,6-dihydro-5H-thiazolo[5',4':4,5]pyrrolo[2,3-d]pyridazin-5-one | LCMS: (ESI) m/z 415 (M + H)$^+$.<br>$^1$H NMR (400 MHz, DMSO-d$_6$) δ 12.82 (s, 1H), 8.52 (s, 1H), 7.92 (s, 1H), 7.76 (s, 1H), 6.31 (s, 1H), 5.34 (s, 2H), 4.53 (s, 2H), 4.31 (s, 3H), 3.79 (s, 3H) |
| E7-93 | 2-((1H-pyrazol-3-yl)methyl)-6-((2-aminothiazol-4-yl)methyl)-4-methyl-4,6-dihydro-5H-thiazolo[5',4':4,5]pyrrolo[2,3-d]pyridazin-5-one | LCMS: (ESI) m/z 399 (M + H)$^+$.<br>$^1$H NMR (400 MHz, DMSO-d$_6$) δ 12.79 (s, 1H), 8.49 (s, 1H), 7.71 (s, 1H), 6.91 (s, 2H), 6.27 (s, 1H), 6.18 (s, 1H), 5.12 (s, 2H), 4.49 (s, 2H), 4.27 (s, 3H). |
| E7-94 | 2-((1H-pyrazol-3-yl)methyl)-6-((6-methoxypyridin-2-yl)methyl)-4-methyl-4,6-dihydro-5H-thiazolo[5',4':4,5]pyrrolo[2,3-d]pyridazin-5-one | LCMS: (ESI) m/z 408 (M + H)$^+$.<br>$^1$H NMR (400 MHz, DMSO-d$_6$) δ 12.79 (s, 1H), 8.56 (s, 1H), 7.71 (s, 1H), 7.63 (dd, 1H), 6.68 (d, 1H), 6.60 (d, 1H), 6.27 (d, 1H), 5.36 (s, 2H), 4.51 (s, 2H), 4.26 (s, 3H), 3.76 (s, 3H). |
| E7-95 | 3-((2-((1H-pyrazol-3-yl)methyl)-4-methyl-5-oxo-4H-thiazolo[5',4':4,5]pyrrolo[2,3-d]pyridazin-6(5H)-yl)methyl)-1-methyl-1H-pyrazole-4-carbonitrile | LC-MS: m/z 406 (M + H)$^+$.<br>$^1$H NMR (400 MHz, DMSO-d6) δ: 12.79 (s, 1H), 8.53 (s, 1H), 8.44 (s, 1H), 7.72 (s, 1H), 6.27 (s, 1H), 5.40 (s, 2H), 4.48 (s, 2H), 4.26 (s, 3H), 3.83 (s, 3H). |

| Cpd No. | Structure | Characterization |
|---|---|---|
| E7-96 | 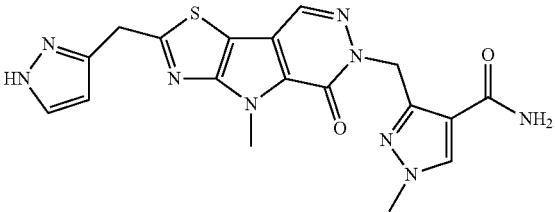 [SMILES: Cn1cc(C(N)=O)c(Cn2ncc3c4sc(Cc5cc[nH]n5)nc4n(C)c3c2=O)n1]<br>3-((2-((1H-pyrazol-3-yl)methyl)-4-methyl-5-oxo-4H-thiazolo[5',4':4,5]pyrrolo[2,3-d]pyridazin-6(5H)-yl)methyl)-1-methyl-1H-pyrazole-4-carboxamide | LC-MS: m/z 424 (M + H)$^+$.<br>$^1$H NMR (400 MHz, DMSO-d6) δ: 12.79 (s, 1H), 8.46 (s, 1H), 8.10 (s, 1H), 7.72 (s, 1H), 7.57 (s, 1H), 7.02 (s, 1H), 6.27 (s, 1H), 5.53 (s, 2H), 4.48 (s, 2H), 4.26 (s, 3H), 3.69 (s, 3H). |
| E7-97 | 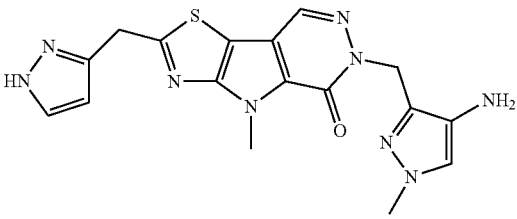 [SMILES: Cn1cc(N)c(Cn2ncc3c4sc(Cc5cc[nH]n5)nc4n(C)c3c2=O)n1]<br>2-((1H-pyrazol-3-yl)methyl)-6-((4-amino-1-methyl-1H-pyrazol-3-yl)methyl)-4-methyl-4H-thiazolo[5',4':4,5]pyrrolo[2,3-d]pyridazin-5(6H)-one | LC-MS: m/z 396 (M + H)$^+$.<br>$^1$H NMR (400 MHz, DMSO-d6) δ: 8.51 (s, 1H), 7.67 (s, 1H), 6.95 (s, 1H), 6.27 (d, 1H), 5.17 (s, 2H), 4.50 (s, 2H), 4.27 (s, 3H), 3.61 (s, 3H). |
| E7-98 | 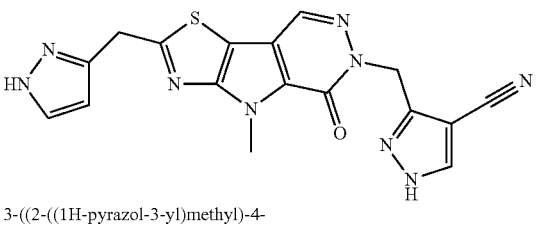<br>3-((2-((1H-pyrazol-3-yl)methyl)-4-methyl-5-oxo-4H-thiazolo[5',4':4,5]pyrrolo[2,3-d]pyridazin-6(5H)-yl)methyl)-1H-pyrazole-4-carbonitrile | LC-MS: m/z 392 (M + H)$^+$.<br>$^1$H NMR (400 MHz, DMSO-d6) δ: 13.62 (s, 1H), 12.79 (s, 1H), 8.54 (m, 2H), 7.71 (s, 1H), 6.27 (d, 1H), 5.45 (s, 2H), 4.49 (s, 2H), 4.26 (s, 3H). |
| E7-99 | 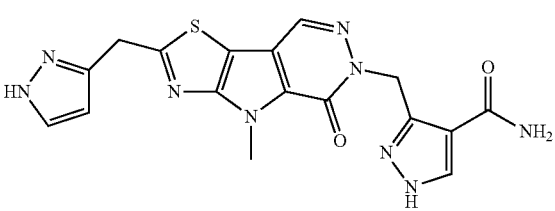 [SMILES: Cn1c2nc(Cc3cc[nH]n3)sc2c2cnn(Cc3n[nH]cc3C(N)=O)c(=O)c21]<br>3-((2-((1H-pyrazol-3-yl)methyl)-4-methyl-5-oxo-4H-thiazolo[5',4':4,5]pyrrolo[2,3-d]pyridazin-6(5H)-yl)methyl)-1H-pyrazole-4-carboxamide | LC-MS: m/z 410 (M + H)$^+$.<br>$^1$H NMR (400 MHz, DMSO-d6) δ: 12.75 (s, 2H), 8.48 (s, 1H), 8.17 (s, 1H), 7.68 (s, 1H), 7.56 (s, 1H), 7.01 (s, 1H), 6.27 (d, 1H), 5.57 (s, 2H), 4.50 (s, 2H), 4.26 (s, 3H). |
| E7-100 | 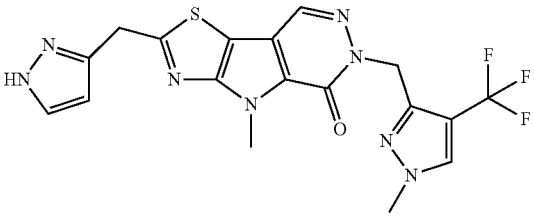 [SMILES: Cn1cc(C(F)(F)F)c(Cn2ncc3c4sc(Cc5cc[nH]n5)nc4n(C)c3c2=O)n1]<br>2-((1H-pyrazol-3-yl)methyl)-4-methyl-6-((1-methyl-4-(trifluoromethyl)-1H-pyrazol-3-yl)methyl)-4H-thiazolo[5',4':4,5]pyrrolo[2,3-d]pyridazin-5(6H)-one | LC-MS: m/z 449 (M + H)$^+$.<br>$^1$H NMR (400 MHz, DMSO-d6) δ: 12.85 (s, 1H), 8.54 (s, 1H), 8.34 (d, 1H), 7.77 (s, 1H), 6.32 (s, 1H), 5.44 (d, 2H), 4.54 (s, 2H), 4.32 (s, 3H), 3.83 (s, 3H). |

-continued

| Cpd No. | Structure | Characterization |
|---|---|---|
| E7-101 | 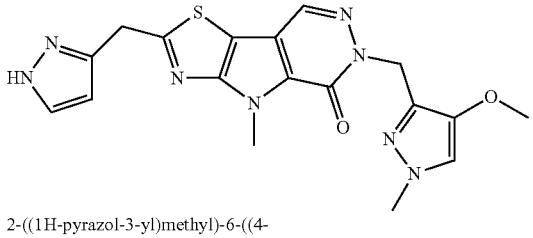<br>2-((1H-pyrazol-3-yl)methyl)-6-((4-methoxy-1-methyl-1H-pyrazol-3-yl)methyl)-4-methyl-4H-thiazolo[5',4':4,5]pyrrolo[2,3-d]pyridazin-5(6H)-one | LC-MS: m/z 411 (M + H)$^+$.<br>$^1$H NMR (400 MHz, DMSO-d6) δ: 12.77 (s, 1H), 8.43 (s, 1H), 7.71 (s, 1H), 7.41 (s, 1H), 6.26 (d, 1H), 5.20 (s, 2H), 4.48 (s, 2H), 4.26 (s, 3H), 3.65 (s, 3H), 3.61 (s, 3H). |
| E7-102 | 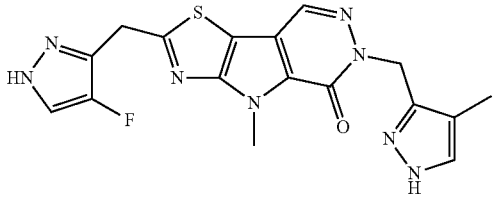 [SMILES: Cc1c[nH]nc1Cn1ncc2c3sc(Cc4n[nH]cc4F)nc3n(C)c2c1=O]<br>2-((4-fluoro-1H-pyrazol-3-yl)methyl)-4-methyl-6-((4-methyl-1H-pyrazol-3-yl)methyl)-4H-thiazolo[5',4':4,5]pyrrolo[2,3-d]pyridazin-5(6H)-one | LC-MS: m/z 399 (M + H)$^+$.<br>$^1$H NMR (400 MHz, DMSO-d6) δ: 12.90-12.30 (m, 2H), 8.49 (s, 1H), 7.81 (s, 1H), 7.34 (s, 1H), 5.30 (s, 2H), 4.50 (s, 2H), 4.26 (s, 3H), 1.96 (s, 3H). |
| E7-103 | 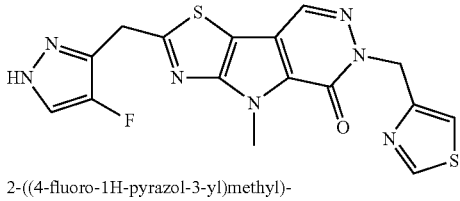<br>2-((4-fluoro-1H-pyrazol-3-yl)methyl)-4-methyl-6-(thiazol-4-ylmethyl)-4,6-dihydro-5H-thiazolo[5',4':4,5]pyrrolo[2,3-d]pyridazin-5-one | LC-MS: m/z 402 (M + H)$^+$.<br>$^1$H NMR (400 MHz, DMSO-d6) δ: 12.80 (s, 1H), 9.04 (d, 1H), 8.54 (s, 1H), 7.88 (s, 1H), 7.49-7.39 (m, 1H), 5.48 (s, 2H), 4.50 (s, 2H), 4.26 (s, 3H). |
| E7-104 | 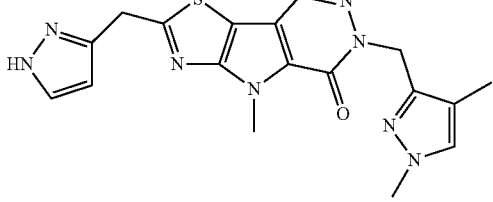<br>2-((1H-pyrazol-3-yl)methyl)-6-((1,4-dimethyl-1H-pyrazol-3-yl)methyl)-4-methyl-4H-thiazolo[5',4':4,5]pyrrolo[2,3-d]pyridazin-5(6H)-one | LC-MS: m/z 395 (M + H)$^+$.<br>$^1$H NMR (400 MHz, DMSO-d6) δ: 12.86 (s, 1H), 8.51 (s, 1H), 7.72 (s, 1H), 7.41 (s, 1H), 6.32 (s, 1H), 5.29 (s, 2H), 4.55 (s, 2H), 4.32 (s, 3H), 3.74 (s, 3H), 1.99 (s, 3H). |
| E7-105 | 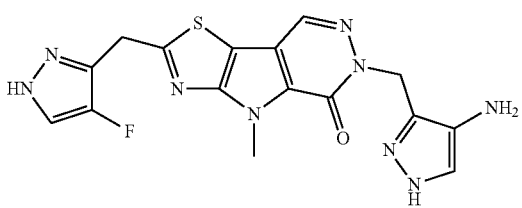 [SMILES: Cn1c2nc(Cc3n[nH]cc3F)sc2c2cnn(Cc3n[nH]cc3N)c(=O)c21]<br>6-((4-amino-1H-pyrazol-3-yl)methyl)-2-((4-fluoro-1H-pyrazol-3-yl)methyl)-4-methyl-4H-thiazolo[5',4':4,5]pyrrolo[2,3-d]pyridazin-5(6H)-one | LC-MS: m/z 400 (M + H)$^+$.<br>$^1$H NMR (400 MHz, DMSO-d6) δ: 8.53 (s, 1 H), 7.80 (s, 1 H), 6.96 (s, 1 H), 5.23 (s, 2 H), 4.50 ( s, 2 H), 4.27 (s, 3 H). |

| Cpd No. | Structure | Characterization |
|---|---|---|
| E7-106 | 2-((1H-pyrazol-3-yl)methyl)-6-((4-(hydroxymethyl)-1-methyl-1H-pyrazol-3-yl)methyl)-4-methyl-4H-thiazolo[5',4':4,5]pyrrolo[2,3-d]pyridazin-5(6H)-one | LC-MS: m/z 411 (M + H)$^+$. $^1$H NMR (400 MHz, DMSO-d6) δ: 12.82 (s, 1H), 8.48 (s, 1H), 7.67 (s, 1H), 7.50 (s, 1H), 6.27 (d, 1H), 5.28 (s, 2H), 4.50 (s, 2H), 4.38 (s, 2H), 4.27 (s, 3H), 3.71 (s, 3H). |
| E7-107 | 4-((2-((1H-pyrazol-3-yl)methyl)-4-methyl-5-oxo-4H-thiazolo[5',4':4,5]pyrrolo[2,3-d]pyridazin-6(5H)-yl)methyl)oxazole-5-carboxamide | LC-MS: m/z 411 (M + H)$^+$. $^1$H NMR (400 MHz, DMSO-d6) δ: 12.80 (s, 1H), 8.49 (s, 1H), 8.38 (s, 1H), 8.09 (s, 1H), 7.80 (s, 1H), 7.72 (s, 1H), 6.27 (d, 1H), 5.56 (s, 2H), 4.49 (s, 2H), 4.26 (s, 3H). |
| E7-108 | 6-((2-((1H-pyrazol-3-yl)methyl)-4-methyl-5-oxo-4H-thiazolo[5',4':4,5]pyrrolo[2,3-d]pyridazin-6(5H)-yl)methyl)nicotinonitrile | LC-MS: m/z 403 (M + H)$^+$. $^1$H NMR (400 MHz, DMSO-d6) δ: 12.82 (s, 1H), 8.94 (d, 1H), 8.57 (s, 1H), 8.26 (dd, 1H), 7.69 (s, 1H), 7.42 (d, 1H), 6.27 (d, 1H), 5.55 (s, 2H), 4.51 (s, 2H), 4.25 (s, 3H). |
| E7-109 | 6-((2-((1H-pyrazol-3-yl)methyl)-4-methyl-5-oxo-4H-thiazolo[5',4':4,5]pyrrolo[2,3-d]pyridazin-6(5H)-yl)methyl)nicotinamide | LC-MS: m/z 421 (M + H)$^+$. $^1$H NMR (400 MHz, DMSO-d6) δ: 12.82 (s, 1H), 8.92 (d, 1H), 8.56 (s, 1H), 8.14 (dd, 2H), 7.69 (s, 1H), 7.57 (s, 1H), 7.23 (d, 1H), 6.27 (d, 1H), 5.50 (s, 2H), 4.51 (s, 2H), 4.26 (s, 3H). |

| Cpd No. | Structure | Characterization |
|---|---|---|
| E7-110 | 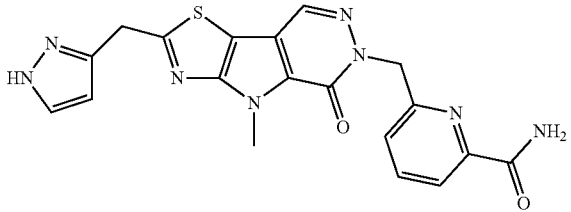 [SMILES: Cn1c2nc(Cc3cc[nH]n3)sc2c2cnn(Cc3cccc(C(N)=O)n3)c(=O)c21]<br>6-((2-((1H-pyrazol-3-yl)methyl)-4-methyl-5-oxo-4H-thiazolo[5',4':4,5]pyrrolo[2,3-d]pyridazin-6(5H)-yl)methyl)picolinamide | LC-MS: m/z 421 (M + H)⁺.<br>¹H NMR (400 MHz, DMSO-d6) δ: 12.79 (s, 1H), 8.59 (s, 1H), 7.97-7.82 (m, 3H), 7.75-7.60 (m, 2H), 7.26 (dd, 1H), 6.27 (d, 1H), 5.53 (s, 2H), 4.51 (s, 2H), 4.26 (s, 3H). |
| E7-111 | 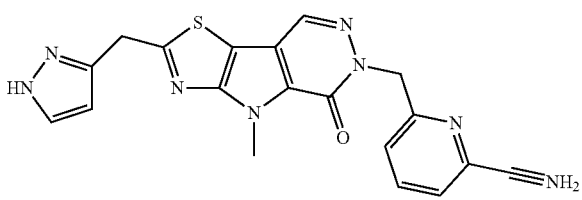 [SMILES: Cn1c2nc(Cc3cc[nH]n3)sc2c2cnn(Cc3cccc(C#N)n3)c(=O)c21]<br>6-((2-((1H-pyrazol-3-yl)methyl)-4-methyl-5-oxo-4H-thiazolo[5',4':4,5]pyrrolo[2,3-d]pyridazin-6(5H)-yl)methyl)picolinonitrile | LC-MS: m/z 403 (M + H)⁺.<br>¹H NMR (400 MHz, DMSO-d6) δ: 8.64 (s, 1H), 8.12-7.98 (m, 2H), 7.74 (s, 1H), 7.60 (d, 1H), 6.33 (d, 1H), 5.57 (s, 2H), 4.57 (s, 2H), 4.32 (s, 3H). |
| E7-112 | 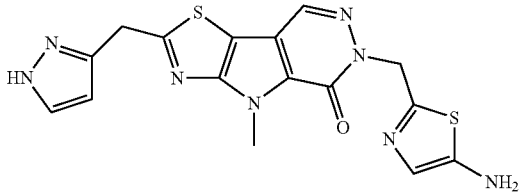<br>2-((1H-pyrazol-3-yl)methyl)-6-((5-aminothiazol-2-yl)methyl)-4-methyl-4H-thiazolo[5',4':4,5]pyrrolo[2,3-d]pyridazin-5(6H)-one | LC-MS: m/z 399 (M + H)⁺.<br>¹H NMR (400 MHz, DMSO-d6) δ: 12.79 (s, 1H), 8.55 (s, 1H), 7.68 (s, 1H), 6.89 (s, 1H), 6.27 (s, 1H), 5.58 (s, 2H), 5.36 (s, 2H), 4.50 (s, 2H), 4.27 (s, 3H). |
| E7-113 | 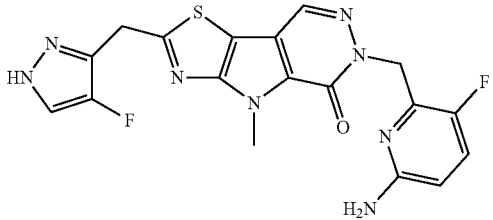 [SMILES: Cn1c2nc(Cc3n[nH]cc3F)sc2c2cnn(Cc3nc(N)ccc3F)c(=O)c21]<br>6-((6-amino-3-fluoropyridin-2-yl)methyl)-2-((4-fluoro-1H-pyrazol-3-yl)methyl)-4-methyl-4H-thiazolo[5',4':4,5]pyrrolo[2,3-d]pyridazin-5(6H)-one | LC-MS: m/z 429 (M + H)⁺.<br>¹H NMR (400 MHz, DMSO-d6) δ: 12.84 (s, 1H), 8.48 (s, 1H), 7.88 (d, 1H), 7.29 (t, 1H), 6.34 (dd, 1H), 5.76 (s, 2H), 5.31 (s, 2H), 4.51 (s, 2H), 4.23 (s, 3H). |
| E7-114 | 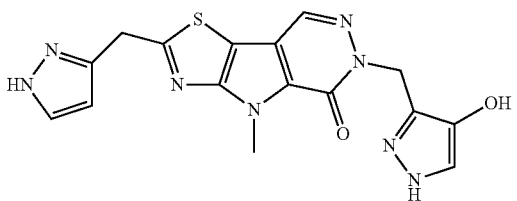 [SMILES: Cn1c2nc(Cc3cc[nH]n3)sc2c2cnn(Cc3n[nH]cc3O)c(=O)c21]<br>2-((1H-pyrazol-3-yl)methyl)-6-((4-hydroxy-1H-pyrazol-3-yl)methyl)-4-methyl-4H-thiazolo[5',4':4,5]pyrrolo[2,3-d]pyridazin-5(6H)-one | LC-MS: m/z 383 (M + H)⁺.<br>¹H NMR (400 MHz, DMSO-d6) δ: 12.85 (s, 1H), 12.10 (s, 1H), 8.57 (s, 1H), 8.32 (s, 1H), 7.77 (s, 1H), 7.21 (s, 1H), 6.33 (d, 1H), 5.32 (s, 2H), 4.55 (s, 2H), 4.34 (s, 3H). |

-continued

| Cpd No. | Structure | Characterization |
|---|---|---|
| E7-115 | 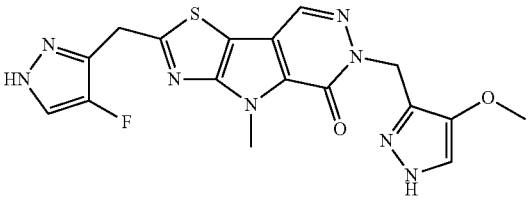 [SMILES: COc1c[nH]nc1Cn1ncc2c3sc(Cc4n[nH]cc4F)nc3n(C)c2c1=O]<br>2-((4-fluoro-1H-pyrazol-3-yl)methyl)-6-((4-methoxy-1H-pyrazol-3-yl)methyl)-4-methyl-4H-thiazolo[5',4':4,5]pyrrolo[2,3-d]pyridazin-5(6H)-one | LC-MS: m/z 415 (M + H)+.<br>$^1$H NMR (400 MHz, DMSO-d6) δ: 12.76 (s, 1H), 12.13 (s, 1H), 8.45 (s, 1H), 7.87 (s, 1H), 7.39 (s, 1H), 5.25 (s, 2H), 4.49 (s, 2H), 4.26 (s, 3H), 3.63 (s, 3H). |
| E7-116 | 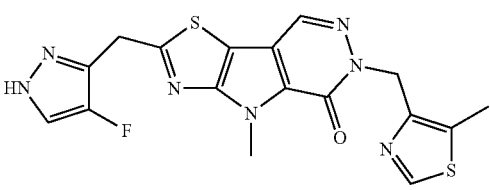 [SMILES: Cc1scnc1Cn1ncc2c3sc(Cc4n[nH]cc4F)nc3n(C)c2c1=O]<br>2-((4-fluoro-1H-pyrazol-3-yl)methyl)-4-methyl-6-((5-methylthiazol-4-yl)methyl)-4H-thiazolo[5',4':4,5]pyrrolo[2,3-d]pyridazin-5(6H)-one | LC-MS: m/z 416 (M + H)+.<br>$^1$H NMR (400 MHz, DMSO-d6) δ: 12.78 (s, 1H), 8.75 (s, 1H), 8.49 (s, 1H), 7.85 (s, 1H), 5.39 (s, 2H), 4.50 (s, 2H), 4.26 (s, 3H), 2.51 (s, 3H). |
| E7-117 | 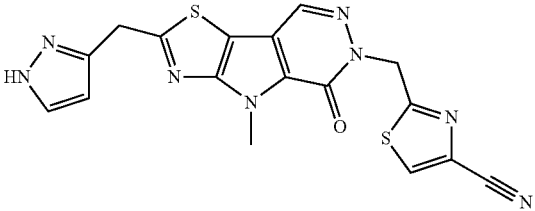 [SMILES: Cn1c2nc(Cc3cc[nH]n3)sc2c2cnn(Cc3nc(C#N)cs3)c(=O)c21]<br>2-((2-((1H-pyrazol-3-yl)methyl)-4-methyl-5-oxo-4H-thiazolo[5',4':4,5]pyrrolo[2,3-d]pyridazin-6(5H)-yl)methyl)thiazole-4-carbonitrile | LC-MS: m/z 409 (M + H)+.<br>$^1$H NMR (400 MHz, DMSO-d6) δ: 12.80 (s, 1H), 8.82 (s, 1H), 8.63 (s, 1H), 7.69 (s, 1H), 6.27 (d, 1H), 5.69 (s, 2H), 4.51 (s, 2H), 4.27 (s, 3H). |
| E7-118 | 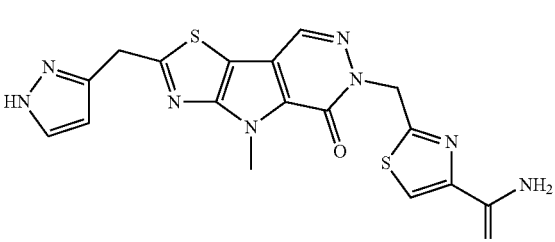<br>2-((2-((1H-pyrazol-3-yl)methyl)-4-methyl-5-oxo-4H-thiazolo[5',4':4,5]pyrrolo[2,3-d]pyridazin-6(5H)-yl)methyl)thiazole-4-carboxamide | LC-MS: m/z 427 (M + H)+.<br>$^1$H NMR (400 MHz, DMSO-d6) δ: 8.63 (s, 1H), 8.19 (s, 1H), 7.76-7.63 (m, 2H), 7.57 (s, 1H), 6.27 (s, 1H), 5.67 (s, 2H), 4.51 (s, 2H), 4.28 (s, 3H). |
| E7-119 | 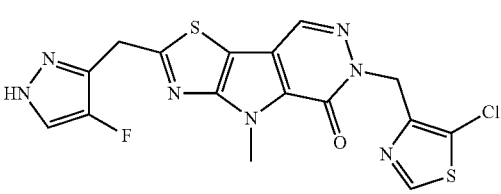 [SMILES: Cn1c2nc(Cc3n[nH]cc3F)sc2c2cnn(Cc3ncsc3Cl)c(=O)c21]<br>6-((5-chlorothiazol-4-yl)methyl)-2-((4-fluoro-1H-pyrazol-3-yl)methyl)-4-methyl-4H-thiazolo[5',4':4,5]pyrrolo[2,3-d]pyridazin-5(6H)-one | LC-MS: m/z 436 (M + H)+.<br>$^1$H NMR (400 MHz, DMSO-d6) δ: 12.83 (s, 1H), 8.94 (s, 1H), 8.51 (s, 1H), 7.83 (s, 1H), 5.43 (s, 2H), 4.51 (s, 2H), 4.26 (s, 3H). |

| Cpd No. | Structure | Characterization |
|---|---|---|
| E7-120 | 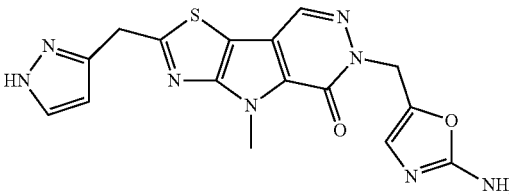<br>2-((1H-pyrazol-3-yl)methyl)-6-((2-aminooxazol-5-yl)methyl)-4-methyl-4H-thiazolo[5',4':4,5]pyrrolo[2,3-d]pyridazin-5(6H)-one | LC-MS: m/z 383 (M + H)⁺<br>¹H NMR (400 MHz, DMSO-d6) δ: 12.79 (s, 1H), 8.50 (s, 1H), 7.70 (s, 1H), 6.65 (s, 1H), 6.57 (s, 2H), 6.23 (d, 1H), 5.21 (s, 2H), 4.49 (s, 2H), 4.27 (s, 3H). |
| E7-121 | 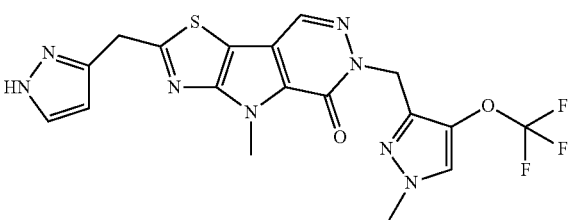 [SMILES: Cn1cc(OC(F)(F)F)c(Cn2ncc3c4sc(Cc5cc[nH]n5)nc4n(C)c3c2=O)n1]<br>2-((1H-pyrazol-3-yl)methyl)-4-methyl-6-((1-methyl-4-(trifluoromethoxy)-1H-pyrazol-3-yl)methyl)-4H-thiazolo[5',4':4,5]pyrrolo[2,3-d]pyridazin-5 (6H)-one | LC-MS: m/z 465 (M + H) .<br>¹H NMR (400 MHz, DMSO-d6) δ: 12.78 (s, 1H), 8.48 (s, 1H), 7.99 (s, 1H), 7.72 (s, 1H), 6.27 (d, 1H), 5.31 (s, 2H), 4.49 (s, 2H), 4.27 (s, 3H), 3.76 (s, 3H). |
| E7-122 | 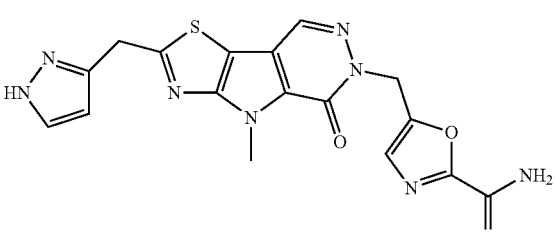<br>5-((2-((1H-pyrazol-3-yl)methyl)-4-methyl-5-oxo-4H-thiazolo[5',4':4,5]pyrrolo[2,3-d]pyridazin-6(5H)-yl)methyl)oxazole-2-carboxamide | LC-MS: m/z 411 (M + H)⁺.<br>¹H NMR (400 MHz, DMSO-d6) δ: 12.78 (s, 1H), 8.56 (s, 1H), 8.17 (s, 1H), 7.84 (s, 1H), 7.72 (s, 1H), 7.34 (s, 1H), 6.27 (s, 1H), 5.48 (s, 2H), 4.49 (s, 2H), 4.27 (s, 3H). |
| E7-123 | 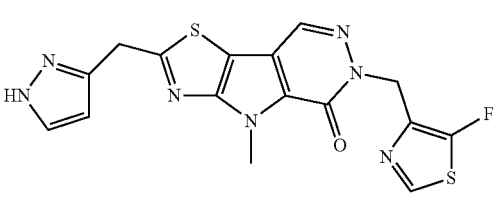 [SMILES: Cn1c2nc(Cc3cc[nH]n3)sc2c2cnn(Cc3ncsc3F)c(=O)c21]<br>2-((1H-pyrazol-3-yl)methyl)-6-((5-fluorothiazol-4-yl)methyl)-4-methyl-4H-thiazolo[5',4':4,5]pyrrolo[2,3-d]pyridazin-5(6H)-one | LC-MS: m/z 402 (M + H)⁺.<br>¹H NMR (400 MHz, DMSO-d6) δ: 12.78 (s, 1H), 8.57 (d, 1H), 8.50 (s, 1H), 7.71 (s, 1H), 6.26 (d, 1H), 5.38 (d, 2H), 4.49 (s, 2H), 4.26 (s, 3H). |
| E7-124 | 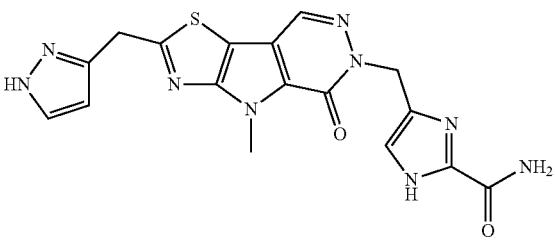 [SMILES: Cn1c2nc(Cc3cc[nH]n3)sc2c2cnn(Cc3c[nH]c(C(N)=O)n3)c(=O)c21]<br>4-((2-((1H-pyrazol-3-yl)methyl)-4-methyl-5-oxo-4H-thiazolo[5',4':4,5]pyrrolo[2,3-d]pyridazin-6(5H)-yl)methyl)-1H-imidazole-2-carboxamide | LC-MS: m/z 410 (M + H)⁺.<br>¹H NMR (400 MHz, DMSO-d6) δ: 12.83 (s, 1H), 8.49 (s, 1H), 7.67 (s, 2H), 7.38 (s, 1H), 7.06 (s, 1H), 6.26 (d, 1H), 5.30 (s, 2H), 4.49 (s, 2H), 4.27 (s, 3H). |

| Cpd No. | Structure | Characterization |
|---|---|---|
| E7-125 | 2-((1H-pyrazol-3-yl)methyl)-6-((2-chlorooxazol-4-yl)methyl)-4-methyl-4H-thiazolo[5',4':4,5]pyrrolo[2,3-d]pyridazin-5(6H)-one | LC-MS: m/z 402 (M + H)⁺.<br>¹H NMR (400 MHz, DMSO-d6) δ: 12.79 (s, 1H), 8.52 (s, 1H), 8.17 (s, 1H), 7.71 (s, 1H), 6.26 (d, 1H), 5.23 (s, 2H), 4.49 (s, 2H), 4.27 (s, 3H). |
| E7-126 | 2-((1H-pyrazol-3-yl)methyl)-6-((2-chlorothiazol-4-yl)methyl)-4-methyl-4H-thiazolo[5',4':4,5]pyrrolo[2,3-d]pyridazin-5(6H)-one | LC-MS: m/z 418 (M + H)⁺.<br>¹H NMR (400 MHz, DMSO-d6) δ: 12.82 (s, 1H), 8.58 (s, 1H), 7.75 (s, 1H), 7.49 (s, 1H), 6.31 (d, 1H), 5.42 (s, 2H), 4.54 (s, 2H), 4.31 (s, 3H). |
| E7-127 | 2-((1H-pyrazol-3-yl)methyl)-6-((1-amino-1H-pyrazol-3-yl)methyl)-4-methyl-4H-thiazolo[5',4':4,5]pyrrolo[2,3-d]pyridazin-5(6H)-one | LC-MS: m/z 382 (M + H)⁺.<br>¹H NMR (400 MHz, DMSO-d6) δ: 8.48 (s, 1H), 7.67 (s, 1H), 7.37 (d, 1H), 6.34 (d, 2H), 6.27 (d, 1H), 6.00 (d, 1H), 5.24 (s, 2H), 4.50 (s, 2H), 4.27 (s, 3H). |
| E7-128 | 2-((1H-pyrazol-3-yl)methyl)-6-((4-(methoxymethyl)-1-methyl-1H-pyrazol-3-yl)methyl)-4-methyl-4H-thiazolo[5',4':4,5]pyrrolo[2,3-d]pyridazin-5(6H)-one | LC-MS: m/z 425 (M + H)⁺.<br>¹H NMR (400 MHz, DMSO-d6) δ: 12.79 (s, 1H), 8.46 (s, 1H), 7.72 (s, 1H), 7.59 (s, 1H), 6.27 (s, 1H), 5.28 (s, 2H), 4.48 (s, 2H), 4.29-4.25 (m, 5H), 3.73 (s, 3H), 3.11 (s, 3H). |
| E7-129 | 2-((1H-pyrazol-3-yl)methyl)-6-((5-chlorooxazol-4-yl)methyl)-4-methyl-4H-thiazolo[5',4':4,5]pyrrolo[2,3-d]pyridazin-5(6H)-one | LC-MS: m/z 402 (M + H)⁺.<br>¹H NMR (400 MHz, DMSO-d6) δ: 12.78 (s, 1H), 8.52 (s, 1H), 8.39 (s, 1H), 7.68 (s, 1H), 6.27 (d, 1H), 5.24 (s, 2H), 4.50 (s, 2H), 4.26 (s, 3H). |

| Cpd No. | Structure | Characterization |
|---|---|---|
| E7-130 | 2-((4-fluoro-1H-pyrazol-3-yl)methyl)-4-methyl-6-((4-(trifluoromethoxy)-1H-pyrazol-3-yl)methyl)-4H-thiazolo[5',4':4,5]pyrrolo[2,3-d]pyridazin-5(6H)-one | LC-MS: m/z 469 (M + H)+. 1H NMR (400 MHz, DMSO-d6) δ: 13.37-12.75 (m, 2H), 8.65-8.50 (m, 1H), 8.15-7.58 (m, 2H), 5.49-5.36 (m, 2H), 4.67-4.50 (m, 2H), 4.32 (s, 3H). |
| E7-131 | 2-((1H-pyrazol-3-yl)methyl)-6-((2-aminooxazol-4-yl)methyl)-4-methyl-4H-thiazolo[5',4':4,5]pyrrolo[2,3-d]pyridazin-5(6H)-one | LC-MS: m/z 383 (M + H)+. 1H NMR (400 MHz, DMSO-d6) δ: 12.84 (s, 1H), 8.53 (s, 1H), 7.77 (s, 1H), 7.25 (s, 1H), 6.58 (s, 2H), 6.32 (d, 1H), 5.10 (s, 2H), 4.54 (s, 2H), 4.32 (s, 3H). |
| E7-132 | 2-((1H-pyrazol-3-yl)methyl)-6-((4-(aminomethyl)-1-methyl-1H-pyrazol-3-yl)methyl)-4-methyl-4H-thiazolo[5',4':4,5]pyrrolo[2,3-d]pyridazin-5(6H)-one | LC-MS: m/z 410 (M + H)+. 1H NMR (400 MHz, DMSO-d6) δ: 12.89 (s, 1H), 8.58 (s, 1H), 8.45 (s, 1H), 7.77-7.64 (m, 2H), 6.33 (d, 1H), 5.39 (s, 2H), 4.57 (s, 2H), 4.33 (s, 3H), 3.96 (s, 2H), 3.82 (s, 3H). |
| E7-133 | 2-(3-((2-((1H-pyrazol-3-yl)methyl)-4-methyl-5-oxo-4H-thiazolo[5',4':4,5]pyrrolo[2,3-d]pyridazin-6(5H)-yl)methyl)-1-methyl-1H-pyrazol-4-yl)acetamide | LC-MS: m/z 438 (M + H)+. 1H NMR (400 MHz, DMSO-d6) δ: 12.78 (s, 1H), 8.46 (s, 1H), 7.72 (s, 1H), 7.44 (s, 1H), 7.25 (s, 1H), 6.80 (s, 1H), 6.26 (d, 1H), 5.26 (s, 2H), 4.48 (s, 2H), 4.26 (s, 3H), 3.70 (s, 3H), 3.31 (s, 2H). |
| E7-134 | 4-((2-((1H-pyrazol-3-yl)methyl)-4-methyl-5-oxo-4,5-dihydro-6H-thiazolo[5',4':4,5]pyrrolo[2,3-d]pyridazin-6-yl)methyl)-1H-imidazole-5-carboxamide | LC-MS: m/z 410 (M + H)+. 1H NMR (400 MHz, DMSO-d6) δ: 12.79 (s, 1H), 12.10 (s, 1H), 8.51 (s, 1H), 7.72 (s, 1H), 7.53 (s, 1H), 7.29 (s, 1H), 7.08 (s, 1H), 6.27 (d, 1H), 5.72 (s, 2H), 4.50 (s, 2H), 4.30 (s, 3H) |

-continued

| Cpd No. | Structure | Characterization |
|---|---|---|
| E7-135 | 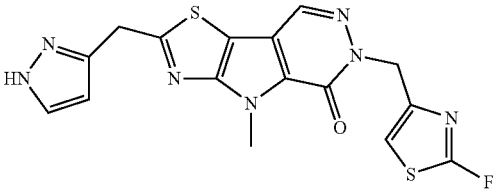 [SMILES: Cn1c2nc(Cc3cc[nH]n3)sc2c2cnn(Cc3csc(F)n3)c(=O)c21]<br>2-((1H-pyrazol-3-yl)methyl)-6-((2-fluorothiazol-4-yl)methyl)-4-methyl-4,6-dihydro-5H-thiazolo[5',4':4,5]pyrrolo[2,3-d]pyridazin-5-one | LC-MS: m/z 402 (M + H)$^+$.<br>$^1$H NMR (400 MHz, DMSO-d6) δ: 12.85 (s, 1H), 8.59 (s, 1H), 7.80 (d, 1H), 7.14 (s, 1H), 6.33 (d, 1H), 5.36 (d, 2H), 4.53 (d, 2H), 4.33 (s, 3H) |
| E7-136 | 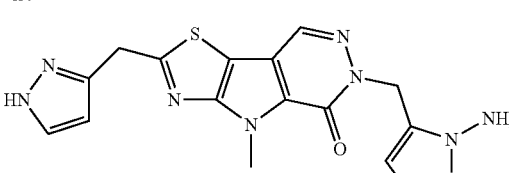<br>2-((1H-pyrazol-3-yl)methyl)-6-((1-amino-1H-pyrazol-5-yl)methyl)-4-methyl-4,6-dihydro-5H-thiazolo[5',4':4,5]pyrrolo[2,3-d]pyridazin-5-one | LC-MS: m/z 382 (M + H)$^+$.<br>$^1$H NMR (400 MHz, DMSO-d6) δ: 12.80 (s, 1H), 8.53 (s, 1H), 7.69 (s, 1H), 7.16 (d, 1H), 6.30 (s, 2H), 6.27 (s, 1H), 5.88 (s, 1H), 5.41 (s, 2H), 4.50 (s, 2H), 4.27 (s, 3H). |
| E7-137 | 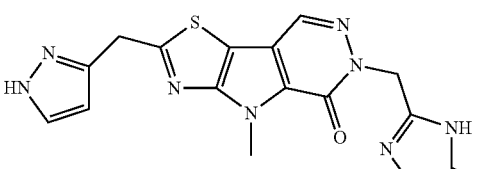<br>2-((1H-pyrazol-3-yl)methyl)-4-methyl-6-((5-oxo-4,5-dihydro-1H-1,2,4-triazol-3-yl)methyl)-4,6-dihydro-5H-thiazolo[5',4':4,5]pyrrolo[2,3-d]pyridazin-5-one | LC-MS: m/z 384 (M + H)$^+$.<br>$^1$H NMR (400 MHz, DMSO-d6) δ: 12.79 (s, 1H), 11.31 (s, 1H), 8.54 (d, 1H), 7.69 (s, 1H), 6.27 (d, 1H), 5.17 (d, 2H), 4.51 (s, 2H), 4.27 (s, 3H). |
| E7-138 | 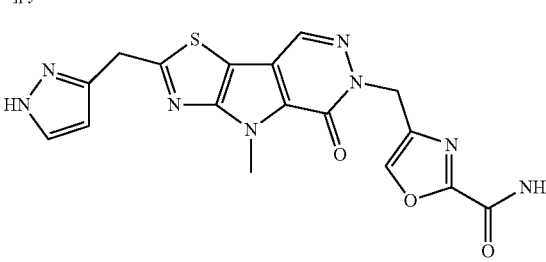<br>4-((2-((1H-pyrazol-3-yl)methyl)-4-methyl-5-oxo-4,5-dihydro-6H-thiazolo[5',4':4,5]pyrrolo[2,3-d]pyridazin-6-yl)methyl)oxazole-2-carboxamide | LC-MS: m/z 411 (M + H)$^+$.<br>$^1$H NMR (400 MHz, DMSO-d6) δ: 12.78 (s, 1H), 8.52 (s, 1H), 8.25-8.12 (m, 2H), 7.84 (s, 1H), 7.70 (s, 1H), 6.26 (d, 1H), 5.30 (s, 2H), 4.48 (s, 2H), 4.26 (s, 3H) |
| E7-139 | 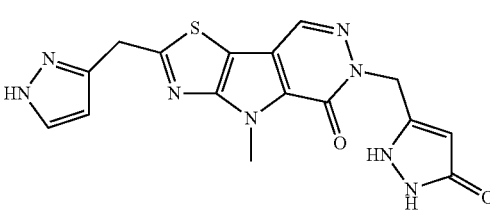 [SMILES: Cn1c2nc(Cc3cc[nH]n3)sc2c2cnn(Cc3cc(=O)[nH][nH]3)c(=O)c21]<br>2-((1H-pyrazol-3-yl)methyl)-4-methyl-6-((5-oxo-2,5-dihydro-1H-pyrazol-3-yl)methyl)-4,6-dihydro-5H-thiazolo[5',4':4,5]pyrrolo[2,3-d]pyridazin-5-one | LC-MS: m/z 383 (M + H)$^+$.<br>$^1$H NMR (400 MHz, DMSO-d6) δ: 12.79 (s, 1H), 8.51 (s, 1H), 8.36 (s, 2H), 7.67 (s, 1H), 6.26 (d, 1H), 5.31 (s, 1H), 5.19 (s, 2H), 4.49 (s, 2H), 4.27 (s, 3H). |

| Cpd No. | Structure | Characterization |
|---|---|---|
| E7-140 | 2-((1H-pyrazol-3-yl)methyl)-6-((5-amino-1H-imidazol-4-yl)methyl)-4-methyl-4,6-dihydro-5H-thiazolo[5',4':4,5]pyrrolo[2,3-d]pyridazin-5-one | LC-MS: m/z 382 (M + H)$^+$. $^1$H NMR (400 MHz, DMSO-d6) δ: 12.79 (s, 1H), 11.47 (s, 1H), 8.52 (s, 1H), 7.68 (s, 1H), 7.04 (s, 1H), 6.27 (s, 1H), 5.17 (s, 2H), 4.50 (s, 2H), 4.28 (s, 3H) |
| E7-141 | 2-((1H-pyrazol-3-yl)methyl)-6-((2-aminopyrimidin-4-yl)methyl)-4-methyl-4,6-dihydro-5H-thiazolo[5',4':4,5]pyrrolo[2,3-d]pyridazin-5-one | LC-MS: m/z 394 (M + H)$^+$. $^1$H NMR (400 MHz, DMSO-d6) δ: 12.78 (s, 1H), 8.56 (s, 1H), 8.11 (d, 1H), 7.71 (s, 1H), 6.60 (s, 2H), 6.27 (d, 1H), 6.18 (d, 1H), 5.19 (s, 2H), 4.50 (s, 2H), 4.26 (s, 3H) |
| E7-142 | 2-((1H-pyrazol-3-yl)methyl)-6-((4-aminopyrimidin-2-yl)methyl)-4-methyl-4,6-dihydro-5H-thiazolo[5',4':4,5]pyrrolo[2,3-d]pyridazin-5-one | LC-MS: m/z 394 (M + H)$^+$. $^1$H NMR (400 MHz, DMSO-d6) δ: 12.84 (s, 1H), 8.55 (s, 1H), 7.99 (d, 1H), 7.77 (s, 1H), 6.86 (s, 2H), 6.44-6.16 (m, 2H), 5.28 (s, 2H), 4.57 (s, 2H), 4.32 (s, 3H) |

Example 7F. Synthesis of 2-((1H-pyrazol-3-yl)methyl)-4-methyl-6-(2-(thiazol-4-yl)ethyl)-4H-thiazolo[5',4':4,5]pyrrolo[2,3-d]pyridazin-5(6H)-one

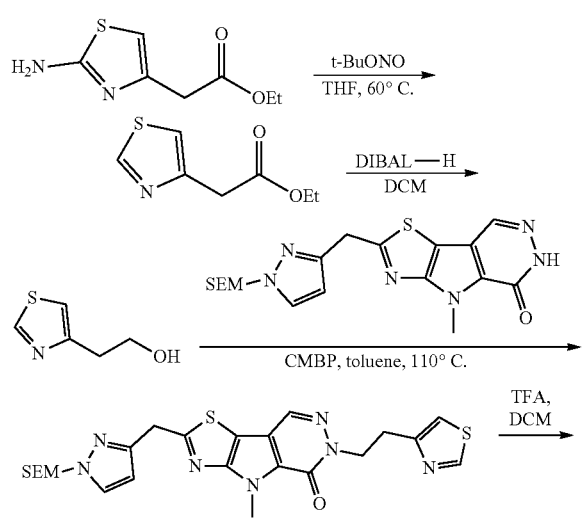

E7-143

Step A. Synthesis of ethyl 2-(thiazol-4-yl)acetate

To a solution of ethyl 2-(2-aminothiazol-4-yl)acetate (2 g, 10.7 mmol) in THF (30 mL) was added t-BuONO (1.6 g, 16.1 mmol). The reaction mixture was stirred at 50° C. for 16 hrs. After cooled to room temperature, the reaction mixture was diluted with EtOAc, washed with water and brine, dried over anhy. Na$_2$SO$_4$, concentrated in vacuum. The residue was purified by flash chromatography (silica gel, 80-100% EtOAc in PE) to afford ethyl 2-(thiazol-4-yl)acetate (400 mg). LC-MS (ESI): m/z 172 (M+1)$^+$.

Step B. Synthesis of 2-(thiazol-4-yl) Ethanol

To a stirred solution of ethyl 2-(thiazol-4-yl)acetate (400 mg, 2.3 mmol) in DCM (20 mL) was added DIBAL-H (4.7 mL, 7.0 mmol). The reaction mixture was stirred at room temperature under N₂ for 3 hrs. The reaction was quenched with satd. NaHCO₃, extracted with DCM and the organic layer was washed with brine, dried over anhy. Na₂SO₄, concentrated in vacuum. The residue was purified by flash chromatography (silica gel, 50-100% EtOAc in PE) to afford 2-(thiazol-4-yl) ethanol (200 mg). LC-MS (ESI): m/z 130 (M+1)⁺.

Step C. Synthesis of 4-methyl-6-(2-(thiazol-4-yl) ethyl)-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one To a mixture of 4-methyl-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (60 mg, 0.14 mmol) and 2-(thiazol-4-yl) ethanol (55 mg, 0.4 mmol) in toluene (5 mL) was added CMBP (104 mg, 0.4 mmol). The reaction mixture was stirred at 110° C. under N₂ for 3 hrs. After cooled to room temperature, the reaction mixture was diluted with EtOAc, washed with water and brine, dried over anhy. Na₂SO₄, concentrated in vacuum. The residue was purified by flash chromatography (silica gel, 80-100% EtOAc in PE) to afford 60 mg of 4-methyl-6-(2-(thiazol-4-yl)ethyl)-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one. LC-MS: m/z 528 (M+1)⁺.

Step D. Synthesis of 2-((1H-pyrazol-3-yl)methyl)-4-methyl-6-(2-(thiazol-4-yl)ethyl)-4H-thiazolo[5',4':4,5]pyrrolo[2,3-d]pyridazin-5(6H)-one To a solution of 4-methyl-6-(2-(thiazol-4-yl)ethyl)-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (60 mg, 0.1 mmol) in DCM (1 mL) was added TFA (0.5 mL). The reaction mixture was stirred at room temperature for 3 hrs. The reaction mixture was adjusted pH=7.5 with satd. NaHCO₃, extracted with DCM, washed with brine, dried over anhy. Na₂SO₄, concentrated in vacuum. The residue was purified by prep-TLC (10% MeOH in DCM) to afford 10 mg of 2-((I H-pyrazol-3-yl)methyl)-4-methyl-6-(2-(thiazol-4-yl)ethyl)-4H-thiazolo[5',4':4,5]pyrrolo[2,3-d]pyridazin-5(6H)-one. LC-MS: m/z 398 (M+H)⁺. ¹H NMR (400 MHz, DMSO-d6) δ 9.03 (s, 1H), 8.47 (s, 1H), 7.67 (s, 1H), 7.41 (s, 1H), 6.27 (s, 1H), 4.58-4.40 (m, 4H), 4.26 (s, 3H), 3.23 (t, 2H).

| Cpd No. | Structure | Characterization |
| --- | --- | --- |
| E7-144 | 2-((1H-pyrazol-3-yl)methyl)-4-methyl-6-(2-(pyridin-3-yl)ethyl)-4,6-dihydro-5H-thiazolo[5',4':4,5]pyrrolo[2,3-d]pyridazin-5-one | LC-MS: m/z 392 (M + H)⁺. ¹H NMR (400 MHz, DMSO-d6) δ: 8.47 (s, 1H), 8.39 (dd, 2H), 7.79-7.47 (m, 2H), 7.28 (dd, 1H), 6.26 (d, 1H), 4.49 (s, 2H), 4.41 (t, 2H), 4.25 (s, 3H), 3.09 (t, 2H) |
| E7-145 | 2-((1H-pyrazol-3-yl)methyl)-4-methyl-6-(2-(1-methyl-1H-pyrazol-3-yl)ethyl)-4,6-dihydro-5H-thiazolo[5',4':4,5]pyrrolo[2,3-d]pyridazin-5-one | LC-MS: m/z 395 (M + H)⁺. ¹H NMR (400 MHz, DMSO-d6) δ: 12.77 (s, 1H), 8.50 (s, 1H), 7.72 (s, 1H), 7.54 (d, 1H), 6.26 (m, 1H), 6.04 (d, 1H), 4.48 (s, 2H), 4.43-4.31 (m, 2H), 4.27 (s, 3H), 3.76 (s, 3H), 3.01-2.90 (m, 2H). |
| E7-146 | 2-((1H-pyrazol-3-yl)methyl)-6-(2-(6-aminopyridin-2-yl)ethyl)-4-methyl-4H-thiazolo[5',4':4,5]pyrrolo[2,3-d]pyridazin-5(6H)-one | LC-MS: m/z 407 (M + H)⁺. ¹H NMR (400 MHz, DMSO-d6) δ: 12.80 (s, 1H), 8.49 (s, 1H), 7.71 (s, 1H), 7.26 (t, 1H), 6.35 (d, 1H), 6.31-6.25 (m, 2H), 5.85 (s, 2H), 4.49 (s, 2H), 4.42 (t, 2H), 4.28 (s, 3H), 2.93 (t, 2H). |

Example 8. Synthesis of Compounds E8-v, E8-vi, and E8-viii

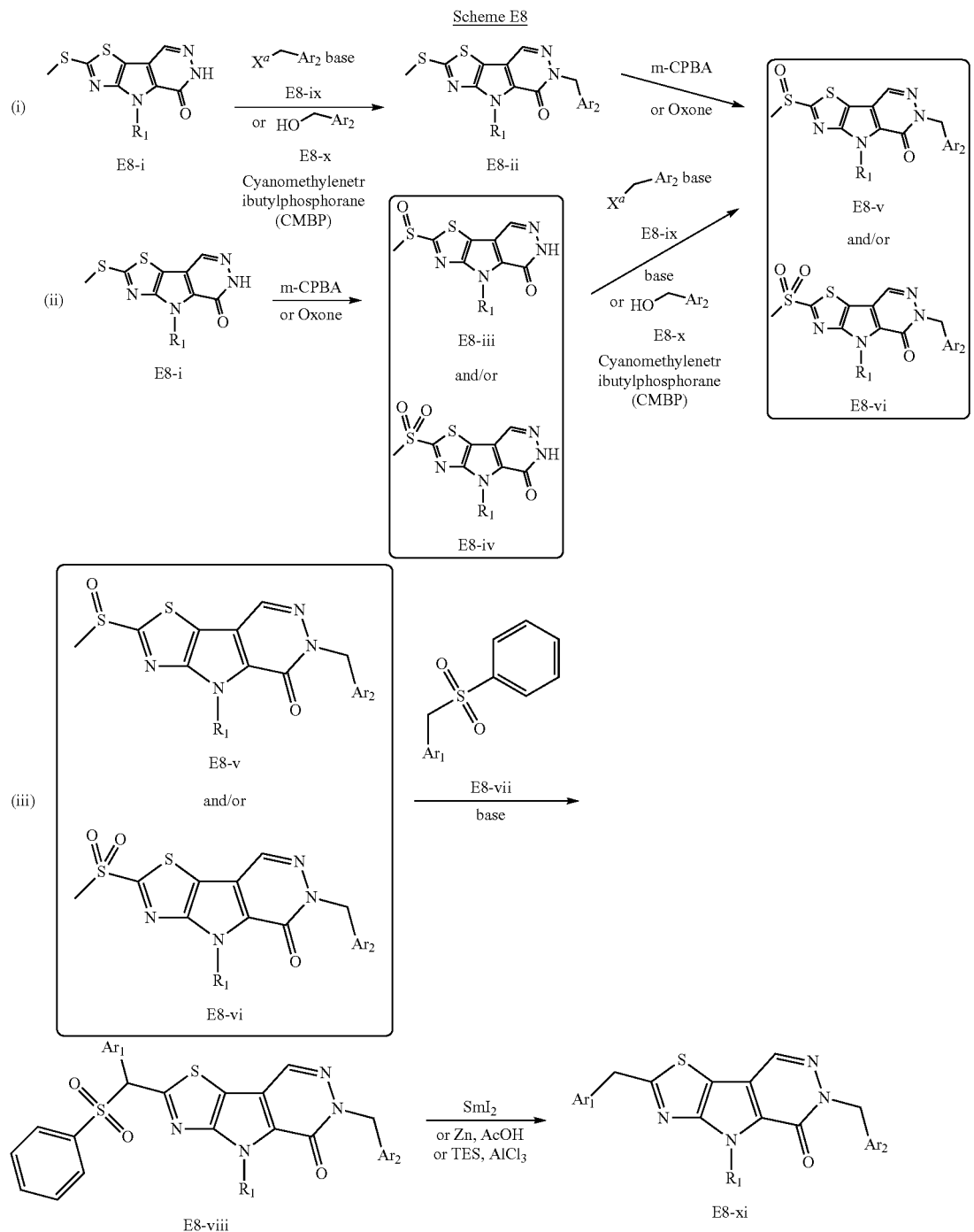

Scheme E8

Compound E8-i can be converted to intermediate E8-ii through either alkylation or Mitsunobu reaction like in example E7-v to E7-viii. Oxidation of E8-ii with either mCPBA or oxone generate compounds E8-v and E8-vi. Both compounds of E8-v and E8-vi can also be formed from E8-i by oxidation first followed by alkylation or Mitsunobu reaction. Wherein $X^a$ is a leaving group (e.g. Cl, Br, I, OMs, OTs); Compounds E8-v and E8-vi can be converted to intermediate E8-viii through nucleophilic aromatic substitution reaction with compound E8-vii, using LiHMDS or t-BuOK as a base. Compound E8-xi can be synthesized from compound E8-viii using either SmI2 or Zn in AcOH or TES with AlCl3. As used herein, R1 is optionally substituted alkyl, optionally substituted aryl, optionally substituted heteroaryl, optionally substituted carbocycle or optionally substituted heterocyclyl; Ar1 and Ar2 are each independently optionally substituted aryl, optionally substituted heteroaryl, optionally substituted carbocycle or optionally substituted heterocyclyl; optionally substituted alkyl, optionally substituted alkylaryl, optionally substituted alkylheteroaryl, optionally substituted alkyenyl, and optionally substituted alkynyl. In certain embodiments, R1 is optionally substituted C1-6 alkyl (e.g. methyl or ethyl). In certain embodiments, R1 is C1-6 alkyl; and Ar1 and Ar2 are each independently optionally substituted heteroaryl Example 8A. Synthesis of 6-((1H-indazol-4-yl)methyl)-2-((5-chloro-1H-pyrazol-3-yl)methyl)-4-methyl-4H-thiazolo[5',4' 4,5]pyrrolo[2,3-d]pyridazin-5(6H)-one Ethyl 5-chloro-1-trityl-1H-pyrazole-3-carboxylate To a stirred mixture of ethyl 5-chloro-1H-pyrazole-3-carboxylate (100 mg, 0.575 mmol) and TEA (0.24 mL, 1.44 mmol) in dry DCM (10 mL) was added TrtCl (192 mg, 0.689 mmol) at r.t. The reaction mixture was stirred at r.t. for 2 h and then poured into H₂O. The resulting mixture was extracted with DCM. The organic layer was washed with brine (30 mL), dried over anhydrous Na₂SO₄ and concentrated under reduced pressure. The residue was purified by flash chromatography (silica gel, 0~4% ethyl acetate in petroleum ether) to give the desired product (crude, 240 mg, 100%).

(5-chloro-1-trityl-1H-pyrazol-3-yl)methanol

To a stirred mixture of ethyl 5-chloro-1-trityl-1H-pyrazole-3-carboxylate (1.20 g, 2.88 mmol) in dry THF (10 mL)

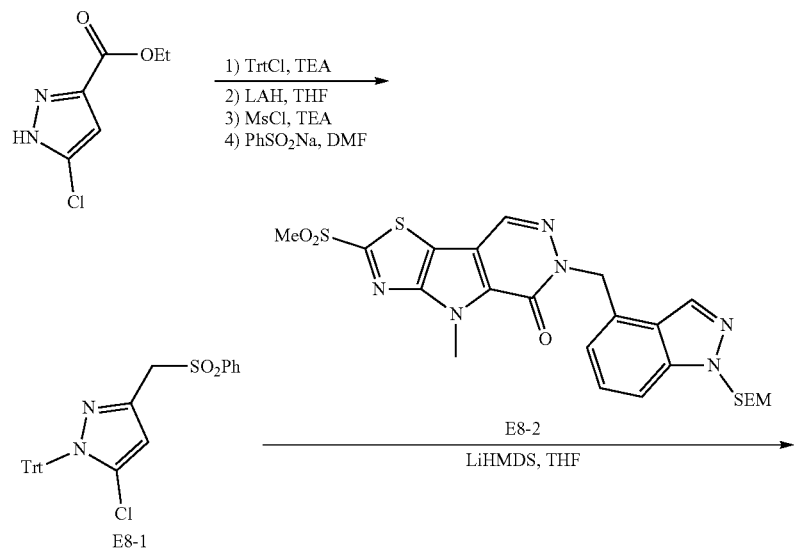

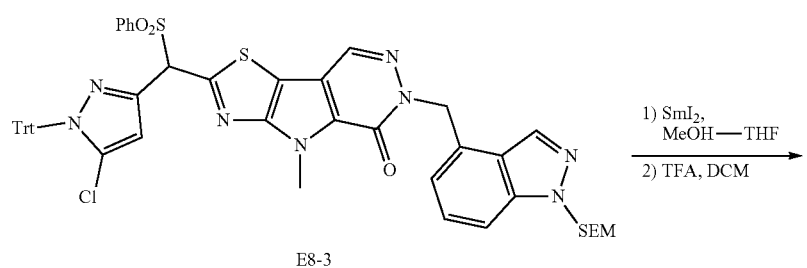

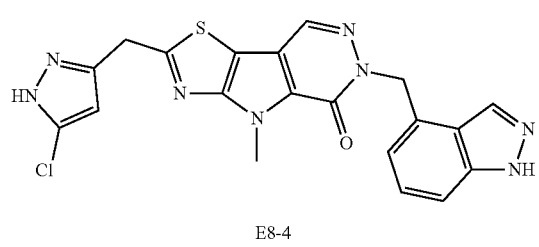

E8-4 was added LAH (400 mg, 10.5 mmol) at −30° C. The reaction mixture was stirred at −30° C. for 0.5 h. Na$_2$SO$_4$10H$_2$O (2 g) was added slowly to quench reaction. The resulting mixture was diluted with EtOAc and filtered through a pad of celite. The filtrate was concentrated and residue was purified by flash chromatography (silica gel, 10%~15% ethyl acetate in petroleum ether) to give desired product (540 mg).

(5-chloro-1-trityl-1H-pyrazol-3-yl)methyl methanesulfonate

To a stirred mixture of (5-chloro-1-trityl-1H-pyrazol-3-yl)methanol (100 mg, 0.267 mmol) and DIPEA (0.14 mL, 0.801 mmol) in dry DCM (10 mL) was added MsCl (46 mg, 0.401 mmol) at 10° C. The reaction mixture was stirred at r.t for 1 h. The reaction mixture was quenched with water. The resulting mixture was extracted with DCM (2×). The combined organic layers were washed with brine (30 mL), dried over anhydrous Na2SO4 and concentrated under reduced pressure to give the desired product (crude, 150 mg) as a sticky oil.

5-chloro-3-((phenylsulfonyl)methyl)-1-trityl-1H-pyrazole

To a stirred mixture of (5-chloro-1-trityl-1H-pyrazol-3-yl)methyl methanesulfonate (150 mg crude, 0.267 mmol) in dry DMF (10 mL) was added PhSO$_2$Na (100 mg, 0.610 mmol) at r.t. The reaction mixture was stirred at r.t for 20 h. The reaction mixture was diluted with water. The resulting mixture was extracted with EtOAc (2×). The organic layers were washed with brine (30 mL), dried over anhydrous Na$_2$SO$_4$ and concentrated under reduced pressure. The residue was purified by prep-TLC (eluent: PE/EtOAc=3/1) to give the desired product (80 mg). LCMS: m/z 521 (M+Na)$^+$.

2-((5-chloro-1-trityl-1H-pyrazol-3-yl)(phenylsulfonyl)methyl)-4-methyl-6-((1-((2-(trimethylsilyl)ethoxy)methyl)-1H-indazol-4-yl)methyl)-4,6-dihydro-5H-thiazolo[5',4':4,5]pyrrolo[2,3-d]pyridazin-5-one To a mixture of 5-chloro-3-((phenylsulfonyl)methyl)-1-trityl-1H-pyrazole (100 mg, 0.2 mmol) and 4-methyl-2-(methylsulfonyl)-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (100 mg, 0.2 mmol) in dry THF (10 mL) was added dropwise LiHMDS (1 mL, 10 mmol, 1M in THF) at 10° C. The reaction mixture was stirred at r.t for 10 min and poured into aqueous NH$_4$Cl. The following mixture was extracted with EtOAc (2×). The combined organic layers were washed with brine (30 mL), dried over anhydrous Na$_2$SO$_4$ and concentrated under reduced pressure. The residue was purified by flash chromatography (silica gel, 0~30% ethyl acetate in petroleum ether) to give the desired product of E8-3 (75 mg) as yellow oil. LCMS: m/z 985 (M+Na)$^+$.

2-((5-chloro-1-trityl-1H-pyrazol-3-yl)methyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one To a mixture of compound E8-3 (75 mg, 0.0779 mmol) in THF (5 mL) and MeOH (5 mL) at r.t. under N$_2$ was added SmI$_2$ (5 mL, 0.1M in THF). The reaction mixture was stirred at r.t for 10 min and then quenched with water. The following mixture was extracted with EtOAc (2×). The combined organic layers were washed with brine (30 mL), dried over anhydrous Na$_2$SO$_4$ and concentrated under reduced pressure. The residue was purified by prep-TLC (PE/EtOAc=2/1) to give 2-((5-chloro-1-trityl-1H-pyrazol-3-yl)methyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (50 mg). LCMS: m/z 845 (M+23)+.

6-((1H-indazol-4-yl)methyl)-2-((5-chloro-1H-pyrazol-3-yl)methyl)-4-methyl-4H-thiazolo[5',4':4,5]pyrrolo[2,3-d]pyridazin-5(6H)-one To a mixture of 2-((5-chloro-1-trityl-1H-pyrazol-3-yl)methyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (50 mg, 0.0608 mmol) in DCM (6 mL) at r.t. under N$_2$ was added TFA (2 mL). The reaction mixture was stirred at r.t. for 1 h. The following mixture was adjusted to pH=8 with aqueous NaHCO$_3$, extracted with 80% DCM/iPrOH (2×). The combined organic layers were washed with brine (30 mL), dried over anhydrous Na$_2$SO$_4$ and concentrated under reduced pressure. The residue was purified by prep-HPLC (C18, 0~50% acetonitrile in H$_2$O with 0.1% formic acid) to give desire product (10 mg). LCMS: m/z 451 (M+H)+. $^1$H NMR (400 MHz, DMSO-d$_6$) δ 13.10-13.2 (brs, 2H), 8.58 (s, 1H), 8.14 (s, 1H), 7.43-7.46 (m, 1H), 7.25-7.30 (m, 1H), 6.94-6.97 (m, 1H), 6.32 (s, 1H), 5.65 (s, 2H), 4.55 (s, 2H), 4.27 (s, 3H).

Example 8B. Synthesis of 2-((1H-1,2,3-triazol-4-yl)methyl)-4-methyl-6-(3-(trifluoromethoxy)benzyl)-4H-thiazolo[5' 4':4,5]pyrrolo[2,3-d]pyridazin-5(6H)-one

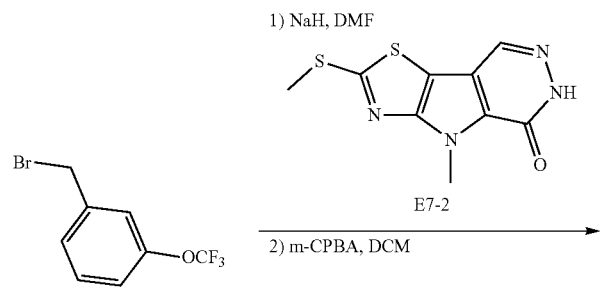

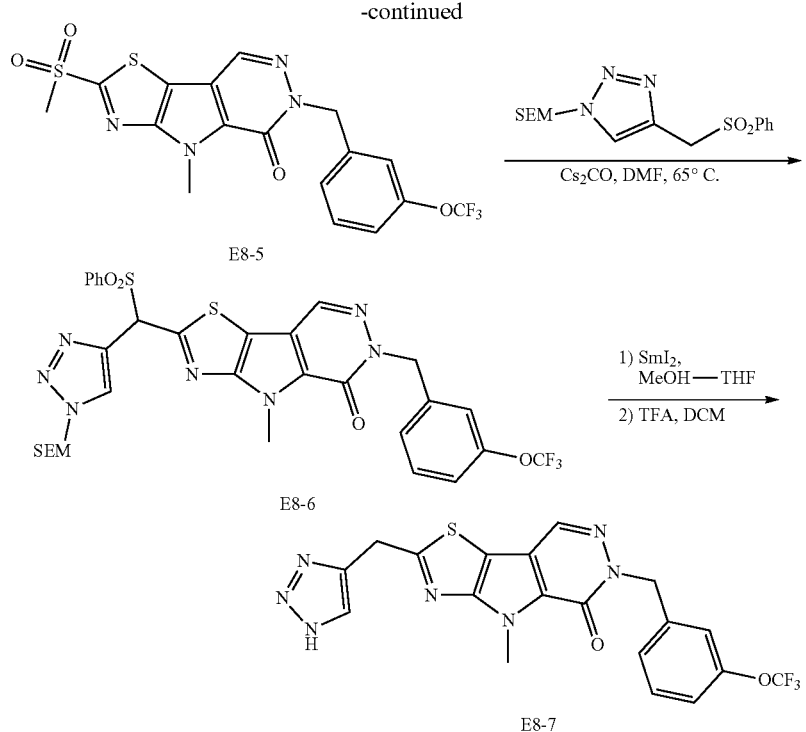

Step A. Synthesis of 4-methyl-2-(methylthio)-6-(3-(trifluoromethoxy)benzyl)-4H-thiazolo[5',4':4,5]pyrrolo[2,3-d]pyridazin-5(6H)-one To a solution of NaH (130 mg, 3.2 mmol) in DMF (4 mL) was added 4-methyl-2-(methylthio)-4H-thiazolo[5',4':4,5]pyrrolo[2,3-d]pyridazin-5(6H)-one (270 mg, 1.1 mmol) at 0° C. under $N_2$. After 5 min, the mixture 1-(bromomethyl)-3-(trifluoromethoxy)benzene (420 mg, 1.65 mmol) in DMF (2 mL) was added to the reaction mixture. The mixture was stirred at r.t. for 2 hr. The reaction was quenched with saturated $NH_4Cl$ and extracted with EA. The organic layer was washed with saturated NaCl (3×), dried over anhydrous $Na_2SO_4$ and concentrated under reduced pressure. The residue was purified by flash chromatography (silica gel, 0~30% ethyl acetate in petroleum ether) to give 4-methyl-2-(methylthio)-6-(3-(trifluoromethoxy)benzyl)-4H-thiazolo[5',4':4,5]pyrrolo[2,3-d]pyridazin-5(6H)-one (420 mg). LCMS: 427 (M+H)$^+$

Step B. Synthesis of 4-methyl-2-(methylsulfonyl)-6-(3-(trifluoromethoxy)benzyl)-4H-thiazolo[5',4':4,5]pyrrolo[2,3-d]pyridazin-5(6H)-one To a solution of 4-methyl-2-(methylthio)-6-(3-(trifluoromethoxy)benzyl)-4H-thiazolo[5',4':4,5]pyrrolo[2,3-d]pyridazin-5(6H)-one (420 mg, 0.99 mmol) in DCM (10 ml) was added mCPBA (520 mg, 3.0 mmol) at 0° C. under $N_2$. The reaction mixture continued to stir overnight. The solution was quenched with saturated $Na_2S_2O_3$ and extracted with DCM (3×). The combined organic layers were dried over anhydrous $Na_2SO_4$ and concentrated under vacuum. The residue was purified by flash chromatography (silica gel, 0~50% ethyl acetate in petroleum ether) to give 4-methyl-2-(methylsulfonyl)-6-(3-(trifluoromethoxy)ben- zyl)-4H-thiazolo[5',4':4,5]pyrrolo[2,3-d]pyridazin-5(6H)-one (330 mg). LCMS: m/z 459 (M+H)$^+$.

Step C. Synthesis of 4-methyl-2-((phenylsulfonyl)(1-((2-(trimethylsilyl)ethoxy) methyl)-1H-1,2,3-triazol-4-yl)methyl)-6-(3-(trifluoromethoxy)benzyl)-4,6-dihydro-5H-thiazolo[5',4':4,5]pyrrolo[2,3-d]pyridazin-5-one To a mixture of 4-methyl-2-(methylsulfonyl)-6-(3-(trifluoromethoxy)benzyl)-4H-thiazolo[5',4':4,5]pyrrolo[2,3-d]pyridazin-5(6H)-one (165 mg, 0.36 mmol) and 4-((phenylsulfonyl)methyl)-1-((2-(trimethylsilyl)ethoxy)methyl)-1H-1,2,3-triazole (50 mg, 0.54 mmol) in dry DMF (10 mL) was added $Cs_2CO_3$ (351 mg, 1.08 mmol) at 65° C. The reaction mixture was stirred at 65° C. for 2 hrs and poured into aqueous $NH_4Cl$. The resulting mixture was extracted with EtOAc (2×). The combined organic layers were washed with brine (30 mL), dried over anhydrous $Na_2SO_4$ and concentrated under reduced pressure. The residue was purified by lash chromatography (silica gel, 0~35% ethyl acetate in petroleum ether) to give the desired product 4-methyl-2-((phenylsulfonyl)(1-((2-(trimethylsilyl)ethoxy) methyl)-1H-1,2,3-triazol-4-yl)methyl)-6-(3-(trifluoromethoxy)benzyl)-4,6-dihydro-5H-thiazolo[5',4':4,5]pyrrolo[2,3-d]pyridazin-5-one (E8-6) (200 mg). LCMS: m/z 732 (M+H)$^+$.

Step D. Synthesis of 2-((1H-1,2,3-triazol-4-yl)methyl)-4-methyl-6-(3-(trifluoromethoxy)benzyl)-4H-thiazolo[5',4':4,5]pyrrolo[2,3-d]pyridazin-5(6H)-one Similar to Example 8A, Compound E8-6 reacted with $SmI_2$, followed by deprotection with TFA, to give the desired product. LCMS: 462 (M+H)$^+$. 1H NMR (400 MHz, DMSO) δ 8.52 (s, 1H), 7.88 (s, 1H), 7.46 (dd, 1H), 7.39-7.2 (m, 3H), 5.40 (s, 2H), 4.63 (s, 2H), 4.26 (s, 3H).

Example 8C. Synthesis of 2,6-bis((1H-indazol-4-yl)methyl)-4-methyl-4H-thiazolo[5',4':4,5]pyrrolo[2,3-d]pyridazin-5(6H)-one

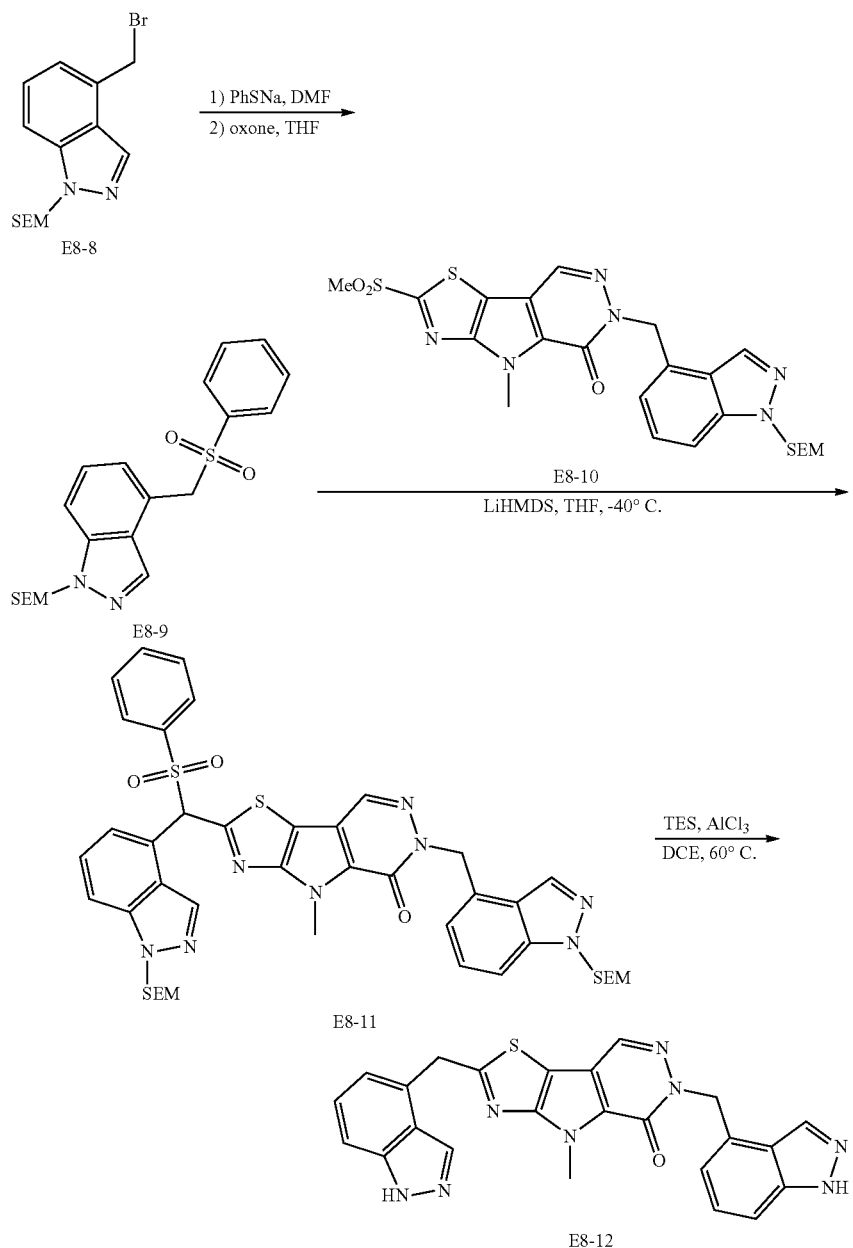

Step A: 4-((phenylthio)methyl)-1-((2-(trimethylsilyl)ethoxy)methyl)-1H-indazole

To a solution of 4-(bromomethyl)-1-((2-(trimethylsilyl)ethoxy)methyl)-1H-indazole (340 mg, 1.0 mmol) in DMF (10 mL) was added sodium benzenethiolate (265 mg, 2 mmol). The mixture was stirred at r.t. for 2 hr. then quenched with ice water (10.0 mL) and extracted with EtOAc. (3×50.0 mL). The combined organic layers were washed with brine, dried over anhydrous $Na_2SO_4$ and concentrated under reduced pressure to afford the crude product (370 mg) which was directly used in the next step. LCMS: m/z 371 (M+H)$^+$.

Step B: 4-((Phenylsulfonyl)methyl)-1-((2-(trimethylsilyl)ethoxy)methyl)-1H-indazole To a solution of 4-((phenylthio)methyl)-1-((2-(trimethylsilyl)ethoxy) methyl)-1H-indazole (370 mg) in THF (20 mL) at 0° C. was added a solution of oxone (2.15 g, 3.5 mmol) in $H_2O$ (20 mL). The mixture was stirred at r.t. for 1 hr. then quenched with ice water (50 mL) and extracted with AcOEt (3×50.0 mL). The combined organic layers were washed with brine, dried over anhydrous $Na_2SO_4$ and concentrated under reduced pressure. The residue was purified by column chromatography on silica gel (eluent: EA/PE=1/5) to afford the desired product (300 mg). LCMS: m/z 403 (M+H)⁺.

Step C: 4-Methyl-2-((phenylsulfonyl)(1-((2-(trimethlyl)ethoxy)methyl)-1H-indazol-4-yl)methyl)-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one To a solution of 4-((phenylsulfonyl)methyl)-1-((2-(trimethylsilyl)ethoxy)methyl)-1H-indazole (163 mg, 0.40 mmol, 2.2 eq) in dry THF (5 mL) at −40° C. was added drop wise LiHMDS (0.46 mL, 0.46 mmol, 2.5 eq). The mixture was stirred at this temperature for 10 min, followed by drop wise addition of a solution of 4-methyl-2-(methylsulfonyl)-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (100 mg, 0.18 mmol, 1.0 eq) in dry THF (3 mL) at −40° C. The mixture was stirred at this temperature for another 30 min till completion. The resulting mixture was poured into icy saturated aqueous NH₄Cl (20 mL) and extracted with EtOAc (3×10 mL). The combined organic layers were washed with water (20 mL), dried over anhydrous Na₂SO₄ and concentrated under reduced pressure. The residue was purified by prep-TLC to give the desired product (100 mg). LCMS: m/z 867 (M+H)⁺.

Step D: 2,6-Bis((1H-indazol-4-yl)methyl)-4-methyl-4H-thiazolo[5,4':4,5]pyrrolo[2,3-d]pyridazin-5(6H)-one To a solution of 4-methyl-2-((phenylsulfonyl)(1-((2-(trimethylsilyl)ethoxy)methyl)-1H-indazol-4-yl)methyl)-6-((1-((2-(trimethylsilyl)ethoxy) methyl)-1H-indazol-4-yl)methyl)-4H-thiazolo[5',4':4,5]pyrrolo[2,3-d]pyridazin-5 (6H)-one (50 mg, 0.06 mmol, 1.0 eq) in dry DCE (2 mL) under N₂ were added AlCl₃ (38 mg, 0.30 mmol, 5.0 eq) and TES (34 mg, 0.30 mmol, 5.0 eq). The mixture was heated to 60° C. for 30 min, then cooled to r.t., poured into water (10 mL) and extracted with DCM/MeOH (V:V=20:1, 3×10 mL). The combined organic layers were dried over anhydrous Na₂SO₄ and concentrated under reduced pressure. The residue was purified by prep-HPLC to give the desired product (5 mg). LCMS: m/z 467 (M+H)⁺. ¹H NMR (400 MHz, DMSO-d₆) δ 13.15 (s, 1H), 13.10 (s, 1H), 8.50 (s, 1H), 8.18 (s, 1H), 8.13 (s, 1H), 7.49 (d, 1H), 7.44 (d, 1H), 7.38-7.30 (m, 1H), 7.29-7.21 (m, 1H), 7.14 (d, 1H), 6.93 (d, 1H), 5.64 (s, 2H), 4.84 (s, 2H), 4.28 (s, 3H).

Example 8D. Synthesis of 2-((1H-pyrazol-3-yl)methyl)-6-((6-aminopyridin-2-yl)methyl)-4-methyl-4H-thiazolo[5',4':4,5]pyrrolo[2,3-d]pyridazin-5(6H)-one and 6-((6-aminopyridin-2-yl)methyl)-4-methyl-2-(1H-pyrazole-3-carbonyl)-4H-thiazolo[5',4': 4,5]pyrrolo[2,3-d]pyridazin-5(6H)-one

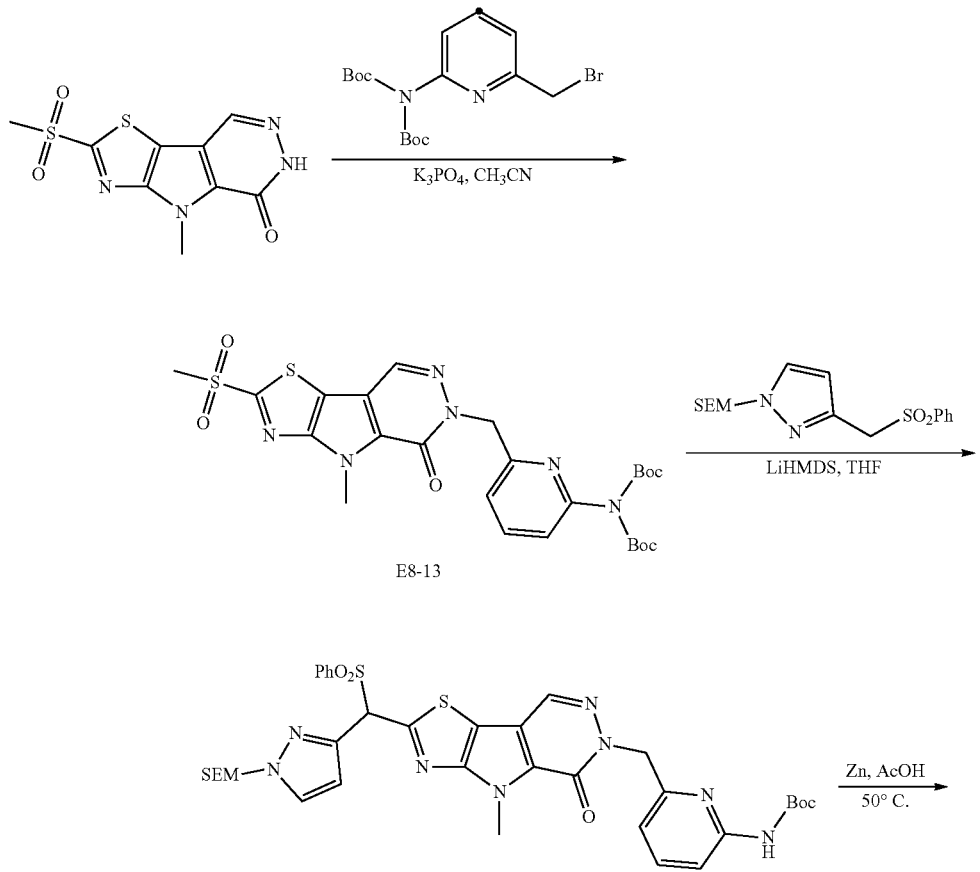

317

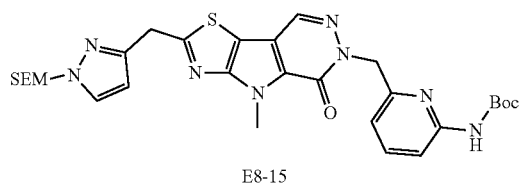

E8-15

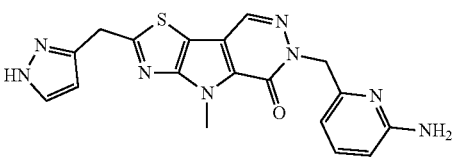

E8-16

-continued

HCl·EtOH
80° C., 1 h

K₂CO₃
DMT

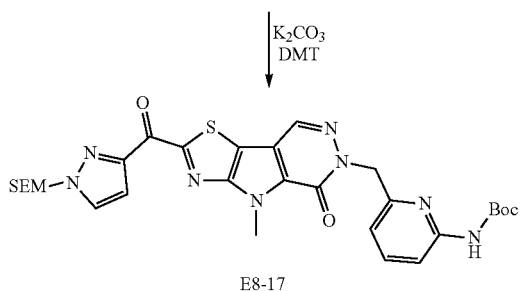

E8-17

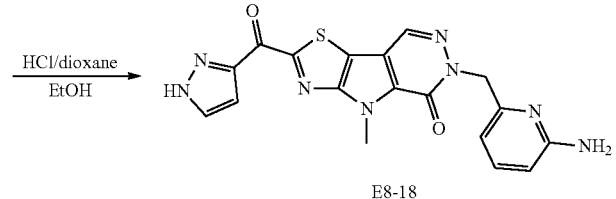

E8-18

HCl/dioxane
EtOH

Step A. tert-butyl N-[(tert-butoxy)carbonyl]-N-[6-({4-methanesulfonyl-7-methyl-9-oxo-3-thia-5,7,10,11-tetraazatricyclo[6.4.0.0 {2,6}]dodeca-1(8),2(6),4,11-tetraen-10-yl}methyl)pyridin-2-yl]carbamate A mixture of 4-methyl-2-(methylsulfonyl)-4H-thiazolo[5',4':4,5]pyrrolo[2,3-d]pyridazin-5(6H)-one (7.5 g, 26.4 mmol) and K₃PO₄ (8.3 g, 39.3 mmol) in anhydrous MeCN (300 mL) was stirred at 70° C. for 1 hr under N₂. Followed a solution of tert-butyl N-[(tert-butoxy)carbonyl]-N-[6-(bromomethyl)pyridin-2-yl]carbamate (11.2 g, 29.0 mmol) in MeCN (30 mL) was added. After stirred at 70° C. for 2.5 hr under N₂, the reaction mixture was quenched with sat. NH₄Cl and extracted with EA (300 mL×3). The combined organic layers were washed with water and brine, dried over Na₂SO₄, filtered and the organic phase was concentrated. The crude product was purified by flash chromatography (silica gel, 0~50% ethyl acetate in petroleum ether) to give tert-butyl N-[(tert-butoxy)carbonyl]-N-[6-({4-methanesulfonyl-7-methyl-9-oxo-3-thia-5,7,10,11-tetraazatricyclo[6.4.0.0 {2,6}]dodeca-1 (8),2(6),4,11-tetraen-10-yl}methyl)pyridin-2-yl]carbamate (5.5 g). LC-MS (ESI) found: 591.1 (M+H)⁺.

Step B. tert-Butyl (6-((4-methyl-5-oxo-2-((phenylsulfonyl)(1-((2-(trimethylsilyl)ethoxy)methyl)-1H-pyrazol-3-yl)methyl)-4H-thiazolo[5',4':4,5]pyrrolo[2,3-d]pyridazin-6(5H)-yl)methyl)pyridin-2-yl)carbamate To a stirred mixture of 3-((phenylsulfonyl)methyl)-1-((2-(trimethylsilyl)ethoxy)methyl)-1H-pyrazole (11.9 g, 33.8 mmol) in anhydrous THF (200 mL) was added LiHMDS (50 mL, 1 M in THF) at −40° C. under argon. After 10 min, the mixture was warmed up to 10° C. and stirred for 1 hr, then tert-butyl N-[(tert-butoxy)carbonyl]-N-[6-({4-methanesulfonyl-7-methyl-9-oxo-3-thia-5,7,10,11-tetraazatricyclo [6.4.0.0 {2,6}]dodeca-1(8),2(6),4,11-tetraen-10-yl}methyl) pyridin-2-yl]carbamate (9.1 g, 15.4 mmol in 35 mL THF) was added. The reaction was stirred at 10° C. for another 30 min. The reaction mixture was poured into aq. NH₄Cl, extracted with EtOAc (200 mL×3). The combined organic layers were washed with water and brine, dried over anhydrous Na₂SO₄ and concentrated. The crude product was purified by flash chromatography (silica gel, 0~50% ethyl acetate in petroleum ether) to give tert-butyl (6-((4-methyl-5-oxo-2-((phenylsulfonyl)(1-((2-(trimethylsilyl)ethoxy) methyl)-1H-pyrazol-3-yl)methyl)-4H-thiazolo[5',4':4,5]pyrrolo[2,3-d]pyridazin-6(5H)-yl)methyl)pyridin-2-yl) carbamate (6.6 g). LC-MS (ESI) found: 763.2 (M+H)⁺.

Step C. tert-Butyl (6-((4-methyl-5-oxo-2-((1-((2-(trimethylsilyl)ethoxy)methyl)-1H-pyrazol-3-yl) methyl)-4H-thiazolo[5',4':4,5]pyrrolo[2,3-d] pyridazin-6(5H)-yl)methyl)pyridin-2-yl)carbamate A solution of tert-butyl (6-((4-methyl-5-oxo-2-((phenylsulfonyl)(1-((2-(trimethylsilyl)ethoxy)methyl)-1H-pyrazol-3-yl)methyl)-4H-thiazolo[5',4':4,5]pyrrolo[2,3-d]pyridazin-6(5H)-yl)methyl)pyridin-2-yl)carbamate (6.0 g, 7.86 mmol) in EtOH/AcOH (35 mL/50 mL) was heated to 50° C. with vigorously stirred in the presence of Zn (2.55 g, 117.9 mmol) for 40 min. Additional zinc were added every 40 min (2.55 g, twice, monitor the reaction by TLC/LC-MS to avoid the byproduct and over reduced product). The solution was filtered and the filter cake was washed with DCM. The filtrate was partly evaporated, neutralized with saturated NaHCO₃ solution, dried over MgSO₄ and the solvent was removed under vacuum. The crude product was purified by flash chromatography (silica gel, DCM: MeOH=40:1) to give tert-butyl (6-((4-methyl-5-oxo-2-((1-((2-(trimethylsilyl)ethoxy)methyl)-1H-pyrazol-3-yl) methyl)-4H-thiazolo[5',4':4,5]pyrrolo[2,3-d]pyridazin-6 (5H)-yl)methyl)pyridin-2-yl)carbamate (3.1 g). LC-MS (ESI) found: 623.3 (M+H)⁺.

Step D. 2-((1H-pyrazol-3-yl)methyl)-6-((6-aminopyridin-2-yl)methyl)-4-methyl-4H-thiazolo[5',4':4,5] pyrrolo[2,3-d]pyridazin-5(6H)-one To a mixture of tert-butyl (6-((4-methyl-5-oxo-2-((1-((2-(trimethylsilyl)ethoxy)methyl)-1H-pyrazol-3-yl)methyl)-4H-thiazolo[5',4':4,5]pyrrolo[2,3-d]pyridazin-6(5H)-yl) methyl)pyridin-2-yl)carbamate (3.0 g, 4.8 mmol) in ethanol (30 mL) was added HCl (30 mL, 4 M in dioxane). The reaction mixture was stirred at 80° C. for 40 min. The reaction mixture was cooled down to r.t., filtered and the solid was collected, suspended in water and neutralized with aqueous NaHCO₃ at 10° C. Filtered to give the desire compound 2-((1H-pyrazol-3-yl)methyl)-6-((6-aminopyridin-2-yl)methyl)-4-methyl-4H-thiazolo[5',4':4,5]pyrrolo[2,3-d]pyridazin-5(6H)-one (1.5 g). LC-MS (ESI) found: 393.2 (M+H)+. 1HNMR (400 MHz, DMSO-d6) δ 12.78 (s, 1H), 8.53 (s, 1H), 7.72 (s, 1H), 7.25 (dd, 1H), 6.33-6.24 (m, 2H), 6.08 (d, 1H), 5.90 (s, 2H), 5.19 (s, 2H), 4.49 (s, 2H), 4.26 (s, 3H).

Step E. Synthesis of tert-butyl (6-((4-methyl-5-oxo-2-(1-((2-(trimethylsilyl)ethoxy)methyl)-1H-pyrazole-3-carbonyl)-4H-thiazolo[5',4':4,5]pyrrolo[2,3-d]pyridazin-6(5H)-yl)methyl)pyridin-2-yl)carbamate To a solution of tert-butyl (6-((4-methyl-5-oxo-2-((1-((2-(trimethylsilyl)ethoxy)methyl)-1H-pyrazol-3-yl)methyl)-4H-thiazolo[5',4':4,5]pyrrolo[2,3-d]pyridazin-6(5H)-yl)methyl)pyridin-2-yl)carbamate (100 mg, 0.16 mmol) in DMF (2 mL) was added K2CO3 (88 mg, 0.64 mmol). The mixture was stirred at 70° C. for 8 hr. The mixture was poured into water, the precipitate was collected by filtration and purified by pre-TLC (2% MeOH in DCM) to afford tert-butyl (6-((4-methyl-5-oxo-2-(1-((2-(trimethylsilyl)ethoxy)methyl)-1H-pyrazole-3-carbonyl)-4H-thiazolo[5',4':4,5]pyrrolo[2,3-d]pyridazin-6(5H)-yl)methyl)pyridin-2-yl)carbamate (20 mg). LC-MS (ESI): m/z 637 (M+H)+.

Step F. Synthesis of 6-((6-aminopyridin-2-yl)methyl)-4-methyl-2-(1H-pyrazole-3-carbonyl)-4H-thiazolo[5',4':4,5]pyrrolo[2,3-d]pyridazin-5(6H)-one To a solution of tert-butyl (6-((4-methyl-5-oxo-2-(1-((2-(trimethylsilyl)ethoxy)methyl)-1H-pyrazole-3-carbonyl)-4H-thiazolo[5',4':4,5]pyrrolo[2,3-d]pyridazin-6(5H)-yl)methyl)pyridin-2-yl)carbamate (20 mg, 0.03 mmol) in EtOH (1 mL) was added HCl (1 mL, 4 mol/L in dioxane). The mixture was stirred at 80° C. for 1 hr and cooled down. The precipitate was collected by filtration and neutralized with sat. NaHCO3, washed with water and dried to afford 5 mg of 6-((6-aminopyridin-2-yl)methyl)-4-methyl-2-(1H-pyrazole-3-carbonyl)-4H-thiazolo[5',4':4,5]pyrrolo[2,3-d]pyridazin-5(6H)-one. LC-MS (ESI): m/z 407 (M+H)+. 1H NMR (400 MHz, DMSO-d6) δ: 8.75 (s, 1H), 7.96 (s, 1H), 7.50 (s, 1H), 7.31-7.22 (m, 1H), 6.31 (d, 1H), 6.14 (d, 1H), 5.91 (s, 2H), 5.23 (s, 2H), 4.38 (s, 3H).

Example 8E. Synthesis of 6-((1H-pyrazol-3-yl)methyl)-2-((6-(dimethylamino)pyridin-2-yl)methyl)-4-methyl-4,6-dihydro-5H-thiazolo[5',4':4,5]pyrrolo[2,3-d]pyridazin-5-one

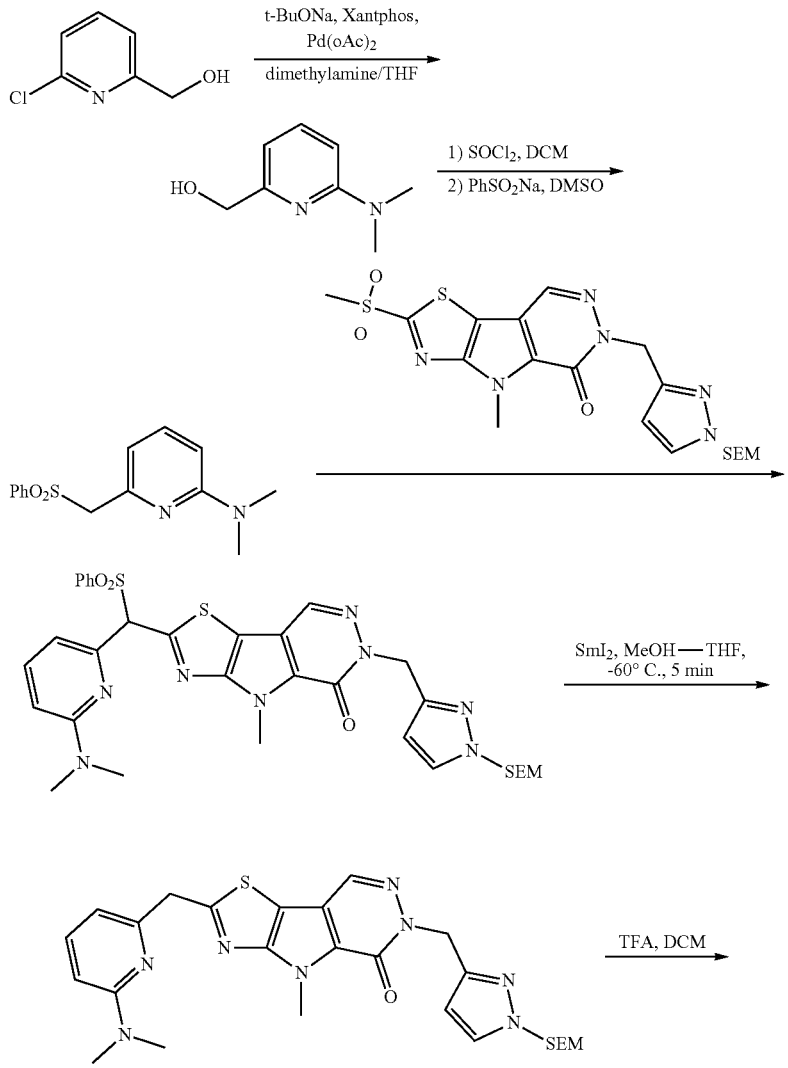

-continued

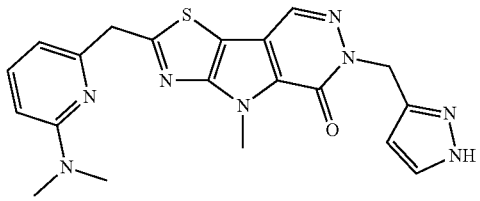

E8-19

Step A. (6-(dimethylamino)pyridin-2-yl)methanol

To a solution of (6-chloropyridin-2-yl)methanol (500 mg, 2.67 mmol) in dimethylamine in THF (35 mL) was added Pd(OAc)$_2$ (78 mg, 0.35 mmol), Xantphos (170 mg, 0.29 mmol) and t-BuONa (385 mg, 4.01 mmol). The reaction mixture was stirred at 100° C. for 18 h. The reaction mixture was filtered and concentrated under reduced pressure. The residue was purified by flash chromatography (silica gel, 0~35% ethyl acetate in petroleum ether) to afford (6-(dimethylamino)pyridin-2-yl)methanol (180 mg). LCMS: 153 (M+H)$^+$.

Step B. 6-(chloromethyl)-N,N-dimethylpyridin-2-amine

To a stirred mixture of (6-(dimethylamino)pyridin-2-yl)methanol (170 mg, 1.1 mmol) in DCM (10 mL) was added SOCl$_2$ (665 mg, 5.6 mmol) at 0° C. The reaction mixture was stirred at r.t for 1 hr. The reaction mixture was adjusted at pH=7~8 with aq. NaHCO$_3$. Then the mixture was extracted with DCM, washed with water and brine. The organic layer was dried over Na$_2$SO$_4$, concentrated under reduced pressure to afford 6-(chloromethyl)-N,N-dimethylpyridin-2-amine (70 mg). LCMS: 171 (M+H)$^+$.

Step C. N,N-dimethyl-6-((phenylsulfonyl)methyl)pyridin-2-amine

To a stirred mixture of 6-(chloromethyl)-N,N-dimethylpyridin-2-amine (500 mg, 2.94 mmol) in DMSO (10 mL) was added PhSO$_2$Na (1.44 g, 8.82 mmol) at r.t. The mixture was stirred at r.t for 18 hr. The reaction mixture was poured into water and extracted with DCM. The mixture was washed with water and the organic layer was concentrated under reduced pressure. The residue was purified by flash chromatography (silica gel, 0~20% ethyl acetate in petroleum ether) to afford N,N-dimethyl-6-((phenylsulfonyl)methyl)pyridine-2-amine (380 mg). LCMS: 277 (M+H)$^+$.

Step D. 2-((6-(dimethylamino)pyridin-2-yl)(phenylsulfonyl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one To a stirred mixture of 4-methyl-2-(methylsulfonyl)-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (180 mg, 0.36 mmol), which was synthesized similar to compound E8-1 in Example 8A, in dry THF (10 mL) was added N,N-dimethyl-6-((phenylsulfonyl)methyl)pyridin-2-amine (120 mg, 0.44 mmol) and t-BuOK (122 mg, 1.1 mmol) at 60° C. under N$_2$. The mixture was stirred at 60° C. for 2 h under N$_2$. Then the mixture was poured into the water and extracted with EtOAc, washed with water and brine. The organic layer was dried over Na$_2$SO$_4$, concentrated under reduced pressure and purified by Prep-TLC (PE:EtOAc=1:1.5) to afford 2-((6-(dimethylamino)pyridin-2-yl)(phenylsulfonyl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (50 mg). LCMS: 691 (M+H)$^+$.

Step E. 2-((6-(dimethylamino)pyridin-2-yl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one To a mixture of 2-((6-(dimethylamino)pyridin-2-yl)(phenylsulfonyl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (50 mg, 0.07 mmol) in THF (5 mL) and MeOH (5 mL) at r.t under N$_2$ was added SmI$_2$ (5 mL, 0.1M in THF) at −40° C. The reaction mixture was stirred at −40° C. for 10 min and then quenched with water. The following mixture was extracted with EtOAc twice. The combined organic layers were washed with brine (30 mL), dried over anhydrous Na$_2$SO$_4$ and concentrated under reduced pressure. The residue was purified by prep-TLC (PE/EtOAc=1/1.5) to give the desired product (10 mg). LCMS: m/z 551 (M+H)$^+$.

Step F. 6-((1H-pyrazol-3-yl)methyl)-2-((6-(dimethylamino)pyridin-2-yl)methyl)-4-methyl-4H-thiazolo[5',4':4,5]pyrrolo[2,3-d]pyridazin-5(6H)-one A mixture of 2-((6-(dimethylamino)pyridin-2-yl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (10 mg, 0.018 mmol) in DCM/TFA (2 mL/2 mL) was stirred at r.t for 1 hour. The reaction mixture was concentrated. The residue was purified by prep-HPLC to afford desired product (1.4 mg). LCMS: 421 (M+H)$^+$. $^1$H NMR (400 MHz, DMSO) δ 8.51 (s, 1H), 7.55 (s, 1H), 7.48 (dd, 1H), 6.64 (d, 1H), 6.54 (d, 1H), 6.11 (d, 1H), 5.32 (s, 2H), 4.44 (s, 2H), 4.26 (s, 3H), 3.05 (s, 6H).

The following compounds were synthesized according to Scheme E8 and Example 8C using the appropriate starting material. Standard protection and deprotection can be used when necessary.

| Cpd No. | Structure | Characterization |
|---|---|---|
| E8-20 | 6-((1H-indazol-4-yl)methyl)-4-methyl-2-(4-((phenylsulfonyl)methyl)-1H-imidazol-1-yl)-4H-thiazolo[5',4':4,5]pyrrolo[2,3-d]pyridazin-5(6H)-one | LCMS: m/z 557 (M + H)$^+$. 1H-NMR (400 MHz, DMSO-d6) δ 13.13 (s, 1H), 8.70 (s, 1H), 8.48 (d, 1H), 8.16 (s, 1H), 7.91-7.72 (m, 4H), 7.63 (t, 2H), 7.47 (d, 1H), 7.36-7.22 (m, 1H), 6.98 (d, 1H), 5.67 (s, 2H), 4.69 (s, 2H), 4.49 (s, 3H) |
| E8-21 | 2-((1H-imidazol-4-yl)methyl)-6-((1H-indazol-4-yl)methyl)-4-methyl-4H-thiazolo[5',4':4,5]pyrrolo[2,3-d]pyridazin-5(6H)-one | LCMS: m/z 417 (M + H)$^+$. 1H NMR (400 MHz, DMSO-d6) δ 13.11 (s, 1H), 12.01 (s, 1H), 8.53 (s, 1H), 8.14 (s, 1H), 7.64 (s, 1H), 7.45 (d, 1H), 7.27 (dd, 1H), 7.09 (s, 1H), 6.96 (d, 1H), 5.65 (s, 2H), 4.39 (s, 2H), 4.27 (s, 3H) |
| E8-22 | 6-((1H-indazol-4-yl)methyl)-2-((2-aminothiazol-5-yl)methyl)-4-methyl-4H-thiazolo[5',4':4,5]pyrrolo[2,3-d]pyridazin-5(6H)-one | LCMS: m/z 449 (M + H)$^+$. 1H NMR (400 MHz, DMSO) δ 8.54 (s, 1H), 8.11 (s, 1H), 7.46 (d, 1H), 7.33-7.24 (m, 1H), 7.08 (s, 1H), 6.96 (d, 1H), 5.64 (s, 2H), 4.53 (s, 2H), 4.24 (s, 3H). |
| E8-23 | 6-((1H-indazol-4-yl)methyl)-4-methyl-2-(oxazol-5-ylmethyl)-4H-thiazolo[5',4':4,5]pyrrolo[2,3-d]pyridazin-5(6H)-one | LCMS: m/z 418 (M + H)$^+$. 1H NMR (400 MHz, DMSO-d6) δ 13.11 (s, 1H), 8.59 (s, 1H), 8.36 (s, 1H), 8.14 (s, 1H), 7.45 (d, 1H), 7.33-7.24 (m, 1H), 7.19 (s, 1H), 6.96 (d, 1H), 5.66 (s, 2H), 4.72 (s, 2H), 4.27 (s, 3H). |

-continued

| Cpd No. | Structure | Characterization |
|---|---|---|
| E8-24 | 3-((6-((1H-indazol-4-yl)methyl)-4-methyl-5-oxo-5,6-dihydro-4H-thiazolo[5′,4′:4,5]pyrrolo[2,3-d]pyridazin-2-yl)methyl)benzenesulfonamide | LC-MS: m/z 506 (M + H)+. 1H NMR (400 MHz, DMSO) δ 13.12 (s, 1H), 8.56 (s, 1H), 8.13 (s, 1H), 7.85 (s, 1H), 7.76 (d, 1H), 7.65 (d, 1H), 7.58 (dd, 1H), 7.45 (d, 1H), 7.38 (s, 2H), 7.30-7.25 (m, 1H), 6.95 (m, 1H), 5.65 (s, 2H), 4.64 (s, 2H), 4.27 (s, 3H). |
| E8-25 | 6-(1H-Indazol-4-ylmethyl)-2-(1H-indazol-6-ylmethyl)-8-methyl-6,8-dihydro-3-thia-1,5,6,8-tetraaza-cyclopenta[a]inden-7-one | LC-MS: m/z 467 (M + H)+. 1H NMR (400 MHz, DMSO) δ 13.13 (s, 1H), 13.09 (s, 1H), 8.52 (s, 1H), 8.13 (s, 1H), 8.05 (s, 1H), 7.75 (d, 1H), 7.59 (s, 1H), 7.45 (d, 1H), 7.30-7.25 (m, 1H), 7.14 (d, 1H), 6.95 (d, 1H), 5.64 (s, 2H), 4.64 (s, 2H), 4.28 (s, 3H). |
| E8-26 | 4-((6-((1H-indazol-4-yl)methyl)-4-methyl-5-oxo-5,6-dihydro-4H-thiazolo[5′,4′:4,5]pyrrolo[2,3-d]pyridazin-2-yl)methyl)thiazole-5-carboxamide | LCMS: m/z 477 (M + H)+. 1H NMR (400 MHz, DMSO-d6) δ 13.11 (s, 1H), 9.14 (s, 1H), 8.54 (s, 1H), 8.13 (s, 1H), 8.01 (s, 1H), 7.70 (s, 1H), 7.45 (d, 1H), 7.27 (dd, 1H), 6.95 (d, 1H), 5.65 (s, 2H), 4.99 (s, 2H), 4.26 (s, 3H) |
| E8-27 | 6-((1H-indazol-4-yl)methyl)-2-((5-fluoro-1H-pyrazol-3-yl)methyl)-4-methyl-4H-thiazolo[5′,4′:4,5]pyrrolo[2,3-d]pyridazin-5(6H)-one | LCMS: m/z 435 (M + H)+. 1H NMR (400 MHz, DMSO-d6) δ 13.12 (s, 1H), 12.53 (s, 1H), 8.59 (s, 1H), 8.14 (s, 1H), 7.45 (d, 1H), 7.28 (d, 1H), 6.96 (d, 1H), 5.96 (d, 1H), 5.66 (s, 2H), 4.53 (s, 2H), 4.27 (s, 3H) |

| Cpd No. | Structure | Characterization |
|---|---|---|
| E8-28 | 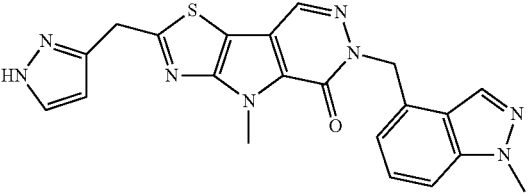<br>2-((1H-pyrazol-3-yl)methyl)-4-methyl-6-((1-methyl-1H-indazol-4-yl)methyl)-4H-thiazolo[5′,4′:4,5]pyrrolo[2,3-d]pyridazin-5(6H)-one | LCMS: m/z 431 (M + H)+.<br>1H NMR (400 MHz, DMSO-d6) δ 12.77 (s, 1H), 8.54 (s, 1H), 8.11 (d, 1H), 7.71 (s, 1H), 7.55 (d, 1H), 7.33 (m, 1H), 6.98 (d, 1H), 6.26 (d, 1H), 5.64 (s, 2H), 4.48 (s, 2H), 4.27 (s, 3H), 4.02 (s, 3H). |
| E8-29 | 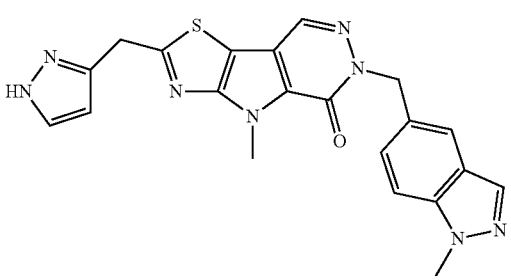<br>2-((1H-pyrazol-3-yl)methyl)-4-methyl-6-((1-methyl-1H-indazol-5-yl)methyl)-4H-thiazolo[5′,4′:4,5]pyrrolo[2,3-d]pyridazin-5(6H)-one | LCMS: m/z 431 (M + H)+.<br>1H NMR (400 MHz, DMSO-d6) δ 12.77 (s, 1H), 8.53 (s, 1H), 8.00 (s, 1H), 7.72-7.64 (m, 2H), 7.58 (d, 1H), 7.43 (dd, 1H), 6.25 (d, 1H), 5.44 (s, 2H), 4.47 (s, 2H), 4.27 (s, 3H), 4.00 (s, 3H) |
| E8-30 | 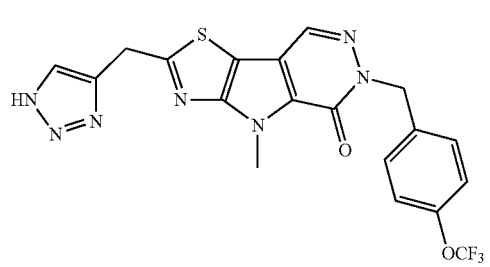<br>2-((1H-1,2,3-triazol-4-yl)methyl)-4-methyl-6-(4-(trifluoromethoxy)benzyl)-4,6-dihydro-5H-thiazolo[5′,4′:4,5]pyrrolo[2,3-d]pyridazin-5-one | LCMS: m/z 462 (M + H )+.<br>1H NMR (400 MHz, DMSO-d6) δ 15.00 (s, 1H), 8.57 (s, 1H), 7.89 (s, 1H), 7.43 (d, 2H), 7.32 (d, 2H), 5.38 (s, 2H), 4.63 (s, 2H), 4.26 (s, 3H). |
| E8-31 | 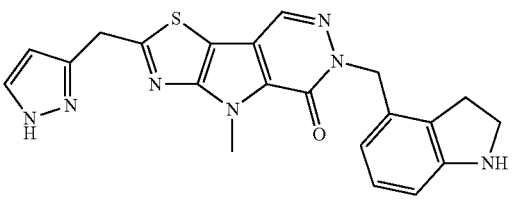<br>2-((1H-pyrazol-3-yl)methyl)-6-(indolin-4-ylmethyl)-4-methyl-4H-thiazolo[5′,4′:4,5]pyrrolo[2,3-d]pyridazin-5(6H)-one | LC-MS: m/z 418 (M + 1)+.<br>1H NMR (400 MHz, DMSO) δ 12.77 (s, 1H), 8.51 (s, 1H), 7.70 (s, 1H), 6.80 (dd, 1H), 6.37 (d, 1H), 6.32 (d, 1H), 6.26 (d, 1H), 5.49 (s, 1H), 5.22 (s, 2H), 4.49 (s, 2H), 4.26 (s, 3H), 3.41 (t, 2H), 2.95 (t, 2H). |

| Cpd No. | Structure | Characterization |
|---|---|---|
| E8-32 | 6-((1H-indazol-4-yl)methyl)-2-((4-fluoro-1H-pyrazol-3-yl)methyl)-4-methyl-4H-thiazolo[5',4':4,5]pyrrolo[2,3-d]pyridazin-5(6H)-one | LC-MS: m/z 435 (M + 1)+. 1H NMR (400 MHz, DMSO) δ 13.12 (s, 1H), 12.77 (s, 1H), 8.56 (s, 1H), 8.14 (s, 1H), 7.86 (s, 1H), 7.45 (d, 1H), 7.35-7.17 (m, 1H), 6.96 (d, 1H), 5.65 (s, 2H), 4.50 (s, 2H), 4.27 (s, 3H). |
| E8-33 | 4-((6-((1H-indazol-4-yl)methyl)-4-methyl-5-oxo-5,6-dihydro-4H-thiazolo[5',4':4,5]pyrrolo[2,3-d]pyridazin-2-yl)methyl)thiazole-2-carboxamide | LCMS: m/z 477 (M + H)+. 1H NMR (400 MHz, DMSO) δ 13.18 (s, 1H), 8.63 (s, 1H), 8.20 (s, 1H), 8.14 (s, 1H), 8.02 (s, 1H), 7.92 (s, 1H), 7.52 (d, 1H), 7.38-7.26 (m, 1H), 7.03 (d, 1H), 5.72 (s, 2H), 4.79 (s, 2H), 4.34 (s, 3H) |
| E8-34 | 2-((1,3,4-oxadiazol-2-yl)methyl)-6-((1H-indazol-4-yl)methyl)-4-methyl-4H-thiazolo[5',4':4,5]pyrrolo[2,3-d]pyridazin-5(6H)-one | LCMS: m/z 419 (M + H)+. 1H NMR (400 MHz, DMSO) δ 13.13 (s, 1H), 9.26 (s, 1H), 8.63 (s, 1H), 8.15 (s, 1H), 7.46 (d, 1H), 7.33-7.20 (m, 1H), 6.97 (d, 1H), 5.67 (s, 2H), 5.02 (s, 2H), 4.27 (s, 3H) |
| E8-35 | 2-((1H-indazol-7-yl)methyl)-6-((1H-pyrazol-3-yl)methyl)-4-methyl-4H-thiazolo[5',4':4,5]pyrrolo[2,3-d]pyridazin-5(6H)-one | LCMS: m/z 417 (M + H)+. 1H NMR (400 MHz, DMSO) δ 13.33 (s, 1H), 12.63 (s, 1H), 8.42 (s, 1H), 8.13 (s, 1H), 7.74 (d, 1H), 7.58 (s, 1H), 7.35 (d, 1H), 7.14 (t, 1H), 6.10 (s, 1H), 5.30 (s, 2H), 4.81 (s, 2H), 4.25 (s, 3H). |

| Cpd No. | Structure | Characterization |
|---|---|---|
| E8-36 | 2-((1H-1,2,4-triazol-3-yl)methyl)-6-((1H-indazol-4-yl)methyl)-4-methyl-4H-thiazolo[5',4':4,5]pyrrolo[2,3-d]pyridazin-5(6H)-one | LC-MS: m/z 418 (M + H)+. 1H NMR (400 MHz, DMSO-d6) δ 13.14 (s, 1H), 8.54 (s, 1H), 8.38-8.37 (m, 1H), 8.13 (s, 1H), 7.46 (d, 1H), 7.31-7.27 (m, 1H), 6.95 (d, 1H), 5.65 (s, 2H), 4.61 (s, 2H), 4.25 (s, 3H). |
| E8-37 | 6-benzyl-4-methyl-2-(pyridin-2-ylmethyl)-4H-thiazolo[5',4':4,5]pyrrolo[2,3-d]pyridazin-5(6H)-one | LCMS: m/z 388 (M + H)+. 1H NMR (400 MHz, DMSO-d6) δ 8.61 (d, 1H), 8.59 (s, 1H), 7.89-7.83 (m, 1H), 7.55 (d, 1H), 7.39-7.30 (m, 6H), 5.39 (s, 2H), 4.71 (s, 2H), 4.30 (s, 3H). |
| E8-38 | 2-((1H-benzo[d][1,2,3]triazol-4-yl)methyl)-6-((1H-indazol-4-yl)methyl)-4-methyl-4H-thiazolo[5',4':4,5]pyrrolo[2,3-d]pyridazin-5(6H)-one | LC-MS: 468 [M + H]+. 1H NMR (400 MHz, DMSO) δ 13.14 (s, 1H), 8.50 (s, 1H), 8.13 (s, 1H), 7.83 (d, 1H), 7.52-7.42 (m, 3H), 7.27 (dd, 1H), 6.94 (d, 1H), 5.64 (s, 2H), 4.95 (s, 2H), 4.26 (s, 3H). |
| E8-39 | 6-((1H-indazol-4-yl)methyl)-2-((2H-1,2,3-triazol-4-yl)methyl)-4-methyl-4H-thiazolo[5',4':4,5]pyrrolo[2,3-d]pyridazin-5(6H)-one | LC-MS: 418 [M + 1]+. 1H NMR (400 MHz, DMSO) δ 13.13 (s, 1H), 8.57 (s, 1H), 8.14 (s, 1H), 7.88 (s, 1H), 7.46 (d, 1H), 7.34-7.23 (m, 1H), 6.96 (d, 1H), 5.66 (s, 2H), 4.63 (s, 2H), 4.28 (s, 3H). |
| E8-40 | 6-benzyl-4-methyl-2-(thiazol-4-ylmethyl)-4H-thiazolo[5',4':4,5]pyrrolo[2,3-d]pyridazin-5(6H)-one | LC-MS: 394 [M + 1]+. 1H NMR (400 MHz, DMSO) δ 9.12 (d, 1H), 8.55 (s, 1H), 7.71 (d, 1H), 7.35-7.22 (m, 5H), 5.35 (s, 2H), 4.70 (s, 2H), 4.26 (s, 3H). |

-continued

| Cpd No. | Structure | Characterization |
|---|---|---|
| E8-41 | 6-((1H-indazol-4-yl)methyl)-2-((5-bromothiazol-4-yl)methyl)-4-methyl-4H-thiazolo[5′,4′:4,5]pyrrolo[2,3-d]pyridazin-5(6H)-one | LCMS: m/z 512 (M + 2H)+. <br> $^1$H NMR (400 MHz, DMSO-$d_6$) δ 13.11 (s, 1H), 9.19 (s, 1H), 8.56 (s, 1H), 8.14 (s, 1H), 7.45 (d, 1H), 7.28 (t, 1H), 6.95 (d, 1H), 5.65 (s, 2H), 4.65 (s, 2H), 4.27 (s, 3H). |
| E8-42 | 6-((1H-indazol-4-yl)methyl)-2-((2-methoxypyridin-3-yl)methyl)-4-methyl-4,6-dihydro-5H-thiazolo[5′,4′:4,5]pyrrolo[2,3-d]pyridazin-5-one | LCMS: m/z 458 (M + H)+. <br> $^1$H NMR (400 MHz, DMSO-$d_6$) δ 13.11 (s, 1H), 8.53 (s, 1H), 8.17-8.11 (m, 2H), 7.78 (d, 1H), 7.44 (d, 1H), 7.28 (d, 1H), 7.02 (dd, 1H), 6.94 (d, 1H), 5.65 (s, 2H), 4.43 (s, 2H), 4.26 (s, 3H), 3.87 (s, 3H). |
| E8-43 | 6-((1H-indazol-4-yl)methyl)-4-methyl-2-((2-oxo-1,2-dihydropyridin-3-yl)methyl)-4H-thiazolo[5′,4′:4,5]pyrrolo[2,3-d]pyridazin-5(6H)-one | LCMS: m/z 444 (M + H)+. <br> $^1$H NMR (400 MHz, DMSO-$d_6$) δ 13.12 (s, 1H), 11.76 (s, 1H), 8.53 (s, 1H), 8.14 (s, 1H), 7.57 (dd, 1H), 7.40 (d, 1H), 7.37 (dd, 1H), 7.28 (dd, 1H), 6.95 (d, 1H), 6.21 (t, 1H), 5.65 (s, 2H), 4.24 (s, 3H), 4.22 (s, 2H). |
| E8-44 | 6-((1H-indazol-4-yl)methyl)-4-methyl-2-((2-oxo-2,3-dihydro-1H-benzo[d]imidazol-4-yl)methyl)-4H-thiazolo[5′,4′:4,5]pyrrolo[2,3-d]pyridazin-5(6H)-one | LCMS: m/z 483 (M + H)+. <br> $^1$H NMR (400 MHz, DMSO) δ 13.11 (s, 1H), 10.93 (s, 1H), 10.71 (s, 1H), 8.52 (s, 1H), 8.13 (s, 1H), 7.45 (d, 1H), 7.33-7.18 (m, 1H), 7.02-6.79 (m, 4H), 5.64 (s, 2H), 4.56 (s, 2H), 4.27 (s, 2H). |

| Cpd No. | Structure | Characterization |
|---|---|---|
| E8-45 | 2-((2H-1,2,3-triazol-4-yl)methyl)-6-(2-fluoro-3-(trifluoromethoxy)benzyl)-4-methyl-4H-thiazolo[5′,4′:4,5]pyrrolo[2,3-d]pyridazin-5(6H)-one | LC-MS: m/z 480 (M + H)+. <br> 1H NMR (400 MHz, DMSO) δ 8.58 (s, 1H), 7.65 (s, 1H), 7.49 (s, 1H), 7.25 (d, 2H), 5.46 (s, 2H), 4.63 (s, 2H), 4.26 (s, 3H). |
| E8-46 | 2-((1H-1,2,3-triazol-4-yl)methyl)-6-benzyl-4-methyl-4,6-dihydro-5H-thiazolo[5′,4′:4,5]pyrrolo[2,3-d]pyridazin-5-one | LC-MS m/z 378 (M + H)+. <br> 1H NMR (400 MHz, DMSO) δ 8.55 (s, 1H), 7.88 (s, 1H), 7.33-7.24 (m, 5H), 5.35 (s, 2H), 4.63 (s, 2H), 4.26 (s, 3H) |
| E8-47 | 2-((1H-indazol-7-yl)methyl)-4-methyl-6-((1-methyl-1H-pyrazol-3-yl)methyl)-4H-thiazolo[5′,4′:4,5]pyrrolo[2,3-d]pyridazin-5(6H)-one | LC-MS m/z 431.0 (M + H)+. <br> 1H NMR (400 MHz, DMSO) δ 13.33 (s, 1H), 8.44 (s, 1H), 8.13 (s, 1H), 7.74 (d, 1H), 7.55 (d, 1H), 7.36 (d, 1H), 7.17-7.10 (m, 1H), 6.06 (d, 1H), 5.25 (s, 2H), 4.84 (s, 2H), 4.27 (s, 3H), 3.75 (s, 3H) |
| E8-48 | 6-((1H-indazol-4-yl)methyl)-2-((1H-indazol-6-yl)methyl)-4-methyl-4,6-dihydro-5H-thiazolo[5′,4′:4,5]pyrrolo[2,3-d]pyridazin-5-one | LCMS: m/z 467 (M + H)+. <br> 1H NMR (400 MHz, DMSO-d6) δ 13.13 (s, 1H), 13.09 (s, 1H), 8.52 (s, 1H), 8.13 (s, 1H), 8.05 (s, 1H), 7.75 (d, 1H), 7.59 (s, 1H), 7.45 (d, 1H), 7.30-7.22 (m, 1H), 7.14 (d, 1H), 6.95 (d, 1H), 5.64 (s, 2H), 4.64 (s, 2H), 4.28 (s, 3H). |

| Cpd No. | Structure | Characterization |
|---|---|---|
| E8-49 | 6-((1H-indazol-4-yl)methyl)-2-((1H-indazol-5-yl)methyl)-4-methyl-4,6-dihydro-5H-thiazolo[5′,4′:4,5]pyrrolo[2,3-d]pyridazin-5-one | LCMS: m/z 467 (M + H)+. <br> 1H NMR (400 MHz, DMSO-d6) δ 13.10 (s, 1H), 13.07 (s, 1H), 8.51 (s, 1H), 8.13 (s, 1H), 8.06 (s, 1H), 7.80 (s, 1H), 7.54 (d, 1H), 7.44 (d, 1H), 7.40-7.34 (m, 1H), 7.30-7.22 (m, 1H), 6.94 (d, 1H), 5.64 (s, 2H), 4.60 (s, 2H), 4.28 (s, 3H). |
| E8-50 | 6-((1H-indazol-4-yl)methyl)-2-((1H-indazol-7-yl)methyl)-4-methyl-4,6-dihydro-5H-thiazolo[5′,4′:4,5]pyrrolo[2,3-d]pyridazin-5-one | LCMS: m/z 467 (M + H)+. <br> 1H NMR (400 MHz, DMSO-d6) δ 13.33 (s, 1H), 13.11 (s, 1H), 8.50 (s, 1H), 8.13 (s, 2H), 7.74 (d, 1H), 7.44 (d, 1H), 7.36 (d, 1H), 7.26 (d, 1H), 7.13 (t, 1H), 6.95 (d, 1H), 5.64 (s, 2H), 4.84 (s, 2H), 4.28 (s, 3H). |
| E8-51 | 6-((1H-indazol-4-yl)methyl)-2-((4-chloro-1H-pyrazol-3-yl)methyl)-4-methyl-4,6-dihydro-5H-thiazolo[5′,4′:4,5]pyrrolo[2,3-d]pyridazin-5-one | LCMS: m/z 451 (M + H)+. <br> 1H NMR (400 MHz, DMSO) δ 13.20 (s, 1H), 13.14 (s, 1H), 8.52 (s, 1H), 8.12 (s, 1H), 7.96 (s, 1H), 7.46 (d, 1H), 7.28 (dd, 1H), 6.95 (d, 1H), 5.64 (s, 2H), 4.47 (s, 2H), 4.25 (s, 3H). |
| E8-52 | 6-((1H-indazol-4-yl)methyl)-4-methyl-2-((6-methylpyridin-2-yl)methyl)-4,6-dihydro-5H-thiazolo[5′,4′:4,5]pyrrolo[2,3-d]pyridazin-5-one | LCMS: m/z 442 (M + H)+. <br> 1H NMR (400 MHz, DMSO) δ 13.11 (s, 1H), 8.56 (s, 1H), 8.13 (s, 1H), 7.68 (dd, 1H), 7.45 (d, 1H), 7.37-7.25 (m, 2H), 7.18 (d, 1H), 6.95 (d, 1H), 5.65 (s, 2H), 4.61 (s, 2H), 4.27 (s, 3H), 2.47 (s, 3H). |

| Cpd No. | Structure | Characterization |
|---|---|---|
| E8-53 | 6-((1H-indazol-4-yl)methyl)-4-methyl-2-((1-methyl-1H-pyrazol-3-yl)methyl)-4,6-dihydro-5H-thiazolo[5',4':4,5]pyrrolo[2,3-d]pyridazin-5-one | LCMS: m/z 431 (M + H)$^+$. $^1$H NMR (400 MHz, DMSO-d$_6$) δ 13.11 (s, 1H), 8.54 (s, 1H), 8.14 (s, 1H), 7.65 (d, 1H), 7.45 (d, 1H), 7.35-7.16 (m, 1H), 6.96 (d, 1H), 6.22 (d, 1H), 5.65 (s, 2H), 4.43 (s, 2H), 4.27 (s, 3H), 3.81 (s, 3H). |
| E8-54 | 6-((1H-indazol-4-yl)methyl)-4-methyl-2-((5-(trifluoromethyl)-1H-pyrazol-3-yl)methyl)-4,6-dihydro-5H-thiazolo[5',4':4,5]pyrrolo[2,3-d]pyridazin-5-one | LCMS: m/z 485 (M + H)$^+$. $^1$H NMR (400 MHz, DMSO-d$_6$) δ 13.77 (s, 1H), 13.11 (s, 1H), 8.59 (s, 1H), 8.14 (s, 1H), 7.45 (d, 1H), 7.35-7.13 (m, 1H), 6.96 (d, 1H), 6.71 (s, 1H), 5.65 (s, 2H), 4.65 (s, 2H), 4.28 (s, 3H). |
| E8-55 | 6-((1H-indazol-4-yl)methyl)-4-methyl-2-((4-(trifluoromethyl)-1H-pyrazol-3-yl)methyl)-4,6-dihydro-5H-thiazolo[5',4':4,5]pyrrolo[2,3-d]pyridazin-5-one | LCMS: m/z 485 (M + H)$^+$. $^1$H NMR (400 MHz, DMSO-d$_6$) δ 13.58 (s, 1H), 13.11 (s, 1H), 8.55 (s, 1H), 8.42 (s, 1H), 8.14 (s, 1H), 7.45 (d, 1H), 7.27 (t, 1H), 6.95 (d, 1H), 5.65 (s, 2H), 4.58 (s, 2H), 4.26 (s, 3H). |
| E8-56 | 6-((1H-indazol-4-yl)methyl)-2-(isoxazol-3-ylmethyl)-4-methyl-4,6-dihydro-5H-thiazolo[5',4':4,5]pyrrolo[2,3-d]pyridazin-5-one | LCMS: m/z 418 (M + H)$^+$. $^1$H NMR (400 MHz, DMSO-d$_6$) δ 8.98 (d, 1H), 8.66 (s, 1H), 8.20 (d, 1H), 7.52 (d, 1H), 7.34 (dd, 1H), 7.02 (d, 1H), 6.71 (d, 1H), 5.72 (s, 2H), 4.74 (s, 2H), 4.33 (s, 3H). |

| Cpd No. | Structure | Characterization |
|---|---|---|
| E8-57 | 6-((1H-indazol-4-yl)methyl)-2-((2-aminothiazol-4-yl)methyl)-4-methyl-4,6-dihydro-5H-thiazolo[5',4':4,5]pyrrolo[2,3-d]pyridazin-5-one | LCMS: m/z 449 (M + H)$^+$. $^1$H NMR (400 MHz, MeOD) δ 8.40 (s, 1H), 8.22 (s, 1H), 7.46 (d, 1H), 7.33 (dd, 1H), 7.11 (d, 1H), 6.46 (s, 1H), 5.74 (s, 2H), 4.58 (s, 3H), 4.33 (s, 2H). |
| E8-58 | Ethyl4-((6-((1H-indazol-4-yl)methyl)-4-methyl-5-oxo-5,6-dihydro-4H-thiazolo[5',4':4,5]pyrrolo[2,3-d]pyridazin-2-yl)methyl)thiazole-5-carboxylate | LCMS: m/z 506 (M + H)$^+$. $^1$H NMR (400 MHz, DMSO-d$_6$) δ 13.11 (s, 1H), 9.31 (s, 1H), 8.55 (s, 1H), 8.13 (s, 1H), 7.45 (d, 1H), 7.35-7.16 (m, 1H), 6.95 (d, 1H), 5.65 (s, 2H), 5.03 (s, 2H), 4.33 (q, 2H), 4.25 (s, 3H), 1.30 (t, 3H). |
| E8-59 | 4-((2-((1H-pyrazol-3-yl)methyl)-4-methyl-5-oxo-4,5-dihydro-6H-thiazolo[5',4':4,5]pyrrolo[2,3-d]pyridazin-6-yl)methyl)benzonitrile | LCMS: m/z 402 (M + H)$^+$. $^1$H NMR (400 MHz, DMSO-d$_6$) δ 12.77 (s, 1H), 8.56 (s, 1H), 7.80 (d, 2H), 7.72 (s, 1H), 7.45 (d, 2H), 6.26 (s, 1H), 5.44 (s, 2H), 4.53 (s, 2H), 4.26 (s, 3H). |
| E8-60 | 3-((2-((1H-pyrazol-3-yl)methyl)-4-methyl-5-oxo-4,5-dihydro-6H-thiazolo[5',4':4,5]pyrrolo[2,3-d]pyridazin-6-yl)methyl)benzonitrile | LCMS: m/z 402 (M + H)$^+$. $^1$H NMR (400 MHz, DMSO-d$_6$) δ 12.79 (s, 1H), 8.56 (s, 1H), 7.78-7.57 (m, 4H), 7.54 (dd, 1H), 6.26 (d, 1H), 5.41 (s, 2H), 4.49 (s, 2H), 4.26 (s, 3H). |

| Cpd No. | Structure | Characterization |
|---|---|---|
| E8-61 | 4-((2-((1H-pyrazol-3-yl)methyl)-4-methyl-5-oxo-4,5-dihydro-6H-thiazolo[5′,4′:4,5]pyrrolo[2,3-d]pyridazin-6-yl)methyl)benzamide | LCMS: m/z 420 (M + H)+. $^1$H NMR (400 MHz, DMSO-$d_6$) δ 12.78 (s, 1H), 8.55 (s, 1H), 8.07 (s, 1H), 7.93 (s, 1H), 7.81 (d, 2H), 7.34 (d, 3H), 6.27 (d, 1H), 5.40 (s, 2H), 4.49 (s, 2H), 4.27 (s, 3H). |
| E8-62 | 3-((2-((1H-pyrazol-3-yl)methyl)-4-methyl-5-oxo-4,5-dihydro-6H-thiazolo[5′,4′:4,5]pyrrolo[2,3-d]pyridazin-6-yl)methyl)benzamide | LCMS: m/z 420 (M + H)+. $^1$H NMR (400 MHz, DMSO-$d_6$) δ 12.78 (s, 1H), 8.55 (s, 1H), 7.97 (s, 1H), 7.85-7.60 (m, 3H), 7.51-7.27 (m, 3H), 6.26 (d, 1H), 5.39 (s, 2H), 4.49 (s, 2H), 4.27 (s, 3H). |
| E8-63 | 6-((1H-indazol-4-yl)methyl)-2-((5-(hydroxymethyl)thiazol-4-yl)methyl)-4-methyl-4,6-dihydro-5H-thiazolo[5′,4′:4,5]pyrrolo[2,3-d]pyridazin-5-one | LCMS: m/z 464 (M + H)+. $^1$H NMR (400 MHz, DMSO-$d_6$) δ 13.11 (s, 1H), 8.99 (s, 1H), 8.54 (s, 1H), 8.14 (s, 1H), 7.45 (d, 1H), 7.31 (dd, 1H), 6.95 (d, 1H), 5.69 (s, 1H), 5.65 (s, 2H), 4.78 (s, 2H), 4.63 (s, 2H), 4.27 (s, 3H). |
| E8-64 | 6-((1H-indazol-4-yl)methyl)-2-((2-(hydroxymethyl)thiazol-4-yl)methyl)-4-methyl-4,6-dihydro-5H-thiazolo[5′,4′:4,5]pyrrolo[2,3-d]pyridazin-5-one | LCMS: m/z 464 (M + H)+. $^1$H NMR (400 MHz, DMSO-$d_6$) 13.12 (s, 1H), 8.56 (s, 1H), 8.14 (s, 1H), 7.56 (s, 1H), 7.45 (d, 1H), 7.31 (dd, 1H), 6.96 (d, 1H), 6.07 (t, 1H), 5.65 (s, 2H), 4.70 (d, 2H), 4.60 (s, 2H), 4.27 (s, 3H). |

| Cpd No. | Structure | Characterization |
|---|---|---|
| E8-65 | 3-((4-methyl-2-((1-methyl-1H-pyrazol-4-yl)methyl)-5-oxo-4,5-dihydro-6H-thiazolo[5′,4′:4,5]pyrrolo[2,3-d]pyridazin-6-yl)methyl)benzamide | LCMS: m/z 434 (M + H)+. $^1$H NMR (400 MHz, DMSO-d$_6$) 8.55 (s, 1H), 7.97 (s, 1H), 7.81-7.74 (m, 2H), 7.73 (s, 1H), 7.45 (d, 2H), 7.39 (dd, 1H), 7.34 (s, 1H), 5.39 (s, 2H), 4.33 (s, 2H), 4.27 (s, 3H), 3.82 (s, 3H). |
| E8-66 | 6-((1H-pyrazol-3-yl)methyl)-2-((6-aminopyridin-2-yl)methyl)-4-methyl-4H-thiazolo[5′,4′:4,5]pyrrolo[2,3-d]pyridazin-5(6H)-one | LCMS: 393 (M + H)+. $^1$H-NMR (400 MHz, DMSO) δ 12.67 (s, 1H), 8.50 (s, 1H), 7.62 (s, 1H), 7.46 (s, 1H), 6.60 (d, 1H), 6.45 (s, 1H), 6.11 (d, 1H), 5.33 (s, 2H), 4.42 (s, 2H), 4.26 (s, 3H) |
| E8-67 | 2-((1H-1,2,3-triazol-4-yl)methyl)-4-methyl-6-(thiazol-2-ylmethyl)-4H-thiazolo[5′,4′:4,5]pyrrolo[2,3-d]pyridazin-5(6H)-one | LCMS: m/z 385 (M + H)+. 1H NMR (400 MHz, DMSO-d6) δ 8.60 (s, 1H), 7.89 (s, 1H), 7.75 (d, 1H), 7.67 (d, 1H), 5.65 (s, 2H), 4.63 (s, 2H), 4.27 (s, 3H). |
| E8-68 | 2-((1H-pyrazol-3-yl)methyl)-4-methyl-6-(oxazol-4-ylmethyl)-4H-thiazolo[5′,4′:4,5]pyrrolo[2,3-d]pyridazin-5(6H)-one | LCMS: m/z 368 (M + H)+. 1H NMR (400 MHz, DMSO-d6) δ 12.79 (s, 1H), 8.51 (s, 1H), 8.29 (s, 1H), 8.00 (s, 1H), 7.68 (s, 1H), 6.26 (s, 1H), 5.26 (s, 2H), 4.49 (s, 2H), 4.27 (s, 3H). |

-continued

| Cpd No. | Structure | Characterization |
|---|---|---|
| E8-69 | 2-((6-aminopyridin-2-yl)methyl)-4-methyl-6-(thiazol-4-ylmethyl)-4H-thiazolo[5′,4′:4,5]pyrrolo[2,3-d]pyridazin-5(6H)-one | LCMS: m/z 410 (M + H)+. 1H NMR (400 MHz, DMSO-d6) δ 9.03 (s, 1H), 8.52 (s, 1H), 7.42 (d, 1H), 7.36 (t, 1H), 6.55 (d, 1H), 6.35 (d, 1H), 5.98 (s, 2H), 5.48 (s, 2H), 4.37 (s, 2H), 4.26 (s, 3H) |
| E8-70 | 4-methyl-6-(thiazol-2-ylmethyl)-2-(thiazol-4-ylmethyl)-4H-thiazolo[5′,4′:4,5]pyrrolo[2,3-d]pyridazin-5(6H)-one | LC-MS: m/z 401 (M + H)+. 1H NMR (400 MHz, DMSO) δ 9.13 (d, 1H), 8.60 (s, 1H), 7.75 (d, 1H), 7.72 (d, 1H), 7.67 (d, 1H), 5.65 (s, 2H), 4.71 (s, 2H). 4.27 (s, 3H). |
| E8-71 | 4-methyl-2-(pyridin-2-ylmethyl)-6-(thiazol-2-ylmethyl)-4H-thiazolo[5′,4′:4,5]pyrrolo[2,3-d]pyridazin-5(6H)-one | LC-MS: mz 395 (M + H)+. 1H NMR (400 MHz, DMSO) δ 8.60 (s, 1H), 8.57 (dd, 1H), 7.81 (td, 1H), 7.74 (d, 1H), 7.67 (d, 1H), 7.51 (d, 1H), 7.36-7.30 (m, 1H), 5.65 (s, 2H), 4.68 (s, 2H), 4.26 (s, 3H) |
| E8-72 | 4-methyl-2,6-bis(thiazol-4-ylmethyl)-4H-thiazolo[5′,4′:4,5]pyrrolo[2,3-d]pyridazin-5(6H)-one | LC-MS: m/z 401 (M + H)+. 1H NMR (400 MHz, DMSO) δ 9.13 (d, 1H), 9.03 (d, 1H), 8.54 (s, 1H), 7.72 (d, 1H), 7.44-7.41 (m, 1H), 5.48 (s, 2H), 4.71 (s, 2H), 4.27 (s, 3H). |
| E8-73 | 2-((1H-1,2,3-triazol-4-yl)methyl)-4-methyl-6-(thiazol-4-ylmethyl)-4H-thiazolo[5′,4′:4,5]pyrrolo[2,3-d]pyridazin-5(6H)-one | LC-MS: m/z 385 (M + H)+. 1H NMR (400 MHz, DMSO) δ 9.03 (d, 1H), 8.54 (s, 1H), 7.89 (s, 1H), 7.42 (d, 1H), 5.48 (s, 2H), 4.63 (s, 2H), 4.26 (s, 3H). |

| Cpd No. | Structure | Characterization |
|---|---|---|
| E8-74 | 4-methyl-6-((1-methyl-1H-pyrazol-3-yl)methyl)-2-(pyridin-2-ylmethyl)-4H-thiazolo[5',4':4,5]pyrrolo[2,3-d]pyridazin-5(6H)-one | LCMS: m/z 392 (M + H)+.<br>1H NMR (400 MHz, DMSO) δ 8.56 (d, 1H), 8.50 (s, 1H), 7.81 (td, 1H), 7.55 (d, 1H), 7.50 (d, 1H), 7.32 (dd, 1H), 6.07 (d, 1H), 5.26 (s, 2H), 4.67 (s, 2H), 4.26 (s, 3H), 3.76 (s, 3H). |
| E8-75 | 6-((1H-1,2,3-triazol-4-yl)methyl)-4-methyl-2-(pyridin-2-ylmethyl)-4H-thiazolo[5',4':4,5]pyrrolo[2,3-d]pyridazin-5(6H)-one | LCMS: m/z 379 (M + H)+.<br>1H NMR (400 MHz, DMSO) δ 8.56 (d, 1H), 8.52 (s, 1H), 7.84-7.78 (m, 1H), 7.71 (s, 1H), 7.50 (d, 1H), 7.36-7.28 (m, 1H), 5.42 (s, 2H), 4.67 (s, 2H), 4.26 (s, 3H). |
| E8-76 | 6-((1H-pyrazol-3-yl)methyl)-4-methyl-2-(pyridin-2-ylmethyl)-4H-thiazolo[5',4':4,5]pyrrolo[2,3-d]pyridazin-5(6H)-one | LCMS: m/z 378 (M + H)+.<br>1H NMR (400 MHz, DMSO-d6) δ 12.63 (s, 1H), 8.57-8.55 (m, 1H), 8.51 (s, 1H), 7.81 (dd, 1H), 7.59 (s, 1H), 7.50 (d, 1H), 7.34-7.30 (m, 1H), 6.11 (d, 1H), 5.32 (s, 2H), 4.67 (s, 2H), 4.26 (s, 3H). |
| E8-77 | 6-((1H-pyrazol-3-yl)methyl)-2-((2-(hydroxymethyl)thiazol-4-yl)methyl)-4-methyl-4H-thiazolo[5',4':4,5]pyrrolo[2,3-d]pyridazin-5(6H)-one | LC-MS: m/z 414 (M + 1)+.<br>1H NMR (400 MHz, DMSO) δ 12.63 (s, 1H), 8.51 (s, 1H), 7.61 (s, 1H), 7.56 (s, 1H), 6.11 (s, 1H), 6.06 (t, 1H), 5.32 (s, 2H), 4.70 (d, 2H), 4.60 (s, 2H), 4.27 (s, 3H). |

| Cpd No. | Structure | Characterization |
|---|---|---|
| E8-78 | 2-((2-(hydroxymethyl)thiazol-4-yl)methyl)-4-methyl-6-(thiazol-2-ylmethyl)-4H-thiazolo[5',4':4,5]pyrrolo[2,3-d]pyridazin-5(6H)-one | LC-MS: m/z 431 (M + 1)+. 1H NMR (400 MHz, DMSO) δ 8.60 (s, 1H), 7.75 (d, 1H), 7.67 (d, 1H), 7.57 (s, 1H), 6.10-5.97 (m, 1H), 5.65 (s, 2H), 4.70 (d, 2H), 4.61 (s, 2H), 4.26 (s, 3H). |
| E8-79 | 2-((2-(hydroxymethyl)thiazol-4-yl)methyl)-4-methyl-6-((1-methyl-1H-pyrazol-3-yl)methyl)-4H-thiazolo[5',4':4,5]pyrrolo[2,3-d]pyridazin-5(6H)-one | LC-MS: m/z 428 (M + 1)+. 1H NMR (400 MHz, DMSO) δ 8.49 (s, 1H), 7.62-7.58 (m, 2H), 6.07-6.03 (m, 2H), 5.26 (s, 2H), 4.70 (d, 2H), 4.60 (s, 2H), 4.26 (s, 3H), 3.76 (s, 3H). |
| E8-80 | 6-((2H-1,2,3-triazol-4-yl)methyl)-2-((2-(hydroxymethyl)thiazol-4-yl)methyl)-4-methyl-4H-thiazolo[5',4':4,5]pyrrolo[2,3-d]pyridazin-5(6H)-one | LC-MS: m/z 415 (M + 1)+. 1H NMR (400 MHz, DMSO) δ 14.77 (s, 1H), 8.52 (s, 1H), 7.65 (s, 1H), 7.56 (s, 1H), 6.05 (t, 1H), 5.42 (s, 2H), 4.70 (d, 2H), 4.60 (s, 2H), 4.26 (s, 3H). |
| E8-81 | 6-((2-aminothiazol-4-yl)methyl)-4-methyl-2-(thiazol-4-ylmethyl)-4H-thiazolo[5',4':4,5]pyrrolo[2,3-d]pyridazin-5(6H)-one | LCMS: m/z 416 (M + H)+. 1H NMR (400 MHz, DMSO) δ 9.13 (d, 1H), 8.51 (s, 1H), 7.72 (d, 1H), 7.03 (br s, 2H), 6.22 (s, 1H), 5.13 (s, 2H), 4.71 (s, 2H), 4.27 (s, 3H). |

-continued

| Cpd No. | Structure | Characterization |
|---------|-----------|------------------|
| E8-82 | 2-((1H-1,2,3-triazol-4-yl)methyl)-4-methyl-6-((1-methyl-1H-pyrazol-3-yl)methyl)-4H-thiazolo[5',4':4,5]pyrrolo[2,3-d]pyridazin-5(6H)-one | LCMS: m/z 382 (M + H)+. 1H NMR (400 MHz, DMSO-d6) δ 8.50 (s, 1H), 7.89 (s, 1H), 7.56 (d, 1H), 6.07 (d, 1H), 5.26 (s, 2H), 4.63 (s, 2H), 4.26 (s, 3H), 3.76 (s, 3H). |
| E8-83 | 2-((1H-1,2,3-triazol-4-yl)methyl)-6-((1H-pyrazol-3-yl)methyl)-4-methyl-4H-thiazolo[5',4':4,5]pyrrolo[2,3-d]pyridazin-5(6H)-one | LCMS: m/z 368 (M + H)+. 1H NMR (400 MHz, DMSO-d6) δ 14.73 (s, 1H), 12.64 (s, 1H), 8.51 (s, 1H), 7.89 (s, 1H), 7.61 (s, 1H), 6.11 (d, 1H), 5.33 (s, 2H), 4.63 (s, 2H), 4.26 (s, 3H). |
| E8-84 | 6-((1H-pyrazol-3-yl)methyl)-4-methyl-2-(thiazol-4-ylmethyl)-4,6-dihydro-5H-thiazolo[5',4':4,5]pyrrolo[2,3-d]pyridazin-5-one | LC-MS: m/z 384.0 (M + H)+. 1H NMR (400 MHz, DMSO) δ 12.62 (s, 1H), 9.12 (d, 1H), 8.51 (s, 1H), 7.72 (d, 1H), 7.61 (s, 1H), 6.11 (s, 1H), 5.32 (s, 2H), 4.70 (s, 2H), 4.27 (s, 3H). |
| E8-85 | 6-((6-aminopyridin-2-yl)methyl)-2-((2-(hydroxymethyl)thiazol-4-yl)methyl)-4-methyl-4H-thiazolo[5',4':4,5]pyrrolo[2,3-d]pyridazin-5(6H)-one | LC-MS: 440.0 [M + H]+ 1H NMR (400 MHz, DMSO) δ 8.55 (s, 1H), 7.57 (s, 1H), 7.29-7.21 (m, 1H), 6.29 (d, 1H), 6.13-6.07 (m, 2H), 5.92 (s, 2H), 5.19 (s, 2H), 4.70 (d, 2H), 4.61 (s, 2H), 4.26 (s, 3H). |

| Cpd No. | Structure | Characterization |
|---|---|---|
| E8-86 | 6-((1H-1,2,3-triazol-4-yl)methyl)-2-((2-amino-5-fluorothiazol-4-yl)methyl)-4-methyl-4H-thiazolo[5',4':4,5]pyrrolo[2,3-d]pyridazin-5(6H)-one | LCMS: 418 (M + H)+. $^1$H NMR (400 MHz, DMSO) δ 8.53 (s, 1H), 7.74 (s, 1H), 6.92 (s, 2H), 5.43 (s, 2H), 4.27 (s, 2H), 4.26 (s, 3H). |
| E8-87 | 6-((1H-1,2,3-triazol-4-yl)methyl)-2-((5-fluorothiazol-4-yl)methyl)-4-methyl-4,6-dihydro-5H-thiazolo[5',4':4,5]pyrrolo[2,3-d]pyridazin-5-one | LCMS: 403 (M + H)+. $^1$H NMR (400 MHz, DMSO) δ 8.70 (d, 1H), 8.54 (s, 1H), 7.73 (s, 1H), 5.42 (s, 2H), 4.60 (d, 2H), 4.25 (s, 3H). |
| E8-88 | 6-((1H-1,2,3-triazol-4-yl)methyl)-2-(ethoxy(thiazol-4-yl)methyl)-4-methyl-4H-thiazolo[5',4':4,5]pyrrolo[2,3-d]pyridazin-5(6H)-one | LCMS: 429 (M + H)+. $^1$H NMR (400 MHz, DMSO) δ 9.09 (d, 1H), 8.57 (s, 1H), 7.88 (d, 1H), 7.73 (s, 1H), 6.12 (s, 1H), 5.54-5.34 (m, 2H), 4.23 (s, 3H), 3.76-3.61 (m, 2H), 1.20 (q, 3H). |
| E8-89 | 4-methyl-6-((1-methyl-1H-pyrazol-3-yl)methyl)-2-(thiazol-4-ylmethyl)-4H-thiazolo[5',4':4,5]pyrrolo[2,3-d]pyridazin-5(6H)-one | LCMS: m/z 398 (M + H)+. $^1$H NMR (400 MHz, DMSO) δ 9.12 (d, 1H), 8.50 (s, 1H), 7.72 (d, 1H), 7.56 (d, 1H), 6.07 (d, 1H), 5.26 (s, 2H), 4.70 (s, 2H), 4.26 (s, 3H), 3.76 (s, 3H). |

-continued

| Cpd No. | Structure | Characterization |
|---|---|---|
| E8-90 | 2-((1H-1,2,3-triazol-4-yl)methyl)-6-((2-aminothiazol-4-yl)methyl)-4-methyl-4H-thiazolo[5',4':4,5]pyrrolo[2,3-d]pyridazin-5(6H)-one | LCMS: m/z 400 (M + H)+. <br> ¹H NMR (400 MHz, DMSO) δ 8.50 (s, 1H), 7.89 (s, 1H), 6.90 (s, 2H), 6.18 (s, 1H), 5.02 (s, 2H), 4.63 (s, 2H) 4.26 (s, 3H). |
| E8-91 | 6-((1H-1,2,3-triazol-4-yl)methyl)-2-((5-chlorothiazol-4-yl)methyl)-4-methyl-4H-thiazolo[5',4':4,5]pyrrolo[2,3-d]pyridazin-5(6H)-one | LCMS: m/z 419 (M + H)+. <br> ¹H NMR (400 MHz, DMSO) δ 9.09 (s, 1H), 8.53 (s, 1H), 7.73 (s, 1H), 5.42 (s, 2H), 4.65 (s, 2H), 4.25 (s, 3H). |
| E8-92 | 6-((1H-pyrazol-3-yl)methyl)-2-((5-chlorothiazol-4-yl)methyl)-4-methyl-4H-thiazolo[5',4':4,5]pyrrolo[2,3-d]pyridazin-5(6H)-one | LCMS: m/z 418 (M + H)+. <br> ¹H NMR (400 MHz, DMSO) δ 9.09 (s, 1H), 8.51 (s, 1H), 7.55 (s, 1H), 6.11 (d, 1H), 5.32 (s, 2H), 4.65 (s, 2H), 4.26 (s, 3H). |
| E8-93 | 6-((1H-1,2,3-triazol-4-yl)methyl)-2-((4-fluoro-1H-pyrazol-3-yl)methyl)-4-methyl-4,6-dihydro-5H-thiazolo[5',4':4,5]pyrrolo[2,3-d]pyridazin-5-one | LC-MS m/z 386.0 (M + H)⁺. <br> ¹H NMR (400 MHz, DMSO) δ 14.82 (s, 1H), 12.82 (s, 1H), 8.57 (s, 1H), 7.95 (s, 1H), 7.70 (s, 1H), 5.47 (s, 2H), 4.54 (s, 2H), 4.31 (s, 3H) |

| Cpd No. | Structure | Characterization |
|---|---|---|
| E8-94 | 6-((1H-pyrazol-3-yl)methyl)-2-((5-bromothiazol-4-yl)methyl)-4-methyl-4H-thiazolo[5',4':4,5]pyrrolo[2,3-d]pyridazin-5(6H)-one | LCMS: m/z 462 (M + H )+. <br> $^1$H NMR (400 MHz, DMSO-$d_6$) δ 12.64 (s, 1H), 9.19 (s, 1H), 8.51 (s, 1H), 7.57 (s, 1H), 6.11 (d, 1H), 5.33 (s, 2H), 4.65 (s, 2H), 4.26 (s, 3H). |
| E8-95 | 2-((1H-pyrazol-3-yl)methyl)-4-methyl-6-((6-oxo-1,6-dihydropyridin-2-yl)methyl)-4H-thiazolo[5',4':4,5]pyrrolo[2,3-d]pyridazin-5(6H)-one | LCMS: m/z 394 (M + H)+. <br> $^1$H NMR (400 MHz, DMSO) δ 12.77 (s, 1H), 11.71 (s, 1H), 8.58 (s, 1H), 7.70 (s, 1H), 7.32 (s, 1H), 6.25-6.05 (m, 2H), 5.75 (s, 1H), 5.19 (s, 2H), 4.50 (s, 2H), 4.26 (s, 3H). |
| E8-96 | 6-((1H-pyrazol-3-yl)methyl)-2-((2-amino-5-fluorothiazol-4-yl)methyl)-4-methyl-4,6-dihydro-5H-thiazolo[5',4':4,5]pyrrolo[2,3-d]pyridazin-5-one | LCMS: m/z 417 (M + H)+. <br> $^1$H NMR (DMSO-d6 400 MHz) δ 12.65 (s, 1H), 8.51 (s, 1H), 7.57 (s, 1H), 6.92 (s, 2H), 6.12 (d, 1H), 5.33 (s, 2H), 4.26 (s, 5H). |
| E8-97 | 6-((1H-pyrazol-3-yl)methyl)-2-((5-fluorothiazol-4-yl)methyl)-4-methyl-4H-thiazolo[5',4':4,5]pyrrolo[2,3-d]pyridazin-5(6H)-one | LCMS: m/z 402 (M + H)+. <br> $^1$H NMR DMSO-d6 400 MHz δ 12.70 (s, 1H), 8.70 (d, 1H), 8.52 (s, 1H), 7.55 (s, 1H), 6.11 (d, 1H), 5.33 (s, 2H), 4.60 (d, 2H), 4.26 (s, 3H). |

| Cpd No. | Structure | Characterization |
|---|---|---|
| E8-98 | 4-methyl-2,6-bis(pyridin-2-ylmethyl)-4H-thiazolo[5',4':4,5]pyrrolo[2,3-d]pyridazin-5(6H)-one | LCMS: m/z 389 (M + H)$^+$. $^1$H NMR (DMSO-d6 400 MHz δ 8.61-8.54 (m, 2H), 8.51-8.46 (m, 1H), 7.82 (td, 1H), 7.73 (td, 1H), 7.52 (d, 1H), 7.34 (ddd, 1H), 7.27 (dd, 1H), 7.14 (d, 1H), 5.46 (s, 2H), 4.69 (s, 2H), 4.26 (s, 3H). |
| E8-99 | 6-((1H-1,2,3-triazol-4-yl)methyl)-4-methyl-2-(thiazol-4-ylmethyl)-4H-thiazolo[5',4':4,5]pyrrolo[2,3-d]pyridazin-5(6H)-one | LCMS: m/z 385 (M + H)$^+$. $^1$H NMR (400 MHz, DMSO-d$_6$) δ 9.13 (d, 1H), 8.53 (s, 1H), 7.74 (s, 1H), 7.72 (d, 1H), 5.42 (s, 2H), 4.70 (s, 2H), 4.26 (s, 3H). |
| E8-100 | 2-((1H-pyrazol-3-yl)methyl)-4-methyl-6-((1-methyl-1H-pyrazol-3-yl)methyl)-4H-thiazolo[5',4':4,5]pyrrolo[2,3-d]pyridazin-5(6H)-one | LCMS: m/z 381 (M + H)$^+$. $^1$H NMR (400 MHz, DMSO-d$_6$) δ 12.77 (s, 1H), 8.48 (s, 1H), 7.71 (s, 1H), 7.55 (d, 1H), 6.26 (d, 1H), 6.07 (d, 1H), 5.26 (s, 2H), 4.47 (s, 2H), 4.27 (s, 3H), 3.76 (s, 3H). |
| E8-101 | 2-((6-aminopyridin-2-yl)methyl)-4-methyl-6-((1-methyl-1H-pyrazol-3-yl)-methyl)-4H-thiazolo[5',4':4,5]pyrrolo[2,3-d]pyridazin-5(6H)-one | LCMS: m/z 407 (M + H)$^+$. $^1$H NMR (400 MHz, DMSO-d$_6$) δ 8.48 (s, 1H), 7.55 (d, 1H), 7.35 (t, 1H), 6.55 (d, 1H), 6.35 (d, 1H), 6.07 (d, 1H), 5.97 (s, 2H), 5.26 (s, 2H), 4.36 (s, 2H), 4.26 (s, 3H), 3.76 (s, 3H). |

| Cpd No. | Structure | Characterization |
|---|---|---|
| E8-102 | 6-((1H-1,2,3-triazol-4-yl)methyl)-4-methyl-2-((1-methyl-1H-pyrazol-3-yl)methyl)-4H-thiazolo[5',4':4,5]pyrrolo[2,3-d]pyridazin-5(6H)-one | LCMS: m/z 382 (M + H)$^+$. $^1$H NMR (400 MHz, DMSO-d$_6$) δ 14.70 (s, 1H), 8.51 (s, 1H), 7.74 (s, 1H), 7.65 (d, 1H), 6.22 (d, 1H), 5.42 (s, 2H), 4.43 (s, 2H), 4.26 (s, 3H), 3.81 (s, 3H). |
| E8-103 | 4-methyl-2,6-bis((1-methyl-1H-pyrazol-3-yl)methyl)-4H-thiazolo[5',4':4,5]pyrrolo[2,3-d]pyridazin-5(6H)-one | LCMS: m/z 395 (M + H)$^+$. $^1$H NMR (400 MHz, DMSO-d$_6$) δ 8.48 (s, 1H), 7.65 (d, 1H), 7.55 (d, 1H), 6.22 (d, 1H), 6.07 (d, 1H), 5.26 (s, 2H), 4.43 (s, 2H), 4.26 (s, 3H), 3.82 (s, 3H), 3.76 (s, 3H). |
| E8-104 | 2,6-bis((4-fluoro-1H-pyrazol-3-yl)methyl)-4-methyl-4H-thiazolo[5',4':4,5]pyrrolo[2,3-d]pyridazin-5(6H)-one | LCMS: m/z 403 (M + H)$^+$. $^1$H NMR (400 MHz, DMSO-d$_6$) δ 13.02-12.57 (m, 2H), 8.49 (s, 1H), 7.6-7.8 (m, 2H), 5.33 (s, 2H), 4.49 (s, 2H), 4.27 (s, 3H). |
| E8-105 | 6-((6-aminopyridin-2-yl)methyl)-4-methyl-2-(thiazol-4-ylmethyl)-4H-thiazolo[5',4':4,5]pyrrolo[2,3-d]pyridazin-5(6H)-one | LCMS: m/z 410 (M + H)$^+$. $^1$H NMR (400 MHz, DMSO-d$_6$) δ 9.13 (d, 1H), 8.55 (s, 1H), 7.72 (d, 1H), 7.25 (t, 1H), 6.29 (d, 1H), 6.07 (d, 1H), 5.92 (s, 2H), 5.19 (s, 2H), 4.71 (s, 2H), 4.26 (s, 3H). |
| E8-106 | 6-((1H-pyrazol-3-yl)methyl)-2-((4-fluoro-1H-pyrazol-3-yl)methyl)-4-methyl-4H-thiazolo[5',4':4,5]pyrrolo[2,3-d]pyridazin-5(6H)-one | LCMS: m/z 385 (M + H)$^+$. $^1$H NMR (400 MHz, DMSO) δ 12.77 (s, 1H), 12.62 (s, 1H), 8.50 (s, 1H), 7.87 (d, 1H), 7.61 (s, 1H), 6.11 (s, 1H), 5.32 (s, 2H), 4.49 (s, 2H), 4.26 (s, 3H). |

| Cpd No. | Structure | Characterization |
|---|---|---|
| E8-107 | 6-((1H-1,2,3-triazol-4-yl)methyl)-4-methyl-2-((5-methylthiazol-4-yl)methyl)-4H-thiazolo[5',4':4,5]pyrrolo[2,3-d[pyridazin-5(6H)-one | LCMS: m/z 399 (M + H)+. $^1$H NMR (400 MHz, DMSO-d6) δ 8.95 (s, 1H), 8.55 (s, 1H), 7.79 (s, 1H), 5.47 (s, 2H), 4.66 (s, 2H), 4.31 (s, 3H), 2.55 (s, 3H). |
| E8-108 | 6-((1H-pyrazol-5-yl)methyl)-4-methyl-2-((1-methyl-1H-pyrazol-3-yl)methyl)-4H-thiazolo[5',4':4,5]pyrrolo[2,3-d]pyridazin-5(6H)-one | LCMS: m/z 381 (M + H)$^+$. $^1$H NMR (400 MHz, DMSO-d6) δ 12.64 (s, 1H), 8.49 (s, 1H), 7.65 (s, 1H), 7.56 (s, 1H), 6.23 (d, 1H), 6.11 (d, 1H), 5.32 (s, 2H), 4.43 (s, 2H), 4.26 (s, 3H), 3.82 (s, 2H). |
| E8-109 | 6-((1H-pyrazol-5-yl)methyl)-4-methyl-2-((5-methylthiazol-4-yl)methyl)-4H-thiazolo[5',4':4,5]pyrrolo[2,3-d]pyridazin-5(6H)-one | LCMS: m/z 398 (M + H)$^+$. $^1$H NMR (400 MHz, DMSO-d6) δ 12.63 (s, 1H), 8.90 (s, 1H), 8.48 (s, 1H), 7.60 (s, 1H), 6.11 (d, 1H), 5.32 (s, 2H), 4.61 (s, 2H), 4.26 (s, 3H) 2.50 (s, 3H overlap with DMSO-d6). . |
| E8-110 | 2-((4-fluoro-1H-pyrazol-3-yl)methyl)-4-methyl-6-((1-methyl-1H-pyrazol-3-yl)methyl)-4H-thiazolo[5',4':4,5]pyrrolo[2,3-d]pyridazin-5(6H)-one | LCMS: m/z 399 (M + H)$^+$. $^1$H NMR (400 MHz, DMSO-d6) δ 12.83 (s, 1H), 8.54 (s, 1H), 7.91 (s, 1H), 7.61 (s, 1H), 6.13 (s, 1H), 5.32 (s, 2H), 4.54 (s, 2H), 4.34 (s, 3H), 3.81 (s, 3H). |

| Cpd No. | Structure | Characterization |
|---|---|---|
| E8-111 | 6-((1H-pyrazol-3-yl)methyl)-2-((3-fluoro-6-(methylamino)pyridin-2-yl)methyl)-4-methyl-4H-thiazolo[5',4':4,5]pyrrolo[2,3-d]pyridazin-5(6H)-one | LCMS: m/z 425 (M + H)$^+$. $^1$H NMR (400 MHz, DMSO) δ 12.68 (s, 1H), 8.56 (s, 1H), 7.65 (s, 1H), 7.43 (t, 1H), 6.62 (d, 1H), 6.46 (dd, 1H), 6.16 (s, 1H), 5.37 (s, 2H), 4.52 (s, 2H), 4.31 (s, 3H), 2.83 (d, 3H) |
| E8-112 | 6-((1H-pyrazol-3-yl)methyl)-2-((6-amino-3-fluoropyridin-2-yl)methyl)-4-methyl-4H-thiazolo[5',4':4,5]pyrrolo[2,3-d]pyridazin-5(6H)-one | LC-MS: m/z 411 (M + H)$^+$. $^1$H NMR (400 MHz, DMSO-d$_6$) δ 12.64 (s, 1H), 8.50 (s, 1H), 7.57 (s, 1H), 7.36 (t, 1H), 6.41 (dd, 1H), 6.11 (d, 1H), 5.96 (s, 2H), 5.32 (s, 2H), 4.44 (d, 2H), 4.26 (s, 3H) |
| E8-113 | 6-((2-aminothiazol-4-yl)methyl)-4-methyl-2-(pyridin-2-ylmethyl)-4,6-dihydro-5H-thiazolo[5',4':4,5]pyrrolo[2,3-d]pyridazin-5-one | LC-MS: m/z 410 (M + H)$^+$. $^1$H NMR (400 MHz, DMSO-d$_6$) δ 8.52 (s, 1H), 8.49 (s, 1H), 7.83 (d, 1H), 7.51 (d, 1H), 7.40-7.25 (m, 1H), 6.91 (s, 2H), 6.17 (s, 1H), 5.12 (s, 2H), 4.67 (s, 2H), 4.26 (s, 3H) |
| E8-114 | 4-methyl-2-(pyridin-2-ylmethyl)-6-(thiazol-4-ylmethyl)-4,6-dihydro-5H-thiazolo[5',4':4,5]pyrrolo[2,3-d]pyridazin-5-one | LC-MS: m/z 395 (M + H)$^+$. $^1$H NMR (400 MHz, DMSO-d$_6$) δ 9.09 (d, 1H), 8.63 (m, 1H), 8.59 (s, 1H), 7.88 (m, 1H), 7.57 (d, 1H), 7.51 (s, 1H), 7.39 (dd, 1H), 5.54 (s, 2H), 4.73 (s, 2H), 4.32 (s, 3H) |

| Cpd No. | Structure | Characterization |
|---|---|---|
| E8-115 | 2,6-bis((1H-1,2,3-triazol-4-yl)methyl)-4-methyl-4,6-dihydro-5H-thiazolo[5',4':4,5]pyrrolo[2,3-d]pyridazin-5-one | LC-MS: m/z 369 (M + H)$^+$. $^1$H NMR (400 MHz, DMSO-d$_6$) δ 8.53 (s, 1H), 7.89 (s, 1H), 7.74 (s, 1H), 5.43 (s, 2H), 4.63 (s, 2H), 4.26 (s, 3H) |
| E8-116 | 6-((6-aminopyridin-2-yl)methyl)-4-methyl-2-(pyridin-2-ylmethyl)-4,6-dihydro-5H-thiazolo[5',4':4,5]pyrrolo[2,3-d]pyridazin-5-one | LC-MS: m/z 404 (M + H)$^+$. $^1$H NMR (400 MHz, DMSO-d$_6$) δ 8.57 (s, 1H), 8.54 (s, 1H), 7.82 (dd, 1H), 7.51 (d, 1H), 7.33 (dd, 1H), 7.27-7.22 (m, 1H), 6.29 (d 1H), 6.07 (d, 1H), 5.90 (s, 2H), 5.19 (s, 2H), 4.68 (s, 2H), 4.26 (s, 3H) |
| E8-117 | 2-((1H-1,2,3-triazol-4-yl)methyl)-6-((6-aminopyridin-2-yl)methyl)-4-methyl-4,6-dihydro-5H-thiazolo[5',4':4,5]pyrrolo[2,3-d]pyridazin-5-one | LC-MS: m/z 394 (M + H)$^+$. $^1$H NMR (400 MHz, DMSO-d$_6$) δ 8.55 (s, 1H), 7.90 (s, 1H), 7.26 (dd, 1H), 6.30 (d, 1H), 6.07 (d 1H), 5.91 (s, 2H), 5.19 (s, 2H), 4.64 (s, 2H), 4.26 (s, 3H) |
| E8-118 | 6-((4-fluoro-1H-pyrazol-3-yl)methyl)-4-methyl-2-(pyridin-2-ylmethyl)-4,6-dihydro-5H-thiazolo[5',4':4,5]pyrrolo[2,3-d]pyridazin-5-one | LC-MS: m/z 396 (M + H)$^+$. $^1$H NMR (400 MHz, DMSO-d$_6$) δ 12.60 (s, 1H), 8.57 (s, 1H), 8.55 (s, 1H), 7.90-7.80 (m, 1H), 7.68 (s, 1H), 7.49 (d 1H), 7.31 (dd, 1H), 5.32 (s, 2H), 4.65 (s, 2H), 4.24 (s, 3H) |

| Cpd No. | Structure | Characterization |
|---|---|---|
| E8-119 | 6-((4-chloro-1H-pyrazol-3-yl)methyl)-4-methyl-2-(pyridin-2-ylmethyl)-4,6-dihydro-5H-thiazolo[5′,4′:4,5]pyrrolo[2,3-d]pyridazin-5-one | LC-MS: m/z 412 (M + H)+. <br> 1H NMR (400 MHz, DMSO-d6) δ 13.00 (s, 1H), 8.67 (d, 1H), 8.46 (s, 1H), 7.86 (s, 1H), 7.82 (dd, 1H), 7.51 (d, 1H), 7.33 (dd, 1H), 5.34 (s, 2H), 4.67 (s, 2H), 4.26 (s, 3H |
| E8-120 | 6-((1H-pyrazol-3-yl)methyl)-2-((2-bromo-5-methoxythiazol-4-yl)methyl)-4-methyl-4H-thiazolo[5′,4′:4,5]pyrrolo[2,3-d]pyridazin-5(6H)-one | LC-MS: m/z 492 (M + H)+. <br> 1H NMR (400 MHz, DMSO-d6) δ: 12.64 (s, 1H), 8.52 (s, 1H), 7.61 (s, 1H), 6.11 (s, 1H), 5.32 (s, 2H), 4.44 (s, 2H), 4.26 (s, 3H), 3.99 (s, 3H). |
| E8-121 | 6-((1H-pyrazol-3-yl)methyl)-2-((5-methoxythiazol-4-yl)methyl)-4-methyl-4H-thiazolo[5′,4′:4,5]pyrrolo[2,3-d]pyridazin-5(6H)-one | LC-MS: m/z 414 (M + H)+. <br> 1H NMR (400 MHz, DMSO-d6) δ: 12.63 (s, 1H), 8.57 (s, 1H), 8.50 (s, 1H), 7.60 (s, 1H), 6.11 (d, 1H), 5.32 (s, 2H), 4.47 (s, 2H), 4.26 (s, 3H), 3.97 (s, 3H). |
| E8-122 | 3-((2-((1H-pyrazol-3-yl)methyl)-4-methyl-5-oxo-4H-thiazolo[5′,4′:4,5]pyrrolo[2,3-d]pyridazin-6(5H)-yl)methyl)-1-methyl-1H-pyrazole-4-carboxylic acid | LC-MS: m/z 425 (M + H)+. <br> 1H NMR (400 MHz, DMSO-d6) δ: 9.12 (s, 1H), 8.19 (s, 1H), 7.66 (s, 1H), 6.25 (s, 1H), 5.59 (s, 2H), 4.49 (s, 2H), 4.31 (s, 3H), 3.81 (s, 3H). |

-continued

| Cpd No. | Structure | Characterization |
|---|---|---|
| E8-123 | 6-((4-chloro-1H-pyrazol-3-yl)methyl)-2-((4-fluoro-1H-pyrazol-3-yl)methyl)-4-methyl-4H-thiazolo[5',4':4,5]pyrrolo[2,3-d]pyridazin-5(6H)-one | LC-MS: m/z 419 (M + H)$^+$.<br>$^1$H NMR (400 MHz, DMSO-d6) δ: 13.28-12.57 (m, 2H), 8.49 (s, 1H), 7.90-7.50 (m, 2H), 5.34 (s, 2H), 4.50 (s, 2H), 4.26 (s, 3H). |
| E8-124 | 3-((2-((4-fluoro-1H-pyrazol-3-yl)methyl)-4-methyl-5-oxo-4H-thiazolo[5',4':4,5]pyrrolo[2,3-d]pyridazin-6(5H)-yl)methyl)-1H-pyrazole-4-carboxamide | LC-MS: m/z 428 (M + H)$^+$.<br>$^1$H NMR (400 MHz, DMSO-d6) δ: 12.89-12.76 (m, 2H), 8.49 (s, 1H), 8.22 (s, 1H), 7.86 (s, 1H), 7.60 (s, 1H), 7.00 (s, 1H), 5.57 (s, 2H), 4.51 (s, 2H), 4.26 (s, 3H). |
| E8-125 | 2-((4-fluoro-1H-pyrazol-3-yl)methyl)-6-((2-methoxypyridin-3-yl)methyl)-4-methyl-4H-thiazolo[5',4':4,5]pyrrolo[2,3-d]pyridazin-5(6H)-one | LC-MS: m/z 426 (M + H)$^+$.<br>$^1$H NMR (400 MHz, DMSO-d6) δ: 12.80 (s, 1H), 8.57 (d, 1H), 8.08 (dd, 1H), 7.92 (d, 1H), 7.16 (d, 1H), 6.90 (dd, 1H), 5.29 (s, 2H), 4.50 (s, 2H), 4.26 (s, 3H), 3.92 (s, 3H). |
| E8-126 | 2-((4-fluoro-1H-pyrazol-3-yl)methyl)-4-methyl-6-((2-oxo-1,2-dihydropyridin-3-yl)methyl)-4H-thiazolo[5',4':4,5]pyrrolo[2,3-d]pyridazin-5(6H)-one | LC-MS: m/z 412 (M + H)$^+$.<br>$^1$H NMR (400 MHz, DMSO-d6) δ: 12.78 (s, 1H), 11.71 (s, 1H), 8.56 (s, 1H), 7.87 (s, 1H), 7.30 (d, 1H), 6.82 (d, 1H), 6.08 (dd, 1H), 5.10 (s, 2H), 4.50 (s, 2H), 4.26 (s, 3H). |

-continued

| Cpd No. | Structure | Characterization |
|---|---|---|
| E8-127 | 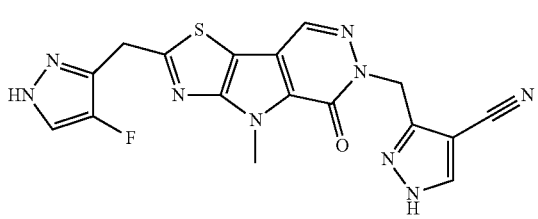<br>3-((2-((4-fluoro-1H-pyrazol-3-yl)methyl)-4-methyl-5-oxo-4H-thiazolo[5′,4′:4,5]pyrrolo[2,3-d]pyridazin-6(5H)-yl)methyl)-1H-pyrazole-4-carbonitrile | LC-MS: m/z 410 (M + H)+.<br>$^1$H NMR (400 MHz, DMSO-d6) δ: 13.63 (s, 1H), 12.81 (s, 1H), 8.55 (s, 1H), 8.37 (s, 1H), 7.81 (s, 1H), 5.45 (s, 2H), 4.51 (s, 2H), 4.25 (s, 3H). |
| E8-128 | 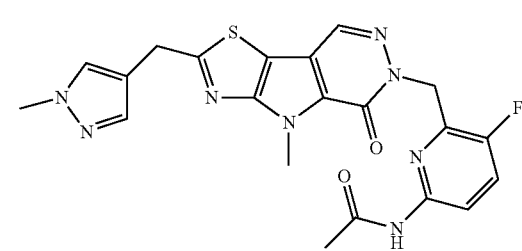<br>N-(5-fluoro-6-((4-methyl-2-((1-methyl-1H-pyrazol-4-yl)methyl)-5-oxo-4,5-dihydro-6H-thiazolo[5′,4′:4,5]pyrrolo[2,3-d]pyridazin-6-yl)methyl)pyridin-2-yl)acetamide | LC-MS: m/z 467 (M + H)+.<br>$^1$H NMR (400 MHz, DMSO-d6) δ: δ10.35 (s, 1H), 8.49 (s, 1H), 8.00 (s, 1H), 7.70 (dd, 2H), 7.45 (s, 1H), 5.45 (s, 2H), 4.34 (s, 2H), 4.26 (s, 3H), 3.83 (s, 3H), 2.01 (s, 3H) |
| E8-129 | 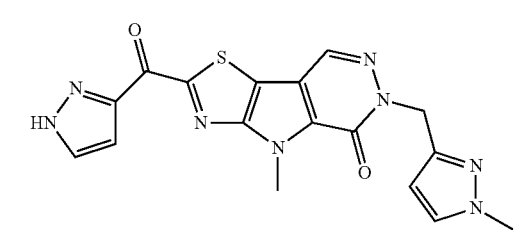<br>4-methyl-6-((1-methyl-1H-pyrazol-3-yl)methyl)-2-(1H-pyrazole-3-carbonyl)-4H-thiazolo[5′,4′:4,5]pyrrolo[2,3-d]pyridazin-5(6H)-one | LC-MS: m/z 395 (M + H)+.<br>$^1$H NMR (400 MHz, DMSO-$d_6$) δ 13.85 (s, 1H), 8.70 (s, 1H), 8.04 (s, 1H), 7.58 (d, 1H), 7.38 (s, 1H), 6.12 (d, 1H), 5.30 (s, 2H), 4.38 (s, 3H), 3.77 (s, 3H). |

Example 8F. Synthesis of 4-methyl-6-(2-(1-methyl-1H-pyrazol-3-yl)ethyl)-2-(pyridin-3-ylmethyl)-4H-thiazolo[5',4':4,5]pyrrolo[2,3-d]pyridazin-5(6H)-one

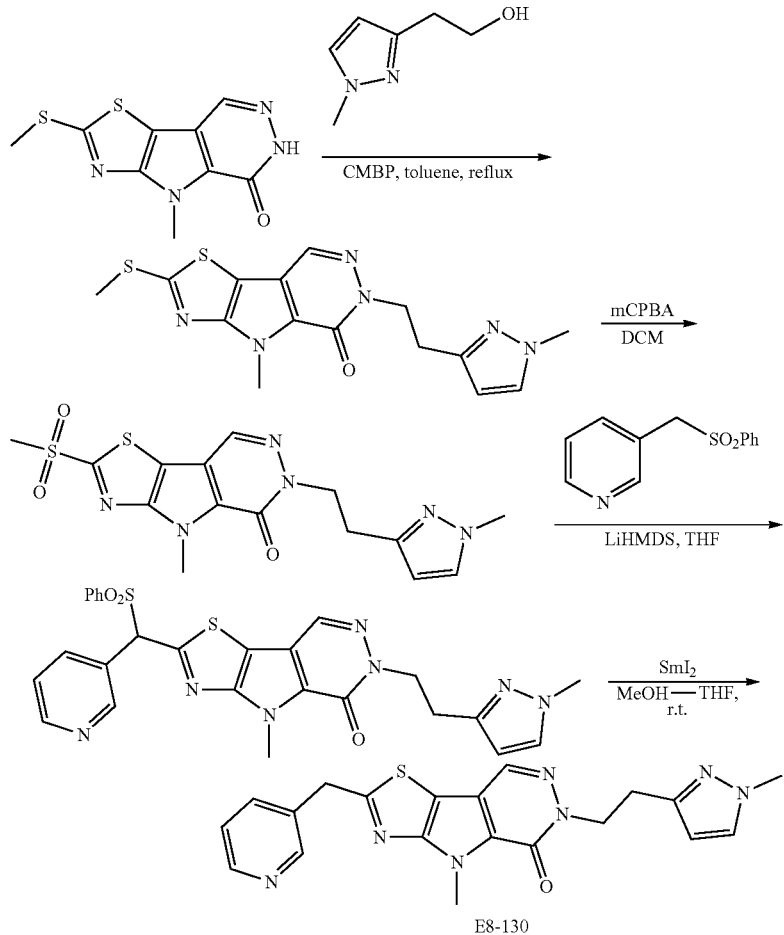

E8-130

Step A. Synthesis of 4-methyl-6-(2-(1-methyl-1H-pyrazol-3-yl)ethyl)-2-(methylthio)-4H-thiazolo[5',4':4,5]pyrrolo[2,3-d]pyridazin-5(6H)-one To a mixture of 4-methyl-2-(methylthio)-4H-thiazolo[5',4':4,5]pyrrolo[2,3-d]pyridazin-5(6H)-one (360 mg, 1.4 mmol) and 2-(1-methyl-1H-pyrazol-3-yl)ethanol (300 mg, 2.4 mmol) in toluene (10 mL) was added CMBP (600 mg, 2.1 mmol). The reaction mixture was stirred at 110° C. under $N_2$ for 3 hrs. After cooled to room temperature, the reaction mixture was diluted with EtOAc, washed with water and brine, dried over anhy. $Na_2SO_4$, concentrated in vacuum. The residue was purified by flash chromatography (silica gel, 80-100% EtOAc in petroleum ether) to afford 4-methyl-6-(2-(1-methyl-1H-pyrazol-3-yl)ethyl)-2-(methylthio)-4H-thiazolo[5',4':4,5]pyrrolo[2,3-d]pyridazin-5(6H)-one (500 mg). LC-MS (ESI): m/z 361 (M+1)$^+$.

Step B. Synthesis of 4-methyl-6-(2-(1-methyl-1H-pyrazol-3-yl)ethyl)-2-(methylsulfonyl)-4H-thiazolo[5',4':4,5]pyrrolo[2,3-d]pyridazin-5(6H)-one To a mixture of 4-methyl-6-(2-(1-methyl-1H-pyrazol-3-yl)ethyl)-2-(methylthio)-4H-thiazolo[5',4':4,5]pyrrolo[2,3-d]pyridazin-5(6H)-one (600 mg, 1.7 mmol) in DCM (20 mL) was added m-CPBA (1.01 g, 5.0 mmol). The reaction mixture was stirred at room temperature for 3 hrs. The reaction mixture was diluted with EtOAc, washed with satd. NaHCO$_3$ and brine, dried over anhy. Na$_2$SO$_4$, concentrated under vacuum. The residue was purified by flash chromatography (silica gel, 80-100% EtOAc in PE) to afford 4-methyl-6-(2-(1-methyl-1H-pyrazol-3-yl)ethyl)-2-(methylsulfonyl)-4H-thiazolo[5',4':4,5]pyrrolo[2,3-d]pyridazin-5(6H)-one (600 mg). LC-MS (ESI): m/z 393 (M+1)$^+$.

Step C. Synthesis of 4-methyl-6-(2-(1-methyl-1H-pyrazol-3-yl)ethyl)-2-((phenylsulfonyl)(pyridin-3-yl)methyl)-4H-thiazolo[5',4':4,5]pyrrolo[2,3-d]pyridazin-5(6H)-one To a mixture of 3-((phenylsulfonyl)methyl)pyridine (300 mg, 1.3 mmol) in THF (20 mL) was added LiHMDS (2 mL, 2.0 mmol) at room temperature. After stirred at room temperature under N$_2$ for 15 min, 4-methyl-6-(2-(1-methyl-1H-pyrazol-3-yl)ethyl)-2-(methylsulfonyl)-4H-thiazolo[5',4':4,5]pyrrolo[2,3-d]pyridazin-5(6H)-one (300 mg, 0.8 mmol) was added to the reaction mixture and the resulting solution was stirred at room temperature for 3 hrs. The reaction mixture was quenched with satd. NH₄Cl, extracted with EtOAc. The organic phase was washed with brine, dried over anhy. Na₂SO₄, concentrated in vacuum. The residue was purified by flash chromatography (silica gel, 80-100% EtOAc in petroleum ether) to afford 110 mg of 4-methyl-6-(2-(1-methyl-1H-pyrazol-3-yl)ethyl)-2-((phenylsulfonyl)(pyridin-3-yl)methyl)-4H-thiazolo[5',4':4,5]pyrrolo[2,3-d]pyridazin-5(6H)-one. LC-MS: m/z 546 (M+1)⁺.

Step D. Synthesis of 4-methyl-6-(2-(1-methyl-1H-pyrazol-3-yl)ethyl)-2-(pyridin-3-ylmethyl)-4H-thiazolo[5',4':4,5]pyrrolo[2,3-d]pyridazin-5(6H)-one To a solution of 4-methyl-6-(2-(1-methyl-1H-pyrazol-3-yl)ethyl)-2-((phenylsulfonyl)(pyridin-3-yl)methyl)-4H-thiazolo[5',4':4,5]pyrrolo[2,3-d]pyridazin-5(6H)-one (110 mg, 0.2 mmol) in THF (5 mL) and MeOH (5 mL) was added SmI₂ (5 mL, 0.1 M in THF) at r.t. Then the reaction mixture was stirred under N₂ at r.t. for 10 min. The reaction solution was quenched with water, diluted with EtOAc, washed with water and brine, dried over anhy. Na₂SO₄, concentrated in vacuum. The residue was purified by flash chromatography (silica gel, 80-100% EtOAc in petroleum ether) to afford 6 mg of 4-methyl-6-(2-(1-methyl-1H-pyrazol-3-yl)ethyl)-2-(pyridin-3-ylmethyl)-4H-thiazolo[5',4':4,5]pyrrolo[2,3-d]pyridazin-5(6H)-one. LC-MS (ESI): m/z 406 (M+1)⁺. ¹H NMR (400 MHz, DMSO-d6) δ 8.66 (s, 1H), 8.52 (d, 2H), 7.84 (d, 1H), 7.54 (d, 1H), 7.41 (dd, 1H), 6.04 (d, 1H), 4.58 (s, 2H), 4.48-4.30 (m, 2H), 4.26 (s, 3H), 3.75 (s, 3H), 3.12-2.75 (m, 2H).

Example 8G. Synthesis of 4-methyl-6-(prop-2-yn-1-yl)-2-(pyridin-2-ylmethyl)-4H-thiazolo[5',4':4,5]pyrrolo[2,3-d]pyridazin-5(6H)-one

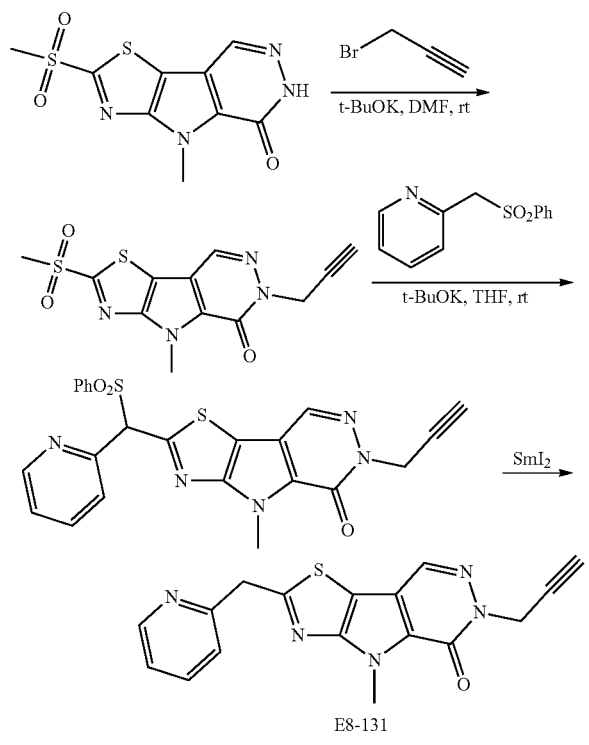

E8-131

Step A. Synthesis of 4-methyl-2-(methylsulfonyl)-6-(prop-2-yn-1-yl)-4H-thiazolo[5',4':4,5]pyrrolo[2,3-d]pyridazin-5(6H)-one To a mixture of 4-methyl-2-(methylsulfonyl)-4H-thiazolo[5',4':4,5]pyrrolo[2,3-d]pyridazin-5(6H)-one (200 mg, 0.70 mmol) in DMF (5 mL) was added t-BuOK (157 mg, 1.4 mmol), followed by 3-bromoprop-1-one (0.12 mL, 1.4 mmol). The reaction was stirred at room temperature for 15 min. Then the suspension was poured into satd. NH₄Cl, extracted with EtOAc. The organic layer was washed with brine, dried over anhy. Na₂SO₄ and concentrated under reduced pressure. The residue was purified by flash chromatography (silica gel, 0~50% EtOAc in PE) to afford 60 mg of 4-methyl-2-(methylsulfonyl)-6-(prop-2-yn-1-yl)-4H-thiazolo[5',4':4,5]pyrrolo[2,3-d]pyridazin-5(6H)-one. LC-MS (ESI): m/z 323 (M+H)⁺.

Step B. Synthesis of 4-methyl-2-((phenylsulfonyl)(pyridin-2-yl)methyl)-6-(prop-2-yn-1-yl)-4H-thiazolo[5',4':4,5]pyrrolo[2,3-d]pyridazin-5(6H)-one To a mixture of 4-methyl-2-(methylsulfonyl)-6-(prop-2-yn-1-yl)-4H-thiazolo[5',4':4,5]pyrrolo[2,3-d]pyridazin-5(6H)-one (60 mg, 0.18 mmol) and 2-((phenylsulfonyl)methyl)pyridine (87 mg, 0.37 mmol) in THF (5 mL) was added t-BuOK (63 mg, 0.57 mmol). After stirred at room temperature for 1 hr under nitrogen, the reaction was poured into satd. NH₄Cl, extracted with EtOAc. The organic layer was washed with brine, dried over anhy. Na₂SO₄ and concentrated under reduced pressure. The residue was purified by prep-TLC (eluant: 70% EtOAc in petroleum ether) to afford 50 mg of 4-methyl-2-((phenylsulfonyl)(pyridin-2-yl)methyl)-6-(prop-2-yn-1-yl)-4H-thiazolo[5',4':4,5]pyrrolo[2,3-d]pyridazin-5(6H)-one. LC-MS (ESI): m/z 476 (M+H)⁺.

Step C. Synthesis of 4-methyl-6-(prop-2-yn-1-yl)-2-(pyridin-2-ylmethyl)-4H-thiazolo[5',4':4,5]pyrrolo[2,3-d]pyridazin-5(6H)-one To a solution of 4-methyl-2-((phenylsulfonyl)(pyridin-2-yl)methyl)-6-(prop-2-yn-1-yl)-4H-thiazolo[5',4':4,5]pyrrolo[2,3-d]pyridazin-5(6H)-one (50 mg, 0.11 mmol) in THF/MeOH (4 mL, 1:1) was added SmI₂ (4.2 mL, 0.1 M in THF) at −70° C. under nitrogen atmosphere. After stirred for 5 min, the reaction was quenched with water. The mixture was diluted with EtOAc and washed with satd. NH₄Cl. The organic layer was washed with brine, dried over anhy. Na₂SO₄ and concentrated under reduced pressure. The residue was purified by prep-HPLC to afford 5 mg of 4-methyl-6-(prop-2-yn-1-yl)-2-(pyridin-2-ylmethyl)-4H-thiazolo[5',4':4,5]pyrrolo[2,3-d]pyridazin-5(6H)-one. LC-MS: m/z 336 (M+H)⁺. ¹H NMR (400 MHz, DMSO-d6) δ 8.60-8.52 (m, 2H), 7.81 (td, 1H), 7.51 (d, 1H), 7.33 (dd, 1H), 4.93 (d, 2H), 4.67 (s, 2H), 4.26 (s, 3H), 3.27 (t, 1H).

Example 8H. Synthesis of 2-((1H-pyrazol-3-yl)methyl)-6-benzyl-4-ethyl-4,6-dihydro-5H-thiazolo[5',4':4,5]pyrrolo[2,3-d]pyridazin-5-one

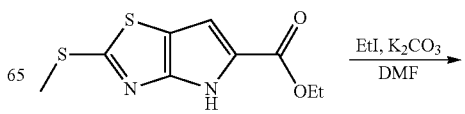

381

-continued

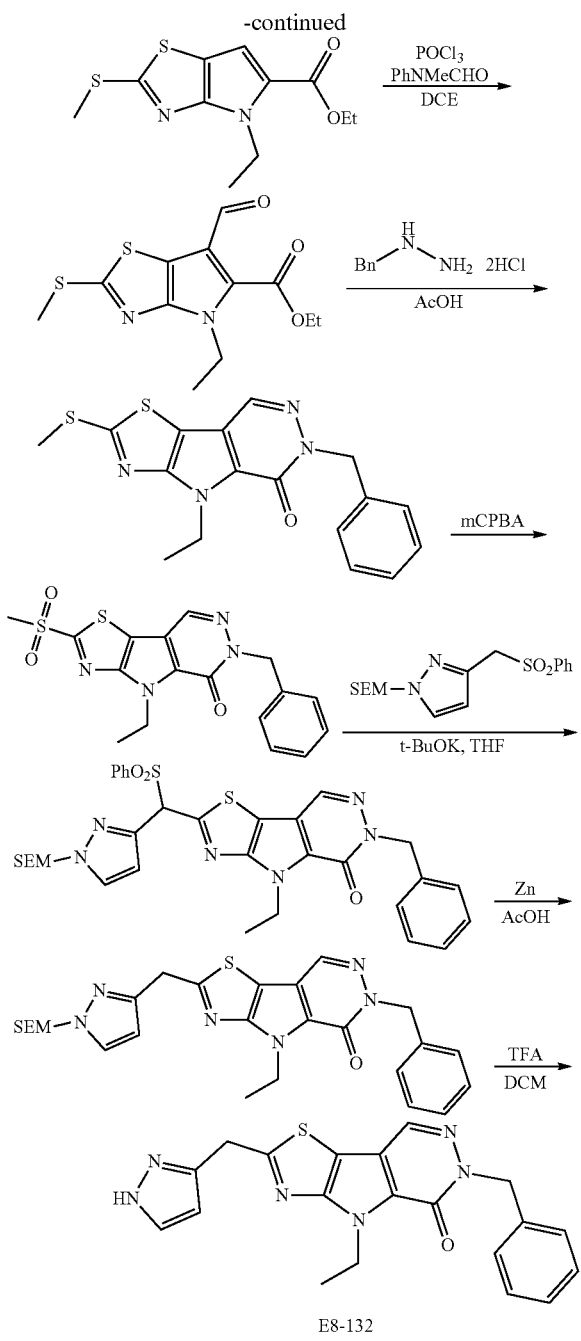

E8-132

Step A. Synthesis of Ethyl 4-ethyl-2-(methylthio)-4H-pyrrolo[2,3-d]thiazole-5-carboxylate To a mixture of ethyl 2-(methylthio)-4H-pyrrolo[2,3-d]thiazole-5-carboxylate (500 mg, 2.06 mmol) in DMF (5 mL) was added $K_2CO_3$ (856 mg, 6.19 mmol). After stirred at 70° C. for 1.5 hrs, EtI (483 mg, 3.10 mmol) was added. The mixture was stirred at 70° C. for another 1 hrs. The reaction mixture was diluted with $H_2O$ and extracted with EtOAc. The combined organic phase was evaporated under reduced pressure. The residue was purified by flash chromatography (silica gel, 0~30% EtOAc in petroleum ether) to give ethyl 4-ethyl-2-(methylthio)-4H-pyrrolo[2,3-d]thiazole-5-carboxylate (400 mg). LC-MS (ESI): m/z 271 (M+1)$^+$.

382

Step B. Synthesis of ethyl 4-ethyl-6-formyl-2-(methylthio)-4H-pyrrolo[2,3-d]thiazole-5-carboxylate A mixture of $POCl_3$ (3.6 ml) and PhNMeCHO (5 mL) was stirred at r.t. for 1 hr, then added to a solution of ethyl 4-ethyl-2-(methylthio)-4H-pyrrolo[2,3-d]thiazole-5-carboxylate (400 mg, 1.48 mmol) in DCE (10 mL). After stirred at 100° C. for 2 hrs, the reaction mixture was diluted with $H_2O$ and extracted with EtOAc twice. The combined organic phases were dried over anhy. $Na_2SO_4$ and evaporated under reduced pressure. The residue was purified by flash chromatography (silica gel, 0~30% EtOAc in PE) to give ethyl 4-ethyl-6-formyl-2-(methylthio)-4H-pyrrolo[2,3-d]thiazole-5-carboxylate (400 mg). LC-MS (ESI): m/z 299 (M+1)$^+$.

Step C. Synthesis of 6-benzyl-4-ethyl-2-(methylthio)-4,6-dihydro-5H-thiazolo[5',4':4,5]pyrrolo[2,3-d]pyridazin-5-one To a mixture of 4-ethyl-6-formyl-2-(methylthio)-4H-pyrrolo[2,3-d]thiazole-5-carboxylate (400 mg, 1.34 mmol) in AcOH (4 mL) was added benzylhydrazine dihydrochloride (260 mg, 1.34 mmol) under $N_2$. The mixture was stirred at 100° C. for 3 hrs. The reaction mixture was evaporated under reduced pressure. The residue was purified by flash chromatography (silica gel, 0~50% EtOAc in petroleum ether) to give 250 mg of 6-benzyl-4-ethyl-2-(methylthio)-4,6-dihydro-5H-thiazolo[5',4':4,5]pyrrolo[2,3-d]pyridazin-5-one. LC-MS: m/z 357 (M+1)$^+$.

Step D. Synthesis of 6-benzyl-4-ethyl-2-(methylsulfonyl)-4,6-dihydro-5H-thiazolo[5',4':4,5]pyrrolo[2,3-d]pyridazin-5-one To a mixture of 6-benzyl-4-ethyl-2-(methylthio)-4,6-dihydro-5H-thiazolo[5',4':4,5]pyrrolo[2,3-d]pyridazin-5-one (250 mg, 0.70 mmol) in DCM (5 mL) was added mCPBA (657.5 mg, 3.8 mmol) at 0° C. After stirred for 1.5 hrs, the reaction mixture was evaporated under reduced pressure. The residue was purified by prep-TLC (10% MeOH in DCM) to give 6-benzyl-4-ethyl-2-(methylsulfonyl)-4,6-dihydro-5H-thiazolo[5',4':4,5]pyrrolo[2,3-d]pyridazin-5-one (90 mg). LC-MS: m/z 389 (M+1)$^+$.

Step E. Synthesis of 6-benzyl-4-ethyl-2-((phenylsulfonyl)(1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one To a mixture of 6-benzyl-4-ethyl-2-(methylsulfonyl)-4,6-dihydro-5H-thiazolo[5',4':4,5]pyrrolo[2,3-d]pyridazin-5-one (90 mg, 0.23 mmol) and 3-((phenylsulfonyl)methyl)-1-((2-(trimethylsilyl)ethoxy)methyl)-1H-pyrazole (123 mg, 0.35 mmol) in THF (3 mL) was added and KO$^t$Bu (85 mg, 0.76 mmol) under $N_2$ at r.t. After stirred at r.t. for 30 min, the reaction mixture was quenched with satd. $NH_4Cl$ and extracted with EtOAc. The combined organic phase was evaporated under reduced pressure. The residue was purified by flash chromatography (silica gel, 0~50% EtOAc in petroleum ether) to give 6-benzyl-4-ethyl-2-((phenylsulfonyl)(1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one (140 mg, 92.2% yield). LC-MS: m/z 661 (M+1)$^+$.

Step F. Synthesis of 6-benzyl-4-ethyl-2-((1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one To a mixture of 6-benzyl-4-ethyl-2-((phenylsulfonyl)(1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one (140 mg, 0.21 mmol) in EtOH (2 mL) and DCE (1 mL) was added acetic acid (0.2 mL, 2.8 mmol) and zinc (360 mg, 5.5 mmol). The mixture was stirred at 80° C. for 3 hrs. The reaction mixture was filtered and the filtrate was evaporated under reduced pressure. The residue was purified by flash chromatography (silica gel, 0~50% EtOAc in petroleum ether) to give 30 mg of 6-benzyl-4-ethyl-2-((1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one. LC-MS (ESI): m/z 521 (M+1)+.

Step G. Synthesis of 2-((1H-pyrazol-3-yl)methyl)-6-benzyl-4-ethyl-4,6-dihydro-5H-thiazolo[5',4':4,5]pyrrolo[2,3-d]pyridazin-5-one To a mixture of 6-benzyl-4-ethyl-2-((1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one (30 mg, 0.06 mmol) in DCM (4 mL) was added TFA (4 mL). After stirred at r.t. for 1.5 hr, the reaction mixture was evaporated under reduced pressure. The residue was purified by prep-TLC (20% MeOH in DCM) to give 2-((1H-pyrazol-3-yl)methyl)-6-benzyl-4-ethyl-4,6-dihydro-5H-thiazolo[5',4':4,5]pyrrolo[2,3-d]pyridazin-5-one (5 mg). LC-MS (ESI): m/z 391 (M+1)+. 1H NMR (400 MHz, DMSO-d6) δ 12.79 (s, 1H), 8.53 (s, 1H), 7.72 (s, 1H), 7.42-7.11 (m, 5H), 6.27 (d, 1H), 5.36 (s, 2H), 4.78 (q, 2H), 4.48 (s, 2H), 1.44 (t, 3H).

Example 8I. Synthesis of 6-benzyl-4-phenyl-2-(pyridin-2-ylmethyl)-4H-thiazolo[5',4':4,5]pyrrolo[2,3-d]pyridazin-5(6H)-one

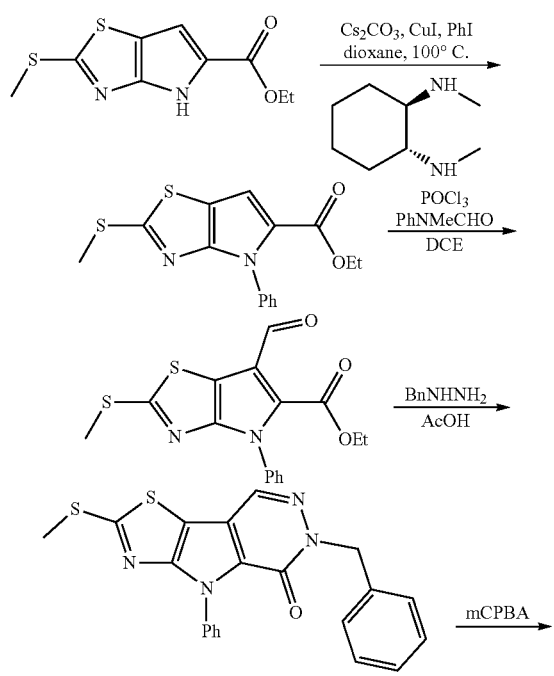

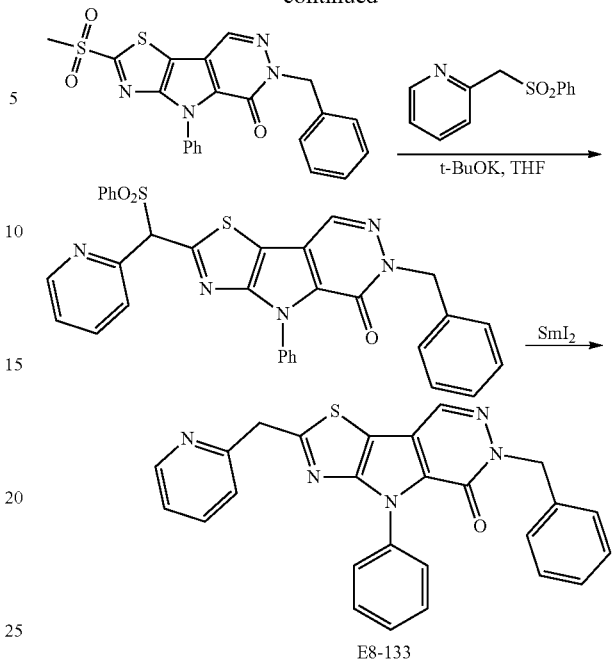

E8-133

Step A. Synthesis of ethyl 2-(methylthio)-4-phenyl-4H-pyrrolo[2,3-d]thiazole-5-carboxylate To a solution of ethyl 2-(methylthio)-4H-pyrrolo[2,3-d]thiazole-5-carboxylate (400 mg, 1.7 mmol) and PhI (265 mg, 2.55 mmol) in dioxane (5 mL) was added Cs2CO3 (1.1 g, 3.4 mmol), followed by CuI (65 mg, 0.34 mmol) and (1R,2R)—N1,N2-dimethylcyclohexane-1,2-diamine (48 mg, 0.34 mmol). The mixture was stirred under nitrogen atmosphere at 100° C. for 7 hr. The mixture was poured into water and extracted with EtOAc twice. The combined organic layers were washed with brine, dried over anhy. Na2SO4 and concentrated under reduced pressure. The residue was purified by flash chromatography (silica gel, 0~10% EtOAc in petroleum ether) to give ethyl 2-(methylthio)-4-phenyl-4H-pyrrolo[2,3-d]thiazole-5-carboxylate (400 mg). LC-MS (ESI): m/z 319 (M+1)+.

Step B. Synthesis of ethyl 6-formyl-2-(methylthio)-4-phenyl-4H-pyrrolo[2,3-d]thiazole-5-carboxylate To a solution of PhNMeCHO (1.5 mL) in DCE (5 mL) was added POCl3 (1.2 mL, 12.5 mmol) under 0° C. The mixture was stirred at r.t. for 30 min. Then ethyl 2-(methylthio)-4-phenyl-4H-pyrrolo[2,3-d]thiazole-5-carboxylate (400 mg, 1.25 mmol) was added to the mixture, the mixture was stirred at 50° C. overnight. The mixture was quenched with sat. NaHCO3 and extracted with DCM twice. The combined organic layers were washed with brine, dried over anhy. Na2SO4 and concentrated under reduced pressure. The residue was purified by flash chromatography (silica gel, 0~50% EtOAc in petroleum ether) to give ethyl 6-formyl-2-(methylthio)-4-phenyl-4H-pyrrolo[2,3-d]thiazole-5-carboxylate (280 mg). LC-MS (ESI): m/z 347 (M+1)+.

Step C. Synthesis of 6-benzyl-2-(methylthio)-4-phenyl-4H-thiazolo[5',4':4,5]pyrrolo[2,3-d]pyridazin-5(6H)-one To a mixture of ethyl 6-formyl-2-(methylthio)-4-phenyl-4H-pyrrolo[2,3-d]thiazole-5-carboxylate (280 mg, 0.81 mmol) in AcOH (6.0 mL) was added benzylhydrazine dihydrochloride (468 mg, 2.4 mmol). The reaction mixture was stirred at 100° C. for 2 hr. The filtrate was evaporated and purified by flash chromatography (silica gel, 0~70% EtOAc in petroleum ether) to give 100 mg of 6-benzyl-2-(methylthio)-4-phenyl-4H-thiazolo[5',4':4,5]pyrrolo[2,3-d]pyridazin-5(6H)-one. LC-MS: m/z 405 (M+1)+.

Step D. Synthesis of 6-benzyl-2-(methylsulfonyl)-4-phenyl-4H-thiazolo[5',4':4,5]pyrrolo[2,3-d]pyridazin-5(6H)-one To a solution of 6-benzyl-2-(methylthio)-4-phenyl-4H-thiazolo[5',4':4,5]pyrrolo[2,3-d]pyridazin-5(6H)-one (100 mg, 0.25 mmol) in DCM (5 mL) was added mCPBA (151 mg, 0.75 mmol). The mixture was stirred at r.t. for 4 hr. The mixture was quenched with aq. Na₂S₂O₃ and extracted with DCM twice. The combined organic layers were washed with brine, dried over anhy. Na₂SO₄ and concentrated under reduced pressure. The residue was purified by flash chromatography (silica gel, 0~100% EtOAc in petroleum ether) to give 6-benzyl-2-(methylsulfonyl)-4-phenyl-4H-thiazolo[5',4':4,5]pyrrolo[2,3-d]pyridazin-5(6H)-one (60 mg). LC-MS (ESI): m/z 437 (M+1)+.

Step E. Synthesis of 6-benzyl-4-phenyl-2-((phenylsulfonyl)(pyridin-2-yl)methyl)-4H-thiazolo[5',4':4,5]pyrrolo[2,3-d]pyridazin-5(6H)-one To a mixture of 6-benzyl-4-phenyl-2-((phenylsulfonyl)(pyridin-2-yl)methyl)-4H-thiazolo[5',4':4,5]pyrrolo[2,3-d]pyridazin-5(6H)-one (60 mg, 0.14 mmol) and 2-((phenylsulfonyl)methyl)pyridine (50 mg, 0.21 mmol) in dry DMF (5 mL) was added t-BuOK (31 mg, 0.28 mmol) under N₂. The reaction mixture was stirred at 60° C. for 1.5 hr. After cooled down to r.t., the mixture was poured into satd. NH₄Cl. The following mixture was extracted with EtOAc twice. The combined organic layers were washed with brine, dried over anhy. Na₂SO₄ and concentrated under reduced pressure. The residue was purified by prep-TLC (petroleum ether/EtOAc=1/4) to give 40 mg of 6-benzyl-4-phenyl-2-((phenylsulfonyl)(pyridin-2-yl)methyl)-4H-thiazolo[5',4':4,5]pyrrolo[2,3-d]pyridazin-5(6H)-one. LC-MS (ESI): m/z 590 (M+1)+.

Step F. Synthesis of 6-benzyl-4-phenyl-2-(pyridin-2-ylmethyl)-4H-thiazolo[5',4':4,5]pyrrolo[2,3-d]pyridazin-5(6H)-one To a mixture of 6-benzyl-4-phenyl-2-((phenylsulfonyl)(pyridin-2-yl)methyl)-4H-thiazolo[5',4':4,5]pyrrolo[2,3-d]pyridazin-5(6H)-one (30 mg, 0.05 mmol) in THF (1.5 mL) and MeOH (1.5 mL) was added SmI₂ (2.5 mL, 0.1 M in THF) at −78° C. under N₂. The reaction mixture was stirred at −78° C. for 10 min and then quenched with water. The mixture was extracted with EtOAc twice. The combined organic layers were washed with brine, dried over anhy. Na₂SO₄ and concentrated under reduced pressure. The residue was purified by HPLC to give 6-benzyl-4-phenyl-2-(pyridin-2-ylmethyl)-4H-thiazolo[5',4':4,5]pyrrolo[2,3-d]pyridazin-5(6H)-one (5 mg). LC-MS (ESI): m/z 450 (M+1)+. ¹H NMR (400 MHz, DMSO-d₆) δ 8.67 (s, 1H), 8.56 (d, 1H), 7.82-7.76 (m, 1H), 7.59-7.45 (m, 6H), 7.34-7.23 (m, 6H), 5.32 (s, 2H), 4.63 (s, 2H).

Example 8J. Synthesis of 2-((1H-pyrazol-3-yl)methyl)-4,6-dibenzyl-4H-thiazolo[5',4':4,5]pyrrolo[2,3-d]pyridazin-5(6H)-one

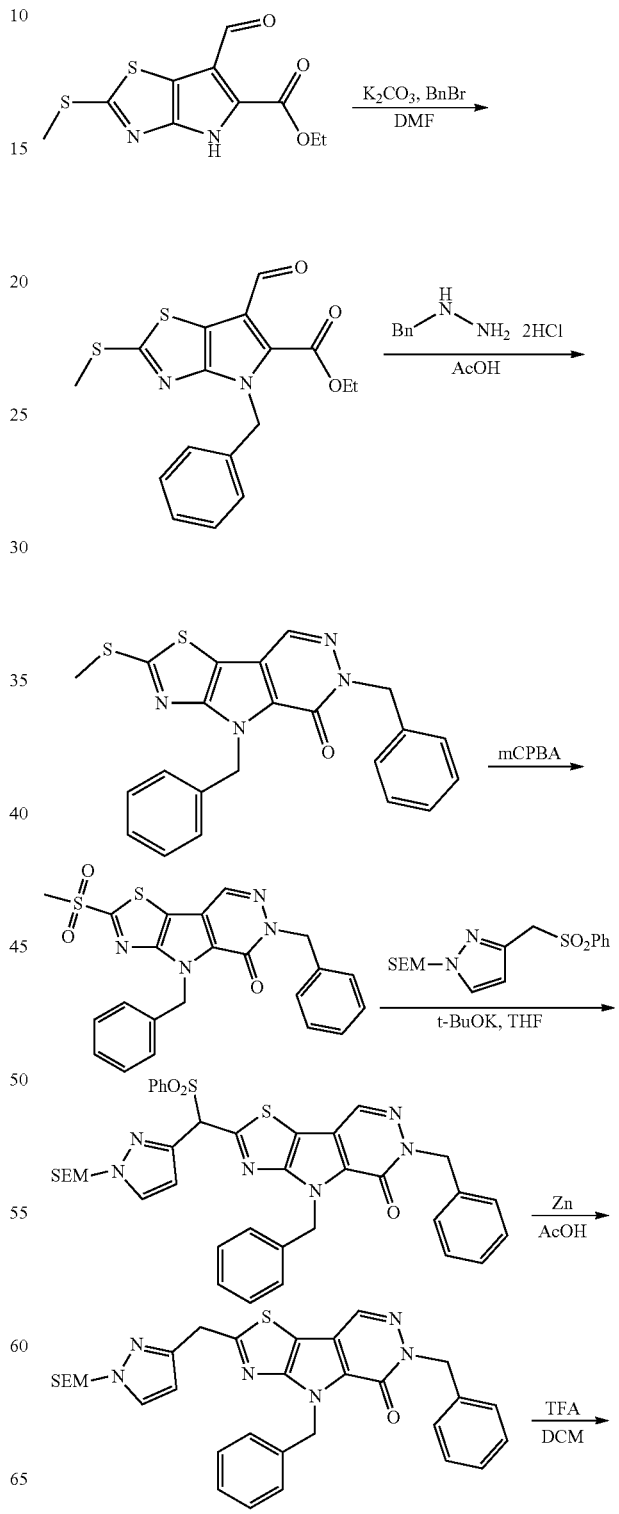

-continued

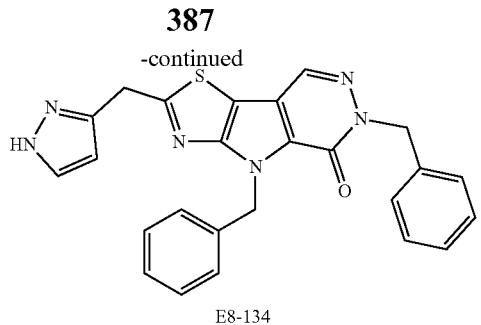

E8-134

Step A. Synthesis of ethyl 4-benzyl-6-formyl-2-(methylthio)-4H-pyrrolo[2,3-d]thiazole-5-carboxylate To a mixture of ethyl 6-formyl-2-(methylthio)-4H-pyrrolo[2,3-d]thiazole-5-carboxylate (300 mg, 1.1 mmol) in DMF (3 mL) was added $K_2CO_3$ (460 mg, 3.3 mmol). After stirred at 70° C. for 1.5 hrs, BnBr (0.2 mL, 1.6 mmol) was added. The mixture was stirred at 70° C. for 1 hr. The reaction mixture was diluted with $H_2O$ and extracted with EtOAc twice. The combined organic phases were dried over anhy. $Na_2SO_4$ and evaporated under reduced pressure. The residue was purified by flash chromatography (silica gel, 0~30% EtOAc in petroleum ether) to give ethyl 4-benzyl-6-formyl-2-(methylthio)-4H-pyrrolo[2,3-d]thiazole-5-carboxylate (370 mg). LC-MS (ESI): m/z 361 (M+1)$^+$.

Step B. Synthesis of 4,6-dibenzyl-2-(methylthio)-4H-thiazolo[5',4':4,5]pyrrolo[2,3-d]pyridazin-5(6H)-one To a mixture of ethyl 4-benzyl-6-formyl-2-(methylthio)-4H-pyrrolo[2,3-d]thiazole-5-carboxylate (370 mg, 1.0 mmol) in AcOH (4 mL) was added benzylhydrazine dihydrochloride (390 mg, 2.0 mmol) under $N_2$. The mixture was stirred at 100° C. for 3 hrs. The reaction mixture was diluted with $H_2O$ and extracted with EtOAc twice. The combined organic phases were dried over anhy. $Na_2SO_4$ and evaporated under reduced pressure. The residue was purified by flash chromatography (silica gel, 0~50% EtOAc in petroleum ether) to give 4,6-dibenzyl-2-(methylthio)-4H-thiazolo[5',4':4,5]pyrrolo[2,3-d]pyridazin-5(6H)-one (320 mg). LC-MS (ESI): m/z 419 (M+1)+.

Step C. Synthesis of 4,6-dibenzyl-2-(methylsulfonyl)-4H-thiazolo[5',4':4,5]pyrrolo[2,3-d]pyridazin-5(6H)-one To a mixture of 4,6-dibenzyl-2-(methylthio)-4H-thiazolo[5',4':4,5]pyrrolo[2,3-d]pyridazin-5(6H)-one (320 mg, 0.76 mmol) in DCM (5 mL) was added mCPBA (657.5 mg, 3.2 mmol). After stirred at 0° C. for 1.5 hrs, the reaction mixture was quenched with satd. $Na_2S_2O_3$, extracted with EtOAc. The organic phase was washed with brine, dried over anhy. $Na_2SO_4$ and evaporated under reduced pressure. The residue was purified by pre-TLC (10% MeOH in DCM) to give 4,6-dibenzyl-2-(methylsulfonyl)-4H-thiazolo[5',4':4,5]pyrrolo[2,3-d]pyridazin-5(6H)-one (170 mg). LC-MS (ESI): m/z 451 (M+1)$^+$.

Step D. Synthesis of 4,6-dibenzyl-2-((phenylsulfonyl)(1-((2-(trimethylsilyl)ethoxy)methyl)-1H-pyrazol-3-yl)methyl)-4H-thiazolo[5',4':4,5]pyrrolo[2,3-d]pyridazin-5(6H)-one To a mixture of 4,6-dibenzyl-2-(methylsulfonyl)-4H-thiazolo[5',4':4,5]pyrrolo[2,3-d]pyridazin-5(6H)-one (170 mg, 0.38 mmol) and 3-((phenylsulfonyl)methyl)-1-((2-(trimethylsilyl)ethoxy)methyl)-1H-pyrazole (160 mg, 0.46 mmol) in THF (3 mL) was added KO$^t$Bu (85 mg, 0.76 mmol) under $N_2$ at r.t. After stirred at r.t. for 3 hr, the reaction mixture was quenched with satd. $NH_4Cl$ and extracted with EtOAc twice. The combined organic phases were dried over anhy. $Na_2SO_4$ and evaporated under reduced pressure. The residue was purified by flash chromatography (silica gel, 0~50% EtOAc in petroleum ether) to give 4,6-dibenzyl-2-((phenylsulfonyl)(1-((2-(trimethylsilyl)ethoxy)methyl)-1H-pyrazol-3-yl)methyl)-4H-thiazolo[5',4':4,5]pyrrolo[2,3-d]pyridazin-5(6H)-one (200 mg). LC-MS (ESI): m/z 723 (M+1)$^+$.

Step E. Synthesis of 4,6-dibenzyl-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one To a mixture of 6-((4-aminopyrimidin-2-yl)methyl)-4-methyl-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (200 mg, 0.28 mmol) in EtOH (2 mL) and DCE (1 mL) were added acetic acid (0.2 mL, 2.8 mmol) and zinc (360 mg, 5.5 mmol). After stirred at 100° C. for 3 hrs, the reaction mixture was filtered and the filtrate was evaporated under reduced pressure. The residue was purified by flash chromatography (silica gel, 0~50% EtOAc in petroleum ether) to give 4,6-dibenzyl-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (120 mg). LC-MS: m/z 583 (M+1)$^+$.

Step F. Synthesis of 2-((1H-pyrazol-3-yl)methyl)-4,6-dibenzyl-4H-thiazolo[5',4':4,5]pyrrolo[2,3-d]pyridazin-5(6H)-one To a mixture of 4,6-dibenzyl-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (120 mg, 0.21 mmol) in DCM (4 mL) was added TFA (4 mL). The mixture was stirred at r.t. for 1.5 hrs. The reaction mixture was evaporated under reduced pressure. The residue was purified by prep-TLC (20% MeOH in DCM) to give 9 mg of 2-((1H-pyrazol-3-yl)methyl)-4,6-dibenzyl-4H-thiazolo[5',4':4,5]pyrrolo[2,3-d]pyridazin-5(6H)-one. LC-MS: m/z 453 (M+1)$^+$. $^1$H NMR (400 MHz, DMSO-$d_6$) δ 12.78 (s, 1H), 8.57 (s, 1H), 7.71 (s, 1H), 7.42-7.04 (m, 10H), 6.25 (d, 1H), 5.98 (s, 2H), 5.37 (s, 2H), 4.48 (s, 2H).

Example 8K. Synthesis of 2-((1H-pyrazol-3-yl)methyl)-6-benzyl-4-cyclopropyl-4,6-dihydro-5H-thiazolo[5',4':4,5]pyrrolo[2,3-d]pyridine-5-one

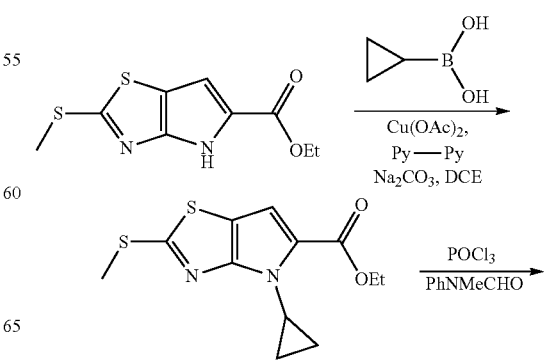

389

-continued

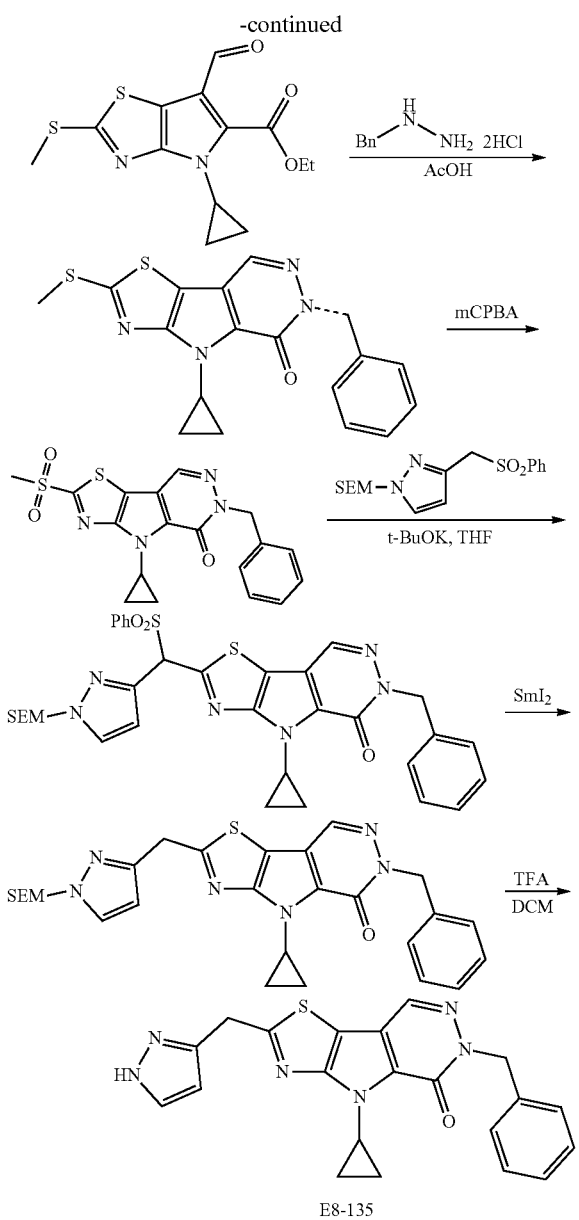

E8-135

Step A. Synthesis of ethyl 4-cyclopropyl-2-(methylthio)-4H-pyrrolo[2,3-d]thiazole-5-carboxylate To a suspension of cyclopropylboronic acid (687 mg, 8 mmol) and ethyl 2-(methylthio)-4H-pyrrolo[2,3-d]thiazole-5-carboxylate (970 mg, 4 mmol) in DCE (10 mL) was added $Na_2CO_3$ (848 mg, 8 mmol), followed by $Cu(OAc)_2$ (727 mg, 4 mmol) and bipyridine (625 mg, 4 mmol). The mixture was stirred at 70° C. for 2 h under air. The resulting mixture was cooled to room temperature, and quenched with satd. $NH_4Cl$, extracted with DCM. The combined organic layers were washed with brine, dried over anhy. $Na_2SO_4$ and concentrated under reduced pressure. The residue was purified by flash chromatography (silica gel, 0~30% EtOAc in petroleum ether) to give ethyl 4-cyclopropyl-2-(methylthio)-4H-pyrrolo[2,3-d]thiazole-5-carboxylate (1.0 g, 88.5% yield). LC-MS (ESI): m/z 283 (M+1)$^+$.

390

Step B. Synthesis of ethyl 4-cyclopropyl-6-formyl-2-(methylthio)-4H-pyrrolo[2,3-d]thiazole-5-carboxylate A mixture of $POCl_3$ (8.6 mL) and PhNMeCHO (12 mL) was stirred at r.t. for 1 hr, then added to a solution of ethyl 4-cyclopropyl-2-(methylthio)-4H-pyrrolo[2,3-d]thiazole-5-carboxylate (1.0 g, 3.54 mmol) in DCE (10 mL). After stirred at 100° C. for 2 hrs, the reaction mixture was diluted with $H_2O$ and extracted with EtOAc twice. The combined organic phases were dried over anhy. $Na_2SO_4$ and evaporated under reduced pressure. The residue was purified by flash chromatography (silica gel, 0~30% EtOAc in petroleum ether) to give ethyl 4-cyclopropyl-6-formyl-2-(methylthio)-4H-pyrrolo[2,3-d]thiazole-5-carboxylate (620 mg). LC-MS (ESI): m/z 311 (M+1)$^+$.

Step C. Synthesis of 6-benzyl-4-cyclopropyl-2-(methylthio)-4,6-dihydro-5H-thiazolo[5',4':4,5]pyrrolo[2,3-d]pyridazin-5-one To a mixture of 4-ethyl-6-formyl-2-(methylthio)-4H-pyrrolo[2,3-d]thiazole-5-carboxylate (620 mg, 2 mmol) in AcOH (4 mL) was added benzylhydrazine dihydrochloride (390 mg, 2 mmol) under $N_2$. The mixture was stirred at 100° C. for 3 hrs. The reaction mixture was evaporated under reduced pressure. The residue was purified by flash chromatography (silica gel, 0~50% EtOAc in petroleum ether) to give 6-benzyl-4-ethyl-2-(methylthio)-4,6-dihydro-5H-thiazolo[5',4':4,5]pyrrolo[2,3-d]pyridazin-5-one (320 mg). LC-MS (ESI): m/z 369 (M+1)+.

Step D. Synthesis of 6-benzyl-4-cyclopropyl-2-(methylsulfonyl)-4,6-dihydro-5H-thiazolo[5',4':4,5]pyrrolo[2,3-d]pyridazin-5-one To a mixture of 6-benzyl-4-cyclopropyl-2-(methylthio)-4,6-dihydro-5H-thiazolo[5',4':4,5]pyrrolo[2,3-d]pyridazin-5-one (320 mg, 0.87 mmol) in DCM (5 mL) was added mCPBA (704 mg, 3.5 mmol). After stirred at 0° C. for 1.5 hrs, the reaction mixture was quenched with satd. $Na_2S_2O_3$, extracted with EtOAc. The organic phase was washed with brine, dried over anhy. $Na_2SO_4$ and evaporated under reduced pressure. The residue was purified by prep-TLC (10% MeOH in DCM) to give 110 mg of 6-benzyl-4-cyclopropyl-2-(methylsulfonyl)-4,6-dihydro-5H-thiazolo[5',4':4,5]pyrrolo[2,3-d]pyridazin-5-one. LC-MS: m/z 401 (M+1)$^+$.

Step E. Synthesis of 6-benzyl-4-cyclopropyl-2-((phenylsulfonyl)(1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one To a mixture of 6-benzyl-4-ethyl-2-(methylsulfonyl)-4,6-dihydro-5H-thiazolo[5',4':4,5]pyrrolo[2,3-d]pyridazin-5-one (110 mg, 0.27 mmol) and 3-((phenylsulfonyl)methyl)-1-((2-(trimethylsilyl)ethoxy)methyl)-1H-pyrazole (123 mg, 0.35 mmol) in THF (3 mL) was added KO$^t$Bu (85 mg, 0.76 mmol) under $N_2$ at r.t. The mixture was stirred at r.t. for 3 hr. The reaction mixture was quenched with satd. $NH_4Cl$ and extracted with EtOAc twice. The combined organic phase was evaporated under reduced pressure. The residue was purified by flash chromatography (silica gel, 0~50% EtOAc in petroleum ether) to give 100 mg of 6-benzyl-4-cyclopropyl-2-((phenylsulfonyl)(1-((2-(trimethylsilyl)ethoxy)

methyl)-1H-pyrazol-3-yl)methyl)-4,6-dihydro-5H-thiazolo [5',4':4,5]pyrrolo[2,3-d]pyridazin-5-one. LC-MS: m/z 673 (M+1)⁺.

Step F. Synthesis of 6-benzyl-4-cyclopropyl-2-((1-((2-(trimethylsilyl)ethoxy)methyl)-1H-pyrazol-3-yl) methyl)-4,6-dihydro-5H-thiazolo[5',4':4,5]pyrrolo[2, 3-d]pyridazin-5-one To a mixture of 6-benzyl-4-cyclopropyl-2-((phenylsulfonyl)(1-((2-(trimethylsilyl)ethoxy)methyl)-1H-pyrazol-3-yl) methyl)-4,6-dihydro-5H-thiazolo[5',4':4,5]pyrrolo[2,3-d] pyridazin-5-one (100 mg, 0.15 mmol) in MeOH (3 mL) and THF (3 mL) was added SmI₂ (4.5 ml, 0.45 mmol) at −60° C. under N₂. The mixture was stirred at −60° C. for 10 min, quenched with H₂O and extracted with EtOAc twice. The combined organic phases were dried over Na₂SO₄ and evaporated under reduced pressure. The residue was purified by flash chromatography (silica gel, 0–50% EtOAc in petroleum ether) to give 40 mg of 6-benzyl-4-cyclopropyl-2-((1-((2-(trimethylsilyl)ethoxy)methyl)-1H-pyrazol-3-yl) methyl)-4,6-dihydro-5H-thiazolo[5',4':4,5]pyrrolo[2,3-d] pyridazin-5-one. LC-MS: m/z 533 (M+1)⁺.

Step G. Synthesis of 2-((1H-pyrazol-3-yl)methyl)-6-benzyl-4-cyclopropyl-4,6-dihydro-5H-thiazolo[5', 4':4,5]pyrrolo[2,3-d]pyridazin-5-one To a mixture of 6-benzyl-4-cyclopropyl-2-((1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one (40 mg, 0.07 mmol) in DCM (4 mL) was added TFA (4 mL). The mixture was stirred at r.t. for 1.5 hrs. The reaction mixture was evaporated under reduced pressure. The residue was purified by prep-TLC (20% MeOH in DCM) to give 5 mg of 2-((1H-pyrazol-3-yl)methyl)-6-benzyl-4-cyclopropyl-4,6-dihydro-5H-thiazolo[5',4':4,5]pyrrolo[2,3-d] pyridazin-5-one. LC-MS (ESI): m/z 403 (M+1)⁺. ¹H NMR (400 MHz, DMSO-d6) δ 12.77 (s, 1H), 8.50 (s, 1H), 7.68 (s, 1H), 7.35-7.23 (m, 5H), 6.26 (d, 1H), 5.35 (s, 2H), 4.48 (s, 2H), 4.19 (tt, 1H), 1.40 (td, 2H), 1.15 (td, 2H).

Example 8L. Synthesis of 4-methyl-6-((1-methyl-1H-pyrazol-3-yl)methyl)-2-(2-(pyridin-3-yl)ethyl)-4H-thiazolo[5',4':4,5]pyrrolo[2,3-d]pyridazin-5(6H)-one

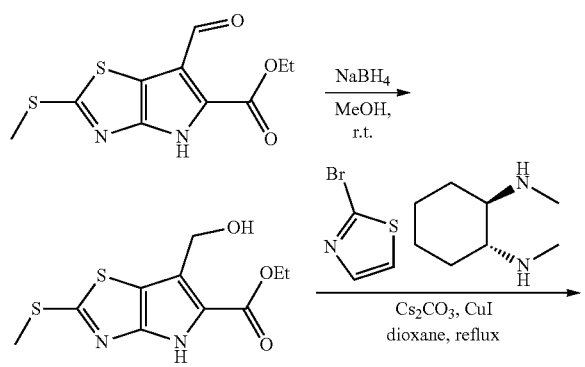

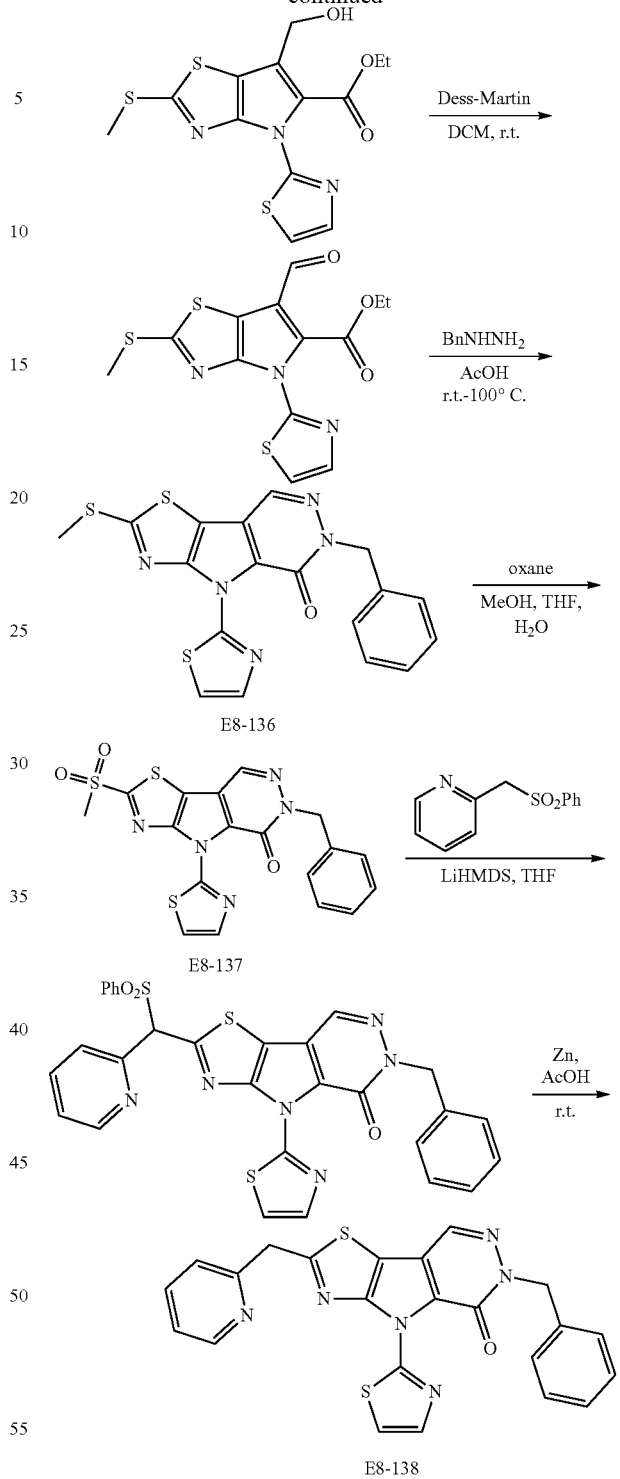

Step A. Synthesis of ethyl 6-(hydroxymethyl)-2-(methylthio)-4H-pyrrolo[2,3-d]thiazole-5-carboxylate To a solution of ethyl 6-formyl-2-(methylthio)-4H-pyrrolo[2,3-d]thiazole-5-carboxylate (1.3 g, 4.8 mmol) in MeOH (20 mL) was added NaBH₄ (274 mg, 7.2 mmol) at 0° C. After stirred at 0° C. for 20 min, the reaction solution was diluted with EtOAc, washed with water and brine, dried over Na₂SO₄, concentrated in vacuum. The residue was purified by flash chromatography (silica gel, 0~10% MeOH in DCM) to give ethyl 6-(hydroxymethyl)-2-(methylthio)-4H-pyrrolo[2,3-d]thiazole-5-carboxylate (1 g). LC-MS (ESI): m/z 273 (M+1)+.

Step B. Synthesis of ethyl 6-(hydroxymethyl)-2-(methylthio)-4-(thiazol-2-yl)-4H-pyrrolo[2,3-d]thiazole-5-carboxylate To a solution of ethyl 6-(hydroxymethyl)-2-(methylthio)-4H-pyrrolo[2,3-d]thiazole-5-carboxylate (1 g, 3.7 mmol) and 2-bromothiazole (3 g, 18.4 mmol) in dioxane (30 mL) was added Cs₂CO₃ (3 g, 9.2 mmol), followed by CuI (700 mg, 3.7 mmol) and $N^1,N^2$-dimethylcyclohexane-1,2-diamine (520 mg, 3.7 mmol). The reaction mixture was stirred at 110° C. under N₂ atmosphere for 16 hr. The reaction mixture was cooled to room temperature, filtered. The filtrate was diluted with EtOAc, washed with water and brine, dried over anhydrous Na₂SO₄, concentrated. The residue was purified by flash chromatography (silica gel, 30~50% EtOAc in petroleum ether) to give ethyl 6-(hydroxymethyl)-2-(methylthio)-4-(thiazol-2-yl)-4H-pyrrolo[2,3-d]thiazole-5-carboxylate (1 g). LC-MS (ESI): m/z 356 (M+1)⁺.

Step C. Synthesis of ethyl 6-formyl-2-(methylthio)-4-(thiazol-2-yl)-4H-pyrrolo[2,3-d]thiazole-5-carboxylate To a solution of ethyl 6-(hydroxymethyl)-2-(methylthio)-4-(thiazol-2-yl)-4H-pyrrolo[2,3-d]thiazole-5-carboxylate (1 g, 2.8 mmol) in DCM (20 mL) was added Dess-martin (1.3 g, 3.4 mmol). After stirred at r.t. for 2 hrs, the reaction solution was diluted with DCM, washed with satd. NaHCO₃ and brine, dried over anhy. Na₂SO₄ and concentrated. The residue was purified by flash chromatography (silica gel, 20~30% EtOAc in petroleum ether) to give ethyl 6-formyl-2-(methylthio)-4-(thiazol-2-yl)-4H-pyrrolo[2,3-d]thiazole-5-carboxylate (800 mg). LC-MS (ESI): m/z 354 (M+1)⁺.

Step D. Synthesis of 6-benzyl-2-(methylthio)-4-(thiazol-2-yl)-4H-thiazolo[5',4':4,5]pyrrolo[2,3-d]pyridazin-5(6H)-one To a solution of ethyl 6-formyl-2-(methylthio)-4-(thiazol-2-yl)-4H-pyrrolo[2,3-d]thiazole-5-carboxylate (800 mg, 2.3 mmol) in AcOH (10 mL) was added benzylhydrazine dihydrochloride (449 mg, 2.3 mmol). After stirred at r.t. for 1 hr, the reaction mixture was heated to 100° C. for 2 hrs. The reaction mixture was cooled to 0° C., neutralized with 1 M aq. NaOH, extracted with DCM. The organic phase was washed with brine, dried over anhy. Na₂SO₄ and concentrated in vacuum. The residue was purified by flash chromatography (silica gel, 0~5% MeOH in DCM) to give 6-benzyl-2-(methylthio)-4-(thiazol-2-yl)-4H-thiazolo[5',4': 4,5]pyrrolo[2,3-d]pyridazin-5(6H)-one (300 mg). LC-MS (ESI): m/z 412 (M+1)⁺. ¹H NMR (400 MHz, DMSO-d6) δ 8.72 (s, 1H), 7.98 (d, 1H), 7.87 (d, 1H), 7.40-7.15 (m, 5H), 5.31 (s, 2H), 2.76 (s, 3H).

Step E. Synthesis of 6-benzyl-2-(methylsulfonyl)-4-(thiazol-2-yl)-4H-thiazolo[5',4':4,5]pyrrolo[2,3-d]pyridazin-5(6H)-one To a mixture of 6-benzyl-2-(methylthio)-4-(thiazol-2-yl)-4H-thiazolo[5',4':4,5]pyrrolo[2,3-d]pyridazin-5(6H)-one (300 mg, 0.73 mmol) in MeOH (5 mL) and THF (5 mL) was added a solution of oxone (2.2 g, 3.6 mmol) in H₂O (5 mL) at 0° C. The reaction mixture was stirred at r.t. for 2 hrs. The reaction mixture was diluted with DCM, washed with satd. NaHCO₃ and brine, dried over anhy. Na₂SO₄ and concentrated in vacuum. The residue was purified by flash chromatography (silica gel, 0~5% MeOH in DCM) to give 6-benzyl-2-(methylsulfonyl)-4-(thiazol-2-yl)-4H-thiazolo[5',4':4,5]pyrrolo[2,3-d]pyridazin-5(6H)-one (260 mg). LC-MS (ESI): m/z 444 (M+1)⁺. ¹H NMR (400 MHz, DMSO-d6) δ 8.93 (s, 1H), 8.04 (d, 1H), 7.91 (d, 1H), 7.40-7.18 (m, 5H), 5.35 (s, 2H), 3.53 (s, 3H).

Step F. Synthesis of 6-benzyl-2-((phenylsulfonyl)(pyridin-2-yl)methyl)-4-(thiazol-2-yl)-4H-thiazolo[5',4':4,5]pyrrolo[2,3-d]pyridazin-5(6H)-one To a stirring solution of 2-((phenylsulfonyl)methyl)pyridine (120 mg, 0.51 mmol) in THF (3 mL) was added LiHMDS (0.7 mL, 0.7 mmol) at 0° C. under N₂ atmosphere. After stirred at 0° C. for 30 min, a solution of 6-benzyl-2-(methylsulfonyl)-4-(thiazol-2-yl)-4H-thiazolo[5',4':4,5]pyrrolo[2,3-d]pyridazin-5(6H)-one (150 mg, 0.34 mmol) in THF (3 mL) was added. The resulting mixture was stirred at r.t. for 1 hr. The reaction was quenched with satd. NH₄Cl, extracted with DCM. The organic phase was washed with brine, dried over anhy. Na₂SO₄ and concentrated in vacuum. The residue was purified by flash chromatography (silica gel, 0~5% MeOH in DCM) to give 6-benzyl-2-((phenylsulfonyl)(pyridin-2-yl)methyl)-4-(thiazol-2-yl)-4H-thiazolo[5',4':4,5]pyrrolo[2,3-d]pyridazin-5(6H)-one (100 mg). LC-MS (ESI): m/z 597 (M+1)⁺.

Step G. Synthesis of 6-benzyl-2-(pyridin-2-ylmethyl)-4-(thiazol-2-yl)-4H-thiazolo[5',4':4,5]pyrrolo[2,3-d]pyridazin-5(6H)-one To a solution of 6-benzyl-2-((phenylsulfonyl)(pyridin-2-yl)methyl)-4-(thiazol-2-yl)-4H-thiazolo[5',4':4,5]pyrrolo[2,3-d]pyridazin-5(6H)-one (100 mg, 0.17 mmol) in AcOH (5 mL) was added Zn (110 mg, 1.7 mmol). The reaction mixture was stirred at r.t. for 15 min. The reaction mixture was diluted with DCM, washed with satd. NaHCO₃ and brine, dried over anhy. Na₂SO₄ and concentrated in vacuum. The residue was purified by pre-TLC (65% EtOAc in petroleum ether) to give 5 mg of 6-benzyl-2-(pyridin-2-ylmethyl)-4-(thiazol-2-yl)-4H-thiazolo[5',4':4,5]pyrrolo[2,3-d]pyridazin-5(6H)-one. LC-MS (ESI): m/z 457 (M+1)⁺. ¹H NMR (400 MHz, DMSO-d6) δ 8.72 (s, 1H), 8.61 (d, 1H), 7.98 (d, 1H), 7.92-7.84 (m, 2H), 7.55 (d, 1H), 7.41 (dd, 1H), 7.35-7.23 (m, 5H), 5.32 (s, 2H), 4.70 (s, 2H).

Example 9. Synthesis of Compounds E9-vi and E9-vii

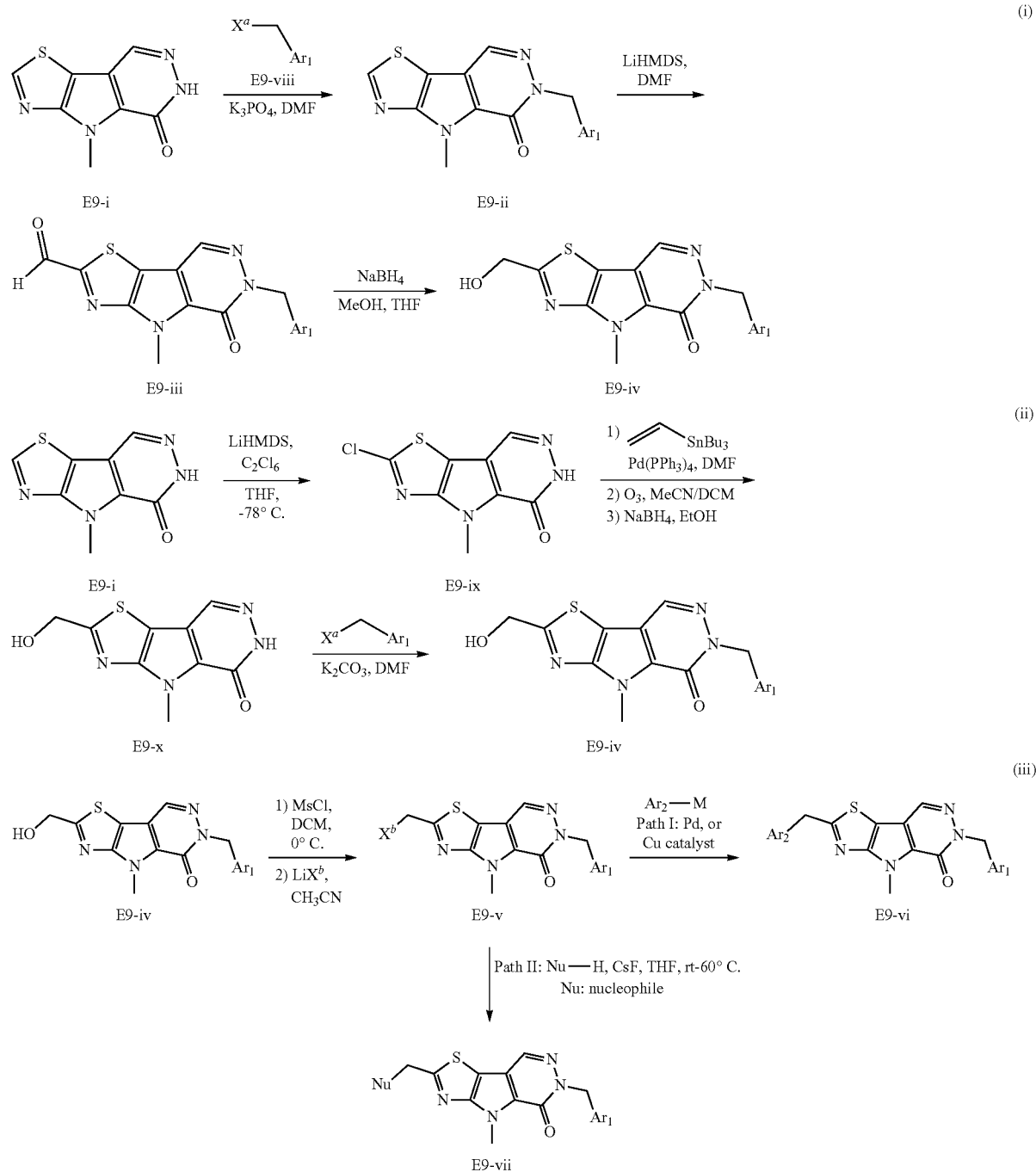

Scheme E9

Compound E9-iv can be synthesized by two approaches, (i) and (ii) in Scheme 9. For approach (i), compound E9-ii can be synthesized from compound E9-i through alkylation reaction as showed in Example 7 or Example 8. As used herein, $X^a$ is a leaving group (e.g. Br, I, OMs, or OTs). Formylation reaction of compound E9-ii with LiHMDS and DMF provides intermediate E9-iii. E9-iii reacts with a reducing agent (e.g. NaBH$_4$) to provide compound E9-iv. Alternatively in approach (ii), halogenation of compound E9-i generates compound E9-ix. Compound E9-ix undergoes Stille reaction, ozonolysis, and reduction to furnish compound E9-x. Compound E9-x can be alkylated with E9-viii to provide compound E9-iv. In Scheme 9, (iii), Compound E9-iv undergoes halogenation to give interme diate E9-v ($X^b$ is halogen such as Cl or Br). A metal (e.g. Pd or Cu) catalyzed coupling of E9-v with organic Tin, boron, zinc or magnesium provides compound E9-vi. As used herein; Compound E9-v can also react with some nucleophiles such as nitrogen in a heterocycle to give product E9-vii. As used herein, M is an organic metal complex (e.g. organoboron complex such as boronic acid or pinaco boron complex, organotin complex such as —Sn(Bu$^r$)$_3$; organozinc complex such as —Zn (halogen)); Ar$_1$ and Ar$_2$ are each independently optionally substituted aryl, optionally substituted heteroaryl, optionally substituted carbocycle or optionally substituted heterocyclyl. In certain embodiments, Ar$_1$ and Ar$_2$ are each independently optionally substituted heteroaryl.

Example 9A. Synthesis of 6-((1H-indazol-4-yl) methyl)-4-methyl-2-(thiazol-4-ylmethyl)-4H-thiazolo[5',4':4,5]pyrrolo[2,3-d]pyridazin-5(6H)-one

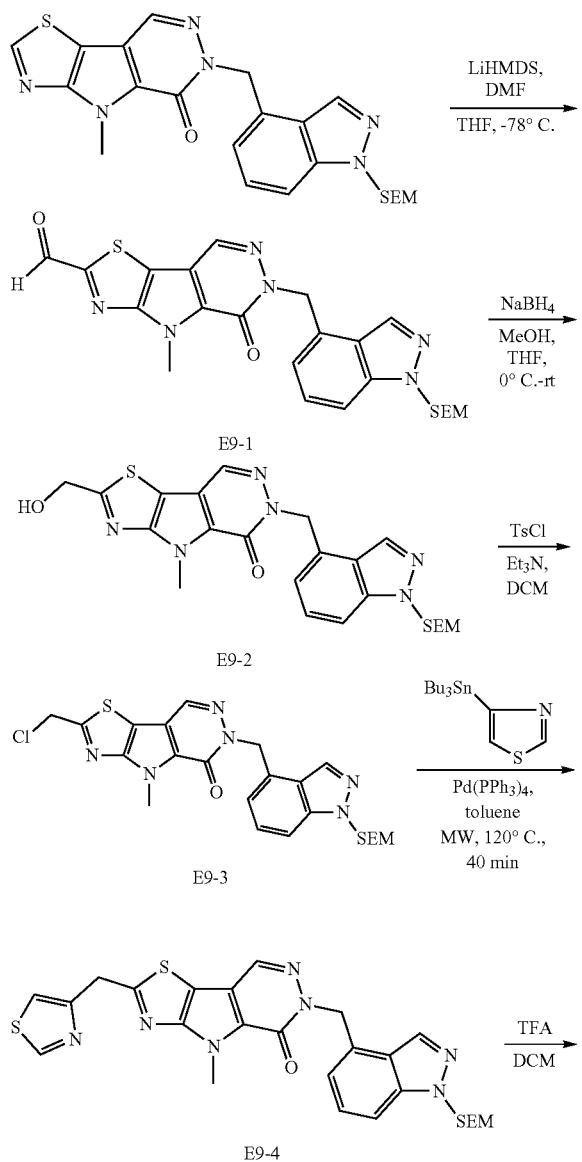

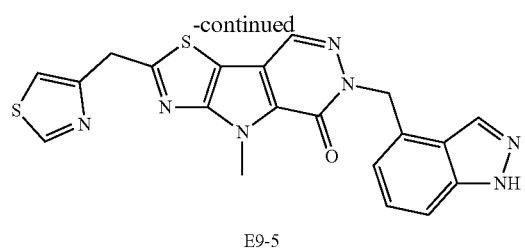

Step A. Synthesis of 4-methyl-5-oxo-6-((1-((2-(trimethylsilyl)ethoxy)methyl)-1H-indazol-4-yl) methyl)-5,6-dihydro-4H-thiazolo[5',4':4,5]pyrrolo[2,3-d]pyridazine-2-carbaldehyde To a mixture of 4-methyl-6-((1-((2-(trimethylsilyl) ethoxy)methyl)-1H-indazol-4-yl)methyl)-4H-thiazolo[5',4':4,5]pyrrolo[2,3-d]pyridazin-5(6H)-one (2.6 g, 5.57 mmol, 1 eq) in dry THF (30 mL) was added LiHMDS (1 M, 11.14 mL, 2.0 eq) at −78° C. The mixture was stirred at −78° C. for 2 hr. Then DMF (2.04 g, 27.86 mmol, 2.14 mL, 5.0 eq) was added dropwise to the above mixture. The mixture was stirred at −78° C. for 2 hr. TLC (PE:EA=2:1, UV=254 nm) showed that one main new spot was formed. The mixture was poured into cold sat. NH$_4$Cl (20 mL). Then the mixture was warmed to room temperature. The mixture was extracted with EtOAc (40 mL×3). The organic layer was washed by water (20 mL×3) and concentrated in vacuo to give the desired product (2.6 g, crude). LCMS: m/z 495.2 [M+H]$^+$ Step B. Synthesis of 2-(hydroxymethyl)-4-methyl-6-((1-((2-(trimethylsilyl)ethoxy) methyl)-1H-indazol-4-yl)methyl)-4H-thiazolo[5',4':4,5]pyrrolo[2,3-d] pyridazin-5(6H)-one To a mixture of crude 4-methyl-5-oxo-6-((1-((2-(trimethylsilyl)ethoxy) methyl)-1H-indazol-4-yl)methyl)-5,6-dihydro-4H-thiazolo[5',4':4,5]pyrrolo[2,3-d]pyridazine-2-carbaldehyde (1.0 g, 2.02 mmol, 1 eq) in THF (10 mL) and MeOH (10 mL) was added NaBH$_4$ (152.97 mg, 4.04 mmol, 2 eq). The mixture was stirred at 30° C. for 14 hr. TLC (DCM:MeOH=10:1, UV=254 nm) showed that the starting material was consumed completely and one main new spot was formed. The reaction was quenched by addition of water (20 mL) and extracted with EtOAc (30 mL×3). The combined organic layers were washed with brine (20 mL). The organic phase was concentrated in vacuo. The residue was purified by flash silica gel chromatography (ISCO®; 40 g SepaFlash® Silica Flash Column, Eluent of 0~5% MeOH/ DCM @ 30 mL/min). The eluent was concentrated in vacuo to give the desired product (382 mg). LCMS: m/z 497.1 [M+H]$^+$. $^1$H NMR (400 MHz, DMSO-d$_6$) δ ppm 8.61 (s, 1H), 8.25 (s, 1H), 7.66 (d, 1H), 7.38 (t, 1H), 7.05 (d), 6.36 (t, 1H), 5.74 (s, 2H), 5.68 (s, 2H), 4.89 (d, 2H), 4.26 (s, 3H), 3.50 (t, 2H), 0.78 (t, 2H), −0.12 (s, 9H).

Step C. Synthesis of 2-(chloromethyl)-4-methyl-6-((1-((2-(trimethylsilyl)ethoxy) methyl)-1H-indazol-4-yl)methyl)-4H-thiazolo[5',4':4,5]pyrrolo[2,3-d] pyridazin-5(6H)-one To a mixture of 2-(hydroxymethyl)-4-methyl-6-((1-((2-(trimethylsilyl) ethoxy)methyl)-1H-indazol-4-yl)methyl)-4H-thiazolo[5',4':4,5]pyrrolo[2,3-d]pyridazin-5(6H)-one (150.0 mg, 302.02 umol, 1 eq) and Et₃N (61.12 mg, 604.04 umol, 84.08 μL, 2.0 eq) in DCM (5 mL) was added 4-methylbenzenesulfonyl chloride (75.0 mg, 393.40 umol, 1.30 eq). The mixture was stirred at 30° C. for 5 hr. TLC (PE:EA=4:1, UV=254 nm) showed the starting material was consumed completely. Water (10 mL) and DCM (20 mL) was added to the mixture. The organic layers were concentrated in vacuo to give a yellow gum (0.1 g). The residue was purified by flash silica gel chromatography (ISCO®; 4 g SepaFlash® Silica Flash Column, Eluent of 0~20% Ethyl acetate/Petroleum ether gradient @ 30 mL/min). The desired fraction was concentrated in vacuo to give the desired product (40.0 mg, 76.88 umol). LCMS: m/z 515.1 [M+H]⁺. ¹H NMR (400 MHz, CHLOROFORM-d) δ ppm 8.27 (d, 1H), 8.26 (s, 1H), 7.52 (d, 1H), 7.39 (dd, 1H), 7.25 (s, 1H), 5.76 (s, 2H), 5.72 (s, 2H), 4.96 (s, 2H), 4.40 (s, 3H), 3.50-3.57 (m, 2H), 0.84-0.90 (m, 2H), −0.09 to −0.06 (m, 9H).

Step D. Synthesis of 4-methyl-2-(thiazol-4-ylmethyl)-6-((1-((2-(trimethylsilyl)ethoxy)methyl)-1H-indazol-4-yl)methyl)-4,6-dihydro-5H-thiazolo[5',4':4,5]pyrrolo[2,3-d]pyridazin-5-one To a solution of 2-(chloromethyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (50 mg, 0.97 mmol) and 4-(tributylstannyl)thiazole (114 mg, 2.91 mmol) in toluene (4 mL) was added Pd(PPh₃)₄ (402 mg, 2.91 mmol). Then the mixture was heated in MW reactor at 120° C. for 30 min under N₂. The solution was poured into water and extracted with EtOAc, dried over anhydrous Na₂SO₄. The organic layer was concentrated under reduced pressure. The residue was purified by flash chromatography (silica gel, 0~50% ethyl acetate in petroleum ether) to give 4-methyl-2-(thiazol-4-ylmethyl)-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (compound E9-4) (30 mg). LCMS: 564 (M+H)⁺.

Step E. Synthesis of 6-((1H-indazol-4-yl)methyl)-4-methyl-2-(thiazol-4-ylmethyl)-4,6-dihydro-5H-thiazolo[5',4':4,5]pyrrolo[2,3-d]pyridazin-5-one To a mixture of compound E9-4 (30 mg, 0.05 mmol) in DCM (3 mL) at r.t. under N₂ was added TFA (3 mL). The reaction mixture was stirred at r.t. for 1 h. The mixture was concentrated under reduced pressure. The residue was purified by prep. HPLC (C18, 0~90% acetonitrile in H₂O with 0.1% formic acid) to give the desired product (3.9 mg). LCMS: 434 (M+H)⁺. ¹H NMR (400 MHz, DMSO) δ 13.12 (s, 1H), 9.12 (d, 1H), 8.56 (s, 1H), 8.14 (s, 1H), 7.71 (d, 1H), 7.45 (d, 1H), 7.35-7.24 (m, 1H), 6.96 (d, 1H), 5.65 (s, 2H), 4.70 (s, 2H), 4.27 (s, 3H).

Example 9B. Synthesis of 2-((1H-imidazol-1-yl)methyl)-6-((1H-indazol-4-yl)methyl)-4-methyl-4,6-dihydro-5H-thiazolo[5',4':4,5]pyrrolo[2,3-d]pyridazin-5-one

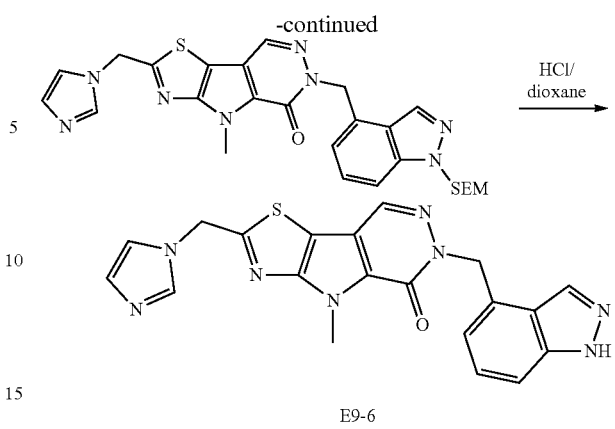

Step A. Synthesis of 2-((1H-imidazol-1-yl)methyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one To a mixture of 2-(chloromethyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (25.0 mg, 48.53 umol, 1 eq) and KI (8.06 mg, 48.53 umol, 1 eq) in THF (0.3 mL) was added Imidazole (33.04 mg, 485.34 umol, 10.0 eq). The mixture was warmed up to 60° C. and stirred at 60° C. for 12 hr. LCMS showed that the desired product was generated and the starting material was consumed completely. The reaction mixture was combined with another batch (25 mg). The mixture was concentrated in vacuo to give a yellow crude gum (50.0 mg). The product would be used to next step reaction without any purification. LCMS: m/z 547.2 [M+H]⁺.

Step B. Synthesis of 2-((1H-imidazol-1-yl)methyl)-6-((1H-indazol-4-yl)methyl)-4-methyl-4H-thiazolo[5',4':4,5]pyrrolo[2,3-d]pyridazin-5(6H)-one To a solution of 2-((1H-imidazol-1-yl)methyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (50.0 mg, 64.02 umol, 1 eq) in dioxane (1 mL) was added HCl/dioxane (4 M, 2 mL, 124.96 eq) and 2 drops of water. The mixture was stirred at 30° C. for 12 hr. TLC (PE:EA=1:1, UV=254 nm) showed that the starting material was consumed completely. The mixture was concentrated in vacuo to give a yellow gum (0.2 g) which was purified by Preparative HPLC (basic) to give the title product (4.0 mg). LCMS: m/z 417.0 [M+H]⁺. ¹H NMR (400 MHz, METHANOL-d₄) ppm 8.43 (s, 1H), 8.22 (s, 1H), 7.89 (s, 1H), 7.43-7.49 (m, 1H), 7.29-7.36 (m, 2H), 7.12 (d, 1H), 7.04 (s, H), 5.74 (s, 2H), 5.73 (s, 2H), 4.34 (s, 3H).

Example 9C. Synthesis of 4-methyl-2-(pyridin-2-ylmethyl)-6-(pyridin-3-ylmethyl)-4H-thiazolo[5',4':4,5]pyrrolo[2,3-d]pyridazin-5(6H)-one

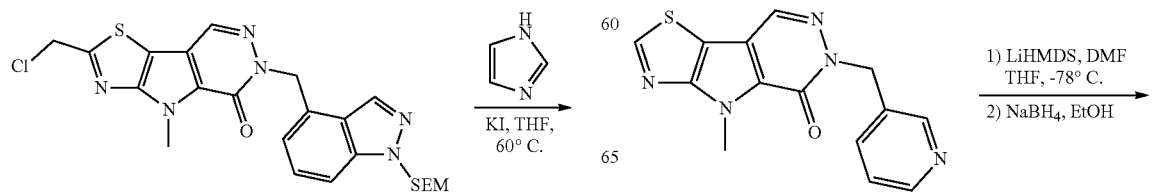

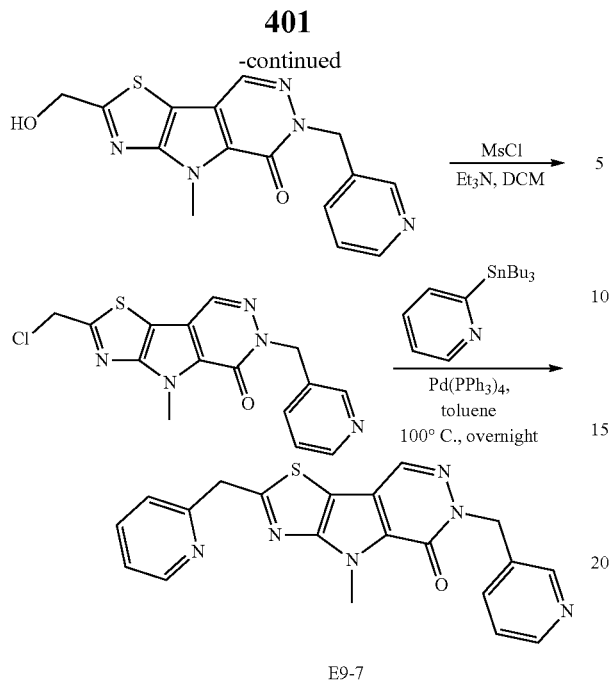

E9-7

Step A. Synthesis of 2-(hydroxymethyl)-4-methyl-6-(pyridin-3-ylmethyl)-4H-thiazolo[5',4':4,5]pyrrolo[2,3-d]pyridazin-5(6H)-one At −78° C., to a mixture of 4-methyl-6-(pyridin-3-ylmethyl)-4H-thiazolo[5',4':4,5]pyrrolo[2,3-d]pyridazin-5(6H)-one (640 mg, 2.15 mmol) in THF (10 mL) was added LiHMDS (4.3 mL, 1 M in THF). After 30 min, dry DMF (0.84 mL, 10.8 mmol) was added to the mixture. After the completely consumption of starting material, a mixture of NaBH$_4$ (164 mg, 4.3 mmol) in EtOH (4 mL) was added and stirred for 5 min. Then the mixture was poured into satd. NH$_4$Cl, extracted with EtOAc. The organic layer was washed with brine, dried over anhy. Na$_2$SO$_4$, filtered and concentrated. The residue was purified by flash chromatography (silica gel, 0~5% MeOH in DCM) to afford 2-(hydroxymethyl)-4-methyl-6-(pyridin-3-ylmethyl)-4H-thiazolo[5',4':4,5]pyrrolo[2,3-d]pyridazin-5(6H)-one (220 mg). LC-MS (ESI): m/z 328 (M+H)$^+$.

Step B. Synthesis of 2-(chloromethyl)-4-methyl-6-(pyridin-3-ylmethyl)-4H-thiazolo[5',4':4,5]pyrrolo[2,3-d]pyridazin-5(6H)-one To a mixture of 2-(hydroxymethyl)-4-methyl-6-(pyridin-3-ylmethyl)-4H-thiazolo[5',4':4,5]pyrrolo[2,3-d]pyridazin-5(6H)-one (100 mg, 0.31 mmol) in DCM (5 mL) were added Et$_3$N (0.43 mL, 3.1 mmol) and MsCl (0.12 mL, 1.5 mmol). The reaction was stirred at room temperature for 6 hr. Then the mixture was washed with satd. NH$_4$Cl (aq.), dried over anhy. Na$_2$SO$_4$, filtered and concentrated. The residue was purified by flash chromatography (silica gel, 0~50% EtOAc in PE) to afford 65 mg of 2-(chloromethyl)-4-methyl-6-(pyridin-3-ylmethyl)-4H-thiazolo[5',4':4,5]pyrrolo[2,3-d]pyridazin-5(6H)-one. LC-MS (ESI): m/z 346 (M+H)$^+$.

Step C. Synthesis of 4-methyl-2-(pyridin-2-ylmethyl)-6-(pyridin-3-ylmethyl)-4H-thiazolo[5',4':4,5]pyrrolo[2,3-d]pyridazin-5(6H)-one Under nitrogen, to a mixture of 2-(chloromethyl)-4-methyl-6-(pyridin-3-ylmethyl)-4H-thiazolo[5',4':4,5]pyrrolo[2,3-d]pyridazin-5(6H)-one (50 mg, 0.14 mmol) and 2-(tributylstannyl)pyridine (0.14 mL, 0.43 mmol) in toluene (3 mL) was added Pd(PPh$_3$)$_4$(17 mg, 0.014 mmol). The reaction mixture was stirred at 100° C. overnight. Then the mixture was cooled, concentrated under reduced pressure and the residue was purified by prep-TLC (eluant: 10% MeOH in DCM) to afford 2 mg of 4-methyl-2-(pyridin-2-ylmethyl)-6-(pyridin-3-ylmethyl)-4H-thiazolo[5',4':4,5]pyrrolo[2,3-d]pyridazin-5(6H)-one. LC-MS (ESI): m/z 389 (M+H)$^+$. $^1$H NMR (400 MHz, DMSO-d6) δ 8.56 (m, 3H), 8.48 (dd, 1H), 7.81 (td, 1H), 7.71 (d, 1H), 7.50 (d, 1H), 7.37-7.30 (m, 2H), 5.38 (s, 2H), 4.67 (s, 2H), 4.25 (s, 3H).

Example 9D. Synthesis of 2-((1H-1,2,4-triazol-1-yl)methyl)-6-((1H-pyrazol-3-yl)methyl)-4-methyl-4H-thiazolo[5',4':4,5]pyrrolo[2,3-d]pyridazin-5(6H)-one and 6-((1H-pyrazol-3-yl)methyl)-2-((4H-1,2,4-triazol-4-yl)methyl)-4-methyl-4H-thiazolo[5',4':4,5]pyrrolo[2,3-d]pyridazin-5(6H)-one

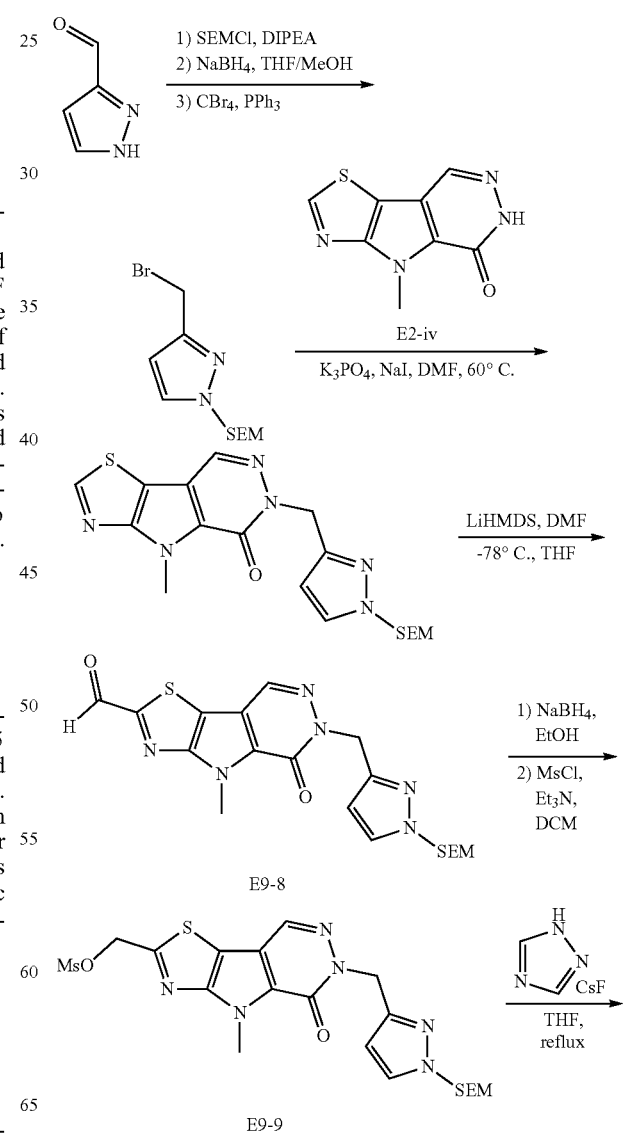

E9-8

E9-9

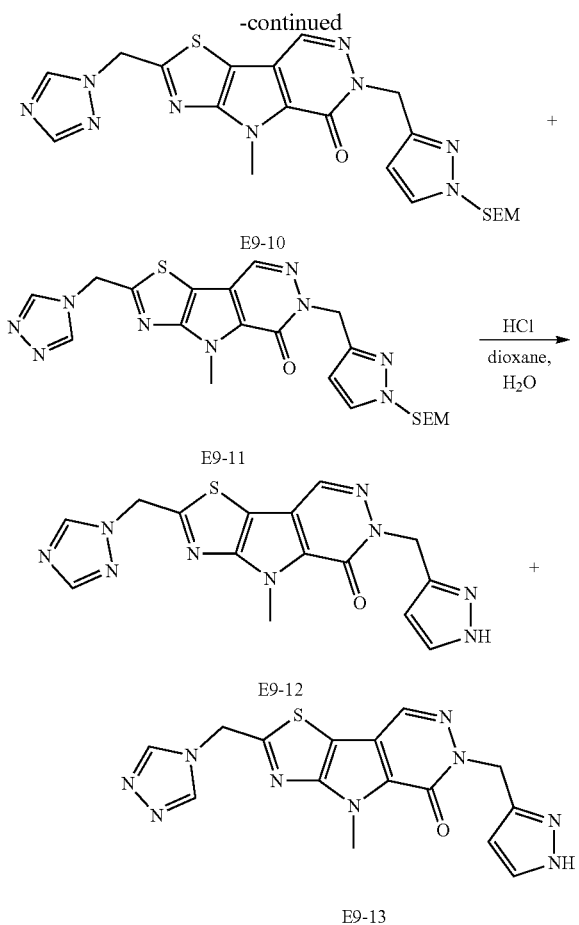

E9-10

E9-11

E9-12

E9-13

Step A. Synthesis of 1-((2-(trimethylsilyl)ethoxy)methyl)-1H-pyrazole-3-carbaldehyde To a suspension of 1H-pyrazole-3-carbaldehyde (10.0 g, 104.07 mmol, 1 eq) and DIPEA (33.63 g, 260.18 mmol, 45.32 mL, 2.5 eq) in DCM (500 mL) was added dropwise 2-(chloromethoxy)ethyl-trimethyl-silane (26.03 g, 156.11 mmol, 27.63 mL, 1.5 eq) at −40° C. Then the reaction mixture was warmed to room temperature and stirred for 16 hr. TLC (petroleum ether:EtOAc=5:1) showed the starting material was consumed completely, and two new spots were formed. The reaction mixture was concentrated in vacuo. The residue was combined with another 2 batches (10.0 g each) and purified by Combiflash (from 100% of petroleum ether to 40% of EtOAc in petroleum ether) to give desired product 60.0 g. (note: mixture of 2 regioisomers with ~5/4 ratio). $^1$H NMR (400 MHz, CHLOROFORM-d) δ ppm 10.06 (s, 1H), 10.00 (s, 1H), 7.68 (d, 1H), 7.67 (d, 1H), 7.03 (d, 1H), 6.92 (d, 1H), 5.87 (s, 2H), 5.56 (s, 2H), 3.61-3.67 (m, 4H), 0.91-1.01 (m, 4H), −0.09-0.05 (m, 18H).

Step B. Synthesis of (1-((2-(trimethylsilyl)ethoxy)methyl)-1H-pyrazol-3-yl)methanol To a solution of 1-((2-(trimethylsilyl)ethoxy)methyl)-1H-pyrazole-3-carbaldehyde (30 g, 132.54 mmol, 1 eq, mixture of 2 regioisomers with ~5/4 ratio) in THF (200 mL)/MeOH (100 mL) was added NaBH$_4$ (7.52 g, 198.81 mmol, 1.50 eq) in portions at 0° C., the reaction mixture was stirred at 0° C. to room temperature for 18 hr. TLC (petroleum ether:EtOAc=2:1) showed the starting materials were consumed completely, and two new spots were formed. The solvent was concentrated in vacuo. The residue was purified by Combiflash (100% of petroleum ether to 100% of EtOAc) to give 25 g of the desired product. (Note: mixture of 2 regioisomers ratio ~3/2). $^1$H NMR (400 MHz, CHLOROFORM-d) δ ppm 7.55 (d, 1H), 7.47 (brs, 1H), 6.36 (d, 1H), 6.34 (d, 1H), 5.57 (s, 2H), 5.42 (s, 2H), 4.74-4.76 (m, 4H), 3.55-3.60 (m, 4H), 0.85-0.96 (m, 4H), 0.00-0.06 (m, 18H).

Step C. Synthesis of 3-(bromomethyl)-1-((2-(trimethylsilyl)ethoxy)methyl)-1H-pyrazole To a solution of (1-((2-(trimethylsilyl)ethoxy)methyl)-1H-pyrazol-3-yl)methanol (23 g, 100.72 mmol, 1 eq, mixture of 2 regioisomers ratio ~3/2) and PPh$_3$ (36.98 g, 141.00 mmol, 1.4 eq) in DCM (200 mL) was added CBr$_4$ (46.76 g, 141.00 mmol, 1.4 eq) at 0° C. and the reaction mixture was stirred at 0° C. for 3 hr. TLC (petroleum ether:EtOAc=5:1) showed the starting materials were consumed completely, and a new spot was formed. The reaction mixture was concentrated in vacuo. The residue was combined with another batch (2.0 g) and purified by Combiflash (from 100% of petroleum ether to 50% of EtOAc in petroleum ether) to give desired product 22.0 g (75.53 mmol). $^1$H NMR (400 MHz, CHLOROFORM-d) δ ppm 7.51 (d, 1H), 6.39 (d, 1H), 5.38 (s, 2H), 4.50 (s, 2H), 3.52-3.57 (m, 2H), 0.86-0.96 (m, 2H), −0.03-0.02 (m, 9H).

Step D. Synthesis of 4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one A suspension of 4-methyl-4H-thiazolo[5',4':4,5]pyrrolo[2,3-d]pyridazin-5(6H)-one (1.0 g, 4.85 mmol, 1 eq), 3-(bromomethyl)-1-((2-(trimethylsilyl)ethoxy)methyl)-1H-pyrazole (2.12 g, 7.27 mmol, 1.5 eq), K$_3$PO$_4$ (2.57 g, 12.12 mmol, 2.5 eq) and NaI (218.05 mg, 1.45 mmol, 0.3 eq) in DMF (15 mL) was stirred at 60° C. for 18 hr under N$_2$. TLC (petroleum ether:EtOAc=1:1) showed the starting material was consumed completely, and a new spot was formed. The reaction mixture was combined with another 3 batches (1.0 g each) and poured into ice-water (250 mL). The mixture was extracted with EtOAc (150 mL×3). The combined organic layers were washed with water (120 mL×2), brine (120 mL), and dried over Na$_2$SO$_4$. The solvent was concentrated in vacuo. The crude product was purified by combiflash (form 100% of petroleum ether to 80% of EtOA in petroleum ether) to give the desired product (3.6 g). $^1$H NMR (400 MHz, CHLOROFORM-d) δ ppm 8.91 (s, 1H), 8.27 (s, 1H), 7.49 (d, 1H), 6.36 (d, 1H), 5.51 (s, 2H), 5.40 (m, 2H), 4.45 (s, 3H), 3.52-3.58 (m, 2H), 0.85-0.90 (m, 2H), −0.05 (s, 9H).

Step E. Synthesis of 4-methyl-5-oxo-6-((1-((2-(trimethylsilyl)ethoxy)methyl)-1H-pyrazol-3-yl)methyl)-5,6-dihydro-4H-thiazolo[5',4':4,5]pyrrolo[2,3-d]pyridazine-2-carbaldehyde Under argon, to a solution of 4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (1.7 g, 4.09 mmol, 1 eq) in THF (30 mL) was slowly added LiHMDS (1.0 M, 8.18 mL, 2 eq) at −78° C., the reaction mixture was stirred at −70° C. for 1 hr. Then a solution of DMF (1.49 g, 20.45 mmol, 1.57 mL, 5 eq) in THF (3 mL)

was added dropwise to the mixture. The resulting mixture was stirred at −70° C. for 1 h. TLC (petroleum ether: EtOAc=1:1) showed a new spot was formed. The reaction mixture was drop-wise added to aq. NH$_4$Cl (50 mL) at 0° C., then the mixture was extracted with EtOAc (30 mL×3). The combined organic layers were washed with brine (40 mL), and dried over Na$_2$SO$_4$. The solvent was removed in vacuo to afford crude desired product (1.8 g) which was used for the next step without further purification.

Step F. Synthesis of 2-(hydroxymethyl)-4-methyl-6-((1-((2-(trimethylsilyl)ethoxy) methyl)-1H-pyrazol-3-yl)methyl)-4H-thiazolo[5',4':4,5]pyrrolo[2,3-d] pyridazin-5(6H)-one To a solution of 4-methyl-5-oxo-6-((1-((2-(trimethylsilyl)ethoxy)methyl)-1H-pyrazol-3-yl)methyl)-5,6-dihydro-4H-thiazolo[5',4':4,5]pyrrolo[2,3-d]pyridazine-2-carbaldehyde (1.8 g, 3.24 mmol, 1 eq) in THF (20 mL) MeOH (10 mL) was added NaBH$_4$ (245.08 mg, 6.48 mmol, 2 eq) at 0° C. and the reaction mixture was stirred at room temperature for 18 hr. TLC (petroleum ether:EtOAc=1:2) showed the starting material was consumed completely, and a new spot was formed. The reaction mixture was concentrated in vacuo, the residue was purified by combiflash (from 100% DCM to 5% of MeOH in DCM). The desired product (1.1 g) was obtained. $^1$H NMR (400 MHz, DMSO-d$_6$) δ ppm 8.63 (s, 1H), 7.86 (d, 1H), 6.44 (t, 1H), 6.27 (d, 1H), 5.40-5.42 (m, 4H), 4.98 (d, 2H), 4.34 (s, 3H), 3.55-3.61 (m, 2H), 0.86-0.91 (m, 2H), 0.00 (s, 9H).

Step G. Synthesis of (4-methyl-5-oxo-6-((1-((2-(trimethylsilyl)ethoxy)methyl)-1H-pyrazol-3-yl) methyl)-5,6-dihydro-4H-thiazolo[5',4':4,5]pyrrolo[2,3-d]pyridazin-2-yl)methyl methanesulfonate To a solution of 2-(hydroxymethyl)-4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (700 mg, 1.57 mmol, 1 eq) and Et$_3$N (317.21 mg, 3.13 mmol, 436.33 uL, 2.0 eq) in DCM (15 mL) was added dropwise MsCl (269.32 mg, 2.35 mmol, 181.97 uL, 1.5 eq) at 0° C. and the reaction mixture was stirred at room temperature for 1 h. TLC (petroleum ether:EtOAc=1:1) showed the starting material was consumed completely, and a new spot was formed. The reaction mixture was diluted with EtOAc (80 mL), and washed with water (30 mL×4), brine (40 mL), and dried over Na$_2$SO$_4$. The solvent was removed in vacuo to afford crude product (700 mg). LCMS: (m/z 525.5 (M+H).

Step H. Synthesis of 2-((1H-1,2,4-triazol-1-yl) methyl)-4-methyl-6-((1-((2-(trimethylsilyl)ethoxy) methyl)-1H-pyrazol-3-yl)methyl)-4H-thiazolo[5',4': 4,5]pyrrolo[2,3-d]pyridazin-5(6H)-one and 2-((4H-1,2,4-triazol-4-yl)methyl)-4-methyl-6-((1-((2-(trimethylsilyl)ethoxy)methyl)-1H-pyrazol-3-yl) methyl)-4H-thiazolo[5',4':4,5]pyrrolo[2,3-d] pyridazin-5(6H)-one A mixture of (4-methyl-5-oxo-6-((1-((2-(trimethylsilyl) ethoxy)methyl)-1H-pyrazol-3-yl)methyl)-5,6-dihydro-4H-thiazolo[5',4':4,5]pyrrolo[2,3-d]pyridazin-2-yl)methyl methanesulfonate (150 mg, 285.88 umol, 1 eq) 1H-1,2,4-triazole (197.45 mg, 2.86 mmol, 10 eq) and CsF (86.85 mg, 571.77 umol, 21.08 uL, 2 eq) in MeCN (8 mL) was stirred at 60° C. under N$_2$ for 18 hr. LCMS showed the starting material was consumed completely, and two new peaks were formed. The reaction mixture was concentrated in vacuo, and the residue was purified by Combiflash (from 100% of DCM to 8% of MeOH in DCM). The product 2-((1H-1,2, 4-triazol-1-yl)methyl)-4-methyl-6-((1-((2-(trimethylsilyl) ethoxy)methyl)-1H-pyrazol-3-yl)methyl)-4H-thiazolo[5',4': 4,5]pyrrolo[2,3-d]pyridazin-5(6H)-one (55 mg) and 2-((4H-1,2,4-triazol-4-yl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (30 mg) were obtained.

Step I. Synthesis of 2-((1H-1,2,4-triazol-1-yl) methyl)-6-((1H-pyrazol-3-yl)methyl)-4-methyl-4H-thiazolo[5',4':4,5]pyrrolo[2,3-d]pyridazin-5(6H)-one To a suspension of 2-((1H-1,2,4-triazol-1-yl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d] pyridazin-5(6H)-one (55 mg, 110.52 umol, 1 eq) and HCl/dioxane (4 M, 1 mL, 36.19 eq) in DCM (3 mL) was added H$_2$O (1.99 mg, 110.52 umol, 0.05 mL, 1 eq) and the reaction mixture was stirred at room temperature for 18 hr. LCMS showed the starting material was consumed completely, and 84% of desired product was found. The reaction mixture was concentrated in vacuo, and the residue was purified by Prep-HPLC to give the desired product (24.1 mg, 65.60 umol, 59.35% yield). Column: Xtimate C18 150*25 mm*5 um, mobile phase: [water (0.225% FA)-ACN]; B %: 13%-43%, 11.2 min. LCMS: m/z 367.9 (M+H)$^{+1}$H NMR (400 MHz, METHANOL-d$_4$) δ ppm 8.72 (s, 1H), 8.35 (s, 1H), 8.05 (s, 1H), 7.52 (brs, 1H), 6.26 (d, 1H), 5.92 (s, 2H), 5.43 (s, 2H), 4.30 (s, 3H).

Step J. Synthesis of 6-((1H-pyrazol-3-yl)methyl)-2-((4H-1,2,4-triazol-4-yl)methyl)-4-methyl-4H-thiazolo[5',4':4,5]pyrrolo[2,3-d]pyridazin-5(6H)-one To a suspension of 2-((4H-1,2,4-triazol-4-yl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d] pyridazin-5(6H)-one (30 mg, 60.28 umol, 1 eq) and HCl/dioxane (4 M, 1 mL, 66.35 eq) in DCM (3 mL) was added H$_2$O (50.00 mg, 2.78 mmol, 0.05 mL, 46.04 eq) and the reaction mixture was stirred at room temperature for 18 hr. LCMS showed the starting material was consumed completely, the desired product was found. The reaction mixture was concentrated in vacuo, and the residue was purified by Prep-HPLC to give the desired product (2.1 mg, 5.72 umol). Column: Xtimate C18 150*25 mm*5 um; mobile phase: [water (0.225% FA)-ACN]; B %: 13%-43%,11.2 min. LCMS: m/z 368.0 (M+H)$^+$. $^1$H NMR (400 MHz, METHA-NOL-d$_4$) δ ppm 8.74 (s, 2H), 8.38 (s, 1H), 7.52 (d, 1H), 6.26 (d, 1H), 5.84 (s, 2H), 5.44 (s, 2H), 4.31 (s, 3H).

The following compounds were synthesized according to Scheme E9 and the procedure of Examples 9A-9B using the appropriate starting material.

| Cpd No. | Structure | Characterization |
|---|---|---|
| E9-14 | 6-((1H-indazol-4-yl)methyl)-4-methyl-2-(pyridin-4-ylmethyl)-4,6-dihydro-5H-thiazolo[5′,4′:4,5]pyrrolo[2,3-d]pyridazin-5-one | LCMS: 428 (M + H)+. 1H NMR (400 MHz, DMSO-d6) δ 13.12 (s, 1H), 8.57 (s, 1H), 8.55 (d, 2H), 8.13 (s, 1H), 7.46 (s, 1H), 7.44-7.41 (m, 2H), 7.29-7.26 (m, 1H), 6.95 (d, 1H), 5.65(s, 2H), 4.58(s, 2H), 4.26 (s, 3H). |
| E9-15 | 6-((1H-indazol-4-yl)methyl)-2-(isoxazol-4-ylmethyl)-4-methyl-4,6-dihydro-5H-thiazolo[5′,4′:4,5]pyrrolo[2,3-d]pyridazin-5-one | LCMS: 418 (M + H)+. 1H NMR (400 MHz, DMSO-d6) 13.12 (s, 1H), 9.00 (s, 1H), 8.70 (s, 1H), 8.58 (s, 1H), 8.14 (s, 1H), 7.45 (d, 1H), 7.40-7.21 (m, 1H), 6.96 (d, 1H), 5.66 (s, 2H), 4.44 (s, 2H), 4.27 (s, 3H). |
| E9-16 | 2-(2-Hydroxy-pyrimidin-5-ylmethyl)-6-(1H-indazol-4-ylmethyl)-8-methyl-6,8-dihydro-3-thia-1,5,6,8-tetraaza-cyclopenta[a]inden-7-one | LC-MS: m/z 445 (M + H)+. 1H NMR (400 MHz, DMSO) δ 13.12 (s, 1H), 8.57 (s, 1H), 8.35 (s, 2H), 8.14 (s, 1H), 7.45 (d, 1H), 7.28 (dd, 1H), 6.96 (d, 1H), 5.65 (s, 2H), 4.32 (s, 2H), 4.26 (s, 3H). |
| E9-17 | 6-((1H-indazol-4-yl)methyl)-2-((2-methoxypyrimidin-5-yl)methyl)-4-methyl-4H-thiazolo[5′,4′:4,5]pyrrolo[2,3-d]pyridazin-5(6H)-one | LC-MS: m/z 459 (M + H)+. 1H NMR (400 MHz, DMSO) δ 13.11 (s, 1H), 8.69 (s, 2H), 8.57 (s, 1H), 8.13 (s, 1H), 7.45 (d, 1H), 7.31-7.24 (m, 1H), 6.96 (d, 1H), 5.65 (s, 2H), 4.52 (s, 2H), 4.26 (s, 3H), 3.92 (s, 3H) |

-continued

| Cpd No. | Structure | Characterization |
|---|---|---|
| E9-18 | 6-((1H-indazol-4-yl)methyl)-2-(isothiazol-5-ylmethyl)-4-methyl-4H-thiazolo[5',4':4,5]pyrrolo[2,3-d]pyridazin-5(6H)-one | LC-MS: m/z 434 (M + H)+. 1H NMR (400 MHz, DMSO) δ 13.13 (s, 1H), 8.60 (s, 1H), 8.52 (d, 1H), 8.15 (s, 1H), 7.48-7.41 (m, 2H), 7.31-7.25 (m, 1H), 6.96 (d, 1H), 5.66 (s, 2H), 5.00 (s, 2H), 4.29 (s, 3H) |
| E9-19 | 6-((1H-indazol-4-yl)methyl)-4-methyl-2-(thiazol-2-ylmethyl)-4H-thiazolo[5',4':4,5]pyrrolo[2,3-d]pyridazin-5(6H)-one | LC-MS: m/z 434 (M + H)+. 1H NMR (400 MHz, DMSO) δ 13.11 (s, 1H), 8.59 (s, 1H), 8.14 (s, 1H), 7.81 (d, 1H), 7.72 (d, 1H), 7.45 (d, 1H), 7.34-7.23 (m, 1H), 6.96 (d, 1H), 5.66 (s, 2H), 4.99 (s, 2H), 4.28 (s, 3H). |
| E9-20 | 6-((1H-indazol-4-yl) methyl)-4-methyl-2-(pyridin-3-ylmethyl)-4H-thiazolo[5',4':4,5]pyrrolo[2,3-d]pyridazin-5(6H)-one | LCMS: 428 (M + H)+. 1H NMR (400 MHz, DMSO-d6) δ 13.11 (s, 1H), 8.65 (d, 1H), 8.56 (s, 1H), 8.51 (dd, 1H), 8.13 (s, 1H), 7.84 (d, 1H), 7.47-7.38 (m, 2H), 7.31-7.25 (m, 1H), 6.95 (d, 1H), 5.65 (s, 2H), 4.58 (s, 2H), 4.27 (s, 3H). |
| E9-21 | 6-((1H-indazol-4-yl)methyl)-4-methyl-2-((2-oxo-1,2-dihydropyridin-4-yl)methyl)-4H-thiazolo[5',4':4,5]pyrrolo[2,3-d]pyridazin-5(6H)-one | LCMS m/z 444 (M + H)+. 1H NMR (400 MHz, DMSO-d6) δ 13.11 (s, 1H), 11.52 (s, 1H), 8.58 (s, 1H), 8.14 (s, 1H), 7.45 (d, 1H), 7.33 (d, 1H), 7.30-7.25 (m, 1H), 6.95 (d, 1H), 6.32 (s, 1H), 6.16 (d, 1H), 5.66 (s, 2H), 4.35 (s, 2H), 4.28 (s, 3H). |
| E9-22 | 6-((1H-indazol-4-yl)methyl)-2-((1H-pyrazol-4-yl)methyl)-4-methyl-4H-thiazolo[5',4':4,5]pyrrolo[2,3-d]pyridazin-5(6H)-one | LCMS: m/z 417 (M + H)+. 1H NMR (400 MHz, DMSO) δ 13.12 (s, 1H), 12.82 (s, 1H), 8.54 (s, 1H), 8.14 (s, 1H), 7.79 (s, 1H), 7.53 (s, 1H), 7.45 (d, 1H), 7.28 (dd, 1H), 6.96 (d, 1H), 5.65 (s, 2H), 4.36 (s, 2H), 4.28 (s, 3H) |

-continued

| Cpd No. | Structure | Characterization |
|---|---|---|
| E9-23 | 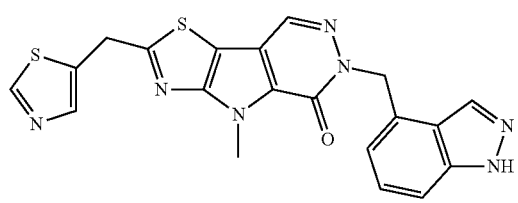<br>6-((1H-indazol-4-yl)methyl)-4-methyl-2-(thiazol-5-ylmethyl)-4H-thiazolo[5',4':4,5]pyrrolo[2,3-d]pyridazin-5(6H)-one | LCMS: m/z 434(M + H)$^+$.<br>1H NMR (400 MHz, DMSO) δ 13.12 (s, 1H), 9.06 (s, 1H), 8.58 (s, 1H), 8.14 (s, 1H), 7.93 (s, 1H), 7.44 (d, 1H), 7.32-7.22 (m, 1H), 6.96 (d, 1H), 5.65 (s, 2H), 4.85 (s, 2H), 4.27 (s, 3H). |
| E9-24 | 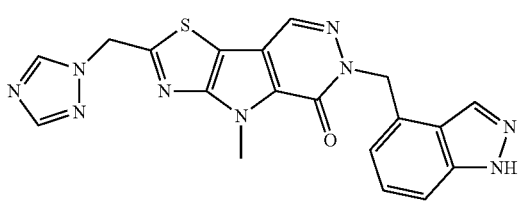<br>2-((1H-1,2,4-triazol-1-yl)methyl)-6-((1H-indazol-4-yl)methyl)-4-methyl-4H-thiazolo[5',4':4,5]pyrrolo[2,3-d]pyridazin-5(6H)-one | LCMS: m/z 418.0 [M + H]$^+$. $^1$H NMR (400 MHz, CDCl3) δ ppm 8.18 (s, 1H), 7.94 (s, 1H), 7.85 (s, 1H), 7.65 (s, 1H), 7.11 (d, 1H), 6.94 (t, 1H), 6.76 (d, 1H), 5.53 (s, 2H), 5.38 (s, 2H), 4.03 (s, 3H) |
| E9-25 | 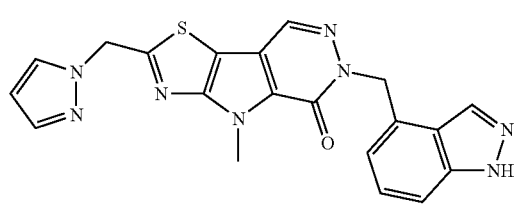<br>6-((1H-indazol-4-yl)methyl)-2-((1H-pyrazol-1-yl)methyl)-4-methyl-4H-thiazolo[5',4':4,5]pyrrolo[2,3-d]pyridazin-5(6H)-one | LC-MS: 417.0 [M + H]$^+$.<br>$^1$H NMR (400 MHz, CDCl3) δ ppm 10.19 (brs, 1H), 8.34 (s, 1H), 8.21 (s, 1H), 7.62-7.67 (m, 2H), 7.40-7.44 (m, 1H), 7.38 (t, 1H), 7.26 (brd, 1H), 6.38-6.41 (m, 1H), 5.78 (s, 2H), 5.76 (s, 2H), 4.42 (s, 3H). |
| E9-26 | 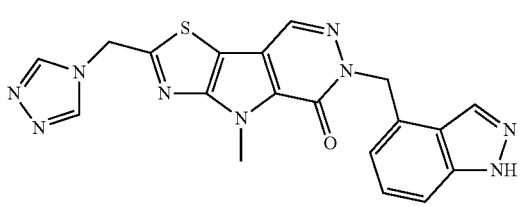<br>6-((1H-indazol-4-yl)methyl)-2-((4H-1,2,4-triazol-4-yl)methyl)-4-methyl-4H-thiazolo[5',4':4,5]pyrrolo[2,3-d]pyridazin-5(6H)-one | LCMS: m/z 418.0 [M + H]$^+$.<br>$^1$H NMR (400 MHz, CDCl3) δ ppm 12.28 (brs, 1H), 8.27 (s, 2H), 7.97-8.08 (m, 2H), 7.23 (brd, 1H), 7.02-7.09 (m, 1H), 6.90 (brd, 1 H), 5.51 (s, 2H), 5.49 (s, 2H), 4.15 (s, 3H). |

-continued

| Cpd No. | Structure | Characterization |
|---|---|---|
| E9-27 | 6-((1H-indazol-4-yl)methyl)-2-((6-aminopyridin-2-yl)methyl)-4-methyl-4H-thiazolo[5',4':4,5]pyrrolo[2,3-d]pyridazin-5(6H)-one | LCMS: m/z 443 [M + H]$^+$. $^1$H NMR (400 MHz, DMSO-d$_6$) δ 8.60 (s, 1H), 8.11 (s, 1H), 7.86 (t, 2H), 7.42 (d, 1H), 7.24-7.28 (m, 1H), 6.95 (d, 1H), 6.83-6.89 (m, 2H), 5.63 (s, 2H), 4.68 (s, 2H), 4.24 (s, 3H) |
| E9-28 | 6-((1H-indazol-4-yl)methyl)-2-((2-methoxypyridin-4-yl)methyl)-4-methyl-4H-thiazolo[5',4':4,5]pyrrolo[2,3-d]pyridazin-5(6H)-one | LCMS: m/z 458 (M + H)$^+$. 1H NMR (400 MHz, DMSO-d6) δ 13.11 (s, 1H), 8.57 (s, 1H), 8.15-8.12 (m, 2H), 7.45 (d, 1H), 7.30-7.25 (m, 1H), 7.01 (dd, 1H), 6.95 (d, 1H), 6.86 (s, 1H), 5.65 (s, 2H), 4.52 (s, 2H), 4.27 (s, 3H), 3.84 (s, 3H). |
| E9-29 | 6-((1H-indazol-4-yl)methyl)-4-methyl-2-(pyridin-2-ylmethyl)-4,6-dihydro-5H-thiazolo[5',4':4,5]pyrrolo[2,3-d]pyridazin-5-one | LCMS: 428 (M + H)$^+$. $^1$H NMR (400 MHz, DMSO-d$_6$) δ 13.12 (s, 1H), 8.56 (s, 2H), 8.14 (s, 1H), 7.83-7.79 (m, 1H), 7.51-7.44 (m, 2H), 7.35-7.23 (m, 2H), 6.96 (d, 1H), 5.65 (s, 2H), 4.67 (s, 2H), 4.27 (s, 3H). |
| E9-30 | 6-((1H-indazol-4-yl)methyl)-4-methyl-2-(pyridin-3-ylmethyl)-4,6-dihydro-5H-thiazolo[5',4':4,5]pyrrolo[2,3-d]pyridazin-5-one | LCMS: m/z 428 (M + H)$^+$. $^1$H NMR (400 MHz, DMSO-d$_6$) δ 13.11 (s, 1H), 8.65 (d, 1H), 8.56 (s, 1H), 8.51 (dd, 1H), 8.13 (s, 1H), 7.84 (d, 1H), 7.49-7.35 (m, 2H), 7.30-7.19 (m, 1H), 6.95 (d, 1H), 5.65 (s, 2H), 4.58 (s, 2H), 4.27 (s, 3H). |
| E9-31 | 6-((1H-indazol-4-yl)methyl)-4-methyl-2-(pyrimidin-5-ylmethyl)-4,6-dihydro-5H-thiazolo[5',4':4,5]pyrrolo[2,3-d]pyridazin-5-one | LCMS: m/z 429 (M + H)$^+$. $^1$H NMR (400 MHz, DMSO-d$_6$) δ 13.13 (s, 1H), 9.14 (s, 1H), 8.90 (s, 2H), 8.58 (s, 1H), 8.14 (s, 1H), 7.45 (d, 1H), 7.28 (t, 1H), 6.96 (d, 1H), 5.65 (s, 2H), 4.62 (s, 2H), 4.25 (s, 3H). |

| Cpd No. | Structure | Characterization |
|---|---|---|
| E9-32 | 6-((1H-indazol-4-yl)methyl)-2-((6-methoxypyridin-2-yl)methyl)-4-methyl-4,6-dihydro-5H-thiazolo[5',4':4,5]pyrrolo[2,3-d]pyridazin-5-one | LCMS: m/z 458 (M + H)+. 1H NMR (400 MHz, DMSO-d6) δ 13.11 (s, 1H), 8.57 (s, 1H), 8.14 (s, 1H), 7.71 (dd, 1H), 7.45 (d, 1H), 7.35-7.18 (m, 1H), 7.08 (d, 1H), 6.96 (d, 1H), 6.75 (d, 1H), 5.65 (s, 2H), 4.58 (s, 2H), 4.27 (s, 3H), 3.89 (s, 3H). |
| E9-33 | 6-((1H-indazol-4-yl)methyl)-2-((6-methoxypyridin-3-yl)methyl)-4-methyl-4,6-dihydro-5H-thiazolo[5',4':4,5]pyrrolo[2,3-d]pyridazin-5-one | LCMS: m/z 458 (M + H)+. 1H NMR (400 MHz, DMSO-d6) δ 13.11 (s, 1H), 8.55 (s, 1H), 8.24 (d, 1H), 8.13 (d, 1H), 7.75 (dd, 1H), 7.45 (d, 1H), 7.27 (dd, 1H), 6.95 (d, 1H), 6.83 (d, 1H), 5.65 (s, 2H), 4.47 (s, 2H), 4.27 (s, 3H), 3.85 (s, 3H). |
| E9-34 | 6-((1H-indazol-4-yl)methyl)-2-((1H-pyrazol-4-yl)methyl)-4-methyl-4,6-dihydro-5H-thiazolo[5',4':4,5]pyrrolo[2,3-d]pyridazin-5-one | LCMS: m/z 417 (M + H)+. 1H NMR (400 MHz, DMSO-d6) δ 13.12 (s, 1H), 12.82 (s, 1H), 8.54 (s, 1H), 8.14 (s, 1H), 7.79 (s, 1H), 7.53 (s, 1H), 7.45 (d, Hz, 1H), 7.28 (dd, 1H), 6.96 (d, 1H), 5.65 (s, 2H), 4.36 (s, 2H), 4.28 (s, 3H). |
| E9-35 | 6-((1H-indazol-4-yl)methyl)-4-methyl-2-((6-oxo-1,6-dihydropyridin-3-yl)methyl)-4,6-dihydro-5H-thiazolo[5',4':4,5]pyrrolo[2,3-d]pyridazin-5-one | LCMS: m/z 444 (M + H)+. 1H NMR (400 MHz, DMSO-d6) δ 13.11 (s, 1H), 11.58 (s, 1H), 8.56 (s, 1H), 8.13 (s, 1H), 7.43-7.49 (m, 3H), 7.27 (t, 1H), 6.95 (d, 1H), 6.33 (d, 1H), 5.65 (s, 2H), 4.25-4.27 (m, 5H). |
| E9-36 | 6-((1H-indazol-4-yl)methyl)-4-methyl-2-((6-oxo-1,6-dihydropyridin-2-yl)methyl)-4,6-dihydro-5H-thiazolo[5',4':4,5]pyrrolo[2,3-d]pyridazin-5-one | LCMS: m/z 444 (M + H)+. 1H NMR (400 MHz, DMSO-d6) δ 13.11 (s, 1H), 11.83 (s, 1H), 8.59 (s, 1H), 8.14 (s, 1H), 7.43 (m, 2H), 7.28 (dd, 1H), 6.96 (d, 1H), 6.28 (d, 2H), 5.65 (s, 2H), 4.39 (s, 2H), 4.27 (s, 3H). |

-continued

| Cpd No. | Structure | Characterization |
|---|---|---|
| E9-37 | 6-((1H-indazol-4-yl)methyl)-4-methyl-2-((1-methyl-1H-pyrazol-4-yl)methyl-4,6-dihydro-5H-thiazolo[5',4':4,5]pyrrolo[2,3-d]pyridazin-5-one | LCMS: m/z 431 (M + H)+. ¹H NMR (400 MHz, DMSO-d₆) δ 8.56 (s, 1H), 8.14 (s, 1H), 7.49 (d, 1H), 7.41 (s, 1H), 7.32 (dd, 1H), 6.98 (d, 1H), 6.29 (d, 1H), 5.67 (s, 2H), 4.66 (s, 2H), 4.27 (s, 3H), 3.24 (s, 3H). |
| E9-38 | 3-((2-((1H-imidazol-1-yl)methyl)-4-methyl-5-oxo-4,5-dihydro-6H-thiazolo[5',4':4,5]pyrrolo[2,3-d]pyridazin-6-yl)methyl)benzamide | LC-MS: m/z 420 (M + H)+. ¹H NMR (400 MHz, DMSO-d6) δ: δ 8.60 (s, 1H), 7.96 (s, 1H), 7.87 (s, 1H), 7.80-7.74 (m, 2H), 7.46-7.37 (m, 2H), 7.35 (s, 2H), 6.99 (s, 1H), 5.78 (s, 2H), 5.39 (s, 2H), 4.27 (s, 3H). |
| E9-39 | 6-allyl-4-methyl-2-(pyridin-2-ylmethyl)-4,6-dihydro-5H-thiazolo[5',4':4,5]pyrrolo[2,3-d]pyridazin-5-one | LC-MS: m/z 338 (M + H)+. ¹H NMR (400 MHz, DMSO-d6) δ: 8.56 (d, 1H), 8.53 (s, 1H), 7.81 (td, 1H), 7.51 (d, 1H), 7.33 (dd, 1H), 5.99 (dq, 1H), 5.12 (ddd, 2H), 4.76 (d, 2H), 4.67 (s, 2H), 4.26 (s, 3H) |
| E9-40 | 4-methyl-2-(pyridin-2-ylmethyl)-6-((tetrahydro-2H-pyran-4-yl)methyl)-4,6-dihydro-5H-thiazolo[5',4':4,5]pyrrolo[2,3-d]pyridazin-5-one | LC-MS: m/z 396 (M + H)+. ¹H NMR (400 MHz, DMSO-d6) δ: 8.56 (d, 1H), 8.51 (s, 1H), 7.81 (td, 1H), 7.50 (d, 1H), 7.38-7.27 (m, 1H), 4.67 (s, 2H), 4.26 (s, 3H), 4.05 (d, 2H), 3.82 (d, 2H), 3.23 (d, 2H), 2.13 (d, 1H), 1.46 (d, 2H), 1.35-1.26 (m, 2H) |
| E9-41 | 2-((1H-pyrazol-1-yl)methyl)-6-((1H-pyrazol-3-yl)methyl)-4-methyl-4H-thiazolo[5',4':4,5]pyrrolo[2,3-d]pyridazin-5(6H)-one | LCMS: m/z 367.0 [M + H]+. ¹H NMR (400 MHz, METHANOL-d₄) δ ppm 8.39 (s, 1H), 7.90 (d, 1H), 7.63 (d, 1H), 7.59 (brs, 1H), 6.43 (t, 1H), 6.29 (brs, 1H), 5.85 (s, 2H), 5.48 (s, 2H), 4.37 (s, 3H). |

| Cpd No. | Structure | Characterization |
|---|---|---|
| E9-42 | 6-((1H-pyrazol-3-yl)methyl)-4-methyl-2-((2-oxo-2,3-dihydro-1H-imidazol-1-yl)methyl)-4H-thiazolo[5′,4′:4,5]pyrrolo[2,3-d]pyridazin-5(6H)-one | LCMS: m/z 383.0 [M + H]$^+$. $^1$H NMR (400 MHz, METHANOL-d$_4$) δ ppm 8.41 (s, 1H), 7.55-7.57 (m, 1H), 6.64 (d, 1H), 6.51 (d, 1H), 6.30 (s, 1H), 5.48 (s, 2H), 5.28 (s, 2H), 4.37 (s, 3H). |
| E9-43 | 6-((1H-pyrazol-3-yl)methyl)-4-methyl-2-((3-nitro-1H-pyrazol-1-yl)methyl)-4,6-dihydro-5H-thiazolo[5′,4′:4,5]pyrrolo[2,3-d]pyridazin-5(6H)-one | LCMS: m/z 412.0 [M + H]$^+$. $^1$H NMR (400 MHz, DMSO-d$_6$) δ ppm 12.61 (brs, 1H), 8.55 (s, 1H), 8.28 (d, 1H), 7.58 (brs, 1H), 7.13 (d, 1H), 6.08 (d, 1H), 6.03 (s, 2H), 5.30 (brs, 2H), 4.24 (s, 3H). |
| E9-44 | 6-((1H-pyrazol-3-yl)methyl)-2-((3-amino-1H-pyrazol-1-yl)methyl)-4-methyl-4H-thiazolo[5′,4′:4,5]pyrrolo[2,3-d]pyridazin-5(6H)-one | LCMS: m/z 382.0 [M + H]$^+$ $^1$H NMR (400 MHz, METHANOL-d$_4$) δ ppm 8.35 (s, 1H), 7.53 (d, 2H), 6.26 (brs, 1H), 5.71 (d, 1H), 5.54 (s, 2H), 5.44 (s, 2H), 4.33 (s, 3H). |
| E9-45 | 2-((1H-imidazol-1-yl)methyl)-6-((1H-pyrazol-3-yl)methyl)-4-methyl-4H-thiazolo[5′,4′:4,5]pyrrolo[2,3-d]pyridazin-5(6H)-one | LCMS: m/z 366.9 [M + H]$^+$. $^1$H NMR(400 MHz, METHANOL-d$_4$) δ ppm 8.36 (s, 1H), 7.89 (s, 1H), 7.54 (brs, 1H), 7.30 (s, 1H), 7.03 (s, 1H), 6.26 (s, 1H), 5.72 (s, 2H), 5.44 (s, 2H), 4.33 (s, 3H). |
| E9-46 | 2-((1H-1,2,3-triazol-1-yl)methyl)-6-((1H-pyrazol-3-yl)methyl)-4-methyl-4H-thiazolo[5′,4′:4,5]pyrrolo[2,3-d]pyridazin-5(6H)-one | LCMS: m/z 368 [M + H]$^+$. $^1$H NMR (400 MHz, DMSO-d$_6$) δ ppm 8.53 (brs, 1H), 8.32 (s, 1H), 7.81 (s, 1H), 7.58 (brs, 1H), 6.17 (s, 2H), 6.07 (brs, 1H), 5.29 (brs, 2H), 4.23 (s, 3H). |

| Cpd No. | Structure | Characterization |
|---|---|---|
| E9-47 | 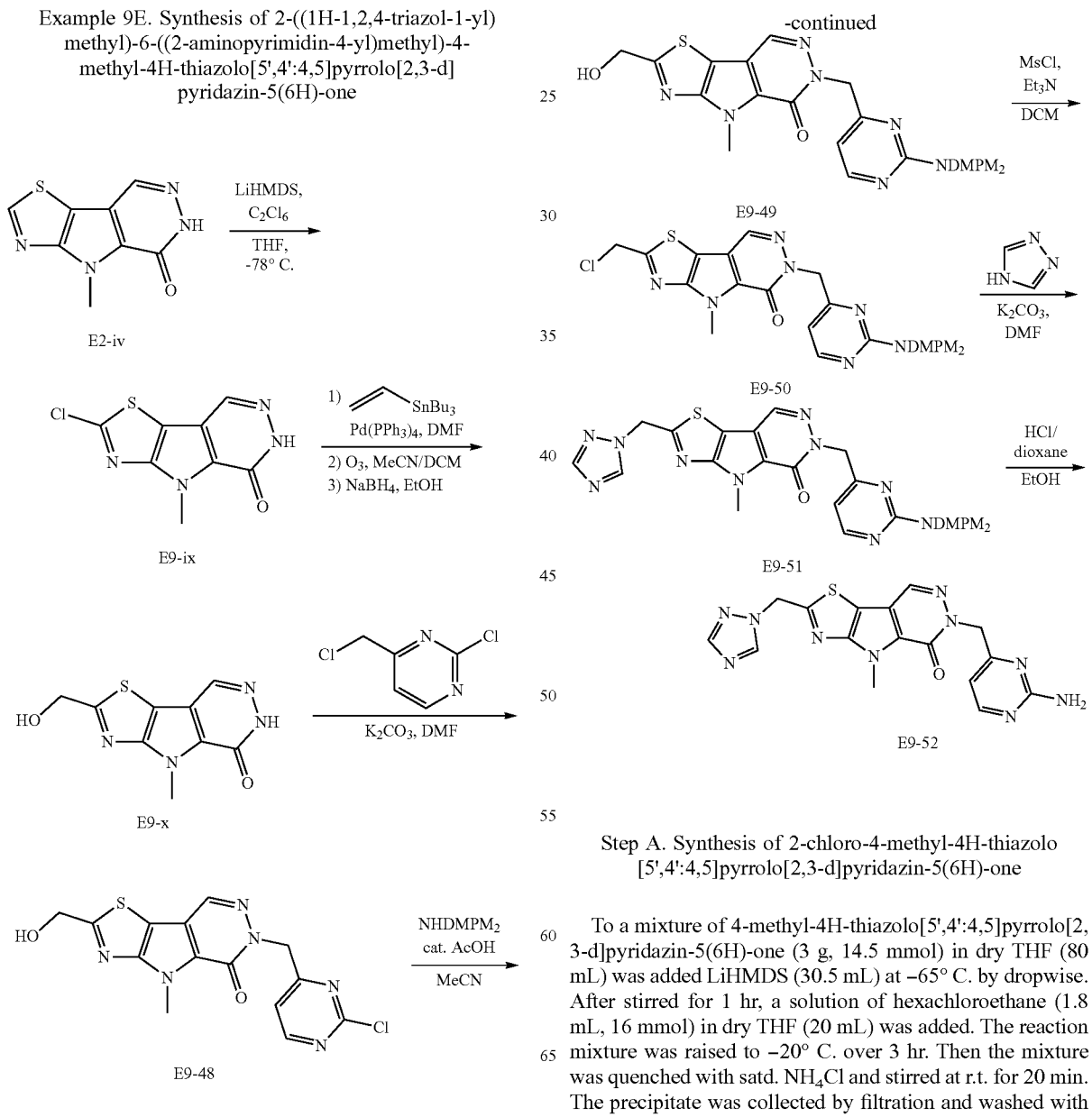

N-(6-((2-((1H-imidazol-1-yl)methyl)-4-methyl-5-oxo-4,5-dihydro-6H-thiazolo[5',4':4,5]pyrrolo[2,3-d]pyridazin-6-yl)methyl)-5-fluoropyridin-2-yl)acetamide | LC-MS: m/z 453 (M + H)+.
1H NMR (400 MHz, DMSO-d6) δ: 10.36 (s, 1H), 8.55 (s, 1H), 8.07-7.84 (m, 2H), 7.70 (t, 1H), 7.37 (s, 1H), 7.00 (s, 1H), 5.79 (s, 2H), 5.45 (s, 2H), 4.26 (s, 3H), 2.01 (s, 3H). |

Example 9E. Synthesis of 2-((1H-1,2,4-triazol-1-yl)methyl)-6-((2-aminopyrimidin-4-yl)methyl)-4-methyl-4H-thiazolo[5',4':4,5]pyrrolo[2,3-d]pyridazin-5(6H)-one Step A. Synthesis of 2-chloro-4-methyl-4H-thiazolo[5',4':4,5]pyrrolo[2,3-d]pyridazin-5(6H)-one To a mixture of 4-methyl-4H-thiazolo[5',4':4,5]pyrrolo[2,3-d]pyridazin-5(6H)-one (3 g, 14.5 mmol) in dry THF (80 mL) was added LiHMDS (30.5 mL) at −65° C. by dropwise. After stirred for 1 hr, a solution of hexachloroethane (1.8 mL, 16 mmol) in dry THF (20 mL) was added. The reaction mixture was raised to −20° C. over 3 hr. Then the mixture was quenched with satd. NH4Cl and stirred at r.t. for 20 min. The precipitate was collected by filtration and washed with EtOAc to give 3.5 g of 2-chloro-4-methyl-4H-thiazolo[5', 4':4,5]pyrrolo[2,3-d]pyridazin-5(6H)-one. LC-MS (ESI): m/z 241 (M+H)+.

Step B. Synthesis of 4-methyl-2-vinyl-4H-thiazolo [5',4':4,5]pyrrolo[2,3-d]pyridazin-5(6H)-one Under nitrogen, to a mixture of 2-chloro-4-methyl-4H-thiazolo[5',4':4,5]pyrrolo[2,3-d]pyridazin-5(6H)-one (1.5 g, 6.2 mmol) and tributyl(ethenyl)stannane (5.5 mL, 18.7 mmol) in DMF (30 mL) was added Pd(PPh$_3$)$_4$ (0.36 g, 0.31 mmol). The reaction mixture was stirred at 100° C. for 2 hr. Then the mixture was cooled down and diluted with EtOAc, washed with water and brine, dried over anhy. Na$_2$SO$_4$ and concentrated. The residue was purified by flash chromatography (silica gel, 0~10% MeOH in DCM) to give 1.4 g of 4-methyl-2-vinyl-4H-thiazolo[5',4':4,5]pyrrolo[2,3-d]pyridazin-5(6H)-one. LC-MS (ESI): m/z 233 (M+H)+.

Step C. Synthesis of 4-methyl-5-oxo-5,6-dihydro-4H-thiazolo[5',4':4,5]pyrrolo[2,3-d]pyridazine-2-carbaldehyde Under –60° C., a mixture of 4-methyl-2-vinyl-4H-thiazolo[5',4':4,5]pyrrolo[2,3-d]pyridazin-5(6H)-one (500 mg, 2.15 mmol) in DCM/MeCN (500 mL, 1:1 volume) was purged with O$_3$ for 20 min. Then the reaction was quenched with dimethylsolfane and concentrated to give 500 mg of 4-methyl-5-oxo-5,6-dihydro-4H-thiazolo[5',4':4,5]pyrrolo[2,3-d]pyridazine-2-carbaldehyde. LC-MS (ESI): m/z 235 (M+H)+.

Step D. Synthesis of 2-(hydroxymethyl)-4-methyl-4H-thiazolo[5',4':4,5]pyrrolo[2,3-d]pyridazin-5(6H)-one To a mixture of 4-methyl-5-oxo-5,6-dihydro-4H-thiazolo[5',4':4,5]pyrrolo[2,3-d]pyridazine-2-carbaldehyde (500 mg, 2.13 mmol) in EtOH (3 mL) was added NaBH$_4$ (81 mg, 2.13 mmol) at 0° C. The reaction was stirred at room temperature for 5 min. Then the mixture was poured into satd. NH$_4$Cl, extracted with EtOAc. The organic layer was washed with brine, dried over anhy. Na$_2$SO$_4$ and concentrated. The residue was purified by flash chromatography (silica gel, 0~8% MeOH in DCM) to give 120 mg of 2-(hydroxymethyl)-4-methyl-4H-thiazolo[5',4':4,5]pyrrolo[2,3-d]pyridazin-5(6H)-one. LC-MS (ESI): m/z 237 (M+H)+.

Step E. Synthesis of 6-((2-chloropyrimidin-4-yl)methyl)-2-(hydroxymethyl)-4-methyl-4H-thiazolo[5',4':4,5]pyrrolo[2,3-d]pyridazin-5(6H)-one To a mixture of 2-(hydroxymethyl)-4-methyl-4H-thiazolo[5',4':4,5]pyrrolo[2,3-d]pyridazin-5(6H)-one (200 mg, 0.85 mmol) in DMF (8 mL) was added K$_2$CO$_3$ (351 mg, 2.54 mmol). After stirred at 60° C. for 30 min, a solution of 2-chloro-4-(chloromethyl)pyrimidine (276 mg, 1.7 mmol) in DMF (2 mL) was added. The reaction mixture was stirred for another 4 hr, poured into satd. NH$_4$Cl, extracted with EtOAc. The organic layer was washed with brine, dried over anhy. Na$_2$SO$_4$ and concentrated. The residue was purified by flash chromatography (silica gel, 0~8% MeOH in DCM) to give 160 mg of 6-((2-chloropyrimidin-4-yl)methyl)-2-(hydroxymethyl)-4-methyl-4H-thiazolo[5',4':4,5]pyrrolo[2,3-d]pyridazin-5(6H)-one. LC-MS (ESI): m/z 363 (M+H)+.

Step F. Synthesis of 6-((2-(bis(2,4-dimethoxybenzyl)amino)pyrimidin-4-yl)methyl)-2-(hydroxymethyl)-4-methyl-4H-thiazolo[5',4':4,5]pyrrolo[2,3-d]pyridazin-5(6H)-one To a mixture of 6-((2-chloropyrimidin-4-yl)methyl)-2-(hydroxymethyl)-4-methyl-4H-thiazolo[5',4':4,5]pyrrolo[2,3-d]pyridazin-5(6H)-one (160 mg, 0.44 mmol) in MeCN (5 mL) was added bis(2,4-dimethoxybenzyl)amine (280 mg, 0.88 mmol) and AcOH (1 drop). The reaction mixture was stirred at 80° C. overnight. The reaction mixture was evaporated and the residue was purified by prep-TLC (eluant: 5% MeOH in DCM) to give 75 mg of 6-((2-(bis(2,4-dimethoxybenzyl)amino)pyrimidin-4-yl)methyl)-2-(hydroxymethyl)-4-methyl-4H-thiazolo[5',4':4,5]pyrrolo[2,3-d]pyridazin-5(6H)-one. LC-MS (ESI): m/z 644 (M+H)+.

Step G. Synthesis of 6-((2-(bis(2,4-dimethoxybenzyl)amino)pyrimidin-4-yl)methyl)-2-(chloromethyl)-4-methyl-4H-thiazolo[5',4':4,5]pyrrolo[2,3-d]pyridazin-5(6H)-one Under 0° C., to a solution of 6-((2-(bis(2,4-dimethoxybenzyl)amino)pyrimidin-4-yl)methyl)-2-(hydroxymethyl)-4-methyl-4H-thiazolo[5',4':4,5]pyrrolo[2,3-d]pyridazin-5(6H)-one (75 mg, 0.12 mmol) in DCM (5 mL) was added Et$_3$N (0.16 mL, 1.16 mmol) and MsCl (0.05 mL, 0.58 mmol). The mixture was stirred at r.t. overnight. The reaction mixture was diluted with DCM, washed with satd. NH$_4$Cl and brine, dried over anhy. Na$_2$SO$_4$ and concentrated to give 70 mg of crude product of 6-((2-(bis(2,4-dimethoxybenzyl)amino)pyrimidin-4-yl)methyl)-2-(chloromethyl)-4-methyl-4H-thiazolo[5',4':4,5]pyrrolo[2,3-d]pyridazin-5(6H)-one. LC-MS (ESI): m/z 662 (M+H)+.

Step H. Synthesis of 2-((1H-1,2,4-triazol-1-yl)methyl)-6-((2-(bis(2,4-dimethoxybenzyl)amino)pyrimidin-4-yl)methyl)-4-methyl-4H-thiazolo[5',4':4,5]pyrrolo[2,3-d]pyridazin-5(6H)-one A mixture of 4H-1,2,4-triazole (39 mg, 0.57 mmol) and K$_2$CO$_3$ (78 mg, 0.57 mmol) in DMF (3 mL) was stirred at 60° C. for 30 min. 6-((2-(bis(2,4-dimethoxybenzyl)amino)pyrimidin-4-yl)methyl)-2-(chloromethyl)-4-methyl-4H-thiazolo[5',4':4,5]pyrrolo[2,3-d]pyridazin-5(6H)-one (75 mg, 0.11 mmol) was added and stirred for another 30 min. The suspension was poured into satd. NH$_4$Cl, extracted with EtOAc. The organic layer was washed with brine, dried over anhy. Na$_2$SO$_4$ and concentrated. The residue was purified by flash chromatography (silica gel, 0~10% DCM in MeOH) to give 60 mg of 2-((1H-1,2,4-triazol-1-yl)methyl)-6-((2-(bis(2,4-dimethoxybenzyl)amino)pyrimidin-4-yl)methyl)-4-methyl-4H-thiazolo[5',4':4,5]pyrrolo[2,3-d]pyridazin-5(6H)-one. LC-MS (ESI): m/z 695 (M+H)+.

Step I. Synthesis of 2-((1H-1,2,4-triazol-1-yl)methyl)-6-((2-aminopyrimidin-4-yl)methyl)-4-methyl-4H-thiazolo[5',4':4,5]pyrrolo[2,3-d]pyridazin-5(6H)-one To a mixture of 2-((1H-1,2,4-triazol-1-yl)methyl)-6-((2-(bis(2,4-dimethoxybenzyl)amino) pyrimidin-4-yl)methyl)-4-methyl-4H-thiazolo[5',4':4,5]pyrrolo[2,3-d]pyridazin-5(6H)-one (30 mg, 0.043 mmol) in EtOH (2 mL) was added HCl (0.5 mL, 4 M in dioxane). The reaction mixture was stirred at 80° C. overnight. Then the mixture was cooled down and poured into satd. NaHCO$_3$, extracted with EtOAc.

The organic layer was washed with brine, dried over anhy. Na₂SO₄ and concentrated. The residue was purified by prep-HPLC to give 8 mg of 2-((1H-1,2,4-triazol-1-yl)methyl)-6-((2-aminopyrimidin-4-yl)methyl)-4-methyl-4H-thiazolo[5',4':4,5]pyrrolo[2,3-d]pyridazin-5(6H)-one.
LC-MS (ESI): m/z 395 (M+H)⁺._¹H NMR (400 MHz, DMSO-d6) δ 8.80 (s, 1H), 8.62 (s, 1H), 8.12-8.10 (m, 2H), 6.60 (s, 2H), 6.19 (d, 1H), 6.01 (s, 2H), 5.19 (s, 2H), 4.26 (s, 3H).

As shown in Scheme E10, reaction of E10-i with an aldehyde in the presence of a base (e.g. LiHMDS) generates compound E10-ii, which can be separated with chiral HPLC or SFC to give two enantiomers. As used herein, Ar1 and Ar2 are each independently optionally substituted alkyl, optionally substituted haloalkyl, optionally substituted alkenyl, optionally substituted alkynyl, optionally substituted cycloalkyl, optionally substituted heterocyclyl, optionally substituted aryl.

| Cpd No. | Structure and chemical name | Charaterization |
|---|---|---|
| E9-53 | 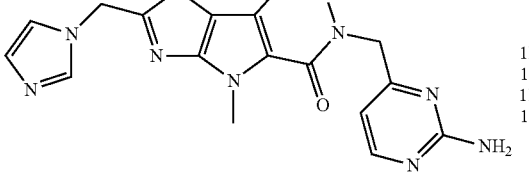<br>2-((1H-imidazol-1-yl)methyl)-6-((2-aminopyrimidin-4-yl)methyl)-4-methyl-4H-thiazolo[5',4':4,5]pyrrolo[2,3-d]pyridazin-5(6H)-one | LC-MS: m/z 394 (M + H)⁺.<br>¹H NMR (400 MHz, DMSO-d6) δ: 8.62 (s, 1H), 8.11 (d, 1H), 7.88 (s, 1H), 7.36 (s, 1H), 6.99 (s, 1H), 6.61 (s, 2H), 6.18 (d, 1H), 5.79 (s, 2H), 5.19 (s, 2H), 4.26 (s, 3H). |
| E9-54 | 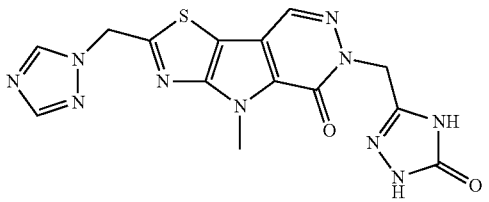<br>2-((1H-1,2,4-triazol-1-yl)methyl)-4-methyl-6-((5-oxo-4,5-dihydro-1H-1,2,4-triazol-3-yl)methyl)-4H-thiazolo[5',4':4,5]pyrrolo[2,3-d]pyridazin-5(6H)-one | LC-MS: m/z 385 (M + H)⁺.<br>¹H NMR (400 MHz, DMSO-d6) δ: 11.32-11.28 (m, 2H), 8.80 (s, 1H), 8.59 (s, 1H), 8.11 (s, 1H), 6.01 (s, 2H), 5.14 (s, 2H), 4.26 (s, 3H). |

Example 10. Synthesis of Compound E10-ii

Example 10A. Synthesis of (S)-6-((1H-indazol-4-yl)methyl)-2-(hydroxy(1H-pyrazol-3-yl)methyl)-4-methyl-4,6-dihydro-5H-thiazolo[5',4':4,5]pyrrolo[2,3-d]pyridazin-5-one and (R)-6-((1H-indazol-4-yl)methyl)-2-(hydroxy(1H-pyrazol-3-yl)methyl)-4-methyl-4,6-dihydro-5H-thiazolo[5',4':4,5]pyrrolo[2,3-d]pyridazin-5-one

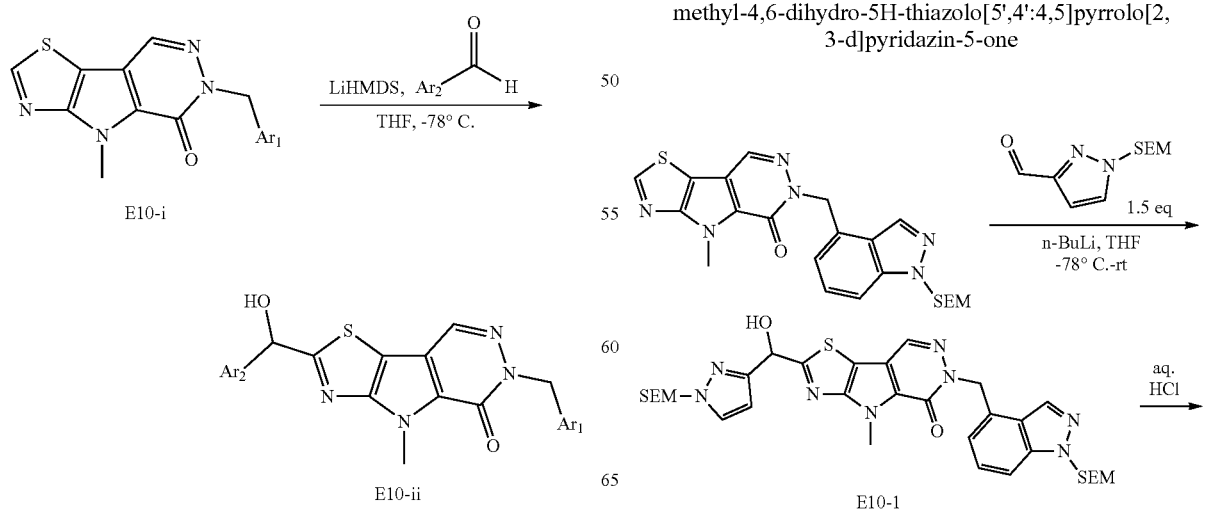

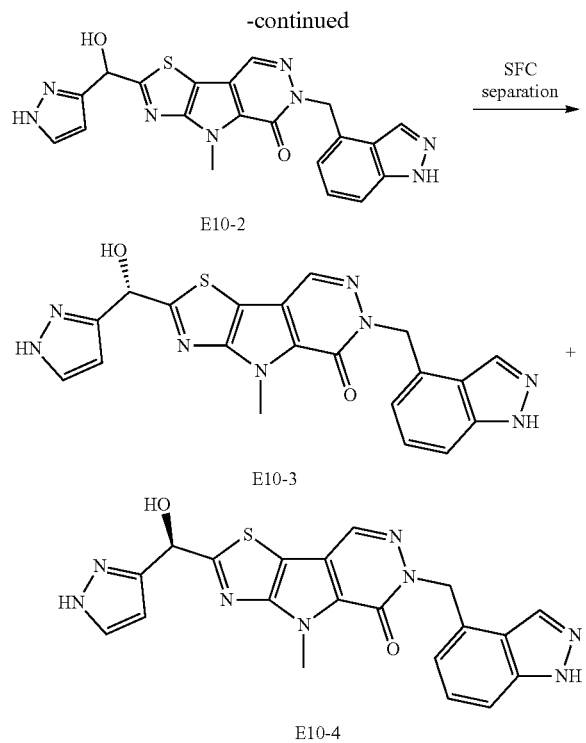

E10-2

E10-3

E10-4

Step A. Synthesis of 2-(hydroxy(1-((2-(trimethylsilyl)ethoxy)methyl)-1H-pyrazol-3-yl)methyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one Under argon, to a solution of 4-methyl-6(1-((1-((2-(trimethylsilyl)ethoxy)methyl)-1H-indazol-4-yl)methyl)-4H-thiazolo[5',4':4,5]pyrrolo[2,3-d]pyridazin-5(6H)-one (0.5 g, 1.07 mmol, 1 eq) in THF (15 mL) was slowly added LiHMDS (1.0 M, 2.14 mL, 2.0 eq) at −78° C., and the reaction mixture was stirred at −78° C. for 1 hr. Then a solution of 1-(2-trimethylsilylethoxymethyl) pyrazole-3-carbaldehyde (1.21 g, 5.36 mmol, 5 eq) in THF (2 mL) was added dropwise to the reaction mixture. The resulting mixture was stirred at −78° C. for 1 hr. TLC (petroleum ether:EtOAc 2:1) showed two new spots formed. The reaction mixture was quenched by aq NH$_4$Cl (15 mL) at −70° C., and diluted with water (20 m). The mixture was extracted with EtOAc (20 mL×3). The combined organic layers were washed with brine (20 mL), and dried over Na$_2$SO$_4$. The solvent was concentrated in vacuo. The residue was purified by Combiflash (from 100% of petroleum ether to 100% of EtOAc) to afford desired product (70 mg, 101.01 umol). LCMS: m/z 693.2 (M+H)$^+$ Step B. Synthesis of 6-((1H-indazol-4-yl)methyl)-2-(hydroxy(1H-pyrazol-3-yl)methyl)-4-methyl-4H-thiazolo[5',4':4,5]pyrrolo[2,3-d]pyridazin-5(6H)-one To a solution of 2-(hydroxy(1-((2-(trimethylsilyl)ethoxy)methyl)-1H-pyrazol-3-yl)methyl)-4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (0.04 g, 57.72 umol, 1 eq) in DCM (3 mL) was added TFA (65.82 mg, 577.22 umol, 42.74 uL, 10 eq) at 0° C., and the reaction mixture was stirred at room temperature for 36 hr. LCMS showed the starting material was consumed completely, and 57% of desired product was formed. The reaction mixture was concentrated in vacuo, and the residue was purified by Prep-HPLC to give the desired product (11 mg). LCMS: m/z 432.9 [M+H]+. $^1$H NMR (400 MHz, DMSO-d$_6$) δ ppm 13.10 (brs, 2H), 8.58 (s, 1H), 8.12 (s, 1H), 7.60 (s, 1H), 7.43 (d, 1H), 7.26 (dd, 1H), 6.93 (d, 2H), 6.19 (d, 1H), 6.07 (s, 1H), 5.63 (s, 2H), 4.20 (s, 3H).

Step C. Synthesis of (S)-6-((1H-indazol-4-yl)methyl)-2-(hydroxy(1H-pyrazol-3-yl)methyl)-4-methyl-4H-thiazolo[5',4':4,5]pyrrolo[2,3-d]pyridazin-5(6H)-one and (R)-6-((1H-indazol-4-yl)methyl)-2-(hydroxy(1H-pyrazol-3-yl)methyl)-4-methyl-4H-thiazolo[5',4':4,5]pyrrolo[2,3-d]pyridazin-5(6H)-one The compound 6-((1H-indazol-4-yl)methyl)-2-(hydroxy(1H-pyrazol-3-yl)methyl)-4-methyl-4H-thiazolo[5',4':4,5]pyrrolo[2,3-d]pyridazin-5(6H)-one was separated by SFC. SFC condition: Column is DAICEL CHIRALCEL OJ-H (250 mm*30 mm, 5 um); mobile phase: A: 55% of CO2; B: 45% [0.1% NH$_3$H$_2$O in EtOH]/min. The SFC separation afforded two enantiomers. One enantiomer (2.6 mg): LCMS: m/z 433.0 [M+H]$^+$. $^1$H NMR (400 MHz, DMSO-d$_6$) δ ppm 8.63 (s, 1H), 8.16 (s, 1H), 7.64 (brs, 1H), 7.47 (brd, 1H), 7.27-7.32 (m, 1H), 6.97 (brd, 1H), 6.22 (d, 1H), 6.11 (s, 1H), 5.64 (s, 2H), 5.34 (brs, 1H), 4.24 (s, 3H). And 3.5 mg of another enantiomer: LCMS: m/z 433.0 (M+H)$^+$. $^1$H NMR (400 MHz, DMSO-d$_6$) ppm 8.63 (s, 1H), 8.17 (s, 1H), 7.64 (brs, 1H), 7.48 (brd, 1H), 7.28-7.32 (m, 1H), 6.98 (brd, 1H), 6.23 (d, 1H), 6.11 (s, 1H), 5.64 (s, 2H), 5.34 (brs, 1H), 4.25 (s, 3H).

Example 10B. Synthesis of (R)-6-((1H-pyrazol-3-yl)methyl)-2-(hydroxy(1H-pyrazol-3-yl)methyl)-4-methyl-4H-thiazolo[5',4':4,5]pyrrolo[2,3-d]pyridazin-5(6H)-one and (S)-6-((1H-pyrazol-3-yl)methyl)-2-(hydroxy(1H-pyrazol-3-yl)methyl)-4-methyl-4H-thiazolo[5',4':4,5]pyrrolo[2,3-d]pyridazin-5(6H)-one

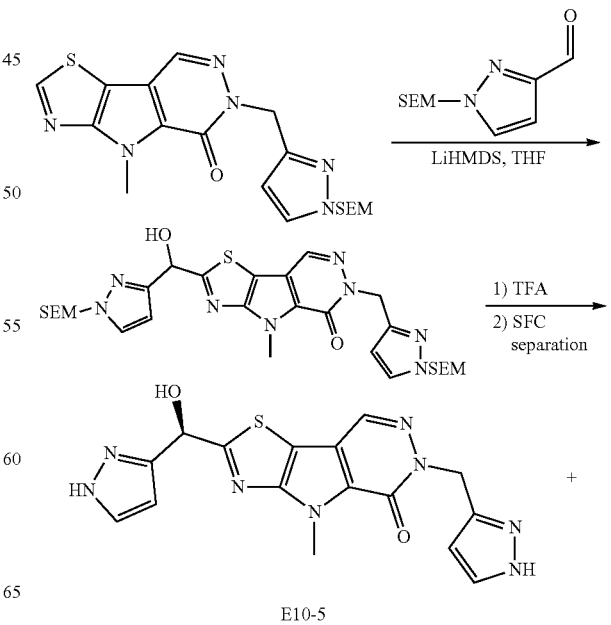

E10-5

-continued

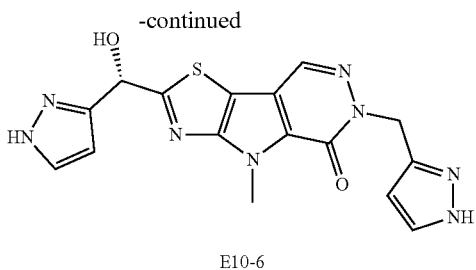

E10-6

Step A. Synthesis of 2-(hydroxy(1-((2-(trimethylsilyl)ethoxy)methyl)-1H-pyrazol-3-yl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one Under argon, to a solution of 4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (0.5 g, 1.20 mmol, 1 eq) in THF (10 mL) was slowly added LiHMDS (1.0 M, 2.41 mL, 2 eq) at −78° C., and the reaction mixture was stirred at −70° C. for 1 hr. Then a solution of 1-(2-trimethylsilylethoxymethyl) pyrazole-3-carbaldehyde (816.97 mg, 3.61 mmol, 3 eq) in THF (1 mL) was added to the reaction mixture. The resulting mixture was stirred at −70° C. for 1 hr. TLC (petroleumether:EtOAc=1:1) showed two new spot was formed. The reaction mixture was quenched by aq NH$_4$Cl (5 mL) at −70° C., and then warmed to room temperature. The mixture was diluted with water (10 mL), and extracted with EtOAc (8 mL×3). The combined organic layers were washed with brine (10 mL), and dried over Na$_2$SO$_4$. The solvent was concentrated in vacuo. The residue was purified by Combiflash (from 100% of petroleum ether to 100% of EtOAc) to give crude product (130 mg) as pale brown gum, which was used for the next step without further purification. LCMS: m/z 643.2 [M+H]$^+$ Step B. Synthesis of 6-((1H-pyrazol-3-yl)methyl)-2-(hydroxy(1H-pyrazol-3-yl)methyl)-4-methyl-4H-thiazolo[5',4':4,5]pyrrolo[2,3-d]pyridazin-5(6H)-one To a solution of 2-(hydroxy(1-((2-(trimethylsilyl)ethoxy)methyl)-1H-pyrazol-3-yl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (0.13 g, 202.20 umol, 1 eq) in DCM (8 mL) was added TFA (4.62 g, 40.52 mmol, 3 mL, 200.38 eq), followed by H$_2$O (500.00 mg, 27.75 mmol, 0.5 mL, 137.26 eq), then the reaction mixture was stirred at room temperature for 18 hr, then heated to 40° C. for 18 hr. LCMS showed the starting material was consumed completely. The reaction mixture was concentrated in vacuo, and the residue was purified by Prep-HPLC to give the desired product (20.5 mg). LCMS: m/z 382.9 [M+H]$^+$. $^1$H NMR (400 MHz, DMSO-d$_6$) δ ppm 12.72 (brs, 1H), 12.61 (brs, 1H), 8.52 (s, 1H), 7.56-7.62 (m, 2H), 6.82 (brs, 1H), 6.18 (d, 1H), 5.99-6.09 (m, 2H), 5.24-5.32 (m, 2H), 4.19 (s, 3H).

Step C. Synthesis of (R)-6-((1H-pyrazol-3-yl)methyl)-2-(hydroxy(1H-pyrazol-3-yl)methyl)-4-methyl-4H-thiazolo[5',4':4,5]pyrrolo[2,3-d]pyridazin-5(6H)-one and (S)-6-((1H-pyrazol-3-yl)methyl)-2-(hydroxy(1H-pyrazol-3-yl)methyl)-4-methyl-4H-thiazolo[5',4':4,5]pyrrolo[2,3-d]pyridazin-5(6H)-one The compound 6-((1H-pyrazol-3-yl)methyl)-2-(hydroxy(1H-pyrazol-3-yl)methyl)-4-methyl-4H-thiazolo[5',4':4,5]pyrrolo[2,3-d]pyridazin-5(6H)-one was separated by SFC. SFC condition: Column is DAICEL CHIRALCEL OJ-H (250 mm*30 mm, 5 um); mobile phase: A: 55% of CO2; B: 45% [0.1% NH$_3$H$_2$O in EtOH]/min. The SFC separation afforded 2-[(R)-hydroxy(1H-pyrazol-3-yl)methyl]-4-methyl-6-(1H-pyrazol-3-ylmethyl)thiazolo[3,4]pyrrolo[1,3-d]pyridazin-5-one and 2-[(S)-hydroxy(1H-pyrazol-3-yl)methyl]-4-methyl-6-(1H-pyrazol-3-ylmethyl)thiazolo[3,4]pyrrolo[1,3-d]pyridazin-5-one. One isomer (4.4 mg): LCMS: m/z 383 [M+H]$^+$. $^1$H NMR (400 MHz, Methanol-d$_4$) δ ppm 8.39 (s, 1H), 7.61 (brs, 1H), 7.55 (brs, 1H), 6.34 (brs, 1H), 6.25 (brs, 1H), 6.18 (brs, 1H), 5.44 (s, 2H), 4.29 (s, 3H). Another isomer (4.1 mg): LCMS: m/z 383 (M+H)$^+$. $^1$H NMR (400 MHz, METHANOL-d$_4$) δ ppm 8.40 (s, 1H), 7.59 (brs, 1H), 7.54 (brs, 1H), 6.34 (brs, 1H), 6.26 (brs, 1H), 6.19 (brs, 1H), 5.44 (s, 2H), 4.29 (s, 3H).

Example 10C: Synthesis of 6-((1H-pyrazol-3-yl)methyl)-2-(difluoro(1H-pyrazol-3-yl)methyl)-4-methyl-4,6-dihydro-5H-thiazolo[5',4':4,5]pyrrolo[2,3-d]pyridazin-5-one

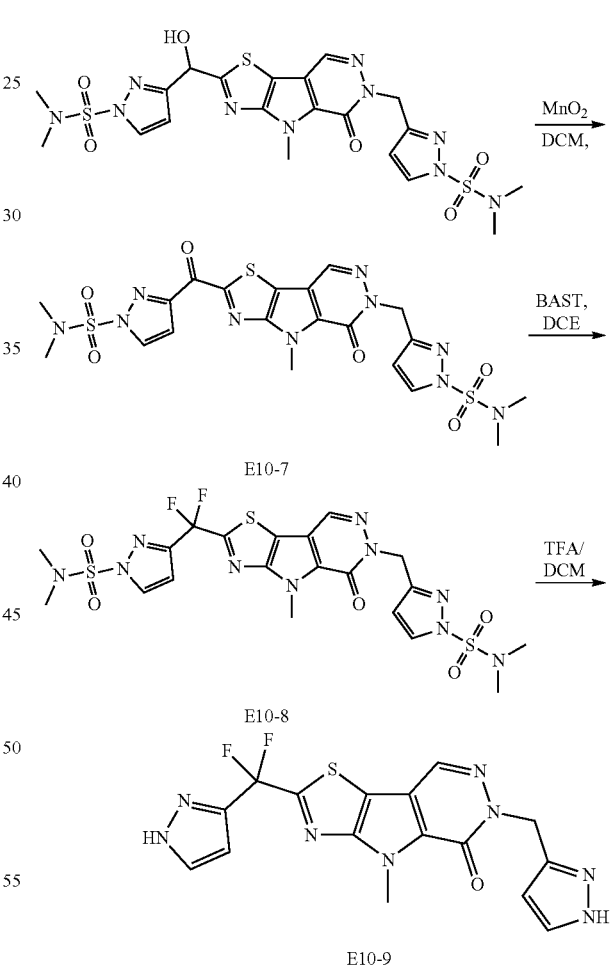

Step A. 3-(6-((1-(N,N-dimethylsulfamoyl)-1H-pyrazol-3-yl)methyl)-4-methyl-5-oxo-5,6-dihydro-4H-thiazolo[5',4':4,5]pyrrolo[2,3-d]pyridazine-2-carbonyl)-N,N-dimethyl-1H-pyrazole-1-sulfonamide To a mixture of 3-((2-((1-(N,N-dimethylsulfamoyl)-1H-pyrazol-3-yl)(hydroxy)methyl)-4-methyl-5-oxo-4,5-dihydro-6H-thiazolo[5',4':4,5]pyrrolo[2,3-d]pyridazin-6-yl) methyl)-N,N-dimethyl-1H-pyrazole-1-sulfonamide (50 mg, 83.80 umol, made similarly to E10-1) in DCM (1.5 mL) was added MnO$_2$ (72.85 mg, 838.00 umol) and the mixture was stirred at 15° C. for 1.5 hours. The reaction mixture was filtered and concentrated under reduced pressure to give a crude product (60 mg, crude). LCMS: m/z 595.1 (M+H)$^+$. $^1$H NMR (400 MHz, CDCl3) δ 8.34 (s, 1H), 8.12 (d, 1H), 7.90 (d, 1H), 7.41 (d, 1H), 6.38 (d, 1H), 5.54 (s, 2H), 4.49 (s, 3H), 3.10 (s, 6H) 2.93 (s, 6H).

Step B. 3-((2-((1-(N,N-dimethylsulfamoyl)-1H-pyrazol-3-yl)difluoromethyl)-4-methyl-5-oxo-4,5-dihydro-6H-thiazolo[5',4':4,5]pyrrolo[2,3-d]pyridazin-6-yl)methyl)-N,N-dimethyl-1H-pyrazole-1-sulfonamide To a solution of 3-(6-((1-(N,N-dimethylsulfamoyl)-1H-pyrazol-3-yl)methyl)-4-methyl-5-oxo-5,6-dihydro-4H-thiazolo[5',4':4,5]pyrrolo[2,3-d]pyridazine-2-carbonyl)-N,N-dimethyl-1H-pyrazole-1-sulfonamide (240 mg, 403.60 umol) in DCE (4 mL) was added BAST (1.34 g, 6.05 mmol, 1.33 mL), and the mixture was stirred at 50° C. for 12 h. The reaction mixture was diluted with dichloromethane (20 mL) and washed with saturated NaHCO$_3$ (10 mL*2), dried over anhydrous Na$_2$SO$_4$, filtered and concentrated under reduced pressure to give a crude product (300 mg, crude) which was used in the next step without further purification. LCMS: m/z 617.1 (M+H)$^+$.

Step C. 6-((1H-pyrazol-3-yl)methyl)-2-(difluoro (1H-pyrazol-3-yl)methyl)-4-methyl-4,6-dihydro-5H-thiazolo[5',4':4,5]pyrrolo[2,3-d]pyridazin-5-one To a mixture of 3-((2-((1-(N,N-dimethylsulfamoyl)-1H-pyrazol-3-yl)difluoromethyl)-4-methyl-5-oxo-4,5-dihydro-6H-thiazolo[5',4':4,5]pyrrolo[2,3-d]pyridazin-6-yl)methyl)-N,N-dimethyl-1H-pyrazole-1-sulfonamide (240 mg, 163.47 umol) in DCM (2 mL) was added TFA (2.07 g, 18.15 mmol, 1.34 mL) and the mixture was warmed up to 50° C. for 5 h. The reaction mixture was concentrated under reduced pressure. The residue was purified by prep-HPLC (column: Agela ASB 150*25 mm*5 um; mobile phase: [water (0.05% HCl)-ACN]; B %: 30%-60%, 8 min) to give desired product (3.9 mg, 5.45% yield, 92% purity) as a white solid. LCMS: m/z 403.1 (M+H)$^+$. $^1$H NMR (400 MHz, DMSO-d$_6$) δ 8.67 (s, 1H), 7.95 (s, 1H), 7.61 (s, 1H), 6.72 (s, 1H), 6.16 (s, 1H), 5.36 (s, 2H), 4.28 (s, 3H).

Example 10D: Synthesis of 2-(1-(1H-pyrazol-3-yl) ethyl)-6-((1H-pyrazol-3-yl)methyl)-4-methyl-4,6-dihydro-5H-thiazolo[5',4':4,5]pyrrolo[2,3-d] pyridazin-5-one

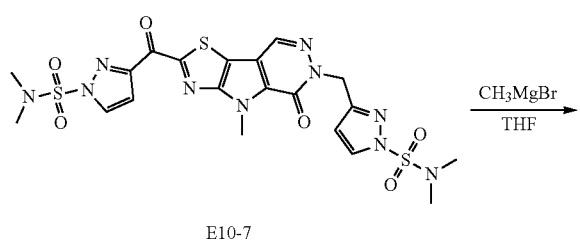

E10-7

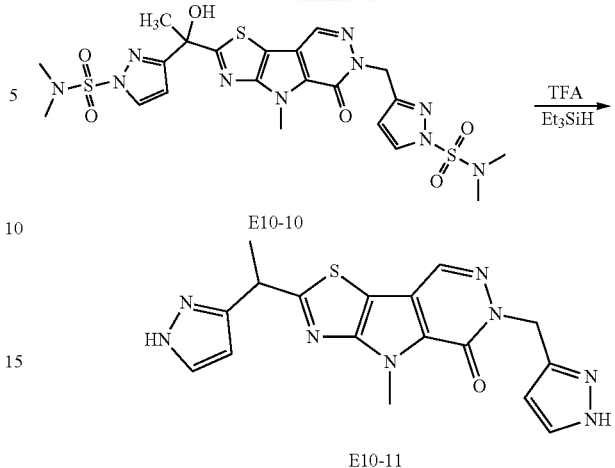

Step A: 3-((2-(1-(1-(N,N-dimethylsulfamoyl)-1H-pyrazol-3-yl)-1-hydroxyethyl)-4-methyl-5-oxo-4,5-dihydro-6H-thiazolo[5',4':4,5]pyrrolo[2,3-d]pyridazin-6-yl)methyl)-N,N-dimethyl-1H-pyrazole-1-sulfonamide To a solution of 3-(6-((1-(N,N-dimethylsulfamoyl)-1H-pyrazol-3-yl)methyl)-4-methyl-5-oxo-5,6-dihydro-4H-thiazolo[5',4':4,5]pyrrolo[2,3-d]pyridazine-2-carbonyl)-N,N-dimethyl-1H-pyrazole-1-sulfonamide (160 mg, 269.07 umol) in THF (3 mL) was added CH3MgBr (3 M, 179.38 uL) and the reaction mixture was stirred at 0° C. for 3 h. The reaction mixture was poured into saturated NH4Cl (10 mL) at 0° C., extracted with ethyl acetate (20 mL*3). The combined organic layers were washed with brine (10 mL), dried over anhydrous Na2SO4, filtered and concentrated under reduced pressure. The residue was purified by flash silica gel chromatography (ISCO®; 12 g SepaFlash® Silica Flash Column, Eluent of 0~90% Ethyl acetate/Petroleum ether gradient @ 40 mL/min) to give desired product (50 mg, 81.87 umol). LCMS: m/z 611.1 (M+H)$^+$.

Step B: 2-(1-(1H-pyrazol-3-yl)ethyl)-6-((1H-pyrazol-3-yl)methyl)-4-methyl-4,6-dihydro-5H-thiazolo [5',4':4,5]pyrrolo[2,3-d]pyridazin-5-one To a mixture of 3-((2-(1-(1-(N,N-dimethylsulfamoyl)-1H-pyrazol-3-yl)-1-hydroxyethyl)-4-methyl-5-oxo-4,5-dihydro-6H-thiazolo[5',4':4,5]pyrrolo[2,3-d]pyridazin-6-yl)methyl)-N,N-dimethyl-1H-pyrazole-1-sulfonamide (50 mg, 81.87 umol) in DCE (0.5 mL) was added Et3SiH (19.04 mg, 163.75 umol, 26.15 uL) at 0° C., followed by TFA (1.54 g, 13.51 mmol, 1 mL, 164.96 eq) and stirred at 0° C. for 1 h. The mixture was warmed up to 50° C. for another 1 h. The reaction mixture was concentrated under reduced pressure. The residue was purified by prep-HPLC (column: Agela ASB 150*25 mm*5 um; mobile phase: [water (0.05% HCl)-ACN]; B %: 25%-55%, 7 min) to give 7.0 mg of desired product. LCMS: m/z 381.2 (M+H)$^+$. $^1$H NMR (400 MHz, CD$_3$OD) δ 8.46 (s, 1H), 8.15 (d, 2H), 6.78 (d, 1H), 6.74 (d, 1H), 5.60 (s, 2H), 5.00 (q, 1H), 4.33 (s, 3H), 1.94 (d, 3H).

Example 10E: Synthesis of 6-((1H-pyrazol-3-yl)methyl)-4-methyl-2-(1H-pyrazole-3-carbonyl)-4,6-dihydro-5H-thiazolo[5',4':4,5]pyrrolo[2,3-d]pyridazin-5-one

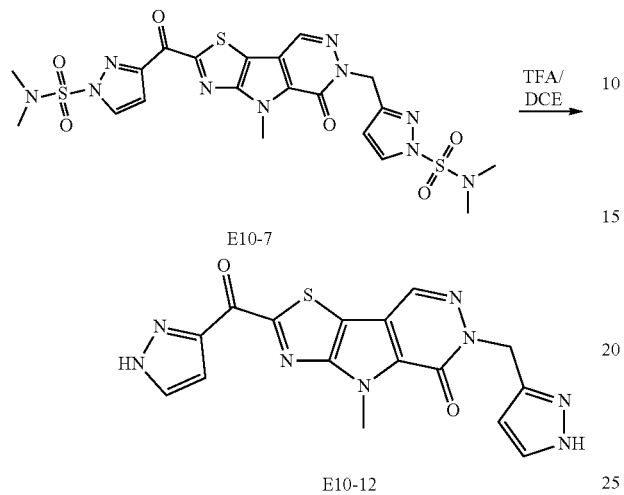

Step A. 4-methyl-2-(1H-pyrazole-3-carbonyl)-6-(1H-pyrazol-3-ylmethyl)thiazolo[3,4]pyrrolo[1,3-d]pyridazin-5-one To a solution of 3-(6-((1-(N,N-dimethylsulfamoyl)-1H-pyrazol-3-yl)methyl)-4-methyl-5-oxo-5,6-dihydro-4H-thiazolo[5',4':4,5]pyrrolo[2,3-d]pyridazine-2-carbonyl)-N,N-dimethyl-1H-pyrazole-1-sulfonamide (50 mg, 84.08 umol) in DCE (1.5 mL) was added TFA (2.31 g, 20.26 mmol, 1.5 mL) and the reaction mixture was warmed up to 50° C. for 12 h. The reaction mixture was concentrated under vacuum. The residue was purified by prep-HPLC to give 6.0 mg of desired product. LCMS: m/z 381.1 (M+H)+. $^1$H NMR (400 MHz, DMSO-$d_6$) δ 8.72 (s, 1H), 7.96 (d, 1H), 7.64 (d, 1H), 7.49 (d, 1H), 6.19 (d, 1H), 5.37 (s, 2H), 4.38 (s, 3H).

Example 11. PKM2 Assay

Procedure:

PKM2 enzyme stock solution was diluted to prepare a 1.11× Reaction Mix (without ADP). 1 μL of test compound was first added to the wells followed by 40 μL of 1.11× Reaction Mix (without ADP) and incubated at room temperature (25° C.) for 60 min. The reaction was initiated with 10 μL ADP (0.4 mM final concentration), bringing the final Reaction Mix to 1×, and the reaction progress was measured as changes in absorbance at 340 nm wavelength at room temperature.

Test compound preparation: Test compounds were prepared at 50× final concentration in DMSO. 1 to 3 dilutions were made for 11 points (for example 50 μL of 5000 LM compound was added to 100 μL 100% DMSO to yield a 1667 μM, 50 μL of this added to 100 μL DMSO to yield 556 μM, and so forth). The compounds were added to the assay as a 1 to 50 dilution (1 μL in 50 μL) to yield a top concentration of 100 μM, decreasing 3-fold for 11 points.

Reaction Mix: PKM2 (5 ng/well, 0.1 μg/ml), ADP (0.4 mM), PEP (0.11 mM), NADH (180 μM), LDH (0.005 U/μL, Sigma #L3888), 1 mM DTT, 0.03% BSA in 1× Reaction Buffer Reaction Buffer: 100 mM KCl, 50 mM Tris pH 7.5, 5 mM $MgCl_2$.

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A method of activating pyruvate kinase M2 (PKM2) activity in a subject in need thereof comprising administering to the subject an effective amount of a compound of Formula (I):

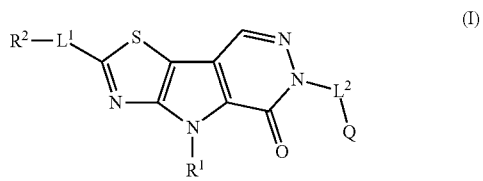

or a pharmaceutically acceptable salt thereof, wherein:

Q is hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl;

$R^1$ is hydrogen, optionally substituted alkyl, optionally substituted haloalkyl, optionally substituted alkenyl, optionally substituted alkynyl, optionally substituted cycloalkyl, optionally substituted heterocyclyl, optionally substituted aryl, —$OR^{o1}$, —$C(=O)R^{c1}$, or a nitrogen protecting group;

$L^1$ is a bond, optionally substituted alkylene, —O—, —S—, —S—$CH_2$—, —$S(=O)CH_2$—, —$S(=O)_2CH_2$—, —$NR^3$—, —$NR^3C(=O)$—, —$C(=O)NR^3$—, —$C(=O)$—, —$OC(=O)$—, —$C(=O)O$—, —$NR^3C(=O)O$—, —$OC(=O)NR^3$—, —$NR^3C(=O)NR^3$—, —$OC(R^4)_2$—, —$C(R^4)_2O$—, —$NR^3C(R^4)_2$—, —$C(R^4)_2NR^3$—, —$S(=O)_2$—, —$S(=O)$—, —$S(=O)_2O$—, —$OS(=O)_2$—, —$S(=O)O$—, —$OS(=O)$—, —$S(=O)_2NR^3$—, —$NR^3S(=O)_2$—, —$S(=O)NR^3$—, —$NR^3S(=O)$—, —$NR^3S(=O)_2O$—, —$OS(=O)_2NR^3$—, —$NR^3S(=O)O$—, —$OS(=O)NR^3$—, or —$S(=O)(=NR^3)$—, wherein the point of the attachment to $R^2$ is on the left-hand side;

$L^2$ is a bond, optionally substituted alkylene, —$C(=O)$—, —$S(=O)_2$—, or —$S(=O)$—, wherein the point of the attachment to Q is on the right-hand side;

$R^2$ is hydrogen, halogen, optionally substituted alkyl, optionally substituted alkoxy, optionally substituted alkenyl, optionally substituted alkynyl, optionally substituted cycloalkyl, optionally substituted heterocyclyl, optionally substituted aryl, or optionally substituted heteroaryl, or a nitrogen protecting group when $L^1$ is —$NR^3$—, —$NR^3C(=O)$—, —$NR^3C(=O)O$—, —$NR^3C(R^4)_2$—, —$NR^3S(=O)_2$—, —$NR^3S(=O)$—, —$NR^3C(=O)NR^3$—, —$NR^3S(=O)_2O$—, or —$NR^3S(=O)O$—, an oxygen protecting group when $L^1$ is —O—, —$OC(=O)$—, —OC(=O)NR$^3$—, —OC(R$^4$)$_2$—, —OS(=O)$_2$—, —OS(=O)$_2$NR$^3$—, —OS(=O)NR$^3$—, or —OS(=O)—, or a sulfur protecting group when L$^1$ is —S—;

each instance of R$^3$ is independently hydrogen, —OR$^{o2}$, optionally substituted alkyl, optionally substituted alkenyl, optionally substituted alkynyl, optionally substituted cycloalkyl, optionally substituted heterocyclyl, optionally substituted aryl, optionally substituted heteroaryl, or a nitrogen protecting group;

each instance of R$^{o1}$, and R$^{o2}$ is independently hydrogen, optionally substituted alkyl, or an oxygen protecting group;

each instance of R$^{c1}$ is independently optionally substituted alkyl or —N(R$^{cn}$)$_2$, wherein each instance of R$^{cn}$ is independently hydrogen, —C$_{1-6}$ alkyl, or a nitrogen protecting group; and each instance of R$^4$ is independently hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl.

2. The method of claim 1, wherein:

Q is hydrogen, optionally substituted —C$_1$-C$_6$ alkyl, optionally substituted C$_3$-C$_{12}$ cycloalkyl, optionally substituted 3- to 14-membered heterocyclyl, optionally substituted 6- to 14-membered aryl, or optionally substituted 5- to 14-membered heteroaryl;

R$^1$ is hydrogen, optionally substituted —C$_1$-C$_6$ alkyl, optionally substituted —C$_1$-C$_6$ haloalkyl, optionally substituted —C$_2$-C$_6$ alkenyl, optionally substituted —C$_2$-C$_6$ alkynyl, optionally substituted C$_3$-C$_{12}$ cycloalkyl, optionally substituted 3- to 14-membered heterocyclyl, optionally substituted 6- to 12-membered aryl, —OR$^{o1}$, —C(=O)R$^{c1}$, or a nitrogen protecting group;

L$^1$ is a bond, optionally substituted C$_{1-6}$ alkylene, —O—, —S—, —S—CH$_2$—, —S(=O)CH$_2$—, —S(=O)$_2$CH$_2$—, —NR$^3$—, —NR$^3$C(=O)—, —C(=O)NR$^3$—, —C(=O)—, —OC(=O)—, —C(=O)O—, —NR$^3$C(=O)O—, —OC(=O)NR$^3$—, —NR$^3$C(=O)NR$^3$—, —OC(R$^4$)$_2$—, —C(R$^4$)$_2$O—, —NR$^3$C(R$^4$)$_2$—, —C(R$^4$)$_2$NR$^3$—, —S(=O)$_2$—, —S(=O)—, —S(=O)$_2$O—, —OS(=O)$_2$—, —S(=O)O—, —OS(=O)—, —S(=O)$_2$NR$^3$—, —NR$^3$S(=O)$_2$—, —S(=O)NR$^3$—, —NR$^3$S(=O)—, —NR$^3$S(=O)$_2$O—, —OS(=O)$_2$NR$^3$—, —NR$^3$S(=O)O—, —OS(=O)NR$^3$—, or —S(=O)(=NR$^3$)—, wherein the point of the attachment to R$^2$ is on the left-hand side;

L$^2$ is a bond, optionally substituted C$_1$-C$_6$ alkylene, —C(=O)—, —S(=O)$_2$—, or —S(=O)—, wherein the point of the attachment to Q is on the right-hand side;

R$^2$ is hydrogen, halogen, optionally substituted —C$_1$-C$_6$ alkyl, optionally substituted —C$_1$-C$_6$ alkoxy, optionally substituted —C$_3$-C$_{12}$ cycloalkyl, optionally substituted 3- to 14-membered heterocyclyl, optionally substituted —C$_6$-C$_{12}$ aryl, or optionally substituted 3- to 14-membered heteroaryl, or a nitrogen protecting group when L$^1$ is —NR$^3$—, —NR$^3$C(=O)—, —NR$^3$C(=O)O—, —NR$^3$C(R$^4$)$_2$—, —NR$^3$S(=O)$_2$—, —NR$^3$S(=O)—, —NR$^3$C(=O)NR$^3$—, —NR$^3$S(=O)$_2$O—, or —NR$^3$S(=O)O—, an oxygen protecting group when L$^1$ is —O—, —OC(=O)—, —OC(=O)NR$^3$—, —OC(R$^4$)$_2$—, —OS(=O)—, —OS(=O)$_2$—, —OS(=O)NR$^3$—, or —OS(=O)—, or a sulfur protecting group when L$^1$ is —S—;

each instance of R$^3$ is independently hydrogen, —OR$^{o2}$, optionally substituted —C$_1$-C$_6$ alkyl, optionally substituted —C$_2$-C$_6$ alkenyl, optionally substituted —C$_2$-C$_6$ alkynyl, optionally substituted C$_3$-C$_{12}$ cycloalkyl, optionally substituted C$_3$-C$_{12}$ heterocyclyl, optionally substituted C$_6$-C$_{12}$ aryl, optionally substituted C$_5$-C$_{12}$ heteroaryl, or a nitrogen protecting group;

each instance of R$^{o1}$ and R$^{o2}$ is independently hydrogen, optionally substituted —C$_1$-C$_6$ alkyl, or an oxygen protecting group;

each instance of R$^{c1}$ is independently optionally substituted —C$_1$-C$_6$ alkyl or —N(R$^{cn}$)$_2$, wherein each instance of R$^{cn}$ is independently hydrogen, —C$_1$-C$_6$ alkyl, or a nitrogen protecting group;

each instance of R$^4$ is independently hydrogen, optionally substituted —C$_1$-C$_6$ alkyl, optionally substituted —C$_2$-C$_6$ alkenyl, optionally substituted —C$_2$-C$_6$ alkynyl, optionally substituted C$_3$-C$_{12}$ cycloalkyl, optionally substituted 3- to 14-membered heterocyclyl, optionally substituted C$_6$-C$_{12}$ aryl, or optionally substituted 5- to 14-membered heteroaryl.

3. The method of claim 1, wherein:

Q is C$_6$-C$_{12}$ aryl, 5- to 6-membered monocyclic heteroaryl, or 8- to 12-membered bicyclic heteroaryl, each of which is substituted with 0-3 occurrences of R$^c$, R$^1$ is selected from hydrogen, —C$_1$-C$_6$ alkyl, —C$_1$-C$_6$ haloalkyl, C$_3$-C$_7$ monocyclic cycloalkyl and 3- to 14-membered heterocyclyl, —OR$^{o1}$, —C(=O)R$^{c1}$, or a nitrogen protecting group; wherein each alkyl, cycloalkyl or heterocyclyl is substituted with 0-3 occurrences of R$^d$;

R$^2$ is selected from hydrogen, halogen, —C$_1$-C$_6$ alkyl, —C$_1$-C$_6$ alkoxy, C$_3$-C$_7$ monocyclic cycloalkyl, C$_6$-C$_{12}$ bicyclic cycloalkyl, 3- to 14-membered heterocyclyl, C$_6$-C$_{12}$ aryl, 5- to 6-membered monocyclic heteroaryl, 8- to 12-membered bicyclic heteroaryl, wherein each alkyl, cycloalkyl, heterocyclyl, aryl and heteroaryl is substituted with 0-3 occurrences of R$^e$, or a nitrogen protecting group when L$^1$ is —NR$^3$—, —NR$^3$C(=O)—, —NR$^3$C(=O)O—, —NR$^3$C(R$^4$)$_2$—, —NR$^3$S(=O)$_2$—, —NR$^3$S(=O)—, —NR$^3$C(=O)NR$^3$—, —NR$^3$S(=O)$_2$O—, or —NR$^3$S(=O)O—, an oxygen protecting group when L$^1$ is —O—, —OC(=O)—, —OC(=O)NR$^3$—, —OC(R$^4$)$_2$—, —OS(=O)—, —OS(=O)$_2$—, —OS(=O)$_2$NR$^3$—, —OS(=O)NR$^3$—, or —OS(=O)—, or a sulfur protecting group when L$^1$ is —S—;

R$^3$ is selected from hydrogen, —OR$^{o2}$, —C$_1$-C$_6$ alkyl, C$_3$-C$_7$ monocyclic cycloalkyl, C$_6$-C$_{12}$ bicyclic cycloalkyl, 3- to 14-membered heterocyclyl, C$_6$-C$_{12}$ aryl, 5- to 6-membered monocyclic heteroaryl, and 8- to 12-membered bicyclic heteroaryl, wherein each alkyl, cycloalkyl, heterocycloalkyl, aryl and heteroaryl is substituted with 0-3 occurrences of R$^f$;

R$^4$ is selected from hydrogen, —C$_1$-C$_6$ alkyl, C$_3$-C$_7$ monocyclic cycloalkyl, and 3- to 14-membered heterocyclyl, wherein each alkyl, cycloalkyl or heterocyclyl is substituted with 0-1 occurrences of R$^g$;

L$^1$ is a bond, an alkylene substituted with 0-3 occurrences of R$^h$, —O—, —S—, —S—CH$_2$—, —S(=O)CH$_2$—, —S(=O)$_2$CH$_2$—, —NR$^3$—, —NR$^3$C(=O)—, —C(=O)NR$^3$—, —C(=O)—, —OC(=O)—, —C(=O)O—, —NR$^3$C(=O)O—, —OC(=O)NR$^3$—, —NR$^3$C(=O)NR$^3$—, —OC(R$^4$)$_2$—, —C(R⁴)₂O—, —NR³C(R⁴)₂—, —C(R⁴)₂NR³—, —S(=O)₂—, —S(=O)—, —S(=O)₂O—, —OS(=O)₂—, —S(=O)O—, —OS(=O)—, —S(=O)₂NR³—, —NR³S(=O)₂—, —S(=O)NR³—, —NR³S(=O)—, —NR³S(=O)₂O—, —OS(=O)₂NR³—, —NR³S(=O)O—, —OS(=O)NR³—, or —S(=O)(=NR³)—, wherein the point of the attachment to R² is on the left-hand side;

L² is a bond, an alkylene substituted with 0-3 occurrences of Rʰ, —C(=O)—, —S(=O)₂—, or —S(=O)—, wherein the point of the attachment to Q is on the right-hand side;

each Rᶜ is independently selected from halo, —C₁-C₆ alkyl, —C₁-C₆ haloalkyl, —C₁-C₆ hydroxyalkyl, —OH, —OC₁-C₆ alkyl, —C₁-C₆ aminoalkyl, —NH(C₁-C₆ alkyl), —N(C₁-C₆ alkyl)₂, —C(=O)OC₁-C₆ alkyl, —C(=O)OH, —C(=O)C₁-C₆ alkyl, —C(=O)NH₂, —C(=O)NH(C₁-C₆ alkyl), —C(=O)N(C₁-C₆ alkyl)₂, —NHC(=O)NH₂, —NHC(=O)NH(C₁-C₆ alkyl), —NH(C=O)N(C₁-C₆ alkyl)₂, —NHC(=O)(C₁-C₆ alkyl), —N(C₁-C₆ alkyl)C(=O)(C₁-C₆ alkyl), —S(=O)₂NH₂, —S(=O)₂NH(C₁-C₆ alkyl), —S(=O)₂N(C₁-C₆ alkyl)₂, —NHS(=O)₂(C₁-C₆ alkyl), —NH₂, —CN, and —NO₂; or two instances of Rᶜ attached to the same or adjacent carbon atoms, are taken together with the carbon atoms to which they are attached form a cycloalkyl or a heterocyclylC(=O)OH;

each Rᵈ is independently selected from halo, —C₁-C₆ alkyl, —OH, —OC₁-C₆ alkyl, —NH₂ and —CN;

each Rᵉ is independently selected from halo, —C₁-C₆ alkyl, —C₁-C₆ haloalkyl, —C₁-C₆ hydroxyalkyl, —OH, —OC₁-C₆ alkyl, —C₁-C₆ aminoalkyl, —NH(C₁-C₆ alkyl), —N(C₁-C₆ alkyl)₂, —C(=O)OC₁-C₆ alkyl, —C(=O)OH, —C(=O)C₁-C₆ alkyl, —C(=O)NH₂, —C(=O)NH(C₁-C₆ alkyl), —C(=O)N(C₁-C₆ alkyl)₂, —NHC(=O)NH₂, —NHC(=O)NH(C₁-C₆ alkyl), —NH(C=O)N(C₁-C₆ alkyl)₂, —NHC(=O)(C₁-C₆ alkyl), —N(C₁-C₆ alkyl)C(=O)(C₁-C₆ alkyl), —S(=O)₂NH₂, —S(=O)₂NH(C₁-C₆ alkyl), —S(=O)₂N(C₁-C₆ alkyl)₂, —NHS(=O)₂(C₁-C₆ alkyl), —NH₂, —CN, and —NO₂; or two instances of Rᵉ attached to the same or adjacent carbon atoms, are taken together with the carbon atoms to which they are attached form a cycloalkyl or a heterocyclyl;

each Rᶠ is independently selected from halo, —C₁-C₆ alkyl, —C₁-C₆ haloalkyl, —C₁-C₆ alkoxy, —OH, —NH₂, —CN and —NO₂;

each Rᵍ is independently selected from halo, —C₁-C₆ alkyl, —C₁-C₆ haloalkyl, —C₁-C₆ alkoxy, —OH, NH₂, —CN and NO₂ and;

each Rʰ is independently selected from halo, —C₁-C₆ alkyl, —C₁-C₆ haloalkyl, —C₁-C₆ hydroxyalkyl, —OH, —OC₁-C₆ alkyl, —C₁-C₆ aminoalkyl, —NH(C₁-C₆ alkyl), —N(C₁-C₆ alkyl)₂, —C(=O)OC₁-C₆ alkyl, —C(=O)OH, —C(=O)C₁-C₆ alkyl, —C(=O)NH₂, —C(=O)NH(C₁-C₆ alkyl), —C(=O)N(C₁-C₆ alkyl)₂, —NHC(=O)NH₂, —NHC(=O)NH(C₁-C₆ alkyl), —NH(C=O)N(C₁-C₆ alkyl)₂, —NHC(=O)(C₁-C₆ alkyl), —N(C₁-C₆ alkyl)C(=O)(C₁-C₆ alkyl), —S(=O)₂NH₂, —S(=O)₂NH(C₁-C₆ alkyl), —S(=O)₂N(C₁-C₆ alkyl)₂, —NHS(=O)₂(C₁-C₆ alkyl), —NH₂, —CN, and —NO₂, S(=O)₂aryl, S(=O)₂heteroaryl and =NOH or two instances of Rʰ attached to the same or adjacent carbon atoms, are taken together with the carbon atoms to which they are attached form a cycloalkyl or a heterocyclyl.

4. The method of claim 1, wherein the compound is of Formula (II):

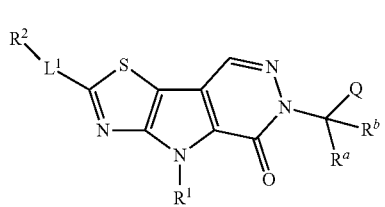

(II)

or a pharmaceutically acceptable salt thereof, wherein:

Rᵃ and Rᵇ are each independently hydrogen, halogen, —CN, —NO₂, —N₃, optionally substituted alkyl, —ORᵒ³, —N(Rⁿ¹)₂, —C(=O)N(Rⁿ¹)₂, or —C(=O)Rᶜ², or Rᵃ and Rᵇ can be taken together with the carbon atom to form optionally substituted cycloalkyl or optionally substituted heterocyclyl;

each instance of Rⁿ¹ is independently hydrogen, optionally substituted —C₁-C₆ alkyl, or a nitrogen protecting group;

each instance of Rᵒ³ is independently hydrogen, optionally substituted —C₁-C₆ alkyl, or an oxygen protecting group; and each instance of Rᶜ² is independently optionally substituted —C₁-C₆ alkyl.

5. The method of claim 1, wherein L¹ is C₁₋₆ alkylene substituted with Rʲ and Rᵏ;

wherein each instance of Rʲ and Rᵏ is independently selected from H, halogen, —CN, —ORᵒ⁷, —N(Rⁿ⁵)₂, —N(Rⁿ⁵)C(=O) Rᶜ⁵, —C(=O)N(Rⁿ⁵)₂, —C(=O)Rᶜ⁵, —C(=O)ORᵒ⁷, —SRʲˢ, —S(=O)₂Rʲˢ, or —S(=O)Rʲˢ, optionally substituted —C₁-C₆ alkyl; or Rʲ and Rᵏ can be taken together with the carbon atom to form C=O, C=NRʲⁿ, an optionally substituted C₃-C₆ monocyclic cycloalkyl ring or an optionally substituted C₃-C₆ monocyclic heterocyclyl ring;

each of Rⁿ⁵ and Rⱼₙ is independently hydrogen, optionally substituted —C₁-C₆ alkyl, —ORᵒ⁸, or a nitrogen protecting group;

each instance of Rᵒ⁷ is independently hydrogen, optionally substituted —C₁-C₆ alkyl, or an oxygen protecting group;

each instance of Rᶜ⁵ is independently optionally substituted —C₁-C₆ alkyl; and each instance of Rʲˢ is independently optionally substituted —C₁-C₆ alkyl, optionally substituted C₆₋₁₂ aryl, optionally substituted heteroaryl, or a sulfur protecting group.

6. The method of claim 1, wherein Q is of one of the following formulae:

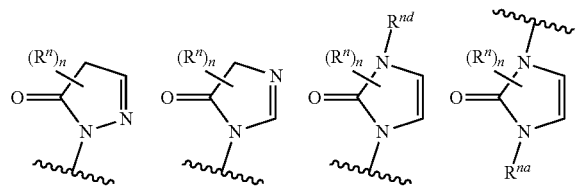

-continued

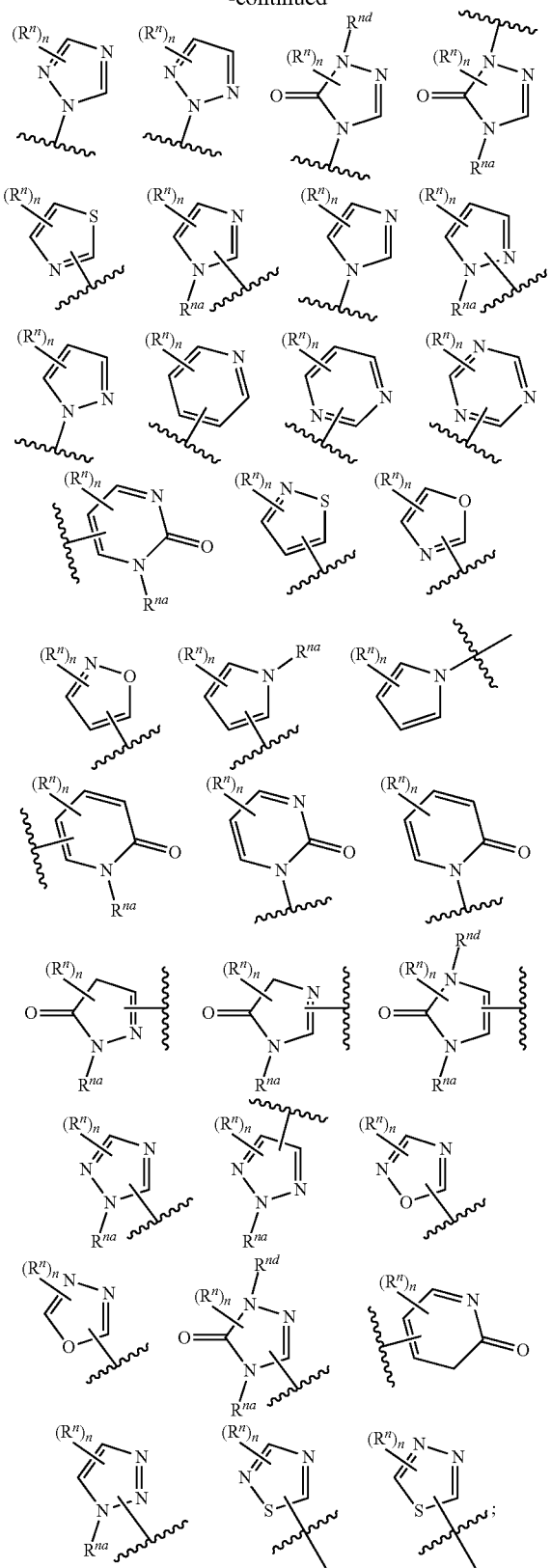

wherein:
each instance of R" is independently hydrogen, a halogen, —CN, —NO$_2$, —N$_3$, an optionally substituted alkyl, an optionally substituted alkenyl, an optionally substituted alkynyl, an optionally substituted cycloalkyl, an optionally substituted aryl, an optionally substituted heterocyclyl, an optionally substituted heteroaryl, —OR$^{o4}$, —SR$^{s1}$, —N(R$^{n2}$)$_2$, —C(=O)N(R$^{n2}$)$_2$, —N(R$^{n2}$)C(=O)R$^{c3}$, —C(=O)R$^{c3}$, —C(=O)OR$^{o4}$, —OC(=O)R$^{c3}$, —S(=O)R$^{s1}$, —S(=O)$_2$R$^{s1}$, —S(=O)OR$^{o4}$, —OS(=O)R$^{c3}$, —S(=O)$_2$OR$^{o4}$, —OS(=O)$_2$R$^{c3}$, —S(=O)N(R$^{n2}$)$_2$, —S(=O)$_2$N(R$^{n2}$)$_2$, —N(R$^{n2}$)S(=O)R$^{s1}$, —N(R$^{n2}$)S(=O)$_2$R$^{s1}$, —N(R$^{n2}$)C(=O)OR$^{o4}$, —OC(=O)N(R$^{n2}$)$_2$, —N(R$^{n2}$)C(=O)N(R$^{n2}$)$_2$, —N(R$^{n2}$)S(=O)N(R$^{n2}$)$_2$, —N(R$^{n2}$)S(=O)$_2$N(R$^{n2}$)$_2$, —N(R$^{n2}$)S(=O)OR$^{o4}$, —N(R$^{n2}$)S(=O)$_2$OR$^{o4}$, —OS(=O)N(R$^{n2}$)$_2$, or —OS(=O)$_2$N(R$^{n2}$)$_2$; or two instances of R" attached to the same or adjacent carbon atoms, taken together with the carbon atoms to which they are attached to form an optionally substituted cycloalkyl or a heterocycloalkyl; wherein:

each instance of R$^{n2}$ is independently hydrogen, an optionally substituted —C$_1$-C$_6$ alkyl, or a nitrogen protecting group;

each instance of R$^{o4}$ is independently hydrogen, an optionally substituted —C$_1$-C$_6$ alkyl, or an oxygen protecting group;

each instance of R$^{c3}$ is independently an optionally substituted —C$_1$-C$_6$ alkyl;

each instance of R$^{s1}$ is independently an optionally substituted —C$_1$-C$_6$ alkyl or a sulfur protecting group;

n is 0, 1, 2, or 3, as valency permits; and each of R$^{na}$, R$^{nb}$, and R$^{nd}$ is independently hydrogen, an optionally substituted —C$_1$-C$_6$ alkyl, or a nitrogen protecting group.

7. The method of claim 1, wherein Q is of one of the following formulae:

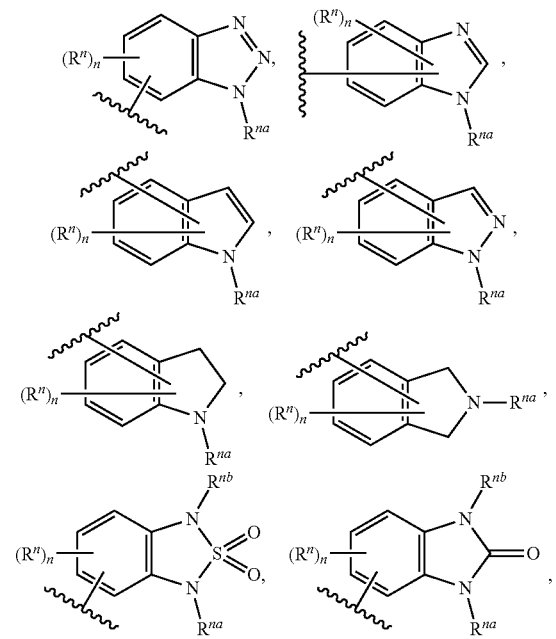

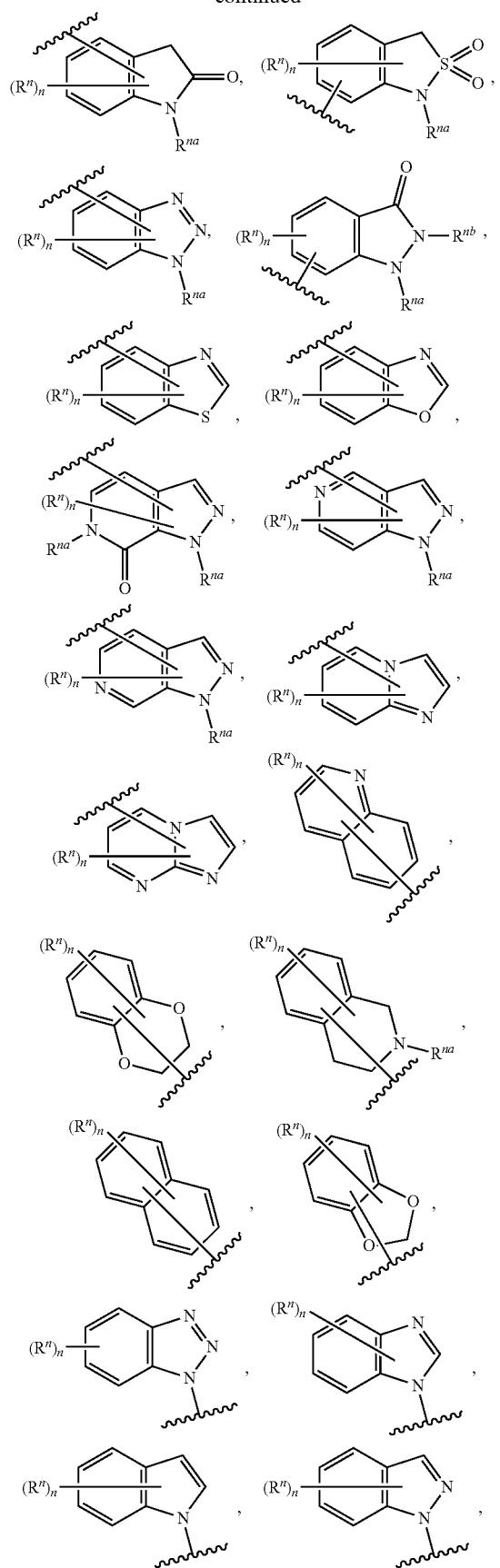
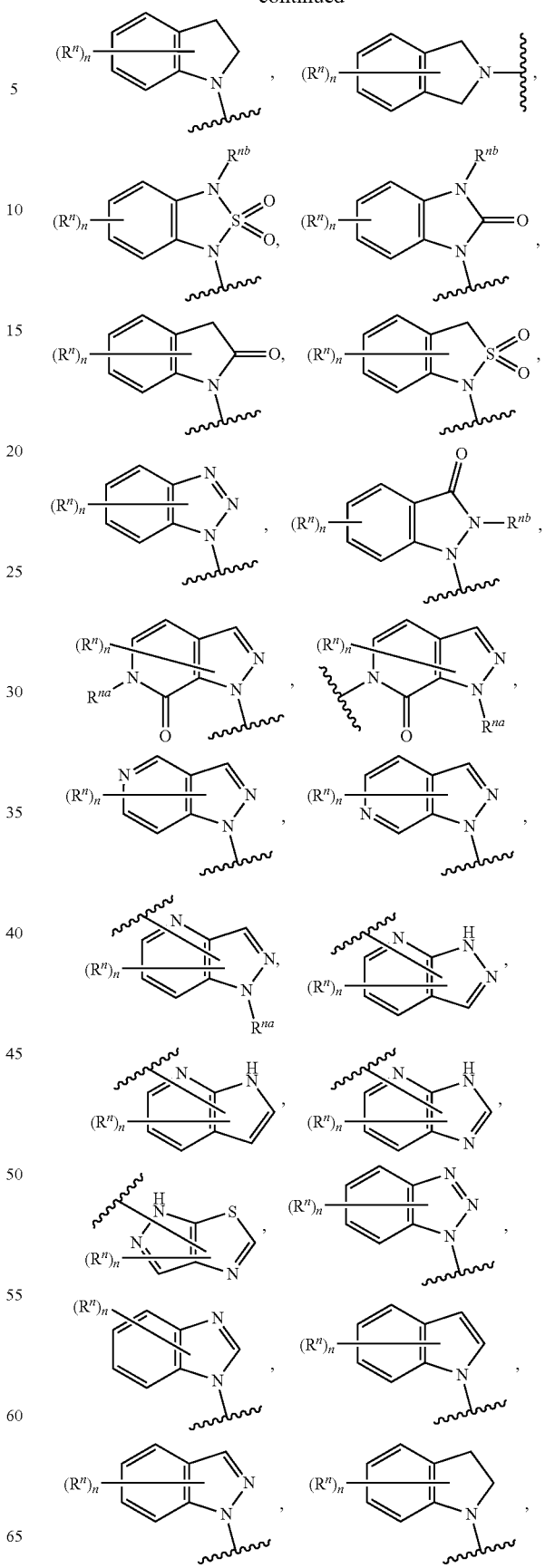

-continued

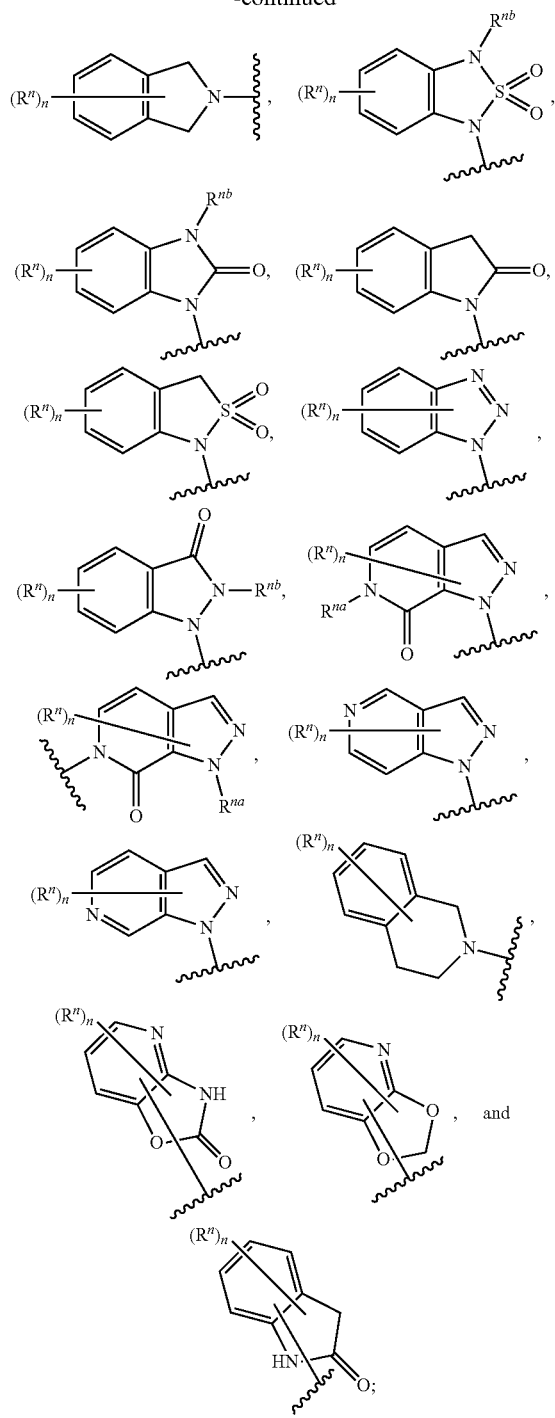

wherein each instance of R'' is independently selected from hydrogen, halogen, —CN, —NO$_2$, —N$_3$, optionally substituted alkyl, optionally substituted alkenyl, optionally substituted alkynyl, optionally substituted cycloalkyl, optionally substituted aryl, optionally substituted heterocyclyl, optionally substituted heteroaryl, —OR$^{o4}$, —SR$^{s1}$, —N(R$^{n2}$)$_2$, —C(=O)N(R$^{n2}$)$_2$, —N(R$^{n2}$)C(=O)R$^{c3}$, —C(=O)R$^{c3}$, —C(=O)OR$^{o4}$, —OC(=O)R$^{c3}$, —S(=O) R$^{s1}$, —S(=O)$_2$R$^{s1}$, —S(=O)OR$^{o4}$, —OS(=O)R$^{c3}$, —S(=O)$_2$OR$^{o4}$, —OS(=O)$_2$R$^{c3}$, —S(=O)N(R$^{n2}$)$_2$, —S(=O)$_2$N(R$^{n2}$)$_2$, —N(R$^{n2}$)S(=O)R$^{s1}$, —N(R$^{n2}$) S(=O)$_2$R$^{s1}$, —N(R$^{n2}$)C(=O)OR$^{o4}$, —OC(=O)N(R$^{n2}$)$_2$, —N(R$^{n2}$)C(=O)N(R$^{n2}$)$_2$, —N(R$^{n2}$)S(=O)N(R$^{n2}$)$_2$, —N(R$^{n2}$)S(=O)$_2$N(R$^{n2}$)$_2$, —N(R$^{n2}$)S(=O)OR$^{o4}$, —N(R$^{n2}$)S(=O)$_2$OR$^{o4}$, —OS(=O)N(R$^{n2}$)$_2$, —OS(=O)$_2$N (R$^{n2}$)$_2$, or two instances of R'' attached to the same or adjacent carbon atoms, taken together with the atoms to which they are attached form an optionally substituted cycloalkyl or a heterocycloalkyl;

each instance of R$^{na}$ and R$^{nb}$ is independently hydrogen, optionally substituted —C$_1$-C$_6$ alkyl, or a nitrogen protecting group;

each instance of R$^{n2}$ is independently hydrogen, optionally substituted —C$_1$-C$_6$ alkyl, or a nitrogen protecting group;

each instance of R$^{o4}$ is independently hydrogen, optionally substituted —C$_1$-C$_6$ alkyl, or an oxygen protecting group;

each instance of R$^{c3}$ is independently optionally substituted —C$_1$-C$_6$ alkyl;

each instance of R$^{s1}$ is independently optionally substituted —C$_1$-C$_6$ alkyl, or a sulfur protecting group; and n is 0, 1, 2, or 3, as valency permits.

8. The method according to claim 1, wherein R$^2$ is selected from hydrogen, hydroxyl, halogen, —C$_1$-C$_6$ alkyl, —C$_2$-C$_6$ alkenyl, —C$_2$-C$_6$ alkoxyl, phenyl, naphthalenyl, C$_{3-6}$ cycloalkyl, 5-membered heteroaryl, 6-membered heteroaryl, 8-membered bicyclic heteroaryl, and 9-membered bicyclic heteroaryl, wherein each alkyl, alkenyl, phenyl, and heteroaryl is substituted with 0-3 occurrences of R$^e$.

9. The method according to claim 1, wherein R$^2$ is of one of the following formulae:

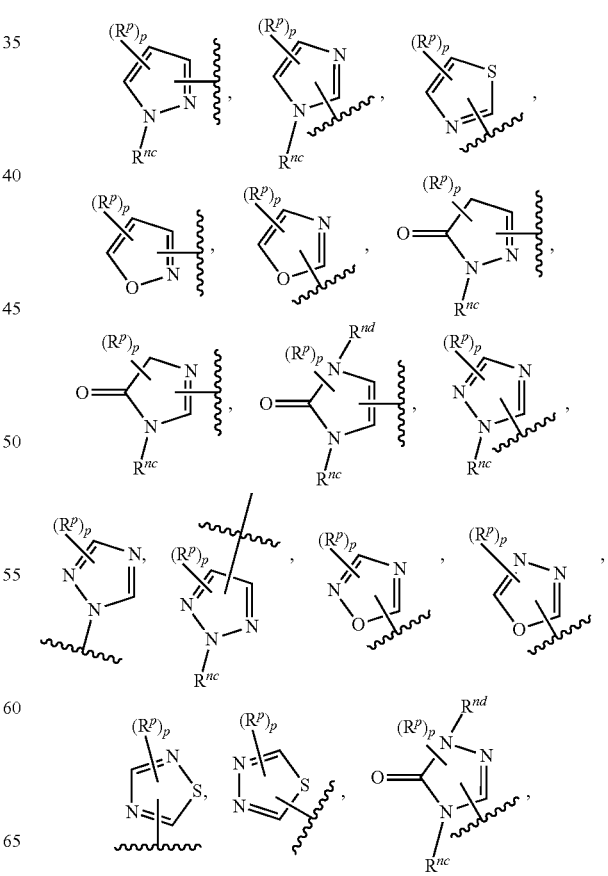

-continued
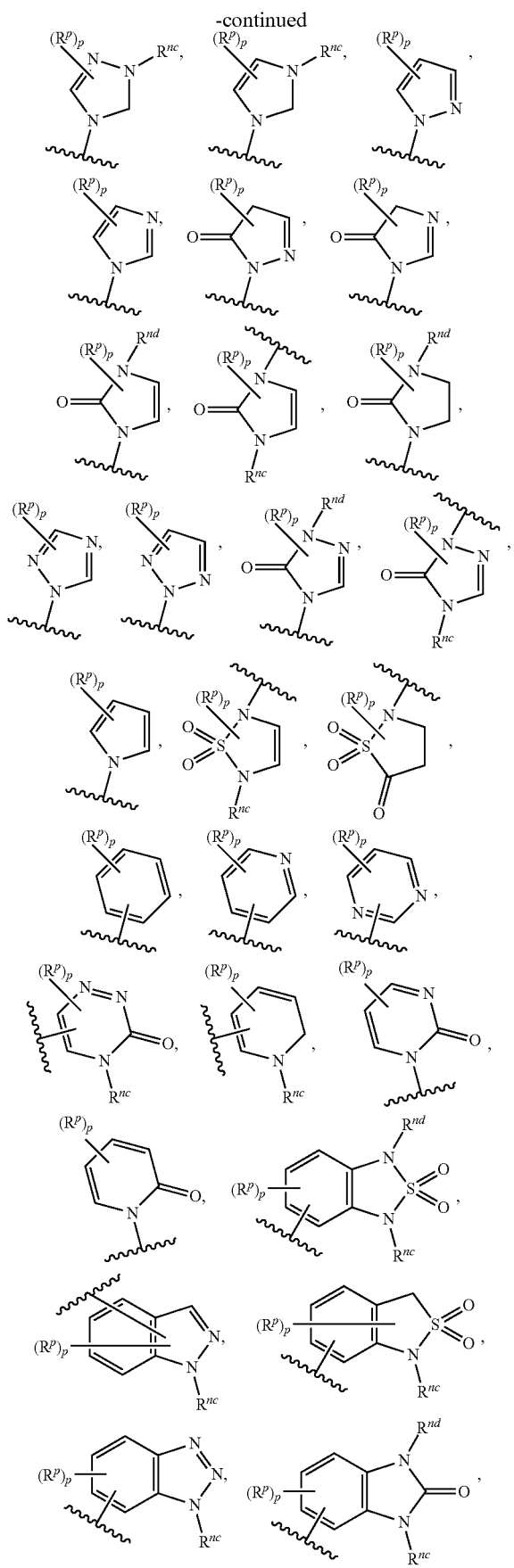
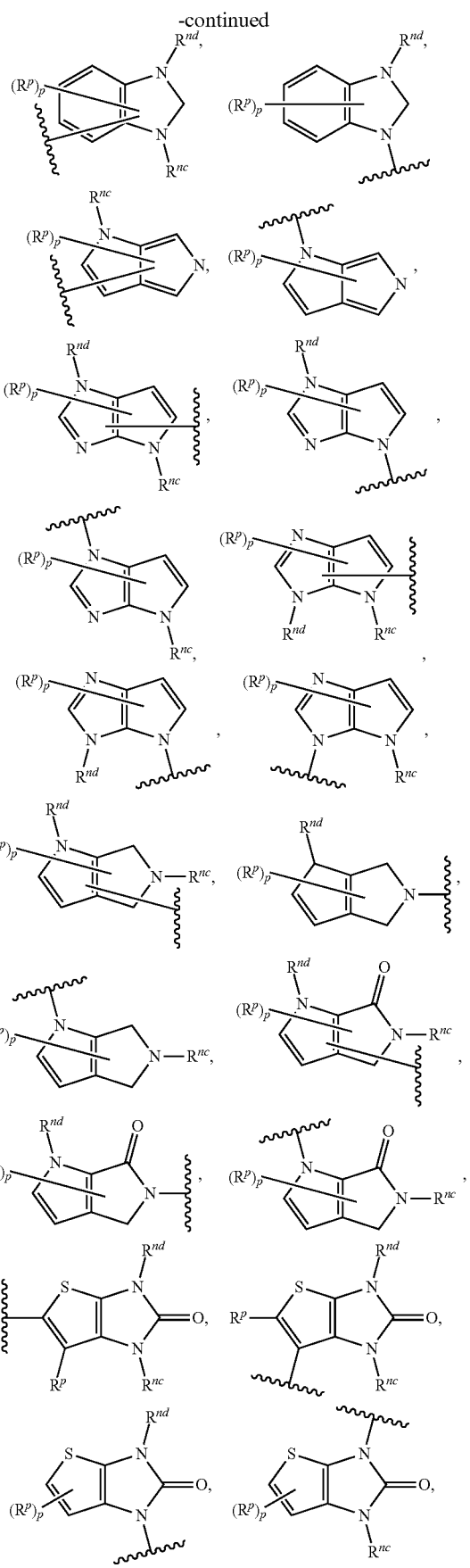

-continued

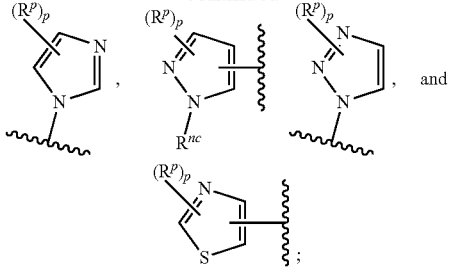
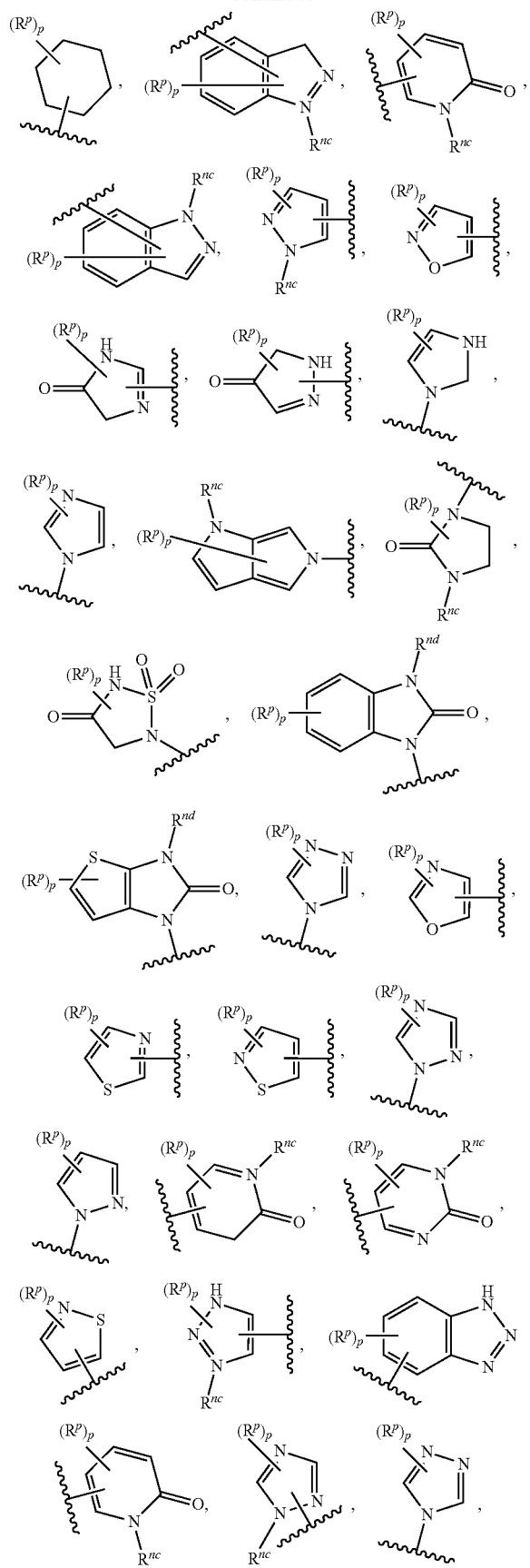

wherein each instance of $R^p$ is independently selected from hydrogen, halogen, —CN, —NO$_2$, —N$_3$, optionally substituted alkyl, optionally substituted alkenyl, optionally substituted alkynyl, optionally substituted cycloalkyl, optionally substituted aryl, optionally substituted heterocyclyl, optionally substituted heteroaryl, —OR$^{o6}$, —SR$^{s2}$, —N(R$^{n3}$)$_2$, —C(=O)N(R$^{n3}$)$_2$, —N(R$^{n3}$)C(=O)R$^{c4}$, —C(=O)R$^{c4}$, —C(=O)OR$^{o6}$, —OC(=O)R$^{c4}$, —S(=O)R$^{s2}$, —S(=O)$_2$R$^{s2}$, —S(=O)OR$^{o6}$, —OS(=O)R$^{c4}$, —S(=O)$_2$OR$^{o6}$, —OS(=O)$_2$R$^{c4}$, —S(=O)N(R$^{n3}$)$_2$, —S(=O)$_2$N(R$^{n3}$)$_2$, —N(R$^{n3}$)S(=O)R$^{s2}$, —N(R$^{n3}$)S(=O)$_2$R$^{s2}$, —N(R$^{n3}$)C(=O)OR$^{o6}$, —OC(=O)N(R$^{n3}$)$_2$, —N(R$^{n3}$)C(=O)N(R$^{n3}$)$_2$, —N(R$^{n3}$)S(=O)N(R$^{n3}$)$_2$, —N(R$^{n3}$)S(=O)$_2$N(R$^{n3}$)$_2$, —N(R$^{n3}$)S(=O)OR$^{o6}$, —N(R$^{n3}$)S(=O)$_2$OR$^{o6}$, —OS(=O)N(R$^{n3}$)$_2$, —OS(=O)$_2$N(R$^{n3}$)$_2$, or two instances of $R^p$ attached to the same or adjacent carbon atoms, taken together with the atoms to which they are attached form an optionally substituted cycloalkyl or a heterocycloalkyl;

each instance of $R^{n3}$, $R^{nc}$, and $R^{nd}$ is independently hydrogen, optionally substituted —C$_1$-C$_6$ alkyl, or a nitrogen protecting group;

each instance of $R^{o6}$ is independently hydrogen, optionally substituted —C$_1$-C$_6$ alkyl, or an oxygen protecting group;

each instance of $R^{c4}$ is independently optionally substituted —C$_1$-C$_6$ alkyl;

each instance of $R^{s2}$ is independently optionally substituted —C$_1$-C$_6$ alkyl, or a sulfur protecting group; and p is 0, 1, 2, or 3, as valency permits.

10. The method according to claim 9, wherein each instance of $R^p$ is independently hydrogen, halogen, optionally substituted C$_{1-4}$ alkyl, —CN, —NO$_2$, —N$_3$, —OR$^{o4}$, —N(R$^{n2}$)$_2$, —C(=O)N(R$^{n2}$)$_2$, —C(=O)R$^{c3}$, or —C(=O)OR$^{o4}$.

11. The method of claim 1, wherein the compound is of Formula (III):

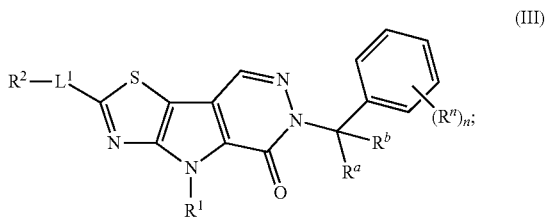

(III)

or a pharmaceutically acceptable salt thereof, wherein:
$R^a$ and $R^b$ are each independently hydrogen, halogen, —CN, —NO$_2$, —N$_3$, optionally substituted alkyl, —OR$^{o3}$, —N(R$^{n1}$)$_2$, —C(=O)N(R$^{n1}$)$_2$, or —C(=O)R$^{c2}$, or R$^a$ and R$^b$ can be taken together with the carbon atom to form optionally substituted cycloalkyl or optionally substituted heterocyclyl;

each instance of R$^{n1}$ is independently hydrogen, optionally substituted —C$_1$-C$_6$ alkyl, or a nitrogen protecting group;

each instance of R$^{o3}$ is independently hydrogen, optionally substituted —C$_1$-C$_6$ alkyl, or an oxygen protecting group;

each instance of R$^{c2}$ is independently optionally substituted —C$_1$-C$_6$ alkyl;

each instance of R" is independently hydrogen, a halogen, —CN, —NO$_2$, —N$_3$, an optionally substituted alkyl, an optionally substituted alkenyl, an optionally substituted alkynyl, an optionally substituted cycloalkyl, an optionally substituted aryl, an optionally substituted heterocyclyl, an optionally substituted heteroaryl, —OR$^{o4}$, —SR$^{s1}$, —N(R$^{n2}$)$_2$, —C(=O)N(R$^{n2}$)$_2$, —N(R$^{n2}$)C(=O)R$^{c3}$, —C(=O)R$^{c3}$, —C(=O)OR$^{o4}$, —OC(=O)R$^{c3}$, —S(=O)R$^{s1}$, —S(=O)$_2$R$^{s1}$, —S(=O)OR$^{o4}$, —OS(=O)R$^{c3}$, —S(=O)$_2$OR$^{o4}$, —OS(=O)$_2$R$^{c3}$, —S(=O)N(R$^{n2}$)$_2$, —S(=O)$_2$N(R$^{n2}$)$_2$, —N(R$^{n2}$)S(=O)R$^{s1}$, —N(R$^{n2}$)S(=O)$_2$R$^{s1}$, —N(R$^{n2}$)C(=O)OR$^{o4}$, —OC(=O)N(R$^{n2}$)$_2$, —N(R$^{n2}$)C(=O)N(R$^{n2}$)$_2$, —N(R$^{n2}$)S(=O)N(R$^{n2}$)$_2$, —N(R$^{n2}$)S(=O)$_2$N(R$^{n2}$)$_2$, —N(R$^{n2}$)S(=O)OR$^{o4}$, —N(R$^{n2}$)S(=O)$_2$OR$^{o4}$, —OS(=O)N(R$^{n2}$)$_2$, or —OS(=O)$_2$N(R$^{n2}$)$_2$; or two instances of R" attached to the same or adjacent carbon atoms, taken together with the carbon atoms to which they are attached to form an optionally substituted cycloalkyl or a heterocycloalkyl; wherein:

each instance of R$^{n2}$ is independently hydrogen, an optionally substituted —C$_1$-C$_6$ alkyl, or a nitrogen protecting group;

each instance of R$^{o4}$ is independently hydrogen, an optionally substituted —C$_1$-C$_6$ alkyl, or an oxygen protecting group;

each instance of R$^{c3}$ is independently an optionally substituted —C$_1$-C$_6$ alkyl;

each instance of R$^{s1}$ is independently an optionally substituted —C$_1$-C$_6$ alkyl or a sulfur protecting group; and n is 0, 1, 2, or 3, as valency permits.

12. The method of claim 1, wherein the compound is of Formula (IV):

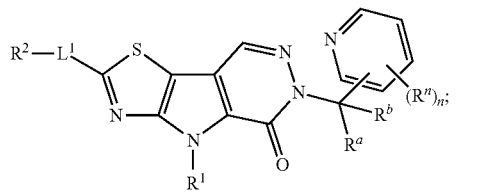

(IV)

or a pharmaceutically acceptable salt thereof, wherein:
R$^a$ and R$^b$ are each independently hydrogen, halogen, —CN, —NO$_2$, —N$_3$, optionally substituted alkyl, —OR$^{o3}$, —N(R$^{n1}$)$_2$, —C(=O)N(R$^{n1}$)$_2$, or —C(=O)R$^{c2}$, or R$^a$ and R$^b$ can be taken together with the carbon atom to form optionally substituted cycloalkyl or optionally substituted heterocyclyl;

each instance of R$^{n1}$ is independently hydrogen, optionally substituted —C$_1$-C$_6$ alkyl, or a nitrogen protecting group;

each instance of R$^{o3}$ is independently hydrogen, optionally substituted —C$_1$-C$_6$ alkyl, or an oxygen protecting group;

each instance of R$^{c2}$ is independently optionally substituted —C$_1$-C$_6$ alkyl;

each instance of R" is independently hydrogen, a halogen, —CN, —NO$_2$, —N$_3$, an optionally substituted alkyl, an optionally substituted alkenyl, an optionally substituted alkynyl, an optionally substituted cycloalkyl, an optionally substituted aryl, an optionally substituted heterocyclyl, an optionally substituted heteroaryl, —OR$^{o4}$, —SR$^{s1}$, —N(R$^{n2}$)$_2$, —C(=O)N(R$^{n2}$)$_2$, —N(R$^{n2}$)C(=O)R$^{c3}$, —C(=O)R$^{c3}$, —C(=O)OR$^{o4}$, —OC(=O)R$^{c3}$, —S(=O)R$^{s1}$, —S(=O)$_2$R$^{s1}$, —S(=O)OR$^{o4}$, —OS(=O)R$^{c3}$, —S(=O)$_2$OR$^{o4}$, —OS(=O)$_2$R$^{c3}$, —S(=O)N(R$^{n2}$)$_2$, —S(=O)$_2$N(R$^{n2}$)$_2$, —N(R$^{n2}$)S(=O)R$^{s1}$, —N(R$^{n2}$)S(=O)$_2$R$^{s1}$, —N(R$^{n2}$)C(=O)OR$^{o4}$, —OC(=O)N(R$^{n2}$)$_2$, —N(R$^{n2}$)C(=O)N(R$^{n2}$)$_2$, —N(R$^{n2}$)S(=O)N(R$^{n2}$)$_2$, —N(R$^{n2}$)S(=O)$_2$N(R$^{n2}$)$_2$, —N(R$^{n2}$)S(=O)OR$^{o4}$, —N(R$^{n2}$)S(=O)$_2$OR$^{o4}$, —OS(=O)N(R$^{n2}$)$_2$, or —OS(=O)$_2$N(R$^{n2}$)$_2$; or two instances of R" attached to the same or adjacent carbon atoms, taken together with the carbon atoms to which they are attached to form an optionally substituted cycloalkyl or a heterocycloalkyl; wherein:

each instance of R$^{n2}$ is independently hydrogen, an optionally substituted —C$_1$-C$_6$ alkyl, or a nitrogen protecting group;

each instance of R$^{o4}$ is independently hydrogen, an optionally substituted —C$_1$-C$_6$ alkyl, or an oxygen protecting group;

each instance of R$^{c3}$ is independently an optionally substituted —C$_1$-C$_6$ alkyl;

each instance of R$^{s1}$ is independently an optionally substituted —C$_1$-C$_6$ alkyl or a sulfur protecting group; and n is 0, 1, 2, or 3, as valency permits.

13. The method of claim 1, wherein the compound is of Formula (V-a):

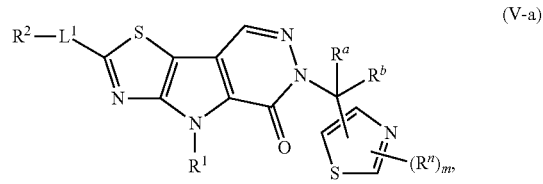

(V-a)

or a pharmaceutically acceptable salt thereof, wherein:
R$^a$ and R$^b$ are each independently hydrogen, halogen, —CN, —NO$_2$, —N$_3$, optionally substituted alkyl, —OR$^{o3}$, —N(R$^{n1}$)$_2$, —C(=O)N(R$^{n1}$)$_2$, or —C(=O)R$^{c2}$, or R$^a$ and R$^b$ can be taken together with the carbon atom to form optionally substituted cycloalkyl or optionally substituted heterocyclyl;

each instance of R$^{n1}$ is independently hydrogen, optionally substituted —C$_1$-C$_6$ alkyl, or a nitrogen protecting group;

each instance of R$^{o3}$ is independently hydrogen, optionally substituted —C$_1$-C$_6$ alkyl, or an oxygen protecting group;

each instance of $R^{c2}$ is independently optionally substituted —$C_1$-$C_6$ alkyl;

each instance of $R''$ is independently hydrogen, a halogen, —CN, —$NO_2$, —$N_3$, an optionally substituted alkyl, an optionally substituted alkenyl, an optionally substituted alkynyl, an optionally substituted cycloalkyl, an optionally substituted aryl, an optionally substituted heterocyclyl, an optionally substituted heteroaryl, —$OR^{o4}$, —$SR^{s1}$, —$N(R^{n2})_2$, —C(=O)$N(R^{n2})_2$, —$N(R^{n2})$C(=O)$R^{c3}$, —C(=O)$R^{c3}$, —C(=O)$OR^{o4}$, —OC(=O)$R^{c3}$, —S(=O)$R^{s1}$, —S(=O)$_2R^{s1}$, —S(=O)$OR^{o4}$, —OS(=O)$R^{c3}$, —S(=O)$_2OR^{o4}$, —OS(=O)$_2R^{c3}$, —S(=O)$N(R^{n2})_2$, —S(=O)$_2N(R^{n2})_2$, —$N(R^{n2})$S(=O)$R^{s1}$, —$N(R^{n2})$S(=O)$_2R^{s1}$, —$N(R^{n2})$C(=O)$OR^{o4}$, —OC(=O)$N(R^{n2})_2$, —$N(R^{n2})$C(=O)$N(R^{n2})_2$, —$N(R^{n2})$S(=O)$N(R^{n2})_2$, —$N(R^{n2})$S(=O)$_2N(R^{n2})_2$, —$N(R^{n2})$S(=O)$OR^{o4}$, —$N(R^{n2})$S(=O)$_2OR^{o4}$, —OS(=O)$N(R^{n2})_2$, or —OS(=O)$_2N(R^{n2})_2$; or two instances of $R''$ attached to the same or adjacent carbon atoms, taken together with the carbon atoms to which they are attached to form an optionally substituted cycloalkyl or a heterocycloalkyl; wherein:

each instance of $R^{n2}$ is independently hydrogen, an optionally substituted —$C_1$-$C_6$ alkyl, or a nitrogen protecting group;

each instance of $R^{o4}$ is independently hydrogen, an optionally substituted —$C_1$-$C_6$ alkyl, or an oxygen protecting group;

each instance of $R^{c3}$ is independently an optionally substituted —$C_1$-$C_6$ alkyl;

each instance of $R^{s1}$ is independently an optionally substituted —$C_1$-$C_6$ alkyl or a sulfur protecting group;

n is 0, 1, 2, or 3, as valency permits; and m is 0, 1, or 2.

14. The method of claim 1, wherein the compound is of Formula (V-b):

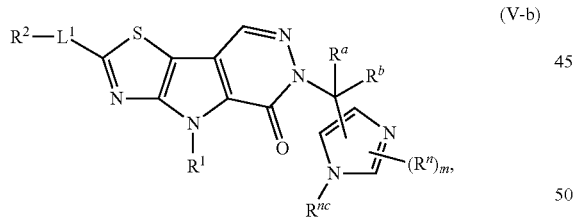

(V-b)

or a pharmaceutically acceptable salt thereof, wherein:

$R^a$ and $R^b$ are each independently hydrogen, halogen, —CN, —$NO_2$, —$N_3$, optionally substituted alkyl, —$OR^{o3}$, —$N(R^{n1})_2$, —C(=O)$N(R^{n1})_2$, or —C(=O)$R^{c2}$, or $R^a$ and $R^b$ can be taken together with the carbon atom to form optionally substituted cycloalkyl or optionally substituted heterocyclyl;

each instance of $R^{n1}$ is independently hydrogen, optionally substituted —$C_1$-$C_6$ alkyl, or a nitrogen protecting group;

each instance of $R^{o3}$ is independently hydrogen, optionally substituted —$C_1$-$C_6$ alkyl, or an oxygen protecting group;

each instance of $R^{c2}$ is independently optionally substituted —$C_1$-$C_6$ alkyl;

each instance of $R''$ is independently hydrogen, a halogen, —CN, —$NO_2$, —$N_3$, an optionally substituted alkyl, an optionally substituted alkenyl, an optionally substituted alkynyl, an optionally substituted cycloalkyl, an optionally substituted aryl, an optionally substituted heterocyclyl, an optionally substituted heteroaryl, —$OR^{o4}$, —$SR^{s1}$, —$N(R^{n2})_2$, —C(=O)$N(R^{n2})_2$, —$N(R^{n2})$C(=O)$R^{c3}$, —C(=O)$R^{c3}$, —C(=O)$OR^{o4}$, —OC(=O)$R^{c3}$, —S(=O)$R^{s1}$, —S(=O)$_2R^{s1}$, —S(=O)$OR^{o4}$, —OS(=O)$R^{c3}$, —S(=O)$_2OR^{o4}$, —OS(=O)$_2R^{c3}$, —S(=O)$N(R^{n2})_2$, —S(=O)$_2N(R^{n2})_2$, —$N(R^{n2})$S(=O)$R^{s1}$, —$N(R^{n2})$S(=O)$_2R^{s1}$, —$N(R^{n2})$C(=O)$OR^{o4}$, —OC(=O)$N(R^{n2})_2$, —$N(R^{n2})$C(=O)$N(R^{n2})_2$, —$N(R^{n2})$S(=O)$N(R^{n2})_2$, —$N(R^{n2})$S(=O)$_2N(R^{n2})_2$, —$N(R^{n2})$S(=O)$OR^{o4}$, —$N(R^{n2})$S(=O)$_2OR^{o4}$, —OS(=O)$N(R^{n2})_2$, or —OS(=O)$_2N(R^{n2})_2$; or two instances of $R''$ attached to the same or adjacent carbon atoms, taken together with the carbon atoms to which they are attached to form an optionally substituted cycloalkyl or a heterocycloalkyl; wherein:

each instance of $R^{n2}$ is independently hydrogen, an optionally substituted —$C_1$-$C_6$ alkyl, or a nitrogen protecting group;

each instance of $R^{o4}$ is independently hydrogen, an optionally substituted —$C_1$-$C_6$ alkyl, or an oxygen protecting group;

each instance of $R^{c3}$ is independently an optionally substituted —$C_1$-$C_6$ alkyl;

each instance of $R^{s1}$ is independently an optionally substituted —$C_1$-$C_6$ alkyl or a sulfur protecting group;

n is 0, 1, 2, or 3, as valency permits;

m is 0, 1, or 2; and $R^{nc}$ is independently hydrogen, optionally substituted —$C_1$-$C_6$ alkyl, or a nitrogen protecting group.

15. The method of claim 1, wherein the compound is of Formula (VI):

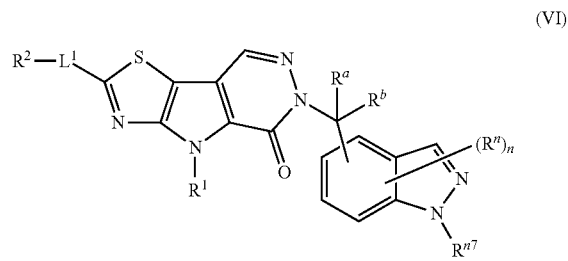

(VI)

or a pharmaceutically acceptable salt thereof, wherein:

$R^a$ and $R^b$ are each independently hydrogen, halogen, —CN, —$NO_2$, —$N_3$, optionally substituted alkyl, —$OR^{o3}$, —$N(R^{n1})_2$, —C(=O)$N(R^{n1})_2$, or —C(=O)$R^{c2}$, or $R^a$ and $R^b$ can be taken together with the carbon atom to form optionally substituted cycloalkyl or optionally substituted heterocyclyl;

each instance of $R^{n1}$ is independently hydrogen, optionally substituted —$C_1$-$C_6$ alkyl, or a nitrogen protecting group;

each instance of $R^{o3}$ is independently hydrogen, optionally substituted —$C_1$-$C_6$ alkyl, or an oxygen protecting group;

each instance of $R^{c2}$ is independently optionally substituted —$C_1$-$C_6$ alkyl;

each instance of R″ is independently hydrogen, a halogen, —CN, —NO₂, —N₃, an optionally substituted alkyl, an optionally substituted alkenyl, an optionally substituted alkynyl, an optionally substituted cycloalkyl, an optionally substituted aryl, an optionally substituted heterocyclyl, an optionally substituted heteroaryl, —OR^{o4}, —SR^{s1}, —N(R^{n2})₂, —C(=O)N(R^{n2})₂, —N(R^{n2})C(=O)R^{c3}, —C(=O)R^{c3}, —C(=O)OR^{o4}, —OC(=O)R^{c3}, —S(=O)R^{s1}, —S(=O)₂R^{s1}, —S(=O)OR^{o4}, —OS(=O)R^{c3}, —S(=O)₂OR^{o4}, —OS(=O)₂R^{c3}, —S(=O)N(R^{n2})₂, —S(=O)₂N(R^{n2})₂, —N(R^{n2})S(=O)R^{s1}, —N(R^{n2})S(=O)₂R^{s1}, —N(R^{n2})C(=O)OR^{o4}, —OC(=O)N(R^{n2})₂, —N(R^{n2})C(=O)N(R^{n2})₂, —N(R^{n2})S(=O)N(R^{n2})₂, —N(R^{n2})S(=O)₂N(R^{n2})₂, —N(R^{n2})S(=O)OR^{o4}, —N(R^{n2})S(=O)₂OR^{o4}, —OS(=O)N(R^{n2})₂, or —OS(=O)₂N(R^{n2})₂; or two instances of R″ attached to the same or adjacent carbon atoms, taken together with the carbon atoms to which they are attached to form an optionally substituted cycloalkyl or a heterocycloalkyl; wherein:

each instance of R^{n2} is independently hydrogen, an optionally substituted —C₁-C₆ alkyl, or a nitrogen protecting group;

each instance of R^{o4} is independently hydrogen, an optionally substituted —C₁-C₆ alkyl, or an oxygen protecting group;

each instance of R^{c3} is independently an optionally substituted —C₁-C₆ alkyl;

each instance of R^{s1} is independently an optionally substituted —C₁-C₆ alkyl or a sulfur protecting group;

n is 0, 1, 2, or 3, as valency permits; and

R^{n7} is hydrogen, optionally substituted —C₁-C₆ alkyl, or a nitrogen protecting group.

16. The method of claim 1, wherein the compound is of Formula (IX):

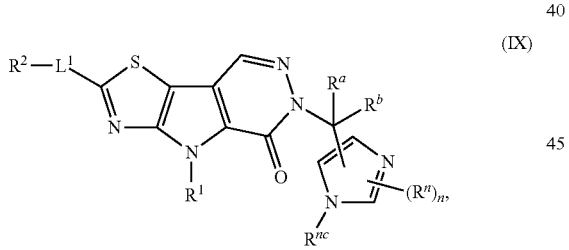

(IX)

or a pharmaceutically acceptable salt thereof, wherein:

R^{a} and R^{b} are each independently hydrogen, halogen, —CN, —NO₂, —N₃, optionally substituted alkyl, —OR^{o3}, —N(R^{n1})₂, —C(=O)N(R^{n1})₂, or —C(=O)R^{c2}, or R^{a} and R^{b} can be taken together with the carbon atom to form optionally substituted cycloalkyl or optionally substituted heterocyclyl;

each instance of R^{n1} is independently hydrogen, optionally substituted —C₁-C₆ alkyl, or a nitrogen protecting group;

each instance of R^{o3} is independently hydrogen, optionally substituted —C₁-C₆ alkyl, or an oxygen protecting group;

each instance of R^{c2} is independently optionally substituted —C₁-C₆ alkyl;

each instance of R″ is independently hydrogen, a halogen, —CN, —NO₂, —N₃, an optionally substituted alkyl, an optionally substituted alkenyl, an optionally substituted alkynyl, an optionally substituted cycloalkyl, an optionally substituted aryl, an optionally substituted heterocyclyl, an optionally substituted heteroaryl, —OR^{o4}, —SR^{s1}, —N(R^{n2})₂, —C(=O)N(R^{n2})₂, —N(R^{n2})C(=O)R^{c3}, —C(=O)R^{c3}, —C(=O)OR^{o4}, —OC(=O)R^{c3}, —S(=O)R^{s1}, —S(=O)₂R^{s1}, —S(=O)OR^{o4}, —OS(=O)R^{c3}, —S(=O)₂OR^{o4}, —OS(=O)₂R^{c3}, —S(=O)N(R^{n2})₂, —S(=O)₂N(R^{n2})₂, —N(R^{n2})S(=O)R^{s1}, —N(R^{n2})S(=O)₂R^{s1}, —N(R^{n2})C(=O)OR^{o4}, —OC(=O)N(R^{n2})₂, —N(R^{n2})C(=O)N(R^{n2})₂, —N(R^{n2})S(=O)N(R^{n2})₂, —N(R^{n2})S(=O)₂N(R^{n2})₂, —N(R^{n2})S(=O)OR^{o4}, —N(R^{n2})S(=O)₂OR^{o4}, —OS(=O)N(R^{n2})₂, or —OS(=O)₂N(R^{n2})₂; or two instances of R″ attached to the same or adjacent carbon atoms, taken together with the carbon atoms to which they are attached to form an optionally substituted cycloalkyl or a heterocycloalkyl; wherein:

each instance of R^{n2} is independently hydrogen, an optionally substituted —C₁-C₆ alkyl, or a nitrogen protecting group;

each instance of R^{o4} is independently hydrogen, an optionally substituted —C₁-C₆ alkyl, or an oxygen protecting group;

each instance of R^{c3} is independently an optionally substituted —C₁-C₆ alkyl;

each instance of R^{s1} is independently an optionally substituted —C₁-C₆ alkyl or a sulfur protecting group;

n is 0, 1, 2, or 3, as valency permits; and

R^{nc} is independently hydrogen, optionally substituted —C₁-C₆ alkyl, or a nitrogen protecting group.

17. The method of claim 1, wherein the compound is of Formula (II'):

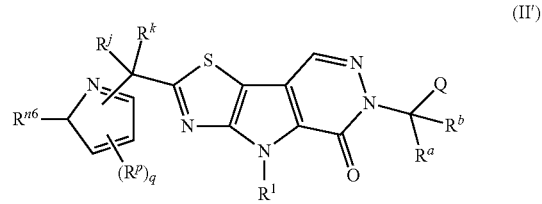

(II')

or a pharmaceutically acceptable salt thereof, wherein:

R^{a} and R^{b} are each independently hydrogen, halogen, —CN, —NO₂, —N₃, optionally substituted alkyl, —OR^{o3}, —N(R^{n1})₂, —C(=O)N(R^{n1})₂, or —C(=O)R^{c2}, or R^{a} and R^{b} can be taken together with the carbon atom to form optionally substituted cycloalkyl or optionally substituted heterocyclyl;

each instance of R^{n1} is independently hydrogen, optionally substituted —C₁-C₆ alkyl, or a nitrogen protecting group;

each instance of R^{o3} is independently hydrogen, optionally substituted —C₁-C₆ alkyl, or an oxygen protecting group;

each instance of R^{c2} is independently optionally substituted —C₁-C₆ alkyl;

each instance of R^{j} and R^{k} is independently selected from H, halogen, —CN, —OR^{o7}, —N(R^{n5})₂, —N(R^{n5})C(=O) R^{c5}, —C(=O)N(R^{n5})₂, —C(=O)R^{c5}, —C(=O)OR^{o7}, —SR^{js}, —S(=O)₂R^{js}, or —S(=O)R$^{js}$, optionally substituted —C$_1$-C$_6$ alkyl; or R$^j$ and R$^k$ can be taken together with the carbon atom to form C=O, C=NR$^{jn}$, an optionally substituted C$_3$-C$_6$ monocyclic cycloalkyl ring or an optionally substituted C$_3$-C$_6$ monocyclic heterocyclyl ring;

each of R$^{n5}$ and R$^{jn}$ is independently hydrogen, optionally substituted —C$_1$-C$_6$ alkyl, —OR$^{o8}$, or a nitrogen protecting group;

each instance of R$^{o7}$ is independently hydrogen, optionally substituted —C$_1$-C$_6$ alkyl, or an oxygen protecting group;

each instance of R$^{c5}$ is independently optionally substituted —C$_1$-C$_6$ alkyl;

each instance of R$^{js}$ is independently optionally substituted —C$_1$-C$_6$ alkyl, optionally substituted C$_{6-12}$ aryl, optionally substituted heteroaryl, or a sulfur protecting group;

each instance of R$^p$ is independently selected from hydrogen, halogen, —CN, —NO$_2$, —N$_3$, optionally substituted alkyl, optionally substituted alkenyl, optionally substituted alkynyl, optionally substituted cycloalkyl, optionally substituted aryl, optionally substituted heterocyclyl, optionally substituted heteroaryl, —OR$^{o6}$, —SR$^{s2}$, —N(R$^{n3}$)$_2$, —C(=O)N(R$^{n3}$)$_2$, —N(R$^{n3}$)C(=O)R$^{c4}$, —C(=O)R$^{c4}$, —C(=O)OR$^{o6}$, —OC(=O)R$^{c4}$, —S(=O)R$^{s2}$, —S(=O)$_2$R$^{s2}$, —S(=O)OR$^{o6}$, —OS(=O)R$^{c4}$, —S(=O)$_2$OR$^{o6}$, —OS(=O)$_2$R$^{c4}$, —S(=O)N(R$^{n3}$)$_2$, —S(=O)$_2$N(R$^{n3}$)$_2$, —N(R$^{n3}$)S(=O)R$^{s2}$, —N(R$^{n3}$)S(=O)$_2$R$^{s2}$, —N(R$^{n3}$)C(=O)OR$^{o6}$, —OC(=O)N(R$^{n3}$)$_2$, —N(R$^{n3}$)C(=O)N(R$^{n3}$)$_2$, —N(R$^{n3}$)S(=O)N(R$^{n3}$)$_2$, —N(R$^{n3}$)S(=O)$_2$N(R$^{n3}$)$_2$, —N(R$^{n3}$)S(=O)OR$^{o6}$, —N(R$^{n3}$)S(=O)$_2$OR$^{o6}$, —OS(=O)N(R$^{n3}$)$_2$, —OS(=O)$_2$N(R$^{n3}$)$_2$, or two instances of R$^p$ attached to the same or adjacent carbon atoms, taken together with the atoms to which they are attached form an optionally substituted cycloalkyl or a heterocycloalkyl;

each instance of R$^{n3}$, R$^{nc}$, and R$^{nd}$ is independently hydrogen, optionally substituted —C$_1$-C$_6$ alkyl, or a nitrogen protecting group;

each instance of R$^{o6}$ is independently hydrogen, optionally substituted —C$_1$-C$_6$ alkyl, or an oxygen protecting group;

each instance of R$^{c4}$ is independently optionally substituted —C$_1$-C$_6$ alkyl;

each instance of R$^{s2}$ is independently optionally substituted —C$_1$-C$_6$ alkyl, or a sulfur protecting group; and q is 0, 1, 2, or 3.

18. The method of claim 1, wherein the compound is of Formula (III'):

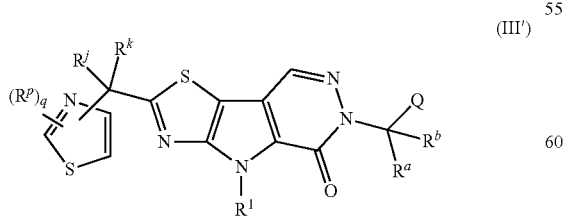

(III')

or a pharmaceutically acceptable salt thereof, wherein:
R$^a$ and R$^b$ are each independently hydrogen, halogen, —CN, —NO$_2$, —N$_3$, optionally substituted alkyl, —OR$^{o3}$, —N(R$^{n1}$)$_2$, —C(=O)N(R$^{n1}$)$_2$, or —C(=O)R$^{c2}$, or R$^a$ and R$^b$ can be taken together with the carbon atom to form optionally substituted cycloalkyl or optionally substituted heterocyclyl;

each instance of R$^{n1}$ is independently hydrogen, optionally substituted —C$_1$-C$_6$ alkyl, or a nitrogen protecting group;

each instance of R$^{o3}$ is independently hydrogen, optionally substituted —C$_1$-C$_6$ alkyl, or an oxygen protecting group;

each instance of R$^{c2}$ is independently optionally substituted —C$_1$-C$_6$ alkyl;

each instance of R$^j$ and R$^k$ is independently selected from H, halogen, —CN, —OR$^{o7}$, —N(R$^{n5}$)$_2$, —N(R$^{n5}$)C(=O) R$^{c5}$, —C(=O)N(R$^{n5}$)$_2$, —C(=O)R$^{c5}$, —C(=O)OR$^{o7}$, —SR$^{js}$, —S(=O)$_2$R$^{js}$, or —S(=O)R$^{js}$, optionally substituted —C$_1$-C$_6$ alkyl; or R$^j$ and R$^k$ can be taken together with the carbon atom to form C=O, C=NR$^{jn}$, an optionally substituted C$_3$-C$_6$ monocyclic cycloalkyl ring or an optionally substituted C$_3$-C$_6$ monocyclic heterocyclyl ring;

each of R$^{n5}$ and R$^{jn}$ is independently hydrogen, optionally substituted —C$_1$-C$_6$ alkyl, —OR$^{o8}$, or a nitrogen protecting group;

each instance of R$^{o7}$ is independently hydrogen, optionally substituted —C$_1$-C$_6$ alkyl, or an oxygen protecting group;

each instance of R$^{c5}$ is independently optionally substituted —C$_1$-C$_6$ alkyl;

each instance of R$^{js}$ is independently optionally substituted —C$_1$-C$_6$ alkyl, optionally substituted C$_{6-12}$ aryl, optionally substituted heteroaryl, or a sulfur protecting group;

each instance of R$^p$ is independently selected from hydrogen, halogen, —CN, —NO$_2$, —N$_3$, optionally substituted alkyl, optionally substituted alkenyl, optionally substituted alkynyl, optionally substituted cycloalkyl, optionally substituted aryl, optionally substituted heterocyclyl, optionally substituted heteroaryl, —OR$^{o6}$, —SR$^{s2}$, —N(R$^{n3}$)$_2$, —C(=O)N(R$^{n3}$)$_2$, —N(R$^{n3}$)C(=O)R$^{c4}$, —C(=O)R$^{c4}$, —C(=O)OR$^{o6}$, —OC(=O)R$^{c4}$, —S(=O)R$^{s2}$, —S(=O)$_2$R$^{s2}$, —S(=O)OR$^{o6}$, —OS(=O)R$^{c4}$, —S(=O)$_2$OR$^{o6}$, —OS(=O)$_2$R$^{c4}$, —S(=O)N(R$^{n3}$)$_2$, —S(=O)$_2$N(R$^{n3}$)$_2$, —N(R$^{n3}$)S(=O)R$^{s2}$, —N(R$^{n3}$)S(=O)$_2$R$^{s2}$, —N(R$^{n3}$)C(=O)OR$^{o6}$, —OC(=O)N(R$^{n3}$)$_2$, —N(R$^{n3}$)C(=O)N(R$^{n3}$)$_2$, —N(R$^{n3}$)S(=O)N(R$^{n3}$)$_2$, —N(R$^{n3}$)S(=O)$_2$N(R$^{n3}$)$_2$, —N(R$^{n3}$)S(=O)OR$^{o6}$, —N(R$^{n3}$)S(=O)$_2$OR$^{o6}$, —OS(=O)N(R$^{n3}$)$_2$, —OS(=O)$_2$N(R$^{n3}$)$_2$, or two instances of R$^p$ attached to the same or adjacent carbon atoms, taken together with the atoms to which they are attached form an optionally substituted cycloalkyl or a heterocycloalkyl;

each instance of R$^{n3}$, R$^{nc}$, and R$^{nd}$ is independently hydrogen, optionally substituted —C$_1$-C$_6$ alkyl, or a nitrogen protecting group;

each instance of R$^{o6}$ is independently hydrogen, optionally substituted —C$_1$-C$_6$ alkyl, or an oxygen protecting group;

each instance of R$^{c4}$ is independently optionally substituted —C$_1$-C$_6$ alkyl;

each instance of R$^{s2}$ is independently optionally substituted —C$_1$-C$_6$ alkyl, or a sulfur protecting group; and q is 0, 1, 2, or 3.

19. The method of claim 1, wherein the compound is of Formula (IV'):

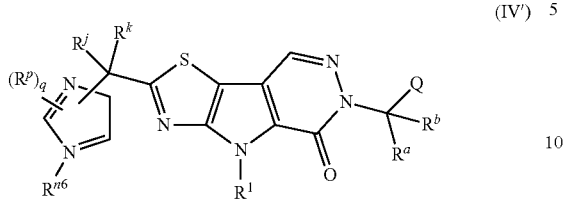

(IV')

or a pharmaceutically acceptable salt thereof, wherein:
$R^a$ and $R^b$ are each independently hydrogen, halogen, —CN, —NO$_2$, —N$_3$, optionally substituted alkyl, —OR$^{o3}$, —N(R$^{n1}$)$_2$, —C(=O)N(R$^{n1}$)$_2$, or —C(=O)R$^{c2}$, or $R^a$ and $R^b$ can be taken together with the carbon atom to form optionally substituted cycloalkyl or optionally substituted heterocyclyl;
each instance of R$^{n1}$ is independently hydrogen, optionally substituted —C$_1$-C$_6$ alkyl, or a nitrogen protecting group;
each instance of R$^{o3}$ is independently hydrogen, optionally substituted —C$_1$-C$_6$ alkyl, or an oxygen protecting group;
each instance of R$^{c2}$ is independently optionally substituted —C$_1$-C$_6$ alkyl;
each instance of R$^j$ and R$^k$ is independently selected from H, halogen, —CN, —OR$^{o7}$, —N(R$^{n5}$)$_2$, —N(R$^{n5}$)C(=O) R$^{c5}$, —C(=O)N(R$^{n5}$)$_2$, —C(=O) R$^{c5}$, —C(=O)OR$^{o7}$, —SR$^{js}$, —S(=O)$_2$R$^{js}$, or —S(=O)R$^{js}$, optionally substituted —C$_1$-C$_6$ alkyl; or R$^j$ and R$^k$ can be taken together with the carbon atom to form C=O, C=NR$^{jn}$, an optionally substituted C$_3$-C$_6$ monocyclic cycloalkyl ring or an optionally substituted C$_3$-C$_6$ monocyclic heterocyclyl ring;
each of R$^{n5}$ and R$^{jn}$ is independently hydrogen, optionally substituted —C$_1$-C$_6$ alkyl, —OR$^{o8}$, or a nitrogen protecting group;
each instance of R$^{o7}$ is independently hydrogen, optionally substituted —C$_1$-C$_6$ alkyl, or an oxygen protecting group;
each instance of R$^{c5}$ is independently optionally substituted —C$_1$-C$_6$ alkyl;
each instance of R$^{js}$ is independently optionally substituted —C$_1$-C$_6$ alkyl, optionally substituted C$_{6-12}$ aryl, optionally substituted heteroaryl, or a sulfur protecting group;
each instance of R$^p$ is independently selected from hydrogen, halogen, —CN, —NO$_2$, —N$_3$, optionally substituted alkyl, optionally substituted alkenyl, optionally substituted alkynyl, optionally substituted cycloalkyl, optionally substituted aryl, optionally substituted heterocyclyl, optionally substituted heteroaryl, —OR$^{o6}$, —SR$^{s2}$, —N(R$^{n3}$)$_2$, —C(=O)N(R$^{n3}$)$_2$, —N(R$^{n3}$)C(=O)R$^{c4}$, —C(=O)R$^{c4}$, —C(=O)OR$^{o6}$, —OC(=O)R$^{c4}$, —S(=O)R$^{s2}$, —S(=O)$_2$R$^{s2}$, —S(=O)OR$^{o6}$, —OS(=O)R$^{c4}$, —S(=O)$_2$OR$^{o6}$, —OS(=O)$_2$R$^{c4}$, —S(=O)N(R$^{n3}$)$_2$, —S(=O)$_2$N(R$^{n3}$)$_2$, —N(R$^{n3}$)S(=O)R$^{s2}$, —N(R$^{n3}$)S(=O)$_2$R$^{s2}$, —N(R$^{n3}$)C(=O)OR$^{o6}$, —OC(=O)N(R$^{n3}$)$_2$, —N(R$^{n3}$)C(=O)N(R$^{n3}$)$_2$, —N(R$^{n3}$)S(=O)N(R$^{n3}$)$_2$, —N(R$^{n3}$)S(=O)$_2$N(R$^{n3}$)$_2$, —N(R$^{n3}$)S(=O)OR$^{o6}$, —N(R$^{n3}$)S(=O)$_2$OR$^{o6}$, —OS(=O)N(R$^{n3}$)$_2$, —OS(=O)$_2$N(R$^{n3}$)$_2$, or two instances of R$^p$ attached to the same or adjacent carbon atoms, taken together with the atoms to which they are attached form an optionally substituted cycloalkyl or a heterocycloalkyl;
each instance of R$^{n3}$, R$^{nc}$, and R$^{nd}$ is independently hydrogen, optionally substituted —C$_1$-C$_6$ alkyl, or a nitrogen protecting group;
each instance of R$^{o6}$ is independently hydrogen, optionally substituted —C$_1$-C$_6$ alkyl, or an oxygen protecting group;
each instance of R$^{c4}$ is independently optionally substituted —C$_1$-C$_6$ alkyl;
each instance of R$^{s2}$ is independently optionally substituted —C$_1$-C$_6$ alkyl, or a sulfur protecting group;
q is 0, 1, 2, or 3; and
R$^{n6}$ is hydrogen, an optionally substituted —C$_1$-C$_6$ alkyl, or a nitrogen protecting group.

20. The method of claim 1, wherein the compound is of Formula (V'):

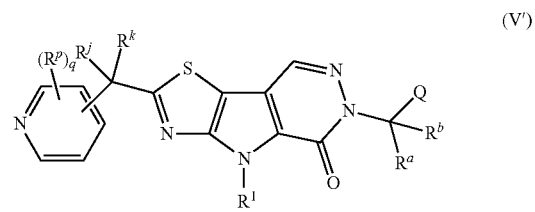

(V')

or a pharmaceutically acceptable salt thereof, wherein:
$R^a$ and $R^b$ are each independently hydrogen, halogen, —CN, —NO$_2$, —N$_3$, optionally substituted alkyl, —OR$^{o3}$, —N(R$^{n1}$)$_2$, —C(=O)N(R$^{n1}$)$_2$, or —C(=O)R$^{c2}$, or $R^a$ and $R^b$ can be taken together with the carbon atom to form optionally substituted cycloalkyl or optionally substituted heterocyclyl;
each instance of R$^{n1}$ is independently hydrogen, optionally substituted —C$_1$-C$_6$ alkyl, or a nitrogen protecting group;
each instance of R$^{o3}$ is independently hydrogen, optionally substituted —C$_1$-C$_6$ alkyl, or an oxygen protecting group;
each instance of R$^{c2}$ is independently optionally substituted —C$_1$-C$_6$ alkyl;
each instance of R$^j$ and R$^k$ is independently selected from H, halogen, —CN, —OR$^{o7}$, —N(R$^{n5}$)$_2$, —N(R$^{n5}$)C(=O) R$^{c5}$, —C(=O)N(R$^{n5}$)$_2$, —C(=O) R$^{c5}$, —C(=O)OR$^{o7}$, —SR$^{js}$, —S(=O)$_2$R$^{js}$, or —S(=O)R$^{js}$, optionally substituted —C$_1$-C$_6$ alkyl; or R$^j$ and R$^k$ can be taken together with the carbon atom to form C=O, C=NR$^{jn}$, an optionally substituted C$_3$-C$_6$ monocyclic cycloalkyl ring or an optionally substituted C$_3$-C$_6$ monocyclic heterocyclyl ring;
each of R$^{n5}$ and R$^{jn}$ is independently hydrogen, optionally substituted —C$_1$-C$_6$ alkyl, —OR$^{o8}$, or a nitrogen protecting group;
each instance of R$^{o7}$ is independently hydrogen, optionally substituted —C$_1$-C$_6$ alkyl, or an oxygen protecting group;
each instance of R$^{c5}$ is independently optionally substituted —C$_1$-C$_6$ alkyl;
each instance of R$^{js}$ is independently optionally substituted —C$_1$-C$_6$ alkyl, optionally substituted C$_{6-12}$ aryl, optionally substituted heteroaryl, or a sulfur protecting group;

each instance of $R^p$ is independently selected from hydrogen, halogen, —CN, —NO$_2$, —N$_3$, optionally substituted alkyl, optionally substituted alkenyl, optionally substituted alkynyl, optionally substituted cycloalkyl, optionally substituted aryl, optionally substituted heterocyclyl, optionally substituted heteroaryl, —OR$^{o6}$, —SR$^{s2}$, —N(R$^{n3}$)$_2$, —C(=O)N(R$^{n3}$)$_2$, —N(R$^{n3}$)C(=O)R$^{c4}$, —C(=O)R$^{c4}$, —C(=O)OR$^{o6}$, —OC(=O)R$^{c4}$, —S(=O)R$^{s2}$, —S(=O)$_2$R$^{s2}$, —S(=O)OR$^{o6}$, —OS(=O)R$^{c4}$, —S(=O)$_2$OR$^{o6}$, —OS(=O)$_2$R$^{c4}$, —S(=O)N(R$^{n3}$)$_2$, —S(=O)$_2$N(R$^{n3}$)$_2$, —N(R$^{n3}$)S(=O)R$^{s2}$, —N(R$^{n3}$)S(=O)$_2$R$^{s2}$, —N(R$^{n3}$)C(=O)OR$^{o6}$, —OC(=O)N(R$^{n3}$)$_2$, —N(R$^{n3}$)C(=O)N(R$^{n3}$)$_2$, —N(R$^{n3}$)S(=O)N(R$^{n3}$)$_2$, —N(R$^{n3}$)S(=O)$_2$N(R$^{n3}$)$_2$, —N(R$^{n3}$)S(=O)OR$^{o6}$, —N(R$^{n3}$)S(=O)$_2$OR$^{o6}$, —OS(=O)N(R$^{n3}$)$_2$, —OS(=O)$_2$N(R$^{n3}$)$_2$, or two instances of $R^p$ attached to the same or adjacent carbon atoms, taken together with the atoms to which they are attached form an optionally substituted cycloalkyl or a heterocycloalkyl;

each instance of R$^{n3}$, R$^{nc}$, and R$^{nd}$ is independently hydrogen, optionally substituted —C$_1$-C$_6$ alkyl, or a nitrogen protecting group;

each instance of R$^{o6}$ is independently hydrogen, optionally substituted —C$_1$-C$_6$ alkyl, or an oxygen protecting group;

each instance of R$^{c4}$ is independently optionally substituted —C$_1$-C$_6$ alkyl;

each instance of R$^{s2}$ is independently optionally substituted —C$_1$-C$_6$ alkyl, or a sulfur protecting group; and q is 0, 1, 2, or 3.

21. The method of claim 1, wherein the compound is selected from

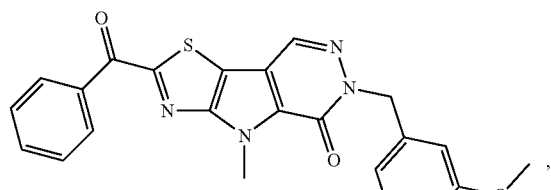

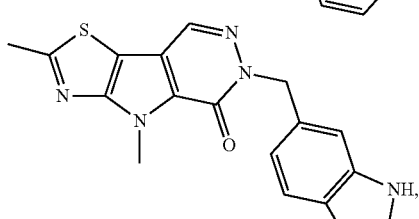

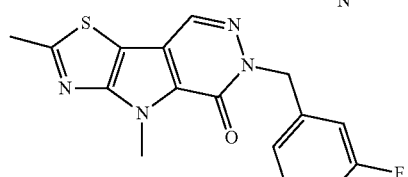

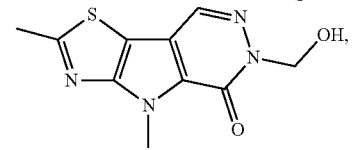

-continued

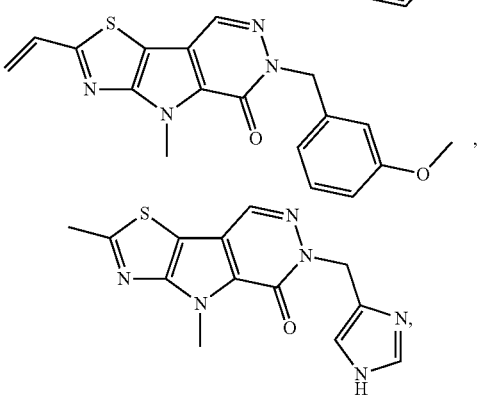

461
-continued
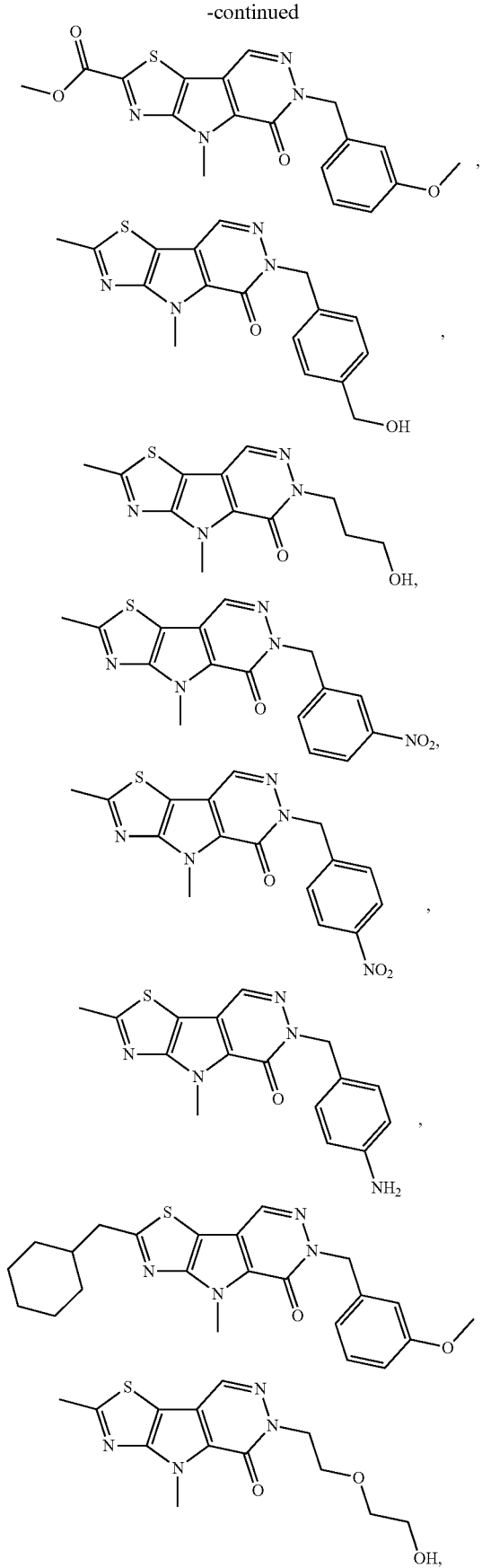
462
-continued
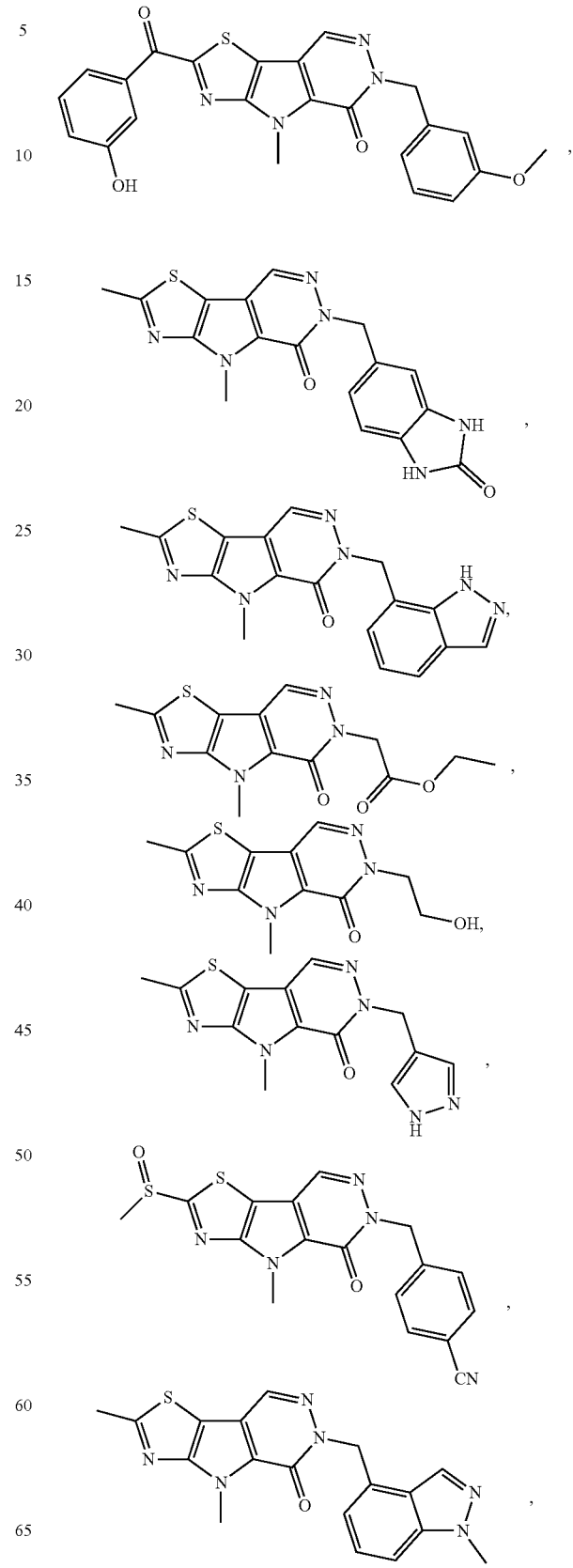

463
-continued
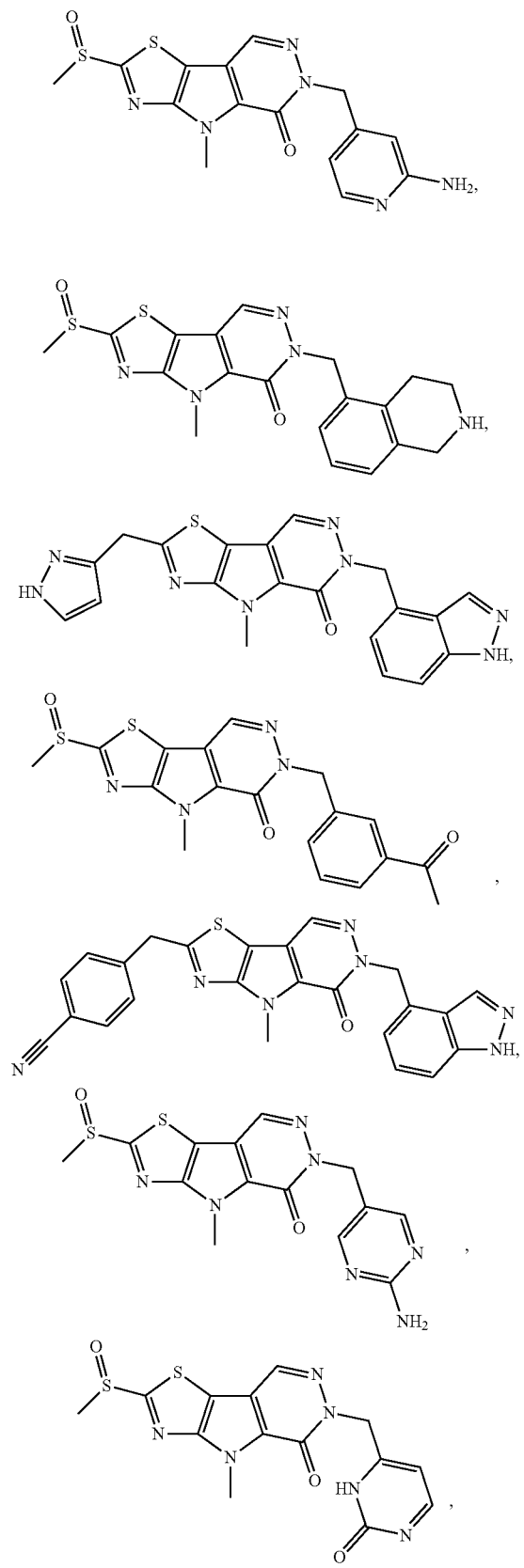
464
-continued
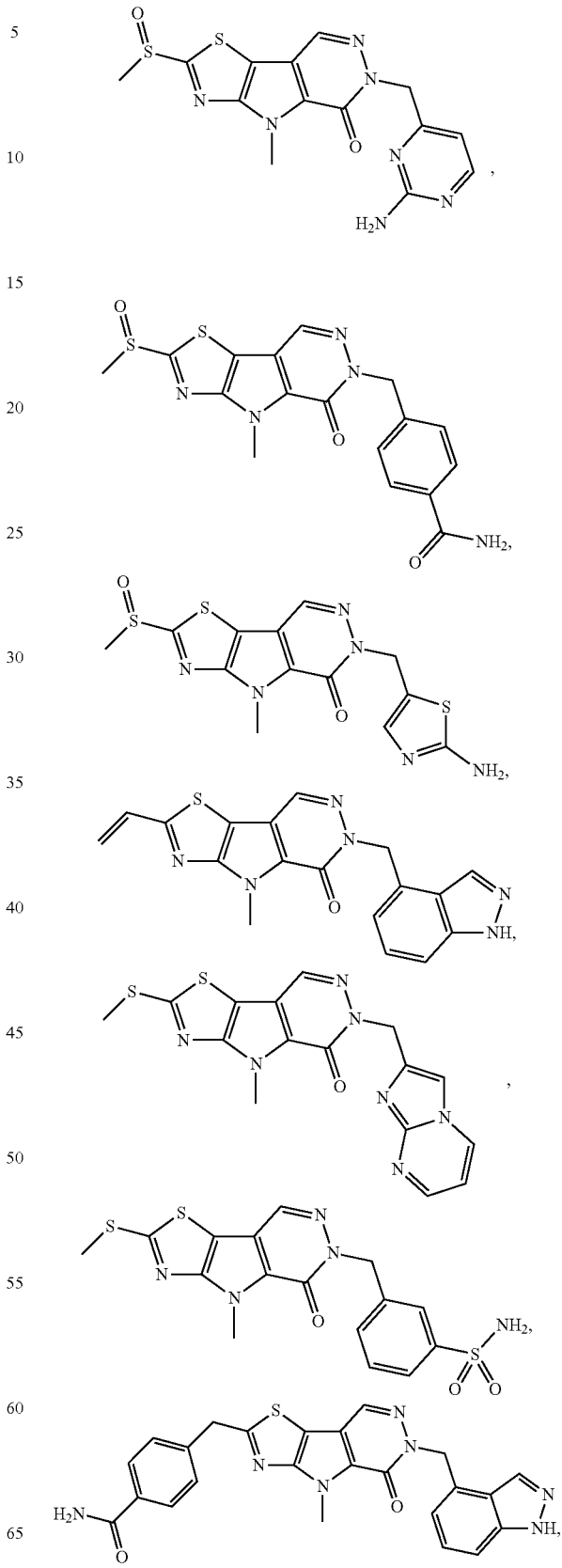

465
-continued
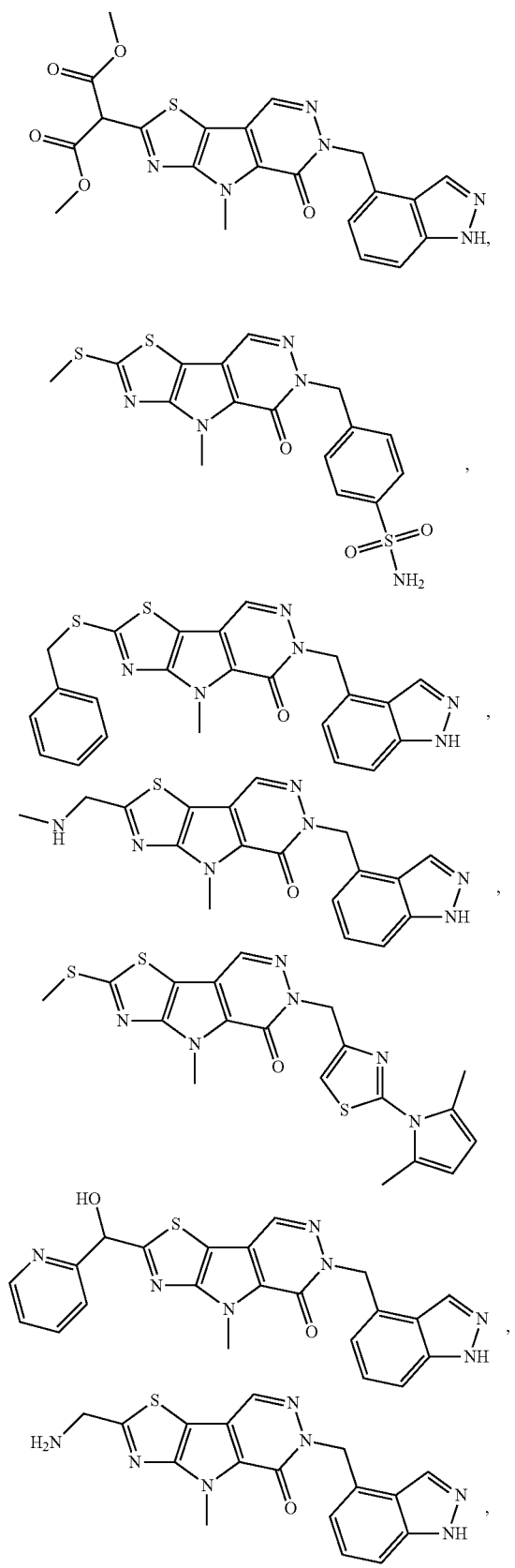
466
-continued
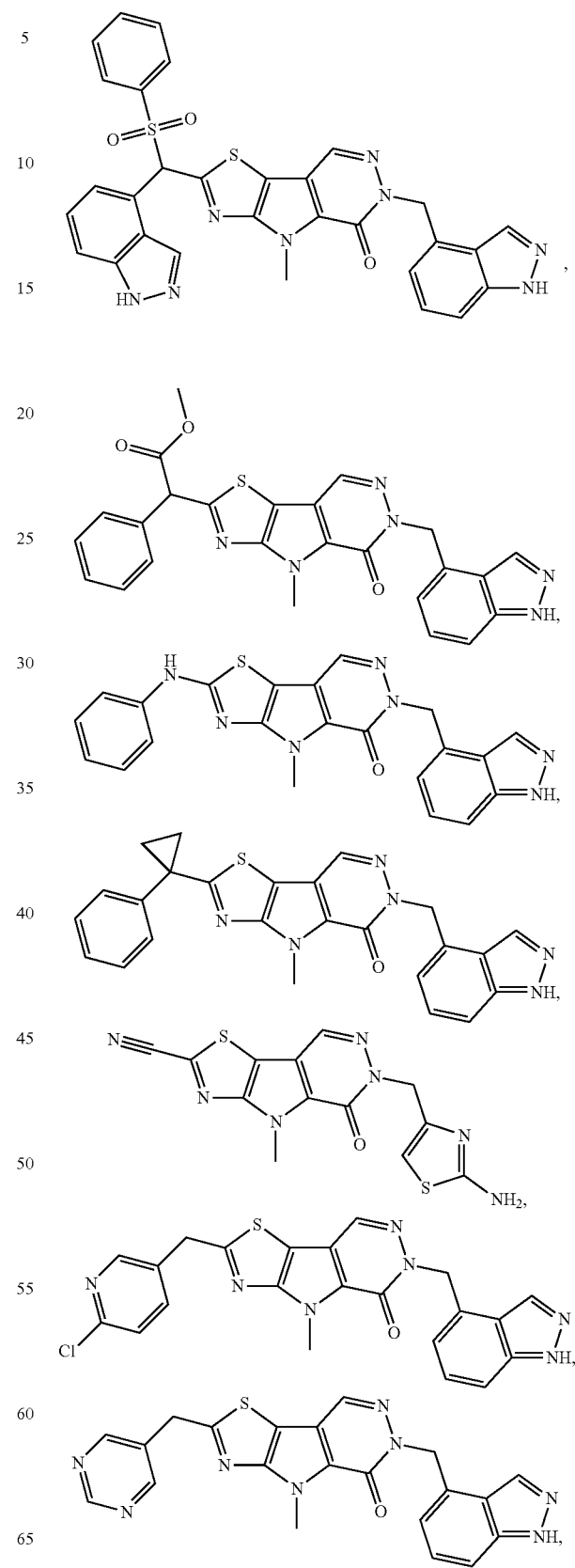

467
-continued
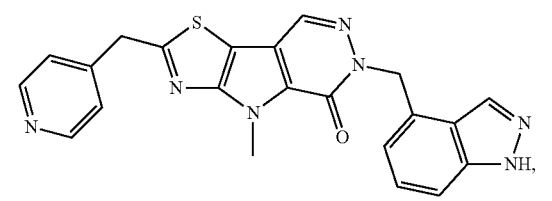
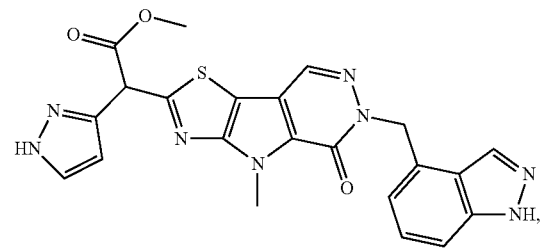
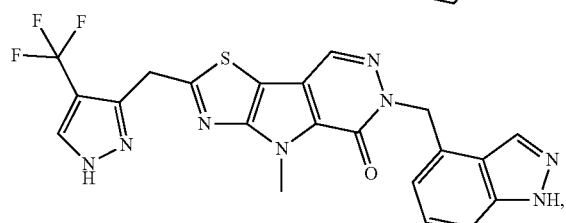
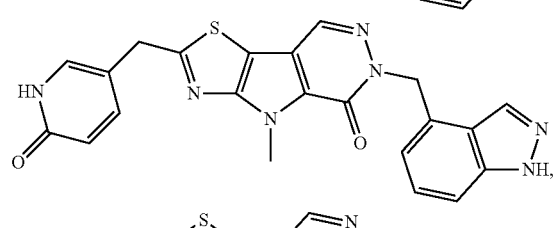
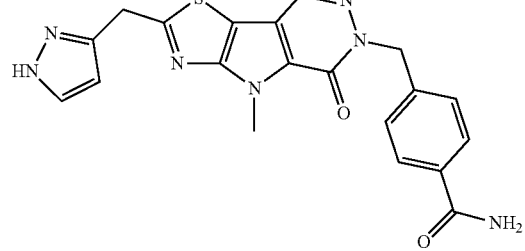
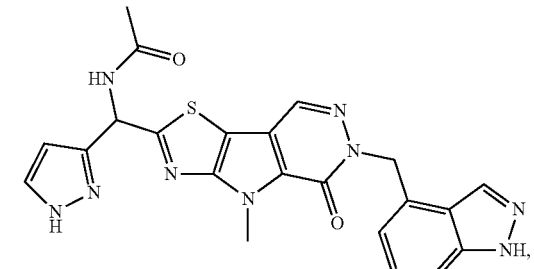
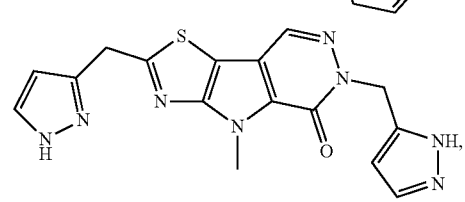
468
-continued
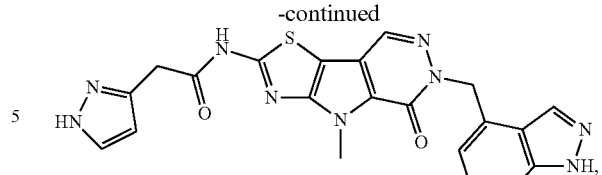
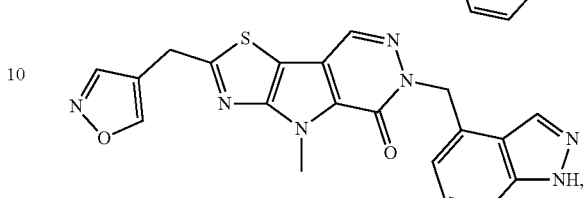
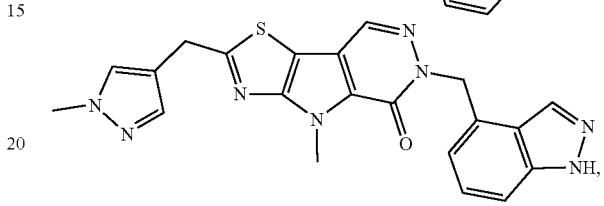
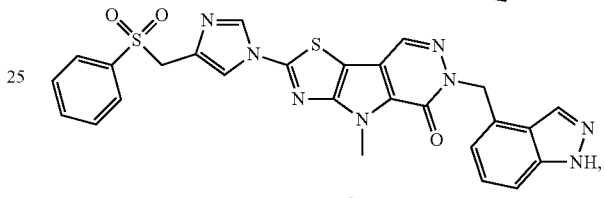
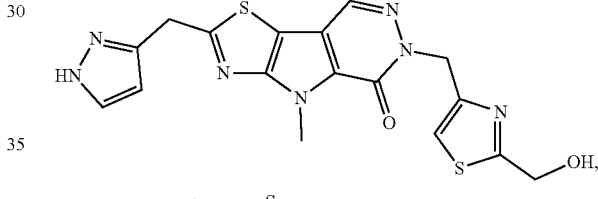
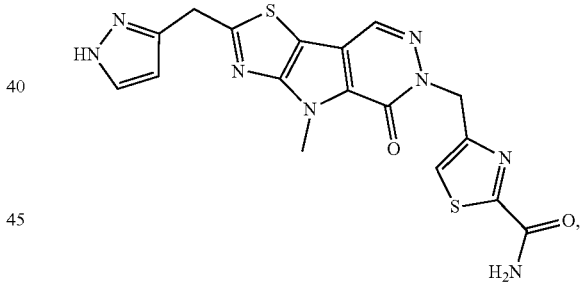
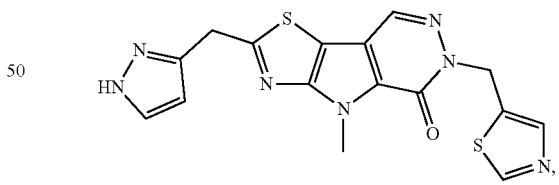
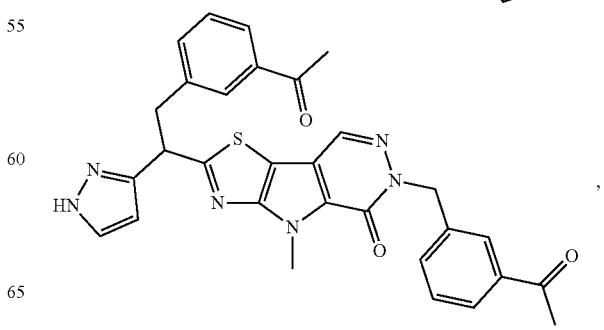

469
-continued
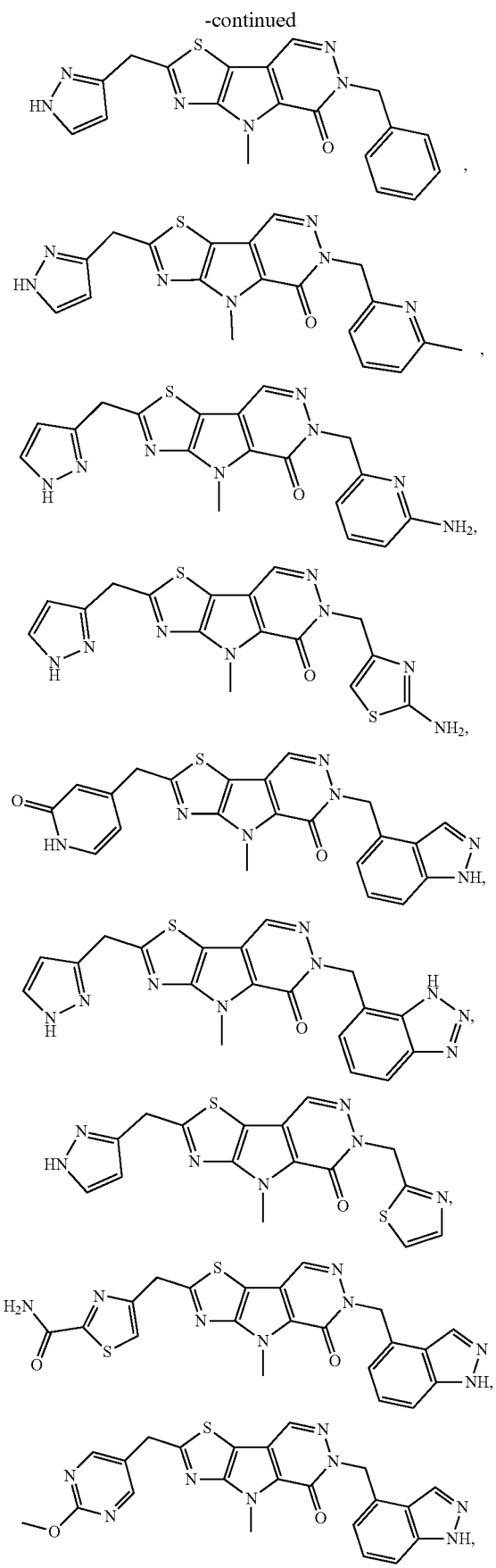
470
-continued
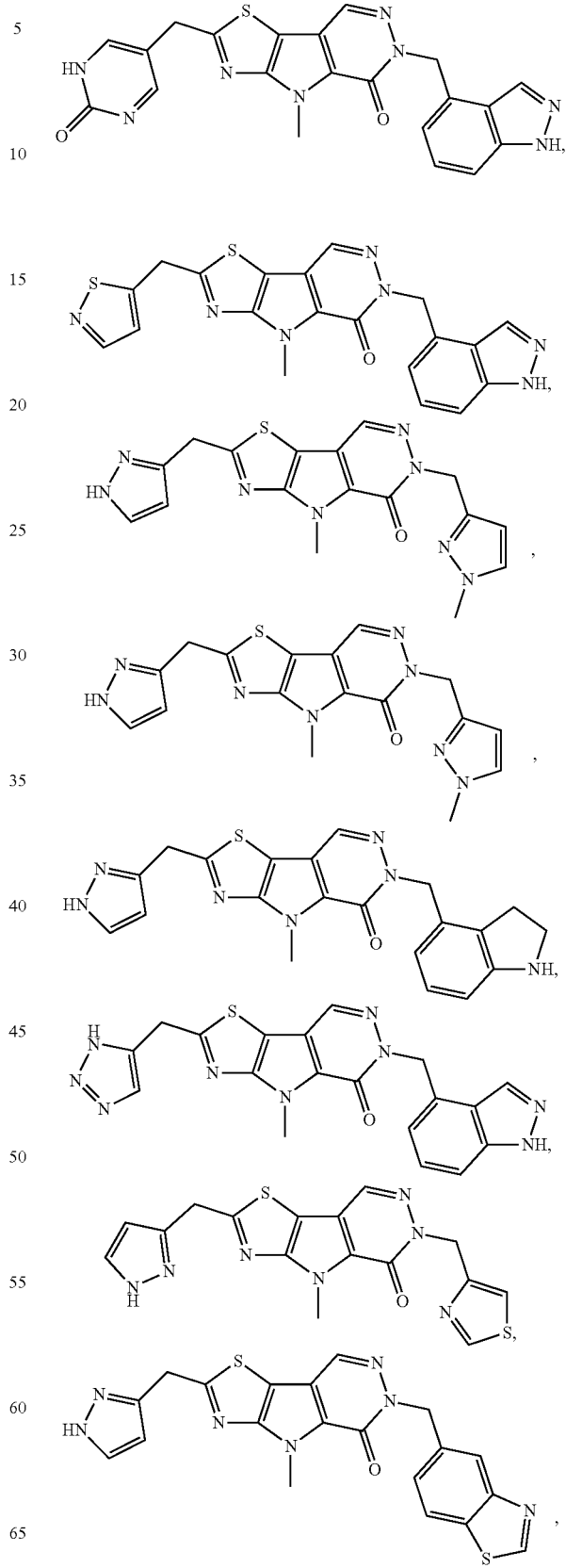

-continued
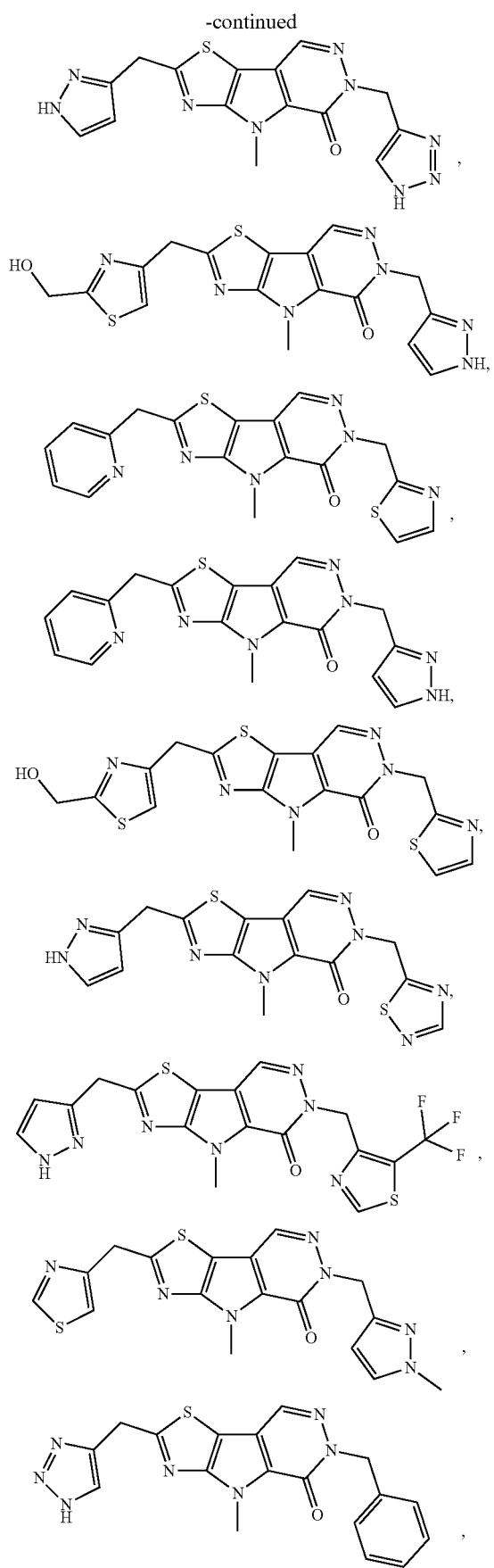
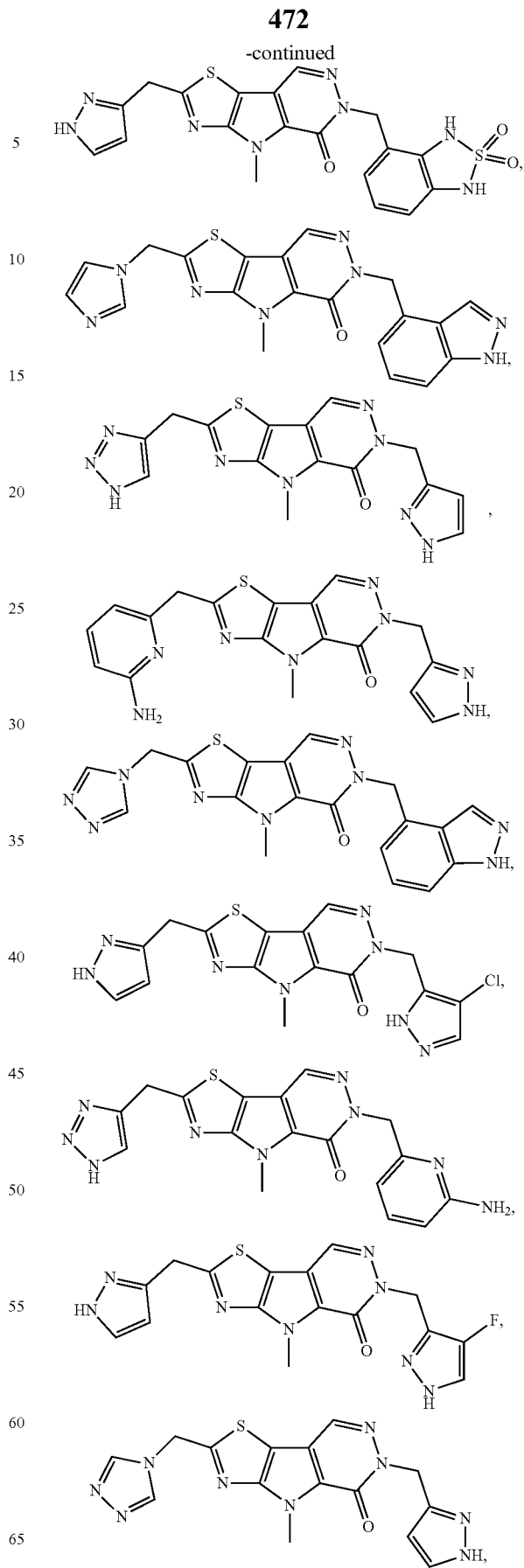

473
-continued
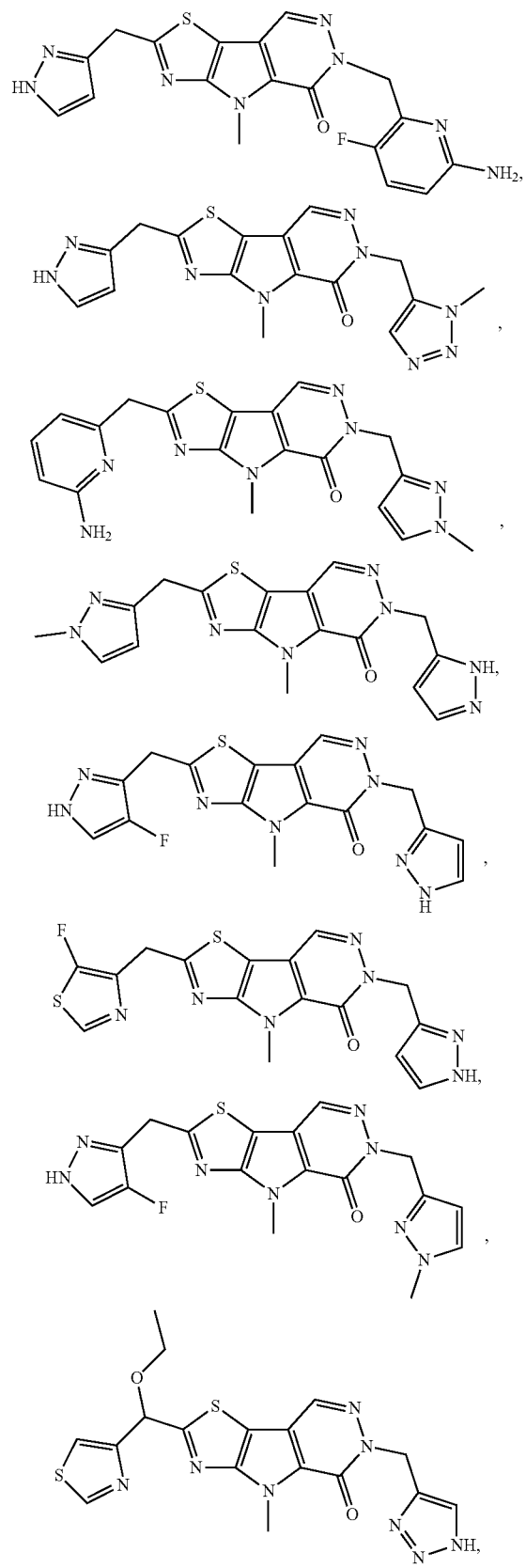
474
-continued
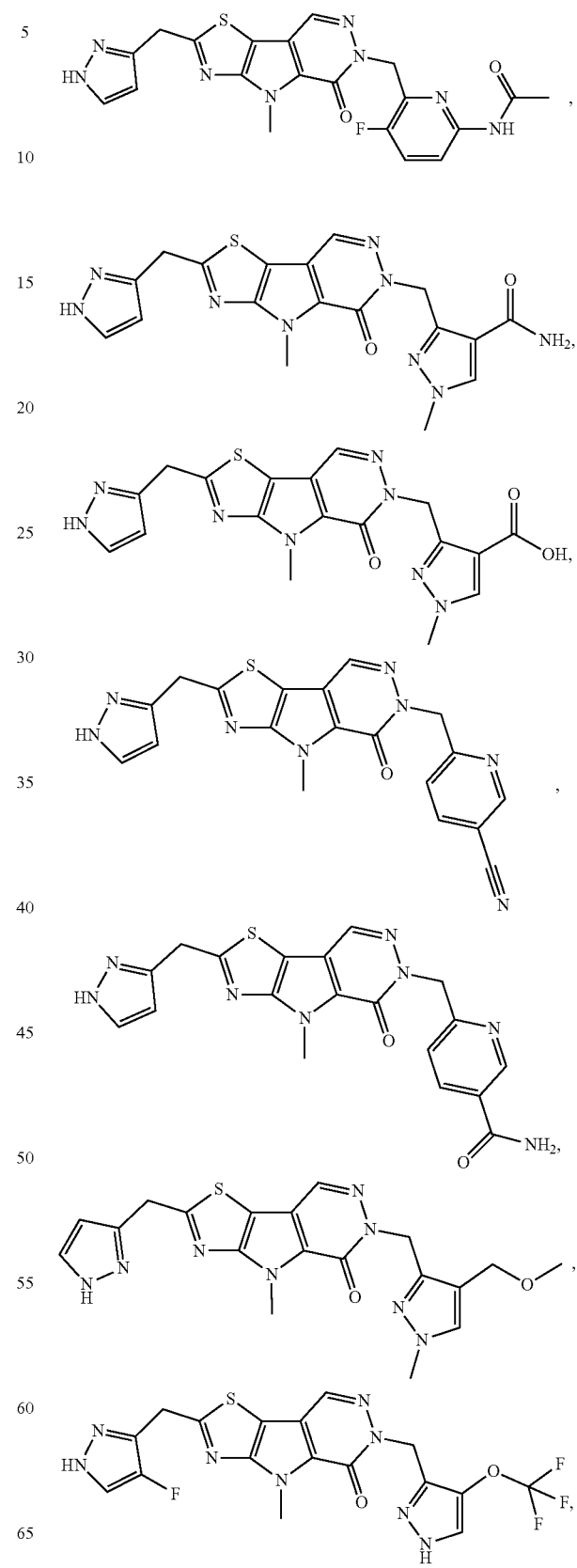

475
-continued
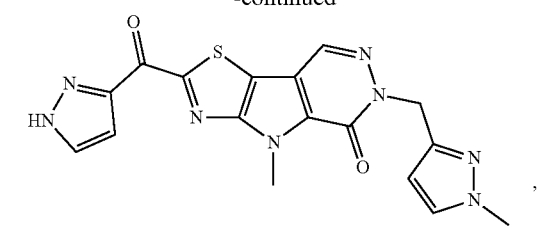
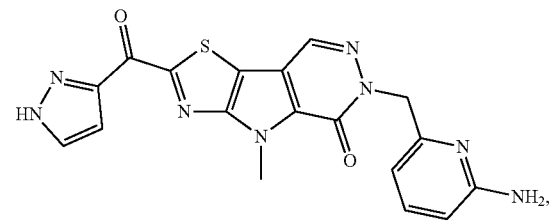
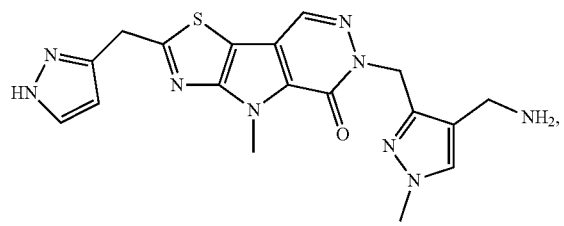
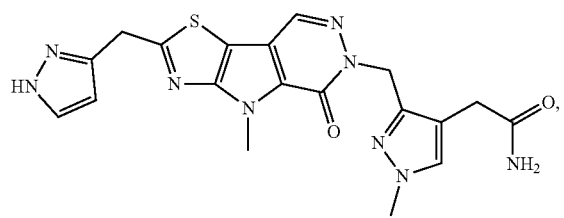
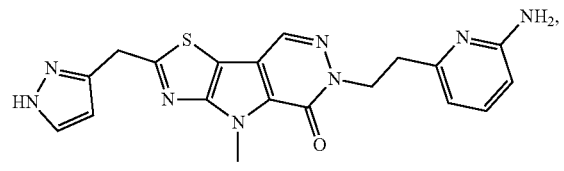
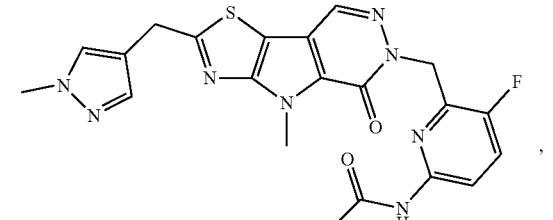
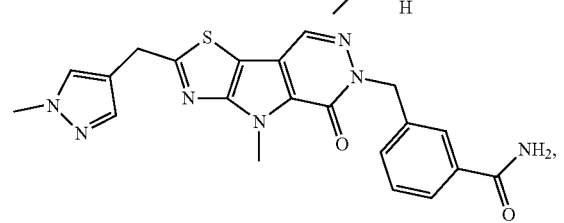
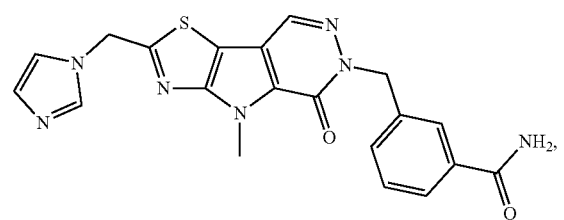
476
-continued
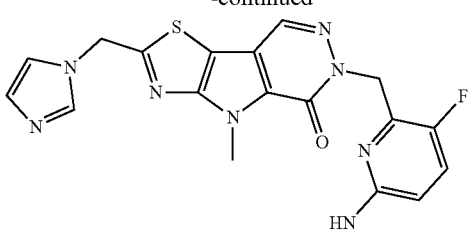
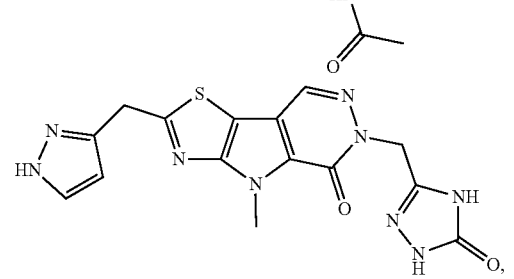
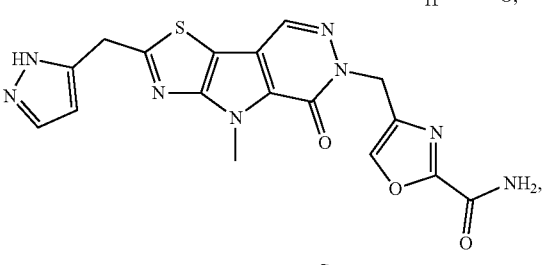
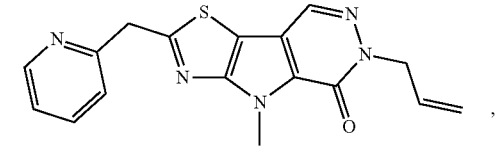
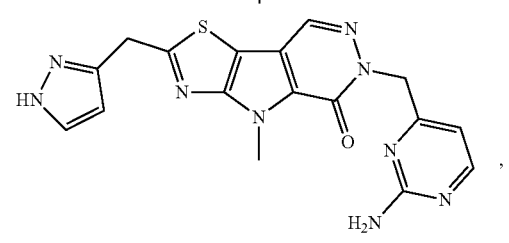
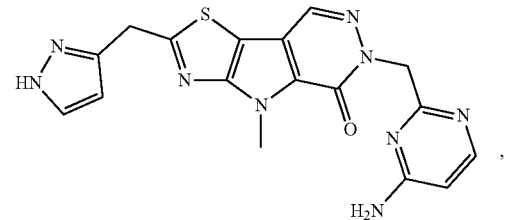
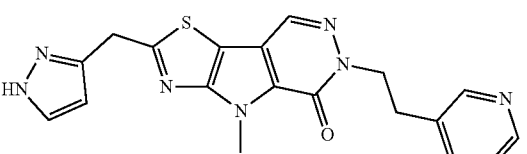
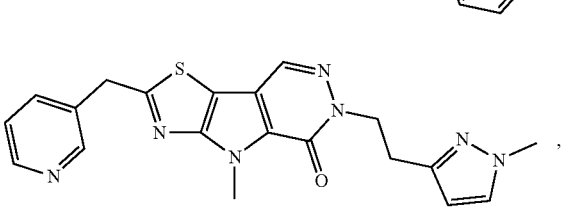

477
-continued
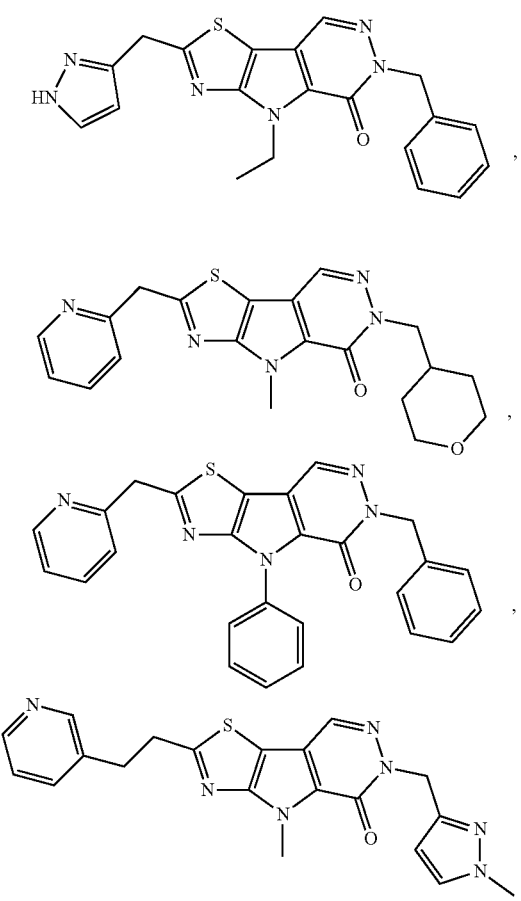
478
-continued
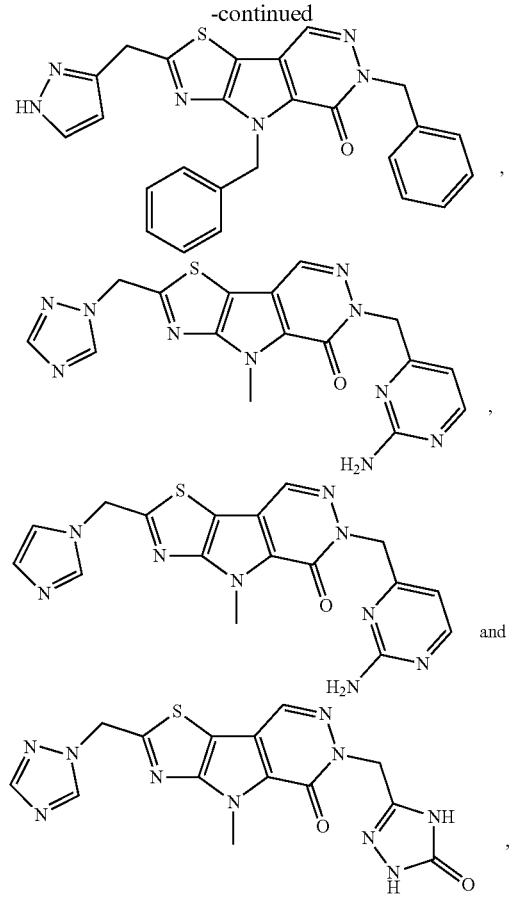
or a pharmaceutically acceptable salt thereof.
* * * * *